(12) United States Patent
Schrepfer et al.

(10) Patent No.: US 11,987,628 B2
(45) Date of Patent: May 21, 2024

(54) METHODS AND COMPOSITIONS FOR MODULATING CAR-T ACTIVITY

(71) Applicant: Sana Biotechnology, Inc., Seattle, WA (US)

(72) Inventors: Sonja Schrepfer, San Mateo, CA (US); Lindong Weng, Seattle, WA (US); Terry J. Fry, Denver, CO (US)

(73) Assignee: Sana Biotechnology, Inc., Seattle, WA (US)

( * ) Notice: Subject to any disclaimer, the term of this patent is extended or adjusted under 35 U.S.C. 154(b) by 0 days.

(21) Appl. No.: 18/339,157

(22) Filed: Jun. 21, 2023

(65) Prior Publication Data

US 2024/0002507 A1 Jan. 4, 2024

Related U.S. Application Data

(63) Continuation of application No. 17/666,523, filed on Feb. 7, 2022, now Pat. No. 11,802,157, which is a continuation of application No. 17/561,659, filed on Dec. 23, 2021.

(60) Provisional application No. 63/288,477, filed on Dec. 10, 2021, provisional application No. 63/255,795, filed on Oct. 14, 2021, provisional application No. 63/175,003, filed on Apr. 14, 2021, provisional application No. 63/136,172, filed on Jan. 11, 2021, provisional application No. 63/133,171, filed on Dec. 31, 2020.

(51) Int. Cl.
| | |
|---|---|
| *A61K 35/17* | (2015.01) |
| *A61P 35/00* | (2006.01) |
| *C07K 14/705* | (2006.01) |
| *C07K 14/725* | (2006.01) |
| *C07K 14/74* | (2006.01) |
| *C07K 16/28* | (2006.01) |
| *C12N 5/0783* | (2010.01) |
| *C12N 15/86* | (2006.01) |
| *A61K 39/00* | (2006.01) |

(52) U.S. Cl.
CPC .......... *C07K 16/2803* (2013.01); *A61K 35/17* (2013.01); *A61P 35/00* (2018.01); *C07K 14/70503* (2013.01); *C07K 14/7051* (2013.01); *C07K 14/70539* (2013.01); *C12N 5/0636* (2013.01); *C12N 15/86* (2013.01); *A61K 2039/505* (2013.01); *A61K 2039/5156* (2013.01); *A61K 2039/5158* (2013.01); *C07K 2317/76* (2013.01); *C07K 2319/02* (2013.01); *C07K 2319/03* (2013.01); *C07K 2319/30* (2013.01); *C07K 2319/33* (2013.01); *C12N 2510/00* (2013.01); *C12N 2740/15043* (2013.01)

(58) Field of Classification Search
None
See application file for complete search history.

(56) References Cited

U.S. PATENT DOCUMENTS

| | | |
|---|---|---|
| 6,140,081 A | 10/2000 | Barbas |
| 6,453,242 B1 | 9/2002 | Eisenberg et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,689,558 B2 | 2/2004 | Case |
| 6,794,136 B1 | 9/2004 | Eisenberg et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,253,273 B2 | 8/2007 | Collingwood |
| 7,262,054 B2 | 8/2007 | Jamieson et al. |
| 7,355,012 B2 | 4/2008 | Pastan et al. |
| 7,361,635 B2 | 4/2008 | Miller et al. |
| 7,541,034 B1 | 6/2009 | Fitzgerald et al. |
| 7,982,011 B2 | 7/2011 | Pastan et al. |
| 8,906,682 B2 | 12/2014 | June et al. |
| 11,026,975 B2 | 6/2021 | Zhou et al. |
| 11,162,079 B2 | 11/2021 | Schrepfer et al. |
| 11,802,157 B2 | 10/2023 | Schrepfer et al. |
| 2005/0064474 A1 | 3/2005 | Urnov et al. |
| 2005/0267061 A1 | 12/2005 | Martin |

(Continued)

FOREIGN PATENT DOCUMENTS

| | | |
|---|---|---|
| WO | WO-97/15664 A1 | 5/1997 |
| WO | WO-98/53058 A1 | 11/1998 |

(Continued)

OTHER PUBLICATIONS

Arnould et al., Engineering of Large Numbers of Highly Specific Homing Endonucleases that Induce Recombination on Novel DNA Targets, J. Mol. Biol., 1-16 (2005).

(Continued)

*Primary Examiner* — Michael D Burkhart
(74) *Attorney, Agent, or Firm* — Choate, Hall & Stewart LLP; Stephanie L. Schonewald; Meaghan E. Bychowski

(57) ABSTRACT

Disclosed herein are engineered cells and/or hypoimmunogenic cells including engineered and/or hypoimmunogenic stem cells, engineered and/or hypoimmunogenic cells differentiated therefrom, engineered and/or hypoimmunogenic CAR-T cells (primary or differentiated from engineered and/or hypoimmunogenic stem cells) and related methods of their use and generation. Provided herein are engineered and/or hypoimmunogenic cells exhibiting reduced expression of MHC class I and/or MHC class II human leukocyte antigens and T-cell receptors. In some embodiments, such cells also exogenously express one or more tolerogenic factors such as CD47 and one or more chimeric antigen receptors (CAR)s.

30 Claims, 62 Drawing Sheets

Specification includes a Sequence Listing.

(56) References Cited

U.S. PATENT DOCUMENTS

| | | | |
|---|---|---|---|
| 2007/0117128 | A1 | 5/2007 | Smith et al. |
| 2007/0218528 | A1 | 9/2007 | Miller |
| 2011/0301073 | A1 | 12/2011 | Gregory et al. |
| 2016/0348073 | A1 | 12/2016 | Meissner et al. |
| 2020/0246381 | A1 | 8/2020 | Zhou et al. |
| 2020/0339699 | A1 | 10/2020 | Li et al. |
| 2021/0308183 | A1 | 10/2021 | Schrepfer et al. |
| 2022/0227865 | A1 | 7/2022 | Schrepfer et al. |
| 2022/0331358 | A1 | 10/2022 | Schrepfer et al. |

FOREIGN PATENT DOCUMENTS

| | | |
|---|---|---|
| WO | WO-98/53059 A1 | 11/1998 |
| WO | WO-98/53060 A1 | 11/1998 |
| WO | WO-02/016536 A1 | 2/2002 |
| WO | WO-03/016496 A2 | 2/2003 |
| WO | WO-2010/104949 A2 | 9/2010 |
| WO | WO-2012/079000 A1 | 6/2012 |
| WO | WO-2012/163805 A1 | 12/2012 |
| WO | WO-2013/040557 A2 | 3/2013 |
| WO | WO-2014/165825 A2 | 10/2014 |
| WO | WO-2016/030414 A1 | 3/2016 |
| WO | WO-2016/057821 A2 | 4/2016 |
| WO | WO-2016/073955 A2 | 5/2016 |
| WO | WO-2016/126608 A1 | 8/2016 |
| WO | WO-2016/149578 A1 | 9/2016 |
| WO | WO-2016/160721 A1 | 10/2016 |
| WO | WO-2016/183041 A2 | 11/2016 |
| WO | WO-2018/132783 A1 | 7/2018 |
| WO | WO-2018/175390 A1 | 9/2018 |
| WO | WO-2018/176390 A1 | 10/2018 |
| WO | WO-2018/213337 A1 | 11/2018 |
| WO | WO-2019/097305 A2 | 5/2019 |
| WO | WO-2020/014482 A1 | 1/2020 |
| WO | WO-2020/018615 A2 | 1/2020 |
| WO | WO-2020/018620 A1 | 1/2020 |
| WO | WO-2020/168317 A2 | 8/2020 |
| WO | WO-2020/231882 A2 | 11/2020 |
| WO | WO-2021/022223 A1 | 2/2021 |
| WO | WO-2021/222285 A2 | 11/2021 |
| WO | WO-2022/036150 A1 | 2/2022 |
| WO | WO-2022/146891 A2 | 7/2022 |

OTHER PUBLICATIONS

Asgari et al., Differentiation and Transplantation of Human Induced Pluripotent Stem Cell-derived Hepatocyte-like Cells, Stem Cell Rev, 1-12 (2011).
Ashworth et al., Computational redesign of endonuclease DNA binding and cleavage specificity, Nature, 441(7093):656-659 (2006).
Bang et al., HA22 (R490A) Is a Recombinant Immunotoxin with Increased Antitumor Activity without an Increase in Animal Toxicity, Clin. Cancer Res., 11:1545-1550 (2005).
Beerli et al., Engineering polydactyl zinc-finger transcription factors, Nature Biotechnol., 20:135-141 (2002).
Beerli et al., Toward controlling gene expression at will: Specific regulation of the erbB-2 I Her-2 promoter by using polydactyl zinc finger proteins constructed from modular building blocks, Proc. Natl. Acad. Sci. USA, 95:14628-14633 (1998).
Bejcek et al., Development and Characterization of Three Recombinant Single Chain Antibody Fragments (scFvs) Directed against the CD19 Antigen1, Cancer Res. 55:2346-2351 (1995).
Berg and Shi, The Galvanization of Biology: A Growing Appreciation for the Roles of Zinc, Science, 271:1081-1085 (1996).
Bernareggi et al., Development of innate immune cells from human pluripotent stem cells, Exp. Hematol., 71:13-23 (2019).
Berndsen and Denu, Catalysis and Substrate Selection by Histone/Protein Lysine Acetyltransferases, Curr. Opin. Struct. Biol., 18(6):682-689 (2008).
Bird et al., Methylation-Induced Repression-Belts, Braces, and Chromatin, Cell, 99:451-454 (1999).
Bitinaite et al., FokI dimerization is required for DNA cleavage, Proc. Natl. Acad. Sci. USA 95:10570-10575 (1998).
Blazar et al., Strategies to Inhibit Alloantibody Production in Alloprimed Murine Recipients of Hematopoietic Stem Cell Grafts, Am. J. Transplant, 15(4):931-941 (2015).
Boch et al., Breaking the Code of DNA Binding Specificity of TAL-Type III Effectors, Science, 326:1509-1512 (2009).
Boch, TALEs of genome targeting, Nature Biotech. 29(2):135-136 (2011).
Callard et al., CD19 regulation of human B cell responses. B cell proliferation and antibody secretion are inhibited or enhanced by ligation of the CD19 surface glycoprotein depending on the stimulating signal used, J. Immunology, 148(10): 2983-2987 (1992).
Carpenter et al., B-cell Maturation Antigen is a Promising Target for Adoptive T-cell Therapy of Multiple Myeloma, Clin. Cancer Res., 19(8):2048-2060 (2013).
Carroll et al., Genome Engineering With Zinc-Finger Nucleases, Genetics Society of America, 188:773-782 (2011).
Cermak et al., Efficient design and assembly of custom Talen and other TAL effector-based constructs for DNA targeting, Nucl. Acids Res. 39(12):e82 1-11 (2011).
Charlop-Powers et al., Global biogeographic sampling of bacterial secondary metabolism, eLIFE, 1-10 (2015).
Chen et al., Directed evolution of homing endonuclease I-SeeI with altered sequence specificity, Protein Eng. Des. Sel., 22(4):249-256 (2009).
Chen et al., Siglec-G/10 in self-nonself discrimination of innate and adaptive immunity, Glycobiology, 24(9):800-806 (2017).
Chern et al., The Regulator of MAT2 (ROM2) Protein Binds to Early Maturation Promoters and Represses PvALF-Activated Transcription, Plant Cell, 8:305-321 (1996).
Chevalier et al., Design, Activity, and Structure of a Highly Specific Artificial Endonuclease, Molec. Cell, 10:895-905 (2002).
Chevalier, B.S. and B.L. Stoddard, Homing endonucleases: structural functional insight into the catalysts of intron/intein mobility, Nucleic Acids Res., 29(18): 3757-3774 (2001).
Cho et al., Analysis of the C-terminal region of *Arabidopsis thaliana* APETALA 1 as a transcription activation domain, Plant Mol. Biol., 40:419-429 (1999).
Choo et al., Advances in zinc finger engineering, Curr. Opin. Struct. Biol., 10:411-416 (2000).
Choulika et al., Inducation of Homologous Recombination in Mammalian Chormosomes by Using the I-SeeI System of *Saccharomyces cerevisiae*, Mol. Cell. Biol., 15(4):1968-1973 (1995).
Cohen-Tannoudji et al., I-SeeI-Induced Gene Replacement at a Natural Locus in Embryonic Stem Cells, Mol. Cell. Biol., 18(3): 1444-1448 (1998).
Collingwood et al., Nuclear receptors: coactivators, corepressors and chromatin remodeling in the control of transcription, J. Mol. Endocrinol, 23:255-275 (1999).
De Laco et al., A family of double-homeodomain transcription factors regulates zygotic genome activation in placental mammals, Nat. Genet, 49(6):941-945 (2017).
De Rie et al., Regulatory Role of CD19 Molecules in B-Cell Activation and Differentiation, Cell. Immunol., 118:368-381 (1989).
Deuse et al., Hypoimmunogenic derivatives of induced pluripotent stem cells evade immune rejection in fully immunocompetent allogeneic recipients, Nature Biotechnology, 37:252-258 (2019).
Donoho et al., Analysis of Gene Targeting and Intrachromosomal Homologous Recombination Stimulated by Genomic Double-Strand Breaks in Mouse Embryonic Stem Cells, Mol. Cell. Biol, 18(7):4070-4078 (1998).
Doyle and Hunt, Reduced nuclear factor KB (p65) expression in rat primary sensory neurons after peripheral nerve injury, Neuroreport, 8:2937-2942 (1997).
Doyon et al., Directed Evolution and Substrate Specificity Profile of Homing Endonucleases I-SeeI, J. Am. Chem. Soc., 128:2477-2484 (2006).
Doyon et al., Enhancing zinc-finger-nuclease activity with improved obligate heterodimeric architechtures, Nature Methods, 8(1):74-79 (2011).
Elliott et al., Gene Conversion Tracts from Double-Strand Break Repair in Mammalian Cells, Mol. Cell. Biol., 18(1):93-101 (1998).

(56) References Cited

OTHER PUBLICATIONS

Epinat et al., A novel engineered meganuclease induces homologous recombination in yeast and mammalian cells, Nucleic Acids Res. 31(11):2952-2962 (2003).
Fiers et al., Complete nucleotide sequence SV40 DNA, Nature, 273:113-120 (1978).
Freedman et al., Normal cellular counterparts of B cell chronic lymphocytic leukemia, Blood, 70(2):418-427 (1987).
Friedman et al., Effective Targeting of Multiple B-Cell Maturation Antigen-Expressing Hematological Malignances by Anti-B-Cell Maturation Antigen Chimeric Antigen Receptor T Cells, Hum. Gene Ther. 29(5):585-601 (2018).
Gaj et al., ZFN, Talen, and CRISPR/Cas-based methods for genome engineering, Trends in Biotechnology, 31(7):397-405 (2013).
Geng et al., DUX4 Activates Germline Genes, Retroelements, and Immune Mediators: Implications for Facioscapulohumeral Dystrophy, Dev. Cell, 22:38-51 (2012).
Goff et al., Identification of functional domains in the maize transcriptional activator C1: comparison of wild-type and dominant inhibitor proteins, Genes Dev., 5:298-309 (1991).
Gong et al., A constitutively expressed Myc-like gene involved in anthocyanin biosynthesis from Perilla frutescens: molecular characterization, heterologous expression in transgenic plants and transactivation in yeast cells, Plant Mol. Biol., 41:33-44 (1999).
Greenaway et al., Human cytomegalovirus DNA: BamHI, EcoRI and PstI restriction endonuclease cleavage maps, Gene, 18:355-360 (1982).
Guo et al., Directed Evolution of an Enhanced and Highly Efficient FokI Cleavage Domain for Zinc Finger Nucleases, J. Mol. Biol. 400:96-107 (2010).
Hagmann et al., The VP16 Paradox: Herpes Simplex Virus VP16 Contains a Long-Range Activation Domain but within the Natural Multiprotein Complex Activates Only from Promoter-Proximal Positions, J. Virol., 71(8):5952-5962 (1997).
Han et al., Generation of hypoimmunogenic human pluripotent stem cells, Proc. Natl. Acad. Sci. USA, 116(21):10441-10446 (2019).
Hendrickson et al., Conserved roles for murine DUX and human DUX4 in activating cleavage stage genes and MERVL/HERVL retrotransposons, Nat. Genet., 49(6):925-934 (2017).
Herbst et al., B-Cell Depletion In Vitro and In Vivo with an Afucosylated Anti-CD19 Antibody, J. Pharmacol. Exp. Ther., 335:213-222 (2010).
Ho et al., In Vitro Antibody Evolution Targeting Germline Hot Spots to Increase Activity of an Anti-CD22 Immunotoxin, J. Biol. Chem., 280(1):607-617 (2005).
Hobo et al., A bZIP factor, TRAB1, interacts with VP1 and mediates abscisic acid-induced transcription, Proc. Natl. Acad. Sci. USA, 96(26):15348-15353 (1999).
Hockemeyer et al., Genetic engineering of human ES and iPS cells using TALE nucleases, Nat. Biotechnol., 29(8):731-734 (2011).
Hu, X. et al., Engineered Hypoimmune Allogeneic CART Cells Exhibit Innate and Adaptive Immune Evasion Even after Sensitization in Humanized Mice and Retain Potent Anti-Tumor Activity, BLOOD, 138(Supplement 1): 1690-1690 (2021).
Huangfu, D. et al., Induction of pluripotent stem cells by defined factors is greatly improved by small molecule compounds, Nature Biotechnol., 26(7):795-797 (2008).
International Search Report for PCT/US2021/065157, 9 pages (dated Dec. 7, 2022).
Jagannathan et al., Model systems of DUX4 expression recapitulate the transcriptional profile of FSHD cells, Human Molecular Genetics, 25(20):4419-4431 (2016).
Kagoya, Y. et al., Genetic Ablation of HLA Class I, Class II, and the T-cell Receptor Enables Allogeneic T Cells to be Used for Adoptive T-cell Therapy, Cancer Immunology Research, 8(7): 926-936 (2020).
Kansas and Tedder, Transmembrane signals generated through MHC class II, CD19, CD20, CD39, and CD40 antigens induce LFA-1-dependent and independent adhesion in human B cells through a tyrosine kinase-dependent pathway, J. Immunol., 147:4094-4102 (1991).

Kim et al., Hybrid restriction enzymes: Zinc finger fusions to Fok I cleavage domain, Proc. Natl. Acad. Sci. USA, 93:1156-1160 (1996).
Knoepfler et al., Sin Meets NuRD and Other Tails of Repression, Cell, 99:447-450 (1999).
Knorr et al., Clinical-Scale Derivation of Natural Killer Cells From Human Pluripotent Stem Cells for Cancer Therapy, Stem Cells Transl Med., 2:274-283 (2013).
Kouzarides, Chromatin Modifications and Their Funtion, Cell, 128:693-705 (2007).
Lakshmupathy and Vermuri, editors, Pluripotent Stem Cells—Methods and Protocols, Humana Press—Springer (2013).
Lanza R. et al., Engineering universal cells that evade immune detection, Nature Reviews Immunology, Nature Publishing Group UK, London, 19(12):723-733 (2019).
Lemon et al., Nuclear receptor cofactors as chromatin remodelers, Curr. Opin. Genet. Dev., 9:499-504 (1999).
Leo et al, The SRC family of nuclear receptor coactivators, Gene, 245:1-11 (2000).
Liu et al., Context-dependent DNA recognition code for C2H2 zinc-finger transcription factors, Bioinformatics 24(17):1850-1857 (2008).
Liu et al., Suppression of growth and transformation and induction of apoptosis by EGR-1, Cancer Gene Ther., 5(1):3-28 (1998).
Lriguchi et al., A clinically applicable and scalable method to regenerate T-cells from iPSCs for off-the-shelf T-cell immunotherapy, Nature Communications, 12:430:1-15 (2021).
Lsalan et al., A rapid, generally applicable method to engineer zinc fingers illustrated by targeting the HIV-1 promoter, Nature Biotechnol., 19(7):656-660 (2001).
Mali et al., Cas9 as a versatile tool for engineering biology, Nature Methods, 10(10):957-963 (2013).
Mali et al., CAS9 transcriptional activators for target specificity screening and paired nickases for cooperative genome engineering, Nat. Biotech., 1-8 (2013).
Mali et al., RNA-Guided Human Genome Engineering via Cas9, Science, 339(6121):823-826 (2013).
Malik et al., Transcriptional regulation through Mediator-like coactivators in yeast and metazoan cells, Trends Biochem. Sci., 277-283 (2000).
Manteuffel-Cymborowska, Nuclear receptors, their coactivators and modulation of transcription, Acta Biochim. Pol. 46(1):77-89 (1999).
Mapp et al., Activation of gene expression by small molecule transcription factors, Proc. Natl. Acad. Sci. USA, 97(8):3930-3935 (2000).
McKenna et al., Nuclear receptor coactivators: multiple enzymes, multiple complexes, multiple functions, J. Steroid Biochem. Mol. Biol., 69:3-12 (1999).
Meeker et al., A Unique Human B Lymphocyte Antigen Defined by a Monoclonal Antibody, Hybridoma, 3(4):305-320 (1984).
Miller et al., A Tale nuclease architecture for efficient genome editing, Nat. Biotechnol., 29(2):143-148 (2011).
Molinari et al., Proteasome-mediated degradation of transcriptional activators correlates with activation domain potency in vivo, EMBO J., 18(22):6439-6447 (1999).
Moscou et al., A Simple Cipher Governs DNA Recognition by TAL Effectors, Science, 326:1501 (2009).
Ni et al., Hematopoietic and Nature Killer Cell Development from Human Pluripotent Stem Cells, Methods Mol. Biol., 1029:33-41 (2013).
Nicholson et al., Construction and Characterisation of a Functional CD19 Specific Single Chain Fv Fragment for Immunotherapy of B Lineage Leukaemia and Lymphoma, Mol. Immun., 34(16-17):1157-1165 (1997).
Ogawa et al., Rice gibberellin-insensitive gene homolog, OsGAI, encodes a nuclear-localized protein capable of gene activation at transcriptional level, Gene, 245:21-29 (2000).
Okanami et al., HALF-1, a bZIP-type protein, interacting with the wheat transcription factor HBP-1 a contains a novel transcriptional activation domain, Genes Cells, 1:87-99 (1996).
Pabo et al. Design and Selection of Novel CYS2HIS2 Zinc Finger Proteins, Ann. Rev. Biochem., 70:313-340 (2001).

(56) References Cited

OTHER PUBLICATIONS

Paques et al., Meganucleases and DNA Double-Strand Break-Induced Recombination: Perspectives for Gene Therapy, Current Gene Therapy, 7:49-66 (2007).
Pettinato et al., Scalable Differentiation of Human iPSCs in a Multicellular Spheroid-based 3D Culture into Hepatocyte-like Cells through Direct WnUI3-catenin Pathway Inhibition, Science Rep., 1-16 (2016).
Pezzutto et al., CD19 Monoclonal Antibody HD37 Inhibits Anti-Immunoglobulin-Induced B Cell Activation and Proliferation1, J. Immunol., 138(9):2793-2799 (1987).
Pirruccello et al., The Human B Cell-Associated Antigen CD24 is a Single Chain Sialoglycoprotein1, J Immunol., 136(10):3779-3784 (1986).
Puchta et al., Homologous recombination in plant cells is enhanced by in vivo induction of double strand breaks into DNA by a site-specific endonuclease, Nuc. Ac. Res., 21(22):5034-5040 (1993).
Puchta et al., Two different but related mechanisms are used in plants for the repair of genomic double-strand breaks by homologous recombination, Proc. Natl. Acad. Sci. USA, 93:5055-5060 (1996).
Ran et al., Double nicking by RNA-guided CRISPR Cas9 for enhanced genome editing specificity, Cell, 154(6):1380-1389 (2013).
Robertson et al., DNMT1 forms a complex with Rb, E2F1 and HDAC1 and represses transcription from E2F-responsive promoters, Nature Genet., 25:338-342 (2000).
Robyr et al., Nuclear Hormone Receptor, Mol. Endocrinol., 14(3):329-347 (2000).
Rouet et al., Introduction of Double-Strand Breaks ino the Genome of Mouse Cells by Expression of a Rare-Cutting Endonuclease, Mol. Cell. Biol., 14(12):8096-8106 (1994).
Sanjana et al., Improved vectors and genome-wide libraries for CRISPR screening, Nat. Methods, 11(8):783-784 (2014).
Sargent et al., Repair of Site-Specific Double-Strand Breaks in a Mammalian Chromosome by Homologous and Illegitimate Recombination, Mol. Cell. Biol., 17(1):267-77 (1997).
Segal et al. Custom DNA-binding proteins come of age: polydactyl zinc-finger proteins, Curr. Opin. Biotechnol., 12:632-637 (2001).
Seipel et al., Different activation domains stimulate transcription from remote ('enhancer') and proximal ('promoter') positions, EMBO J., 11(13):4961-4968 (1992).
Seki et al., Methods of induced pluripotent stem cells for clinical application, World J. Stem Cells, 7(1):116-125 (2015).
Seligman et al., Mutations altering the cleavage specificity of a homing endonuclease, Nucleic Acids Res., 30(17):3870-3879 (2002).
Sera et al., Rational Design of Artificial Zinc-Finger Proteins Using a Nondegenerate Recognition Code Table, Biochemistry, 41:7074-7081 (2002).
Sha, H. et al., Chimaeric antigen receptor T-cell therapy for tumour immunotherapy, Bioscience Reports, 37:1-12 (2017).
Shankar et al., Genome engineering of induced pluripotent stem cells to manufacture natural killer cell therapies, Stem Cell Res. Ther., 11(1):234 (2020).
Silva et al., From Mononumeric to Homodimeric Endonucleases and Back: Engineering Novel Specificity of LAGLIDADG Enzymes, J. Mol. Biol., 361:744-754 (2006).
Silva et al., Meganucleases and Other Tools for Targeted Genome Engineering: Perspectives and Challenges for Gene Therapy, Current Gene Therapy, 11:11-27 (2011).
Si-Tayeb et al., Highly Efficient Generation of Human Hepatocyte-Like Cells from Induced Pluripotent Stem Cells, Hepatology, 51:297-305 (2010).
Sitko and Barik, Persistent Activation of RelA by Respiratory Syncytial Virus Involves Protein Kinase C, Underphosphorylated IKBI3, and Sequestration of Protein Phosphatase 2A by the Viral Phosphoprotein, J. Virol., 72:5610-5618 (1998).
Smith et al., A combinatorial approach to create artificial homing endonucleases cleaving chosen sequences, Nucleic Acids Res., 34(22) e149:1-12 (2006).
Smith T. et al., In situ programming of leukaemia-specific T cells using synthetic DNA nanocarriers, Nature Nanotechnology, 12(8):813-820 (2017).
Snider et al., Facioscapulohumeral Dystrophy: Incomplete Suppression of a Retrotransposed Gene, PLoS Genet., 1-13 (2010).
Snykers et al., Hepatic Differentiation of Mesenchymal Stem Cells: In Vitro Strategies, Methods Mol. Biol., 698:305-314 (2011).
Sprenger-Haussels et al., Transactivation properties of parsley praline-rich bZIP transcription factors, Plant J., 22(1):1-8 (2000).
Sussman et al., Isolation and Characterization of New Homing Endonuclease Specificites at Individual Target Site Positions, J. Mol. Biol., 342:31-41 (2004).
Szczepek et al., Structure-based redesign of the dimerization interface reduces the toxicity of zinc-finger nucleases, Nature Biotech., 25(7):1-28 (2007).
Takahashi and Yamanaka, Induction of Pluripotent Stem Cells from Mouse Embryonic and Adult Fibroblast Cultures by Defined Factors, Cell, 126:663-676 (2006).
Themeli et al., Generation of tumor-targeted human T lymphocytes from induced pluripotent stem cells for cancer therapy, Nature Biotechnology, 31(10):928-933 (2013).
Themeli et al., New Cell Sources for T Cell Engineering and Adoptive Immunotherapy, Cell Stem Cell, 16(4):357-366 (2015).
Torchia et al., Co-activators and co-repressors in the integration of transcriptional responses, Curr. Opin. Cell. Biol., 10:373-383 (1998).
Tyler et al., The "Dark Side" of Chromatin Remodeling: Repressive Effects on Transcription, Cell, 99:443-446 (1999).
Ulmasov et al., Activation and repression of transcription by auxin-response factors, Proc. Natl. Acad. Sci. USA, 96:5844-5849 (1999).
Van Roey et al., Catalytic domain structure and hypothesis for function of GIY-YIG intron endonuclease I-Tevl, Nature Struct. Biol., 9(11):806-811 (2002).
Whiddon et al., Conservation and innovation in the DUX4-family gene network, Nat Genet., 49(6):935-940 (2017).
Woltjen, K. et al., piggyBac transposition reprograms fibroblasts to induced pluripotent stem cells, Nature, 458(7239):766-770 (2009).
Wood et al., Targeted Genome Editing Across Species Using ZFNs and TALENs, Science, 333(6040):307 (2011).
Written Opinion for PCT/US2021/065157, 15 pages (dated Dec. 7, 2022).
Wu et al., Functional analysis of HD2 histone deacetylase homologues in *Arabidopsis thaliana*, Plant J. 22(1):19-27 (2000).
Wu et al., Multimerization of chimeric anti-CD20 single-chain Fv-Fc fusion protein is mediated through variable domain exchange, Protein Engineering, 14(12):1025-1033 (2001).
Yazawa et al., Immunotherapy using unconjugated CD19 monoclonal antibodies in animal models for B lymphocyte malignancies and autoimmune disease, Proc. Natl. Acad. Sci. USA, 102(42):15178-15183 (2005).
Zeng et al., Generation of 'Off-the-Shelf Natural Killer Cells from Peripheral Blood Cell-Derived Induced Pluripotent Stem Cells, Stem Cell Reports, 9:1796-1812 (2017).
Zhang C. et al., Engineering CAR-T cells, Biomarker Research, 5:22 (2017).
Zhang, Efficient construction of sequence-specific TAL effectors for modulating mammalian transcription, Nature Biotech., 29(2):149-153 (2011).
Zhao et al., A phase 1, open-label study of LCAR-B38M, a chimeric antigen receptor T cell therapy directed against B cell maturation antigen, in patients with relapsed or refractory multiple myeloma, J. Hematol. Oncol., 11(1):141 (2018).
Zhou, H. et al., Generation of Induced Pluripotent Stem Cells Using Recombinant Proteins, Cell Stem Cell, 4(5):381-384 (2009).
Zhou, W. and Freed, C.R., Adenoviral Gene Delivery Can Reprogram Human Fibroblasts to Induced Pluripotent Stem Cells, Stem Cells, 27(11):2667-2674 (2009).
Zhu et al., An improved method to produce clinical scale natural killer cells from human pluripotent stem cells, Methods Mol Biol., 1-14 (2019).

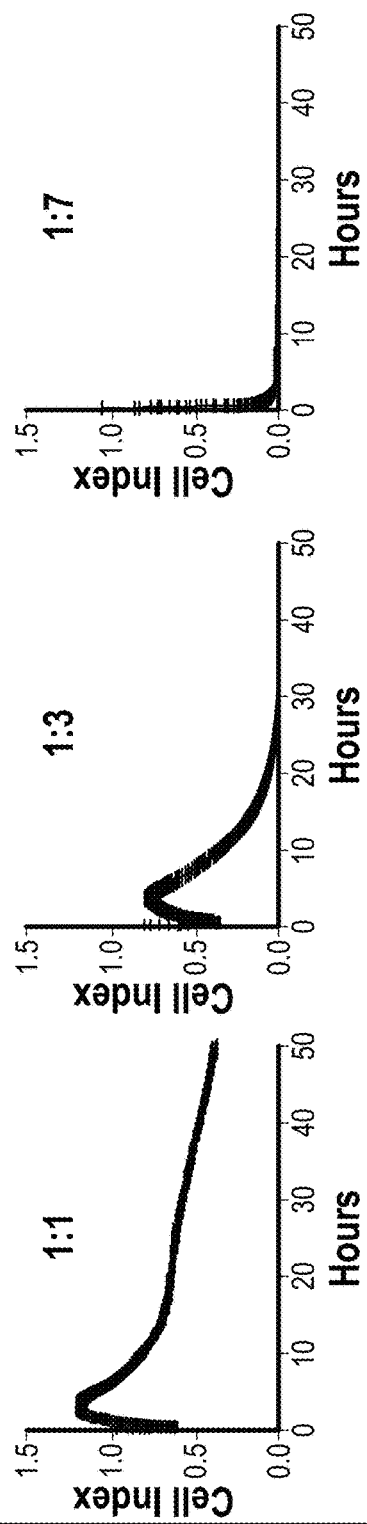
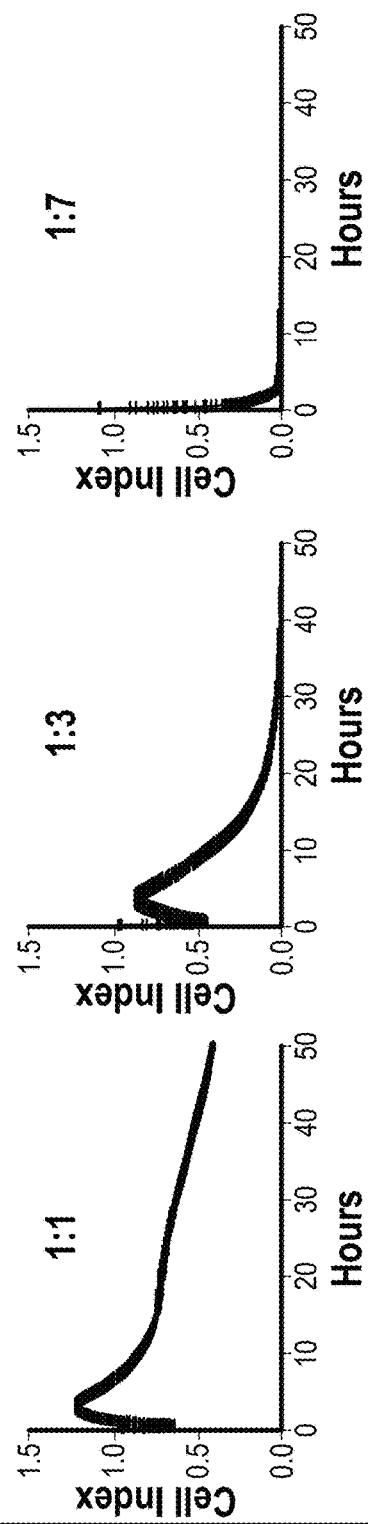
FIG. 5A

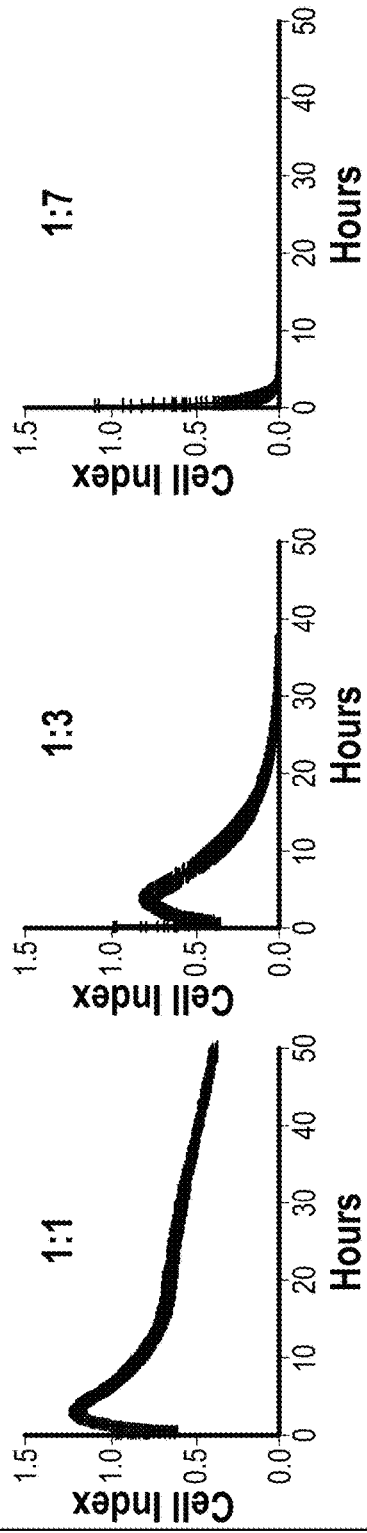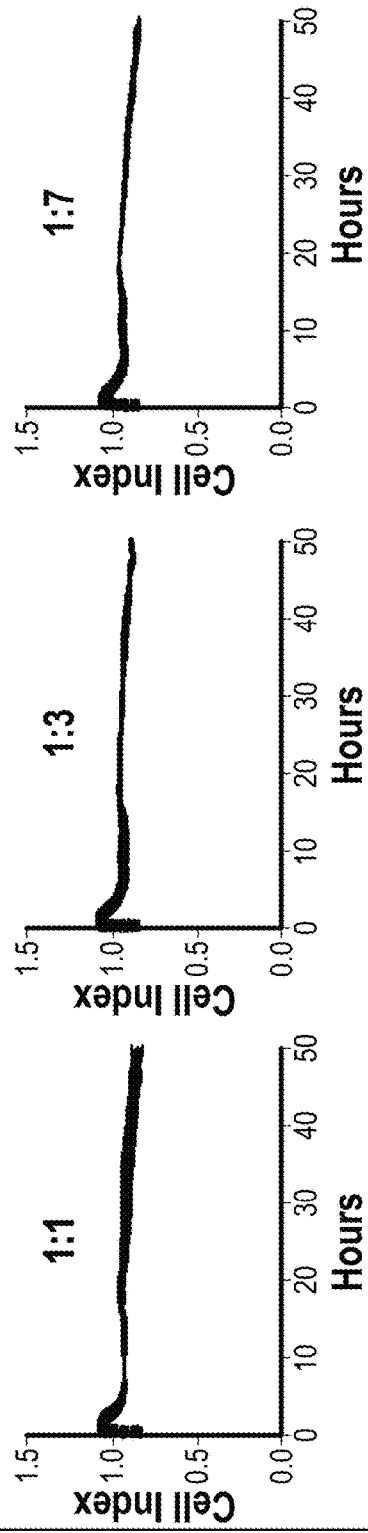
FIG. 5B

Tested Cell Lines

| Cell Line | Transgene (Via Lentiviral Transduction) | Genome Edits | % Triple Knockout | % CAR+ Cells | % CD47+ | % CAR+CD47+ (Double Positive) |
|---|---|---|---|---|---|---|
| HIP CAR-T | CD19-Specific CAR-CD47 | B2M, CIITA, TRAC | 69.3 | 61.7 | 55.8 | 53.9 |
| CAR+ Only | CD47-EGFRt | None | NA | 51.3 | NA | NA |
| CAR+ Only | Tisagenlecleucel Biosimilar/Surrogate | None | NA | 68.9 | NA | NA |

FIG. 25

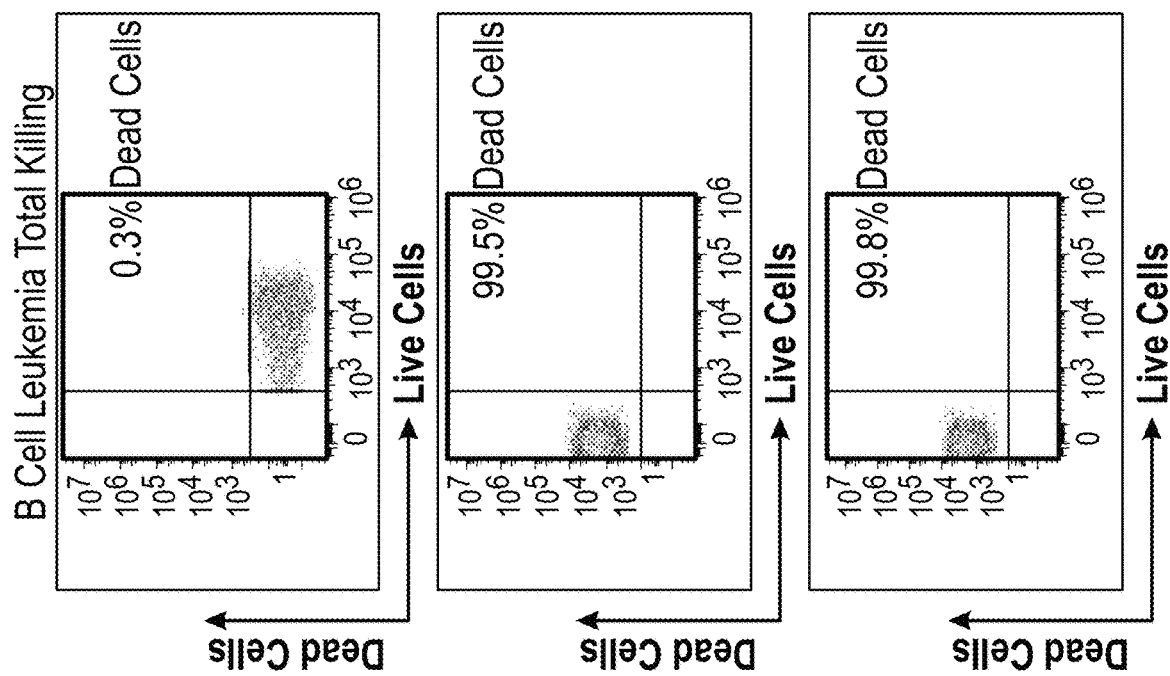
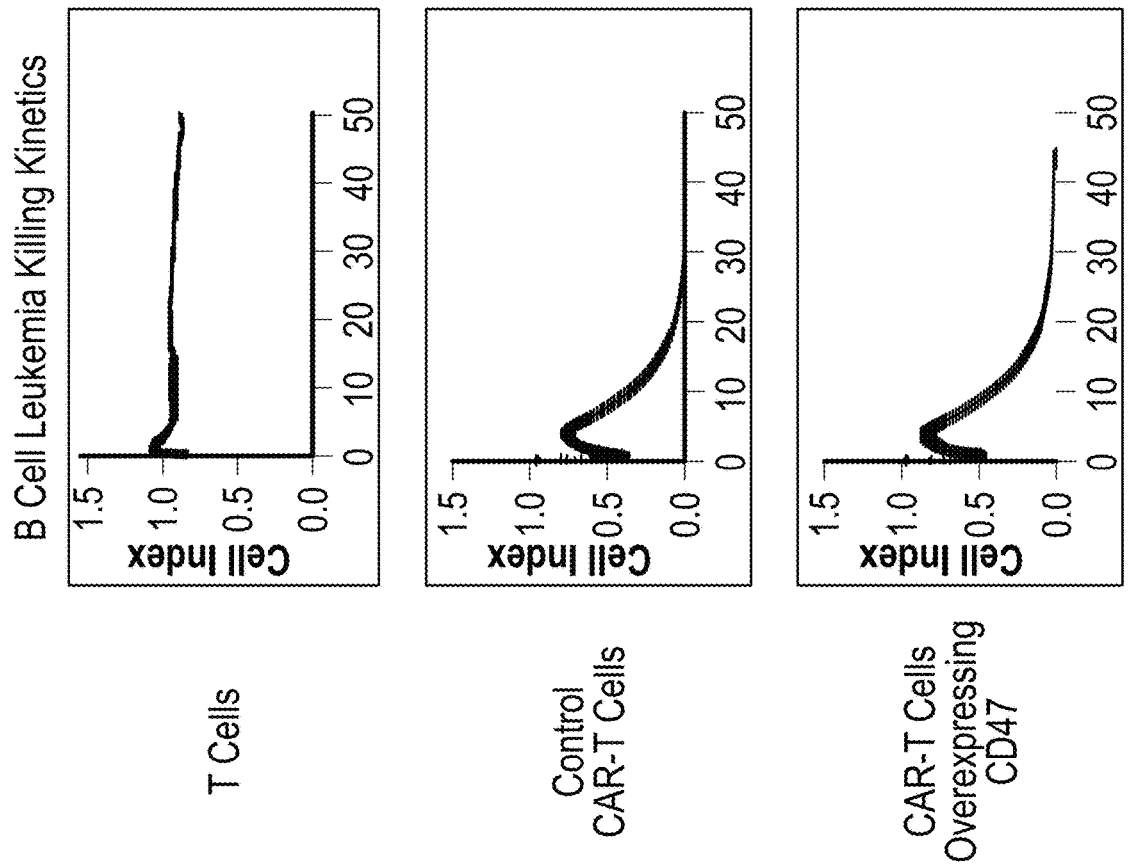
FIG. 30

| T Cell Line | %CD19 CAR+ Cells | %CD47+ | Fold-Change CD47+ MFI Over Unedited T Cells | %CAR+ CD47+ | %CD3-neg | %HLA-ABC-neg | %HLA-DR-DP-DQ-neg | %TKO | %CD8+ | %CD4+ |
|---|---|---|---|---|---|---|---|---|---|---|
| Unedited T Cells | 0.2 | 0.2 | N/A | 0.02 | 0.30 | 0.36 | 58.4 | 0.0 | 70.4 | 28.3 |
| Control CAR-T Cells | 74.7 | 0.1 | N/A | 0.51 | 0.25 | 0.35 | 41.0 | 0.0 | 69.2 | 29.4 |
| TKO/CD47 CAR-T Cells | 70.1 | 74.0 | 4.4 | 68.40 | 99.9 | 88.4 | 83.7 | 73.5 | 46.0 | 52.0 |

FIG. 38

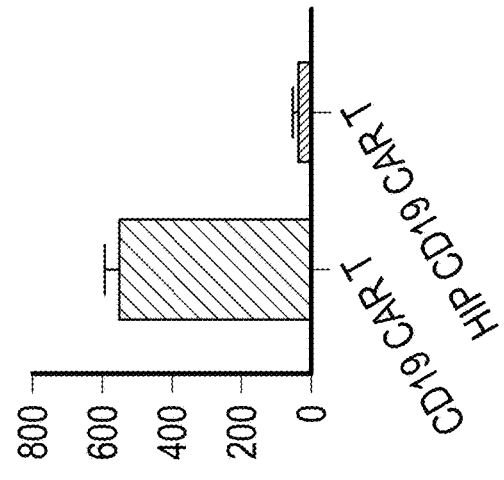
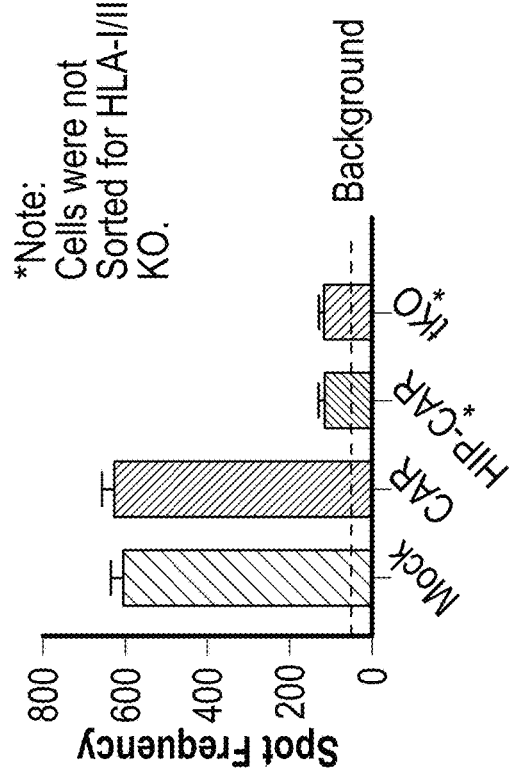
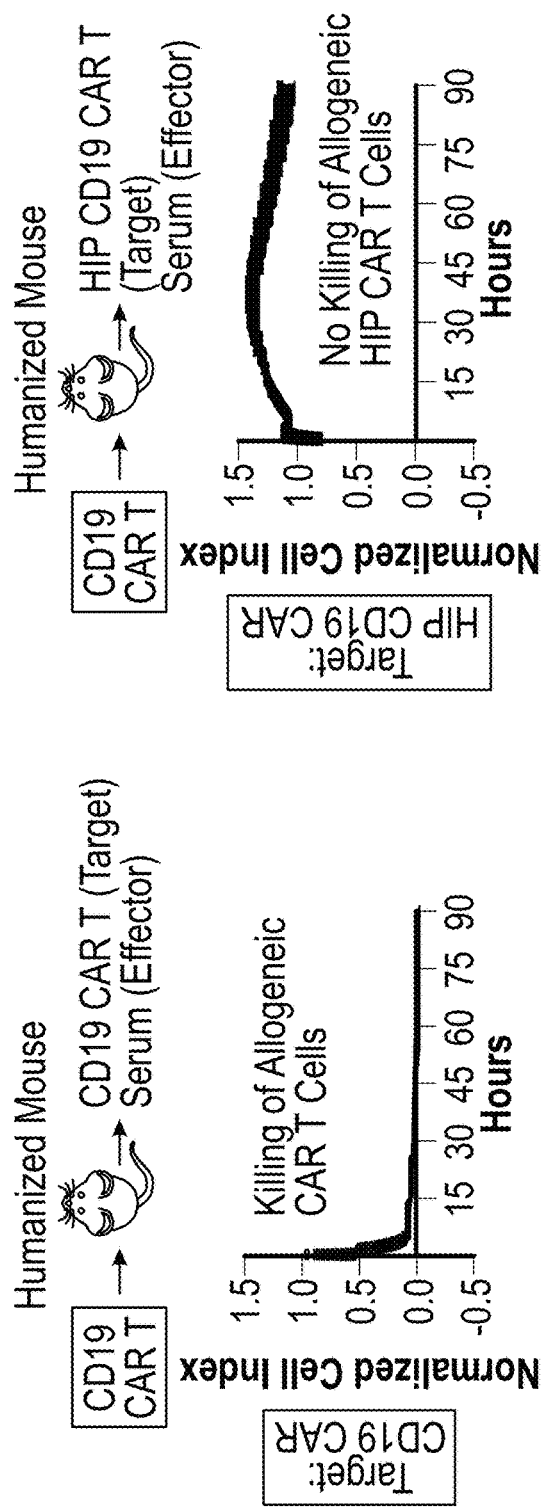

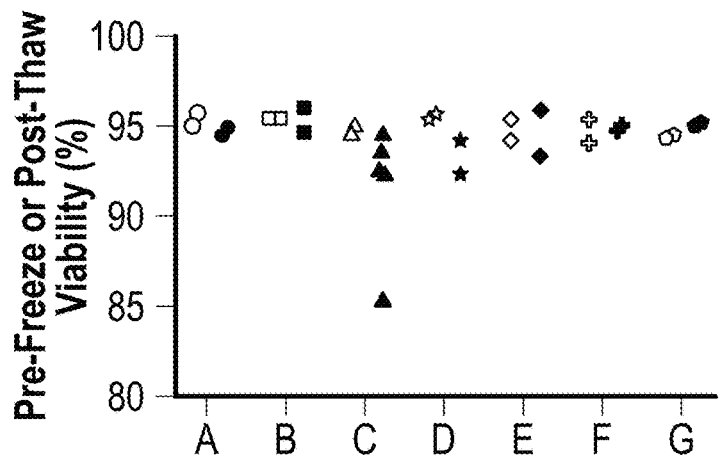
FIG. 40A
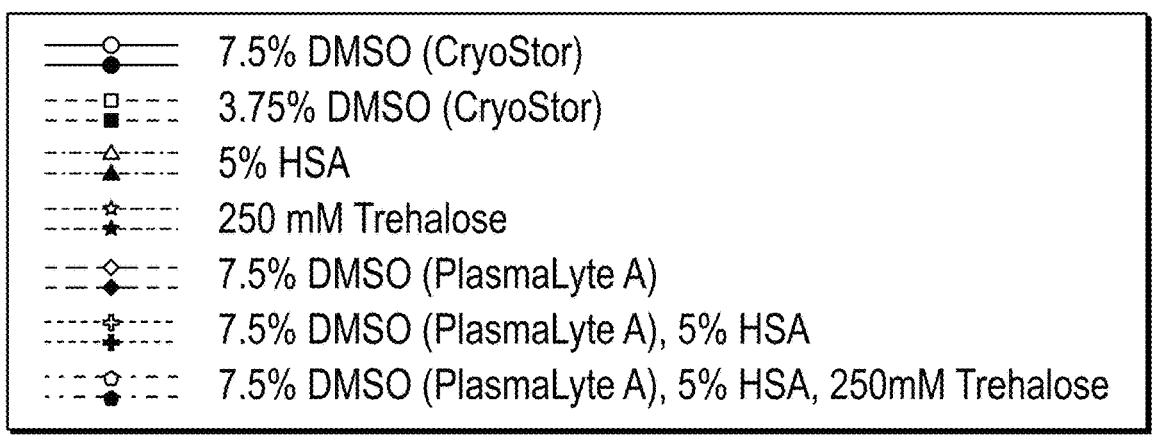
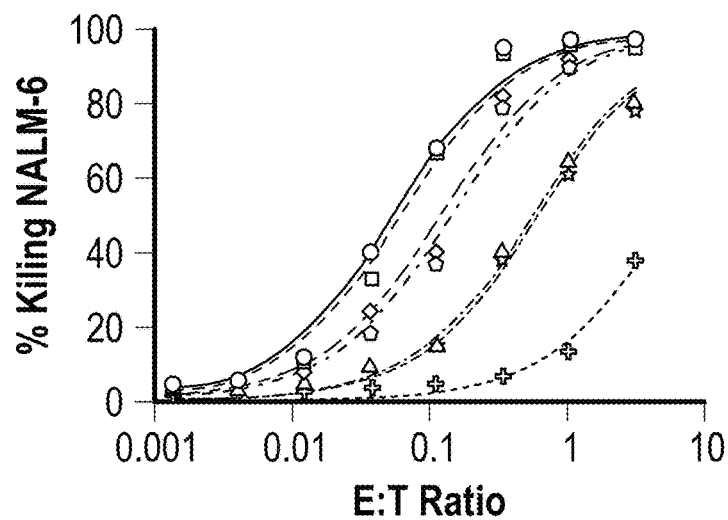
FIG. 40B

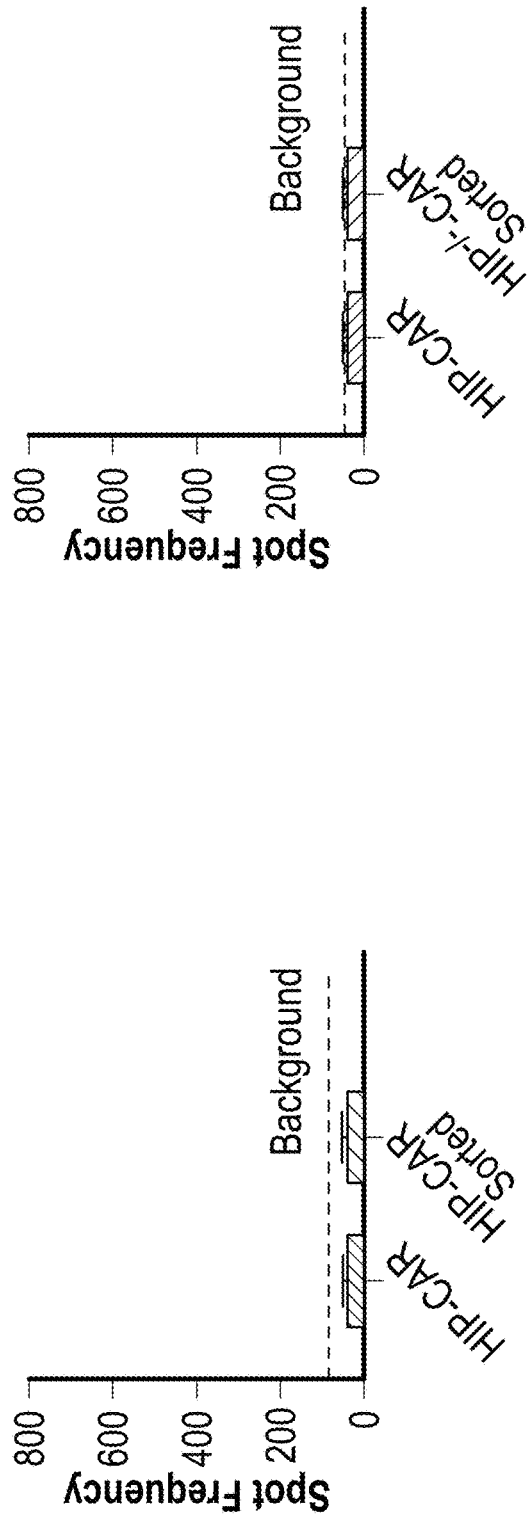

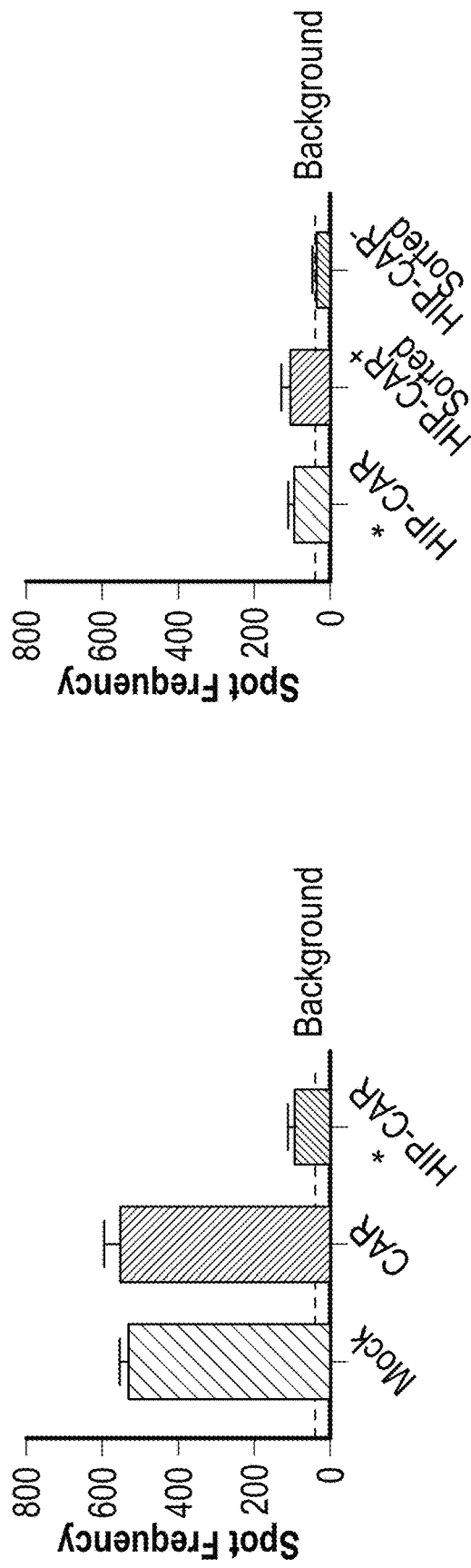

METHODS AND COMPOSITIONS FOR MODULATING CAR-T ACTIVITY

CROSS-REFERENCE TO RELATED APPLICATIONS

This application is a continuation of U.S. application Ser. No. 17/666,523, filed on Feb. 7, 2022, which is a continuation of U.S. application Ser. No. 17/561,659, filed on Dec. 23, 2021, which claims priority under 35 U.S.C. § 119(e) to U.S. Provisional Application Nos. 63/133,171 filed Dec. 31, 2020; 63/136,172 filed Jan. 11, 2021; 63/175,003 filed Apr. 14, 2021; 63/255,795 filed Oct. 14, 2021; and 63/288,477 filed Dec. 10, 2021, the disclosures of which are herein incorporated by reference in their entireties.

SEQUENCE LISTING

In accordance with 37 CFR § 1.52(e)(5), the present specification makes reference to a Sequence Listing (submitted electronically as a .xml file named "2017428-0514_SL.xml"). The .xml file was generated on Jun. 21, 2023 and is 168,172 bytes in size. The entire contents of the Sequence Listing are herein incorporated by reference.

SUMMARY

Off-the-shelf CAR-T cells and other therapeutic cells can offer advantages over autologous cell-based strategies, including ease of manufacturing, quality control and avoidance of malignant contamination and T cell dysfunction. However, the vigorous host-versus-graft immune response against histoincompatible T cells prevents expansion and persistence of allogeneic CAR-T cells and mitigates the efficacy of this approach.

There is substantial evidence in both animal models and human patients that hypoimmunogenic cell transplantation is a scientifically feasible and clinically promising approach to the treatment of numerous disorders, conditions, and diseases.

There remains a need for novel approaches, compositions and methods for producing cell-based therapies that avoid detection by the recipient's immune system.

In some embodiments, provided herein is an engineered cell comprising reduced expression of HLA-A, HLA-B, HLA-C, HLA-DP, HLA-DQ, HLA-DR, B2M, CIITA, TCR-alpha, and/or TCR-beta relative to a wild-type cell or a control cell, the engineered cell further comprising a set of exogenous polynucleotides comprising a first exogenous polynucleotide encoding CD47 and a second exogenous polynucleotide encoding a chimeric antigen receptor (CAR), wherein the first and/or second exogenous polynucleotides are inserted into a specific locus of at least one allele of the cell. In some embodiments, the exogenous polynucleotide is inserted into at least one allele of the cell using viral transduction, for example, with a vector. In some embodiments, the vector is a pseudotyped, self-inactivating lentiviral vector that carries the exogenous polynucleotide. In some embodiments, the vector is a self-inactivating lentiviral vector pseudotyped with a vesicular stomatitis virus glycoprotein (VSV-G) envelope, and which carries the exogenous polynucleotide. In some embodiments, the exogenous polynucleotide is inserted into at least one allele of the cell using viral transduction. In some embodiments, the exogenous polynucleotide is inserted into at least one allele of the cell using a lentivirus based viral vector.

In some embodiments, the specific locus is selected from the group consisting of a safe harbor or target locus, a B2M locus, a CIITA locus, a TRAC locus and a TRB locus. In many embodiments, the first exogenous polynucleotide encoding CD47 is inserted into the specific locus selected from the group consisting of a safe harbor or target locus, a B2M locus, a CIITA locus, a TRAC locus and a TRB locus. In some embodiments, the second exogenous polynucleotide encoding the CAR is inserted into the specific locus selected from the group consisting of a safe harbor or target locus, a B2M locus, a CIITA locus, a TRAC locus and a TRB locus. In some embodiments, the exogenous polynucleotide is inserted into at least one allele of the cell using viral transduction, for example, with a vector. In some embodiments, the vector is a pseudotyped, self-inactivating lentiviral vector that carries the exogenous polynucleotide. In some embodiments, the vector is a self-inactivating lentiviral vector pseudotyped with a vesicular stomatitis VSV-G envelope, and which carries the exogenous polynucleotide. In some embodiments, the exogenous polynucleotide is inserted into at least one allele of the cell using viral transduction. In some embodiments, the exogenous polynucleotide is inserted into at least one allele of the cell using a lentivirus based viral vector.

In some embodiments, the first exogenous polynucleotide encoding CD47 and the second exogenous polynucleotide encoding the CAR are inserted into different loci. In many embodiments, the first exogenous polynucleotide encoding CD47 and the second exogenous polynucleotide encoding the CAR are inserted into the same locus. In several embodiments, the first exogenous polynucleotide encoding CD47 and the second exogenous polynucleotide encoding the CAR are inserted into the B2M locus. In some embodiments, the first exogenous polynucleotide encoding CD47 and the second exogenous polynucleotide encoding the CAR are inserted into the CIITA locus. In many embodiments, the first exogenous polynucleotide encoding CD47 and the second exogenous polynucleotide encoding the CAR are inserted into the TRAC locus. In some embodiments, the first exogenous polynucleotide encoding CD47 and the second exogenous polynucleotide encoding the CAR are inserted into the TRB locus. In some embodiments, the first exogenous polynucleotide encoding CD47 and the second exogenous polynucleotide encoding the CAR are inserted into the safe harbor or target locus. In some embodiments, the safe harbor or target locus is selected from the group consisting of a CCR5 gene locus, a CXCR4 gene locus, a PPP1R12C (also known as AAVS1) gene locus, an albumin gene locus, a SHS231 gene locus, a CLYBL gene locus, a Rosa gene locus (e.g., ROSA26 gene locus), an F3 gene locus (also known as CD142), a MICA gene locus, a MICB gene locus, a LRP1 gene locus (also known as a CD91 gene locus), a HMGB1 gene locus, an ABO gene locus, ad RHD gene locus, a FUT1 locus, and a KDM5D gene locus. In various embodiments, the safe harbor or target locus is selected from the group consisting of the AAVS1 locus, the CCR5 locus, and the ROSA26 locus. In some embodiments, the exogenous polynucleotide is inserted into at least one allele of the cell using viral transduction, for example, with a vector. In some embodiments, the vector is a pseudotyped, self-inactivating lentiviral vector that carries the exogenous polynucleotide. In some embodiments, the vector is a self-inactivating lentiviral vector pseudotyped with a vesicular stomatitis VSV-G envelope, and which carries the exogenous polynucleotide. In some embodiments, the exogenous polynucleotide is inserted into at least one allele of the cell using viral transduction. In some embodiments, the exogenous polynucleotide is inserted into at least one allele of the cell using a lentivirus based viral vector.

In some embodiments, the CAR is selected from the group consisting of a CD19-specific CAR and a CD22-specific CAR. In some embodiments, the CAR is a bispecific CAR. In some embodiments, the CAR is a CD19-specific CAR. In some embodiments, the CAR is a CD22-specific CAR. In some embodiments, the CAR is a bispecific CAR. In some embodiments, the CAR is a CD19/CD22-bispecific CAR.

In many embodiments, the engineered cell does not express HLA-A, HLA-B, and/or HLA-C antigens. In some embodiments, the engineered cell does not express B2M. In other embodiments, the engineered cell does not express HLA-DP, HLA-DQ, and/or HLA-DR antigens. In some embodiments, the engineered cell does not express CIITA. In some embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell does not express TCR-alpha and/or TCR-beta.

In many embodiments, the engineered cell is a pluripotent stem cell. In some embodiments, the engineered cell is an induced pluripotent stem cell.

In some embodiments, the engineered cell is a differentiated cell derived from an induced pluripotent stem cell. In various embodiments, the differentiated cell is selected from the group consisting of an NK cell and a T cell.

In some embodiments, the engineered cell is a cell derived from a primary T cell. In many embodiments, the cell derived from the primary T cell is derived from a pool of T cells comprising primary T cells from one or more donor subjects who are different from a recipient subject.

In some embodiments, the engineered cell is a cell derived from a primary NK cell. In many embodiments, the cell derived from the primary NK cell is derived from a pool of NK cells comprising primary NK cells from one or more donor subjects who are different from a recipient subject.

In some embodiments, the engineered cell retains pluripotency and/or retains differentiation potential.

In many embodiments, following transfer into a first subject, the engineered cell exhibits one or more responses selected from the group consisting of (a) a T cell response, (b) an NK cell response, and (c) a macrophage response, that are reduced as compared to a wild-type cell following transfer into a second subject. In some instances, the first subject and the second subject are different subjects. In some instances, the macrophage response is engulfment. In various embodiments, following transfer into a subject the engineered cell exhibits one or more selected from the group consisting of (a) reduced TH1 activation in the subject, (b) reduced NK cell killing in the subject, and (c) reduced killing by whole PBMCs in the subject, as compared to a wild-type cell following transfer into the subject. In many embodiments, following transfer into a subject the engineered cell elicits one or more selected from the group consisting of (a) reduced donor specific antibodies in the subject, (b) reduced IgM or IgG antibodies in the subject, and (c) reduced complement-dependent cytotoxicity (CDC) in a subject, as compared to a wild-type cell following transfer into the subject.

In some embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a $B2M^{indel/indel}$, $CIITA^{indel/indel}$, and/or $TRAC^{indel/indel}$ cell comprising first exogenous polynucleotide encoding CD47 and/or the second exogenous polynucleotide encoding CAR. In some embodiments, the first and/or second exogenous polynucleotides are inserted into at least one allele of the T cell using viral transduction. In some embodiments, the first and/or second exogenous polynucleotides are inserted into at least one allele of the T cell using a lentivirus based viral vector. In some embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a $B2M^{indel/indel}$, $CIITA^{indel/indel}$, and/or $TRAC^{indel/indel}$ cell comprising first exogenous polynucleotide encoding CD47 and/or the second exogenous polynucleotide encoding CAR inserted into the TRAC locus. In many embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a $B2M^{indel/indel}$, $CIITA^{indel/indel}$, and/or $TRAC^{indel/indel}$ cell comprising the first exogenous polynucleotide encoding CD47 and the second exogenous polynucleotide encoding CAR inserted into the TRAC locus. In many embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a $B2M^{indel/indel}$, $CIITA^{indel/indel}$, and/or $TRAC^{indel/indel}$ cell comprising first exogenous polynucleotide encoding CD47 and/or the second exogenous polynucleotide encoding CAR inserted into the TRB locus. In some embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a $B2M^{indel/indel}$, $CIITA^{indel/indel}$, and/or $TRAC^{indel/indel}$ cell comprising the first exogenous polynucleotide encoding CD47 and the second exogenous polynucleotide encoding CAR inserted into the TRB locus. In numerous embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a $B2M^{indel/indel}$, $CIITA^{indel/indel}$, and/or $TRAC^{indel/indel}$ cell comprising first exogenous polynucleotide encoding CD47 and/or the second exogenous polynucleotide encoding CAR inserted into the B2M locus. In many embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a $B2M^{indel/indel}$, $CIITA^{indel/indel}$, and/or $TRAC^{indel/indel}$ cell comprising the first exogenous polynucleotide encoding CD47 and the second exogenous polynucleotide encoding CAR inserted into a B2M locus. In some embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a $B2M^{indel/indel}$, $CIITA^{indel/indel}$, and/or $TRAC^{indel/indel}$ cell comprising first exogenous polynucleotide encoding CD47 and/or the second exogenous polynucleotide encoding CAR inserted into the CIITA locus. In many embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a B2M$^{indel/indel}$ CIITA$^{indel/indel}$, and/or TRAC$^{indel/indel}$ cell comprising the first exogenous polynucleotide encoding CD47 and the second exogenous polynucleotide encoding CAR inserted into a CIITA locus. In some embodiments, the exogenous polynucleotide is inserted into at least one allele of the cell using viral transduction, for example, with a vector. In some embodiments, the vector is a pseudotyped, self-inactivating lentiviral vector that carries the exogenous polynucleotide. In some embodiments, the vector is a self-inactivating lentiviral vector pseudotyped with a vesicular stomatitis VSV-G envelope, and which carries the exogenous polynucleotide. In some embodiments, the exogenous polynucleotide is inserted into at least one allele of the cell using viral transduction. In some embodiments, the exogenous polynucleotide is inserted into at least one allele of the cell using a lentivirus based viral vector.

In some embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a B2M$^{indel/indel}$, CIITA$^{indel/indel}$ and/or TRB$^{indel/indel}$ cell comprising first exogenous polynucleotide encoding CD47 and/or the second exogenous polynucleotide encoding CAR inserted into the TRAC locus. In many embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a B2M$^{indel/indel}$, CIITA$^{indel/indel}$, and/or TRB$^{indel/indel}$ cell comprising the first exogenous polynucleotide encoding CD47 and the second exogenous polynucleotide encoding CAR inserted into the TRAC locus. In many embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a B2M$^{indel/indel}$, CIITA$^{indel/indel}$, and/or TRB$^{indel/indel}$ cell comprising first exogenous polynucleotide encoding CD47 and/or the second exogenous polynucleotide encoding CAR inserted into the TRB locus. In some embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a B2M$^{indel/indel}$, CIITA$^{indel/indel}$, and/or TRB$^{indel/indel}$ cell comprising the first exogenous polynucleotide encoding CD47 and the second exogenous polynucleotide encoding CAR inserted into the TRB locus. In numerous embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a B2M$^{indel/indel}$, CIITA$^{indel/indel}$ and/or TRB$^{indel/indel}$ cell comprising first exogenous polynucleotide encoding CD47 and/or the second exogenous polynucleotide encoding CAR inserted into the B2M locus. In many embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a B2M$^{indel/indel}$, CIITA$^{indel/indel}$, and/or TRB$^{indel/indel}$ cell comprising the first exogenous polynucleotide encoding CD47 and the second exogenous polynucleotide encoding CAR inserted into a B2M locus. In some embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a B2M$^{indel/indel}$, CIITA$^{indel/indel}$, and/or TRB$^{indel/indel}$ cell comprising first exogenous polynucleotide encoding CD47 and/or the second exogenous polynucleotide encoding CAR inserted into the CIITA locus. In many embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a B2M$^{indel/indel}$, CIITA$^{indel/indel}$, and/or TRB$^{indel/indel}$ cell comprising the first exogenous polynucleotide encoding CD47 and the second exogenous polynucleotide encoding CAR inserted into a CIITA locus. In some embodiments, the exogenous polynucleotide is inserted into at least one allele of the cell using viral transduction, for example, with a vector. In some embodiments, the vector is a pseudotyped, self-inactivating lentiviral vector that carries the exogenous polynucleotide. In some embodiments, the vector is a self-inactivating lentiviral vector pseudotyped with a vesicular stomatitis VSV-G envelope, and which carries the exogenous polynucleotide. In some embodiments, the exogenous polynucleotide is inserted into at least one allele of the cell using viral transduction. In some embodiments, the exogenous polynucleotide is inserted into at least one allele of the cell using a lentivirus based viral vector.

In some embodiments, the engineered cell is a B2M$^{indel/indel}$, CIITA$^{indel/indel}$ TRAC$^{indel/indel}$, and/or TRB$^{indel/indel}$ cell comprising first exogenous polynucleotide encoding CD47 and/or the second exogenous polynucleotide encoding CAR inserted into the TRAC locus. In many embodiments, the engineered cell is a B2M$^{indel/indel}$, CIITA$^{indel/indel}$, TRAC$^{indel/indel}$, and/or TRB$^{indel/indel}$ cell comprising the first exogenous polynucleotide encoding CD47 and the second exogenous polynucleotide encoding CAR inserted into the TRAC locus. In many embodiments, the engineered cell is a B2M$^{indel/indel}$, CIITA$^{indel/indel}$, TRAC$^{indel/indel}$, and/or TRB$^{indel/indel}$ cell comprising first exogenous polynucleotide encoding CD47 and/or the second exogenous polynucleotide encoding CAR inserted into the TRB locus. In some embodiments, the engineered cell is a B2M$^{indel/indel}$, CIITA$^{indel/indel}$, TRAC$^{indel/indel}$, and/or TRB$^{indel/indel}$ cell comprising the first exogenous polynucleotide encoding CD47 and the second exogenous polynucleotide encoding CAR inserted into the TRB locus. In numerous embodiments, the engineered cell is a B2M$^{indel/indel}$, CIITA$^{indel/indel}$, TRAC$^{indel/indel}$, and/or TRB$^{indel/indel}$ cell comprising first exogenous polynucleotide encoding CD47 and/or the second exogenous polynucleotide encoding CAR inserted into the B2M locus. In many embodiments, the engineered cell is a B2M$^{indel/indel}$, CIITA$^{indel/indel}$, TRAC$^{indel/indel}$, and/or TRB$^{indel/indel}$ cell comprising the first exogenous polynucleotide encoding CD47 and the second exogenous polynucleotide encoding CAR inserted into a B2M locus. In some embodiments, the engineered cell is a B2M$^{indel/indel}$, CIITA$^{indel/indel}$, TRAC$^{indel/indel}$ and/or TRB$^{indel/indel}$ cell comprising first exogenous polynucleotide encoding CD47 and/or the second exogenous polynucleotide encoding CAR inserted into the CIITA locus. In many embodiments, the engineered cell is a B2M$^{indel/indel}$, CIITA$^{indel/indel}$, TRAC$^{indel/indel}$, and/or TRB$^{indel/indel}$ cell comprising the first exogenous polynucleotide encoding CD47 and the second exogenous polynucleotide encoding CAR inserted into a CIITA locus. In some embodiments, the exogenous polynucleotide is inserted into at least one allele of the cell using viral transduction, for example, with a vector. In some embodiments, the vector is a pseudotyped, self-inactivating lentiviral vector that carries the exogenous polynucleotide. In some embodiments, the vector is a self-inactivating lentiviral vector pseudotyped with a vesicular stomatitis VSV-G envelope, and which carries the exogenous polynucleotide. In some embodiments, the exogenous polynucleotide is inserted into at least one allele of the cell using viral transduction. In some embodiments, the exogenous polynucleotide is inserted into at least one allele of the cell using a lentivirus based viral vector.

In some embodiments, provided is an engineered cell comprising reduced expression of HLA-A, HLA-B, HLA-C, HLA-DP, HLA-DQ, HLA-DR, B2M, CIITA, TCR-alpha, and/or TCR-beta relative to a wild-type cell or a control cell.

In some embodiments, the engineered cell does not express HLA-A, HLA-B and/or HLA-C antigens. In many embodiments, the engineered cell does not express CIITA.

In many embodiments, the engineered cell does not express HLA-DP, HLA-DQ, and/or HLA-DR antigens. In some embodiments, the engineered cell does not express B2M.

In many embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell does not express TCR-alpha. In many embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell does not express TCR-beta.

In various embodiments, the engineered cell overexpresses CD47 relative to a wild-type cell or a control cell.

In some embodiments, the engineered cell is a pluripotent stem cell. In many embodiments, the engineered cell is an induced pluripotent stem cell.

In many embodiments, the engineered cell is a differentiated cell derived from an induced pluripotent stem cell. In some embodiments, the differentiated cell is selected from the group consisting of an NK cell and a T cell.

In many embodiments, the engineered cell is a cell derived from a primary T cell. In several embodiments, the cell derived from the primary T cell is derived from a pool of T cells comprising primary T cells from one or more donor subjects who are different from a recipient subject.

In various embodiments, the engineered cell retains pluripotency and/or retains differentiation potential.

In some embodiments, following transfer into a subject the engineered cell elicits one or more response selected from the group consisting of (a) a T cell response, (b) an NK cell response, and (c) a macrophage response, that are reduced as compared to a wild-type cell following transfer into a second subject. In some instances, the first subject and the second subject are different subjects. In some instances, the macrophage response is engulfment.

In various embodiments, following transfer into a subject the engineered cell exhibits one or more selected from the group consisting of (a) reduced TH1 activation in the subject, (b) reduced NK cell killing in the subject, and (c) reduced killing by whole PBMCs in the subject, as compared to a wild-type cell following transfer into the subject. In many embodiments, following transfer into a subject the engineered cell elicits one or more selected from the group consisting of (a) reduced donor specific antibodies in the subject, (b) reduced IgM or IgG antibodies in the subject, and (c) reduced complement-dependent cytotoxicity (CDC) in a subject, as compared to a wild-type cell following transfer into the subject.

In some embodiments, the engineered cell is a B2M$^{indel/indel}$, CIITA$^{indel/indel}$, TRAC$^{indel/indel}$, and/or TRB$^{indel/indel}$ cell. In some instances, the engineered cell is a B2M$^{indel/indel}$, CIITA$^{indel/indel}$, TRAC$^{indel/indel}$, and/or TRB$^{indel/indel}$ primary T cell. In some instances, the engineered cell is a B2M$^{indel/indel}$, CIITA$^{indel/indel}$, TRAC$^{indel/indel}$, and/or TRB$^{indel/indel}$ T cell differentiated from a hypoimmunogenic induced pluripotent stem cell. In some embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a B2M$^{indel/indel}$, CIITA$^{indel/indel}$, TRAC$^{indel/indel}$ cell. In some instances, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a B2M$^{indel/indel}$, CIITA$^{indel/indel}$, TRAC$^{indel/indel}$ primary T cell. In some embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a B2M$^{indel/indel}$, CIITA$^{indel/indel}$, TRB$^{indel/indel}$ cell. In some instances, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a B2M$^{indel/indel}$, CIITA$^{indel/indel}$, TRB$^{indel/indel}$ primary T cell. In some instances, the engineered cell is a B2M$^{indel/indel}$, CIITA$^{indel/indel}$, and/or TRAC$^{indel/indel}$ T cell differentiated from a hypoimmunogenic induced pluripotent stem cell. In some embodiments, the engineered cell is a B2M$^{indel/indel}$, CIITA$^{indel/indel}$, and/or TRB$^{indel/indel}$ cell. In some instances, the engineered cell is a B2M$^{indel/indel}$, CIITA$^{indel/indel}$, and/or TRB$^{indel/indel}$ primary T cell. In some instances, the engineered cell is a B2M$^{indel/indel}$, CIITA$^{indel/indel}$, and/or TRB$^{indel/indel}$ T cell differentiated from a hypoimmunogenic induced pluripotent stem cell.

In some embodiments, the engineered cell is a hypoimmunogenic cell.

In some embodiments, provided is a pharmaceutical composition comprising a population of any of the engineered cells described herein and a pharmaceutically acceptable additive, carrier, diluent or excipient.

In some embodiments, the pharmaceutically acceptable additive, carrier, diluent or excipient comprises one or more selected from the group consisting of Plasma-Lyte A®, dextrose, dextran, sodium chloride, human serum albumin (HSA), dimethylsulfoxide (DMSO), and a combination thereof. In some embodiments, the pharmaceutical composition further comprises a pharmaceutically acceptable buffer. In some embodiments, the pharmaceutically acceptable buffer is neutral buffer saline or phosphate buffered saline.

In some embodiments, provided is a pharmaceutical composition comprising a population of any of the engineered cells described herein, a base solution of CryoStor® CSB at a concentration of about 70-80% w/w, and one or more of about 20-30% w/w PlasmaLyte-A™, about 0.3-5.3% w/v human serum albumin (HSA), about 0-20% v/v dimethylsulfoxide (DMSO), and about 100-400 mM trehalose.

In some embodiments, provided is a pharmaceutical composition comprising a population of any of the engineered cells described herein, a base solution of PlasmaLyte-A™ at a concentration of about 20-30% w/w, and one or more of about 70-80% w/w CryoStor® CSB, about 0.3-5.3% w/v human serum albumin (HSA), about 0-20% v/v dimethylsulfoxide (DMSO), and about 100-400 mM trehalose.

In some embodiments, provided is a pharmaceutical composition comprising a population of any of the engineered cells described herein, about 0.3-5.3% w/v human serum albumin (HSA), and one or more of about 70-80% w/w CryoStor® CSB, about 20-30% w/w PlasmaLyte-A™, about 0-20% v/v dimethylsulfoxide (DMSO), and about 100-400 mM trehalose.

In some embodiments, provided is a pharmaceutical composition comprising a population of any of the engineered cells described herein, about 0-20% v/v dimethylsulfoxide (DMSO), and one or more of about 70-80% w/w CryoStor® CSB, about 20-30% w/w PlasmaLyte-A™, about 0.3-5.3% w/v human serum albumin (HSA), and about 100-400 mM trehalose.

In some embodiments, provided is a pharmaceutical composition comprising a population of any of the engineered cells described herein, about 100-400 mM trehalose, and one or more of about 70-80% w/w CryoStor® CSB, about 20-30% w/w PlasmaLyte-A™, about 0.3-5.3% w/v human serum albumin (HSA), and about 0-20% v/v dimethylsulfoxide (DMSO).

In some embodiments, the pharmaceutical composition comprises about 75% w/w of CryoStor® CSB. In some embodiments, the pharmaceutical composition comprises about 25% w/w of PlasmaLyte-A™. In some embodiments, the pharmaceutical composition comprises about 0.3% w/v of HSA. In some embodiments, the pharmaceutical composition comprises about 7.5% v/v of DMSO.

In some embodiments, provided is a pharmaceutical composition comprising a population of any of the engineered cells described herein, a base solution of CryoStor® CSB at a concentration of about 75% w/w, about 25% w/w PlasmaLyte-A™, about 0.3% w/v human serum albumin (HSA), and about 7.5% v/v dimethylsulfoxide (DMSO).

In some embodiments, the population of the engineered cells is up to about $8.0\times10^8$ cells. In many embodiments, the population of the engineered cells is up to about $6.0\times10^8$ cells. In other embodiments, the population of the engineered cells is from about $1.0\times10^6$ to about $2.5\times10^8$ cells. In some embodiments, the population of the engineered cells is from about $2.0\times10^6$ to about $2.0\times10^8$ cells.

In various embodiments, the population of the engineered cells ranges from about 5 ml to about 80 ml. In many embodiments, the population of the engineered cells ranges from about 10 ml to about 70 ml. In some embodiments, the population of the engineered cells ranges from about 10 ml to about 50 ml.

In some embodiments, the composition is formulated for administration in a single dose. In many embodiments, the composition is formulated for administration in up to three doses.

In some embodiments, the composition is formulated for administration of a single dose to a subject takes a duration of time of about 60 minutes or less. In many embodiments, the composition is formulated for administration of a single dose to a subject takes a duration of time of about 30 minutes or less.

In some embodiments, the population of engineered cells of the pharmaceutical composition or progeny thereof exhibit at least 40% survival in a subject after 10 days following administration. In various embodiments, the population of engineered cells of the pharmaceutical composition or progeny thereof exhibit at least 80% survival in a subject after about 2 weeks following administration. In several embodiments, the population of engineered cells of the pharmaceutical composition or progeny thereof exhibit at least 100% survival in a subject after about 3 weeks following administration. In many embodiments, the population of engineered cells of the pharmaceutical composition or progeny thereof exhibit at least 150% survival in a subject after about 4 weeks following administration.

In another embodiment, provided is a dosage regimen for treating a disease or disorder in a subject comprising administration of a pharmaceutical composition comprising a population of any of the engineered cells described herein and a pharmaceutically acceptable additive, carrier, diluent or excipient, wherein the pharmaceutical composition is administered in about 1-3 doses.

In some embodiments, the pharmaceutical composition administered is up to about $6.0\times10^8$ cells in about 1-3 doses. In some embodiments, the pharmaceutical composition administered is from about $0.6\times10^6$ to about $6.0\times10^8$ cells in about 1-3 doses. In some embodiments, the pharmaceutical composition administered is from about $0.2\times10^6$ to about $5.0\times10^6$ cells per kg of the subject's body weight in about 1-3 doses, if the subject has a body weight of 50 kg or less. In some embodiments, the pharmaceutical composition administered is from about $0.1\times10^8$ to about $2.5\times10^8$ cells in about 1-3 doses, if the subject has a body weight greater than 50 kg. In some embodiments, the pharmaceutical composition administered is from about $2.0\times10^6$ cells per kg of the subject's body weight and up to about $2\times10^8$ cells in about 1-3 doses.

In some embodiments, the administration of a single dose to the subject takes a duration of time of about 60 minutes or less. In some embodiments, the administration of a single dose to the subject takes a duration of time of about 30 minutes or less.

In some embodiments, the pharmaceutically acceptable additive, carrier, diluent or excipient comprises one or more selected from the group consisting of Plasma-Lyte A®, dextrose, dextran, sodium chloride, human serum albumin (HSA), dimethylsulfoxide (DMSO), and a combination thereof.

In some embodiments, the pharmaceutical composition further comprises a pharmaceutically acceptable buffer. In some embodiments, the pharmaceutically acceptable buffer is neutral buffer saline or phosphate buffered saline.

In some embodiments, after the administration of the pharmaceutical composition, the population of cells or progeny thereof are present in the subject up to 9 months. In some embodiments, after the administration of the pharmaceutical composition, the population of cells or progeny thereof are present in the subject at least 2 years or more.

In some embodiments, after the administration of the pharmaceutical composition, the population of engineered cells or progeny thereof exhibit at least 40% survival in a subject after about 10 days following administration. In some embodiments, after the administration of the pharmaceutical composition, the population of engineered cells or progeny thereof exhibit at least 80% survival in a subject after about 2 weeks following administration. In some embodiments, after the administration of the pharmaceutical composition, the population of engineered cells or progeny thereof exhibit at least 100% survival in a subject after about 3 weeks following administration. In some embodiments, after the administration of the pharmaceutical composition, the population of engineered cells or progeny thereof exhibit at least 150% survival in a subject after about 4 weeks following administration.

In some embodiments, the administration of 2-3 doses to the subject occurs such that each dose is administered ranging from 1 to 24 hours apart. In some embodiments, the administration of 2-3 doses to the subject occurs such that each dose is administered ranging from 1 to 28 days apart. In some embodiments, the administration of 2-3 doses to the subject occurs such that each dose is administered ranging from 1 to 6 weeks apart. In some embodiments, the administration of 2-3 doses to the subject occurs such that each dose is administered ranging from 1 to 12 months or more apart.

Provided herein is a dosage regimen for treating a disease or disorder in a subject comprising administering a pharmaceutical composition comprising (i) an engineered cell comprising reduced expression of HLA-A, HLA-B, HLA-C, HLA-DP, HLA-DQ, HLA-DR, B2M, CIITA, TCR-alpha, and/or TCR-beta, the engineered cell further comprising a set of exogenous polynucleotides encoding CD47 and a chimeric antigen receptor (CAR). In some embodiments, the set of exogenous polynucleotides are inserted into at least one allele of the T cell using viral transduction, for example, with a vector. In some embodiments, the vector is a pseudotyped, self-inactivating lentiviral vector that carries the set of exogenous polynucleotides. In some embodiments, the vector is a self-inactivating lentiviral vector pseudotyped with a vesicular stomatitis VSV-G envelope, and which carries the set of exogenous polynucleotides. In some embodiments, set of exogenous polynucleotides are inserted into at least one allele of the T cell using a lentivirus based viral vector. In some embodiments, the set of exogenous polynucleotides are inserted into a safe harbor or target locus of at least one allele of the cell; and (ii) a pharmaceutically acceptable additive, carrier, diluent or excipient, wherein the pharmaceutical composition comprises up to about $6.0 \times 10^8$ cells. In some embodiments, the exogenous polynucleotide is inserted into at least one allele of the cell using viral transduction, for example, with a vector. In some embodiments, the vector is a pseudotyped, self-inactivating lentiviral vector that carries the exogenous polynucleotide. In some embodiments, the vector is a self-inactivating lentiviral vector pseudotyped with a vesicular stomatitis VSV-G envelope, and which carries the exogenous polynucleotide. In some embodiments, the exogenous polynucleotide is inserted into at least one allele of the cell using viral transduction. In some embodiments, the exogenous polynucleotide is inserted into at least one allele of the cell using a lentivirus based viral vector.

Provided herein is a dosage regimen for treating a disease or disorder in a subject comprising administering a pharmaceutical composition comprising (i) an engineered cell comprising reduced expression of HLA-A, HLA-B, HLA-C, HLA-DP, HLA-DQ, HLA-DR, B2M, CIITA, TCR-alpha, and/or TCR-beta, the engineered cell further comprising a set of exogenous polynucleotides encoding CD47 and a chimeric antigen receptor (CAR). In some embodiments, the set of exogenous polynucleotides are inserted into at least one allele of the T cell using viral transduction. In some embodiments, set of exogenous polynucleotides are inserted into at least one allele of the T cell using a lentivirus based viral vector. In some embodiments, the set of exogenous polynucleotides are inserted into a safe harbor or target locus of at least one allele of the cell; and (ii) a pharmaceutically acceptable additive, carrier, diluent or excipient, wherein the pharmaceutical composition is administered in 1-3 doses. In some embodiments, the exogenous polynucleotide is inserted into at least one allele of the cell using viral transduction, for example, with a vector. In some embodiments, the vector is a pseudotyped, self-inactivating lentiviral vector that carries the exogenous polynucleotide. In some embodiments, the vector is a self-inactivating lentiviral vector pseudotyped with a vesicular stomatitis VSV-G envelope, and which carries the exogenous polynucleotide. In some embodiments, the exogenous polynucleotide is inserted into at least one allele of the cell using viral transduction. In some embodiments, the exogenous polynucleotide is inserted into at least one allele of the cell using a lentivirus based viral vector.

Provided herein is a dosage regimen for treating a disease or disorder in a subject comprising administering a pharmaceutical composition comprising (i) an engineered cell comprising reduced expression of HLA-A, HLA-B, HLA-C, HLA-DP, HLA-DQ, HLA-DR, B2M, CIITA, TCR-alpha, and/or TCR-beta, the engineered cell further comprising a set of exogenous polynucleotides encoding CD47 and a chimeric antigen receptor (CAR), wherein the set of exogenous polynucleotides are inserted into a safe harbor or target locus of at least one allele of the cell; and (ii) a pharmaceutically acceptable additive, carrier, diluent or excipient, wherein a dose of the pharmaceutical composition is administered for a duration of time of about 60 minutes or less. In some embodiments, the exogenous polynucleotide is inserted into at least one allele of the cell using viral transduction, for example, with a vector. In some embodiments, the vector is a pseudotyped, self-inactivating lentiviral vector that carries the exogenous polynucleotide. In some embodiments, the vector is a self-inactivating lentiviral vector pseudotyped with a vesicular stomatitis VSV-G envelope, and which carries the exogenous polynucleotide. In some embodiments, the exogenous polynucleotide is inserted into at least one allele of the cell using viral transduction. In some embodiments, the exogenous polynucleotide is inserted into at least one allele of the cell using a lentivirus based viral vector.

Provided herein is a dosage regimen for treating a disease or disorder in a subject comprising administering a pharmaceutical composition comprising (i) an engineered cell comprising reduced expression of HLA-A, HLA-B, HLA-C, HLA-DP, HLA-DQ, HLA-DR, B2M, CIITA, TCR-alpha, and/or TCR-beta; and (ii) a pharmaceutically acceptable additive, carrier, diluent or excipient, wherein the pharmaceutical composition comprises up to about $6.0 \times 10^8$ cells.

Provided herein is a dosage regimen for treating a disease or disorder in a subject comprising administering a pharmaceutical composition comprising (i) an engineered cell comprising reduced expression of HLA-A, HLA-B, HLA-C, HLA-DP, HLA-DQ, HLA-DR, B2M, CIITA, TCR-alpha, and/or TCR-beta; and (ii) a pharmaceutically acceptable additive, carrier, diluent or excipient, wherein the pharmaceutical composition is administered in 1-3 doses.

Provided herein is a dosage regimen for treating a disease or disorder in a subject comprising administering a pharmaceutical composition comprising (i) an engineered cell comprising reduced expression of HLA-A, HLA-B, HLA-C, HLA-DP, HLA-DQ, HLA-DR, B2M, CIITA, TCR-alpha, and/or TCR-beta; and (ii) a pharmaceutically acceptable additive, carrier, diluent or excipient, wherein a dose of the pharmaceutical composition is administered for a duration of 60 minutes or less.

In some embodiments, provided is a method of treating a cancer in a subject comprising administration of any of the engineered cells described herein or any of the pharmaceutical compositions described herein or any of the dosage regimens described herein to the subject. In some embodiments, the cancer is a CD19$^+$ cancer.

In some embodiments, provided is a method of preventing T cell exhaustion or treating a disease in a subject comprising administration of any of the engineered cells described herein to the subject, wherein the CAR is a CD19/CD22-bispecific CAR.

In some embodiments, provided herein is a method of preventing T cell exhaustion or treating a disease in a subject comprising: (i) administration of a first dosage regimen comprising a first population of any of the engineered cells described herein to the subject at a first timepoint, and (ii) administration of a second dosage regimen comprising a second population of any of the engineered cells described herein to the subject at a second timepoint, wherein the first dosage regimen and the second dosage regimen are different.

In some embodiments, provided herein is a method of preventing T cell exhaustion or treating a disease in a subject comprising: (i) administration of a first dosage regimen comprising a first population of any of the engineered cells described herein to the subject at a first timepoint, and (ii) administration of a second dosage regimen comprising a second population of any of the engineered cells described herein to the subject at a second timepoint, wherein the first population of engineered cells and the second population of engineered cells both comprise the same chimeric antigen receptor.

In some embodiments, provided herein is a method of preventing T cell exhaustion or treating a disease in a subject comprising: (i) administration of a first dosage regimen comprising a first population of any of the engineered cells described herein to the subject at a first timepoint, and (ii) administration of a second dosage regimen comprising a second population of any of the engineered cells described herein to the subject at a second timepoint, wherein the first population of engineered cells and the second population of engineered cells both comprise different chimeric antigen receptors.

In some embodiments, provided herein is a method of preventing T cell exhaustion or treating a disease in a subject comprising: (i) administration of a first dosage regimen comprising a first population of any of the engineered cells described herein to the subject at a first timepoint, and (ii) administration of a second dosage regimen comprising a second population of any of the engineered cells described herein to the subject at a second timepoint, wherein the engineered cells of the first population comprise a first chimeric antigen receptor that binds a first antigen and the engineered cells of the second population comprise a second chimeric antigen receptor that binds a second antigen, and wherein the first antigen and the second antigen are the same.

In some embodiments, provided herein is a method of preventing T cell exhaustion or treating a disease in a subject comprising: (i) administration of a first dosage regimen comprising a first population of any of the engineered cells described herein to the subject at a first timepoint, and (ii) administration of a second dosage regimen comprising a second population of any of the engineered cells described herein to the subject at a second timepoint, wherein the engineered cells of the first population comprise a first chimeric antigen receptor that binds a first antigen and the engineered cells of the second population comprise a second chimeric antigen receptor that binds a second antigen, and wherein the first antigen and the second antigen are different.

Provided herein are non-activated T cells comprising reduced expression of HLA-A, HLA-B, HLA-C, HLA-DP, HLA-DQ, HLA-DR, B2M, CIITA, TCR-alpha, and/or TCR-beta relative to a wild-type T cell, and a first exogenous polynucleotide encoding a chimeric antigen receptor (CAR). In some embodiments, the exogenous polynucleotide is inserted into at least one allele of the cell using viral transduction, for example, with a vector. In some embodiments, the vector is a pseudotyped, self-inactivating lentiviral vector that carries the exogenous polynucleotide. In some embodiments, the vector is a self-inactivating lentiviral vector pseudotyped with a vesicular stomatitis VSV-G envelope, and which carries the exogenous polynucleotide. In some embodiments, the exogenous polynucleotide is inserted into at least one allele of the cell using viral transduction. In some embodiments, the exogenous polynucleotide is inserted into at least one allele of the cell using a lentivirus based viral vector.

In some embodiments, the non-activated T cell is a primary T cell. In other embodiments, the non-activated T cell is differentiated from the engineered cells of the present technology.

In some embodiments, the T cell is a CD8$^+$ T cell.

In some embodiments, the non-activated T cell has not been treated with an anti-CD3 antibody, an anti-CD28 antibody, a T cell activating cytokine, or a soluble T cell costimulatory molecule.

In some embodiments, the anti-CD3 antibody is OKT3. In some embodiments, the anti-CD28 antibody is CD28.2. In some embodiments, the T cell activating cytokine is selected from the group of T cell activating cytokines consisting of IL-2, IL-7, IL-15, and IL-21. In some embodiments, the soluble T cell costimulatory molecule is selected from the group of soluble T cell costimulatory molecules consisting of an anti-CD28 antibody, an anti-CD80 antibody, an anti-CD86 antibody, an anti-CD137L antibody, and an anti-ICOS-L antibody.

In some embodiments, the non-activated T cell does not express activation markers.

In some embodiments, the non-activated T cell expresses CD3 and CD28, and wherein the CD3 and/or CD28 are inactive.

In some embodiments, the first exogenous polynucleotide is carried by a lentiviral vector comprising a CD8 binding agent.

In some embodiments, the non-activated T cell further comprises a second exogenous polynucleotide encoding CD47.

In some embodiments, the first and/or second exogenous polynucleotides are inserted into a specific locus of at least one allele of the T cell. In some embodiments, the first and/or second exogenous polynucleotides are inserted into at least one allele of the T cell using viral transduction. In some embodiments, the first and/or second exogenous polynucleotides are inserted into at least one allele of the T cell using a lentivirus based viral vector. In some embodiments, the vector is a pseudotyped, self-inactivating lentiviral vector that carries the first and/or second exogenous polynucleotides. In some embodiments, the vector is a self-inactivating lentiviral vector pseudotyped with a vesicular stomatitis VSV-G envelope, and which carries the first and/or second exogenous polynucleotides. In some embodiments, the specific locus is selected from the group consisting of a safe harbor or target locus, a B2M locus, a CIITA locus, a TRAC locus, and a TRB locus. In some embodiments, the second exogenous polynucleotide encoding CD47 is inserted into the specific locus selected from the group consisting of a safe harbor or target locus, a B2M locus, a CIITA locus, a TRAC locus and a TRB locus. In some embodiments, the first exogenous polynucleotide encoding the CAR is inserted into the specific locus selected from the group consisting of a safe harbor or target locus, a B2M locus, a CIITA locus, a TRAC locus and a TRB locus. In some embodiments, the second exogenous polynucleotide encoding CD47 and the first exogenous polynucleotide encoding the CAR are inserted into different loci. In some embodiments, the second exogenous polynucleotide encoding CD47 and the first exogenous polynucleotide encoding the CAR are inserted into the same locus. In some embodiments, the second exogenous polynucleotide encoding CD47 and the first exogenous polynucleotide encoding the CAR are inserted into the B2M locus. In some embodiments, the second exogenous polynucleotide encoding CD47 and the first exogenous polynucleotide encoding the CAR are inserted into the CIITA locus. In some embodiments, the second exogenous polynucleotide encoding CD47 and the first exogenous polynucleotide encoding the CAR are inserted into the TRAC locus. In some embodiments, the second exogenous polynucleotide encoding CD47 and the first exogenous polynucleotide encoding the CAR are inserted into the TRB locus. In some embodiments, the second exogenous polynucleotide encoding CD47 and the first exogenous polynucleotide encoding the CAR are inserted into the safe harbor or target locus. In some embodiments, the safe harbor or target locus is selected from the group consisting of a CCR5 gene locus, a CXCR4 gene locus, a PPP1R12C (also known as AAVS1) gene locus, an albumin gene locus, a SHS231 gene locus, a CLYBL gene locus, a Rosa gene locus (e.g., ROSA26 gene locus), an F3 gene locus (also known as CD142), a MICA gene locus, a MICB gene locus, a LRP1 gene locus (also known as a CD91 gene locus), a HMGB1 gene locus, an ABO gene locus, ad RHD gene locus, a FUT1 locus, and a KDM5D gene locus. In some embodiments, the safe harbor or target locus is selected from the group consisting of the AAVS1 locus, the CCR5 locus, and the ROSA26 locus. In some embodiments, the exogenous polynucleotide is inserted into at least one allele of the cell using viral transduction, for example, with a vector. In some embodiments, the vector is a pseudotyped, self-inactivating lentiviral vector that carries the exogenous polynucleotide. In some embodiments, the vector is a self-inactivating lentiviral vector pseudotyped with a vesicular stomatitis VSV-G envelope, and which carries the exogenous polynucleotide. In some embodiments, the exogenous polynucleotide is inserted into at least one allele of the cell using viral transduction. In some embodiments, the exogenous polynucleotide is inserted into at least one allele of the cell using a lentivirus based viral vector.

In some embodiments, the CAR is selected from the group consisting of a CD19-specific CAR and a CD22-specific CAR. In some embodiments, the CAR is a bispecific CAR. In some embodiments, the bispecific CAR is a CD19/CD22-bispecific CAR.

In some embodiments, the non-activated T cell does not express HLA-A, HLA-B, and/or HLA-C antigens. In some embodiments, the non-activated T cell does not express B2M. In some embodiments, the non-activated T cell does not express HLA-DP, HLA-DQ, and/or HLA-DR antigens.

In some embodiments, the non-activated T cell does not express CIITA. In some embodiments, the non-activated T cell does not express TCR-alpha and TCR-beta.

In some embodiments, the non-activated T cell is a $B2M^{indel/indel}$, $CIITA^{indel/indel}$, $TRAC^{indel/indel}$ cell comprising second exogenous polynucleotide encoding CD47 and/or the first exogenous polynucleotide encoding CAR inserted into the TRAC locus.

In some embodiments, the non-activated T cell is a $B2M^{indel/indel}$, $CIITA^{indel/indel}$, $TRAC^{indel/indel}$ cell comprising the second exogenous polynucleotide encoding CD47 and the first exogenous polynucleotide encoding CAR inserted into the TRAC locus.

In some embodiments, the non-activated T cell is a $B2M^{indel/indel}$, $CIITA^{indel/indel}$, $TRAC^{indel/indel}$ cell comprising second exogenous polynucleotide encoding CD47 and/or the first exogenous polynucleotide encoding CAR inserted into the TRB locus.

In some embodiments, the non-activated T cell is a $B2M^{indel/indel}$, $CIITA^{indel/indel}$, $TRAC^{indel/indel}$ cell comprising the second exogenous polynucleotide encoding CD47 and the first exogenous polynucleotide encoding CAR inserted into the TRB locus.

In some embodiments, the non-activated T cell is a $B2M^{indel/indel}$, $CIITA^{indel/indel}$, $TRAC^{indel/indel}$ cell comprising second exogenous polynucleotide encoding CD47 and/or the first exogenous polynucleotide encoding CAR inserted into the B2M locus.

In some embodiments, the non-activated T cell is a $B2M^{indel/indel}$, $CIITA^{indel/indel}$, $TRAC^{indel/indel}$ cell comprising the second exogenous polynucleotide encoding CD47 and the first exogenous polynucleotide encoding CAR inserted into a B2M locus.

In some embodiments, the non-activated T cell is a $B2M^{indel/indel}$, $CIITA^{indel/indel}$, $TRAC^{indel/indel}$ cell comprising second exogenous polynucleotide encoding CD47 and/or the first exogenous polynucleotide encoding CAR inserted into the CIITA locus.

In some embodiments, the non-activated T cell is a $B2M^{indel/indel}$, $CIITA^{indel/indel}$, $TRAC^{indel/indel}$ cell comprising the second exogenous polynucleotide encoding CD47 and the first exogenous polynucleotide encoding CAR inserted into a CIITA locus.

In some embodiments, the exogenous polynucleotide is inserted into at least one allele of the cell using viral transduction, for example, with a vector. In some embodiments, the vector is a pseudotyped, self-inactivating lentiviral vector that carries the exogenous polynucleotide. In some embodiments, the vector is a self-inactivating lentiviral vector pseudotyped with a vesicular stomatitis VSV-G envelope, and which carries the exogenous polynucleotide. In some embodiments, the exogenous polynucleotide is inserted into at least one allele of the cell using viral transduction. In some embodiments, the exogenous polynucleotide is inserted into at least one allele of the cell using a lentivirus based viral vector.

Provided herein are engineered T cells comprising reduced expression of HLA-A, HLA-B, HLA-C, HLA-DP, HLA-DQ, HLA-DR, B2M, CIITA, TCR-alpha, and/or TCR-beta relative to a wild-type T cell, wherein the engineered T cell further comprises a first exogenous polynucleotide encoding a chimeric antigen receptor (CAR) carried by a lentiviral vector. Provided herein are engineered T cells comprising reduced expression of HLA-A, HLA-B, HLA-C, HLA-DP, HLA-DQ, HLA-DR, B2M, CIITA, TCR-alpha, and/or TCR-beta relative to a wild-type T cell, wherein the engineered T cell further comprises a first exogenous polynucleotide encoding a chimeric antigen receptor (CAR) carried by a lentiviral vector that comprises a CD8 binding agent. In some embodiments, the exogenous polynucleotide is inserted into at least one allele of the cell using viral transduction, for example, with a vector. In some embodiments, the vector is a pseudotyped, self-inactivating lentiviral vector that carries the exogenous polynucleotide. In some embodiments, the vector is a self-inactivating lentiviral vector pseudotyped with a vesicular stomatitis VSV-G envelope, and which carries the exogenous polynucleotide. In some embodiments, the exogenous polynucleotide is inserted into at least one allele of the cell using viral transduction. In some embodiments, the exogenous polynucleotide is inserted into at least one allele of the cell using a lentivirus based viral vector.

In some embodiments, the engineered T cell is a primary T cell. In other embodiments, the engineered T cell is differentiated from the engineered cell of the present technology. In some embodiments, the T cell is a CD8$^+$ T cell.

In some embodiments, the engineered T cell has not been treated with an anti-CD3 antibody, an anti-CD28 antibody, a T cell activating cytokine, or a soluble T cell costimulatory molecule. In some embodiments, the anti-CD3 antibody is OKT3, wherein the anti-CD28 antibody is CD28.2, wherein the T cell activating cytokine is selected from the group of T cell activating cytokines consisting of IL-2, IL-7, IL-15, and IL-21, and wherein soluble T cell costimulatory molecule is selected from the group of soluble T cell costimulatory molecules consisting of an anti-CD28 antibody, an anti-CD80 antibody, an anti-CD86 antibody, an anti-CD137L antibody, and an anti-ICOS-L antibody.

In some embodiments, the engineered T cell does not express activation markers. In some embodiments, the engineered T cell expresses CD3 and CD28, and wherein the CD3 and/or CD28 are inactive.

In some embodiments, the engineered T cell further comprises a second exogenous polynucleotide encoding CD47. In some embodiments, the first and/or second exogenous polynucleotides are inserted into a specific locus of at least one allele of the T cell. In some embodiments, the specific locus is selected from the group consisting of a safe harbor or target locus, a B2M locus, a CIITA locus, a TRAC locus, and a TRB locus. In some embodiments, the second exogenous polynucleotide encoding CD47 is inserted into the specific locus selected from the group consisting of a safe harbor or target locus, a B2M locus, a CIITA locus, a TRAC locus and a TRB locus. In some embodiments, the first exogenous polynucleotide encoding the CAR is inserted into the specific locus selected from the group consisting of a safe harbor or target locus, a B2M locus, a CIITA locus, a TRAC locus and a TRB locus. In some embodiments, the second exogenous polynucleotide encoding CD47 and the first exogenous polynucleotide encoding the CAR are inserted into different loci. In some embodiments, the second exogenous polynucleotide encoding CD47 and the first exogenous polynucleotide encoding the CAR are inserted into the same locus. In some embodiments, the second exogenous polynucleotide encoding CD47 and the first exogenous polynucleotide encoding the CAR are inserted into the B2M locus, the CIITA locus, the TRAC locus, the TRB locus, or the safe harbor or target locus. In some embodiments, the safe harbor or target locus is selected from the group consisting of a CCR5 gene locus, a CXCR4 gene locus, a PPP1R12C (also known as AAVS1) gene locus, an albumin gene locus, a SHS231 gene locus, a CLYBL gene locus, a Rosa gene locus (e.g., ROSA26 gene locus), an F3 gene locus (also known as CD142), a MICA gene locus, a MICB gene locus, a LRP1 gene locus (also known as a CD91 gene locus), a HMGB1 gene locus, an ABO gene locus, ad RHD gene locus, a FUT1 locus, and a KDM5D gene locus. In some embodiments, the safe harbor or target locus is selected from the group consisting of the AAVS1 locus, the CCR5 locus, and the ROSA26 locus. In some embodiments, the exogenous polynucleotide is inserted into at least one allele of the cell using viral transduction, for example, with a vector. In some embodiments, the vector is a pseudotyped, self-inactivating lentiviral vector that carries the exogenous polynucleotide. In some embodiments, the vector is a self-inactivating lentiviral vector pseudotyped with a vesicular stomatitis VSV-G envelope, and which carries the exogenous polynucleotide. In some embodiments, the exogenous polynucleotide is inserted into at least one allele of the cell using viral transduction. In some embodiments, the exogenous polynucleotide is inserted into at least one allele of the cell using a lentivirus based viral vector.

In some embodiments, the CAR is selected from the group consisting of a CD19-specific CAR and a CD22-specific CAR.

In some embodiments, the engineered T cell does not express HLA-A, HLA-B, and/or HLA-C antigens, wherein the engineered T cell does not express B2M, wherein the engineered T cell does not express HLA-DP, HLA-DQ, and/or HLA-DR antigens, wherein the engineered T cell does not express CIITA, and/or wherein the engineered T cell does not express TCR-alpha and TCR-beta.

In some embodiments, the engineered T cell is a $B2M^{indel/indel}$, $CIITA^{indel/indel}$, $TRAC^{indel/indel}$ cell comprising the second exogenous polynucleotide encoding CD47 and/or the first exogenous polynucleotide encoding CAR inserted into the TRAC locus, into the TRB locus, into the B2M locus, or into the CIITA locus. In some embodiments, the exogenous polynucleotide is inserted into at least one allele of the cell using viral transduction, for example, with a vector. In some embodiments, the vector is a pseudotyped, self-inactivating lentiviral vector that carries the exogenous polynucleotide. In some embodiments, the vector is a self-inactivating lentiviral vector pseudotyped with a vesicular stomatitis VSV-G envelope, and which carries the exogenous polynucleotide. In some embodiments, the exogenous polynucleotide is inserted into at least one allele of the cell using viral transduction. In some embodiments, the exogenous polynucleotide is inserted into at least one allele of the cell using a lentivirus based viral vector.

In some embodiments, the non-activated T cell and/or the engineered T cell of the present technology are in a subject. In other embodiments, the non-activated T cell and/or the engineered T cell of the present technology are in vitro.

In some embodiments, the non-activated T cell and/or the engineered T cell of the present technology express a CD8 binding agent. In some embodiments, the CD8 binding agent is an anti-CD8 antibody. In some embodiments, the anti-CD8 antibody is selected from the group consisting of a mouse anti-CD8 antibody, a rabbit anti-CD8 antibody, a human anti-CD8 antibody, a humanized anti-CD8 antibody, a camelid (e.g., llama, alpaca, camel) anti-CD8 antibody, and a fragment thereof. In some embodiments, the fragment thereof is an scFV or a VHH. In some embodiments, the CD8 binding agent binds to a CD8 alpha chain and/or a CD8 beta chain.

In some embodiments, the CD8 binding agent is fused to a transmembrane domain incorporated in the viral envelope. In some embodiments, the lentivirus vector is pseudotyped with a viral fusion protein. In some embodiments, the viral fusion protein comprises one or more modifications to reduce binding to its native receptor.

In some embodiments, the viral fusion protein is fused to the CD8 binding agent. In some embodiments, the viral fusion protein comprises Nipah virus F glycoprotein and Nipah virus G glycoprotein fused to the CD8 binding agent. In some embodiments, the lentivirus vector does not comprise a T cell activating molecule or a T cell costimulatory molecule. In some embodiments, the lentivirus vector encodes the first exogenous polynucleotide and/or the second exogenous polynucleotide.

In some embodiments, the exogenous polynucleotide is inserted into at least one allele of the cell using viral transduction, for example, with a vector. In some embodiments, the vector is a pseudotyped, self-inactivating lentiviral vector that carries the exogenous polynucleotide. In some embodiments, the vector is a self-inactivating lentiviral vector pseudotyped with a vesicular stomatitis VSV-G envelope, and which carries the exogenous polynucleotide. In some embodiments, the exogenous polynucleotide is inserted into at least one allele of the cell using viral transduction. In some embodiments, the exogenous polynucleotide is inserted into at least one allele of the cell using a lentivirus based viral vector.

In some embodiments, following transfer into a first subject, the non-activated T cell or the engineered T cell exhibits one or more responses selected from the group consisting of (a) a T cell response, (b) an NK cell response, and (c) a macrophage response, that are reduced as compared to a wild-type cell following transfer into a second subject. In some embodiments, the first subject and the second subject are different subjects. In some embodiments, the macrophage response is engulfment.

In some embodiments, following transfer into a subject, the non-activated T cell or the engineered T cell exhibits one or more selected from the group consisting of (a) reduced TH1 activation in the subject, (b) reduced NK cell killing in the subject, and (c) reduced killing by whole PBMCs in the subject, as compared to a wild-type cell following transfer into the subject.

In some embodiments, following transfer into a subject, the non-activated T cell or the engineered T cell elicits one or more selected from the group consisting of (a) reduced donor specific antibodies in the subject, (b) reduced IgM or IgG antibodies in the subject, and (c) reduced complement-dependent cytotoxicity (CDC) in a subject, as compared to a wild-type cell following transfer into the subject.

In some embodiments, the non-activated T cell or the engineered T cell is transduced with a lentivirus vector comprising a CD8 binding agent within the subject. In some embodiments, the lentivirus vector carries a gene encoding the CAR and/or CD47.

Provided herein are pharmaceutical compositions comprising a population of the non-activated T cells and/or the engineered T cells of the present technology and a pharmaceutically acceptable additive, carrier, diluent or excipient.

Provided herein are methods comprising administering to a subject a composition comprising a population of the non-activated T cells and/or the engineered T cells of the present technology, or one or more the pharmaceutical compositions of the present technology.

In some embodiments, the subject is not administered a T cell activating treatment before, after, and/or concurrently with administration of the composition. In some embodiments, the T cell activating treatment comprises lymphodepletion.

Provided herein are methods of treating a subject suffering from cancer, comprising administering to a subject a composition comprising a population of the non-activated T cells and/or the engineered T cells of the present technology, or one or more the pharmaceutical compositions of the present technology, wherein the subject is not administered a T cell activating treatment before, after, and/or concurrently with administration of the composition. In some embodiments, the T cell activating treatment comprises lymphodepletion.

Provided herein are methods for expanding T cells capable of recognizing and killing tumor cells in a subject in need thereof within the subject, comprising administering to a subject a composition comprising a population of the non-activated T cells and/or the engineered T cells of the present technology, or one or more the pharmaceutical compositions of the present technology, wherein the subject is not administered a T cell activating treatment before, after, and/or concurrently with administration of the composition. In some embodiments, the T cell activating treatment comprises lymphodepletion.

Provided herein are dosage regimens for treating a disease or disorder in a subject comprising administration of a pharmaceutical composition comprising a population of the non-activated T cells and/or the engineered T cells of the present technology, or one or more the pharmaceutical compositions of the present technology, and a pharmaceutically acceptable additive, carrier, diluent or excipient, wherein the pharmaceutical composition is administered in about 1-3 doses.

Provided herein is an engineered cell comprising reduced expression of HLA-A, HLA-B, HLA-C, HLA-DP, HLA-DQ, HLA-DR, B2M, CIITA, TCR-alpha, and/or TCR-beta relative to a wild-type cell or a control cell, the engineered cell further comprising a set of exogenous polynucleotides comprising a first exogenous polynucleotide encoding CD47 and a second exogenous polynucleotide encoding a chimeric antigen receptor (CAR), wherein the first and/or second exogenous polynucleotides are inserted into a specific locus of at least one allele of the cell.

In some embodiments, the specific locus is selected from the group consisting of a safe harbor or target locus, a B2M locus, a CIITA locus, a TRAC locus and a TRB locus.

In some embodiments, the first exogenous polynucleotide encoding CD47 is inserted into the specific locus selected from the group consisting of a safe harbor or target locus, a B2M locus, a CIITA locus, a TRAC locus and a TRB locus.

In some embodiments, the second exogenous polynucleotide encoding the CAR is inserted into the specific locus selected from the group consisting of a safe harbor or target locus, a B2M locus, a CIITA locus, a TRAC locus and a TRB locus.

In some embodiments, the first exogenous polynucleotide encoding CD47 and the second exogenous polynucleotide encoding the CAR are inserted into different loci.

In some embodiments, the first exogenous polynucleotide encoding CD47 and the second exogenous polynucleotide encoding the CAR are inserted into the same locus.

In some embodiments, the first exogenous polynucleotide encoding CD47 and the second exogenous polynucleotide encoding the CAR are inserted into the B2M locus.

In some embodiments, the first exogenous polynucleotide encoding CD47 and the second exogenous polynucleotide encoding the CAR are inserted into the CIITA locus.

In some embodiments, the first exogenous polynucleotide encoding CD47 and the second exogenous polynucleotide encoding the CAR are inserted into the TRAC locus.

In some embodiments, the first exogenous polynucleotide encoding CD47 and the second exogenous polynucleotide encoding the CAR are inserted into the TRB locus.

In some embodiments, the first exogenous polynucleotide encoding CD47 and the second exogenous polynucleotide encoding the CAR are inserted into the safe harbor or target locus.

In some embodiments, the safe harbor locus is selected from the group consisting of a CCR5 gene locus, a PPP1R12C gene locus, a CLYBL gene locus, and a Rosa gene locus, and the target locus is selected from the group consisting of a CXCR4 gene locus, an albumin gene locus, a SHS231 gene locus, an F3 (CD142) gene locus, a MICA gene locus, a MICB gene locus, a LRP1 (CD91) gene locus, a HMGB1 gene locus, an ABO gene locus, ad RHD gene locus, a FUT1 locus, and a KDM5D gene locus.

In some embodiments, the CAR is selected from the group consisting of a CD19-specific CAR and a CD22-specific CAR.

In some embodiments, the CD19-specific CAR is substantially equivalent to the CD19-specific CAR of any one of the CAR-T cell based therapies selected from the group consisting of axicabtagene ciloleucel, lisocabtagene maraleucel, brexucabtagene autoleucel, and tisagenlecleucel.

In some embodiments, the CAR is a bispecific CAR.

In some embodiments, the CAR is a CD19/CD22-bispecific CAR.

In some embodiments, the engineered cell does not express HLA-A, HLA-B, and/or HLA-C antigens.

In some embodiments, the engineered cell does not express B2M.

In some embodiments, the engineered cell does not express HLA-DP, HLA-DQ, and/or HLA-DR antigens.

In some embodiments, the engineered cell does not express CIITA.

In some embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell does not express TCR-alpha and/or TCR-beta.

In some embodiments, the engineered cell is a pluripotent stem cell.

In some embodiments, the engineered cell is an induced pluripotent stem cell.

In some embodiments, the engineered cell is a differentiated cell derived from an induced pluripotent stem cell.

In some embodiments, the differentiated cell is selected from the group consisting of an NK cell and a T cell.

In some embodiments, the engineered cell is a cell derived from a primary T cell.

In some embodiments, the cell derived from the primary T cell is derived from a pool of T cells comprising primary T cells from one or more donor subjects who are different from a recipient subject.

In some embodiments, the engineered cell retains pluripotency and/or retains differentiation potential.

In some embodiments, following transfer into a first subject, the engineered cell exhibits one or more responses selected from the group consisting of (a) a T cell response, (b) an NK cell response, and (c) a macrophage response, that are reduced as compared to a wild-type cell following transfer into a second subject.

In some embodiments, the first subject and the second subject are different subjects.

In some embodiments, the macrophage response is engulfment.

In some embodiments, following transfer into a subject the engineered cell exhibits one or more selected from the group consisting of (a) reduced TH1 activation in the subject, (b) reduced NK cell killing in the subject, and (c) reduced killing by whole PBMCs in the subject, as compared to a wild-type cell following transfer into the subject.

In some embodiments, following transfer into a subject the engineered cell elicits one or more selected from the group consisting of (a) reduced donor specific antibodies in the subject, (b) reduced IgM or IgG antibodies in the subject, and (c) reduced complement-dependent cytotoxicity (CDC) in a subject, as compared to a wild-type cell following transfer into the subject.

In some embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a $B2M^{indel/indel}$, $CIITA^{indel/indel}$, $TRAC^{indel/indel}$ cell comprising first exogenous polynucleotide encoding CD47 and/or the second exogenous polynucleotide encoding CAR inserted into the TRAC locus.

In some embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a $B2M^{indel/indel}$, $CIITA^{indel/indel}$, $TRAC^{indel/indel}$ cell comprising the first exogenous polynucleotide encoding CD47 and the second exogenous polynucleotide encoding CAR inserted into the TRAC locus.

In some embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a $B2M^{indel/indel}$, $CIITA^{indel/indel}$, $TRAC^{indel/indel}$ cell comprising first exogenous polynucleotide encoding CD47 and/or the second exogenous polynucleotide encoding CAR inserted into the TRB locus.

In some embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a $B2M^{indel/indel}$, $CIITA^{indel/indel}$, $TRAC^{indel/indel}$ cell comprising the first exogenous polynucleotide encoding CD47 and the second exogenous polynucleotide encoding CAR inserted into the TRB locus.

In some embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a $B2M^{indel/indel}$, $CIITA^{indel/indel}$, $TRAC^{indel/indel}$ cell comprising first exogenous polynucleotide encoding CD47 and/or the second exogenous polynucleotide encoding CAR inserted into the B2M locus.

In some embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a $B2M^{indel/indel}$, $CIITA^{indel/indel}$, $TRAC^{indel/indel}$ cell comprising the first exogenous polynucleotide encoding CD47 and the second exogenous polynucleotide encoding CAR inserted into a B2M locus.

In some embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a B2M$^{indel/indel}$, CIITA$^{indel/indel}$, TRAC$^{indel/indel}$ cell comprising first exogenous polynucleotide encoding CD47 and/or the second exogenous polynucleotide encoding CAR inserted into the CIITA locus.

In some embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a B2M$^{indel/indel}$, CIITA$^{indel/indel}$, TRAC$^{indel/indel}$ cell comprising the first exogenous polynucleotide encoding CD47 and the second exogenous polynucleotide encoding CAR inserted into a CIITA locus.

Provided herein is an engineered cell comprising reduced expression of HLA-A, HLA-B, HLA-C, HLA-DP, HLA-DQ, HLA-DR, B2M, CIITA, TCR-alpha, and/or TCR-beta relative to a wild-type cell or a control cell.

In some embodiments, the engineered cell does not express HLA-A, HLA-B and/or HLA-C antigens.

In some embodiments, the engineered cell does not express CIITA.

In some embodiments, the engineered cell does not express HLA-DP, HLA-DQ, and/or HLA-DR antigens.

In some embodiments, the engineered cell does not express B2M.

In some embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell does not express TCR-alpha.

In some embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell does not express TCR-beta.

In some embodiments, the engineered cell overexpresses CD47 relative to a wild-type cell or a control cell.

In some embodiments, the engineered cell is a pluripotent stem cell.

In some embodiments, the engineered cell is an induced pluripotent stem cell.

In some embodiments, the engineered cell is a differentiated cell derived from an induced pluripotent stem cell.

In some embodiments, the differentiated cell is selected from the group consisting of an NK cell and a T cell.

In some embodiments, the engineered cell is a cell derived from a primary T cell.

In some embodiments, the cell derived from the primary T cell is derived from a pool of T cells comprising primary T cells from one or more donor subjects who are different from a recipient subject.

In some embodiments, the engineered cell retains pluripotency and/or retains differentiation potential.

In some embodiments, following transfer into a first subject, the engineered cell exhibits one or more responses selected from the group consisting of (a) a T cell response, (b) an NK cell response, and (c) a macrophage response, that are reduced as compared to a wild-type cell following transfer into a second subject.

In some embodiments, the first subject and the second subject are different subjects.

In some embodiments, the macrophage response is engulfment.

In some embodiments, following transfer into a subject the engineered cell exhibits one or more selected from the group consisting of (a) reduced TH1 activation in the subject, (b) reduced NK cell killing in the subject, and (c) reduced killing by whole PBMCs in the subject, as compared to a wild-type cell following transfer into the subject.

In some embodiments, following transfer into a subject the engineered cell elicits one or more selected from the group consisting of (a) reduced donor-specific antibodies in the subject, (b) reduced IgM or IgG antibodies in the subject, and (c) reduced complement-dependent cytotoxicity (CDC) in the subject, as compared to a wild-type cell following transfer into the subject.

In some embodiments, the engineered cell is selected from the group consisting a pluripotent stem cell, an induced pluripotent stem cell, a T cell differentiated from an induced pluripotent stem cell, a primary T cell, and a cell derived from a primary T cell, and the engineered cell is a B2M$^{indel/indel}$, CIITA$^{indel/indel}$, TRACindeindel and/or TRBindevindel cell.

In some embodiments, the engineered cell is a hypoimmunogenic cell.

In some embodiments, the wild type cell or the control cell is a starting material.

In some embodiments, the first and/or second exogenous polynucleotide is inserted into at least one allele of the cell using viral transduction.

In some embodiments, the viral transduction is via a lentivirus based viral vector.

In some embodiments, the lentivirus based viral vector is a pseudotyped, self-inactivating lentiviral vector that carries the first and/or second exogenous polynucleotides.

In some embodiments, the lentivirus based viral vector is a self-inactivating lentiviral vector pseudotyped with a vesicular stomatitis VSV-G envelope, and which carries the first and/or second exogenous polynucleotides.

Provided herein is a pharmaceutical composition comprising a population of the engineered cells as described herein and a pharmaceutically acceptable additive, carrier, diluent or excipient.

In some embodiments, the pharmaceutically acceptable additive, carrier, diluent or excipient comprises one or more selected from the group consisting of Plasma-Lyte A®, dextrose, dextran, sodium chloride, human serum albumin (HSA), dimethylsulfoxide (DMSO), and a combination thereof.

In some embodiments of the composition, the composition further comprises a pharmaceutically acceptable buffer.

In some embodiments, the pharmaceutically acceptable buffer is neutral buffer saline or phosphate buffered saline.

Provided herein is a pharmaceutical composition comprising a population of the engineered cells as described herein, a base solution of CryoStor® CSB at a concentration of about 70-80% w/w, and one or more of about 20-30% w/w PlasmaLyte-A™, about 0.3-5.3% w/v human serum albumin (HSA), about 0-20% v/v dimethylsulfoxide (DMSO), and about 100-400 mM trehalose.

Provided herein is a pharmaceutical composition comprising a population of the engineered cells as described herein, a base solution of PlasmaLyte-A™ at a concentration of about 20-30% w/w, and one or more of about 70-80% w/w CryoStor® CSB, about 0.3-5.3% w/v human serum albumin (HSA), about 0-20% v/v dimethylsulfoxide (DMSO), and about 100-400 mM trehalose.

Provided herein is a pharmaceutical composition comprising a population of the engineered cells as described herein, about 0.3-5.3% w/v human serum albumin (HSA), and one or more of about 70-80% w/w CryoStor® CSB, about 20-30% w/w PlasmaLyte-A™, about 0-20% v/v dimethylsulfoxide (DMSO), and about 100-400 mM trehalose.

Provided herein is a pharmaceutical composition comprising a population of the engineered cells as described herein, about 0-20% v/v dimethylsulfoxide (DMSO), and one or more of about 70-80% w/w CryoStor® CSB, about 20-30% w/w PlasmaLyte-A™, about 0.3-5.3% w/v human serum albumin (HSA), and about 100-400 mM trehalose.

Provided herein is a pharmaceutical composition comprising a population of the engineered cells as described herein, about 100-400 mM trehalose, and one or more of about 70-80% w/w CryoStor® CSB, about 20-30% w/w PlasmaLyte-A™, about 0.3-5.3% w/v human serum albumin (HSA), and about 0-20% v/v dimethylsulfoxide (DMSO).

In some embodiments, the pharmaceutical composition comprises about 75% w/w of CryoStor® CSB.

In some embodiments, the pharmaceutical composition comprises about 25% w/w of PlasmaLyte-A™.

In some embodiments, the pharmaceutical composition comprises about 0.3% w/v of HSA.

In some embodiments, the pharmaceutical composition comprises about 7.5% v/v of DMSO.

Provided herein is a pharmaceutical composition comprising a population of the engineered cells as described herein, a base solution of CryoStor® CSB at a concentration of about 75% w/w, about 25% w/w PlasmaLyte-A™, about 0.3% w/v human serum albumin (HSA), and about 7.5% v/v dimethylsulfoxide (DMSO).

In some embodiments, the population of the engineered cells is up to about $8.0 \times 10^8$ cells.

In some embodiments, the population of the engineered cells is up to about $6.0 \times 10^8$ cells.

In some embodiments, the population of the engineered cells is from about $1.0 \times 10^6$ to about $2.5 \times 10^8$ cells.

In some embodiments, the population of the engineered cells is from about $2.0 \times 10^6$ to about $2.0 \times 10^8$ cells.

In some embodiments, the population of the engineered cells ranges from about 5 ml to about 80 ml.

In some embodiments, the population of the engineered cells ranges from about 10 ml to about 70 ml.

In some embodiments, the population of the engineered cells ranges from about 10 ml to about 50 ml.

In some embodiments, the composition is formulated for administration in a single dose.

In some embodiments, the composition is formulated for administration in up to three doses.

In some embodiments, the composition is formulated for administration of a single dose to a subject takes a duration of time of about 60 minutes or less.

In some embodiments, the composition is formulated for administration of a single dose to a subject takes a duration of time of about 30 minutes or less.

In some embodiments, the population of engineered cells of the pharmaceutical composition or progeny thereof exhibit at least 40% survival in a subject after 10 days following administration.

In some embodiments, the population of engineered cells of the pharmaceutical composition or progeny thereof exhibit at least 80% survival in a subject after about 2 weeks following administration.

In some embodiments, the population of engineered cells of the pharmaceutical composition or progeny thereof exhibit at least 100% survival in a subject after about 3 weeks following administration.

In some embodiments, the population of engineered cells of the pharmaceutical composition or progeny thereof exhibit at least 150% survival in a subject after about 4 weeks following administration.

Provided herein is a dosage regimen for treating a disease or disorder in a subject comprising administration of a pharmaceutical composition comprising a population of engineered cells as described herein and a pharmaceutically acceptable additive, carrier, diluent or excipient, wherein the pharmaceutical composition is administered in about 1-3 doses.

In some embodiments, the pharmaceutical composition administered is up to about $6.0 \times 10^8$ cells in about 1-3 doses.

In some embodiments, the pharmaceutical composition administered is from about $0.6 \times 10^6$ to about $6.0 \times 10^8$ cells in about 1-3 doses.

In some embodiments, the pharmaceutical composition administered is from about $0.2 \times 10^6$ to about $5.0 \times 10^6$ cells per kg of the subject's body weight in about 1-3 doses, if the subject has a body weight of 50 kg or less.

In some embodiments, the pharmaceutical composition administered is from about $0.1 \times 10^8$ to about $2.5 \times 10^8$ cells in about 1-3 doses, if the subject has a body weight greater than 50 kg.

In some embodiments, the pharmaceutical composition administered is from about $2.0 \times 10^6$ cells per kg of the subject's body weight and up to about $2 \times 10^8$ cells in about 1-3 doses.

In some embodiments, the administration of a single dose to the subject takes a duration of time of about 60 minutes or less.

In some embodiments, the administration of a single dose to the subject takes a duration of time of about 30 minutes or less.

In some embodiments, the pharmaceutically acceptable additive, carrier, diluent or excipient comprises one or more selected from the group consisting of Plasma-Lyte A®, dextrose, dextran, sodium chloride, human serum albumin (HSA), dimethylsulfoxide (DMSO), and a combination thereof.

In some embodiments, the pharmaceutical composition further comprises a pharmaceutically acceptable buffer.

In some embodiments, the pharmaceutically acceptable buffer is neutral buffer saline or phosphate buffered saline.

In some embodiments, the administration of the pharmaceutical composition, the population of cells or progeny thereof are present in the subject up to 9 months.

In some embodiments, the administration of the pharmaceutical composition, the population of cells or progeny thereof are present in the subject at least 2 years or more.

In some embodiments, the administration of the pharmaceutical composition, the population of engineered cells or progeny thereof exhibit at least 40% survival in a subject after about 10 days following administration.

In some embodiments, the administration of the pharmaceutical composition, the population of engineered cells or progeny thereof exhibit at least 80% survival in a subject after about 2 weeks following administration.

In some embodiments, the administration of the pharmaceutical composition, the population of engineered cells or progeny thereof exhibit at least 100% survival in a subject after about 3 weeks following administration.

In some embodiments, the administration of the pharmaceutical composition, the population of engineered cells or progeny thereof exhibit at least 150% survival in a subject after about 4 weeks following administration.

In some embodiments, the administration of 2-3 doses to the subject occurs such that each dose is administered ranging from 1 to 24 hours apart.

In some embodiments, the administration of 2-3 doses to the subject occurs such that each dose is administered ranging from 1 to 28 days apart.

In some embodiments, the administration of 2-3 doses to the subject occurs such that each dose is administered ranging from 1 to 6 weeks apart.

In some embodiments, the administration of 2-3 doses to the subject occurs such that each dose is administered ranging from 1 to 12 months or more apart.

Provided herein is a dosage regimen for treating a disease or disorder in a subject comprising administering a pharmaceutical composition comprising
(i) an engineered cell comprising reduced expression of HLA-A, HLA-B, HLA-C, HLA-DP, HLA-DQ, HLA-DR, B2M, CIITA, TCR-alpha, and/or TCR-beta, the engineered cell further comprising a set of exogenous polynucleotides encoding CD47 and a chimeric antigen receptor (CAR), wherein the set of exogenous polynucleotides are inserted into a safe harbor or target locus of at least one allele of the cell; and
(ii) a pharmaceutically acceptable additive, carrier, diluent or excipient,
wherein the pharmaceutical composition comprises up to about $6.0 \times 10^8$ cells.

Provided herein is a dosage regimen for treating a disease or disorder in a subject comprising administering a pharmaceutical composition comprising
(i) an engineered cell comprising reduced expression of HLA-A, HLA-B, HLA-C, HLA-DP, HLA-DQ, HLA-DR, B2M, CIITA, TCR-alpha, and/or TCR-beta, the engineered cell further comprising a set of exogenous polynucleotides encoding CD47 and a chimeric antigen receptor (CAR), wherein the set of exogenous polynucleotides are inserted into a safe harbor or target locus of at least one allele of the cell; and
(ii) a pharmaceutically acceptable additive, carrier, diluent or excipient,
wherein the pharmaceutical composition is administered in 1-3 doses.

Provided herein is a dosage regimen for treating a disease or disorder in a subject comprising administering a pharmaceutical composition comprising
(i) an engineered cell comprising reduced expression of HLA-A, HLA-B, HLA-C, HLA-DP, HLA-DQ, HLA-DR, B2M, CIITA, TCR-alpha, and/or TCR-beta, the engineered cell further comprising a set of exogenous polynucleotides encoding CD47 and a chimeric antigen receptor (CAR), wherein the set of exogenous polynucleotides are inserted into a safe harbor or target locus of at least one allele of the cell; and
(ii) a pharmaceutically acceptable additive, carrier, diluent or excipient,
wherein a dose of the pharmaceutical composition is administered for a duration of time of about 60 minutes or less.

Provided herein is a dosage regimen for treating a disease or disorder in a subject comprising administering a pharmaceutical composition comprising
(i) an engineered cell comprising reduced expression of HLA-A, HLA-B, HLA-C, HLA-DP, HLA-DQ, HLA-DR, B2M, CIITA, TCR-alpha, and/or TCR-beta; and
(ii) a pharmaceutically acceptable additive, carrier, diluent or excipient,
wherein the pharmaceutical composition comprises up to about $6.0 \times 10^8$ cells.

Provided herein is a dosage regimen for treating a disease or disorder in a subject comprising administering a pharmaceutical composition comprising
(i) an engineered cell comprising reduced expression of HLA-A, HLA-B, HLA-C, HLA-DP, HLA-DQ, HLA-DR, B2M, CIITA, TCR-alpha, and/or TCR-beta; and
(ii) a pharmaceutically acceptable additive, carrier, diluent or excipient,
wherein the pharmaceutical composition is administered in 1-3 doses.

Provided herein is a dosage regimen for treating a disease or disorder in a subject comprising administering a pharmaceutical composition comprising
(i) an engineered cell comprising reduced expression of HLA-A, HLA-B, HLA-C, HLA-DP, HLA-DQ, HLA-DR, B2M, CIITA, TCR-alpha, and/or TCR-beta; and
(ii) a pharmaceutically acceptable additive, carrier, diluent or excipient,
wherein a dose of the pharmaceutical composition is administered for a duration of 60 minutes or less.

Provided herein is a method of treating a cancer in a subject comprising administration of the engineered cell as described herein, the pharmaceutical composition as described herein, or the dosage regimen as described herein to the subject.

In some embodiments, the cancer is a CD19+ cancer.

Provided herein is a method of preventing T cell exhaustion in a subject comprising administration of the engineered cell as described herein to the subject, wherein the CAR is a CD19-specific CAR or a CD22-specific CAR.

In some embodiments, the CD19-specific CAR is substantially equivalent to the CD19-specific CAR of any one of the CAR-T cell based therapies selected from the group consisting of axicabtagene ciloleucel, lisocabtagene maraleucel, brexucabtagene autoleucel, and tisagenlecleucel.

Provided herein is a method of preventing T cell exhaustion or treating a disease in a subject comprising:
(i) administration of a first dosage regimen comprising a first population of engineered cells as described herein to the subject at a first timepoint, and
(ii) administration of a second dosage regimen comprising a second population of engineered cells as described herein to the subject at a second timepoint,
wherein the first dosage regimen and the second dosage regimen are different.

A method of preventing T cell exhaustion or treating a disease in a subject comprising:
(i) administration of a first dosage regimen comprising a first population of engineered cells as described herein to the subject at a first timepoint, and
(ii) administration of a second dosage regimen comprising a second population of engineered cells as described herein to the subject at a second timepoint,
wherein the first population of engineered cells and the second population of engineered cells both comprise the same chimeric antigen receptor.

Provided herein is a method of preventing T cell exhaustion or treating a disease in a subject comprising:
(i) administration of a first dosage regimen comprising a first population of engineered cells as described herein to the subject at a first timepoint, and
(ii) administration of a second dosage regimen comprising a second population of engineered cells as described herein to the subject at a second timepoint,
wherein the first population of engineered cells and the second population of engineered cells both comprise different chimeric antigen receptors.

Provided herein is a method of preventing T cell exhaustion or treating a disease in a subject comprising:
(i) administration of a first dosage regimen comprising a first population of engineered cells as described herein to the subject at a first timepoint, and
(ii) administration of a second dosage regimen comprising a second population of engineered cells as described herein to the subject at a second timepoint,
wherein the engineered cells of the first population comprise a first chimeric antigen receptor that binds a first antigen and the engineered cells of the second population comprise a second chimeric antigen receptor that binds a second antigen, and wherein the first antigen and the second antigen are the same.

Provided herein is a method of preventing T cell exhaustion or treating a disease in a subject comprising:
(i) administration of a first dosage regimen comprising a first population of engineered cells as described herein to the subject at a first timepoint, and
(ii) administration of a second dosage regimen comprising a second population of engineered cells as described herein to the subject at a second timepoint,
wherein the engineered cells of the first population comprise a first chimeric antigen receptor that binds a first antigen and the engineered cells of the second population comprise a second chimeric antigen receptor that binds a second antigen, and wherein the first antigen and the second antigen are different.

In some embodiments, the engineered cell is not activated.

Provided herein is a non-activated T cell comprising reduced expression of HLA-A, HLA-B, HLA-C, HLA-DP, HLA-DQ, HLA-DR, B2M, CIITA, TCR-alpha, and/or TCR-beta relative to a wild-type T cell, and a first exogenous polynucleotide encoding a chimeric antigen receptor (CAR).

In some embodiments, the non-activated T cell is a primary T cell.

In some embodiments, the non-activated T cell is differentiated from the engineered cell as described herein.

In some embodiments, the T cell is a CD8$^+$ T cell.

In some embodiments, the non-activated T cell has not been treated with an anti-CD3 antibody, an anti-CD28 antibody, a T cell activating cytokine, or a soluble T cell costimulatory molecule.

In some embodiments, the anti-CD3 antibody is OKT3.

In some embodiments, the anti-CD28 antibody is CD28.2.

In some embodiments, the T cell activating cytokine is selected from the group consisting of IL-2, IL-7, IL-15, and IL-21.

In some embodiments, the soluble T cell costimulatory molecule is selected from the group consisting of an anti-CD28 antibody, an anti-CD80 antibody, an anti-CD86 antibody, an anti-CD137L antibody, and an anti-ICOS-L antibody.

In some embodiments, the non-activated T cell does not express activation markers.

In some embodiments, the non-activated T cell expresses CD3 and CD28, and wherein the CD3 and/or CD28 are inactive.

In some embodiments, the first exogenous polynucleotide is carried by a lentiviral vector that comprises a CD8 binding agent.

In some embodiments, the non-activated T cell further comprises a second exogenous polynucleotide encoding CD47.

In some embodiments, the first and/or second exogenous polynucleotides are inserted into a specific locus of at least one allele of the T cell.

In some embodiments, the specific locus is selected from the group consisting of a safe harbor or target locus, a B2M locus, a CIITA locus, a TRAC locus, and a TRB locus.

In some embodiments, the second exogenous polynucleotide encoding CD47 is inserted into the specific locus selected from the group consisting of a safe harbor or target locus, a B2M locus, a CIITA locus, a TRAC locus and a TRB locus.

In some embodiments, the first exogenous polynucleotide encoding the CAR is inserted into the specific locus selected from the group consisting of a safe harbor or target locus, a B2M locus, a CIITA locus, a TRAC locus and a TRB locus.

In some embodiments, the second exogenous polynucleotide encoding CD47 and the first exogenous polynucleotide encoding the CAR are inserted into different loci.

In some embodiments, the second exogenous polynucleotide encoding CD47 and the first exogenous polynucleotide encoding the CAR are inserted into the same locus.

In some embodiments, the second exogenous polynucleotide encoding CD47 and the first exogenous polynucleotide encoding the CAR are inserted into the B2M locus.

In some embodiments, the second exogenous polynucleotide encoding CD47 and the first exogenous polynucleotide encoding the CAR are inserted into the CIITA locus.

In some embodiments, the second exogenous polynucleotide encoding CD47 and the first exogenous polynucleotide encoding the CAR are inserted into a TCR gene locus.

In some embodiments, the second exogenous polynucleotide encoding CD47 and the first exogenous polynucleotide encoding the CAR are inserted into the TRAC locus.

In some embodiments, the second exogenous polynucleotide encoding CD47 and the first exogenous polynucleotide encoding the CAR are inserted into the TRB locus.

In some embodiments, the second exogenous polynucleotide encoding CD47 and the first exogenous polynucleotide encoding the CAR are inserted into the safe harbor or target locus.

In some embodiments, the safe harbor or target locus is selected from the group consisting of a CCR5 gene locus, a CXCR4 gene locus, a PPP1R12C gene locus, an albumin gene locus, a SHS231 gene locus, a CLYBL gene locus, a Rosa gene locus, an F3 (CD142) gene locus, a MICA gene locus, a MICB gene locus, a LRP1 (CD91) gene locus, a HMGB1 gene locus, an ABO gene locus, an RHD gene locus, a FUT1 locus, and a KDM5D gene locus.

In some embodiments, the CAR is selected from the group consisting of a CD19-specific CAR and a CD22-specific CAR.

In some embodiments, the CD19-specific CAR is substantially equivalent to the CD19-specific CAR of any one of the CAR-T cell based therapies selected from the group consisting of axicabtagene ciloleucel, lisocabtagene maraleucel, brexucabtagene autoleucel, and tisagenlecleucel.

In some embodiments, the CAR is a bispecific CAR.

In some embodiments, the bispecific CAR is a CD19/CD22 bispecific CAR.

In some embodiments, the non-activated T cell does not express HLA-A, HLA-B, and/or HLA-C antigens.

In some embodiments, the non-activated T cell does not express B2M.

In some embodiments, the non-activated T cell does not express HLA-DP, HLA-DQ, and/or HLA-DR antigens.

In some embodiments, the non-activated T cell does not express CIITA.

In some embodiments, the non-activated T cell does not express TCR-alpha and/or TCR-beta.

In some embodiments, the non-activated T cell is a $B2M^{indel/indel}$, $CIITA^{indel/indel}$, $TRAC^{indel/indel}$ cell comprising second exogenous polynucleotide encoding CD47 and/or the first exogenous polynucleotide encoding CAR inserted into the TRAC locus.

In some embodiments, the non-activated T cell is a $B2M^{indel/indel}$, $CIITA^{indel/indel}$, $TRAC^{indel/indel}$ cell comprising the second exogenous polynucleotide encoding CD47 and the first exogenous polynucleotide encoding CAR inserted into the TRAC locus.

In some embodiments, the non-activated T cell is a $B2M^{indel/indel}$, $CIITA^{indel/indel}$, $TRAC^{indel/indel}$ cell comprising second exogenous polynucleotide encoding CD47 and/or the first exogenous polynucleotide encoding CAR inserted into the TRB locus.

In some embodiments, the non-activated T cell is a $B2M^{indel/indel}$, $CIITA^{indel/indel}$, $TRAC^{indel/indel}$ cell comprising the second exogenous polynucleotide encoding CD47 and the first exogenous polynucleotide encoding CAR inserted into the TRB locus.

In some embodiments, the non-activated T cell is a $B2M^{indel/indel}$, $CIITA^{indel/indel}$, $TRAC^{indel/indel}$ cell comprising the second exogenous polynucleotide encoding CD47 and/or the first exogenous polynucleotide encoding CAR inserted into the B2M locus.

In some embodiments, the non-activated T cell is a $B2M^{indel/indel}$, $CIITA^{indel/indel}$, $TRAC^{indel/indel}$ cell comprising the second exogenous polynucleotide encoding CD47 and the first exogenous polynucleotide encoding CAR inserted into a B2M locus.

In some embodiments, the non-activated T cell is a $B2M^{indel/indel}$, $CIITA^{indel/indel}$, $TRAC^{indel/indel}$ cell comprising second exogenous polynucleotide encoding CD47 and/or the first exogenous polynucleotide encoding CAR inserted into the CIITA locus.

In some embodiments, the non-activated T cell is a $B2M^{indel/indel}$, $CIITA^{indel/indel}$, $TRAC^{indel/indel}$ cell comprising the second exogenous polynucleotide encoding CD47 and the first exogenous polynucleotide encoding CAR inserted into a CIITA locus.

Provided herein is an engineered T cell comprising reduced expression of HLA-A, HLA-B, HLA-C, HLA-DP, HLA-DQ, HLA-DR, B2M, CIITA, TCR-alpha, and/or TCR-beta relative to a wild-type T cell, wherein the engineered T cell further comprises a first exogenous polynucleotide encoding a chimeric antigen receptor (CAR) carried by a lentiviral vector comprising a CD8 binding agent.

In some embodiments, the engineered T cell is a primary T cell.

In some embodiments, the engineered T cell is differentiated from the engineered cell as described herein.

In some embodiments, the T cell is a $CD8^+$ T cell.

In some embodiments, the engineered T cell has not been treated with an anti-CD3 antibody, an anti-CD28 antibody, a T cell activating cytokine, or a soluble T cell costimulatory molecule.

In some embodiments, the anti-CD3 antibody is OKT3, wherein the anti-CD28 antibody is CD28.2, wherein the T cell activating cytokine is selected from the group consisting of IL-2, IL-7, IL-15, and IL-21, and wherein the soluble T cell costimulatory molecule is selected from the group consisting of an anti-CD28 antibody, an anti-CD80 antibody, an anti-CD86 antibody, an anti-CD137L antibody, and an anti-ICOS-L antibody.

In some embodiments, the engineered T cell does not express activation markers.

In some embodiments, the engineered T cell expresses CD3 and CD28, and wherein the CD3 and/or CD28 are inactive.

In some embodiments, the engineered T cell further comprises a second exogenous polynucleotide encoding CD47.

In some embodiments, the first and/or second exogenous polynucleotides are inserted into a specific locus of at least one allele of the T cell.

In some embodiments, the specific locus is selected from the group consisting of a safe harbor or target locus, a B2M locus, a CIITA locus, a TRAC locus, and a TRB locus.

In some embodiments, the second exogenous polynucleotide encoding CD47 is inserted into the specific locus selected from the group consisting of a safe harbor or target locus, a B2M locus, a CIITA locus, a TRAC locus and a TRB locus.

In some embodiments, the first exogenous polynucleotide encoding the CAR is inserted into the specific locus selected from the group consisting of a safe harbor or target locus, a B2M locus, a CIITA locus, a TRAC locus and a TRB locus.

In some embodiments, the second exogenous polynucleotide encoding CD47 and the first exogenous polynucleotide encoding the CAR are inserted into different loci.

In some embodiments, the second exogenous polynucleotide encoding CD47 and the first exogenous polynucleotide encoding the CAR are inserted into the same locus.

In some embodiments, the second exogenous polynucleotide encoding CD47 and the first exogenous polynucleotide encoding the CAR are inserted into the B2M locus, the CIITA locus, the TRAC locus, the TRB locus, or the safe harbor or target locus.

In some embodiments, the safe harbor or target locus is selected from the group consisting of a CCR5 gene locus, a CXCR4 gene locus, a PPP1R12C gene locus, an albumin gene locus, a SHS231 gene locus, a CLYBL gene locus, a Rosa gene locus, an F3 (CD142) gene locus, a MICA gene locus, a MICB gene locus, a LRP1 (CD91) gene locus, a HMGB1 gene locus, an ABO gene locus, an RHD gene locus, a FUT1 locus, and a KDM5D gene locus.

In some embodiments, the CAR is selected from the group consisting of a CD19-specific CAR and a CD22-specific CAR.

In some embodiments, the CD19-specific CAR is substantially equivalent to the CD19-specific CAR of any one of the CAR-T cell based therapies selected from the group consisting of axicabtagene ciloleucel, lisocabtagene maraleucel, brexucabtagene autoleucel, and tisagenlecleucel.

In some embodiments, the engineered T cell does not express HLA-A, HLA-B, and/or HLA-C antigens, wherein the engineered T cell does not express B2M, wherein the engineered T cell does not express HLA-DP, HLA-DQ, and/or HLA-DR antigens, wherein the engineered T cell does not express CIITA, and/or wherein the engineered T cell does not express TCR-alpha and/or TCR-beta.

In some embodiments, the engineered T cell is a $B2M^{indel/indel}$, $CIITA^{indel/indel}$, $TRAC^{indel/indel}$ cell comprising the second exogenous polynucleotide encoding CD47 and/or the first exogenous polynucleotide encoding CAR inserted into the TRAC locus, into the TRB locus, into the B2M locus, or into the CIITA locus.

In some embodiments, the non-activated T cell is as described herein or the engineered T cell is as described herein, wherein the non-activated T cell or the engineered T cell is in a subject.

In some embodiments, the non-activated T cell is as described herein or the engineered T cell is as described herein, wherein the non-activated T cell or the engineered T cell is in vitro.

In some embodiments, the non-activated T cell is as described herein or the engineered T cell is as described herein, wherein the CD8 binding agent is an anti-CD8 antibody.

In some embodiments, the non-activated T cell or the engineered T cell is as described herein, wherein the anti-CD8 antibody is selected from the group consisting of a mouse anti-CD8 antibody, a rabbit anti-CD8 antibody, a human anti-CD8 antibody, a humanized anti-CD8 antibody, a camelid anti-CD8 antibody, and a fragment thereof.

In some embodiments, the non-activated T cell or the engineered T cell is as described herein, wherein the fragment thereof is an scFV or a VHH.

In some embodiments, the non-activated T cell or the engineered T cell is as described herein, wherein the CD8 binding agent binds to a CD8 alpha chain and/or a CD8 beta chain.

In some embodiments, the non-activated T cell or the engineered T cell is as described herein, wherein the CD8 binding agent is fused to a transmembrane domain incorporated in a viral envelope.

In some embodiments, the non-activated T cell or the engineered T cell is as described herein, wherein the lentivirus vector is pseudotyped with a viral fusion protein.

In some embodiments, the non-activated T cell or the engineered T cell is as described herein, wherein the viral fusion protein comprises one or more modifications to reduce binding to its native receptor.

In some embodiments, the non-activated T cell or the engineered T cell is as described herein, wherein the viral fusion protein is fused to the CD8 binding agent.

In some embodiments, the non-activated T cell or the engineered T cell is as described herein, wherein the viral fusion protein comprises Nipah virus F glycoprotein and Nipah virus G glycoprotein fused to the CD8 binding agent.

In some embodiments, the non-activated T cell or the engineered T cell is as described herein, wherein the lentivirus vector does not comprise a T cell activating molecule or a T cell costimulatory molecule.

In some embodiments, the non-activated T cell or the engineered T cell is as described herein, wherein the lentivirus vector encodes the first exogenous polynucleotide and/or the second exogenous polynucleotide.

In some embodiments, the non-activated T cell or the engineered T cell is as described herein, wherein, following transfer into a first subject, the non-activated T cell or the engineered T cell exhibits one or more responses selected from the group consisting of (a) a T cell response, (b) an NK cell response, and (c) a macrophage response, that are reduced as compared to a wild-type cell following transfer into a second subject.

In some embodiments, the non-activated T cell or the engineered T cell is as described herein, wherein the first subject and the second subject are different subjects.

In some embodiments, the non-activated T cell or the engineered T cell is as described herein, wherein the macrophage response is engulfment.

In some embodiments, the non-activated T cell or the engineered T cell is as described herein, wherein, following transfer into a subject, the non-activated T cell or the engineered T cell exhibits one or more selected from the group consisting of (a) reduced TH1 activation in the subject, (b) reduced NK cell killing in the subject, and (c) reduced killing by whole PBMCs in the subject, as compared to a wild-type cell following transfer into the subject.

In some embodiments, the non-activated T cell or the engineered T cell is as described herein, wherein, following transfer into a subject, the non-activated T cell or the engineered T cell elicits one or more selected from the group consisting of (a) reduced donor specific antibodies in the subject, (b) reduced IgM or IgG antibodies in the subject, and (c) reduced complement-dependent cytotoxicity (CDC) in a subject, as compared to a wild-type cell following transfer into the subject.

In some embodiments, the non-activated T cell or the engineered T cell is as described herein, wherein the non-activated T cell or the engineered T cell is transduced with a lentivirus vector comprising a CD8 binding agent within the subject.

In some embodiments, the non-activated T cell or the engineered T cell is as described herein, wherein the lentivirus vector carries a gene encoding the CAR and/or CD47.

Provided herein is a pharmaceutical composition comprising a population of the non-activated T cell or the engineered T cell is as described herein and a pharmaceutically acceptable additive, carrier, diluent or excipient.

Provided herein is a method comprising administering to a subject a composition comprising the non-activated T cell as described herein, the engineered T cell as described herein, or the pharmaceutical composition as described herein.

In some embodiments, the subject is not administered a T cell activating treatment before, after, and/or concurrently with the administration of the composition.

In some embodiments, the T cell activating treatment comprises lymphodepletion.

Provided herein is a method of treating a subject suffering from cancer, comprising administering to a subject a composition comprising the non-activated T cell as described herein, the engineered T cell as described herein, or the pharmaceutical composition as described herein, wherein the subject is not administered a T cell activating treatment before, after, and/or concurrently with the administration of the composition.

In some embodiments, the T cell activating treatment comprises lymphodepletion.

A method for expanding T cells capable of recognizing and killing tumor cells in a subject in need thereof within the subject, comprising administering to a subject a composition comprising the non-activated T cell as described herein, the engineered T cell as described herein, or the pharmaceutical composition as described herein, wherein the subject is not administered a T cell activating treatment before, after, and/or concurrently with the administration of the composition.

In some embodiments, the T cell activating treatment comprises lymphodepletion.

Provided herein is a dosage regimen for treating a disease or disorder in a subject comprising administration of a pharmaceutical composition comprising a population of subject a composition comprising the non-activated T cell as described herein, and/or the engineered T cell as described herein, and a pharmaceutically acceptable additive, carrier, diluent or excipient, wherein the pharmaceutical composition is administered in about 1-3 doses.

Detailed descriptions of engineered and/or hypoimmunogenic cells, methods of producing thereof, and methods of using thereof are found in U.S. Provisional Application No. 63/065,342 filed on Aug. 13, 2020, WO2016/183041 filed May 9, 2015, WO2018/132783 filed Jan. 14, 2018, WO2020/018615 filed Jul. 17, 2019, WO2020/018620 filed Jul. 17, 2019, WO2020/168317 filed Feb. 16, 2020, the disclosures of which including the examples, sequence listings and figures are incorporated herein by reference in their entireties.

BRIEF DESCRIPTION OF THE DRAWINGS

FIGS. 5A and 5B depict killing of CD19+ tumor cells by exemplary hypoimmunogenic CAR-T cells (CD19-specific CAR-CD47 T cells) in vitro in a dose-dependent manner. CD47 overexpression seemed not to affect CD19-specific CAR activity. CD19-specific CAR-CD47 T cells showed similar killing as control CD19-specific CAR-T cells ("CAR low" (FIG. 5A) and "CAR high" (FIG. 5B) cells).

FIG. 25 shows exemplary test cells and control cells used in the study. Exemplary test cells include hypoimmunogenic CD19-specific CAR-CD47 T cells that harbor genome edits of the B2M, CIITA and TRAC genes and overexpress CD47 molecules and CD19-specific chimeric antigen receptors. Control cells include immunogenic CD19-specific CAR-T cells co-expressing CD47 and EGFR as well as a tisagenlecleucel biosimilar or surrogate.

FIG. 30 shows that hypoimmunogenic CD19-specific CAR-CD47 T cells were able to kill tumor cells equivalently to control CD19-specific CAR-T cells in vitro. B cell leukemia killing kinetics and B cell leukemia total killing are depicted.

FIG. 38 provides a table of flow cytometry data that characterizes the HIP CAR-T cells (HIP CD19-CAR-T cells), control CAR-T cells (CD19-CAR-T cells), and unedited T cells produced according to the method outlined in FIG. 36.

FIG. 39A-D show the experimental results of Example 6. FIGS. 39A-B show Elispot analysis of the Th1 (IFNg) response, and FIGS. 39C-D show the results of the killing assay using CD19-CAR-T cells (FIG. 39C) or HIP CD19-CAR-T cells (FIG. 39D).

FIG. 40A and FIG. 40B show the viability and killing potency of HIP cells formulated in exemplary formulations described in Table 20. FIG. 40A shows the pre-freeze (empty markers) or post-thaw (solid markers) viability of HIP cells prepared in the formulations, and FIG. 40B shows the NALM-6 killing potency of the HIP cells prepared in the formulations.

FIGS. 41A-D show Th1 (IFNg) response as determined by Elispot for unsorted and sorted T cells.

FIGS. 43A-F shows the frequency of HIP CD19-CAR-T cells in blood assessed at interim bleeds and time of sacrifice, and FIG. 43G shows the CD47MFI of CD19-CAR-T cells in blood at Day 108 in groups rechallenged with $5\times10^6$ HIP CD19-CAR-T cells and tKO CD19-CAR-T (HIP CD19-CAR-T) treated groups. One-way ANOVA with Tukey's multiple comparisons test performed on CAR+ cell frequency data and two-way ANOVA with Bonferroni's multiple comparisons test performed on blood CD47MFI data.

Figure 1:
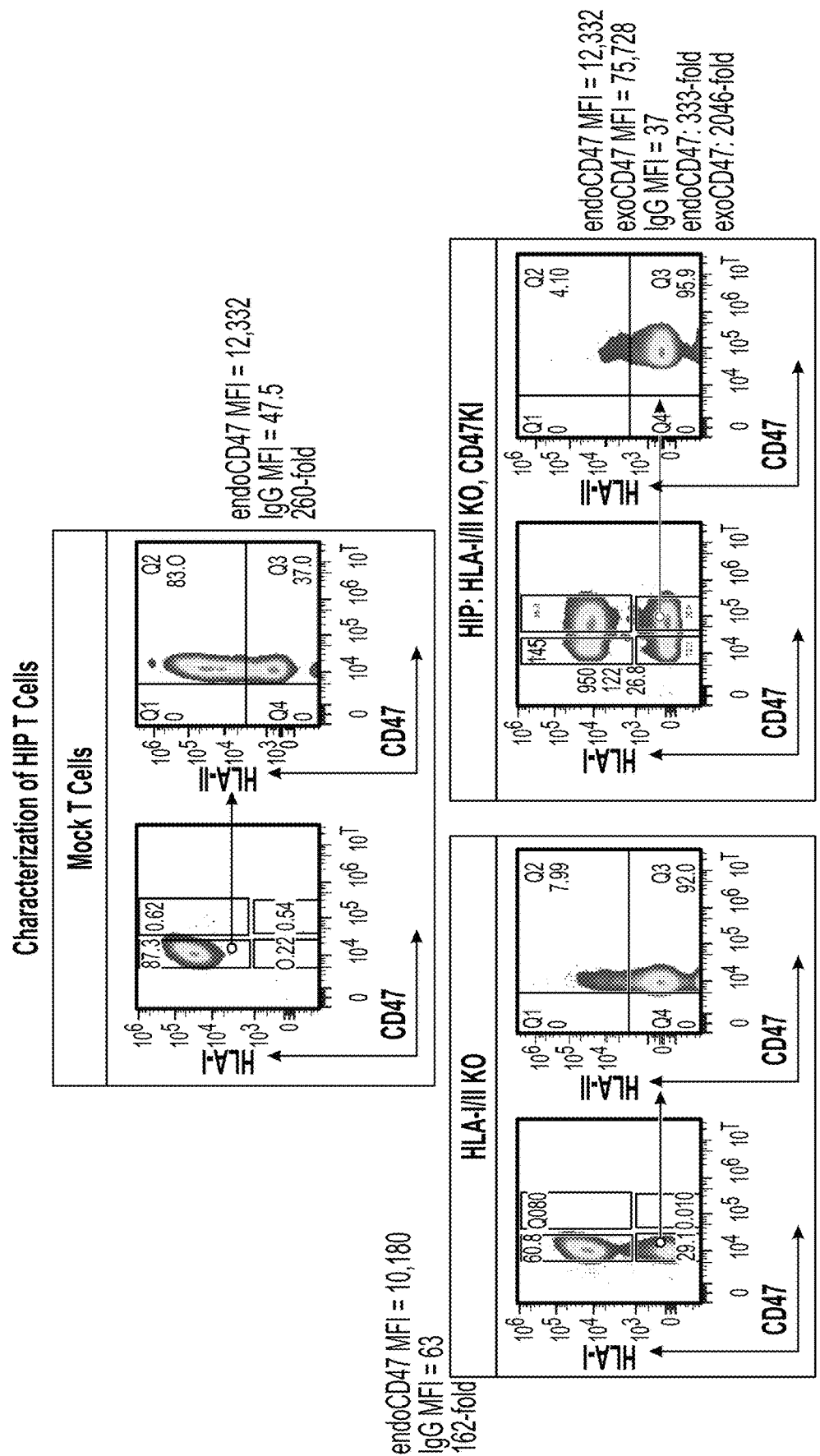
FIG. 1 shows the characterization of hypoimmunogenic T cells described herein. Such cells are HLA-I and HLA-II knock-out and CD47 knock-in cells.
Figure 2:
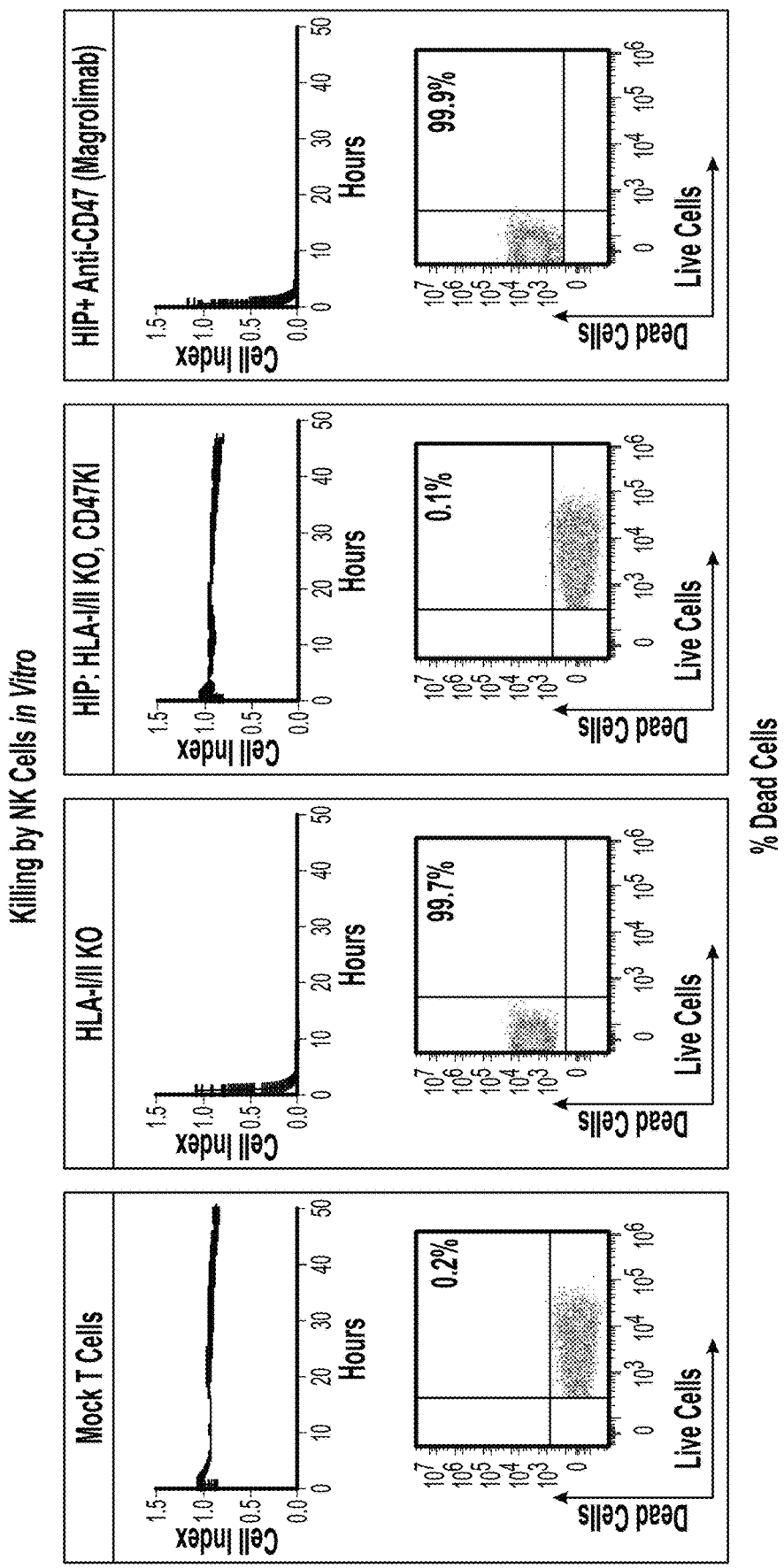
FIG. 2 shows the absence of NK cell mediated killing of the hypoimmunogenic T cells. In contrast, blocking CD47 with an anti-CD47 antibody resulted in NK cell mediated killing of the cells. Mock T cells were not killed by allogeneic NK cells (as expected). T cells lacking HLA-I/II were killed by NK cells. HLA-I/II knockout and CD47 knock-in cells were not killed by NK cells. Blocking CD47 with magrolimab (e.g., an anti-CD47 antibody) resulted in killing of HLA-I/II knockout, CD47 knock-in cells, and thus highlights the protection by CD47.
Figure 3:
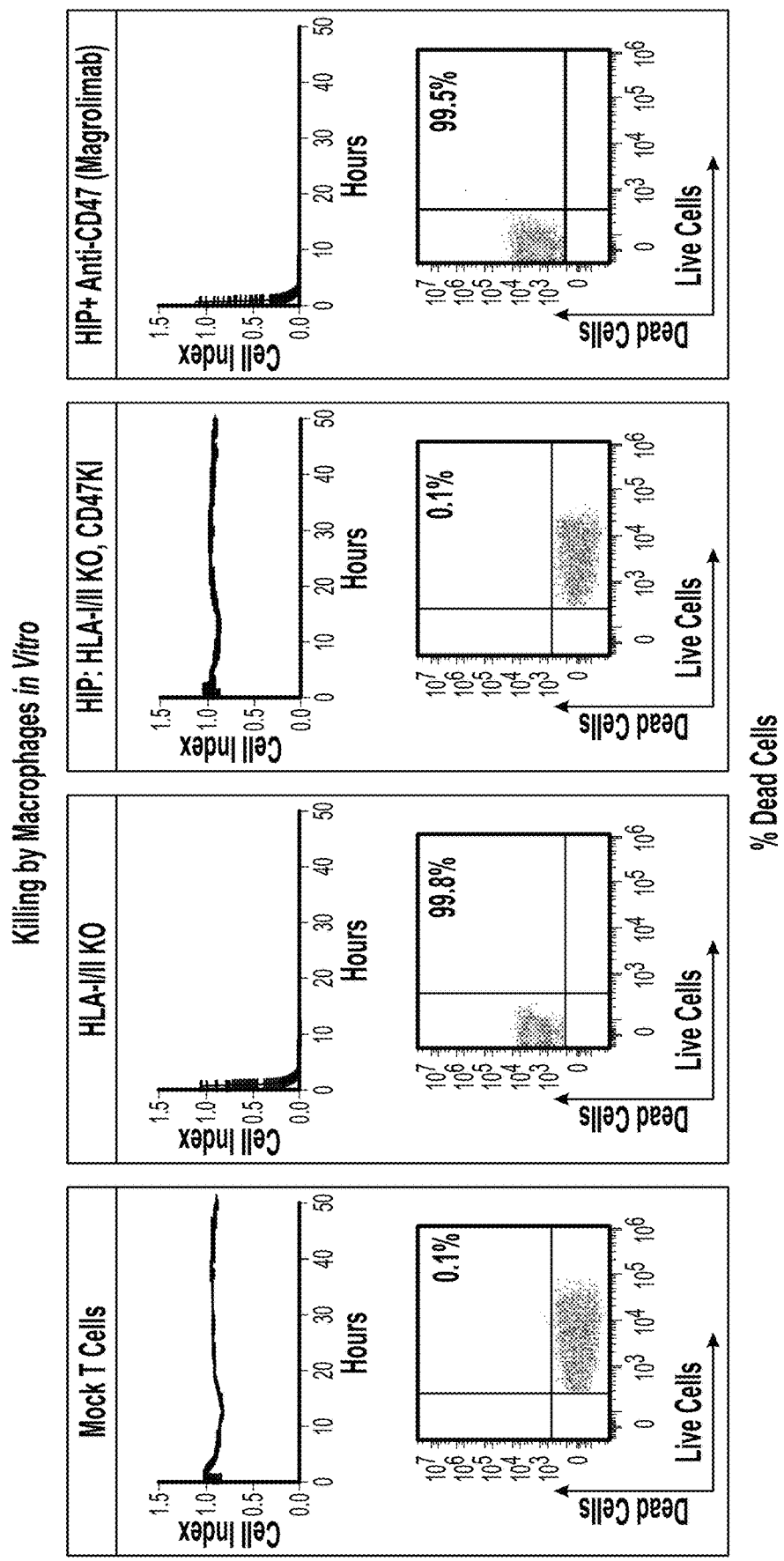
FIG. 3 shows the absence of macrophage mediated killing of the hypoimmunogenic T cells. Control T cells were not killed by allogeneic macrophages and T cells lacking HLA-I/II were killed by macrophages. HLA-I/II knockout and CD47 knock-in cells were not killed by macrophages. Blocking CD47 with magrolimab (e.g., an anti-CD47 antibody) resulted in killing of HLA-I/II knockout, CD47 knock-in cells, and thus highlights the protection by CD47.
Figure 4:
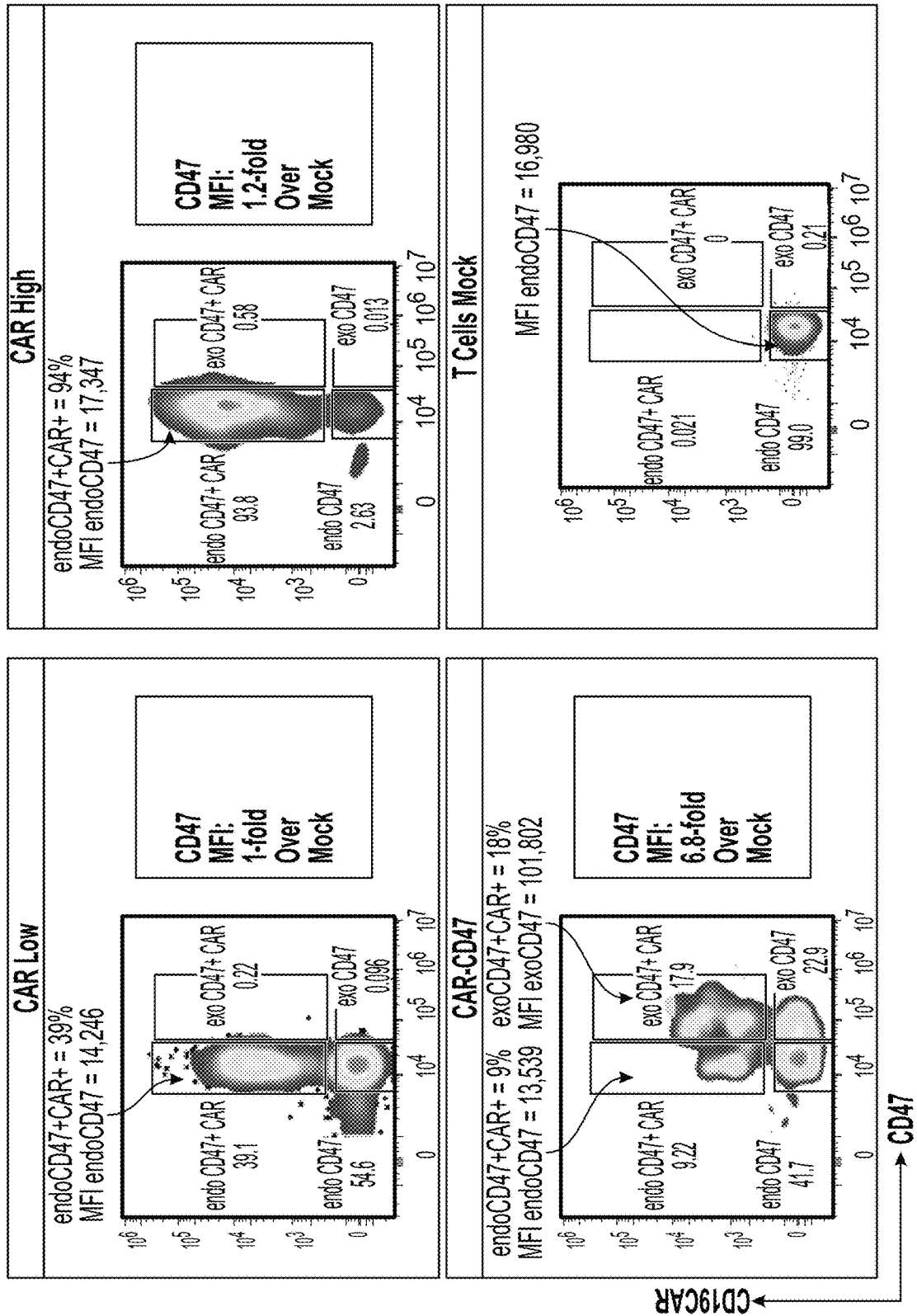
FIG. 4 shows the expression of the CD19-specific CAR and CD47 constructs in exemplary hypoimmunogenic CAR-T cells. The CD19-specific CAR-CD47 T cells expressed exogenous CD47 at high levels. As used herein, the term "CD19-specific CAR-CD47 T cell" refers to a T cell exogenously expressing a CD19-specific CAR and CD47.
Figure 6A:
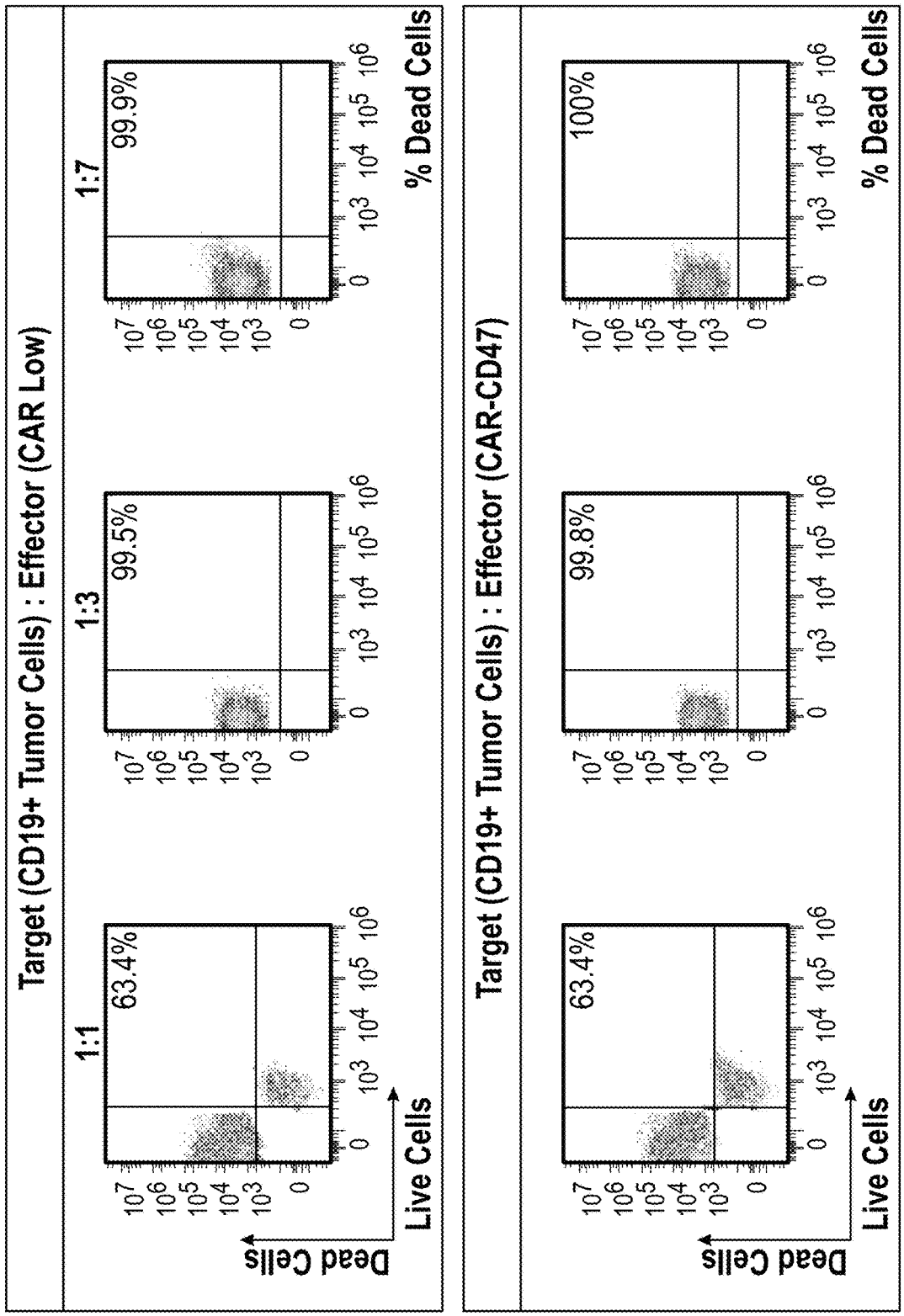
FIGS. 6A and 6B depict flow data confirming real-time cell analysis data showing killing of CD19+ tumor cells by exemplary hypoimmunogenic CAR-T cells (e.g., CD19-specific CAR-CD47 T cells) ("CAR low" (FIG. 6A) and "CAR high" (FIG. 6B) cells) in vitro in a dose-dependent manner. CD47 overexpression did not after CD19-specific CAR activity in in vitro assays.
Figure 6B:
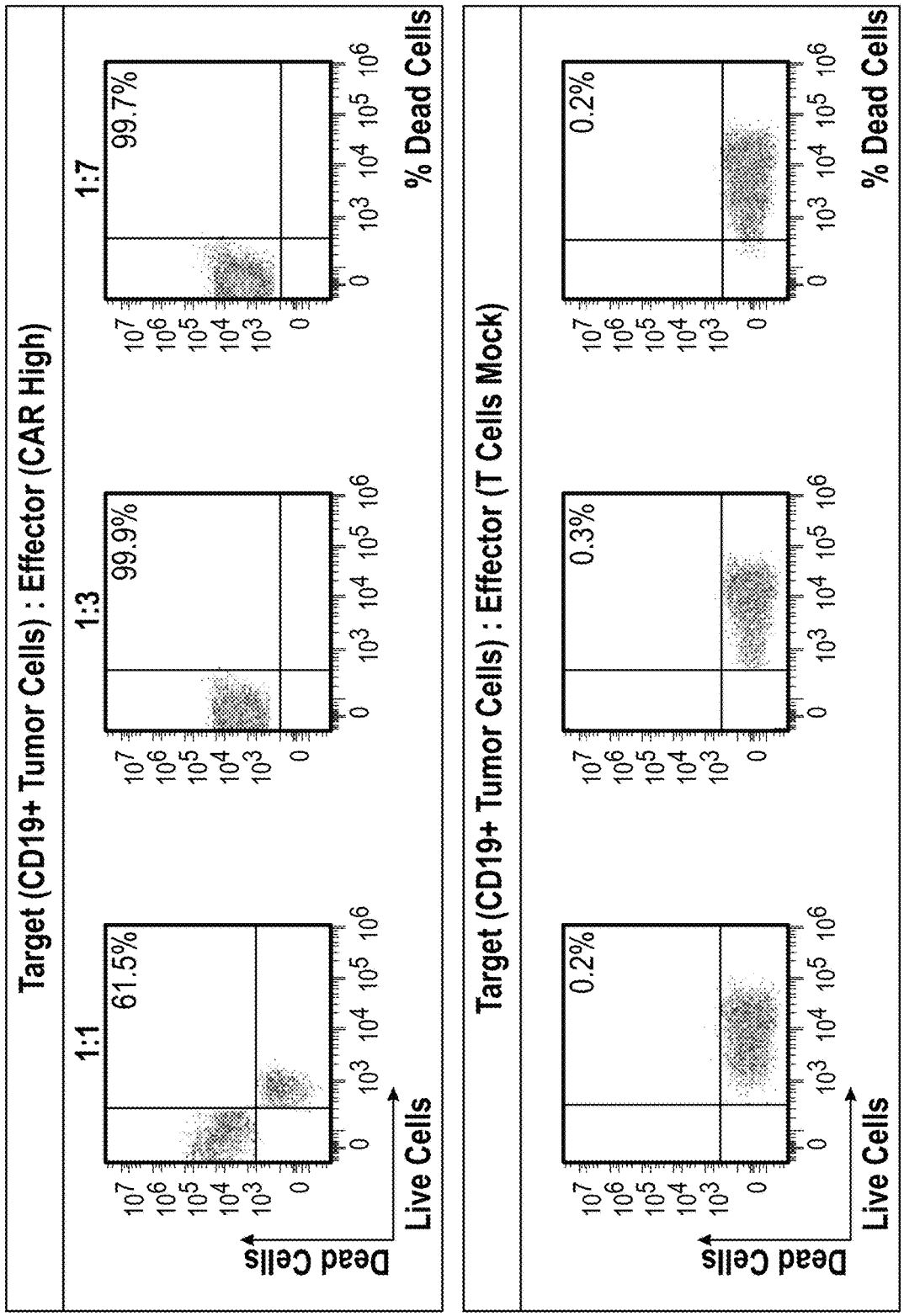
Figure 7:
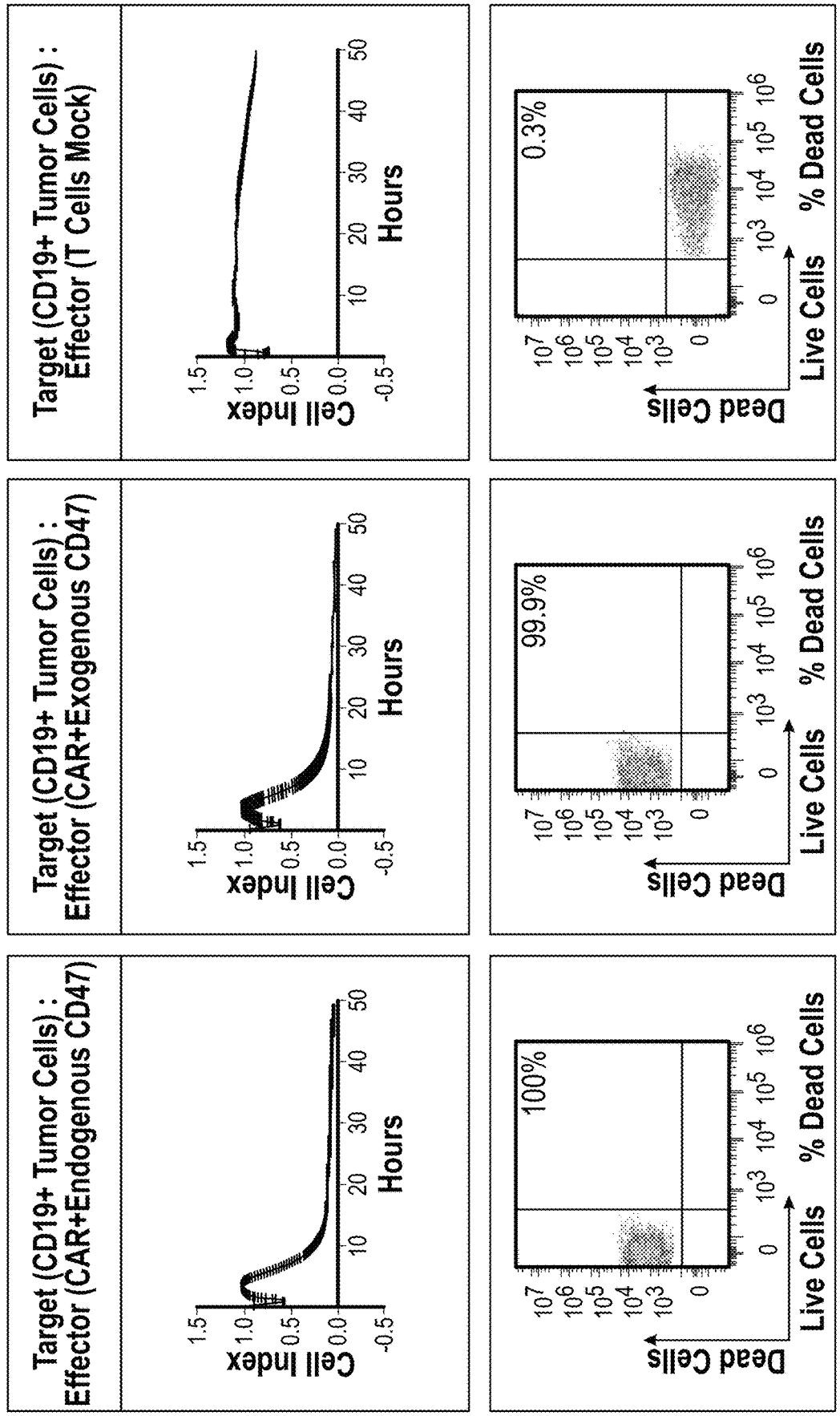
FIG. 7 shows killing of CD19+ tumor cells by exemplary hypoimmunogenic CAR-T cells (CD19-specific CAR-CD47 T cells) that were FACS sorted. The target cell:effector cell ratio was 1:3 and the killing was analyzed using a real-time, quantitative microelectronic biosensor system for cell analysis (xCELLigence® RTCA system, Agilent) for 48 hours and by flow cytometry. The data shows that CD19-specific CAR-T cells with endogenous CD47 expression killed the tumor cells. Also, CD19-specific CAR-T cells with exogenous CD47 expression killed the tumor cells. Control T cells (mock T cells) did not kill the tumor cells. CD47 overexpression does not appear to affect CD19-specific CAR activity in in vitro assays.
Figure 8:
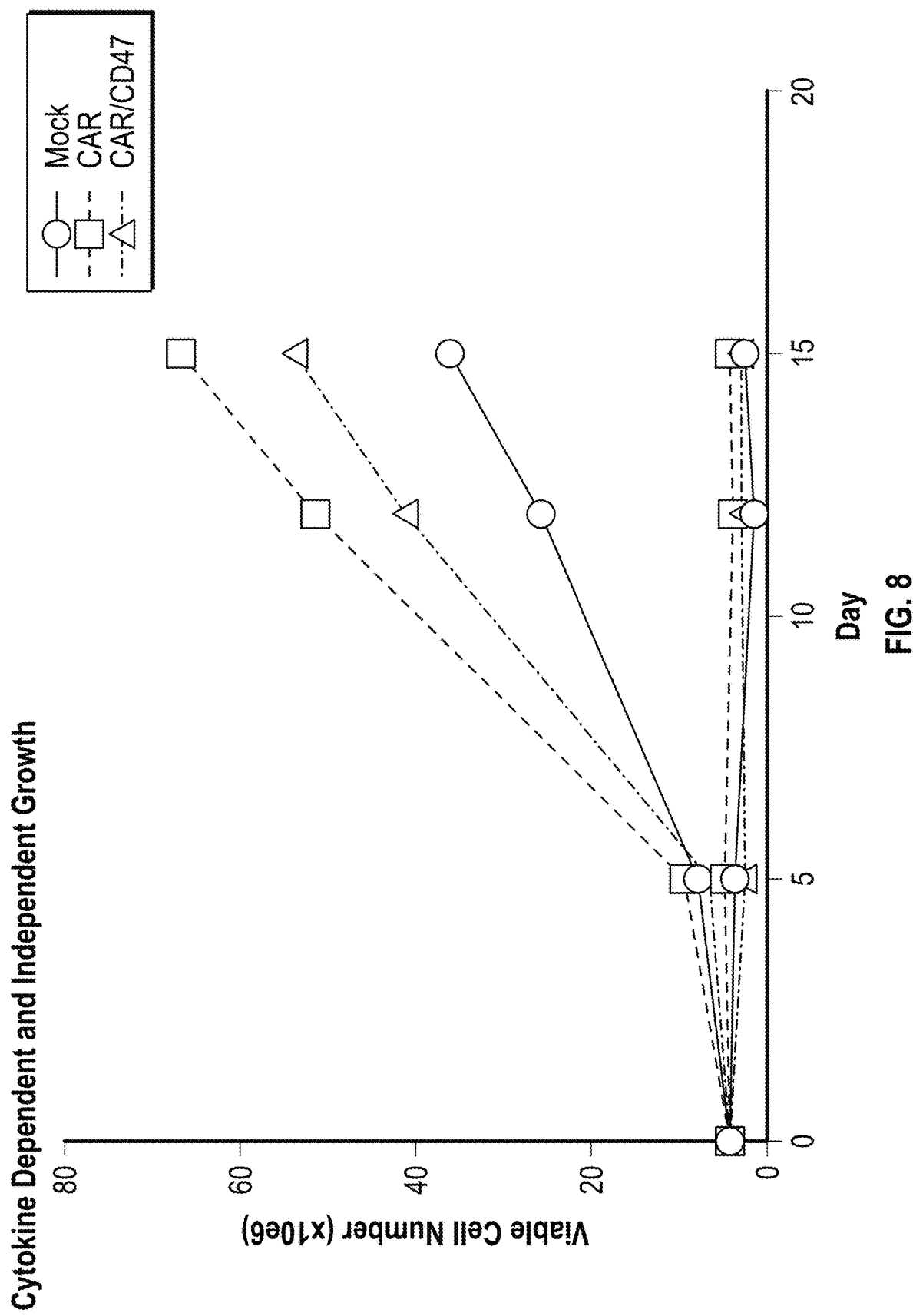
FIG. 8 shows the growth of the cells described herein, in particular, the CD47-dependent and CD47-independent growth of CD19-specific CAR-T cells and CD19-specific CAR-CD47 T cells.
Figure 9A:
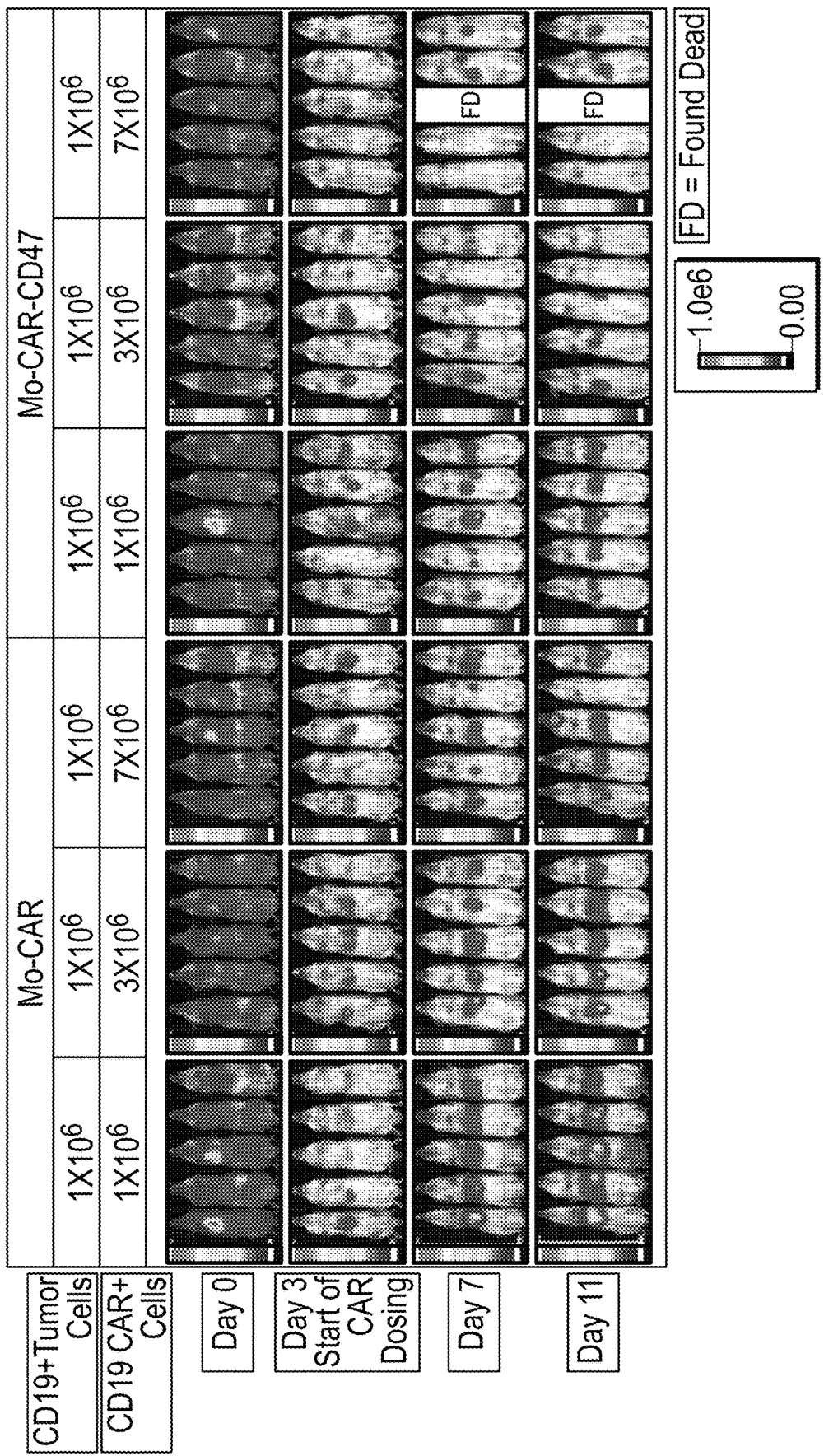
FIG. 9A-B show the efficacy of the exemplary hypoimmunogenic CAR-T cells in a mouse model with human CD19+ tumors. The whole animal scans show the effects of CD19-specific CAR-T cells, CD19-specific CAR-CD47 T cells, and mock T cells on CD19+ tumor cells.
Figure 9B:
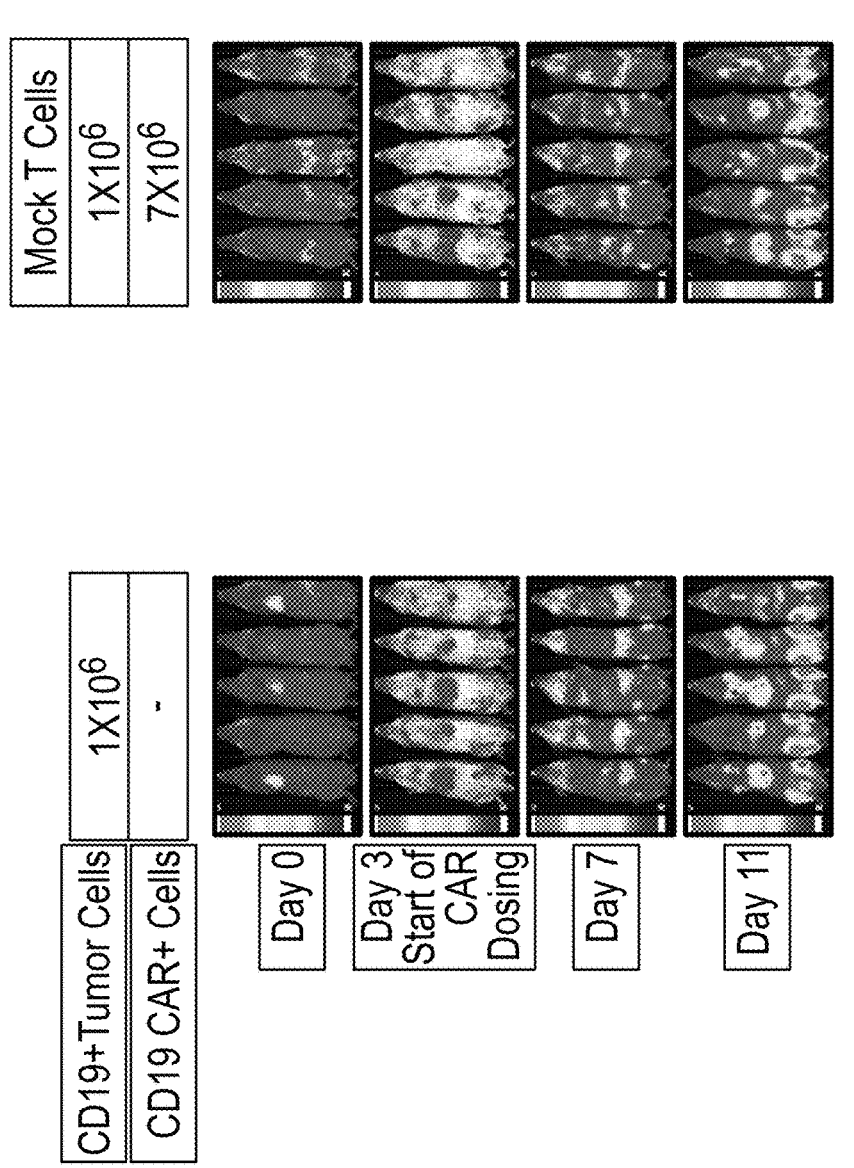
Figure 10:
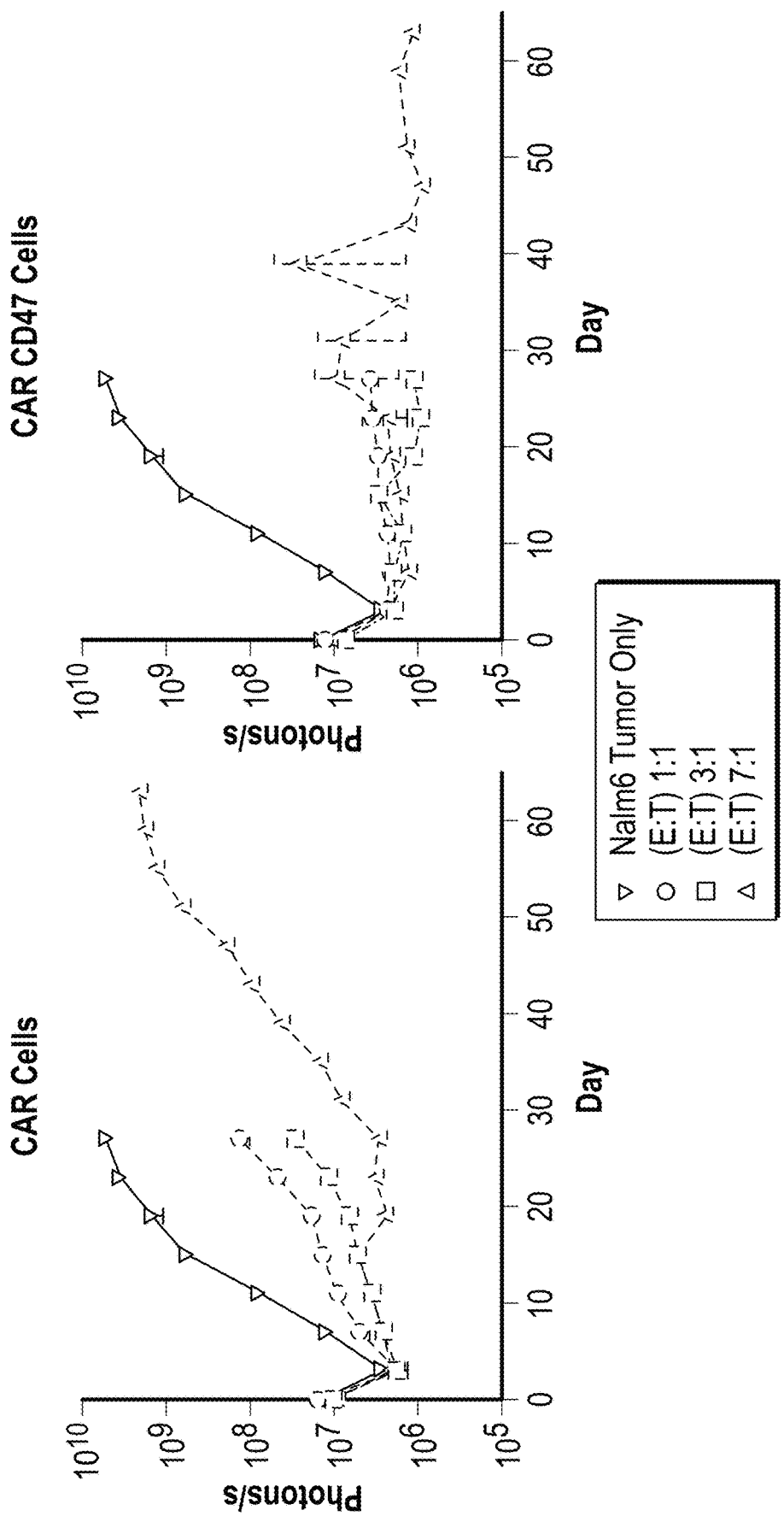
FIG. 10 shows the efficacy of the exemplary hypoimmunogenic CAR-T cells at various effector to Nalm6 target ratios.
Figure 11:
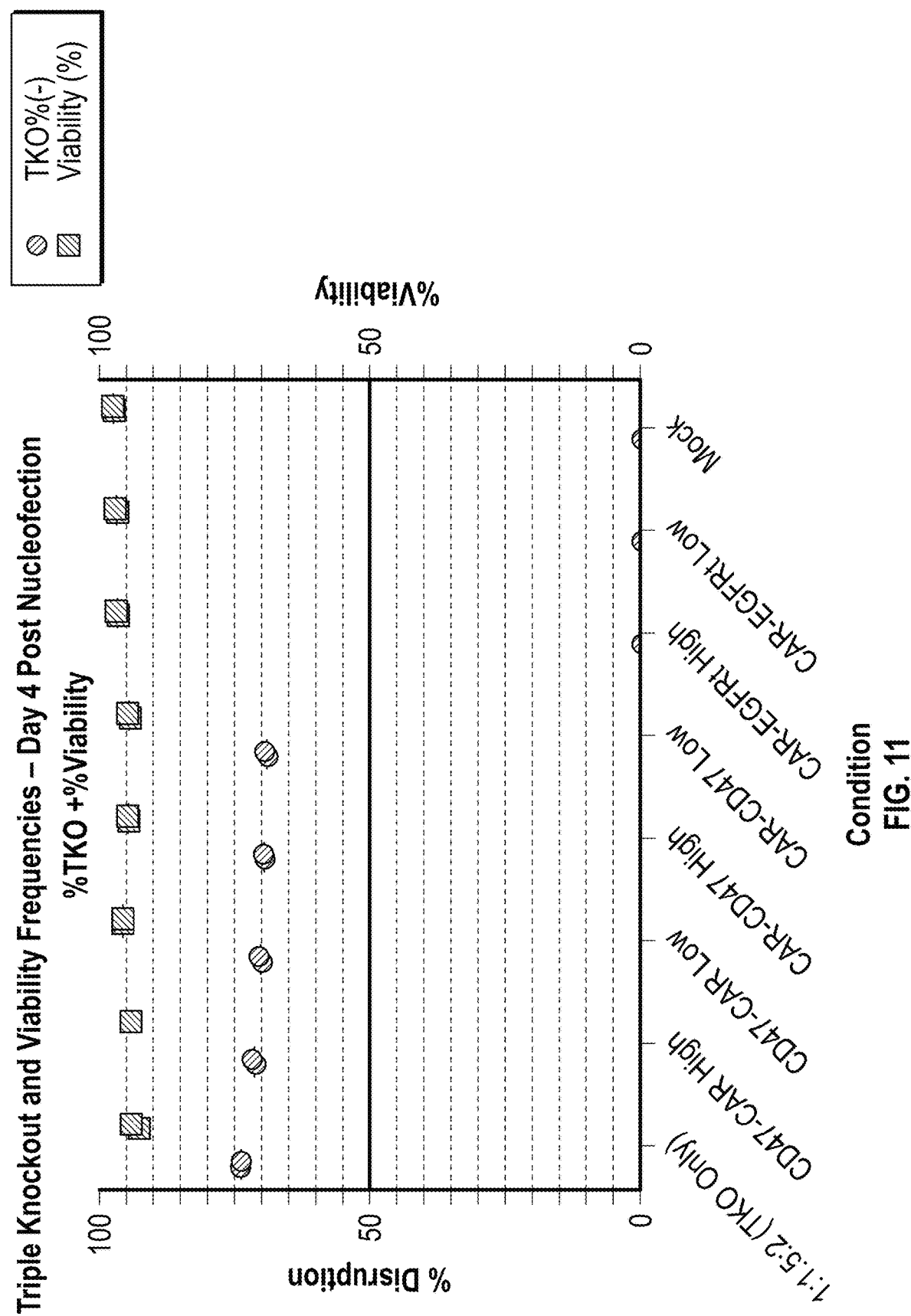
FIG. 11 depicts cell viability and the frequency of TRAC, B2M and CIITA triple knockouts in hypoimmunogenic CD19-specific CAR-CD47 T cells and control T cells (CD19-specific CAR-EGFRt T cells and mock T cells) four days after nucleofection to introduce a CRISPR/Cas9 based gene editing system into the CD19-specific CAR-T cells and CD19-specific CAR-CD47 T cells.
Figure 12A:
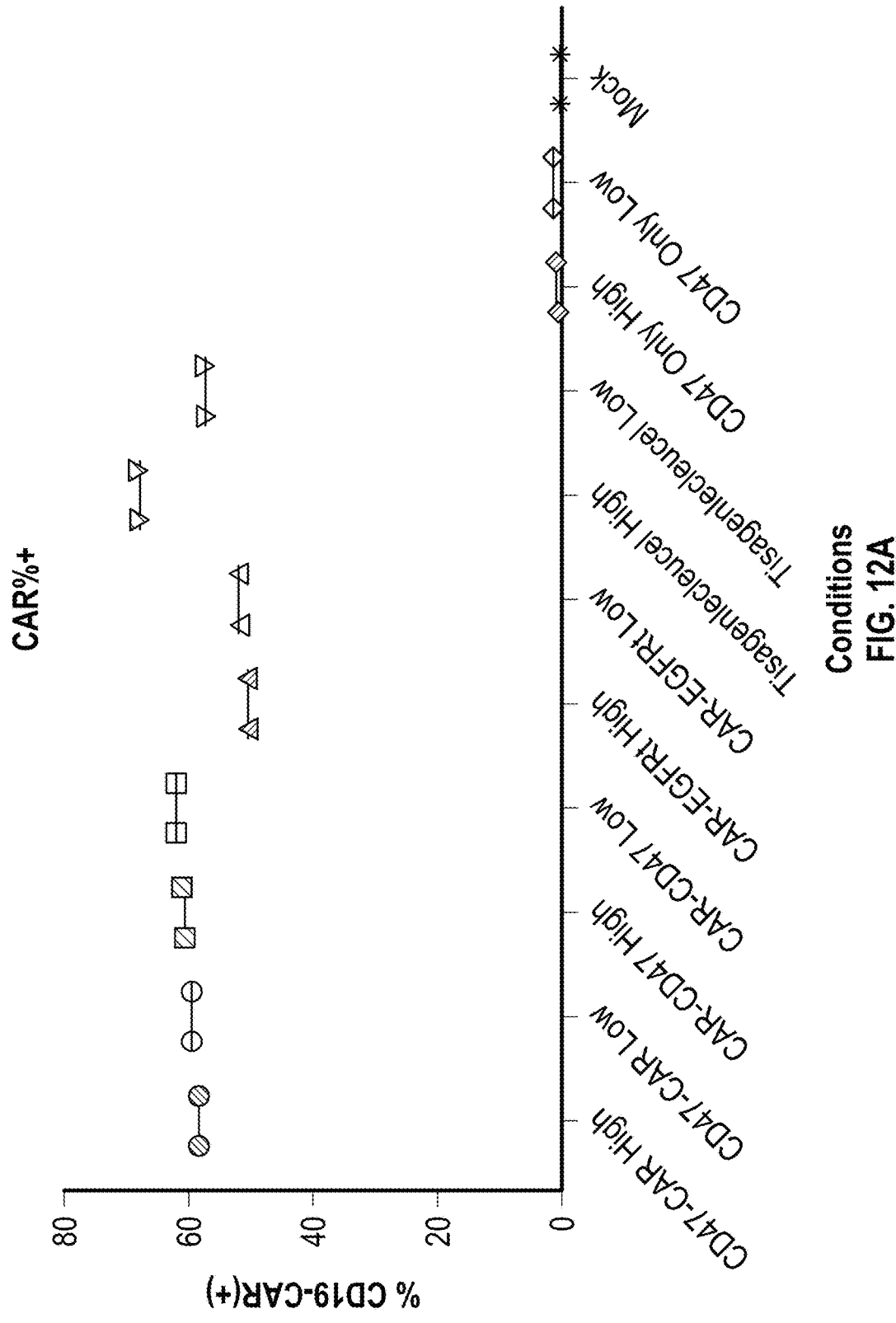
FIGS. 12A and 12B show the frequency (FIG. 12A) and MFI (FIG. 12B) of an exemplary CD19-specific CAR in hypoimmunogenic CD19-specific CAR-CD47 T cells and control T cells (CD19-specific CAR-EGFRt T cells, tisagenlecleucel biosimilar/surrogate cells, and mock T cells).
Figure 12B:
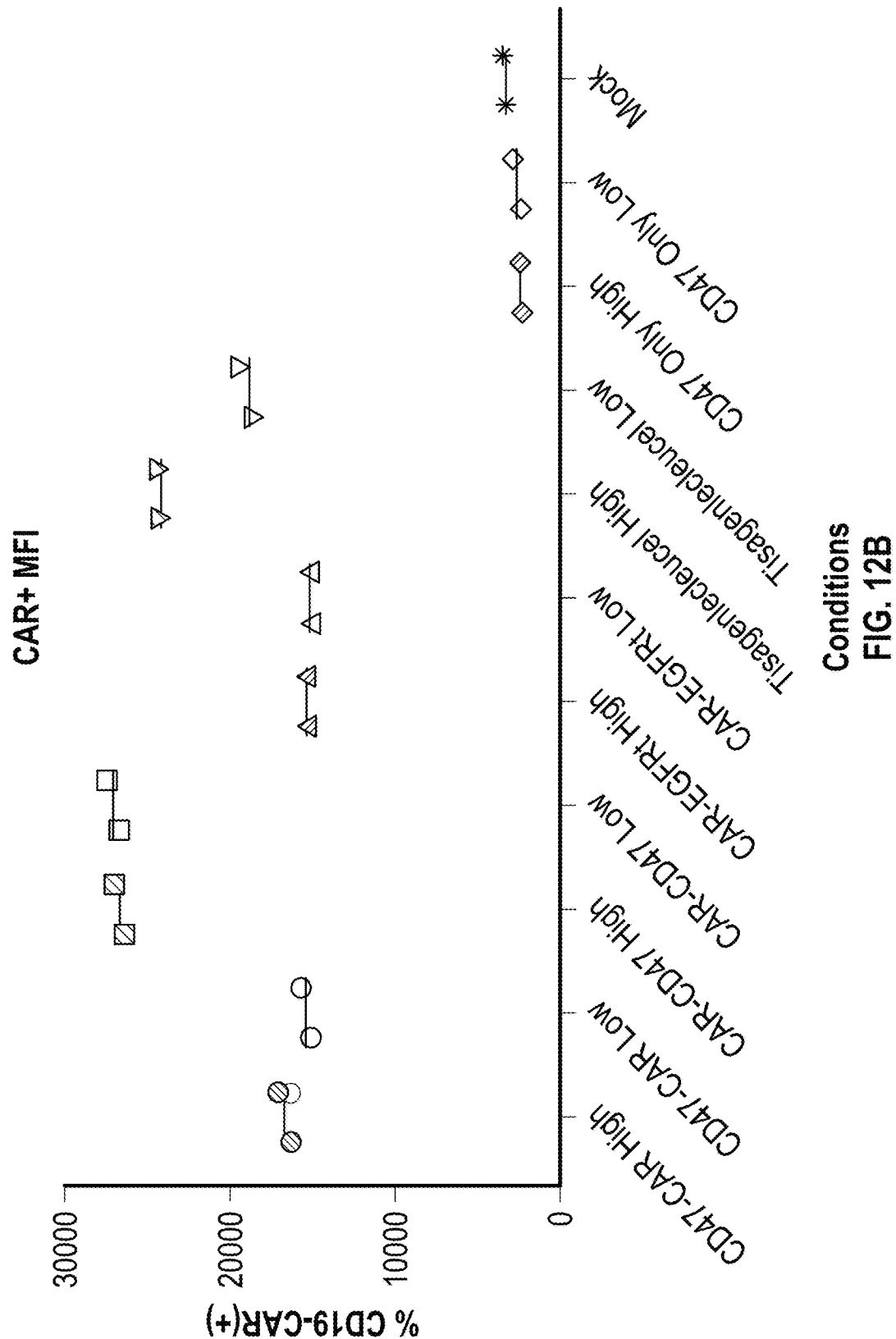

Other objects, advantages and embodiments of the present disclosure will be apparent from the detailed description following.

DETAILED DESCRIPTION

I. Introduction

Described herein are engineered or modified immune evasive cells based, in part, on the hypoimmune editing platform described in WO2018132783, including but not limited to human immune evasive cells. To overcome the problem of a subject's immune rejection of these primary and/or stem cell-derived transplants, the inventors have developed and describe herein hypoimmunogenic cells (e.g., hypoimmunogenic pluripotent cells, differentiated cells derived from such, and primary cells) that represent a viable source for any transplantable cell type. Such cells are protected from adaptive and/or innate immune rejection upon administration to a recipient subject. Advantageously, the cells disclosed herein are not rejected by the recipient subject's immune system, regardless of the subject's genetic make-up, as they are protected from adaptive and innate immune rejection upon administration to a recipient subject. In some embodiments, the engineered and/or hypoimmunogenic cells do not express major histocompatibility complex (MHC) class I and class II antigens and/or T-cell receptors. In certain embodiments, the engineered and/or hypoimmunogenic cells do not express MHC I and II antigens and/or T-cell receptors and overexpress CD47 proteins. In certain embodiments, the engineered and/or hypoimmunogenic cells such as engineered and/or hypoimmunogenic T cells do not express MHC I and II antigens and/or T-cell receptors, overexpress CD47 proteins and express exogenous CARs.

In some embodiments, hypoimmunogenic cells outlined herein are not subject to an innate immune cell rejection. In some instances, hypoimmunogenic cells are not susceptible to NK cell-mediated lysis. In some instances, hypoimmunogenic cells are not susceptible to macrophage engulfment. In some embodiments, hypoimmunogenic cells are useful as a source of universally compatible cells or tissues (e.g., universal donor cells or tissues) that are transplanted into a recipient subject with little to no immunosuppressant agent needed. Such hypoimmunogenic cells retain cell-specific characteristics and features upon transplantation, including, e.g., pluripotency, as well as being capable of engraftment and functioning similarly to a corresponding native cell.

The technology disclosed herein utilizes expression of tolerogenic factors and modulation (e.g., reduction or elimination) of MHC I, MHC II, and/or TCR expression in human cells. In some embodiments, genome editing technologies utilizing rare-cutting endonucleases (e.g., the CRISPR/Cas, TALEN, zinc finger nuclease, meganuclease, and homing endonuclease systems) are also used to reduce or eliminate expression of genes involved in an immune response (e.g., by deleting genomic DNA of genes involved in an immune response or by insertions of genomic DNA into such genes, such that gene expression is impacted) in the cells. In some embodiments, genome editing technologies or other gene modulation technologies are used to insert tolerance-inducing (tolerogenic) factors in human cells, rendering the cells and their progeny (include any differentiated cells prepared therefrom) able to evade immune recognition upon engrafting into a recipient subject. As such, the cells described herein exhibit modulated expression of one or more genes and factors that affect MHC I, MHC II, and/or TCR expression and evade the recipient subject's immune system.

The genome editing techniques enable double-strand DNA breaks at desired locus sites. These controlled double-strand breaks promote homologous recombination at the specific locus sites. This process focuses on targeting specific sequences of nucleic acid molecules, such as chromosomes, with endonucleases that recognize and bind to the sequences and induce a double-stranded break in the nucleic acid molecule. The double-strand break is repaired either by an error-prone non-homologous end-joining (NHEJ) or by homologous recombination (HR).

The practice of the numerous embodiments will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., Molecular Cloning: A Laboratory Manual (3rd Edition, 2001); Sambrook, et al., Molecular Cloning: A Laboratory Manual (2nd Edition, 1989); Maniatis et al., Molecular Cloning: A Laboratory Manual (1982); Ausubel et al., Current Protocols in Molecular Biology (John Wiley and Sons, updated July 2008); Short Protocols in Molecular Biology: A Compendium of Methods from Current Protocols in Molecular Biology, Greene Pub. Associates and Wiley-Interscience; Glover, DNA Cloning: A Practical Approach, vol. I & II (IRL Press, Oxford, 1985); Anand, Techniques for the Analysis of Complex Genomes, (Academic Press, New York, 1992); Transcription and Translation (B. Hames & S. Higgins, Eds., 1984); Perbal, A Practical Guide to Molecular Cloning (1984); Harlow and Lane, Antibodies, (Cold Spring Harbor Laboratory Press, Cold Spring Harbor, N.Y., 1998) Current Protocols in Immunology Q. E. Coligan, A. M. Kruisbeek, D. H. Margulies, E. M. Shevach and W. Strober, eds., 1991); Annual Review of Immunology; as well as monographs in journals such as Advances in Immunology.

II. Definitions

As described in the present disclosure, the following terms will be employed, and are defined as indicated below.

The term "autoimmune disease" refers to any disease or disorder in which the subject mounts an immune response against its own tissues and/or cells. Autoimmune disorders can affect almost every organ system in the subject (e.g., human), including, but not limited to, diseases of the nervous, gastrointestinal, and endocrine systems, as well as skin and other connective tissues, eyes, blood and blood vessels. Examples of autoimmune diseases include, but are not limited to Hashimoto's thyroiditis, Systemic lupus erythematosus, Sjogren's syndrome, Graves' disease, Scleroderma, Rheumatoid arthritis, Multiple sclerosis, Myasthenia gravis and Diabetes.

The term "cancer" as used herein is defined as a hyperproliferation of cells whose unique trait (e.g., loss of normal controls) results in unregulated growth, lack of differentiation, local tissue invasion, and metastasis. With respect to the inventive methods, the cancer can be any cancer, including any of acute lymphocytic cancer, acute myeloid leukemia, alveolar rhabdomyosarcoma, bladder cancer, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, Hodgkin lymphoma, hypopharynx cancer, kidney cancer, larynx cancer, leukemia, liquid tumors, liver cancer, lung cancer, lymphoma, malignant mesothelioma, mastocytoma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, stomach cancer, testicular cancer, thyroid cancer, ureter cancer, and/or urinary bladder cancer. As used herein, the term "tumor" refers to an abnormal growth of cells or tissues of the malignant type, unless otherwise specifically indicated and does not include a benign type tissue.

The term "chronic infectious disease" refers to a disease caused by an infectious agent wherein the infection has persisted. Such a disease may include hepatitis (A, B, or C), herpes virus (e.g., VZV, HSV-1, HSV-6, HSV-II, CMV, and EBV), and HIV/AIDS. Non-viral examples may include chronic fungal diseases such Aspergillosis, Candidiasis, Coccidioidomycosis, and diseases associated with *Cryptococcus* and Histoplasmosis. None limiting examples of chronic bacterial infectious agents may be *Chlamydia pneumoniae, Listeria monocytogenes*, and *Mycobacterium tuberculosis*. In some embodiments, the disorder is human immunodeficiency virus (HIV) infection. In some embodiments, the disorder is acquired immunodeficiency syndrome (AIDS).

As used herein, "clinically effective amount" refers to an amount sufficient to provide a clinical benefit in the treatment and/or management of a disease, disorder, or condition. In some embodiments, a clinically effective amount is an amount that has been shown to produce at least one improved clinical endpoint to the standard of care for the disease, disorder, or condition. In some embodiments, a clinically effective amount is an amount that has been demonstrated, for example in a clinical trial, to be sufficient to provide statistically significant and meaningful effectiveness for treating the disease, disorder, or condition. In some embodiments, the clinically effective amount is also a therapeutically effective amount. In other embodiments, the clinically effective amount is not a therapeutically effective amount.

In some embodiments, an alteration or modification (including, for example, genetic alterations or modifications) described herein results in reduced expression of a target or selected polynucleotide sequence. In some embodiments, an alteration or modification described herein results in reduced expression of a target or selected polypeptide sequence. In some embodiments, an alteration or modification described herein results in increased expression of a target or selected polynucleotide sequence. In some embodiments, an alteration or modification described herein results in increased expression of a target or selected polypeptide sequence.

In additional or alternative embodiments, the present disclosure contemplates altering target polynucleotide sequences in any manner which is available to the skilled artisan, e.g., utilizing a TALEN system or RNA-guided transposases. It should be understood that although examples of methods utilizing CRISPR/Cas (e.g., Cas9 and Cas12a) and TALEN are described in detail herein, the present disclosure is not limited to the use of these methods/systems. Other methods of targeting, e.g., B2M, to reduce or ablate expression in target cells known to the skilled artisan can be utilized herein.

The terms "decrease," "reduced," "reduction," and "decrease" are all used herein generally to mean a decrease by a statistically significant amount. However, for avoidance of doubt, "decrease," "reduced," "reduction," "decrease" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level. In some embodiments, the cells are engineered to have reduced expression of one or more targets relative to an unaltered or unmodified wild-type cell.

In some embodiments, the engineered and hypoimmunogenic cells described are derived from an iPSC or a progeny thereof. As used herein, the term "derived from an iPSC or a progeny thereof" encompasses the initial iPSC that is generated and any subsequent progeny thereof. As used herein, the term "progeny" encompasses, e.g., a first-generation progeny, i.e., the progeny is directly derived from, obtained from, obtainable from or derivable from the initial iPSC by, e.g., traditional propagation methods. The term "progeny" also encompasses further generations such as second, third, fourth, fifth, sixth, seventh, or more generations, i.e., generations of cells which are derived from, obtained from, obtainable from or derivable from the former generation by, e.g., traditional propagation methods. The term "progeny" also encompasses modified cells that result from the modification or alteration of the initial iPSC or a progeny thereof.

The term "donor subject" refers to an animal, for example, a human from whom cells can be obtained. The "non-human animals" and "non-human mammals" as used interchangeably herein, includes mammals such as rats, mice, rabbits, sheep, cats, dogs, cows, pigs, and non-human primates. The term "donor subject" also encompasses any vertebrate including but not limited to mammals, reptiles, amphibians and fish. However, advantageously, the donor subject is a mammal such as a human, or other mammals such as a domesticated mammal, e.g., dog, cat, horse, and the like, or production mammal, e.g., cow, sheep, pig, and the like. A "donor subject" can also refer to more than one donor, for example one or more humans or non-human animals or non-human mammals.

The term "endogenous" refers to a referenced molecule or polypeptide that is naturally present in the cell. Similarly, the term when used in reference to expression of an encoding nucleic acid refers to expression of an encoding nucleic acid naturally contained within the cell and not exogenously introduced. Similarly, the term when used in reference to a promoter sequence refers to a promoter sequence naturally contained within the cell and not exogenously introduced.

The term "engineered cell" as used herein refers to a cell that has been altered in at least some way by human intervention, including, for example, by genetic alterations or modifications such that the engineered cell differs from a wild-type cell.

As used herein, the term "exogenous" in the context of a polynucleotide or polypeptide being expressed is intended to mean that the referenced molecule or the referenced polypeptide is introduced into the cell of interest. The polypeptide can be introduced, for example, by introduction of an encoding nucleic acid into the genetic material of the cells such as by integration into a chromosome or as non-chromosomal genetic material such as a plasmid or expression vector. Therefore, the term as it is used in reference to expression of an encoding nucleic acid refers to introduction of the encoding nucleic acid in an expressible form into the cell. An exogenous polynucleotide can be inserted into at least one allele of the cell using viral transduction, for example, with a vector. In some embodiments, the vector is a pseudotyped, self-inactivating lentiviral vector that carries exogenous polynucleotide. In some embodiments, the vector is a self-inactivating lentiviral vector pseudotyped with a vesicular stomatitis VSV-G envelope, and which carries the exogenous polynucleotide. In some embodiments, the exogenous polynucleotide is inserted into at least one allele of the cell using viral transduction. In some embodiments, exogenous polynucleotide is inserted into at least one allele of the cell using a lentivirus based viral vector. In some embodiments, the exogenous polynucleotide is inserted into a safe harbor or target locus of at least one allele of the cell.

An "exogenous" molecule is a molecule, construct, factor and the like that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of neurons is an exogenous molecule with respect to an adult neuron cell. An exogenous molecule can comprise, for example, a functioning version of a malfunctioning endogenous molecule or a malfunctioning version of a normally-functioning endogenous molecule.

An exogenous molecule or factor can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule or construct can be the same type of molecule as an endogenous molecule, e.g., an exogenous protein or nucleic acid. In such instances, the exogenous molecule is introduced into the cell at greater concentrations than that of the endogenous molecule in the cell. In some instances, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

A "gene," for the purposes of the present disclosure, includes a DNA region encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and/or locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristoylation, and/or glycosylation.

The term "genetic modification" and its grammatical equivalents as used herein can refer to one or more alterations of a nucleic acid, e.g., the nucleic acid within an organism's genome. For example, genetic modification can refer to alterations, additions, and/or deletion of genes or portions of genes or other nucleic acid sequences. A genetically modified cell can also refer to a cell with an added, deleted and/or altered gene or portion of a gene. A genetically modified cell can also refer to a cell with an added nucleic acid sequence that is not a gene or gene portion. Genetic modifications include, for example, both transient knock-in or knock-down mechanisms, and mechanisms that result in permanent knock-in, knock-down, or knock-out of target genes or portions of genes or nucleic acid sequences Genetic modifications include, for example, both transient knock-in and mechanisms that result in permanent knock-in of nucleic acids sequences Genetic modifications also include, for example, reduced or increased transcription, reduced or increased mRNA stability, reduced or increased translation, and reduced or increased protein stability.

As used herein, the terms "grafting", "administering," "introducing", "implanting" and "transplanting" as well as grammatical variations thereof are used interchangeably in the context of the placement of cells (e.g., cells described herein) into a subject, by a method or route which results in localization or at least partial localization of the introduced cells at a desired site or systemic introduction (e.g., into circulation). The cells can be implanted directly to the desired site, or alternatively be administered by any appropriate route which results in delivery to a desired location in the subject where at least a portion of the implanted cells or components of the cells remain viable. The period of viability of the cells after administration to a subject can be as short as a few hours, e.g. twenty-four hours, to a few days, to as long as several years. In some embodiments, the cells can also be administered (e.g., injected) a location other than the desired site, such as in the brain or subcutaneously, for example, in a capsule to maintain the implanted cells at the implant location and avoid migration of the implanted cells.

By "HLA" or "human leukocyte antigen" complex is a gene complex encoding the MHC proteins in humans. These cell-surface proteins that make up the HLA complex are responsible for the regulation of the immune response to antigens. In humans, there are two MHCs, class I and class II, "HLA-I" and "HLA-II". HLA-I includes three proteins, HLA-A, HLA-B and HLA-C, which present peptides from the inside of the cell, and antigens presented by the HLA-I complex attract killer T-cells (also known as CD8+ T-cells or cytotoxic T cells). The HLA-I proteins are associated with 3-2 microglobulin (B2M). HLA-II includes five proteins, HLA-DP, HLA-DM, HLA-DOB, HLA-DQ and HLA-DR, which present antigens from outside the cell to T lymphocytes. This stimulates CD4+ cells (also known as T-helper cells). It should be understood that the use of either "MHC" or "HLA" is not meant to be limiting, as it depends on whether the genes are from humans (HLA) or murine (MHC). Thus, as it relates to mammalian cells, these terms may be used interchangeably herein.

As used herein to characterize a cell, the term "hypoimmunogenic" generally means that such cell is less prone to innate or adaptive immune rejection by a subject into which such cells are transplanted, e.g., the cell is less prone to allorejection by a subject into which such cells are transplanted. For example, relative to a cell of the same cell type that does not comprise the modifications, such a hypoimmunogenic cell may be about 2.5%, 5%, 10%, 20%, 30%, 40%, 50%, 60%, 70%, 80%, 90%, 95%, 97.5%, 99% or more less prone to innate or adaptive immune rejection by a subject into which such cells are transplanted. In some embodiments, genome editing technologies are used to modulate the expression of MHC I and MHC II genes, and thus, contribute to generation of a hypoimmunogenic cell. In some embodiments, a hypoimmunogenic cell evades immune rejection in an MHC-mismatched allogeneic recipient. In some instance, differentiated cells produced from the hypoimmunogenic stem cells outlined herein evade immune rejection when administered (e.g., transplanted or grafted) to an MHC-mismatched allogeneic recipient. In some embodiments, a hypoimmunogenic cell is protected from T cell-mediated adaptive immune rejection and/or innate immune cell rejection. Detailed descriptions of hypoimmunogenic cells, methods of producing thereof, and methods of using thereof are found in WO2016183041 filed May 9, 2015; WO2018132783 filed Jan. 14, 2018; WO2018176390 filed Mar. 20, 2018; WO2020018615 filed Jul. 17, 2019; WO2020018620 filed Jul. 17, 2019; PCT/US2020/44635 filed Jul. 31, 2020; U.S. 62/881,840 filed Aug. 1, 2019; U.S. 62/891,180 filed Aug. 23, 2019; U.S. 63/016,190, filed Apr. 27, 2020; and U.S. 63/052,360 filed Jul. 15, 2020, the disclosures including the examples, sequence listings and figures are incorporated herein by reference in their entirety.

Hypoimmunogenicity of a cell can be determined by evaluating the immunogenicity of the cell such as the cell's ability to elicit adaptive and innate immune responses or to avoid eliciting such adaptive and innate immune responses. Such immune response can be measured using assays recognized by those skilled in the art. In some embodiments, an immune response assay measures the effect of a hypoimmunogenic cell on T cell proliferation, T cell activation, T cell killing, donor specific antibody generation, NK cell proliferation, NK cell activation, and macrophage activity. In some cases, hypoimmunogenic cells and derivatives thereof undergo decreased killing by T cells and/or NK cells upon administration to a subject. In some instances, the cells and derivatives thereof show decreased macrophage engulfment compared to an unmodified or wild-type cell. In some embodiments, a hypoimmunogenic cell elicits a reduced or diminished immune response in a recipient subject compared to a corresponding unmodified wild-type cell. In some embodiments, a hypoimmunogenic cell is nonimmunogenic or fails to elicit an immune response in a recipient subject.

The term percent "identity," in the context of two or more nucleic acid or polypeptide sequences, refers to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information.

"Immune signaling factor" as used herein refers to, in some cases, a molecule, protein, peptide and the like that activates immune signaling pathways.

"Immunosuppressive factor" or "immune regulatory factor" or "tolerogenic factor" as used herein include hypoimmunity factors, complement inhibitors, and other factors that modulate or affect the ability of a cell to be recognized by the immune system of a host or recipient subject upon administration, transplantation, or engraftment. These may be in combination with additional genetic modifications.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In some embodiments, the reference level, also referred to as the basal level, is 0.

In some embodiments, the alteration is an indel. As used herein, "indel" refers to a mutation resulting from an insertion, deletion, or a combination thereof. As will be appreciated by those skilled in the art, an indel in a coding region of a genomic sequence will result in a frameshift mutation, unless the length of the indel is a multiple of three. In some embodiments, the alteration is a point mutation. As used herein, "point mutation" refers to a substitution that replaces one of the nucleotides. A gene editing (e.g., CRISPR/Cas) system of the present disclosure can be used to induce an indel of any length or a point mutation in a target polynucleotide sequence.

As used herein, "knock down" refers to a reduction in expression of the target mRNA or the corresponding target protein. Knock down is commonly reported relative to levels present following administration or expression of a noncontrol molecule that does not mediate reduction in expression levels of RNA (e.g., a non-targeting control shRNA, siRNA, or miRNA). In some embodiments, knock down of a target gene is achieved by way of conditional or inducible shRNAs, conditional or inducible siRNAs, conditional or inducible miRNAs, or conditional or inducible CRISPR interference (CRISPRi). In some embodiments, knock down of a target gene is achieved by way of a protein-based method, such as a conditional or inducible degron method. In some embodiments, knock down of a target gene is achieved by genetic modification, including shRNAs, siRNAs, miRNAs, or use of gene editing systems (e.g., CRISPR/Cas).

Knock down is commonly assessed by measuring the mRNA levels using quantitative polymerase chain reaction (qPCR) amplification or by measuring protein levels by western blot or enzyme-linked immunosorbent assay (ELISA). Analyzing the protein level provides an assessment of both mRNA cleavage as well as translation inhibition. Further techniques for measuring knock down include RNA solution hybridization, nuclease protection, northern hybridization, gene expression monitoring with a microarray, antibody binding, radioimmunoassay, and fluorescence activated cell analysis. Those skilled in the art will readily appreciate how to use the gene editing systems (e.g., CRISPR/Cas) of the present disclosure to knock out a target polynucleotide sequence or a portion thereof based upon the details described herein.

By "knock in" or "knock-in" herein is meant a genetic modification resulting from the insertion of a DNA sequence into a chromosomal locus in a host cell. This causes initiation of or increased levels of expression of the knocked in gene, portion of gene, or nucleic acid sequence inserted product, e.g., an increase in RNA transcript levels and/or encoded protein levels. As will be appreciated by those in the art, this can be accomplished in several ways, including inserting or adding one or more additional copies of the gene or portion thereof to the host cell or altering a regulatory component of the endogenous gene increasing expression of the protein is made or inserting a specific nucleic acid sequence whose expression is desired. This may be accomplished by modifying a promoter, adding a different promoter, adding an enhancer, adding other regulatory elements, or modifying other gene expression sequences.

As used herein, "knock out" or "knock-out" includes deleting all or a portion of a target polynucleotide sequence in a way that interferes with the translation or function of the target polynucleotide sequence. For example, a knock out can be achieved by altering a target polynucleotide sequence by inducing an insertion or a deletion ("indel") in the target polynucleotide sequence, including in a functional domain of the target polynucleotide sequence (e.g., a DNA binding domain). Those skilled in the art will readily appreciate how to use the gene editing systems (e.g., CRISPR/Cas) of the present disclosure to knock out a target polynucleotide sequence or a portion thereof based upon the details described herein.

In some embodiments, a genetic modification or alteration results in a knock out or knock down of the target polynucleotide sequence or a portion thereof. Knocking out a target polynucleotide sequence or a portion thereof using a gene editing system (e.g., CRISPR/Cas) of the present disclosure can be useful for a variety of applications. For example, knocking out a target polynucleotide sequence in a cell can be performed in vitro for research purposes. For ex vivo purposes, knocking out a target polynucleotide sequence in a cell can be useful for treating or preventing a disorder associated with expression of the target polynucleotide sequence (e.g., by knocking out a mutant allele in a cell ex vivo and introducing those cells comprising the knocked out mutant allele into a subject) or for changing the genotype or phenotype of a cell.

"Modulation" of gene expression refers to a change in the expression level of a gene. Modulation of expression can include, but is not limited to, gene activation and gene repression. Modulation may also be complete, i.e., wherein gene expression is totally inactivated or is activated to wild-type levels or beyond; or it may be partial, wherein gene expression is partially reduced, or partially activated to some fraction of wild-type levels.

In additional or alternative aspects, the present disclosure contemplates altering target polynucleotide sequences in any manner which is available to the skilled artisan, e.g., utilizing a nuclease system such as a TAL effector nuclease (TALEN) or zinc finger nuclease (ZFN) system. It should be understood that although examples of methods utilizing CRISPR/Cas (e.g., Cas9 and Cas12a) and TALEN are described in detail herein, the disclosure is not limited to the use of these methods/systems. Other methods of targeting to reduce or ablate expression in target cells known to the skilled artisan can be utilized herein. The methods provided herein can be used to alter a target polynucleotide sequence in a cell. The present disclosure contemplates altering target polynucleotide sequences in a cell for any purpose. In some embodiments, the target polynucleotide sequence in a cell is altered to produce a mutant cell. As used herein, a "mutant cell" refers to a cell with a resulting genotype that differs from its original genotype. In some instances, a "mutant cell" exhibits a mutant phenotype, for example when a normally functioning gene is altered using the gene editing systems (e.g., CRISPR/Cas) systems of the present disclosure. In other instances, a "mutant cell" exhibits a wild-type phenotype, for example when a gene editing system (e.g., CRISPR/Cas) system of the present disclosure is used to correct a mutant genotype. In some embodiments, the target polynucleotide sequence in a cell is altered to correct or repair a genetic mutation (e.g., to restore a normal phenotype to the cell). In some embodiments, the target polynucleotide sequence in a cell is altered to induce a genetic mutation (e.g., to disrupt the function of a gene or genomic element).

The term "native cell" as used herein refers to a cell that is not otherwise modified (e.g., engineered). In some embodiments, a native cell is a naturally occurring wild-type or a control cell.

The term "operatively linked" or "operably linked" are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

"Pluripotent stem cells" as used herein have the potential to differentiate into any of the three germ layers: endoderm (e.g., the stomach linking, gastrointestinal tract, lungs, etc.), mesoderm (e.g., muscle, bone, blood, urogenital tissue, etc.) or ectoderm (e.g., epidermal tissues and nervous system tissues). The term "pluripotent stem cells," as used herein, also encompasses "induced pluripotent stem cells", or "iPSCs", or a type of pluripotent stem cell derived from a non-pluripotent cell. In some embodiments, a pluripotent stem cell is produced or generated from a cell that is not a pluripotent cell. In other words, pluripotent stem cells can be direct or indirect progeny of a non-pluripotent cell. Examples of parent cells include somatic cells that have been reprogrammed to induce a pluripotent, undifferentiated phenotype by various means. Such "iPS" or "iPSC" cells can be created by inducing the expression of certain regulatory genes or by the exogenous application of certain proteins. Methods for the induction of iPS cells are known in the art and are further described below. (See, e.g., Zhou et al., Stem Cells 27 (11): 2667-74 (2009); Huangfu et al., Nature Biotechnol. 26 (7): 795 (2008); Woltjen et al., Nature 458 (7239): 766-770 (2009); and Zhou et al., Cell Stem Cell 8:381-384 (2009); each of which is incorporated by reference herein in their entirety.) The generation of induced pluripotent stem cells (iPSCs) is outlined below. As used herein, "hiPSCs" are human induced pluripotent stem cells. In some embodiments, "pluripotent stem cells," as used herein, also encompasses mesenchymal stem cells (MSCs), and/or embryonic stem cells (ESCs).

As used herein, "promoter," "promoter sequence," or "promoter region" refers to a DNA regulatory region/sequence capable of binding RNA polymerase and involved in initiating transcription of a downstream coding or noncoding sequence. In some examples, the promoter sequence includes the transcription initiation site and extends upstream to include the minimum number of bases or elements necessary to initiate transcription at levels detectable above background. In some embodiments, the promoter sequence includes a transcription initiation site, as well as protein binding domains responsible for the binding of RNA polymerase. Eukaryotic promoters will often, but not always, contain "TATA" boxes and "CAT" boxes.

In some embodiments, the engineered and hypoimmunogenic cells described are propagated from a primary T cell or a progeny thereof. As used herein, the term "propagated from a primary T cell or a progeny thereof" encompasses the initial primary T cell that is isolated from the donor subject and any subsequent progeny thereof. As used herein, the term "progeny" encompasses, e.g., a first-generation progeny, i.e., the progeny is directly derived from, obtained from, obtainable from or derivable from the initial primary T cell by, e.g., traditional propagation methods. The term "progeny" also encompasses further generations such as second, third, fourth, fifth, sixth, seventh, or more generations, i.e., generations of cells which are derived from, obtained from, obtainable from or derivable from the former generation by, e.g., traditional propagation methods. The term "progeny" also encompasses modified cells that result from the modification or alteration of the initial primary T cell or a progeny thereof.

The term "recipient patient" refers to an animal, for example, a human to whom treatment, including prophylactic treatment, with the cells as described herein, is provided. For treatment of those infections, conditions or disease states, which are specific for a specific animal such as a human patient, the term patient refers to that specific animal. The term "recipient patient" also encompasses any vertebrate including but not limited to mammals, reptiles, amphibians and fish. However, advantageously, the recipient patient is a mammal such as a human, or other mammals such as a domesticated mammal, e.g., dog, cat, horse, and the like, or production mammal, e.g., cow, sheep, pig, and the like.

As used herein, the terms "regulatory sequences," "regulatory elements," and "control elements" are interchangeable and refer to polynucleotide sequences that are upstream (5' non-coding sequences), within, or downstream (3' non-translated sequences) of a polynucleotide target to be expressed. Regulatory sequences influence, for example but are not limited to, the timing of transcription, amount or level of transcription, RNA processing or stability, and/or translation of the related structural nucleotide sequence. Regulatory sequences may include activator binding sequences, enhancers, introns, polyadenylation recognition sequences, promoters, repressor binding sequences, stem-loop structures, translational initiation sequences, translation leader sequences, transcription termination sequences, translation termination sequences, primer binding sites, and the like. It is recognized that since in most cases the exact boundaries of regulatory sequences have not been completely defined, nucleotide sequences of different lengths may have identical regulatory or promoter activity.

"Safe harbor locus" as used herein refers to a gene locus that allows expression of a transgene or an exogenous gene in a manner that enables the newly inserted genetic elements to function predictably and that also may not cause alterations of the host genome in a manner that poses a risk to the host cell. Exemplary "safe harbor" loci include, but are not limited to, a CCR5 gene, a PPP1R12C (also known as AAVS1) gene, a CLYBL gene, and/or a Rosa gene (e.g., ROSA26).

"Target locus" as used herein refers to a gene locus that allows expression of a transgene or an exogenous gene. Exemplary "target loci" include, but are not limited to, a CXCR4 gene, an albumin gene, a SHS231 locus, an F3 gene (also known as CD142), a MICA gene, a MICB gene, a LRP1 gene (also known as CD91), a HMGB1 gene, an ABO gene, a RHD gene, a FUT1 gene, and/or a KDM5D gene (also known as HY). The exogenous polynucleotide encoding the exogenous gene can be inserted in the CDS region for B2M, CIITA, TRAC, TRBC, CCR5, F3 (i.e., CD142), MICA, MICB, LRP1, HMGB1, ABO, RHD, FUT1, KDM5D (i.e., HY), PDGFRa, OLIG2, and/or GFAP. The exogenous polynucleotide encoding the exogenous gene can be inserted in introns 1 or 2 for PPP1R12C (i.e., AAVS1) or CCR5. The exogenous polynucleotide encoding the exogenous gene can be inserted in exons 1 or 2 or 3 for CCR5. The exogenous polynucleotide encoding the exogenous gene can be inserted in intron 2 for CLYBL. The exogenous polynucleotide encoding the exogenous gene can be inserted in a 500 bp window in Ch-4:58,976,613 (i.e., SHS231). The exogenous polynucleotide encoding the exogenous gene can be insert in any suitable region of the aforementioned safe harbor or target loci that allows for expression of the exogenous gene, including, for example, an intron, an exon or a coding sequence region in a safe harbor or target locus.

As used herein, a "target" can refer to a gene, a portion of a gene, a portion of the genome, or a protein that is subject to regulatable reduced expression by the methods described herein.

As used herein, "therapeutically effective amount" refers to an amount sufficient to provide a therapeutic benefit in the treatment and/or management of a disease, disorder, or condition. In some embodiments, a therapeutically effective amount is an amount sufficient to ameliorate, palliate, stabilize, reverse, slow, attenuate or delay the progression of a disease, disorder, or condition, or of a symptom or side effect of the disease, disorder, or condition. In some embodiments, the therapeutically effective amount is also a clinically effective amount. In other embodiments, the therapeutically effective amount is not a clinically effective amount.

As used herein, the term "treating" and "treatment" includes administering to a subject a therapeutically or clinically effective amount of cells described herein so that the subject has a reduction in at least one symptom of the disease or an improvement in the disease, for example, beneficial or desired therapeutic or clinical results. For purposes of this technology, beneficial or desired therapeutic or clinical results include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. Treating can refer to prolonging survival as compared to expected survival if not receiving treatment. Thus, one of skill in the art realizes that a treatment may improve the disease condition, but may not be a complete cure for the disease. In some embodiments, one or more symptoms of a condition, disease or disorder are alleviated by at least 5%, at least 10%, at least 20%, at least 30%, at least 40%, or at least 50% upon treatment of the condition, disease or disorder.

For purposes of this technology, beneficial or desired therapeutic or clinical results of disease treatment include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable.

A "vector" or "construct" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors. Methods for the introduction of vectors or constructs into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and/or viral vector-mediated transfer.

In some embodiments, the cells are engineered to have reduced or increased expression of one or more targets relative to an unaltered or unmodified wild-type cell. In some embodiments, the cells are engineered to have constitutive reduced or increased expression of one or more targets relative to an unaltered or unmodified wild-type cell. In some embodiments, the cells are engineered to have regulatable reduced or increased expression of one or more targets relative to an unaltered or unmodified wild-type cell. In some embodiments, the cells comprise increased expression of CD47 relative to a wild-type cell or a control cell of the same cell type. By "wild-type" or "wt" or "control" in the context of a cell means any cell found in nature. Examples of wild type or control cells include primary cells and T cells found in nature. However, by way of example, in the context of an engineered cell, as used herein, "wild-type" or "control" can also mean an engineered cell that may contain nucleic acid changes resulting in reduced expression of MHC I and/or II and/or T-cell receptors, but did not undergo the gene editing procedures to result in overexpression of CD47 proteins. For example, as used herein, "wild-type" or "control" means an engineered cell that comprises reduced or knocked out expression of B2M, CIITA, and/or TRAC. Also as used herein, "wild-type" or "control" means an engineered cell that comprises reduced or knocked out expression of B2M, CIITA, TRAC, and/or TRBC. As used herein, "wild-type" or "control" also means an engineered cell that may contain nucleic acid changes resulting in overexpression of CD47 proteins, but did not undergo the gene editing procedures to result in reduced expression of MHC I and/or II and/or T-cell receptors. In the context of an iPSC or a progeny thereof, "wild-type" or "control" also means an iPSC or progeny thereof that may contain nucleic acid changes resulting in pluripotency but did not undergo the gene editing procedures of the present disclosure to achieve reduced expression of MHC I and/or II and/or T-cell receptors, and/or overexpression of CD47 proteins. For example, as used herein, "wild-type" or "control" means an iPSC or progeny thereof that comprises reduced or knocked out expression of B2M, CIITA, and/or TRAC. Also as used herein, "wild-type" or "control" means an iPSC or progeny thereof that comprises reduced or knocked out expression of B2M, CIITA, TRAC, and/or TRBC. In the context of a primary T cell or a progeny thereof, "wild-type" or "control" also means a primary T cell or progeny thereof that may contain nucleic acid changes resulting in reduced expression of MHC I and/or II and/or T-cell receptors, but did not undergo the gene editing procedures to result in overexpression of CD47 proteins. For example, as used herein, "wild-type" or "control" means a primary T cell or progeny thereof that comprises reduced or knocked out expression of B2M, CIITA, and/or TRAC. Also as used herein, "wild-type" or "control" means a primary T cell or progeny thereof that comprises reduced or knocked out expression of B2M, CIITA, TRAC, and/or TRBC. Also in the context of a primary T cell or a progeny thereof, "wild-type" or "control" also means a primary T cell or progeny thereof that may contain nucleic acid changes resulting in overexpression of CD47 proteins, but did not undergo the gene editing procedures to result in reduced expression of MHC I and/or II and/or T-cell receptors. In some embodiments, the cells are engineered to have regulatable reduced or increased expression of one or more targets relative to a cell of the same cell type that does not comprise the modifications. In some embodiments, the wild-type cell or the control cell is a starting material. In some embodiments, the starting material is a primary cell collected from a donor. In some embodiments, the starting material is a primary blood cell collected from a donor, e.g., via a leukopak. For example, unmodified T cells obtained from a donor is a starting material that are considered wild-type or control cells as contemplated herein. In another example, an iPSC cell line starting material is a starting material that is considered a wild-type or control cell as contemplated herein. In some embodiments, the starting material is otherwise modified or engineered to have altered expression of one or more genes to generate the engineered cell.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features readily separated from or combined with the features of any of the other several embodiments without departing from the scope or spirit of the present disclosure. Any recited method may be carried out in the order of events recited or in any other order that is logically possible. Although any methods and materials similar or equivalent to those described herein may also be used in the practice or testing of the present disclosure, representative illustrative methods and materials are now described.

Unless defined otherwise, all technical and scientific terms used herein have the same meaning as commonly understood by one of ordinary skill in the art to which this technology belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the present disclosure. The upper and lower limits of these smaller ranges may independently be included in the smaller ranges and are also encompassed within the present disclosure, subject to any specifically excluded limit in the stated range. Where the stated range includes one or both of the limits, ranges excluding either or both of those included limits are also included in the present disclosure. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context presented, provides the substantial equivalent of the specifically recited number. The term about is used herein to mean plus or minus ten percent (10%) of a value. For example, "about 100" refers to any number between 90 and 110.

All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the technology described herein is not entitled to antedate such publication by virtue of prior technology. Further, the dates of publication provided might be different from the actual publication dates, which may need to be independently confirmed.

Before the technology is further described, it is to be understood that this technology is not limited to particular embodiments described, as such may, of course, vary. It is also to be understood that the terminology used herein is for the purpose of describing particular embodiments only, and is not intended to be limiting, since the scope of the present disclosure will be limited only by the appended claims. It should also be understood that the headers used herein are not limiting and are merely intended to orient the reader, but the subject matter generally applies to the technology disclosed herein.

III. Detailed Description of the Embodiments

A. Hypoimmunogenic Cells

In some embodiments, the present disclosure is directed to pluripotent stem cells (e.g., pluripotent stem cells and induced pluripotent stem cells (iPSCs)), differentiated cells derived from such pluripotent stem cells (such as, but not limited to, T cells and NK cells), and primary cells (such as, but not limited to, primary T cells and primary NK cells). In some embodiments, the pluripotent stem cells, differentiated cells derived therefrom, such as T cells and NK cells, and primary cells such as primary T cells and primary NK cells, are engineered for reduced expression or lack of expression of MHC class I and/or MHC class II human leukocyte antigens, and in some instances, for reduced expression or lack of expression of a T-cell receptor (TCR) complex. In some embodiments, the hypoimmune (HIP) T cells and primary T cells overexpress CD47 and a chimeric antigen receptor (CAR) in addition to reduced expression or lack of expression of MHC class I and/or MHC class II human leukocyte antigens, and have reduced expression or lack expression of a T-cell receptor (TCR) complex. In some embodiments, the CAR comprises an antigen binding domain that binds to any one selected from the group consisting of CD19, CD22, CD38, CD123, CD138, and BCMA. In some embodiments, the CAR is a CD19-specific CAR. In some embodiments, the CAR is a CD22-specific CAR. In some instances, the CAR is a CD38-specific CAR. In some embodiments, the CAR is a CD123-specific CAR. In some embodiments, the CAR is a CD138-specific CAR. In some instances, the CAR is a BCMA-specific CAR. In some embodiments, the CAR is a bispecific CAR. In some embodiments, the bispecific CAR is a CD19/CD22-bispecific CAR. In some embodiments, the bispecific CAR is a BCMA/CD38-bispecific CAR. In some embodiments, the cells described express a CD19-specific CAR and a different CAR, such as, but not limited to a CD22-specific CAR, a CD38-specific CAR, a CD123-specific CAR, a CD138-specific CAR, and a BCMA-specific CAR. In some embodiments, the cells described express a CD22-specific CAR and a different CAR, such as, but not limited to a CD19-specific CAR, a CD38-specific CAR, a CD123-specific CAR, a CD138-specific CAR, and a BCMA-specific CAR. In some embodiments, the cells described express a CD38-specific CAR and a different CAR, such as, but not limited to a CD22-specific CAR, a CD18-specific CAR, a CD123-specific CAR, a CD138-specific CAR, and a BCMA-specific CAR. In some embodiments, the cells described express a CD123-specific CAR and a different CAR, such as, but not limited to a CD22-specific CAR, a CD38-specific CAR, a CD19-specific CAR, a CD138-specific CAR, and a BCMA-specific CAR. In some embodiments, the cells described express a CD138-specific CAR and a different CAR, such as, but not limited to a CD22-specific CAR, a CD38-specific CAR, a CD123-specific CAR, a CD19-specific CAR, and a BCMA-specific CAR. In some embodiments, the cells described express a BCMA-specific CAR and a different CAR, such as, but not limited to a CD22-specific CAR, a CD38-specific CAR, a CD123-specific CAR, a CD138-specific CAR, and a CD19-specific CAR. In some embodiments, the cells are modified or engineered as compared to a wild-type or control cell, including an unaltered or unmodified wild-type cell or control cell. In some embodiments, the wild-type cell or the control cell is a starting material. In some embodiments, the starting material is a primary cell collected from a donor. In some embodiments, the starting material is a primary blood cell collected from a donor, e.g., via a leukopak. In some embodiments, the starting material is otherwise modified or engineered to have altered expression of one or more genes to generate the engineered cell.

In some embodiments, engineered and/or hypoimmune (HIP) T cells and primary T cells overexpress CD47 and a chimeric antigen receptor (CAR), and include a genomic modification of the B2M gene. In some embodiments, engineered and/or hypoimmune (HIP) T cells and primary T cells overexpress CD47 and include a genomic modification of the CIITA gene. In some embodiments, engineered and/or hypoimmune (HIP) T cells and primary T cells overexpress CD47 and a CAR, and include a genomic modification of the TRAC gene. In some embodiments, engineered and/or hypoimmune (HIP) T cells and primary T cells overexpress CD47 and a CAR, and include a genomic modification of the TRB gene. In some embodiments, engineered and/or hypoimmune (HIP) T cells and primary T cells overexpress CD47 and a CAR, and include one or more genomic modifications selected from the group consisting of the B2M, CIITA, TRAC, and TRB genes. In some embodiments, engineered and/or hypoimmune (HIP) T cells and primary T cells overexpress CD47 and a CAR, and include genomic modifications of the B2M, CIITA, TRAC, and TRB genes. In some embodiments, the cells are $B2M^{-/-}$, $CIITA^{-/-}$, TRAC$^{-/-}$, CD47tg cells that also express CARs. In some embodiments, engineered and/or hypoimmune (HIP) T cells are produced by differentiating induced pluripotent stem cells such as engineered and/or hypoimmunogenic induced pluripotent stem cells. In some embodiments, the cells are modified or engineered as compared to a wild-type or control cell, including an unaltered or unmodified wild-type cell or control cell. In some embodiments, the wild-type cell or the control cell is a starting material. In some embodiments, the starting material is a primary cell collected from a donor. In some embodiments, the starting material is a primary blood cell collected from a donor, e.g., via a leukopak. In some embodiments, the starting material is otherwise modified or engineered to have altered expression of one or more genes to generate the engineered cell.

In some embodiments, the engineered and/or hypoimmune (HIP) T cells and primary T cells are B2M$^{-/-}$, CIITA$^{-/-}$, TRB$^{-/-}$, CD47tg cells that also express CARs. In some embodiments, the cells are B2M$^{-/-}$, CIITA$^{-/-}$, TRAC$^{-/-}$, TRB$^{-/-}$, CD47tg cells that also express CARs. In certain embodiments, the cells are B2M$^{indel/indel}$, CIITA$^{indel/indel}$, TRAC$^{indel/indel}$, CD47tg cells that also express CARs. In certain embodiments, the cells are B2M$^{indel/indel}$, CIITA$^{indel/indel}$, TRB$^{indel/indel}$, CD47tg cells that also express CARs. In certain embodiments, the cells are B2M$^{indel/indel}$, CIITA$^{indel/indel}$, TRAC$^{indel/indel}$, TRB$^{indel/indel}$, CD47tg cells that also express CARs. In some embodiments, the engineered or modified cells described are pluripotent stem cells, induced pluripotent stem cells, NK cells differentiated from such pluripotent stem cells and induced pluripotent stem cells, T cells differentiated from such pluripotent stem cells and induced pluripotent stem cells, or primary T cells. Non-limiting examples of primary T cells include CD3+ T cells, CD4+ T cells, CD8+ T cells, naïve T cells, regulatory T (Treg) cells, non-regulatory T cells, Th1 cells, Th2 cells, Th9 cells, Th17 cells, T-follicular helper (Tfh) cells, cytotoxic T lymphocytes (CTL), effector T (Teff) cells, central memory T (Tcm) cells, effector memory T (Tem) cells, effector memory T cells express CD45RA (TEMRA cells), tissue-resident memory (Trm) cells, virtual memory T cells, innate memory T cells, memory stem cell (Tsc), γδ T cells, and any other subtype of T cells. In some embodiments, the primary T cells are selected from a group that includes cytotoxic T-cells, helper T-cells, memory T-cells, regulatory T-cells, tumor infiltrating lymphocytes, and combinations thereof. Non-limiting examples of NK cells and primary NK cells include immature NK cells and mature NK cells. In some embodiments, the cells are modified or engineered as compared to a wild-type or control cell, including an unaltered or unmodified wild-type cell or control cell. In some embodiments, the wild-type cell or the control cell is a starting material. In some embodiments, the starting material is a primary cell collected from a donor. In some embodiments, the starting material is a primary blood cell collected from a donor, e.g., via a leukopak. In some embodiments, the starting material is otherwise modified or engineered to have altered expression of one or more genes to generate the engineered cell.

In some embodiments, the primary T cells are from a pool of primary T cells from one or more donor subjects that are different than the recipient subject (e.g., the patient administered the cells). The primary T cells can be obtained from 1, 2, 3, 4, 5, 6, 7, 8, 9, 10, 20, 50, 100 or more donor subjects and pooled together. The primary T cells can be obtained from 1 or more, 2 or more, 3 or more, 4 or more, 5 or more, 6 or more, 7 or more, 8 or more, 9 or more, 10, or more 20 or more, 50 or more, or 100 or more donor subjects and pooled together. In some embodiments, the primary T cells are harvested from one or a plurality of individuals, and in some instances, the primary T cells or the pool of primary T cells are cultured in vitro. In some embodiments, the primary T cells or the pool of primary T cells are engineered to exogenously express CD47 and cultured in vitro.

In certain embodiments, the primary T cells or the pool of primary T cells are engineered to express a chimeric antigen receptor (CAR). The CAR can be any known to those skilled in the art. Useful CARs include those that bind an antigen selected from a group that includes CD19, CD20, CD22, CD38, CD123, CD138, and BCMA. In some cases, the CAR is the same or equivalent to those used in FDA-approved CAR-T cell therapies such as, but not limited to, those used in tisagenlecleucel and axicabtagene ciloleucel, or others under investigation in clinical trials.

In some embodiments, the primary T cells or the pool of primary T cells are engineered to exhibit reduced expression of an endogenous T cell receptor compared to unmodified primary T cells. In certain embodiments, the primary T cells or the pool of primary T cells are engineered to exhibit reduced expression of CTLA-4, PD-1, or both CTLA-4 and PD-1, as compared to unmodified primary T cells. Methods of genetically modifying a cell including a T cell are described in detail, for example, in WO2020/018620 and WO2016/183041, the disclosures of which are herein incorporated by reference in their entireties, including the tables, appendices, sequence listing and figures.

In some embodiments, the CAR-T cells comprise a CAR selected from a group including: (a) a first generation CAR comprising an antigen binding domain, a transmembrane domain, and a signaling domain; (b) a second generation CAR comprising an antigen binding domain, a transmembrane domain, and at least two signaling domains; (c) a third generation CAR comprising an antigen binding domain, a transmembrane domain, and at least three signaling domains; and (d) a fourth generation CAR comprising an antigen binding domain, a transmembrane domain, three or four signaling domains, and a domain which upon successful signaling of the CAR induces expression of a cytokine gene.

In some embodiments, the CAR-T cells comprise a CAR comprising an antigen binding domain, a transmembrane, and one or more signaling domains. In some embodiments, the CAR also comprises a linker. In some embodiments, the CAR comprises a CD19 antigen binding domain. In some embodiments, the CAR comprises a CD28 or a CD8α transmembrane domain. In some embodiments, the CAR comprises a CD8α signal peptide. In some embodiments, the CAR comprises a Whitlow linker GSTSGSGKPGSGEG-STKG (SEQ ID NO:24). In some embodiments, the antigen binding domain of the CAR is selected from a group including, but not limited to, (a) an antigen binding domain targets an antigen characteristic of a neoplastic cell; (b) an antigen binding domain that targets an antigen characteristic of a T cell; (c) an antigen binding domain targets an antigen characteristic of an autoimmune or inflammatory disorder; (d) an antigen binding domain that targets an antigen characteristic of senescent cells; (e) an antigen binding domain that targets an antigen characteristic of an infectious disease; and (f) an antigen binding domain that binds to a cell surface antigen of a cell.

In some embodiments, the CAR further comprises one or more linkers. The format of an scFv is generally two variable domains linked by a flexible peptide sequence, or a "linker," either in the orientation VH-linker-VL or VL-linker-VH. Any suitable linker known to those in the art in view of the specification can be used in the CARs. Examples of suitable linkers include, but are not limited to, a GS based linker sequence, and a Whitlow linker GSTSGSGKPGSGEGSTKG (SEQ ID NO:24). In some embodiments, the linker is a GS or a gly-ser linker. Exemplary gly-ser polypeptide linkers comprise the amino acid sequence Ser(Gly$_4$Ser)$_n$ (SEQ ID NO:144), as well as (Gly$_4$Ser)$_n$ (SEQ ID NO:145) and/or (Gly$_4$Ser$_3$)$_n$ (SEQ ID NO:149). In some embodiments, n=1. In some embodiments, n=2. In some embodiments, n=3, i.e., Ser(Gly$_4$Ser)$_3$ (SEQ ID NO:146). In some embodiments, n=4, i.e., Ser(Gly$_4$Ser)$_4$ (SEQ ID NO:147). In some embodiments, n=5. In some embodiments, n=6. In some embodiments, n=7. In some embodiments, n=8. In some embodiments, n=9. In some embodiments, n=10. Another exemplary gly-ser polypeptide linker comprises the amino acid sequence Ser(Gly$_4$Ser)$_n$(SEQ ID NO:144). In some embodiments, n=1. In some embodiments, n=2. In some embodiments, n=3. In another embodiment, n=4. In some embodiments, n=5. In some embodiments, n=6. Another exemplary gly-ser polypeptide linker comprises (Gly$_4$Ser)$_n$ (SEQ ID NO:145). In some embodiments, n=1. In some embodiments, n=2. In some embodiments, n=3. In some embodiments, n=4. In some embodiments, n=5. In some embodiments, n=6. Another exemplary gly-ser polypeptide linker comprises (Gly$_3$Ser)$_n$ (SEQ ID NO:148). In some embodiments, n=1. In some embodiments, n=2. In some embodiments, n=3. In some embodiments, n=4. In another embodiment, n=5. In yet another embodiment, n=6. Another exemplary gly-ser polypeptide linker comprises (Gly$_4$Ser$_3$)$_n$(SEQ ID NO:149). In some embodiments, n=1. In some embodiments, n=2. In some embodiments, n=3. In some embodiments, n=4. In some embodiments, n=5. In some embodiments, n=6. Another exemplary gly-ser polypeptide linker comprises (Gly$_3$Ser)$_n$ (SEQ ID NO:148). In some embodiments, n=1. In some embodiments, n=2. In some embodiments, n=3. In some embodiments, n=4. In another embodiment, n=5. In yet another embodiment, n=6.

In some embodiments, the antigen binding domain is selected from a group that includes an antibody, an antigen-binding portion or fragment thereof, an scFv, and a Fab. In some embodiments, the antigen binding domain binds to CD19, CD20, CD22, CD38, CD123, CD138, or BCMA. In some embodiments, the antigen binding domain is an anti-CD19 scFv such as but not limited to FMC63.

In some embodiments, the transmembrane domain comprises one selected from a group that includes a transmembrane region of TCRα, TCRβ, TCRζ, CD3ε, CD3γ, CD3δ, CD3ζ, CD4, CD5, CD8α, CD8β, CD9, CD16, CD28, CD45, CD22, CD33, CD34, CD37, CD40, CD40L/CD154, CD45, CD64, CD80, CD86, OX40/CD134, 4-1BB/CD137, CD154, FcεRIγ, VEGFR2, FAS, FGFR2B, and functional variant thereof.

In some embodiments, the signaling domain(s) of the CAR comprises a costimulatory domain(s). For instance, a signaling domain can contain a costimulatory domain. Or, a signaling domain can contain one or more costimulatory domains. In certain embodiments, the signaling domain comprises a costimulatory domain. In other embodiments, the signaling domains comprise costimulatory domains. In some cases, when the CAR comprises two or more costimulatory domains, two costimulatory domains are not the same. In some embodiments, the costimulatory domains comprise two costimulatory domains that are not the same. In some embodiments, the costimulatory domain enhances cytokine production, CAR-T cell proliferation, and/or CAR-T cell persistence during T cell activation. In some embodiments, the costimulatory domains enhance cytokine production, CAR-T cell proliferation, and/or CAR-T cell persistence during T cell activation.

As described herein, a fourth generation CAR can contain an antigen binding domain, a transmembrane domain, three or four signaling domains, and a domain which upon successful signaling of the CAR induces expression of a cytokine gene. In some instances, the cytokine gene is an endogenous or exogenous cytokine gene of the hypoimmunogenic cells. In some cases, the cytokine gene encodes a pro-inflammatory cytokine. In some embodiments, the pro-inflammatory cytokine is selected from a group that includes IL-1, IL-2, IL-9, IL-12, IL-18, TNF, IFN-gamma, and a functional fragment thereof. In some embodiments, the domain which upon successful signaling of the CAR induces expression of the cytokine gene comprises a transcription factor or functional domain or fragment thereof.

In some embodiments, the CAR comprises a CD3 zeta (CD3ζ) domain or an immunoreceptor tyrosine-based activation motif (ITAM), or functional variant thereof. In some embodiments, the CAR comprises (i) a CD3 zeta domain, or an immunoreceptor tyrosine-based activation motif (ITAM), or functional variant thereof, and (ii) a CD28 domain, or a 4-1BB domain, or functional variant thereof. In other embodiments, the CAR comprises (i) a CD3 zeta domain, or an immunoreceptor tyrosine-based activation motif (ITAM), or functional variant thereof; (ii) a CD28 domain or functional variant thereof, and (iii) a 4-1BB domain, or a CD134 domain, or functional variant thereof. In certain embodiments, the CAR comprises (i) a CD3 zeta domain, or an immunoreceptor tyrosine-based activation motif (ITAM), or functional variant thereof, (ii) a CD28 domain or functional variant thereof; (iii) a 4-1BB domain, or a CD134 domain, or functional variant thereof, and (iv) a cytokine or costimulatory ligand transgene. In some embodiments, the CAR comprises a (i) an anti-CD19 scFv; (ii) a CD8α hinge and transmembrane domain or functional variant thereof; (iii) a 4-1BB costimulatory domain or functional variant thereof; and (iv) a CD3ζ signaling domain or functional variant thereof.

Methods for introducing a CAR construct or producing a CAR-T cells are well known to those skilled in the art. Detailed descriptions are found, for example, in Vormittag et al., Curr Opin Biotechnol, 2018, 53, 162-181; and Eyquem et al., Nature, 2017, 543, 113-117.

In some embodiments, the cells derived from primary T cells comprise reduced expression of an endogenous T cell receptor, for example by disruption of an endogenous T cell receptor gene (e.g., T cell receptor alpha constant region (TRAC) or T cell receptor beta constant region (TRB)). In some embodiments, an exogenous nucleic acid encoding a polypeptide as disclosed herein (e.g., a chimeric antigen receptor, CD47, or another tolerogenic factor disclosed herein) is inserted at the disrupted T cell receptor gene. In some embodiments, an exogenous nucleic acid encoding a polypeptide is inserted at a TRAC or a TRB gene locus.

In some embodiments, the cells derived from primary T cells comprise reduced expression of cytotoxic T-lymphocyte-associated protein 4 (CTLA4) and/or programmed cell death (PD1). Methods of reducing or eliminating expression of CTLA4, PD1 and both CTLA4 and PD1 can include any recognized by those skilled in the art, such as but not limited to, genetic modification technologies that utilize rare-cutting endonucleases and RNA silencing or RNA interference technologies. Non-limiting examples of a rare-cutting endonuclease include any Cas protein, TALEN, zinc finger nuclease, meganuclease, and/or homing endonuclease. In some embodiments, an exogenous nucleic acid encoding a polypeptide as disclosed herein (e.g., a chimeric antigen receptor, CD47, or another tolerogenic factor disclosed herein) is inserted at a CTLA4 and/or PD1 gene locus. In some embodiments, the cells are modified or engineered as compared to a wild-type or control cell, including an unaltered or unmodified wild-type cell or control cell. In some embodiments, the wild-type cell or the control cell is a starting material. In some embodiments, the starting material is a primary cell collected from a donor. In some embodiments, the starting material is a primary blood cell collected from a donor, e.g., via a leukopak. In some embodiments, the starting material is otherwise modified or engineered to have altered expression of one or more genes to generate the engineered cell. In some embodiments, the exogenous polynucleotide is inserted into at least one allele of the cell using viral transduction, for example, with a vector. In some embodiments, the vector is a pseudotyped, self-inactivating lentiviral vector that carries the exogenous polynucleotide. In some embodiments, the vector is a self-inactivating lentiviral vector pseudotyped with a vesicular stomatitis VSV-G envelope, and which carries the exogenous polynucleotide. In some embodiments, the exogenous polynucleotide is inserted into at least one allele of the cell using viral transduction. In some embodiments, the exogenous polynucleotide is inserted into at least one allele of the cell using a lentivirus based viral vector.

In some embodiments, a CD47 transgene is inserted into a pre-selected locus of the cell. In some embodiments, a CD47 transgene is inserted into a random locus of the cell. In some embodiments, a transgene encoding a CAR is inserted into a pre-selected locus of the cell. In some embodiments, a transgene encoding a CAR is inserted into a random locus of the cell. In certain embodiments, a CD47 transgene and a transgene encoding a CAR are inserted into a pre-selected locus of the cell. In some embodiments, a transgene encoding a CAR is inserted into a random or pre-selected locus of the cell, including a safe harbor locus, via viral vector transduction/integration. In some embodiments, a CD47 transgene and a transgene encoding a CAR are inserted into a random or pre-selected locus of the cell, including a safe harbor locus, via viral vector transduction/integration. In some embodiments, the vector is a self-inactivating lentiviral vector pseudotyped with a vesicular stomatitis VSV-G envelope. In some embodiments, the transgene encoding a CAR is inserted into at least one allele of the cell using viral transduction. In some embodiments, the exogenous polynucleotide is inserted into at least one allele of the cell using a lentivirus based viral vector. The random and/or pre-selected locus can be a safe harbor or target locus. Non-limiting examples of a safe harbor locus include, but are not limited to, a CCR5 gene locus, a PPP1R12C (also known as AAVS1) gene locus, and a CLYBL gene locus, a Rosa gene locus (e.g., ROSA26 gene locus). Non-limiting examples of a target locus include, but are not limited to, a CXCR4 gene locus, an albumin gene locus, a SHS231 gene locus, an F3 gene locus (also known as CD142), a MICA gene locus, a MICB gene locus, a LRP1 gene locus (also known as a CD91 gene locus), a HMGB1 gene locus, an ABO gene locus, ad RHD gene locus, a FUT1 locus, and a KDM5D gene locus. The CD47 transgene can be inserted in Introns 1 or 2 for PPP1R12C (i.e., AAVS1) or CCR5. The CD47 transgene can be inserted in Exons 1 or 2 or 3 for CCR5. The CD47 transgene can be inserted in intron 2 for CLYBL. The CD47 transgene can be inserted in a 500 bp window in Ch-4:58,976,613 (i.e., SHS231). The CD47 transgene can be insert in any suitable region of the aforementioned safe harbor or target loci that allows for expression of the exogenous polynucleotide, including, for example, an intron, an exon or a coding sequence region in a safe harbor or target locus. In some embodiments, the pre-selected locus is selected from the group consisting of the B2M locus, the CIITA locus, the TRAC locus, and the TRB locus. In some embodiments, the pre-selected locus is the B2M locus. In some embodiments, the pre-selected locus is the CIITA locus. In some embodiments, the pre-selected locus is the TRAC locus. In some embodiments, the pre-selected locus is the TRB locus. In some embodiments, the exogenous polynucleotide is inserted into at least one allele of the cell using viral transduction, for example, with a vector. In some embodiments, the vector is a pseudotyped, self-inactivating lentiviral vector that carries the exogenous polynucleotide. In some embodiments, the vector is a self-inactivating lentiviral vector pseudotyped with a vesicular stomatitis VSV-G envelope, and which carries the exogenous polynucleotide. In some embodiments, the exogenous polynucleotide is inserted into at least one allele of the cell using viral transduction. In some embodiments, the exogenous polynucleotide is inserted into at least one allele of the cell using a lentivirus based viral vector.

In some embodiments, a CD47 transgene and a transgene encoding a CAR are inserted into the same locus. In some embodiments, a CD47 transgene and a transgene encoding a CAR are inserted into different loci. In many instances, a CD47 transgene is inserted into a safe harbor or target locus. In many instances, a transgene encoding a CAR is inserted into a safe harbor or target locus. In some instances, a CD47 transgene is inserted into a B2M locus. In some instances, a transgene encoding a CAR is inserted into a B2M locus. In certain instances, a CD47 transgene is inserted into a CIITA locus. In certain instances, a transgene encoding a CAR is inserted into a CIITA locus. In particular instances, a CD47 transgene is inserted into a TRAC locus. In particular instances, a transgene encoding a CAR is inserted into a TRAC locus. In many other instances, a CD47 transgene is inserted into a TRB locus. In many other instances, a transgene encoding a CAR is inserted into a TRB locus. In some embodiments, a CD47 transgene and a transgene encoding a CAR are inserted into a safe harbor or target locus (e.g., a CCR5 gene locus, a CXCR4 gene locus, a PPP1R12C gene locus, an albumin gene locus, a SHS231 gene locus, a CLYBL gene locus, a Rosa gene locus, an F3 (CD142) gene locus, a MICA gene locus, a MICB gene locus, a LRP1 (CD91) gene locus, a HMGB1 gene locus, an ABO gene locus, an RHD gene locus, a FUT1 locus, and a KDM5D gene locus.

In certain embodiments, a CD47 transgene and a transgene encoding a CAR are inserted into a safe harbor or target locus. In certain embodiments, a CD47 transgene and a transgene encoding a CAR are controlled by a single promoter and are inserted into a safe harbor or target locus. In certain embodiments, a CD47 transgene and a transgene encoding a CAR are controlled by their own promoters and are inserted into a safe harbor or target locus. In certain embodiments, a CD47 transgene and a transgene encoding a CAR are inserted into a TRAC locus. In certain embodiments, a CD47 transgene and a transgene encoding a CAR are controlled by a single promoter and are inserted into a TRAC locus. In certain embodiments, a CD47 transgene and a transgene encoding a CAR are controlled by their own promoters and are inserted into a TRAC locus. In some embodiments, a CD47 transgene and a transgene encoding a CAR are inserted into a TRB locus. In some embodiments, a CD47 transgene and a transgene encoding a CAR are controlled by a single promoter and are inserted into a TRB locus. In some embodiments, a CD47 transgene and a transgene encoding a CAR are controlled by their own promoters and are inserted into a TRB locus. In other embodiments, a CD47 transgene and a transgene encoding a CAR are inserted into a B2M locus. In other embodiments, a CD47 transgene and a transgene encoding a CAR are controlled by a single promoter and are inserted into a B2M locus. In other embodiments, a CD47 transgene and a transgene encoding a CAR are controlled by their own promoters and are inserted into a B2M locus. In various embodiments, a CD47 transgene and a transgene encoding a CAR are inserted into a CIITA locus. In various embodiments, a CD47 transgene and a transgene encoding a CAR are controlled by a single promoter and are inserted into a CIITA locus. In various embodiments, a CD47 transgene and a transgene encoding a CAR are controlled by their own promoters and are inserted into a CIITA locus. In some instances, the promoter controlling expression of any transgene described is a constitutive promoter. In other instances, the promoter for any transgene described is an inducible promoter. In some embodiments, the promoter is an EF1α promoter. In some embodiments, the promoter is CAG promoter. In some embodiments, a CD47 transgene and a transgene encoding a CAR are both controlled by a constitutive promoter. In some embodiments, a CD47 transgene and a transgene encoding a CAR are both controlled by an inducible promoter. In some embodiments, a CD47 transgene is controlled by a constitutive promoter and a transgene encoding a CAR is controlled by an inducible promoter. In some embodiments, a CD47 transgene is controlled by an inducible promoter and a transgene encoding a CAR is controlled by a constitutive promoter. In various embodiments, a CD47 transgene is controlled by an EF1α promoter and a transgene encoding a CAR is controlled by an EF1α promoter. In some embodiments, a CD47 transgene is controlled by a CAG promoter and a transgene encoding a CAR is controlled by a CAG promoter. In some embodiments, a CD47 transgene is controlled by a CAG promoter and a transgene encoding a CAR is controlled by an EF1α promoter. In some embodiments, a CD47 transgene is controlled by an EF1α promoter and a transgene encoding a CAR is controlled by a CAG promoter. In some embodiments, expression of both a CD47 transgene and a transgene encoding a CAR is controlled by a single EF1α promoter. In some embodiments, expression of both a CD47 transgene and a transgene encoding a CAR is controlled by a single CAG promoter.

In another embodiment, the present disclosure disclosed herein is directed to pluripotent stem cells, (e.g., pluripotent stem cells and induced pluripotent stem cells (iPSCs)), differentiated cells derived from such pluripotent stem cells (e.g., hypoimmune (HIP) T cells), and primary T cells that overexpress CD47 (such as exogenously express CD47 proteins), have reduced expression or lack expression of MHC class I and/or MHC class II human leukocyte antigens, and have reduced expression or lack expression of a T-cell receptor (TCR) complex. In some embodiments, the hypoimmune (HIP) T cells and primary T cells overexpress CD47 (such as exogenously express CD47 proteins), have reduced expression or lack expression of MHC class I and/or MHC class II human leukocyte antigens, and have reduced expression or lack expression of a T-cell receptor (TCR) complex.

In some embodiments, pluripotent stem cells, (e.g., pluripotent stem cells and induced pluripotent stem cells (iPSCs)), differentiated cells derived from such pluripotent stem cells (e.g., hypoimmune (HIP) T cells), and primary T cells overexpress CD47 and include a genomic modification of the B2M gene. In some embodiments, pluripotent stem cells, differentiated cell derived from such pluripotent stem cells and primary T cells overexpress CD47 and include a genomic modification of the CIITA gene. In some embodiments, pluripotent stem cells, T cells differentiated from such pluripotent stem cells and primary T cells overexpress CD47 and include a genomic modification of the TRAC gene. In some embodiments, pluripotent stem cells, T cells differentiated from such pluripotent stem cells and primary T cells overexpress CD47 and include a genomic modification of the TRB gene. In some embodiments, pluripotent stem cells, T cells differentiated from such pluripotent stem cells and primary T cells overexpress CD47 and include one or more genomic modifications selected from the group consisting of the B2M, CIITA, TRAC and TRB genes. In some embodiments, pluripotent stem cells, T cells differentiated from such pluripotent stem cells and primary T cells overexpress CD47 and include genomic modifications of the B2M, CIITA and TRAC genes. In some embodiments, pluripotent stem cells, T cells differentiated from such pluripotent stem cells and primary T cells overexpress CD47 and include genomic modifications of the B2M, CIITA and TRB genes. In some embodiments, pluripotent stem cells, T cells differentiated from such pluripotent stem cells and primary T cells overexpress CD47 and include genomic modifications of the B2M, CIITA, TRAC and TRB genes. In certain embodiments, the pluripotent stem cells, differentiated cell derived from such pluripotent stem cells and primary T cells are $B2M^{-/-}$, $CIITA^{-/-}$, $TRAC^{-/-}$, CD47tg cells. In certain embodiments, the cells are $B2M^{-/-}$, $CIITA^{-/-}$, $TRB^{-/-}$, CD47tg cells. In certain embodiments, the cells are $B2M^{-/-}$, $CIITA^{-/-}$, $TRAC^{-/-}$, $TRB^{-/-}$, CD47tg cells. In some embodiments, the cells are $B2M^{indel/indel}$, $CIITA^{indel/indel}$, $TRAC^{indel/indel}$, CD47tg cells. In some embodiments, the cells are $B2M^{indel/indel}$, $CIITA^{indel/indel}$, $TRB^{indel/indel}$, CD47tg cells. In some embodiments, the cells are $B2M^{indel/indel}$, $CIITA^{indel/indel}$, $TRAC^{indel/indel}$, $TRB^{indel/indel}$, CD47tg cells. In some embodiments, the engineered or modified cells described are pluripotent stem cells, T cells differentiated from such pluripotent stem cells or primary T cells. Non-limiting examples of primary T cells include CD3+ T cells, CD4+ T cells, CD8+ T cells, naïve T cells, regulatory T (Treg) cells, non-regulatory T cells, Th1 cells, Th2 cells, Th9 cells, Th17 cells, T-follicular helper (Tfh) cells, cytotoxic T lymphocytes (CTL), effector T (Teff) cells, central memory T (Tcm) cells, effector memory T (Tem) cells, effector memory T cells express CD45RA (TEMRA cells), tissue-resident memory (Trm) cells, virtual memory T cells, innate memory T cells, memory stem cell (Tsc), γδ T cells, and any other subtype of T cells. In some embodiments, the cells are modified or engineered as compared to a wild-type or control cell, including an unaltered or unmodified wild-type cell or control cell. In some embodiments, the wild-type cell or the control cell is a starting material. In some embodiments, the starting material is a primary cell collected from a donor. In some embodiments, the starting material is a primary blood cell collected from a donor, e.g., via a leukopak. In some embodiments, the starting material is otherwise modified or engineered to have altered expression of one or more genes to generate the engineered cell.

In some embodiments, a CD47 transgene is inserted into a pre-selected locus of the cell. The pre-selected locus can be a safe harbor or target locus. Non-limiting examples of a safe harbor or target locus includes a CCR5 gene locus, a CXCR4 gene locus, a PPP1R12C gene locus, an albumin gene locus, a SHS231 gene locus, a CLYBL gene locus, a Rosa gene locus, an F3 (CD142) gene locus, a MICA gene locus, a MICB gene locus, a LRP1 (CD91) gene locus, a HMGB1 gene locus, an ABO gene locus, an RHD gene locus, a FUT1 locus, and a KDM5D gene locus. In some embodiments, the pre-selected locus is the TRAC locus. In some embodiments, a CD47 transgene is inserted into a safe harbor or target locus (e.g., a CCR5 gene locus, a CXCR4 gene locus, a PPP1R12C gene locus, an albumin gene locus, a SHS231 gene locus, a CLYBL gene locus, a Rosa gene locus, an F3 (CD142) gene locus, a MICA gene locus, a MICB gene locus, a LRP1 (CD91) gene locus, a HMGB1 gene locus, an ABO gene locus, an RHD gene locus, a FUT1 locus, and a KDM5D gene locus. In certain embodiments, a CD47 transgene is inserted into the B2M locus. In certain embodiments, a CD47 transgene is inserted into the B2M locus. In certain embodiments, a CD47 transgene is inserted into the TRAC locus. In certain embodiments, a CD47 transgene is inserted into the TRB locus. In some embodiments, the CD47 transgene is inserted into a pre-selected locus of the cell, including a safe harbor locus, via viral vector transduction/integration. In some embodiments, the vector is a self-inactivating lentiviral vector pseudotyped with a vesicular stomatitis VSV-G envelope. In some embodiments, the CD47 transgene is inserted into at least one allele of the cell using viral transduction. In some embodiments, the exogenous polynucleotide is inserted into at least one allele of the cell using a lentivirus based viral vector.

In some instances, expression of a CD47 transgene is controlled by a constitutive promoter. In other instances, expression of a CD47 transgene is controlled by an inducible promoter. In some embodiments, the promoter is an EF1alpha (EF1α) promoter. In some embodiments, the promoter a CAG promoter.

In yet another embodiment, the present disclosure disclosed herein is directed to pluripotent stem cells, (e.g., pluripotent stem cells and induced pluripotent stem cells (iPSCs)), T cells derived from such pluripotent stem cells (e.g., hypoimmune (HIP) T cells), and primary T cells that have reduced expression or lack expression of MHC class I and/or MHC class II human leukocyte antigens and have reduced expression or lack expression of a T-cell receptor (TCR) complex. In some embodiments, the cells have reduced or lack expression of MHC class I antigens, MHC class II antigens, and TCR complexes.

In some embodiments, pluripotent stem cells (e.g., iPSCs), differentiated cells derived from such (e.g., T cells differentiated from such), and primary T cells include a genomic modification of the B2M gene. In some embodiments, pluripotent stem cells (e.g., iPSCs), differentiated cells derived from such (e.g., T cells differentiated from such), and primary T cells include a genomic modification of the CIITA gene. In some embodiments, pluripotent stem cells (e.g., iPSCs), T cells differentiated from such, and primary T cells include a genomic modification of the TRAC gene. In some embodiments, pluripotent stem cells (e.g., iPSCs), T cells differentiated from such, and primary T cells include a genomic modification of the TRB gene. In some embodiments, pluripotent stem cells (e.g., iPSCs), T cells differentiated from such, and primary T cells include one or more genomic modifications selected from the group consisting of the B2M, CIITA and TRAC genes. In some embodiments, pluripotent stem cells (e.g., iPSCs), T cells differentiated from such, and primary T cells include one or more genomic modifications selected from the group consisting of the B2M, CIITA and TRB genes. In some embodiments, pluripotent stem cells (e.g., iPSCs), T cells differentiated from such, and primary T cells include one or more genomic modifications selected from the group consisting of the B2M, CIITA, TRAC and TRB genes. In certain embodiments, the cells including iPSCs, T cells differentiated from such, and primary T cells are $B2M^{-/-}$, $CIITA^{-/-}$, $TRAC^{-/-}$ cells. In certain embodiments, the cells including iPSCs, T cells differentiated from such, and primary T cells are $B2M^{-/-}$, $CIITA^{-/-}$, $TRB^{-/-}$ cells. In some embodiments, the cells including iPSCs, T cells differentiated from such, and primary T cells are $B2M^{indel/indel}$, $CIITA^{indel/indel}$, $TRAC^{indel/indel}$ cells. In some embodiments, the cells including iPSCs, T cells differentiated from such, and primary T cells are $B2M^{indel/indel}$, $CIITA^{indel/indel}$, $TRB^{indel/indel}$ cells. In some embodiments, the cells including iPSCs, T cells differentiated from such, and primary T cells are $B2M^{indel/indel}$, $CIITA^{indel/indel}$, $TRAC^{indel/indel}$, $TRB^{indel/indel}$ cells. In some embodiments, the modified cells described are pluripotent stem cells, induced pluripotent stem cells, T cells differentiated from such pluripotent stem cells and induced pluripotent stem cells, or primary T cells. Non-limiting examples of primary T cells include CD3+ T cells, CD4+ T cells, CD8+ T cells, naïve T cells, regulatory T (Treg) cells, non-regulatory T cells, Th1 cells, Th2 cells, Th9 cells, Th17 cells, T-follicular helper (Tfh) cells, cytotoxic T lymphocytes (CTL), effector T (Teff) cells, central memory T (Tcm) cells, effector memory T (Tem) cells, effector memory T cells express CD45RA (TEMRA cells), tissue-resident memory (Trm) cells, virtual memory T cells, innate memory T cells, memory stem cell (Tsc), γδ T cells, and any other subtype of T cells. In some embodiments, the cells are modified or engineered as compared to a wild-type or control cell, including an unaltered or unmodified wild-type cell or control cell. In some embodiments, the wild-type cell or the control cell is a starting material. In some embodiments, the starting material is a primary cell collected from a donor. In some embodiments, the starting material is a primary blood cell collected from a donor, e.g., via a leukopak. In some embodiments, the starting material is otherwise modified or engineered to have altered expression of one or more genes to generate the engineered cell.

Cells of the present disclosure exhibit reduced or lack expression of MHC class I antigens, MHC class II antigens, and/or TCR complexes. Reduction of MHC I and/or MHC II expression can be accomplished, for example, by one or more of the following: (1) targeting the polymorphic HLA alleles (HLA-A, HLA-B, HLA-C) and MHC-II genes directly; (2) removal of B2M, which will prevent surface trafficking of all MHC-I molecules; (3) removal of CIITA, which will prevent surface trafficking of all MHC-II molecules; and/or (4) deletion of components of the MHC enhanceosomes, such as LRC5, RFX5, RFXANK, RFXAP, IRF1, NF-Y (including NFY-A, NFY-B, NFY-C), and CIITA that are critical for HLA expression.

In some embodiments, HLA expression is interfered with by targeting individual HLAs (e.g., knocking out, knocking down, or reducing expression of HLA-A, HLA-B, HLA-C, HLA-DP, HLA-DQ, and/or HLA-DR), targeting transcriptional regulators of HLA expression (e.g., knocking out, knocking down, or reducing expression of NLRC5, CIITA, RFX5, RFXAP, RFXANK, NFY-A, NFY-B, NFY-C and/or IRF-1), blocking surface trafficking of MHC class I molecules (e.g., knocking out, knocking down, or reducing expression of B2M and/or TAP1), and/or targeting with HLA-Razor (see, e.g., WO2016183041).

In some embodiments, the cells disclosed herein including, but not limited to, pluripotent stem cells, induced pluripotent stem cells, differentiated cells derived from such stem cells, and primary T cells do not express one or more human leukocyte antigens (e.g., HLA-A, HLA-B, HLA-C, HLA-DP, HLA-DQ, and/or HLA-DR) corresponding to MHC-I and/or MHC-II and are thus characterized as being hypoimmunogenic. For example, in certain embodiments, the pluripotent stem cells and induced pluripotent stem cells disclosed have been modified such that the stem cell or a differentiated stem cell prepared therefrom do not express or exhibit reduced expression of one or more of the following MHC-I molecules: HLA-A, HLA-B and HLA-C. In some embodiments, one or more of HLA-A, HLA-B and HLA-C may be "knocked-out" of a cell. A cell that has a knocked-out HLA-A gene, HLA-B gene, and/or HLA-C gene may exhibit reduced or eliminated expression of each knocked-out gene.

In some embodiments, guide RNAs, shRNAs, siRNAs, or miRNAs that allow simultaneous deletion of all MHC class I alleles by targeting a conserved region in the HLA genes are identified as HLA Razors. In some embodiments, the gRNAs are part of a CRISPR system. In alternative embodiments, the gRNAs are part of a TALEN system. In some embodiments, an HLA Razor targeting an identified conserved region in HLAs is described in WO2016183041. In some embodiments, multiple HLA Razors targeting identified conserved regions are utilized. It is generally understood that any guide, siRNA, shRNA, or miRNA molecule that targets a conserved region in HLAs can act as an HLA Razor.

Methods provided are useful for inactivation or ablation of MHC class I expression and/or MHC class II expression in cells such as but not limited to pluripotent stem cells, differentiated cells, and primary T cells. In some embodiments, genome editing technologies utilizing rare-cutting endonucleases (e.g., the CRISPR/Cas, TALEN, zinc finger nuclease, meganuclease, and homing endonuclease systems) are also used to reduce or eliminate expression of genes involved in an immune response (e.g., by deleting genomic DNA of genes involved in an immune response or by insertions of genomic DNA into such genes, such that gene expression is impacted) in cells. In certain embodiments, genome editing technologies or other gene modulation technologies are used to insert tolerance-inducing factors in human cells, rendering them and the differentiated cells prepared therefrom hypoimmunogenic cells. As such, the hypoimmunogenic cells have reduced or eliminated expression of MHC I and MHC II expression. In some embodiments, the cells are nonimmunogenic (e.g., do not induce an innate and/or an adaptive immune response) in a recipient subject.

In some embodiments, the cell includes a modification to increase expression of CD47 and one or more factors selected from the group consisting of DUX4, CD24, CD27, CD35, CD46, CD55, CD59, CD200, HLA-C, HLA-E, HLA-E heavy chain, HLA-G, PD-L1, IDO1, CTLA4-Ig, C1-Inhibitor, IL-10, IL-35, IL-39, FasL, CCL21, CCL22, Mfge8, CD16, CD52, H2-M3, CD16 Fc receptor, IL15-RF, and/or Serpinb9.

In some embodiments, the cell comprises a genomic modification of one or more target polynucleotide sequences that regulate the expression of either MHC class I molecules, MHC class II molecules, or MHC class I and MHC class II molecules. In some embodiments, a genetic editing system is used to modify one or more target polynucleotide sequences. In some embodiments, the targeted polynucleotide sequence is one or more selected from the group including B2M, CIITA, and NLRC5. In some embodiments, the cell comprises a genetic editing modification to the B2M gene. In some embodiments, the cell comprises a genetic editing modification to the CIITA gene. In some embodiments, the cell comprises a genetic editing modification to the NLRC5 gene. In some embodiments, the cell comprises genetic editing modifications to the B2M and CIITA genes. In some embodiments, the cell comprises genetic editing modifications to the B2M and NLRC5 genes. In some embodiments, the cell comprises genetic editing modifications to the CIITA and NLRC5 genes. In numerous embodiments, the cell comprises genetic editing modifications to the B2M, CIITA and NLRC5 genes. In certain embodiments, the genome of the cell has been altered to reduce or delete critical components of HLA expression. In some embodiments, the cells are modified or engineered as compared to a wild-type or control cell, including an unaltered or unmodified wild-type cell or control cell. In some embodiments, the wild-type cell or the control cell is a starting material. In some embodiments, the starting material is a primary cell collected from a donor. In some embodiments, the starting material is a primary blood cell collected from a donor, e.g., via a leukopak. In some embodiments, the starting material is otherwise modified or engineered to have altered expression of one or more genes to generate the engineered cell.

In some embodiments, the present disclosure provides a cell (e.g., stem cell, induced pluripotent stem cell, differentiated cell such as a primary NK cell, CAR-NK cell, primary T cell or CAR-T cell) or population thereof comprising a genome in which a gene has been edited to delete a contiguous stretch of genomic DNA, thereby reducing or eliminating surface expression of MHC class I molecules in the cell or population thereof. In certain embodiments, the present disclosure provides a cell (e.g., stem cell, induced pluripotent stem cell, differentiated cell such as a primary NK cell, CAR-NK cell, primary T cell or CAR-T cell) or population thereof comprising a genome in which a gene has been edited to delete a contiguous stretch of genomic DNA, thereby reducing or eliminating surface expression of MHC class II molecules in the cell or population thereof. In numerous embodiments, the present disclosure provides a cell (e.g., stem cell, induced pluripotent stem cell, differentiated cell, hematopoietic stem cell, primary T cell or CAR-T cell) or population thereof comprising a genome in which one or more genes has been edited to delete a contiguous stretch of genomic DNA, thereby reducing or eliminating surface expression of MHC class I and II molecules in the cell or population thereof.

In certain embodiments, the expression of MHC I molecules and/or MHC II molecules is modulated by targeting and deleting a contiguous stretch of genomic DNA, thereby reducing or eliminating expression of a target gene selected from the group consisting of B2M, CIITA, and NLRC5. In some embodiments, described herein are genetically edited cells (e.g., modified human cells) comprising exogenous CD47 proteins and inactivated or modified CIITA gene sequences, and in some instances, additional gene modifications that inactivate or modify B2M gene sequences. In some embodiments, described herein are genetically edited cells comprising exogenous CD47 proteins and inactivated or modified CIITA gene sequences, and in some instances, additional gene modifications that inactivate or modify NLRC5 gene sequences. In some embodiments, described herein are genetically edited cells comprising exogenous CD47 proteins and inactivated or modified B2M gene sequences, and in some instances, additional gene modifications that inactivate or modify NLRC5 gene sequences. In some embodiments, described herein are genetically edited cells comprising exogenous CD47 proteins and inactivated or modified B2M gene sequences, and in some instances, additional gene modifications that inactivate or modify CIITA gene sequences and NLRC5 gene sequences.

Provided herein are cells exhibiting a modification of one or more targeted polynucleotide sequences that regulates the expression of any one of the following: (a) MHC I antigens, (b) MHC II antigens, (c) TCR complexes, (d) both MHC I and II antigens, and (e) MHC I and II antigens and TCR complexes. In certain embodiments, the modification includes increasing expression of CD47. In some embodiments, the cells include an exogenous or recombinant CD47 polypeptide. In certain embodiments, the modification includes expression of a chimeric antigen receptor. In some embodiments, the cells comprise an exogenous or recombinant chimeric antigen receptor polypeptide.

In some embodiments, the cell includes a genomic modification of one or more targeted polynucleotide sequences that regulates the expression of MHC I antigens, MHC II antigens and/or TCR complexes. In some embodiments, a genetic editing system is used to modify one or more targeted polynucleotide sequences. In some embodiments, the polynucleotide sequence targets one or more genes selected from the group consisting of B2M, CIITA, TRAC, and TRB. In certain embodiments, the genome of a T cell (e.g., a T cell differentiated from hypoimmunogenic iPSCs and a primary T cell) has been altered to reduce or delete critical components of HLA and TCR expression, e.g., HLA-A antigen, HLA-B antigen, HLA-C antigen, HLA-DP antigen, HLA-DQ antigen, HLA-DR antigens, TCR-alpha and TCR-beta.

In some embodiments, the present disclosure provides a cell or population thereof comprising a genome in which a gene has been edited to delete a contiguous stretch of genomic DNA, thereby reducing or eliminating surface expression of MHC class I molecules in the cell or population thereof. In certain embodiments, the present disclosure provides a cell or population thereof comprising a genome in which a gene has been edited to delete a contiguous stretch of genomic DNA, thereby reducing or eliminating surface expression of MHC class II molecules in the cell or population thereof. In certain embodiments, the present disclosure provides a cell or population thereof comprising a genome in which a gene has been edited to delete a contiguous stretch of genomic DNA, thereby reducing or eliminating surface expression of TCR molecules in the cell or population thereof. In numerous embodiments, the present disclosure provides a cell or population thereof comprising a genome in which one or more genes has been edited to delete a contiguous stretch of genomic DNA, thereby reducing or eliminating surface expression of MHC class I and II molecules and TCR complex molecules in the cell or population thereof.

In some embodiments, the cells and methods described herein include genomically editing human cells to cleave CIITA gene sequences as well as editing the genome of such cells to alter one or more additional target polynucleotide sequences such as, but not limited to, B2M TRAC, and TRB. In some embodiments, the cells and methods described herein include genomically editing human cells to cleave B2M gene sequences as well as editing the genome of such cells to alter one or more additional target polynucleotide sequences such as, but not limited to, CIITA, TRAC, and TRB. In some embodiments, the cells and methods described herein include genomically editing human cells to cleave TRAC gene sequences as well as editing the genome of such cells to alter one or more additional target polynucleotide sequences such as, but not limited to, B2M, CIITA, and TRB. In some embodiments, the cells and methods described herein include genomically editing human cells to cleave TRB gene sequences as well as editing the genome of such cells to alter one or more additional target polynucleotide sequences such as, but not limited to, B2M, CIITA, and TRAC.

Provided herein are hypoimmunogenic stem cells comprising reduced expression of HLA-A, HLA-B, HLA-C, HLA-DP, HLA-DQ, HLA-DR, B2M, CIITA, TCR-alpha, and TCR-beta relative to a wild-type stem cell, the hypoimmunogenic stem cell further comprising a set of exogenous polynucleotides comprising a first exogenous polynucleotide encoding CD47 and a second exogenous polynucleotide encoding a chimeric antigen receptor (CAR), wherein the first and/or second exogenous polynucleotides are inserted into a specific locus of at least one allele of the cell. Also provided herein are hypoimmunogenic primary T cells including any subtype of primary T cells comprising reduced expression of HLA-A, HLA-B, HLA-C, HLA-DP, HLA-DQ, HLA-DR, B2M, CIITA, TCR-alpha, and TCR-beta relative to a wild-type primary T cell, the hypoimmunogenic stem cell further comprising a set of exogenous polynucleotides comprising a first exogenous polynucleotide encoding CD47 and a second exogenous polynucleotide encoding a chimeric antigen receptor (CAR), wherein the first and/or second exogenous polynucleotides are inserted into a specific locus of at least one allele of the cell. Further provided herein are hypoimmunogenic T cells differentiated from hypoimmunogenic induced pluripotent stem cells comprising reduced expression of HLA-A, HLA-B, HLA-C, HLA-DP, HLA-DQ, HLA-DR, B2M, CIITA, TCR-alpha, and TCR-beta relative to a wild-type primary T cell, the hypoimmunogenic stem cell further comprising a set of exogenous polynucleotides comprising a first exogenous polynucleotide encoding CD47 and a second exogenous polynucleotide encoding a chimeric antigen receptor (CAR), wherein the first and/or second exogenous polynucleotides are inserted into a specific locus of at least one allele of the cell.

In some embodiments, the population of engineered cells described evades NK cell mediated cytotoxicity upon administration to a recipient patient. In some embodiments, the population of engineered cells evades NK cell mediated cytotoxicity by one or more subpopulations of NK cells. In some embodiments, the population of engineered eis protected from cell lysis by NK cells, including immature and/or mature NK cells upon administration to a recipient patient. In some embodiments, the population of engineered cells evades macrophage engulfment upon administration to a recipient patient. In some embodiments, the population of engineered cells does not induce an innate and/or an adaptive immune response to the cell upon administration to a recipient patient.

In some embodiments, the cells described herein comprise a safety switch. The term "safety switch" used herein refers to a system for controlling the expression of a gene or protein of interest that, when downregulated or upregulated, leads to clearance or death of the cell, e.g., through recognition by the host's immune system. A safety switch can be designed to be triggered by an exogenous molecule in case of an adverse clinical event. A safety switch can be engineered by regulating the expression on the DNA, RNA and protein levels. A safety switch includes a protein or molecule that allows for the control of cellular activity in response to an adverse event. In one embodiment, the safety switch is a "kill switch" that is expressed in an inactive state and is fatal to a cell expressing the safety switch upon activation of the switch by a selective, externally provided agent. In one embodiment, the safety switch gene is cis-acting in relation to the gene of interest in a construct. Activation of the safety switch causes the cell to kill solely itself or itself and neighboring cells through apoptosis or necrosis. In some embodiments, the cells described herein, e.g., stem cells, induced pluripotent stem cells, hematopoietic stem cells, primary cells, or differentiated cell, including, but not limited to, T cells, CAR-T cells, NK cells, and/or CAR-NK cells, comprise a safety switch.

In some embodiments, the safety switch comprises a therapeutic agent that inhibits or blocks the interaction of CD47 and SIRPα. In some aspects, the CD47-SIRPα blockade agent is an agent that neutralizes, blocks, antagonizes, or interferes with the cell surface expression of CD47, SIRPα, or both. In some embodiments, the CD47-SIRPα blockade agent inhibits or blocks the interaction of CD47, SIRPα or both. In some embodiments, a CD47-SIRPα blockade agent (e.g., a CD47-SIRPα blocking, inhibiting, reducing, antagonizing, neutralizing, or interfering agent) comprises an agent selected from a group that includes an antibody or fragment thereof that binds CD47, a bispecific antibody that binds CD47, an immunocytokine fusion protein that bind CD47, a CD47 containing fusion protein, an antibody or fragment thereof that binds SIRPα, a bispecific antibody that binds SIRPα, an immunocytokine fusion protein that bind SIRPα, an SIRPα containing fusion protein, and a combination thereof.

In some embodiments, the cells described herein comprise a "suicide gene" (or "suicide switch"). The suicide gene can cause the death of the hypoimmunogenic cells should they grow and divide in an undesired manner. The suicide gene ablation approach includes a suicide gene in a gene transfer vector encoding a protein that results in cell killing only when activated by a specific compound. A suicide gene can encode an enzyme that selectively converts a nontoxic compound into highly toxic metabolites. In some embodiments, the cells described herein, e.g., stem cells, induced pluripotent stem cells, hematopoietic stem cells, primary cells, or differentiated cell, including, but not limited to, T cells, CAR-T cells, NK cells, and/or CAR-NK cells, comprise a suicide gene.

In some embodiments, the population of engineered cells described elicits a reduced level of immune activation or no immune activation upon administration to a recipient subject. In some embodiments, the cells elicit a reduced level of systemic TH1 activation or no systemic TH1 activation in a recipient subject. In some embodiments, the cells elicit a reduced level of immune activation of peripheral blood mononuclear cells (PBMCs) or no immune activation of PBMCs in a recipient subject. In some embodiments, the cells elicit a reduced level of donor-specific IgG antibodies or no donor specific IgG antibodies against the cells upon administration to a recipient subject. In some embodiments, the cells elicit a reduced level of IgM and IgG antibody production or no IgM and IgG antibody production against the cells in a recipient subject. In some embodiments, the cells elicit a reduced level of cytotoxic T cell killing of the cells upon administration to a recipient subject.

B. CIITA

In some embodiments, the technologies disclosed herein modulate (e.g., reduces or eliminates) the expression of MHC II genes by targeting and modulating (e.g., reducing or eliminating) Class II transactivator (CIITA) expression. In some embodiments, the modulation occurs using a CRISPR/Cas system. CIITA is a member of the LR or nucleotide binding domain (NBD) leucine-rich repeat (LRR) family of proteins and regulates the transcription of MHC II by associating with the MHC enhanceosome.

In some embodiments, the target polynucleotide sequence of the present disclosure is a variant of CIITA. In some embodiments, the target polynucleotide sequence is a homolog of CIITA. In some embodiments, the target polynucleotide sequence is an ortholog of CIITA.

In some embodiments, reduced or eliminated expression of CIITA reduces or eliminates expression of one or more of the following MHC class II are HLA-DP, HLA-DM, HLA-DOA, HLA-DOB, HLA-DQ, and HLA-DR.

In some embodiments, the cells described herein comprise gene modifications at the gene locus encoding the CIITA protein. In other words, the cells comprise a genetic modification at the CIITA locus. In some instances, the nucleotide sequence encoding the CIITA protein is set forth in RefSeq. No. NM_000246.4 and NCBI Genbank No. U18259. In some instances, the CIITA gene locus is described in NCBI Gene ID No. 4261. In certain cases, the amino acid sequence of CIITA is depicted as NCBI GenBank No. AAA88861.1. Additional descriptions of the CIITA protein and gene locus can be found in Uniprot No. P33076, HGNC Ref No. 7067, and OMIM Ref No. 600005.

In some embodiments, the hypoimmunogenic cells outlined herein comprise a genetic modification targeting the CIITA gene. In some embodiments, the genetic modification targeting the CIITA gene by the rare-cutting endonuclease comprises a Cas protein or a polynucleotide encoding a Cas protein, and at least one guide ribonucleic acid sequence for specifically targeting the CIITA gene. In some embodiments, the at least one guide ribonucleic acid sequence for specifically targeting the CIITA gene is selected from the group consisting of SEQ ID NOS:5184-36352 of Table 12 of WO2016183041, which is herein incorporated by reference. In some embodiments, the cell has a reduced ability to induce an innate and/or an adaptive immune response in a recipient subject. In some embodiments, an exogenous nucleic acid encoding a polypeptide as disclosed herein (e.g., a chimeric antigen receptor, CD47, or another tolerogenic factor disclosed herein) is inserted at the CIITA gene.

Assays to test whether the CIITA gene has been inactivated are known and described herein. In some embodiments, the resulting genetic modification of the CIITA gene by PCR and the reduction of HLA-II expression can be assays by FACS analysis. In another embodiment, CIITA protein expression is detected using a Western blot of cells lysates probed with antibodies to the CIITA protein. In another embodiment, reverse transcriptase polymerase chain reactions (RT-PCR) are used to confirm the presence of the inactivating genetic modification. In some embodiments, the exogenous polynucleotide is inserted into at least one allele of the cell using viral transduction, for example, with a vector. In some embodiments, the vector is a pseudotyped, self-inactivating lentiviral vector that carries the exogenous polynucleotide. In some embodiments, the vector is a self-inactivating lentiviral vector pseudotyped with a vesicular stomatitis VSV-G envelope, and which carries the exogenous polynucleotide. In some embodiments, the exogenous polynucleotide is inserted into at least one allele of the cell using viral transduction. In some embodiments, the exogenous polynucleotide is inserted into at least one allele of the cell using a lentivirus based viral vector.

C. B2M

In some embodiments, the technologies disclosed herein modulate (e.g., reduce or eliminate) the expression of MHC-I genes by targeting and modulating (e.g., reducing or eliminating) expression of the accessory chain B2M. In some embodiments, the modulation occurs using a CRISPR/Cas system. By modulating (e.g., reducing or deleting) expression of B2M, surface trafficking of MHC-I molecules is blocked and the cell rendered hypoimmunogenic. In some embodiments, the cell has a reduced ability to induce an innate and/or an adaptive immune response in a recipient subject.

In some embodiments, the target polynucleotide sequence of the present disclosure is a variant of B2M. In some embodiments, the target polynucleotide sequence is a homolog of B2M. In some embodiments, the target polynucleotide sequence is an ortholog of B2M.

In some embodiments, decreased or eliminated expression of B2M reduces or eliminates expression of one or more of the following MHC I molecules: HLA-A, HLA-B, and HLA-C.

In some embodiments, the cells described herein comprise gene modifications at the gene locus encoding the B2M protein. In other words, the cells comprise a genetic modification at the B2M locus. In some instances, the nucleotide sequence encoding the B2M protein is set forth in RefSeq. No. NM_004048.4 and Genbank No. AB021288.1. In some instances, the B2M gene locus is described in NCBI Gene ID No. 567. In certain cases, the amino acid sequence of B2M is depicted as NCBI GenBank No. BAA35182.1. Additional descriptions of the B2M protein and gene locus can be found in Uniprot No. P61769, HGNC Ref. No. 914, and OMIM Ref No. 109700.

In some embodiments, the hypoimmunogenic cells outlined herein comprise a genetic modification targeting the B2M gene. In some embodiments, the genetic modification targeting the B2M gene by the rare-cutting endonuclease comprises a Cas protein or a polynucleotide encoding a Cas protein, and at least one guide ribonucleic acid sequence for specifically targeting the B2M gene. In some embodiments, the at least one guide ribonucleic acid sequence for specifically targeting the B2M gene is selected from the group consisting of SEQ ID NOS:81240-85644 of Table 15 of WO2016183041, which is herein incorporated by reference. In some embodiments, an exogenous nucleic acid encoding a polypeptide as disclosed herein (e.g., a chimeric antigen receptor, CD47, or another tolerogenic factor disclosed herein) is inserted at the B2M gene. In some embodiments, the exogenous polynucleotide is inserted into at least one allele of the cell using viral transduction, for example, with a vector. In some embodiments, the vector is a pseudotyped, self-inactivating lentiviral vector that carries the exogenous polynucleotide. In some embodiments, the vector is a self-inactivating lentiviral vector pseudotyped with a vesicular stomatitis VSV-G envelope, and which carries the exogenous polynucleotide. In some embodiments, the exogenous polynucleotide is inserted into at least one allele of the cell using viral transduction. In some embodiments, the exogenous polynucleotide is inserted into at least one allele of the cell using a lentivirus based viral vector.

Assays to test whether the B2M gene has been inactivated are known and described herein. In some embodiments, the resulting genetic modification of the B2M gene by PCR and the reduction of HLA-I expression can be assays by FACS analysis. In another embodiment, B2M protein expression is detected using a Western blot of cells lysates probed with antibodies to the B2M protein. In another embodiment, reverse transcriptase polymerase chain reactions (RT-PCR) are used to confirm the presence of the inactivating genetic modification.

D. NLRC5

In many embodiments, the technologies disclosed herein modulate (e.g., reduce or eliminate) the expression of MHC-I genes by targeting and modulating (e.g., reducing or eliminating) expression of the NLR family, CARD domain containing 5/NOD27/CLR16.1 (NLRC5). In some embodiments, the modulation occurs using a CRISPR/Cas system. NLRC5 is a critical regulator of MHC-I-mediated immune responses and, similar to CIITA, NLRC5 is highly inducible by IFN-γ and can translocate into the nucleus. NLRC5 activates the promoters of MHC-I genes and induces the transcription of MHC-I as well as related genes involved in MHC-I antigen presentation.

In some embodiments, the target polynucleotide sequence is a variant of NLRC5. In some embodiments, the target polynucleotide sequence is a homolog of NLRC5. In some embodiments, the target polynucleotide sequence is an ortholog of NLRC5.

In some embodiments, decreased or eliminated expression of NLRC5 reduces or eliminates expression of one or more of the following MHC I molecules—HLA-A, HLA-B, and HLA-C.

In some embodiments, the cells outlined herein comprise a genetic modification targeting the NLRC5 gene. In some embodiments, the genetic modification targeting the NLRC5 gene by the rare-cutting endonuclease comprises a Cas protein or a polynucleotide encoding a Cas protein, and at least one guide ribonucleic acid sequence for specifically targeting the NLRC5 gene. In some embodiments, the at least one guide ribonucleic acid sequence for specifically targeting the NLRC5 gene is selected from the group consisting of SEQ ID NOS:36353-81239 of Appendix 3 or Table 14 of WO2016183041, the disclosure is incorporated by reference in its entirety.

Assays to test whether the NLRC5 gene has been inactivated are known and described herein. In some embodiments, the resulting genetic modification of the NLRC5 gene by PCR and the reduction of HLA-I expression can be assays by FACS analysis. In another embodiment, NLRC5 protein expression is detected using a Western blot of cells lysates probed with antibodies to the NLRC5 protein. In another embodiment, reverse transcriptase polymerase chain reactions (RT-PCR) are used to confirm the presence of the inactivating genetic modification.

E. TRAC

In many embodiments, the technologies disclosed herein modulate (e.g., reduce or eliminate) the expression of TCR genes including the TRAC gene by targeting and modulating (e.g., reducing or eliminating) expression of the constant region of the T cell receptor alpha chain. In some embodiments, the modulation occurs using a CRISPR/Cas system. By modulating (e.g., reducing or deleting) expression of TRAC, surface trafficking of TCR molecules is blocked. In some embodiments, the cell also has a reduced ability to induce an innate and/or an adaptive immune response in a recipient subject.

In some embodiments, the target polynucleotide sequence of the present disclosure is a variant of TRAC. In some embodiments, the target polynucleotide sequence is a homolog of TRAC. In some embodiments, the target polynucleotide sequence is an ortholog of TRAC.

In some embodiments, decreased or eliminated expression of TRAC reduces or eliminates TCR surface expression.

In some embodiments, the cells, such as, but not limited to, pluripotent stem cells, induced pluripotent stem cells, T cells differentiated from induced pluripotent stem cells, primary T cells, and cells derived from primary T cells comprise gene modifications at the gene locus encoding the TRAC protein. In other words, the cells comprise a genetic modification at the TRAC locus. In some instances, the nucleotide sequence encoding the TRAC protein is set forth in Genbank No. X02592.1. In some instances, the TRAC gene locus is described in RefSeq. No. NG_001332.3 and NCBI Gene ID No. 28755. In certain cases, the amino acid sequence of TRAC is depicted as Uniprot No. P01848. Additional descriptions of the TRAC protein and gene locus can be found in Uniprot No. P01848, HGNC Ref No. 12029, and OMIM Ref. No. 186880.

In some embodiments, the hypoimmunogenic cells outlined herein comprise a genetic modification targeting the TRAC gene. In some embodiments, the genetic modification targeting the TRAC gene by the rare-cutting endonuclease comprises a Cas protein or a polynucleotide encoding a Cas protein, and at least one guide ribonucleic acid sequence for specifically targeting the TRAC gene. In some embodiments, the at least one guide ribonucleic acid sequence for specifically targeting the TRAC gene is selected from the group consisting of SEQ ID NOS:532-609 and 9102-9797 of US20160348073, which is herein incorporated by reference.

Assays to test whether the TRAC gene has been inactivated are known and described herein. In some embodiments, the resulting genetic modification of the TRAC gene by PCR and the reduction of TCR expression can be assays by FACS analysis. In another embodiment, TRAC protein expression is detected using a Western blot of cells lysates probed with antibodies to the TRAC protein. In another embodiment, reverse transcriptase polymerase chain reactions (RT-PCR) are used to confirm the presence of the inactivating genetic modification.

F. TRB

In many embodiments, the technologies disclosed herein modulate (e.g., reduce or eliminate) the expression of TCR genes including the gene encoding T cell antigen receptor, beta chain (e.g., the TRB, TRBC, or TCRB gene) by targeting and modulating (e.g., reducing or eliminating) expression of the constant region of the T cell receptor beta chain. In some embodiments, the modulation occurs using a CRISPR/Cas system. By modulating (e.g., reducing or deleting) expression of TRB, surface trafficking of TCR molecules is blocked. In some embodiments, the cell also has a reduced ability to induce an innate and/or an adaptive immune response in a recipient subject.

In some embodiments, the target polynucleotide sequence of the present disclosure is a variant of TRB. In some embodiments, the target polynucleotide sequence is a homolog of TRB. In some embodiments, the target polynucleotide sequence is an ortholog of TRB.

In some embodiments, decreased or eliminated expression of TRB reduces or eliminates TCR surface expression.

In some embodiments, the cells, such as, but not limited to, pluripotent stem cells, induced pluripotent stem cells, T cells differentiated from induced pluripotent stem cells, primary T cells, and cells derived from primary T cells comprise gene modifications at the gene locus encoding the TRB protein. In other words, the cells comprise a genetic modification at the TRB gene locus. In some instances, the nucleotide sequence encoding the TRB protein is set forth in UniProt No. P0DSE2. In some instances, the TRB gene locus is described in RefSeq. No. NG_001333.2 and NCBI Gene ID No. 6957. In certain cases, the amino acid sequence of TRB is depicted as Uniprot No. P01848. Additional descriptions of the TRB protein and gene locus can be found in GenBank No. L36092.2, Uniprot No. P0DSE2, and HGNC Ref No. 12155.

In some embodiments, the hypoimmunogenic cells outlined herein comprise a genetic modification targeting the TRB gene. In some embodiments, the genetic modification targeting the TRB gene by the rare-cutting endonuclease comprises a Cas protein or a polynucleotide encoding a Cas protein, and at least one guide ribonucleic acid sequence for specifically targeting the TRB gene. In some embodiments, the at least one guide ribonucleic acid sequence for specifically targeting the TRB gene is selected from the group consisting of SEQ ID NOS:610-765 and 9798-10532 of US20160348073, which is herein incorporated by reference.

Assays to test whether the TRB gene has been inactivated are known and described herein. In some embodiments, the resulting genetic modification of the TRB gene by PCR and the reduction of TCR expression can be assays by FACS analysis. In another embodiment, TRB protein expression is detected using a Western blot of cells lysates probed with antibodies to the TRB protein. In another embodiment, reverse transcriptase polymerase chain reactions (RT-PCR) are used to confirm the presence of the inactivating genetic modification.

G. CD142

In many embodiments, the technologies disclosed herein modulate (e.g., reduce or eliminate) the expression of CD142, which is also known as tissue factor, factor III, and F3. In some embodiments, the modulation occurs using a gene editing system (e.g., CRISPR/Cas).

In some embodiments, the target polynucleotide sequence is CD142 or a variant of CD142. In some embodiments, the target polynucleotide sequence is a homolog of CD142. In some embodiments, the target polynucleotide sequence is an ortholog of CD142.

In some embodiments, the cells outlined herein comprise a genetic modification targeting the CD142 gene. In some embodiments, the genetic modification targeting the CD142 gene by the rare-cutting endonuclease comprises a Cas protein or a polynucleotide encoding a Cas protein, and at least one guide ribonucleic acid (gRNA) sequence for specifically targeting the CD142 gene. Useful methods for identifying gRNA sequences to target CD142 are described below.

Assays to test whether the CD142 gene has been inactivated are known and described herein. In some embodiments, the resulting genetic modification of the CD142 gene by PCR and the reduction of CD142 expression can be assays by FACS analysis. In another embodiment, CD142 protein expression is detected using a Western blot of cells lysates probed with antibodies to the CD142 protein. In another embodiment, reverse transcriptase polymerase chain reactions (RT-PCR) are used to confirm the presence of the inactivating genetic modification.

Useful genomic, polynucleotide and polypeptide information about the human CD142 are provided in, for example, the GeneCard Identifier GC01M094530, HGNC No. 3541, NCBI Gene ID 2152, NCBI RefSeq Nos. NM_001178096.1, NM_001993.4, NP_001171567.1, and NP_001984.1, UniProt No. P13726, and the like.

H. CTLA-4

In some embodiments, the target polynucleotide sequence is CTLA-4 or a variant of CTLA-4. In some embodiments, the target polynucleotide sequence is a homolog of CTLA-4. In some embodiments, the target polynucleotide sequence is an ortholog of CTLA-4.

In some embodiments, the cells outlined herein comprise a genetic modification targeting the CTLA-4 gene. In certain embodiments, primary T cells comprise a genetic modification targeting the CTLA-4 gene. The genetic modification can reduce expression of CTLA-4 polynucleotides and CTLA-4 polypeptides in T cells includes primary T cells and CAR-T cells. In some embodiments, the genetic modification targeting the CTLA-4 gene by the rare-cutting endonuclease comprises a Cas protein or a polynucleotide encoding a Cas protein, and at least one guide ribonucleic acid (gRNA) sequence for specifically targeting the CTLA-4 gene. Useful methods for identifying gRNA sequences to target CTLA-4 are described below.

Assays to test whether the CTLA-4 gene has been inactivated are known and described herein. In some embodiments, the resulting genetic modification of the CTLA-4 gene by PCR and the reduction of CTLA-4 expression can be assays by FACS analysis. In another embodiment, CTLA-4 protein expression is detected using a Western blot of cells lysates probed with antibodies to the CTLA-4 protein. In another embodiment, reverse transcriptase polymerase chain reactions (RT-PCR) are used to confirm the presence of the inactivating genetic modification.

Useful genomic, polynucleotide and polypeptide information about the human CTLA-4 are provided in, for example, the GeneCard Identifier GC02P203867, HGNC No. 2505, NCBI Gene ID 1493, NCBI RefSeq Nos. NM_005214.4, NM_001037631.2, NP_001032720.1 and NP_005205.2, UniProt No. P16410, and the like.

I. PD-1

In some embodiments, the target polynucleotide sequence is PD-1 or a variant of PD-1. In some embodiments, the target polynucleotide sequence is a homolog of PD-1. In some embodiments, the target polynucleotide sequence is an ortholog of PD-1.

In some embodiments, the cells outlined herein comprise a genetic modification targeting the gene encoding the programmed cell death protein 1 (PD-1) protein or the PDCD1 gene. In certain embodiments, primary T cells comprise a genetic modification targeting the PDCD1 gene. The genetic modification can reduce expression of PD-1 polynucleotides and PD-1 polypeptides in T cells includes primary T cells and CAR-T cells. In some embodiments, the genetic modification targeting the PDCD1 gene by the rare-cutting endonuclease comprises a Cas protein or a polynucleotide encoding a Cas protein, and at least one guide ribonucleic acid (gRNA) sequence for specifically targeting the PDCD1 gene. Useful methods for identifying gRNA sequences to target PD-1 are described below.

Assays to test whether the PDCD1 gene has been inactivated are known and described herein. In some embodiments, the resulting genetic modification of the PDCD1 gene by PCR and the reduction of PD-1 expression can be assays by FACS analysis. In another embodiment, PD-1 protein expression is detected using a Western blot of cells lysates probed with antibodies to the PD-1 protein. In another embodiment, reverse transcriptase polymerase chain reactions (RT-PCR) are used to confirm the presence of the inactivating genetic modification.

Useful genomic, polynucleotide and polypeptide information about human PD-1 including the PDCD1 gene are provided in, for example, the GeneCard Identifier GC02M241849, HGNC No. 8760, NCBI Gene ID 5133, Uniprot No. Q15116, and NCBI RefSeq Nos. NM_005018.2 and NP_005009.2.

J. CD47

In some embodiments, the present disclosure provides a cell or population thereof that has been modified to express the tolerogenic factor (e.g., immunomodulatory polypeptide) CD47. In some embodiments, the present disclosure provides a method for altering a cell genome to express CD47. In some embodiments, the stem cell expresses exogenous CD47. In some instances, the cell expresses an expression vector comprising a nucleotide sequence encoding a human CD47 polypeptide. In some embodiments, the cell is genetically modified to comprise an integrated exogenous polynucleotide encoding CD47 using homology-directed repair. In some instances, the cell expresses a nucleotide sequence encoding a human CD47 polypeptide such that the nucleotide sequence is inserted into at least one allele of a safe harbor or target locus. In some instances, the cell expresses a nucleotide sequence encoding a human CD47 polypeptide wherein the nucleotide sequence is inserted into at least one allele of an AAVS1 locus. In some instances, the cell expresses a nucleotide sequence encoding a human CD47 polypeptide wherein the nucleotide sequence is inserted into at least one allele of an CCR5 locus. In some instances, the cell expresses a nucleotide sequence encoding a human CD47 polypeptide wherein the nucleotide sequence is inserted into at least one allele of a safe harbor or target gene locus, such as, but not limited to, a CCR5 gene locus, a CXCR4 gene locus, a PPP1R12C gene locus, an albumin gene locus, a SHS231 gene locus, a CLYBL gene locus, a Rosa gene locus, an F3 (CD142) gene locus, a MICA gene locus, a MICB gene locus, a LRP1 (CD91) gene locus, a HMGB1 gene locus, an ABO gene locus, an RHD gene locus, a FUT1 locus, and a KDM5D gene locus. In some instances, the cell expresses a nucleotide sequence encoding a human CD47 polypeptide wherein the nucleotide sequence is inserted into at least one allele of a TRAC locus.

CD47 is a leukocyte surface antigen and has a role in cell adhesion and modulation of integrins. It is expressed on the surface of a cell and signals to circulating macrophages not to eat the cell.

In some embodiments, the cell outlined herein comprises a nucleotide sequence encoding a CD47 polypeptide has at least 95% sequence identity (e.g., 95%, 96%, 97%, 98%, 99%, or more) to an amino acid sequence as set forth in NCBI Ref Sequence Nos. NP_001768.1 and NP_942088.1. In some embodiments, the cell outlined herein comprises a nucleotide sequence encoding a CD47 polypeptide having an amino acid sequence as set forth in NCBI Ref. Sequence Nos. NP_001768.1 and NP_942088.1. In some embodiments, the cell comprises a nucleotide sequence for CD47 having at least 85% sequence identity (e.g., 85%, 86%, 87%, 88%, 89%, 90%, 91%, 92%, 93%, 94%, 95%, 96%, 97%, 98%, 99%, or more) to the sequence set forth in NCBI Ref Nos. NM_001777.3 and NM_198793.2. In some embodiments, the cell comprises a nucleotide sequence for CD47 as set forth in NCBI Ref. Sequence Nos. NM_001777.3 and NM_198793.2. In some embodiments, the nucleotide sequence encoding a CD47 polynucleotide is a codon optimized sequence. In some embodiments, the nucleotide sequence encoding a CD47 polynucleotide is a human codon optimized sequence.

In some embodiments, the cell comprises a CD47 polypeptide having at least 9500 sequence identity (e.g., 95%, 96%, 97%, 98%, 99%, or more) to an amino acid sequence as set forth in NCBI Ref Sequence Nos. NP_001768.1 and NP_942088.1. In some embodiments, the cell outlined herein comprises a CD47 polypeptide having an amino acid sequence as set forth in NCBI Ref Sequence Nos. NP_001768.1 and NP_942088.1.

Exemplary amino acid sequences of human CD47 with a signal sequence and without a signal sequence are provided in Table 1.

TABLE 1

Amino acid sequences of human CD47

| Protein | SEQ ID NO: | Sequence | Amino acid residues |
|---|---|---|---|
| Human CD47 (without signal sequence) | 13 | QLLFNKTKSVEFTFCNDTVVIPCFVTNMEAQNTTEV YVKWKFKGRDIYTFDGALNKSTVPTDFSSAKIEVS QLLKGDASLKMDKSDAVSHTGNYTCEVTELTREG ETIIELKYRVVSWFSPNENILIVIFPIFAILLFWGQFGI KTLKYRSGGMDEKTIALLVAGLVITVIVIVGAILFVP GEYSLKNATGLGLIVTSTGILILLHYYVFSTAIGLTSF VIAILVIQVIAYILAVVGLSLCIAACIPMHGPLLISGL SILALAQLLGLVYMKFVASNQKTIQPPRKAVEEPLN AFKESKGMMNDE | aa 19-323 |
| Human CD47 (with signal sequence) | 14 | MWPLVAALLLGSACCGSAQLLFNKTKSVEFTFCND TVVIPCFVTNMEAQNTTEVYVKWKFKGRDIYTFDG ALNKSTVPTDFSSAKIEVSQLLKGDASLKMDKSDA VSHTGNYTCEVTELTREGETIIELKYRVVSWFSPNE NILIVIFPIFAILLFWGQFGIKTLKYRSGGMDEKTIAL LVAGLVITVIVIVGAILFVPGEYSLKNATGLGLIVTS TGILILLHYYVFSTAIGLTSFVIAILVIQVIAYILAVVG LSLCIAACIPMHGPLLISGLSILALAQLLGLVYMKFV ASNQKTIQPPRKAVEEPLNAFKESKGMMNDE | aa 1-323 |

In some embodiments, the cell comprises a CD47 polypeptide having at least 9500 sequence identity (e.g., 9500, 9600, 9700, 9800, 9900, or more) to the amino acid sequence of SEQ ID NO: 142. In some embodiments, the cell comprises a CD47 polypeptide having the amino acid sequence of SEQ ID NO:142. In some embodiments, the cell comprises a CD47 polypeptide having at least 95% sequence identity (e.g., 95%, 96%, 97%, 98%, 99%, or more) to the amino acid sequence of SEQ ID NO:143. In some embodiments, the cell comprises a CD47 polypeptide having the amino acid sequence of SEQ ID NO:143.

In some embodiments, the cell comprises a nucleotide sequence encoding a CD47 polypeptide having at least 95% sequence identity (e.g., 95%, 96%, 97%, 98%, 99%, or more) to the amino acid sequence of SEQ ID NO:142. In some embodiments, the cell comprises a nucleotide sequence encoding a CD47 polypeptide having the amino acid sequence of SEQ ID NO:142. In some embodiments, the cell comprises a nucleotide sequence encoding a CD47 polypeptide having at least 95% sequence identity (e.g., 95%, 96%, 97%, 98%, 99%, or more) to the amino acid sequence of SEQ ID NO:143. In some embodiments, the cell comprises a nucleotide sequence encoding a CD47 polypeptide having the amino acid sequence of SEQ ID NO:143. In some embodiments, the nucleotide sequence is codon optimized for expression in a particular cell.

In some embodiments, a suitable gene editing system (e.g., CRISPR/Cas system or any of the gene editing systems described herein) is used to facilitate the insertion of a polynucleotide encoding CD47, into a genomic locus of the hypoimmunogenic cell. In some cases, the polynucleotide encoding CD47 is inserted into a safe harbor or target locus, such as but not limited to, an AAVS1, CCR5, CLYBL, ROSA26, SHS231, F3 (CD142), MICA, MICB, LRP1 (CD91), HMGB1, ABO, RHD, FUT1, or KDM5D gene locus. In some embodiments, the polynucleotide encoding CD47 is inserted into a B2M gene locus, a CIITA gene locus, a TRAC gene locus, or a TRB gene locus. In some embodiments, the polynucleotide encoding CD47 is inserted into any one of the gene loci depicted in Table 15 provided herein. In certain embodiments, the polynucleotide encoding CD47 is operably linked to a promoter.

In some embodiments, the polynucleotide encoding CD47 is inserted into at least one allele of the T cell using viral transduction. In some embodiments, the polynucleotide encoding CD47 is inserted into at least one allele of the T cell using a lentivirus based viral vector. In some embodiments, the lentivirus based viral vector is a pseudotyped, self-inactivating lentiviral vector that carries the polynucleotide encoding CD47. In some embodiments, the lentivirus based viral vector is a self-inactivating lentiviral vector pseudotyped with a vesicular stomatitis VSV-G envelope, and which carries the polynucleotide encoding CD47.

In another embodiment, CD47 protein expression is detected using a Western blot of cell lysates probed with antibodies against the CD47 protein. In another embodiment, reverse transcriptase polymerase chain reactions (RT-PCR) are used to confirm the presence of the exogenous CD47 mRNA.

K. CD24

In some embodiments, the present disclosure provides a cell or population thereof that has been modified to express the tolerogenic factor (e.g., immunomodulatory polypeptide) CD24. In some embodiments, the present disclosure provides a method for altering a cell genome to express CD24. In some embodiments, the stem cell expresses exogenous CD24. In some instances, the cell expresses an expression vector comprising a nucleotide sequence encoding a human CD24 polypeptide. In some embodiments, the exogenous polynucleotide is inserted into at least one allele of the cell using viral transduction, for example, with a vector. In some embodiments, the vector is a pseudotyped, self-inactivating lentiviral vector that carries the exogenous polynucleotide. In some embodiments, the vector is a self-inactivating lentiviral vector pseudotyped with a vesicular stomatitis VSV-G envelope, and which carries the exogenous polynucleotide. In some embodiments, the exogenous polynucleotide is inserted into at least one allele of the cell using viral transduction. In some embodiments, the exogenous polynucleotide is inserted into at least one allele of the cell using a lentivirus based viral vector.

CD24 which is also referred to as a heat stable antigen or small-cell lung cancer cluster 4 antigen is a glycosylated glycosylphosphatidylinositol-anchored surface protein (Pirruccello et al., J Immunol, 1986, 136, 3779-3784; Chen et al., Glycobiology, 2017, 57, 800-806). It binds to Siglec-10 on innate immune cells. Recently it has been shown that CD24 via Siglec-10 acts as an innate immune checkpoint (Barkal et al., Nature, 2019, 572, 392-396).

In some embodiments, the cell outlined herein comprises a nucleotide sequence encoding a CD24 polypeptide has at least 95% sequence identity (e.g., 95%, 96%, 97%, 98%, 99%, or more) to an amino acid sequence set forth in NCBI Ref Nos. NP_001278666.1, NP_001278667.1, NP_001278668.1, and NP_037362.1. In some embodiments, the cell outlined herein comprises a nucleotide sequence encoding a CD24 polypeptide having an amino acid sequence set forth in NCBI Ref. Nos. NP_001278666.1, NP_001278667.1, NP_001278668.1, and NP_037362.1.

In some embodiments, the cell comprises a nucleotide sequence having at least 85% sequence identity (e.g., 85%, 86%, 87%, 88%, 89%, 90%, 91%, 92%, 93%, 94%, 95%, 96%, 97%, 98%, 99%, or more) to the sequence set forth in NCBI Ref. Nos. NM_00129737.1, NM_00129738.1, NM_001291739.1, and NM_013230.3. In some embodiments, the cell comprises a nucleotide sequence as set forth in NCBI Ref. Nos. NM_00129737.1, NM_00129738.1, NM_001291739.1, and NM_013230.3.

In some embodiments, a suitable gene editing system (e.g., CRISPR/Cas system or any of the gene editing systems described herein) is used to facilitate the insertion of a polynucleotide encoding CD24, into a genomic locus of the hypoimmunogenic cell. In some cases, the polynucleotide encoding CD24 is inserted into a safe harbor or target locus, such as but not limited to, an AAVS1, CCR5, CLYBL, ROSA26, SHS231, F3 (CD142), MICA, MICB, LRP1 (CD91), HMGB1, ABO, RHD, FUT1, or KDM5D gene locus. In some embodiments, the polynucleotide encoding CD24 is inserted into a B2M gene locus, a CIITA gene locus, a TRAC gene locus, or a TRB gene locus. In some embodiments, the polynucleotide encoding CD24 is inserted into any one of the gene loci depicted in Table 15 provided herein. In certain embodiments, the polynucleotide encoding CD24 is operably linked to a promoter.

In another embodiment, CD24 protein expression is detected using a Western blot of cells lysates probed with antibodies against the CD24 protein. In another embodiment, reverse transcriptase polymerase chain reactions (RT-PCR) are used to confirm the presence of the exogenous CD24 mRNA.

In some embodiments, a suitable gene editing system (e.g., CRISPR/Cas system or any of the gene editing systems described herein) is used to facilitate the insertion of a polynucleotide encoding CD24, into a genomic locus of the hypoimmunogenic cell. In some cases, the polynucleotide encoding CD24 is inserted into a safe harbor or target locus, such as but not limited to, an AAVS1, CCR5, CLYBL, ROSA26, SHS231, F3 (also known as CD142), MICA, MICB, LRP1 (also known as CD91), HMGB1, ABO, RHD, FUT1, or KDM5D gene locus. In some embodiments, the polynucleotide encoding CD24 is inserted into a B2M gene locus, a CIITA gene locus, a TRAC gene locus, or a TRB gene locus. In some embodiments, the polynucleotide encoding CD24 is inserted into any one of the gene loci depicted in Table 15 provided herein. In certain embodiments, the polynucleotide encoding CD24 is operably linked to a promoter.

L. DUX4

In some embodiments, the present disclosure provides a cell (e.g., stem cell, induced pluripotent stem cell, differentiated cell, hematopoietic stem cell, primary T cell or CAR-T cell) or population thereof comprising a genome modified to increase expression of a tolerogenic or immunosuppressive factor such as DUX4. In some embodiments, the present disclosure provides a method for altering a cell's genome to provide increased expression of DUX4, including through a exogenous polynucleotide. In some embodiments, the disclosure provides a cell or population thereof comprising exogenously expressed DUX4 proteins. In some embodiments, increased expression of DUX4 suppresses, reduces or eliminates expression of one or more of the following MHC I molecules—HLA-A, HLA-B, and HLA-C. In some embodiments, the exogenous polynucleotide is inserted into at least one allele of the cell using viral transduction, for example, with a vector. In some embodiments, the vector is a pseudotyped, self-inactivating lentiviral vector that carries the exogenous polynucleotide. In some embodiments, the vector is a self-inactivating lentiviral vector pseudotyped with a vesicular stomatitis VSV-G envelope, and which carries the exogenous polynucleotide. In some embodiments, the exogenous polynucleotide is inserted into at least one allele of the cell using viral transduction. In some embodiments, the exogenous polynucleotide is inserted into at least one allele of the cell using a lentivirus based viral vector.

DUX4 is a transcription factor that is active in embryonic tissues and induced pluripotent stem cells, and is silent in normal, healthy somatic tissues (Feng et al., 2015, ELife4; De Iaco et al., 2017, Nat Genet, 49, 941-945; Hendrickson et al., 2017, Nat Genet, 49, 925-934; Snider et al., 2010, PLoS Genet, e1001181; Whiddon et al., 2017, Nat Genet). DUX4 expression acts to block IFN-gamma mediated induction of major histocompatibility complex (MHC) class I gene expression (e.g., expression of B2M, HLA-A, HLA-B, and HLA-C). DUX4 expression has been implicated in suppressed antigen presentation by MHC class I (Chew et al., Developmental Cell, 2019, 50, 1-14). DUX4 functions as a transcription factor in the cleavage-stage gene expression (transcriptional) program. Its target genes include, but are not limited to, coding genes, noncoding genes, and repetitive elements.

There are at least two isoforms of DUX4, with the longest isoform comprising the DUX4 C-terminal transcription activation domain. The isoforms are produced by alternative splicing. See, e.g., Geng et al., 2012, Dev Cell, 22, 38-51; Snider et al., 2010, PLoS Genet, e1001181. Active isoforms for DUX4 comprise its N-terminal DNA-binding domains and its C-terminal activation domain. See, e.g., Choi et al., 2016, Nucleic Acid Res, 44, 5161-5173.

It has been shown that reducing the number of CpG motifs of DUX4 decreases silencing of a DUX4 transgene (Jagannathan et al., Human Molecular Genetics, 2016, 25(20): 4419-4431). The nucleic acid sequence provided in Jagannathan et al., supra represents a codon altered sequence of DUX4 comprising one or more base substitutions to reduce the total number of CpG sites while preserving the DUX4 protein sequence. The nucleic acid sequence is commercially available from Addgene, Catalog No. 99281.

In many embodiments, at least one or more polynucleotides may be utilized to facilitate the exogenous expression of DUX4 by a cell, e.g., a stem cell, induced pluripotent stem cell, differentiated cell, hematopoietic stem cell, primary T cell or CAR-T cell.

In some embodiments, a suitable gene editing system (e.g., CRISPR/Cas system or any of the gene editing systems described herein) is used to facilitate the insertion of a polynucleotide encoding DUX4, into a genomic locus of the hypoimmunogenic cell. In some cases, the polynucleotide encoding DUX4 is inserted into a safe harbor or target locus, such as but not limited to, an AAVS1, CCR5, CLYBL, ROSA26, SHS231, F3 (CD142), MICA, MICB, LRP1 (CD91), HMGB1, ABO, RHD, FUT1, or KDM5D gene locus. In some embodiments, the polynucleotide encoding DUX4 is inserted into a B2M gene locus, a CIITA gene locus, a TRAC gene locus, or a TRB gene locus. In some embodiments, the polynucleotide encoding DUX4 is inserted into any one of the gene loci depicted in Table 15 provided herein. In certain embodiments, the polynucleotide encoding DUX4 is operably linked to a promoter.

In some embodiments, the polynucleotide encoding DUX4 is inserted into at least one allele of the T cell using viral transduction. In some embodiments, the polynucleotide encoding DUX4 is inserted into at least one allele of the T cell using a lentivirus based viral vector. In some embodiments, the lentivirus based viral vector is a pseudotyped, self-inactivating lentiviral vector that carries the polynucleotide encoding DUX4. In some embodiments, the lentivirus based viral vector is a self-inactivating lentiviral vector pseudotyped with a vesicular stomatitis VSV-G envelope, and which carries the polynucleotide encoding DUX4.

In some embodiments, the polynucleotide sequence encoding DUX4 comprises a polynucleotide sequence comprising a codon altered nucleotide sequence of DUX4 comprising one or more base substitutions to reduce the total number of CpG sites while preserving the DUX4 protein sequence. In some embodiments, the polynucleotide sequence encoding DUX4 comprising one or more base substitutions to reduce the total number of CpG sites has at least 85% (e.g., 85%, 86%, 87%, 88%, 89%, 90%, 91%, 92%, 93%, 94%, 95%, 96%, 97%, 98%, 99% or 100%) sequence identity to SEQ ID NO:1 of PCT/US2020/44635, filed Jul. 31, 2020. In some embodiments, the polynucleotide sequence encoding DUX4 is SEQ ID NO:1 of PCT/US2020/44635.

In some embodiments, the polynucleotide sequence encoding DUX4 is a nucleotide sequence encoding a polypeptide sequence having at least 95% (e.g., 95%, 96%, 97%, 98%, 99% or 100%) sequence identity to a sequence selected from a group including SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, and SEQ ID NO:29, as provided in PCT/US2020/44635. In some embodiments, the polynucleotide sequence encoding DUX4 is a nucleotide sequence encoding a polypeptide sequence is selected from a group including SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, and SEQ ID NO:29. Amino acid sequences set forth as SEQ ID NOS:2-29 are shown in FIG. 1A-1G of PCT/US2020/44635.

In some instances, the DUX4 polypeptide comprises an amino acid sequence having at least 95% sequence identity to the sequence set forth in GenBank Accession No. ACN62209.1 or an amino acid sequence set forth in GenBank Accession No. ACN62209.1. In some instances, the DUX4 polypeptide comprises an amino acid sequence having at least 95% sequence identity to the sequence set forth in NCBI RefSeq No. NP_001280727.1 or an amino acid sequence set forth in NCBI RefSeq No. NP_001280727.1. In some instances, the DUX4 polypeptide comprises an amino acid sequence having at least 95% sequence identity to the sequence set forth in GenBank Accession No. ACP30489.1 or an amino acid sequence set forth in GenBank Accession No. ACP30489.1. In some instances, the DUX4 polypeptide comprises an amino acid sequence having at least 95% sequence identity to the sequence set forth in UniProt No. P0CJ85.1 or an amino acid sequence set forth in UniProt No. P0CJ85.1. In some instances, the DUX4 polypeptide comprises an amino acid sequence having at least 95% sequence identity to the sequence set forth in GenBank Accession No. AUA60622.1 or an amino acid sequence set forth in GenBank Accession No. AUA60622.1. In some instances, the DUX4 polypeptide comprises an amino acid sequence having at least 95% sequence identity to the sequence set forth in GenBank Accession No. ADK24683.1 or an amino acid sequence set forth in GenBank Accession No. ADK24683.1. In some instances, the DUX4 polypeptide comprises an amino acid sequence having at least 95% sequence identity to the sequence set forth in GenBank Accession No. ACN62210.1 or an amino acid sequence set forth in GenBank Accession No. ACN62210.1. In some instances, the DUX4 polypeptide comprises an amino acid sequence having at least 95% sequence identity to the sequence set forth in GenBank Accession No. ADK24706.1 or an amino acid sequence set forth in GenBank Accession No. ADK24706.1. In some instances, the DUX4 polypeptide comprises an amino acid sequence having at least 95% sequence identity to the sequence set forth in GenBank Accession No. ADK24685.1 or an amino acid sequence set forth in GenBank Accession No. ADK24685.1. In some instances, the DUX4 polypeptide comprises an amino acid sequence having at least 95% sequence identity to the sequence set forth in GenBank Accession No. ACP30488.1 or an amino acid sequence set forth in GenBank Accession No. ACP30488.1. In some instances, the DUX4 polypeptide comprises an amino acid sequence having at least 95% sequence identity to the sequence set forth in GenBank Accession No. ADK24687.1 or an amino acid sequence set forth in GenBank Accession No. ADK24687.1. In some instances, the DUX4 polypeptide comprises an amino acid sequence having at least 95% sequence identity to the sequence set forth in GenBank Accession No. ACP30487.1 or an amino acid sequence set forth in GenBank Accession No. ACP30487.1. In some instances, the DUX4 polypeptide comprises an amino acid sequence having at least 95% sequence identity to the sequence set forth in GenBank Accession No. ADK24717.1 or an amino acid sequence set forth in GenBank Accession No. ADK24717.1. In some instances, the DUX4 polypeptide comprises an amino acid sequence having at least 95% sequence identity to the sequence set forth in GenBank Accession No. ADK24690.1 or an amino acid sequence set forth in GenBank Accession No. ADK24690.1. In some instances, the DUX4 polypeptide comprises an amino acid sequence having at least 95% sequence identity to the sequence set forth in GenBank Accession No. ADK24689.1 or an amino acid sequence set forth in GenBank Accession No. ADK24689.1. In some instances, the DUX4 polypeptide comprises an amino acid sequence having at least 95% sequence identity to the sequence set forth in GenBank Accession No. ADK24692.1 or an amino acid sequence set forth in GenBank Accession No. ADK24692.1. In some instances, the DUX4 polypeptide comprises an amino acid sequence having at least 95% sequence identity to the sequence set forth in GenBank Accession No. ADK24693.1 or an amino acid sequence of set forth in GenBank Accession No. ADK24693.1. In some instances, the DUX4 polypeptide comprises an amino acid sequence having at least 95% sequence identity to the sequence set forth in GenBank Accession No. ADK24712.1 or an amino acid sequence set forth in GenBank Accession No. ADK24712.1. In some instances, the DUX4 polypeptide comprises an amino acid sequence having at least 95% sequence identity to the sequence set forth in GenBank Accession No. ADK24691.1 or an amino acid sequence set forth in GenBank Accession No. ADK24691.1. In some instances, the DUX4 polypeptide comprises an amino acid sequence having at least 95% sequence identity to the sequence set forth in UniProt No. P0CJ87.1 or an amino acid sequence of set forth in UniProt No. P0CJ87.1. In some instances, the DUX4 polypeptide comprises an amino acid sequence having at least 95% sequence identity to the sequence set forth in GenBank Accession No. ADK24714.1 or an amino acid sequence set forth in GenBank Accession No. ADK24714.1. In some instances, the DUX4 polypeptide comprises an amino acid sequence having at least 95% sequence identity to the sequence set forth in GenBank Accession No. ADK24684.1 or an amino acid sequence of set forth in GenBank Accession No. ADK24684.1. In some instances, the DUX4 polypeptide comprises an amino acid sequence having at least 95% sequence identity to the sequence set forth in GenBank Accession No. ADK24695.1 or an amino acid sequence set forth in GenBank Accession No. ADK24695.1. In some instances, the DUX4 polypeptide comprises an amino acid sequence having at least 95% sequence identity to the sequence set forth in GenBank Accession No. ADK24699.1 or an amino acid sequence set forth in GenBank Accession No. ADK24699.1. In some instances, the DUX4 polypeptide comprises an amino acid sequence having at least 95% sequence identity to the sequence set forth in NCBI RefSeq No. NP_001768.1 or an amino acid sequence set forth in NCBI RefSeq No. NP_001768. In some instances, the DUX4 polypeptide comprises an amino acid sequence having at least 95% sequence identity to the sequence set forth in NCBI RefSeq No. NP_942088.1 or an amino acid sequence set forth in NCBI RefSeq No. NP_942088.1. In some instances, the DUX4 polypeptide comprises an amino acid sequence having at least 95% sequence identity to SEQ ID NO:28 provided in PCT/US2020/44635 or an amino acid sequence of SEQ ID NO:28 provided in PCT/US2020/44635. In some instances, the DUX4 polypeptide comprises an amino acid sequence having at least 95% sequence identity to SEQ ID NO:29 provided in PCT/US2020/44635 or an amino acid sequence of SEQ ID NO:29 provided in PCT/US2020/44635.

In other embodiments, expression of tolerogenic factors is facilitated using an expression vector. In some embodiments, the expression vector comprises a polynucleotide sequence encoding DUX4 is a codon altered sequence comprising one or more base substitutions to reduce the total number of CpG sites while preserving the DUX4 protein sequence. In some cases, the codon altered sequence of DUX4 comprises SEQ ID NO:1 of PCT/US2020/44635. In some cases, the codon altered sequence of DUX4 is SEQ ID NO:1 of PCT/US2020/44635. In other embodiments, the expression vector comprises a polynucleotide sequence encoding DUX4 comprising SEQ ID NO:1 of PCT/US2020/44635. In some embodiments, the expression vector comprises a polynucleotide sequence encoding a DUX4 polypeptide sequence having at least 95% sequence identity to a sequence selected from a group including SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, and SEQ ID NO:29 of PCT/US2020/44635. In some embodiments, the expression vector comprises a polynucleotide sequence encoding a DUX4 polypeptide sequence selected from a group including SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, and SEQ ID NO:29 of PCT/US2020/44635.

An increase of DUX4 expression can be assayed using known techniques, such as Western blots, ELISA assays, FACS assays, immunoassays, and the like.

M. Additional Tolerogenic Factors

In many embodiments, one or more tolerogenic factors can be inserted or reinserted into genome-edited cells to create immune-privileged universal donor cells, such as universal donor stem cells, universal donor T cells, or universal donor cells. In certain embodiments, the hypoimmunogenic cells disclosed herein have been further modified to express one or more tolerogenic factors. Exemplary tolerogenic factors include, without limitation, one or more of CD47, DUX4, CD24, CD27, CD35, CD46, CD55, CD59, CD200, HLA-C, HLA-E, HLA-E heavy chain, HLA-G, PD-L1, IDO1, CTLA4-Ig, C1-Inhibitor, IL-10, IL-35, FasL, CCL21, CCL22, Mfge8, CD16, CD52, H2-M3, CD16 Fc receptor, IL15-RF, and Serpinb9. In some embodiments, the tolerogenic factors are selected from the group consisting of CD200, HLA-G, HLA-E, HLA-C, HLA-E heavy chain, PD-L1, IDO1, CTLA4-Ig, IL-10, IL-35, FasL, Serpinb9, CCL21, CCL22, and Mfge8. In some embodiments, the tolerogenic factors are selected from the group consisting of DUX4, HLA-C, HLA-E, HLA-F, HLA-G, PD-L1, CTLA-4-Ig, C1-inhibitor, and IL-35. In some embodiments, the tolerogenic factors are selected from the group consisting of HLA-C, HLA-E, HLA-F, HLA-G, PD-L1, CTLA-4-Ig, C1-inhibitor, and IL-35. In some embodiments, the tolerogenic factors are selected from a group including CD47, DUX4, CD24, CD27, CD35, CD46, CD55, CD59, CD200, HLA-C, HLA-E, HLA-E heavy chain, HLA-G, PD-L1, IDO1, CTLA4-Ig, C1-Inhibitor, IL-10, IL-35, FasL, CCL21, CCL22, Mfge8, CD16, CD52, H2-M3, CD16 Fc receptor, IL15-RF, and Serpinb9.

In some embodiments, the polynucleotide encoding the one or more tolerogenic factors is inserted into at least one allele of the T cell using viral transduction. In some embodiments, the polynucleotide encoding the one or more tolerogenic factors is inserted into at least one allele of the T cell using a lentivirus based viral vector. In some embodiments, the lentivirus based viral vector is a pseudotyped, self-inactivating lentiviral vector that carries the polynucleotide encoding the one or more tolerogenic factors. In some embodiments, the lentivirus based viral vector is a self-inactivating lentiviral vector pseudotyped with a vesicular stomatitis VSV-G envelope, and which carries the polynucleotide encoding the one or more tolerogenic factors.

Useful genomic, polynucleotide and polypeptide information about human CD27 (which is also known as CD27L receptor, Tumor Necrosis Factor Receptor Superfamily Member 7, TNFSF7, T Cell Activation Antigen S152, Tp55, and T14) are provided in, for example, the GeneCard Identifier GC12P008144, HGNC No. 11922, NCBI Gene ID 939, Uniprot No. P26842, and NCBI RefSeq Nos. NM_001242.4 and NP_001233.1.

Useful genomic, polynucleotide and polypeptide information about human CD46 are provided in, for example, the GeneCard Identifier GC01P207752, HGNC No. 6953, NCBI Gene ID 4179, Uniprot No. P15529, and NCBI RefSeq Nos. NM_002389.4, NM_153826.3, NM_172350.2, NM_172351.2, NM_172352.2 NP_758860.1, NM_172353.2, NM_172359.2, NM_172361.2, NP_002380.3, NP_722548.1, NP_758860.1, NP_758861.1, NP_758862.1, NP_758863.1, NP_758869.1, and NP_758871.1.

Useful genomic, polynucleotide and polypeptide information about human CD55 (also known as complement decay-accelerating factor) are provided in, for example, the GeneCard Identifier GC01P207321, HGNC No. 2665, NCBI Gene ID 1604, Uniprot No. P08174, and NCBI RefSeq Nos. NM_000574.4, NM_001114752.2, NM_001300903.1, NM_001300904.1, NP_000565.1, NP_001108224.1, NP_001287832.1, and NP_001287833.1.

Useful genomic, polynucleotide and polypeptide information about human CD59 are provided in, for example, the GeneCard Identifier GC11M033704, HGNC No. 1689, NCBI Gene ID 966, Uniprot No. P13987, and NCBI RefSeq Nos. NP_000602.1, NM_000611.5, NP_001120695.1, NM_001127223.1, NP_001120697.1, NM_001127225.1, NP_001120698.1, NM_001127226.1, NP_001120699.1, NM_001127227.1, NP_976074.1, NM_203329.2, NP_976075.1, NM_203330.2, NP_976076.1, and NM_203331.2.

Useful genomic, polynucleotide and polypeptide information about human CD200 are provided in, for example, the GeneCard Identifier GC03P112332, HGNC No. 7203, NCBI Gene ID 4345, Uniprot No. P41217, and NCBI RefSeq Nos. NP_001004196.2, NM_001004196.3, NP_001305757.1, NM_001318828.1, NP_005935.4, NM_005944.6, XP_005247539.1, and XM_005247482.2.

Useful genomic, polynucleotide and polypeptide information about human HLA-C are provided in, for example, the GeneCard Identifier GC06M031272, HGNC No. 4933, NCBI Gene ID 3107, Uniprot No. P10321, and NCBI RefSeq Nos. NP_002108.4 and NM_002117.5.

Useful genomic, polynucleotide and polypeptide information about human HLA-E are provided in, for example, the GeneCard Identifier GC06P047281, HGNC No. 4962, NCBI Gene ID 3133, Uniprot No. P13747, and NCBI RefSeq Nos. NP_005507.3 and NM_005516.5.

Useful genomic, polynucleotide and polypeptide information about human HLA-G are provided in, for example, the GeneCard Identifier GC06P047256, HGNC No. 4964, NCBI Gene ID 3135, Uniprot No. P17693, and NCBI RefSeq Nos. NP_002118.1 and NM_002127.5.

Useful genomic, polynucleotide and polypeptide information about human PD-L1 or CD274 are provided in, for example, the GeneCard Identifier GC09P005450, HGNC No. 17635, NCBI Gene ID 29126, Uniprot No. Q9NZQ7, and NCBI RefSeq Nos. NP_001254635.1, NM_001267706.1, NP_054862.1, and NM_014143.3.

Useful genomic, polynucleotide and polypeptide information about human IDO1 are provided in, for example, the GeneCard Identifier GC08P039891, HGNC No. 6059, NCBI Gene ID 3620, Uniprot No. P14902, and NCBI RefSeq Nos. NP_002155.1 and NM_002164.5.

Useful genomic, polynucleotide and polypeptide information about human IL-10 are provided in, for example, the GeneCard Identifier GC01M206767, HGNC No. 5962, NCBI Gene ID 3586, Uniprot No. P22301, and NCBI RefSeq Nos. NP_000563.1 and NM_000572.2.

Useful genomic, polynucleotide and polypeptide information about human Fas ligand (which is known as FasL, FASLG, CD178, TNFSF6, and the like) are provided in, for example, the GeneCard Identifier GC01P172628, HGNC No. 11936, NCBI Gene ID 356, Uniprot No. P48023, and NCBI RefSeq Nos. NP_000630.1, NM_000639.2, NP_001289675.1, and NM_001302746.1.

Useful genomic, polynucleotide and polypeptide information about human CCL21 are provided in, for example, the GeneCard Identifier GC09M034709, HGNC No. 10620, NCBI Gene ID 6366, Uniprot No. 000585, and NCBI RefSeq Nos. NP_002980.1 and NM_002989.3.

Useful genomic, polynucleotide and polypeptide information about human CCL22 are provided in, for example, the GeneCard Identifier GC16P057359, HGNC No. 10621, NCBI Gene ID 6367, Uniprot No. 000626, and NCBI RefSeq Nos. NP_002981.2, NM_002990.4, XP_016879020.1, and XM_017023531.1.

Useful genomic, polynucleotide and polypeptide information about human Mfge8 are provided in, for example, the GeneCard Identifier GC15M088898, HGNC No. 7036, NCBI Gene ID 4240, Uniprot No. Q08431, and NCBI RefSeq Nos. NP_001108086.1, NM_001114614.2, NP_001297248.1, NM_001310319.1, NP_001297249.1, NM_001310320.1, NP_001297250.1, NM_001310321.1, NP_005919.2, and NM_005928.3.

Useful genomic, polynucleotide and polypeptide information about human SerpinB9 are provided in, for example, the GeneCard Identifier GC06M002887, HGNC No. 8955, NCBI Gene ID 5272, Uniprot No. P50453, and NCBI RefSeq Nos. NP_004146.1, NM_004155.5, XP_005249241.1, and XM_005249184.4.

Methods for modulating expression of genes and factors (proteins) include genome editing technologies, RNA or protein expression technologies, and the like. For all of these technologies, well known recombinant techniques are used, to generate recombinant nucleic acids as outlined herein.

In some embodiments, the cells (e.g., stem cell, induced pluripotent stem cell, differentiated cell, hematopoietic stem cell, primary T cell or CAR-T cell) possess genetic modifications that inactivate the B2M and CIITA genes and express a plurality of exogenous polypeptides selected from the group including CD47 and DUX4, CD47 and CD24, CD47 and CD27, CD47 and CD46, CD47 and CD55, CD47 and CD59, CD47 and CD200, CD47 and HLA-C, CD47 and HLA-E, CD47 and HLA-E heavy chain, CD47 and HLA-G, CD47 and PD-L1, CD47 and IDO1, CD47 and CTLA4-Ig, CD47 and C1-Inhibitor, CD47 and IL-10, CD47 and IL-35, CD47 and IL-39, CD47 and FasL, CD47 and CCL21, CD47 and CCL22, CD47 and Mfge8, and CD47 and Serpinb9, and any combination thereof. In some instances, such cells also possess a genetic modification that inactivates the CD142 gene.

In some instances, a gene editing system such as the CRISPR/Cas system is used to facilitate the insertion of tolerogenic factors, such as the tolerogenic factors into a safe harbor or target locus, such as the AAVS1 locus, to actively inhibit immune rejection. In some instances, the tolerogenic factors are inserted into a safe harbor or target locus using an expression vector. In some embodiments, the safe harbor or target locus is an AAVS1, CCR5, CLYBL, ROSA26, SHS231, F3 (also known as CD142), MICA, MICB, LRP1 (also known as CD91), HMGB1, ABO, RHD, FUT1, or KDMSD gene locus.

In some embodiments, expression of a target gene (e.g., DUX4, CD47, or another tolerogenic factor gene) is increased by expression of fusion protein or a protein complex containing (1) a site-specific binding domain specific for the endogenous target gene (e.g., DUX4, CD47, or another tolerogenic factor gene) and (2) a transcriptional activator.

In some embodiments, the regulatory factor is comprised of a site specific DNA-binding nucleic acid molecule, such as a guide RNA (gRNA). In some embodiments, the method is achieved by site specific DNA-binding targeted proteins, such as zinc finger proteins (ZFP) or fusion proteins containing ZFP, which are also known as zinc finger nucleases (ZFNs).

In some embodiments, the regulatory factor comprises a site-specific binding domain, such as using a DNA binding protein or DNA-binding nucleic acid, which specifically binds to or hybridizes to the gene at a targeted region. In some embodiments, the provided polynucleotides or polypeptides are coupled to or complexed with a site-specific nuclease, such as a modified nuclease. For example, in some embodiments, the administration is effected using a fusion comprising a DNA-targeting protein of a modified nuclease, such as a meganuclease or an RNA-guided nuclease such as a clustered regularly interspersed short palindromic nucleic acid (CRISPR)-Cas system, such as CRISPR-Cas9 system. In some embodiments, the nuclease is modified to lack nuclease activity. In some embodiments, the modified nuclease is a catalytically dead dCas9.

In some embodiments, the site specific binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. See also U.S. Pat. Nos. 5,420,032; 6,833,252; Belfort et al., (1997) Nucleic Acids Res. 25:3379-3388; Dujon et al., (1989) Gene 82:115-118; Perler et al, (1994) Nucleic Acids Res. 22, 1125-1127; Jasin (1996) Trends Genet. 12:224-228; Gimble et al., (1996) J. Mol. Biol. 263:163-180; Argast et al, (1998) J. Mol. Biol. 280:345-353 and the New England Biolabs catalogue. In addition, the DNA-binding specificity of homing endonucleases and meganucleases can be engineered to bind non-natural target sites. See, for example, Chevalier et al, (2002) Molec. Cell 10:895-905; Epinat et al, (2003) Nucleic Acids Res. 31:2952-2962; Ashworth et al, (2006) Nature 441:656-659; Paques et al, (2007) Current Gene Therapy 7:49-66; U.S. Patent Publication No. 2007/0117128.

Zinc finger, TALE, and CRISPR system binding domains can be "engineered" to bind to a predetermined nucleotide sequence, for example via engineering (altering one or more amino acids) of the recognition helix region of a naturally occurring zinc finger or TALE protein. Engineered DNA binding proteins (zinc fingers or TALEs) are proteins that are non-naturally occurring. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication No. 20110301073.

In some embodiments, the site-specific binding domain comprises one or more zinc-finger proteins (ZFPs) or domains thereof that bind to DNA in a sequence-specific manner. A ZFP or domain thereof is a protein or domain within a larger protein that binds DNA in a sequence-specific manner through one or more zinc fingers, regions of amino acid sequence within the binding domain whose structure is stabilized through coordination of a zinc ion.

Among the ZFPs are artificial ZFP domains targeting specific DNA sequences, typically 9-18 nucleotides long, generated by assembly of individual fingers. ZFPs include those in which a single finger domain is approximately 30 amino acids in length and contains an alpha helix containing two invariant histidine residues coordinated through zinc with two cysteines of a single beta turn, and having two, three, four, five, or six fingers. Generally, sequence-specificity of a ZFP may be altered by making amino acid substitutions at the four helix positions (−1, 2, 3 and 6) on a zinc finger recognition helix. Thus, in some embodiments, the ZFP or ZFP-containing molecule is non-naturally occurring, e.g., is engineered to bind to a target site of choice. See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

Many gene-specific engineered zinc fingers are available commercially. For example, Sangamo Biosciences (Richmond, CA, USA) has developed a platform (CompoZr) for zinc-finger construction in partnership with Sigma-Aldrich (St. Louis, MO, USA), allowing investigators to bypass zinc-finger construction and validation altogether, and provides specifically targeted zinc fingers for thousands of proteins (Gaj et al., Trends in Biotechnology, 2013, 31(7), 397-405). In some embodiments, commercially available zinc fingers are used or are custom designed.

In some embodiments, the site-specific binding domain comprises a naturally occurring or engineered (non-naturally occurring) transcription activator-like protein (TAL) DNA binding domain, such as in a transcription activator-like protein effector (TALE) protein, See, e.g., U.S. Patent Publication No. 20110301073, incorporated by reference in its entirety herein.

In some embodiments, the site-specific binding domain is derived from the CRISPR/Cas system. In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system, or a "targeting sequence"), and/or other sequences and transcripts from a CRISPR locus.

In general, a guide sequence includes a targeting domain comprising a polynucleotide sequence having sufficient complementarity with a target polynucleotide sequence to hybridize with the target sequence and direct sequence-specific binding of the CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. In some examples, the targeting domain of the gRNA is complementary, e.g., at least 80, 85, 90, 95, 98 or 99% complementary, e.g., fully complementary, to the target sequence on the target nucleic acid.

In some embodiments, the target site is upstream of a transcription initiation site of the target gene. In some embodiments, the target site is adjacent to a transcription initiation site of the gene. In some embodiments, the target site is adjacent to an RNA polymerase pause site downstream of a transcription initiation site of the gene.

In some embodiments, the targeting domain is configured to target the promoter region of the target gene to promote transcription initiation, binding of one or more transcription enhancers or activators, and/or RNA polymerase. One or more gRNA can be used to target the promoter region of the gene. In some embodiments, one or more regions of the gene can be targeted. In certain aspects, the target sites are within 600 base pairs on either side of a transcription start site (TSS) of the gene.

It is within the level of a skilled artisan to design or identify a gRNA sequence that is or comprises a sequence targeting a gene, including the exon sequence and sequences of regulatory regions, including promoters and activators. A genome-wide gRNA database for CRISPR genome editing is publicly available, which contains exemplary single guide RNA (sgRNA) target sequences in constitutive exons of genes in the human genome or mouse genome (see e.g., genescript.com/gRNA-database.html; see also, Sanjana et al. (2014) Nat. Methods, 11:783-4; www.e-crisp.org/E-CRISP/; crispr.mit.edu/). In some embodiments, the gRNA sequence is or comprises a sequence with minimal off-target binding to a non-target gene.

In some embodiments, the regulatory factor further comprises a functional domain, e.g., a transcriptional activator.

In some embodiments, the transcriptional activator is or contains one or more regulatory elements, such as one or more transcriptional control elements of a target gene, whereby a site-specific domain as provided above is recognized to drive expression of such gene. In some embodiments, the transcriptional activator drives expression of the target gene. In some cases, the transcriptional activator, can be or contain all or a portion of an heterologous transactivation domain. For example, in some embodiments, the transcriptional activator is selected from Herpes simplex-derived transactivation domain, Dnmt3a methyltransferase domain, p65, VP16, and VP64.

In some embodiments, the regulatory factor is a zinc finger transcription factor (ZF-TF). In some embodiments, the regulatory factor is VP64-p65-Rta (VPR).

In certain embodiments, the regulatory factor further comprises a transcriptional regulatory domain. Common domains include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g., kinases, acetylases and deacetylases); and DNA modifying enzymes (e.g., methyltransferases such as members of the DNMT family (e.g., DNMT1, DNMT3A, DNMT3B, DNMT3L, etc., topoisomerases, helicases, ligases, kinases, phosphatases, polymerases, endonucleases) and their associated factors and modifiers. See, e.g., U.S. Publication No. 2013/0253040, incorporated by reference in its entirety herein.

Suitable domains for achieving activation include the HSV VP 16 activation domain (see, e.g., Hagmann et al, J. Virol. 71, 5952-5962 (1997)) nuclear hormone receptors (see, e.g., Torchia et al., Curr. Opin. Cell. Biol. 10:373-383 (1998)); the p65 subunit of nuclear factor kappa B (Bitko & Bank, J. Virol. 72:5610-5618 (1998) and Doyle & Hunt, Neuroreport 8:2937-2942 (1997)); Liu et al., Cancer Gene Ther. 5:3-28 (1998)), or artificial chimeric functional domains such as VP64 (Beerli et al., (1998) Proc. Natl. Acad. Sci. USA 95:14623-33), and degron (Molinari et al., (1999) EMBO J. 18, 6439-6447). Additional exemplary activation domains include, Oct 1, Oct-2A, Sp1, AP-2, and CTF1 (Seipel et al, EMBOJ. 11, 4961-4968 (1992) as well as p300, CBP, PCAF, SRC1 PvALF, AtHD2A and ERF-2. See, for example, Robyr et al, (2000) Mol. Endocrinol. 14:329-347; Collingwood et al, (1999) J. Mol. Endocrinol 23:255-275; Leo et al, (2000) Gene 245:1-11; Manteuffel-Cymborowska (1999) Acta Biochim. Pol. 46:77-89; McKenna et al, (1999) J. Steroid Biochem. Mol. Biol. 69:3-12; Malik et al, (2000) Trends Biochem. Sci. 25:277-283; and Lemon et al, (1999) Curr. Opin. Genet. Dev. 9:499-504. Additional exemplary activation domains include, but are not limited to, OsGAI, HALF-1, Cl, AP1, ARF-5, -6, -1, and -8, CPRF1, CPRF4, MYC-RP/GP, and TRAB1, See, for example, Ogawa et al, (2000) Gene 245:21-29; Okanami et al, (1996) Genes Cells 1:87-99; Goff et al, (1991) Genes Dev. 5:298-309; Cho et al, (1999) Plant Mol Biol 40:419-429; Ulmason et al, (1999) Proc. Natl. Acad. Sci. USA 96:5844-5849; Sprenger-Haussels et al, (2000) Plant J. 22:1-8; Gong et al, (1999) Plant Mol. Biol. 41:33-44; and Hobo et al., (1999) Proc. Natl. Acad. Sci. USA 96:15,348-15,353.

Exemplary repression domains that can be used to make genetic repressors include, but are not limited to, KRAB A/B, KOX, TGF-beta-inducible early gene (TIEG), v-erbA, SID, MBD2, MBD3, members of the DNMT family (e.g., DNMT1, DNMT3A, DNMT3B, DNMT3L, etc.), Rb, and MeCP2. See, for example, Bird et al, (1999) Cell 99:451-454; Tyler et al, (1999) Cell 99:443-446; Knoepfler et al, (1999) Cell 99:447-450; and Robertson et al, (2000) Nature Genet. 25:338-342. Additional exemplary repression domains include, but are not limited to, ROM2 and AtHD2A. See, for example, Chem et al, (1996) Plant Cell 8:305-321; and Wu et al, (2000) Plant J. 22:19-27.

In some instances, the domain is involved in epigenetic regulation of a chromosome. In some embodiments, the domain is a histone acetyltransferase (HAT), e.g., type-A, nuclear localized such as MYST family members MOZ, Ybf2/Sas3, MOF, and Tip60, GNAT family members Gcn5 or pCAF, the p300 family members CBP, p300 or Rtt109 (Bemdsen and Denu (2008) Curr Opin Struct Biol 18(6): 682-689). In other instances the domain is a histone deacetylase (HD AC) such as the class I (HDAC-1, 2, 3, and 8), class II (HDAC IIA (HDAC-4, 5, 7 and 9), HD AC IIB (HDAC 6 and 10)), class IV (HDAC-1 1), class III (also known as sirtuins (SIRTs); SIRT1-7) (see Mottamal et al., (2015) Molecules 20(3):3898-3941). Another domain that is used in some embodiments is a histone phosphorylase or kinase, where examples include MSK1, MSK2, ATR, ATM, DNA-PK, Bubl, VprBP, IKK-a, PKCpi, Dik/Zip, JAK2, PKC5, WSTF and CK2. In some embodiments, a methylation domain is used and may be chosen from groups such as Ezh2, PRMT1/6, PRMT5/7, PRMT 2/6, CARM1, set7/9, MLL, ALL-1, Suv 39h, G9a, SETDB1, Ezh2, Set2, Dotl, PRMT 1/6, PRMT 5/7, PR-Set7 and Suv4-20h, Domains involved in sumoylation and biotinylation (Lys9, 13, 4, 18 and 12) may also be used in some embodiments (review see Kousarides (2007) Cell 128:693-705).

Fusion molecules are constructed by methods of cloning and biochemical conjugation that are well known to those of skill in the art. Fusion molecules comprise a DNA-binding domain and a functional domain (e.g., a transcriptional activation or repression domain). Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion.

Fusions between a polypeptide component of a functional domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, IL) Catalogue. Methods and compositions for making fusions between a minor groove binder and a polypeptide have been described. Mapp et al, (2000) Proc. Natl. Acad. Sci. USA 97:3930-3935. Likewise, CRISPR/Cas TFs and nucleases comprising a sgRNA nucleic acid component in association with a polypeptide component function domain are also known to those of skill in the art and detailed herein.

In some embodiments, the present disclosure provides a cell (e.g., a primary T cell and a hypoimmunogenic stem cell and derivative thereof) or population thereof comprising a genome in which the cell genome has been modified to express CD47. In some embodiments, the present disclosure provides a method for altering a cell genome to express CD47. In certain embodiments, at least one ribonucleic acid or at least one pair of ribonucleic acids may be utilized to facilitate the insertion of CD47 into a cell line. In certain embodiments, the at least one ribonucleic acid or the at least one pair of ribonucleic acids is selected from the group consisting of SEQ ID NOS:200784-231885 of Table 29 of WO2016183041, which is herein incorporated by reference.

In some embodiments, the present disclosure provides a cell (e.g., a primary T cell and a hypoimmunogenic stem cell and derivative thereof) or population thereof comprising a genome in which the cell genome has been modified to express HLA-C. In some embodiments, the present disclosure provides a method for altering a cell genome to express HLA-C. In certain embodiments, at least one ribonucleic acid or at least one pair of ribonucleic acids may be utilized to facilitate the insertion of HLA-C into a cell line. In certain embodiments, the at least one ribonucleic acid or the at least one pair of ribonucleic acids is selected from the group consisting of SEQ ID NOS:3278-5183 of Table 10 of WO2016183041, which is herein incorporated by reference.

In some embodiments, the present disclosure provides a cell (e.g., a primary T cell and a hypoimmunogenic stem cell and derivative thereof) or population thereof comprising a genome in which the cell genome has been modified to express HLA-E. In some embodiments, the present disclosure provides a method for altering a cell genome to express HLA-E. In certain embodiments, at least one ribonucleic acid or at least one pair of ribonucleic acids may be utilized to facilitate the insertion of HLA-E into a cell line. In certain embodiments, the at least one ribonucleic acid or the at least one pair of ribonucleic acids is selected from the group consisting of SEQ ID NOS:189859-193183 of Table 19 of WO2016183041, which is herein incorporated by reference.

In some embodiments, the present disclosure provides a cell (e.g., a primary T cell and a hypoimmunogenic stem cell and derivative thereof) or population thereof comprising a genome in which the cell genome has been modified to express HLA-F. In some embodiments, the present disclosure provides a method for altering a cell genome to express HLA-F. In certain embodiments, at least one ribonucleic acid or at least one pair of ribonucleic acids may be utilized to facilitate the insertion of HLA-F into a cell line. In certain embodiments, the at least one ribonucleic acid or the at least one pair of ribonucleic acids is selected from the group consisting of SEQ ID NOS: 688808-399754 of Table 45 of WO2016183041, which is herein incorporated by reference.

In some embodiments, the present disclosure provides a cell (e.g., a primary T cell and a hypoimmunogenic stem cell and derivative thereof) or population thereof comprising a genome in which the cell genome has been modified to express HLA-G. In some embodiments, the present disclosure provides a method for altering a cell genome to express HLA-G. In certain embodiments, at least one ribonucleic acid or at least one pair of ribonucleic acids may be utilized to facilitate the insertion of HLA-G into a stem cell line. In certain embodiments, the at least one ribonucleic acid or the at least one pair of ribonucleic acids is selected from the group consisting of SEQ ID NOS:188372-189858 of Table 18 of WO2016183041, which is herein incorporated by reference.

In some embodiments, the present disclosure provides a cell (e.g., a primary T cell and a hypoimmunogenic stem cell and derivative thereof) or population thereof comprising a genome in which the cell genome has been modified to express PD-L1. In some embodiments, the present disclosure provides a method for altering a cell genome to express PD-L1. In certain embodiments, at least one ribonucleic acid or at least one pair of ribonucleic acids may be utilized to facilitate the insertion of PD-L1 into a stem cell line. In certain embodiments, the at least one ribonucleic acid or the at least one pair of ribonucleic acids is selected from the group consisting of SEQ ID NOS:193184-200783 of Table 21 of WO2016183041, which is herein incorporated by reference.

In some embodiments, the present disclosure provides a cell (e.g., a primary T cell and a hypoimmunogenic stem cell and derivative thereof) or population thereof comprising a genome in which the cell genome has been modified to express CTLA4-Ig. In some embodiments, the present disclosure provides a method for altering a cell genome to express CTLA4-Ig. In certain embodiments, at least one ribonucleic acid or at least one pair of ribonucleic acids may be utilized to facilitate the insertion of CTLA4-Ig into a stem cell line. In certain embodiments, the at least one ribonucleic acid or the at least one pair of ribonucleic acids is selected from any one disclosed in WO2016183041, including the sequence listing.

In some embodiments, the present disclosure provides a cell (e.g., a primary T cell and a hypoimmunogenic stem cell and derivative thereof) or population thereof comprising a genome in which the cell genome has been modified to express CI-inhibitor. In some embodiments, the present disclosure provides a method for altering a cell genome to express CI-inhibitor. In certain embodiments, at least one ribonucleic acid or at least one pair of ribonucleic acids may be utilized to facilitate the insertion of CI-inhibitor into a stem cell line. In certain embodiments, the at least one ribonucleic acid or the at least one pair of ribonucleic acids is selected from any one disclosed in WO2016183041, including the sequence listing.

In some embodiments, the present disclosure provides a cell (e.g., a primary T cell and a hypoimmunogenic stem cell and derivative thereof) or population thereof comprising a genome in which the cell genome has been modified to express IL-35. In some embodiments, the present disclosure provides a method for altering a cell genome to express IL-35. In certain embodiments, at least one ribonucleic acid or at least one pair of ribonucleic acids may be utilized to facilitate the insertion of IL-35 into a stem cell line. In certain embodiments, the at least one ribonucleic acid or the at least one pair of ribonucleic acids is selected from any one disclosed in WO2016183041, including the sequence listing.

In some embodiments, the tolerogenic factors are expressed in a cell using an expression vector. In some embodiments, the tolerogenic factors are introduced to the cell using a viral expression vector that mediates integration of the tolerogenic factor sequence into the genome of the cell. For example, the expression vector for expressing CD47 in a cell comprises a polynucleotide sequence encoding CD47. The expression vector can be an inducible expression vector. The expression vector can be a viral vector, such as but not limited to, a lentiviral vector. In some embodiments, the tolerogenic factors are introduced into the cells using fusogen-mediated delivery or a transposase system selected from the group consisting of conditional or inducible transposases, conditional or inducible PiggyBac transposons, conditional or inducible Sleeping Beauty (SB11) transposons, conditional or inducible Mos1 transposons, and conditional or inducible Tol2 transposons.

In some embodiments, the present disclosure provides a cell (e.g., a primary T cell and a hypoimmunogenic stem cell and derivative thereof) or population thereof comprising a genome in which the cell genome has been modified to express any one of the polypeptides selected from the group consisting of HLA-A, HLA-B, HLA-C, RFX-ANK, CIITA, NFY-A, NLRC5, B2M, RFX5, RFX-AP, HLA-G, HLA-E, NFY-B, PD-L1, NFY-C, IRF1, TAP1, GITR, 4-1BB, CD28, B7-1, CD47, B7-2, OX40, CD27, HVEM, SLAM, CD226, ICOS, LAG3, TIGIT, TIM3, CD160, BTLA, CD244, LFA-1, ST2, HLA-F, CD30, B7-H3, VISTA, TLT, PD-L2, CD58, CD2, HELIOS, and IDO1. In some embodiments, the present disclosure provides a method for altering a cell genome to express any one of the polypeptides selected from the group consisting of HLA-A, HLA-B, HLA-C, RFX-ANK, CIITA, NFY-A, NLRC5, B2M, RFX5, RFX-AP, HLA-G, HLA-E, NFY-B, PD-L1, NFY-C, IRF1, TAP1, GITR, 4-1BB, CD28, B7-1, CD47, B7-2, OX40, CD27, HVEM, SLAM, CD226, ICOS, LAG3, TIGIT, TIM3, CD160, BTLA, CD244, LFA-1, ST2, HLA-F, CD30, B7-H3, VISTA, TLT, PD-L2, CD58, CD2, HELIOS, and IDOL. In certain embodiments, at least one ribonucleic acid or at least one pair of ribonucleic acids may be utilized to facilitate the insertion of the selected polypeptide into a stem cell line. In certain embodiments, the at least one ribonucleic acid or the at least one pair of ribonucleic acids is selected from any one disclosed in Appendices 1-47 and the sequence listing of WO2016183041, the disclosure is incorporated herein by references.

In some embodiments, a suitable gene editing system (e.g., CRISPR/Cas system or any of the gene editing systems described herein) is used to facilitate the insertion of a polynucleotide encoding a tolerogenic factor, into a genomic locus of the hypoimmunogenic cell. In some cases, the polynucleotide encoding the tolerogenic factor is inserted into a safe harbor or target locus, such as but not limited to, an AAVS1, CCR5, CLYBL, ROSA26, SHS231, F3 (CD142), MICA, MICB, LRP1 (CD91), HMGB1, ABO, RHD, FUT1, or KDM5D gene locus. In some embodiments, the polynucleotide encoding the tolerogenic factor is inserted into a B2M gene locus, a CIITA gene locus, a TRAC gene locus, or a TRB gene locus. In some embodiments, the polynucleotide encoding the tolerogenic factor is inserted into any one of the gene loci depicted in Table 15 provided herein. In certain embodiments, the polynucleotide encoding the tolerogenic factor is operably linked to a promoter.

In some embodiments, the cells are engineered to expresses an increased amount of one or more of CD47, DUX4, CD24, CD27, CD35, CD46, CD55, CD59, CD200, HLA-C, HLA-E, HLA-E heavy chain, HLA-G, PD-L1, IDO1, CTLA4-Ig, C1-Inhibitor, IL-10, IL-35, FasL, CCL21, CCL22, Mfge8, CD16, CD52, H2-M3, CD16 Fc receptor, IL15-RF, and/or Serpinb9 relative to a cell of the same cell type that does not comprise the modifications.

N. Chimeric Antigen Receptors

Provided herein are hypoimmunogenic cells comprising a chimeric antigen receptor (CAR). In some embodiments, the CAR binds to CD19. In some embodiments, the CAR binds to CD22. In some embodiments, the CAR binds to CD19. In some embodiments, the CAR binds to CD19 and CD22. In some embodiments, the CAR is selected from the group consisting of a first generation CAR, a second generation CAR, a third generation CAR, and a fourth generation CAR. In some embodiments, the CAR includes a single binding domain that binds to a single target antigen. In some embodiments, the CAR includes a single binding domain that binds to more than one target antigen, e.g., 2, 3, or more target antigens. In some embodiments, the CAR includes two binding domains such that each binding domain binds to a different target antigens. In some embodiments, the CAR includes two binding domains such that each binding domain binds to the same target antigen. Detailed descriptions of exemplary CARs including CD19-specific, CD22-specific and CD19/CD22-bispecific CARs can be found in WO2012/079000, WO2016/149578 and WO2020/014482, the disclosures including the sequence listings and figures are incorporated herein by reference in their entirety.

In some embodiments, the CD19 specific CAR includes an anti-CD19 single-chain antibody fragment (scFv), a transmembrane domain such as one derived from human CD8α, a 4-1BB (CD137) co-stimulatory signaling domain, and a CD3ζ signaling domain. In some embodiments, the CD22 specific CAR includes an anti-CD22 scFv, a transmembrane domain such as one derived from human CD8a, a 4-1BB (CD137) co-stimulatory signaling domain, and a CD3ζ signaling domain. In some embodiments, the CD19/CD22-bispecific CAR includes an anti-CD19 scFv, an anti-CD22 scFv, a transmembrane domain such as one derived from human CD8a, a 4-1BB (CD137) co-stimulatory signaling domain, and a CD3ζ signaling domain.

In some embodiments, the CAR comprises a commercial CAR construct carried by a T cell. Non-limiting examples of commercial CAR-T cell based therapies include brexucabtagene autoleucel (TECARTUS®), axicabtagene ciloleucel (YESCARTA®), idecabtagene vicleucel (ABECMA®), lisocabtagene maraleucel (BREYANZI®), tisagenlecleucel (KYMRIAH®), Descartes-08 and Descartes-11 from Cartesian Therapeutics, CTL110 from Novartis, P-BMCA-101 from Poseida Therapeutics, AUTO4 from Autolus Limited, UCARTCS from Cellectis, PBCAR19B and PBCAR269A from Precision Biosciences, FT819 from Fate Therapeutics, and CYAD-211 from Clyad Oncology.

In some embodiments, a hypoimmunogenic cell described herein comprises a polynucleotide encoding a chimeric antigen receptor (CAR) comprising an antigen binding domain. In some embodiments, a hypoimmunogenic cell described herein comprises a chimeric antigen receptor (CAR) comprising an antigen binding domain. In some embodiments, the polynucleotide is or comprises a chimeric antigen receptor (CAR) comprising an antigen binding domain. In some embodiments, the CAR is or comprises a first generation CAR comprising an antigen binding domain, a transmembrane domain, and at least one signaling domain (e.g., one, two or three signaling domains). In some embodiments, the CAR comprises a second generation CAR comprising an antigen binding domain, a transmembrane domain, and at least two signaling domains. In some embodiments, the CAR comprises a third generation CAR comprising an antigen binding domain, a transmembrane domain, and at least three signaling domains. In some embodiments, a fourth generation CAR comprising an antigen binding domain, a transmembrane domain, three or four signaling domains, and a domain which upon successful signaling of the CAR induces expression of a cytokine gene. In some embodiments, the antigen binding domain is or comprises an antibody, an antibody fragment, an scFv or a Fab.

1. Antigen Binding Domain (ABD) Targets an Antigen Characteristic of a Neoplastic or Cancer Cell In some embodiments, the antigen binding domain (ABD) targets an antigen characteristic of a neoplastic cell. In other words, the antigen binding domain targets an antigen expressed by a neoplastic or cancer cell. In some embodiments, the ABD binds a tumor associated antigen. In some embodiments, the antigen characteristic of a neoplastic cell (e.g., antigen associated with a neoplastic or cancer cell) or a tumor associated antigen is selected from a cell surface receptor, an ion channel-linked receptor, an enzyme-linked receptor, a G protein-coupled receptor, receptor tyrosine kinase, tyrosine kinase associated receptor, receptor-like tyrosine phosphatase, receptor serine/threonine kinase, receptor guanylyl cyclase, histidine kinase associated receptor, epidermal growth factor receptors (EGFR) (including ErbB1/EGFR, ErbB2/HER2, ErbB3/HER3, and ErbB4/HER4), fibroblast growth factor receptors (FGFR) (including FGF1, FGF2, FGF3, FGF4, FGF5, FGF6, FGF7, FGF18, and FGF21), vascular endothelial growth factor receptors (VEGFR) (including VEGF-A, VEGF-B, VEGF-C, VEGF-D, and PIGF), RET Receptor and the Eph Receptor Family (including EphA1, EphA2, EphA3, EphA4, EphA5, EphA6, EphA7, EphA8, EphA9, EphA10, EphB1, EphB2. EphB3, EphB4, and EphB6), CXCR1, CXCR2, CXCR3, CXCR4, CXCR6, CCR1, CCR2, CCR3, CCR4, CCR5, CCR6, CCR8, CFTR, CIC-1, CIC-2, CIC-4, CIC-5, CIC-7, CIC-Ka, CIC-Kb, Bestrophins, TMEM16A, GABA receptor, glycin receptor, ABC transporters, NAV1.1, NAV1.2, NAV1.3, NAV1.4, NAV1.5, NAV1.6, NAV1.7, NAV1.8, NAV1.9, sphingosin-1-phosphate receptor (SiPlR), NMDA channel, transmembrane protein, multispan transmembrane protein, T-cell receptor motifs, T-cell alpha chains, T-cell β chains, T-cell γ chains, T-cell δ chains, CCR7, CD3, CD4, CD5, CD7, CD8, CD11b, CD11c, CD16, CD19, CD20, CD21, CD22, CD25, CD28, CD34, CD35, CD40, CD45RA, CD45RO, CD52, CD56, CD62L, CD68, CD80, CD95, CD117, CD127, CD133, CD137 (4-1BB), CD163, F4/80, IL-4Ra, Sca-1, CTLA-4, GITR, GARP, LAP, granzyme B, LFA-1, transferrin receptor, NKp46, perforin, CD4+, Th1, Th2, Th17, Th40, Th22, Th9, Tfh, canonical Treg. FoxP3+, Trl, Th3, Treg17, $T_{REG}$; CDCP, NT5E, EpCAM, CEA, gpA33, mucins, TAG-72, carbonic anhydrase IX, PSMA, folate binding protein, gangliosides (e.g., CD2, CD3, GM2), Lewis-$γ^2$, VEGF, VEGFR 1/2/3, αVβ, α5β1, ErbB1/EGFR, ErbB1/HIER2, ErB3, c-MET, IGF1R, EphA3, TRAIL-R1, TRAIL-R2, RANKL, FAP, Tenascin, PDL-1, BAFF, HDAC, ABL, FLT3, KIT, MET, RET, IL-10, ALK, RANKL, mTOR, CTLA-4, IL-6, IL-6R, JAK3, BRAF, PTCH, Smoothened, PIGF, ANPEP, TIMP1, PLAUR, PTPRJ, LTBR, ANTXR1, folate receptor alpha (FRa), ERBB2 (Her2/neu), EphA2, IL-13Ra2, epidermal growth factor receptor (EGFR), mesothelin, TSHR, CD19, CD123, CD22, CD30, CD171, CS-1, CLL-1, CD33, EGFRvIII, GD2, GD3, BCMA, MUC16 (CA125), LiCAM, LeY, MSLN, IL13Rα1, L1-CAM, Tn Ag, prostate specific membrane antigen (PSMA), ROR1, FLT3, FAP, TAG72, CD38, CD44v6, CEA, EPCAM, B7H3, KIT, interleukin-11 receptor a (IL-11Ra), PSCA, PRSS21, VEGFR2, LewisY, CD24, platelet-derived growth factor receptor-beta (PDGFR-beta), SSEA-4, CD20, MUC1, NCAM, Prostase, PAP, ELF2M, Ephrin B2, IGF-1 receptor, CAIX, LMP2, gp100, bcr-abl, tyrosinase, Fucosyl GM1, sLe, GM3, TGS5, HMWMAA, o-acetyl-GD2, folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCRI, ADRB3, PANX3, GPR20, LY6K, OR51E2, TARP, WTi, NY-ESO-1, LAGE-la, MAGE-A1, legumain, HPV E6, E7, ETV6-AML, sperm protein 17, XAGEi, Tie 2, MAD-CT-1, MAD-CT-2, major histocompatibility complex class I-related gene protein (MR1), urokinase-type plasminogen activator receptor (uPAR), Fos-related antigen 1, $p^{53}$, $p^{53}$ mutant, prostein, survivin, telomerase, PCTA-1/Galectin 8, MelanA/MARTI, Ras mutant, hTERT, sarcoma translocation breakpoints, ML-IAP, ERG (TMPRSS2 ETS fusion gene), NA17, PAX3, androgen receptor, cyclin B1, MYCN, RhoC, TRP-2, CYPIB I, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, IGLL1, a neoantigen, CD133, CD15, CD184, CD24, CD56, CD26, CD29, CD44, HLA-A, HLA-B, HLA-C, (HLA-A,B,C) CD49f, CD151 CD340, CD200, tkrA, trkB, or trkC, or an antigenic fragment or antigenic portion thereof.

2. ABD Targets an Antigen Characteristic of a T Cell

In some embodiments, the antigen binding domain targets an antigen characteristic of a T cell. In some embodiments, the ABD binds an antigen associated with a T cell. In some instances, such an antigen is expressed by a T cell or is located on the surface of a T cell. In some embodiments, the antigen characteristic of a T cell or the T cell associated antigen is selected from a cell surface receptor, a membrane transport protein (e.g., an active or passive transport protein such as, for example, an ion channel protein, a pore-forming protein, etc.), a transmembrane receptor, a membrane enzyme, and/or a cell adhesion protein characteristic of a T cell. In some embodiments, an antigen characteristic of a T cell may be a G protein-coupled receptor, receptor tyrosine kinase, tyrosine kinase associated receptor, receptor-like tyrosine phosphatase, receptor serine/threonine kinase, receptor guanylyl cyclase, histidine kinase associated receptor, AKT1; AKT2; AKT3; ATF2; BCL10; CALM1; CD3D (CD3δ); CD3E (CD3ε); CD3G (CD3γ); CD4; CD8; CD28; CD45; CD80 (B7-1); CD86 (B7-2); CD247 (CD3ζ); CTLA-4 (CD152); ELK1; ERK1 (MAPK3); ERK2; FOS; FYN; GRAP2 (GADS); GRB2; HLA-DRA; HLA-DRB1; HLA-DRB3; HLA-DRB4; HLA-DRB5; HRAS; IKBKA (CHUK); IKBKB; IKBKE; IKBKG (NEMO); IL2; ITPR1; ITK; JUN; KRAS2; LAT; LCK; MAP2K1 (MEK1);

MAP2K2 (MEK2); MAP2K3 (MKK3); MAP2K4 (MKK4); MAP2K6 (MKK6); MAP2K7 (MKK7); MAP3K1 (MEKK1); MAP3K3; MAP3K4; MAP3K5; MAP3K8; MAP3K14 (NIK); MAPK8 (JNK1); MAPK9 (JNK2); MAPK10 (JNK3); MAPK11 (p38β); MAPK12 (p38γ); MAPK13 (p38δ); MAPK14 (p38α); NCK; NFAT1; NFAT2; NFKB1; NFKB2; NFKBIA; NRAS; PAK1; PAK2; PAK3; PAK4; PIK3C2B; PIK3C3 (VPS34); PIK3CA; PIK3CB; PIK3CD; PIK3R1; PKCA; PKCB; PKCM; PKCQ; PLCY1; PRF1 (Perforin); PTEN; RAC1; RAF1; RELA; SDF1; SHP2; SLP76; SOS; SRC; TBK1; TCRA; TEC; TRAF6; VAV1; VAV2; or ZAP70.

3. ABD Targets an Antigen Characteristic of an Autoimmune or Inflammatory Disorder In some embodiments, the antigen binding domain targets an antigen characteristic of an autoimmune or inflammatory disorder. In some embodiments, the ABD binds an antigen associated with an autoimmune or inflammatory disorder. In some instances, the antigen is expressed by a cell associated with an autoimmune or inflammatory disorder. In some embodiments, the autoimmune or inflammatory disorder is selected from chronic graft-vs-host disease (GVHD), lupus, arthritis, immune complex glomerulonephritis, goodpasture syndrome, uveitis, hepatitis, systemic sclerosis or scleroderma, type I diabetes, multiple sclerosis, cold agglutinin disease, Pemphigus vulgaris, Grave's disease, autoimmune hemolytic anemia, Hemophilia A, Primary Sjogren's Syndrome, thrombotic thrombocytopenia purrpura, neuromyelits optica, Evan's syndrome, IgM mediated neuropathy, cryoglobulinemia, dermatomyositis, idiopathic thrombocytopenia, ankylosing spondylitis, bullous pemphigoid, acquired angioedema, chronic urticarial, antiphospholipid demyelinating polyneuropathy, and autoimmune thrombocytopenia or neutropenia or pure red cell aplasias, while exemplary non-limiting examples of alloimmune diseases include allosensitization (see, for example, Blazar et al., 2015, Am. J. Transplant, 15(4):931-41) or xenosensitization from hematopoietic or solid organ transplantation, blood transfusions, pregnancy with fetal allosensitization, neonatal alloimmune thrombocytopenia, hemolytic disease of the newborn, sensitization to foreign antigens such as can occur with replacement of inherited or acquired deficiency disorders treated with enzyme or protein replacement therapy, blood products, and gene therapy. In some embodiments, the antigen characteristic of an autoimmune or inflammatory disorder is selected from a cell surface receptor, an ion channel-linked receptor, an enzyme-linked receptor, a G protein-coupled receptor, receptor tyrosine kinase, tyrosine kinase associated receptor, receptor-like tyrosine phosphatase, receptor serine/threonine kinase, receptor guanylyl cyclase, or histidine kinase associated receptor.

In some embodiments, an antigen binding domain of a CAR binds to a ligand expressed on B cells, plasma cells, or plasmablasts. In some embodiments, an antigen binding domain of a CAR binds to CD10, CD19, CD20, CD22, CD24, CD27, CD38, CD45R, CD138, CD319, BCMA, CD28, TNF, interferon receptors, GM-CSF, ZAP-70, LFA-1, CD3 gamma, CD5 or CD2. See, e.g., US 2003/0077249; WO 2017/058753; WO 2017/058850, the contents of which are herein incorporated by reference.

4. ABD Targets an Antigen Characteristic of Senescent Cells

In some embodiments, the antigen binding domain targets an antigen characteristic of senescent cells, e.g., urokinase-type plasminogen activator receptor (uPAR). In some embodiments, the ABD binds an antigen associated with a senescent cell. In some instances, the antigen is expressed by a senescent cell. In some embodiments, the CAR may be used for treatment or prophylaxis of disorders characterized by the aberrant accumulation of senescent cells, e.g., liver and lung fibrosis, atherosclerosis, diabetes and osteoarthritis.

5. ABD Targets an Antigen Characteristic of an Infectious Disease

In some embodiments, the antigen binding domain targets an antigen characteristic of an infectious disease. In some embodiments, the ABD binds an antigen associated with an infectious disease. In some instances, the antigen is expressed by a cell affected by an infectious disease. In some embodiments, wherein the infectious disease is selected from HIV, hepatitis B virus, hepatitis C virus, Human herpes virus, Human herpes virus 8 (HHV-8, Kaposi sarcoma-associated herpes virus (KSHV)), Human T-lymphotrophic virus-1 (HTLV-1), Merkel cell polyomavirus (MCV), Simian virus 40 (SV40), Epstein-Barr virus, CMV, human papillomavirus. In some embodiments, the antigen characteristic of an infectious disease is selected from a cell surface receptor, an ion channel-linked receptor, an enzyme-linked receptor, a G protein-coupled receptor, receptor tyrosine kinase, tyrosine kinase associated receptor, receptor-like tyrosine phosphatase, receptor serine/threonine kinase, receptor guanylyl cyclase, histidine kinase associated receptor, HIV Env, gpl20, or CD4-induced epitope on HIV-1 Env.

6. ABD Binds to a Cell Surface Antigen of a Cell

In some embodiments, an antigen binding domain binds to a cell surface antigen of a cell. In some embodiments, a cell surface antigen is characteristic of (e.g., expressed by) a particular or specific cell type. In some embodiments, a cell surface antigen is characteristic of more than one type of cell.

In some embodiments, a CAR antigen binding domain binds a cell surface antigen characteristic of a T cell, such as a cell surface antigen on a T cell. In some embodiments, an antigen characteristic of a T cell may be a cell surface receptor, a membrane transport protein (e.g., an active or passive transport protein such as, for example, an ion channel protein, a pore-forming protein, etc.), a transmembrane receptor, a membrane enzyme, and/or a cell adhesion protein characteristic of a T cell. In some embodiments, an antigen characteristic of a T cell may be a G protein-coupled receptor, receptor tyrosine kinase, tyrosine kinase associated receptor, receptor-like tyrosine phosphatase, receptor serine/threonine kinase, receptor guanylyl cyclase, or histidine kinase associated receptor.

In some embodiments, an antigen binding domain of a CAR binds a T cell receptor. In some embodiments, a T cell receptor may be AKT1; AKT2; AKT3; ATF2; BCL10; CALM1; CD3D (CD3δ); CD3E (CD3ε); CD3G (CD3γ); CD4; CD8; CD28; CD45; CD80 (B7-1); CD86 (B7-2); CD247 (CD3ζ); CTLA-4 (CD152); ELK1; ERK1 (MAPK3); ERK2; FOS; FYN; GRAP2 (GADS); GRB2; HLA-DRA; HLA-DRB1; HLA-DRB3; HLA-DRB4; HLA-DRB5; HRAS; IKBKA (CHUK); IKBKB; IKBKE; IKBKG (NEMO); IL2; ITPR1; ITK; JUN; KRAS2; LAT; LCK; MAP2K1 (MEK1); MAP2K2 (MEK2); MAP2K3 (MKK3); MAP2K4 (MKK4); MAP2K6 (MKK6); MAP2K7 (MKK7); MAP3K1 (MEKK1); MAP3K3; MAP3K4; MAP3K5; MAP3K8; MAP3K14 (NIK); MAPK8 (JNK1); MAPK9 (JNK2); MAPK10 (JNK3); MAPK11 (p38β); MAPK12 (p38γ); MAPK13 (p38δ); MAPK14 (p38α); NCK; NFAT1; NFAT2; NFKB1; NFKB2; NFKBIA; NRAS; PAK1; PAK2; PAK3; PAK4; PIK3C2B; PIK3C3 (VPS34); PIK3CA; PIK3CB; PIK3CD; PIK3R1; PKCA; PKCB; PKCM; PKCQ; PLCY1; PRF1 (Perforin); PTEN; RAC1; RAF1;

RELA; SDF1; SHP2; SLP76; SOS; SRC; TBK1; TCRA; TEC; TRAF6; VAV1; VAV2; or ZAP70.

7. Transmembrane Domain

In some embodiments, the CAR transmembrane domain comprises at least a transmembrane region of the alpha, beta or zeta chain of a T cell receptor, CD28, CD3 epsilon, CD45, CD4, CD5, CD8, CD9, CD16, CD22, CD33, CD37, CD64, CD80, CD86, CD134, CD137, CD154, or functional variant thereof. In some embodiments, the transmembrane domain comprises at least a transmembrane region(s) of CD8a, CD80, 4-1BB/CD137, CD28, CD34, CD4, FcεRIγ, CD16, OX40/CD134, CD3ζ, CD3ε, CD3γ, CD3δ, TCRα, TCRβ, TCRζ, CD32, CD64, CD64, CD45, CD5, CD9, CD22, CD37, CD80, CD86, CD40, CD40L/CD154, VEGFR2, FAS, and FGFR2B, or functional variant thereof. antigen binding domain binds 8. Signaling Domain or Plurality of Signaling Domains In some embodiments, a CAR described herein comprises one or at least one signaling domain selected from one or more of B7-1/CD80; B7-2/CD86; B7-H1/PD-L1; B7-H2; B7-H3; B7-H4; B7-H6; B7-H7; BTLA/CD272; CD28; CTLA-4; Gi24/VISTA/B7-H5; ICOS/CD278; PD-1; PD-L2/B7-DC; PDCD6); 4-1BB/TNFSF9/CD137; 4-1BB Ligand/TNFSF9; BAFF/BLyS/TNFSF13B; BAFF R/TNFRSF13C; CD27/TNFRSF7; CD27 Ligand/TNFSF7; CD30/TNFRSF8; CD30 Ligand/TNFSF8; CD40/TNFRSF5; CD40/TNFSF5; CD40 Ligand/TNFSF5; DR3/TNFRSF25; GITR/TNFRSF18; GITR Ligand/TNFSF18; HVEM/TNFRSF14; LIGHT/TNFSF14; Lymphotoxin-alpha/TNF-beta; OX40/TNFRSF4; OX40 Ligand/TNFSF4; RELT/TNFRSF19L; TACI/TNFRSF13B; TL1A/TNFSF15; TNF-alpha; TNF RII/TNFRSFIB); 2B4/CD244/SLAMF4; BLAME/SLAMF8; CD2; CD2F-10/SLAMF9; CD48/SLAMF2; CD58/LFA-3; CD84/SLAMF5; CD229/SLAMF3; CRACC/SLAMF7; NTB-A/SLAMF6; SLAM/CD150); CD2; CD7; CD53; CD82/Kai-1; CD90/Thy1; CD96; CD160; CD200; CD300a/LMIR1; HLA Class I; HLA-DR; Ikaros; Integrin alpha 4/CD49d; Integrin alpha 4 beta 1; Integrin alpha 4 beta 7/LPAM-1; LAG-3; TCL1A; TCL1B; CRTAM; DAP12; Dectin-1/CLEC7A; DPPIV/CD26; EphB6; TIM-1/KIM-1/HAVCR; TIM-4; TSLP; TSLP R; lymphocyte function associated antigen-1 (LFA-1); NKG2C, a CD3 zeta domain, an immunoreceptor tyrosine-based activation motif (ITAM), CD27, CD28, 4-1BB, CD134/OX40, CD30, CD40, PD-1, ICOS, lymphocyte function-associated antigen-1 (LFA-1), CD2, CD7, LIGHT, NKG2C, B7-H3, a ligand that specifically binds with CD83, or functional fragment thereof.

In some embodiments, the at least one signaling domain comprises a CD3 zeta domain or an immunoreceptor tyrosine-based activation motif (ITAM), or functional variant thereof. In other embodiments, the at least one signaling domain comprises (i) a CD3 zeta domain, or an immunoreceptor tyrosine-based activation motif (ITAM), or functional variant thereof; and (ii) a CD28 domain, or a 4-1BB domain, or functional variant thereof. In yet other embodiments, the at least one signaling domain comprises a (i) a CD3 zeta domain, or an immunoreceptor tyrosine-based activation motif (ITAM), or functional variant thereof, (ii) a CD28 domain or functional variant thereof, and (iii) a 4-1BB domain, or a CD134 domain, or functional variant thereof. In some embodiments, the at least one signaling domain comprises a (i) a CD3 zeta domain, or an immunoreceptor tyrosine-based activation motif (ITAM), or functional variant thereof, (ii) a CD28 domain or functional variant thereof, (iii) a 4-1BB domain, or a CD134 domain, or functional variant thereof, and (iv) a cytokine or costimulatory ligand transgene.

In some embodiments, the at least two signaling domains comprise a CD3 zeta domain or an immunoreceptor tyrosine-based activation motif (ITAM), or functional variant thereof. In other embodiments, the at least two signaling domains comprise (i) a CD3 zeta domain, or an immunoreceptor tyrosine-based activation motif (ITAM), or functional variant thereof; and (ii) a CD28 domain, or a 4-1BB domain, or functional variant thereof. In yet other embodiments, the at least one signaling domain comprises a (i) a CD3 zeta domain, or an immunoreceptor tyrosine-based activation motif (ITAM), or functional variant thereof, (ii) a CD28 domain or functional variant thereof, and (iii) a 4-1BB domain, or a CD134 domain, or functional variant thereof. In some embodiments, the at least two signaling domains comprise a (i) a CD3 zeta domain, or an immunoreceptor tyrosine-based activation motif (ITAM), or functional variant thereof, (ii) a CD28 domain or functional variant thereof, (iii) a 4-1BB domain, or a CD134 domain, or functional variant thereof, and (iv) a cytokine or costimulatory ligand transgene.

In some embodiments, the at least three signaling domains comprise a CD3 zeta domain or an immunoreceptor tyrosine-based activation motif (ITAM), or functional variant thereof. In other embodiments, the at least three signaling domains comprise (i) a CD3 zeta domain, or an immunoreceptor tyrosine-based activation motif (ITAM), or functional variant thereof; and (ii) a CD28 domain, or a 4-1BB domain, or functional variant thereof. In yet other embodiments, the least three signaling domains comprises a (i) a CD3 zeta domain, or an immunoreceptor tyrosine-based activation motif (ITAM), or functional variant thereof, (ii) a CD28 domain or functional variant thereof, and (iii) a 4-1BB domain, or a CD134 domain, or functional variant thereof. In some embodiments, the at least three signaling domains comprise a (i) a CD3 zeta domain, or an immunoreceptor tyrosine-based activation motif (ITAM), or functional variant thereof, (ii) a CD28 domain or functional variant thereof, (iii) a 4-1BB domain, or a CD134 domain, or functional variant thereof, and (iv) a cytokine or costimulatory ligand transgene.

In some embodiments, the CAR comprises a CD3 zeta domain or an immunoreceptor tyrosine-based activation motif (ITAM), or functional variant thereof. In some embodiments, the CAR comprises (i) a CD3 zeta domain, or an immunoreceptor tyrosine-based activation motif (ITAM), or functional variant thereof, and (ii) a CD28 domain, or a 4-1BB domain, or functional variant thereof.

In some embodiments, the CAR comprises a (i) a CD3 zeta domain, or an immunoreceptor tyrosine-based activation motif (ITAM), or functional variant thereof, (ii) a CD28 domain or functional variant thereof, and (iii) a 4-1BB domain, or a CD134 domain, or functional variant thereof.

In some embodiments, the CAR comprises (i) a CD3 zeta domain, or an immunoreceptor tyrosine-based activation motif (ITAM), or functional variant thereof, (ii) a CD28 domain, or a 4-1BB domain, or functional variant thereof, and/or (iii) a 4-1BB domain, or a CD134 domain, or functional variant thereof.

In some embodiments, the CAR comprises a (i) a CD3 zeta domain, or an immunoreceptor tyrosine-based activation motif (ITAM), or functional variant thereof, (ii) a CD28 domain or functional variant thereof, (iii) a 4-1BB domain, or a CD134 domain, or functional variant thereof, and (iv) a cytokine or costimulatory ligand transgene.

9. Domain which Upon Successful Signaling of the CAR Induces Expression of a Cytokine Gene In some embodiments, a first, second, third, or fourth generation CAR further comprises a domain which upon successful signaling of the CAR induces expression of a cytokine gene. In some embodiments, a cytokine gene is endogenous or exogenous to a target cell comprising a CAR which comprises a domain which upon successful signaling of the CAR induces expression of a cytokine gene. In some embodiments, a cytokine gene encodes a pro-inflammatory cytokine. In some embodiments, a cytokine gene encodes IL-1, IL-2, IL-9, IL-12, IL-18, TNF, or IFN-gamma, or functional fragment thereof. In some embodiments, a domain which upon successful signaling of the CAR induces expression of a cytokine gene is or comprises a transcription factor or functional domain or fragment thereof. In some embodiments, a domain which upon successful signaling of the CAR induces expression of a cytokine gene is or comprises a transcription factor or functional domain or fragment thereof. In some embodiments, a transcription factor or functional domain or fragment thereof is or comprises a nuclear factor of activated T cells (NFAT), an NF-kB, or functional domain or fragment thereof. See, e.g., Zhang. C. et al., Engineering CAR-T cells. Biomarker Research. 5:22 (2017); WO 2016126608; Sha, H. et al. Chimaeric antigen receptor T-cell therapy for tumour immunotherapy. Bioscience Reports Jan. 27, 2017, 37 (1).

In some embodiments, the CAR further comprises one or more spacers, e.g., wherein the spacer is a first spacer between the antigen binding domain and the transmembrane domain. In some embodiments, the first spacer includes at least a portion of an immunoglobulin constant region or variant or modified version thereof. In some embodiments, the spacer is a second spacer between the transmembrane domain and a signaling domain. In some embodiments, the second spacer is an oligopeptide, e.g., wherein the oligopeptide comprises glycine and serine residues such as but not limited to glycine-serine doublets. In some embodiments, the CAR comprises two or more spacers, e.g., a spacer between the antigen binding domain and the transmembrane domain and a spacer between the transmembrane domain and a signaling domain.

In some embodiments, any one of the cells described herein comprises a nucleic acid encoding a CAR or a first generation CAR. In some embodiments, a first generation CAR comprises an antigen binding domain, a transmembrane domain, and signaling domain. In some embodiments, a signaling domain mediates downstream signaling during T cell activation.

In some embodiments, any one of the cells described herein comprises a nucleic acid encoding a CAR or a second generation CAR. In some embodiments, a second generation CAR comprises an antigen binding domain, a transmembrane domain, and two signaling domains. In some embodiments, a signaling domain mediates downstream signaling during T cell activation. In some embodiments, a signaling domain is a costimulatory domain. In some embodiments, a costimulatory domain enhances cytokine production, CAR-T cell proliferation, and/or CAR-T cell persistence during T cell activation.

In some embodiments, any one of the cells described herein comprises a nucleic acid encoding a CAR or a third generation CAR. In some embodiments, a third generation CAR comprises an antigen binding domain, a transmembrane domain, and at least three signaling domains. In some embodiments, a signaling domain mediates downstream signaling during T cell activation. In some embodiments, a signaling domain is a costimulatory domain. In some embodiments, a costimulatory domain enhances cytokine production, CAR-T cell proliferation, and or CAR-T cell persistence during T cell activation. In some embodiments, a third generation CAR comprises at least two costimulatory domains. In some embodiments, the at least two costimulatory domains are not the same.

In some embodiments, any one of the cells described herein comprises a nucleic acid encoding a CAR or a fourth generation CAR. In some embodiments, a fourth generation CAR comprises an antigen binding domain, a transmembrane domain, and at least two, three, or four signaling domains. In some embodiments, a signaling domain mediates downstream signaling during T cell activation. In some embodiments, a signaling domain is a costimulatory domain. In some embodiments, a costimulatory domain enhances cytokine production, CAR-T cell proliferation, and or CAR-T cell persistence during T cell activation.

10. ABD Comprising an Antibody or Antigen-Binding Portion Thereof

In some embodiments, a CAR antigen binding domain is or comprises an antibody or antigen-binding portion thereof. In some embodiments, a CAR antigen binding domain is or comprises an scFv or Fab. In some embodiments, a CAR antigen binding domain comprises an scFv or Fab fragment of a CD19 antibody; CD22 antibody; T-cell alpha chain antibody; T-cell β chain antibody; T-cell γ chain antibody; T-cell δ chain antibody; CCR7 antibody; CD3 antibody; CD4 antibody; CD5 antibody; CD7 antibody; CD8 antibody; CD11b antibody; CD11c antibody; CD16 antibody; CD20 antibody; CD21 antibody; CD25 antibody; CD28 antibody; CD34 antibody; CD35 antibody; CD40 antibody; CD45RA antibody; CD45RO antibody; CD52 antibody; CD56 antibody; CD62L antibody; CD68 antibody; CD80 antibody; CD95 antibody; CD117 antibody; CD127 antibody; CD133 antibody; CD137 (4-1 BB) antibody; CD163 antibody; F4/80 antibody; IL-4Ra antibody; Sca-1 antibody; CTLA-4 antibody; GITR antibody GARP antibody; LAP antibody; granzyme B antibody; LFA-1 antibody; MR1 antibody; uPAR antibody; or transferrin receptor antibody.

In some embodiments, a CAR comprises a signaling domain which is a costimulatory domain. In some embodiments, a CAR comprises a second costimulatory domain. In some embodiments, a CAR comprises at least two costimulatory domains. In some embodiments, a CAR comprises at least three costimulatory domains. In some embodiments, a CAR comprises a costimulatory domain selected from one or more of CD27, CD28, 4-1BB, CD134/OX40, CD30, CD40, PD-1, ICOS, lymphocyte function-associated antigen-1 (LFA-1), CD2, CD7, LIGHT, NKG2C, B7-H3, a ligand that specifically binds with CD83. In some embodiments, if a CAR comprises two or more costimulatory domains, two costimulatory domains are different. In some embodiments, if a CAR comprises two or more costimulatory domains, two costimulatory domains are the same.

In addition to the CARs described herein, various chimeric antigen receptors and nucleotide sequences encoding the same are known in the art and would be suitable for fusosomal delivery and reprogramming of target cells in vivo and in vitro as described herein. See, e.g., WO2013040557; WO2012079000; WO2016030414; Smith T, et al., Nature Nanotechnology. 2017. DOI: 10.1038/NNANO.2017.57, the disclosures of which are herein incorporated by reference.

11. Additional Descriptions of CARs

In certain embodiments, the cell may comprise an exogenous polynucleotide encoding a CAR. CARs (also known as chimeric immunoreceptors, chimeric T cell receptors, or artificial T cell receptors) are receptor proteins that have been engineered to give host cells (e.g., T cells) the new ability to target a specific protein. The receptors are chimeric because they combine both antigen-binding and T cell activating functions into a single receptor. The polycistronic vector of the present disclosure may be used to express one or more CARs in a host cell (e.g., a T cell) for use in cell-based therapies against various target antigens. The CARs expressed by the one or more expression cassettes may be the same or different. In these embodiments, the CAR may comprise an extracellular binding domain (also referred to as a "binder") that specifically binds a target antigen, a transmembrane domain, and an intracellular signaling domain. In certain embodiments, the CAR may further comprise one or more additional elements, including one or more signal peptides, one or more extracellular hinge domains, and/or one or more intracellular costimulatory domains. Domains may be directly adjacent to one another, or there may be one or more amino acids linking the domains. The nucleotide sequence encoding a CAR may be derived from a mammalian sequence, for example, a mouse sequence, a primate sequence, a human sequence, or combinations thereof. In the cases where the nucleotide sequence encoding a CAR is non-human, the sequence of the CAR may be humanized. The nucleotide sequence encoding a CAR may also be codon-optimized for expression in a mammalian cell, for example, a human cell. In any of these embodiments, the nucleotide sequence encoding a CAR may be at least 80% identical (e.g., at least 80%, at least 85%, at least 90%, at least 95%, at least 96%, at least 97%, at least 98%, at least 99%, or 100% identical) to any of the nucleotide sequences disclosed herein. The sequence variations may be due to codon-optimalization, humanization, restriction enzyme-based cloning scars, and/or additional amino acid residues linking the functional domains, etc.

In certain embodiments, the CAR may comprise a signal peptide at the N-terminus. Non-limiting examples of signal peptides include CD8α signal peptide, IgK signal peptide, and granulocyte-macrophage colony-stimulating factor receptor subunit alpha (GMCSFR-α, also known as colony stimulating factor 2 receptor subunit alpha (CSF2RA)) signal peptide, and variants thereof, the amino acid sequences of which are provided in Table 2 below.

TABLE 2

Exemplary sequences of signal peptides

| SEQ ID NO: | Sequence | Description |
|---|---|---|
| 6 | MALPVTALLLPLALLLHAARP | CD8α signal peptide |
| 7 | METDTLLLWVLLLWVPGSTG | IgK signal peptide |
| 8 | MLLLVTSLLLCELPHPAFLLIP | GMCSFR-α (CSF2RA) signal peptide |

In certain embodiments, the extracellular binding domain of the CAR may comprise one or more antibodies specific to one target antigen or multiple target antigens. The antibody may be an antibody fragment, for example, an scFv, or a single-domain antibody fragment, for example, a VHH. In certain embodiments, the scFv may comprise a heavy chain variable region ($V_H$) and a light chain variable region ($V_L$) of an antibody connected by a linker. The $V_H$ and the $V_L$ may be connected in either order, i.e., $V_H$-linker-$V_L$ or $V_L$-linker-$V_H$. Non-limiting examples of linkers include Whitlow linker, $(G_4S)_n$ (n can be a positive integer, e.g., 1, 2, 3, 4, 5, 6, etc.) linker, and variants thereof. In certain embodiments, the antigen may be an antigen that is exclusively or preferentially expressed on tumor cells, or an antigen that is characteristic of an autoimmune or inflammatory disease. Exemplary target antigens include, but are not limited to, CD5, CD19, CD20, CD22, CD23, CD30, CD70, Kappa, Lambda, and B cell maturation agent (BCMA), G-protein coupled receptor family C group 5 member D (GPRC5D) (associated with leukemias); CS1/SLAMF7, CD38, CD138, GPRC5D, TACI, and BCMA (associated with myelomas); GD2, HER2, EGFR, EGFRvIII, B7H3, PSMA, PSCA, CAIX, CD171, CEA, CSPG4, EPHA2, FAP, FRα, IL-13Rα, Mesothelin, MUC1, MUC16, and ROR1 (associated with solid tumors). In any of these embodiments, the extracellular binding domain of the CAR can be codon-optimized for expression in a host cell or have variant sequences to increase functions of the extracellular binding domain.

In certain embodiments, the CAR may comprise a hinge domain, also referred to as a spacer. The terms "hinge" and "spacer" may be used interchangeably in the present disclosure. Non-limiting examples of hinge domains include CD8α hinge domain, CD28 hinge domain, IgG4 hinge domain, IgG4 hinge-CH2-CH3 domain, and variants thereof, the amino acid sequences of which are provided in Table 3 below.

TABLE 3

Exemplary sequences of hinge domains

| SEQ ID NO: | Sequence | Description |
|---|---|---|
| 9 | TTTPAPRPPTPAPTIASQPLSLRPEACR PAAGGAVHTRGLDFACD | CD8α hinge domain |
| 10 | IEVMYPPPYLDNEKSNGTIIHVKGKHLC PSPLFPGPSKP | CD28 hinge domain |
| 113 | AAAIEVMYPPPYLDNEKSNGTIIHVKGK HLCPSPLFPGPSKP | CD28 hinge domain |
| 11 | ESKYGPPCPPCP | IgG4 hinge domain |
| 12 | ESKYGPPCPSCP | IgG4 hinge domain |
| 13 | ESKYGPPCPPCPAPEFLGGPSVFLFPPK PKDTLMISRTPEVTCVVVDVSQEDPEVQ FNWYVDGVEVHNAKTKPREEQFNSTYRV VSVLTVLHQDWLNGKEYKCKVSNKGLPS SIEKTISKAKGQPREPQVYTLPPSQEEM TKNQVSLTCLVKGFYPSDIAVEWESNGQ PENNYKTTPPVLDSDGSFFLYSRLTVDK SRWQEGNVFSCSVMHEALHNHYTQKSLS LSLGK | IgG4 hinge-CH2-CH3 domain |

In certain embodiments, the transmembrane domain of the CAR may comprise a transmembrane region of the alpha, beta, or zeta chain of a T cell receptor, CD28, CD3F', CD45, CD4, CD5, CD8, CD9, CD16, CD22, CD33, CD37, CD64, CD80, CD86, CD134, CD137, CD154, or a functional variant thereof, including the human versions of each of these sequences. In other embodiments, the transmembrane domain may comprise a transmembrane region of CD8α, CD8β, 4-1BB/CD137, CD28, CD34, CD4, FcεRIγ, CD16, OX40/CD134, CD3ζ, CD3ε, CD3γ, CD3δ, TCRα, TCRβ, TCRζ, CD32, CD64, CD64, CD45, CD5, CD9, CD22, CD37, CD80, CD86, CD40, CD40L/CD154, VEGFR2, FAS, and FGFR21B, or a functional variant thereof, including the human versions of each of these sequences. Table 4 provides the amino acid sequences of a few exemplary transmembrane domains.

TABLE 4

Exemplary sequences of transmembrane domains

| SEQ ID NO: | Sequence | Description |
|---|---|---|
| 14 | IYIWAPLAGTCGVLLLSLVITLYC | CD8α transmembrane domain |
| 15 | FWVLVVVGGVLACYSLLVTVAFIIFWV | CD28 transmembrane domain |
| 114 | MFWVLVVVGGVLACYSLLVTVAFIIFWV | CD28 transmembrane domain |

In certain embodiments, the intracellular signaling domain and/or intracellular costimulatory domain of the CAR may comprise one or more signaling domains selected from B7-1/CD80, B7-2/CD86, B7-H1/PD-L1, B7-H2, B7-H3, B7-H4, B7-H6, B7-H7, BTLA/CD272, CD28, CTLA-4, Gi24/VISTA/B7-H5, ICOS/CD278, PD-1, PD-L2/B7-DC, PDCD6, 4-1BB/TNFSF9/CD137, 4-1BB Ligand/TNFSF9, BAFF/BLyS/TNFSF13B, BAFF R/TNFRSF13C, CD27/TNFRSF7, CD27 Ligand/TNFSF7, CD30/TNFRSF8, CD30 Ligand/TNFSF8, CD40/TNFRSF5, CD40/TNFSF5, CD40 Ligand/TNFSF5, DR3/TNFRSF25, GITR/TNFRSF18, GITR Ligand/TNFSF18, HVEM/TNFRSF14, LIGHT/TNFSF14, Lymphotoxin-alpha/TNFβ, OX40/TNFRSF4, OX40 Ligand/TNFSF4, RELT/TNFRSF19L, TACI/TNFRSF13B, TL1A/TNFSF15, TNFα, TNF RII/TNFRSF1B, 2B4/CD244/SLAMF4, BLAME/SLAMF8, CD2, CD2F-10/SLAMF9, CD48/SLAMF2, CD58/LFA-3, CD84/SLAMF5, CD229/SLAMF3, CRACC/SLAMF7, NTB-A/SLAMF6, SLAM/CD150, CD2, CD7, CD53, CD82/Kai-1, CD90/Thy1, CD96, CD160, CD200, CD300a/LMIR1, HLA Class I, HLA-DR, Ikaros, Integrin alpha 4/CD49d, Integrin alpha 4 beta 1, Integrin alpha 4 beta 7/LPAM-1, LAG-3, TCL1A, TCL1B, CRTAM, DAP12, Dectin-1/CLEC7A, DPPIV/CD26, EphB6, TIM-1/KIM-1/HAVCR, TIM-4, TSLP, TSLP R, lymphocyte function associated antigen-1 (LFA-1), NKG2C, CD3ζ, an immunoreceptor tyrosine-based activation motif (ITAM), CD27, CD28, 4-1BB, CD134/OX40, CD30, CD40, PD-1, ICOS, lymphocyte function-associated antigen-1 (LFA-1), CD2, CD7, LIGHT, NKG2C, B7-H3, a ligand that specifically binds with CD83, and a functional variant thereof including the human versions of each of these sequences. In some embodiments, the intracellular signaling domain and/or intracellular costimulatory domain comprises one or more signaling domains selected from a CD3ζ domain, an ITAM, a CD28 domain, 4-1BB domain, or a functional variant thereof. Table 5 provides the amino acid sequences of a few exemplary intracellular costimulatory and/or signaling domains. In certain embodiments, as in the case of tisagenlecleucel as described below, the CD3ζ signaling domain of SEQ ID NO:18 may have a mutation, e.g., a glutamine (Q) to lysine (K) mutation, at amino acid position 14 (see SEQ ID NO:115).

TABLE 5

Exemplary sequences of intracellular costimulatory and/or signaling domains

| SEQ ID NO: | Sequence | Description |
|---|---|---|
| 16 | KRGRKKLLYIFKQPFMRPVQTTQEEDGCSCRFPEEEEGGCEL | 4-1BB costimulatory domain |
| 17 | RSKRSRLLHSDYMNMTPRRPGPTRKHYQPYAPPRDFAAYRS | CD28 costimulatory domain |
| 18 | RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | CD3ζ signaling domain |
| 115 | RVKFSRSADAPAYKQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | CD3ζ signaling domain (with Q to K mutation at position 14) |

In certain embodiments where the polycistronic vector encodes two or more CARs, the two or more CARs may comprise the same functional domains, or one or more different functional domains, as described. For example, the two or more CARs may comprise different signal peptides, extracellular binding domains, hinge domains, transmembrane domains, costimulatory domains, and/or intracellular signaling domains, in order to minimize the risk of recombination due to sequence similarities. Or, alternatively, the two or more CARs may comprise the same domains. In the cases where the same domain(s) and/or backbone are used, it is optional to introduce codon divergence at the nucleotide sequence level to minimize the risk of recombination.

CD19 CAR

In some embodiments, the CAR is a CD19 CAR ("CD19-CAR"), and in these embodiments, the polycistronic vector comprises an expression cassette that contains a nucleotide sequence encoding a CD19 CAR. In some embodiments, the CD19 CAR may comprise a signal peptide, an extracellular binding domain that specifically binds CD19, a hinge domain, a transmembrane domain, an intracellular costimulatory domain, and/or an intracellular signaling domain in tandem.

In some embodiments, the signal peptide of the CD19 CAR comprises a CD8α signal peptide. In some embodiments, the CD8α signal peptide comprises or consists of an amino acid sequence set forth in SEQ ID NO:6 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:6. In some embodiments, the signal peptide comprises an IgK signal peptide. In some embodiments, the IgK signal peptide comprises or consists of an amino acid sequence set forth in SEQ ID NO:7 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:7. In some embodiments, the signal peptide comprises a GMCSFR-α or CSF2RA signal peptide. In some embodiments, the GMCSFR-α or CSF2RA signal peptide comprises or consists of an amino acid sequence set forth in SEQ ID NO:8 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:8.

In some embodiments, the extracellular binding domain of the CD19 CAR is specific to CD19, for example, human CD19. The extracellular binding domain of the CD19 CAR can be codon-optimized for expression in a host cell or to have variant sequences to increase functions of the extracellular binding domain. In some embodiments, the extracellular binding domain comprises an immunogenically active portion of an immunoglobulin molecule, for example, an scFv.

In some embodiments, the extracellular binding domain of the CD19 CAR comprises an scFv derived from the FMC63 monoclonal antibody (FMC63), which comprises the heavy chain variable region ($V_H$) and the light chain variable region ($V_L$) of FMC63 connected by a linker. FMC63 and the derived scFv have been described in Nicholson et al., Mol. Immun. 34(16-17):1157-1165 (1997) and PCT Application Publication No. WO2018/213337, the entire contents of each of which are incorporated by reference herein. In some embodiments, the amino acid sequences of the entire FMC63-derived scFv (also referred to as FMC63 scFv) and its different portions are provided in Table 6 below. In some embodiments, the CD19-specific scFv comprises or consists of an amino acid sequence set forth in SEQ ID NO:19, 20, or 25, or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO:19, 20, or 25. In some embodiments, the CD19-specific scFv may comprise one or more CDRs having amino acid sequences set forth in SEQ ID NOs: 21-23 and 26-28. In some embodiments, the CD19-specific scFv may comprise a light chain with one or more CDRs having amino acid sequences set forth in SEQ ID NOs: 21-23. In some embodiments, the CD19-specific scFv may comprise a heavy chain with one or more CDRs having amino acid sequences set forth in SEQ ID NOs: 26-28. In any of these embodiments, the CD19-specific scFv may comprise one or more CDRs comprising one or more amino acid substitutions, or comprising a sequence that is at least 80% identical (e.g., at least 80%, at least 85%, at least 90%, at least 95%, at least 96%, at least 97%, at least 98%, at least 99%, or 100% identical), to any of the sequences identified. In some embodiments, the extracellular binding domain of the CD19 CAR comprises or consists of the one or more CDRs as described herein.

In some embodiments, the linker linking the $V_H$ and the $V_L$ portions of the scFv is a Whitlow linker having an amino acid sequence set forth in SEQ ID NO:24. In some embodiments, the Whitlow linker may be replaced by a different linker, for example, a 3×G$_4$S linker having an amino acid sequence set forth in SEQ ID NO:30, which gives rise to a different FMC63-derived scFv having an amino acid sequence set forth in SEQ ID NO:29. In certain of these embodiments, the CD19-specific scFv comprises or consists of an amino acid sequence set forth in SEQ ID NO:29 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:29.

TABLE 6

Exemplary sequences of anti-CD19 scFv and components

| SEQ ID NO: | Amino Acid Sequence | Description |
|---|---|---|
| 19 | DIQMTQTTSSLSASLGDRVTISCRAS QDISKYLNWYQQKPDGTVKLLIYHT SRLHSGVPSRFSGSGSGTDYSLTISN LEQEDIATYFCQQGNTLPYTFGGGT KLEITGSTSGSGKPGSGEGSTKGEVK LQESGPGLVAPSQSLSVTCTVSGVSL PDYGVSWIRQPPRKGLEWLGVIWGS ETTYYNSALKSRLTIIKDNSKSQVFL | Anti-CD19 FMC63 scFv entire sequence, with Whitlow linker |

TABLE 6-continued

Exemplary sequences of anti-CD19 scFv and components

| SEQ ID NO: | Amino Acid Sequence | Description |
|---|---|---|
| | KMNSLQTDDTAIYYCAKHYYYGGS YAMDYWGQGTSVTVSS | |
| 20 | DIQMTQTTSSLSASLGDRVTISCRAS QDISKYLNWYQQKPDGTVKLLIYHT SRLHSGVPSRFSGSGSGTDYSLTISN LEQEDIATYFCQQGNTLPYTFGGGT KLEIT | Anti-CD19 FMC63 scFv light chain variable region |
| 21 | QDISKY | Anti-CD19 FMC63 scFv light chain CDR1 |
| 22 | HTS | Anti-CD19 FMC63 scFv light chain CDR2 |
| 23 | QQGNTLPYT | Anti-CD19 FMC63 scFv light chain CDR3 |
| 24 | GSTSGSGKPGSGEGSTKG | Whitlow linker |
| 25 | EVKLQESGPGLVAPSQSLSVTCTVS GVSLPDYGVSWIRQPPRKGLEWLG VIWGSETTYYNSALKSRLTIIKDNSK SQVFLKMNSLQTDDTAIYYCAKHY YGGSYAMDYWGQGTSVTVSS | Anti-CD19 FMC63 scFv heavy chain variable region |
| 26 | GVSLPDYG | Anti-CD19 FMC63 scFv heavy chain CDR1 |
| 27 | IWGSETT | Anti-CD19 FMC63 scFv heavy chain CDR2 |
| 28 | AKHYYYGGSYAMDY | Anti-CD19 FMC63 scFv heavy chain CDR3 |
| 29 | DIQMTQTTSSLSASLGDRVTISCRAS QDISKYLNWYQQKPDGTVKLLIYHT SRLHSGVPSRFSGSGSGTDYSLTISN LEQEDIATYFCQQGNTLPYTFGGGT KLEITGGGGSGGGGSGGGGSEVKLQ ESGPGLVAPSQSLSVTCTVSGVSLPD YGVSWIRQPPRKGLEWLGVIWGSET TYYNSALKSRLTIIKDNSKSQVFLK MNSLQTDDTAIYYCAKHYYYGGSY AMDYWGQGTSVTVSS | Anti-CD19 FMC63 scFv entire sequence, with 3xG$_4$S linker |
| 30 | GGGGSGGGGSGGGGS | 3xG$_4$S linker |

In some embodiments, the extracellular binding domain of the CD19 CAR is derived from an antibody specific to CD19, including, for example, SJ25C1 (Bejcek et al., Cancer Res. 55:2346-2351 (1995)), HD37 (Pezutto et al., J. Immunol. 138(9):2793-2799 (1987)), 4G7 (Meeker et al., Hybridoma 3:305-320 (1984)), B43 (Bejcek (1995)), BLY3 (Bejcek (1995)), B4 (Freedman et al., 70:418-427 (1987)), B4 HB12b (Kansas & Tedder, J. Immunol. 147:4094-4102 (1991); Yazawa et al., Proc. Natl. Acad. Sci. USA 102: 15178-15183 (2005); Herbst et al., J. Pharmacol. Exp. Ther. 335:213-222 (2010)), BU12 (Callard et al., J. Immunology, 148(10): 2983-2987 (1992)), and CLB-CD19 (De Rie Cell. Immunol. 118:368-381(1989)). In any of these embodiments, the extracellular binding domain of the CD19 CAR can comprise or consist of the $V_H$, the $V_L$, and/or one or more CDRs of any of the antibodies.

In some embodiments, the hinge domain of the CD19 CAR comprises a CD8α hinge domain, for example, a human CD8α hinge domain. In some embodiments, the CD8α hinge domain comprises or consists of an amino acid sequence set forth in SEQ ID NO:9 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:9. In some embodiments, the hinge domain comprises a CD28 hinge domain, for example, a human CD28 hinge domain. In some embodiments, the CD28 hinge domain comprises or consists of an amino acid sequence set forth in SEQ ID NO:10 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:10. In some embodiments, the hinge domain comprises an IgG4 hinge domain, for example, a human IgG4 hinge domain. In some embodiments, the IgG4 hinge domain comprises or consists of an amino acid sequence set forth in SEQ ID NO:11 or SEQ ID NO:12, or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:11 or SEQ ID NO:12. In some embodiments, the hinge domain comprises a IgG4 hinge-Ch2-Ch3 domain, for example, a human IgG4 hinge-Ch2-Ch3 domain. In some embodiments, the IgG4 hinge-Ch2-Ch3 domain comprises or consists of an amino acid sequence set forth in SEQ ID NO:13 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:13.

In some embodiments, the transmembrane domain of the CD19 CAR comprises a CD8α transmembrane domain, for example, a human CD8α transmembrane domain. In some embodiments, the CD8α transmembrane domain comprises or consists of an amino acid sequence set forth in SEQ ID NO:14 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO:14. In some embodiments, the transmembrane domain comprises a CD28 transmembrane domain, for example, a human CD28 transmembrane domain. In some embodiments, the CD28 transmembrane domain comprises or consists of an amino acid sequence set forth in SEQ ID NO:15 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO:15.

In some embodiments, the intracellular costimulatory domain of the CD19 CAR comprises a 4-1BB costimulatory domain. 4-1BB, also known as CD137, transmits a potent costimulatory signal to T cells, promoting differentiation and enhancing long-term survival of T lymphocytes. In some embodiments, the 4-1BB costimulatory domain is human. In some embodiments, the 4-1BB costimulatory domain comprises or consists of an amino acid sequence set forth in SEQ ID NO:16 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO:16. In some embodiments, the intracellular costimulatory domain comprises a CD28 costimulatory domain. CD28 is another co-stimulatory molecule on T cells. In some embodiments, the CD28 costimulatory domain is human. In some embodiments, the CD28 costimulatory domain comprises or consists of an amino acid sequence set forth in SEQ ID NO:17 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO:17. In some embodiments, the intracellular costimulatory domain of the CD19 CAR comprises a 4-1BB costimulatory domain and a CD28 costimulatory domain as described.

In some embodiments, the intracellular signaling domain of the CD19 CAR comprises a CD3 zeta (ζ) signaling domain. CD3ζ associates with T cell receptors (TCRs) to produce a signal and contains immunoreceptor tyrosine-based activation motifs (ITAMs). The CD3ζ signaling domain refers to amino acid residues from the cytoplasmic domain of the zeta chain that are sufficient to functionally transmit an initial signal necessary for T cell activation. In some embodiments, the CD3ζ signaling domain is human. In some embodiments, the CD3ζ signaling domain comprises or consists of an amino acid sequence set forth in SEQ ID NO:18 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO:18.

In some embodiments, the polycistronic vector comprises an expression cassette that contains a nucleotide sequence encoding a CD19 CAR, including, for example, a CD19 CAR comprising the CD19-specific scFv having sequences set forth in SEQ ID NO:19 or SEQ ID NO:29, the CD8α hinge domain of SEQ ID NO:9, the CD8α transmembrane domain of SEQ ID NO:14, the 4-1BB costimulatory domain of SEQ ID NO:16, the CD3ζ signaling domain of SEQ ID NO:18, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof. In any of these embodiments, the CD19 CAR may additionally comprise a signal peptide (e.g., a CD8α signal peptide) as described.

In some embodiments, the polycistronic vector comprises an expression cassette that contains a nucleotide sequence encoding a CD19 CAR, including, for example, a CD19 CAR comprising the CD19-specific scFv having sequences set forth in SEQ ID NO:19 or SEQ ID NO:29, the IgG4 hinge domain of SEQ ID NO:11 or SEQ ID NO:12, the CD28 transmembrane domain of SEQ ID NO:15, the 4-1BB costimulatory domain of SEQ ID NO:16, the CD3ζ signaling domain of SEQ ID NO:18, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof. In any of these embodiments, the CD19 CAR may additionally comprise a signal peptide (e.g., a CD8α signal peptide) as described.

In some embodiments, the polycistronic vector comprises an expression cassette that contains a nucleotide sequence encoding a CD19 CAR, including, for example, a CD19 CAR comprising the CD19-specific scFv having sequences set forth in SEQ ID NO:19 or SEQ ID NO:29, the CD28 hinge domain of SEQ ID NO:10, the CD28 transmembrane domain of SEQ ID NO:15, the CD28 costimulatory domain of SEQ ID NO:17, the CD3ζ signaling domain of SEQ ID NO:18, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof. In any of these embodiments, the CD19 CAR may additionally comprise a signal peptide (e.g., a CD8α signal peptide) as described.

In some embodiments, the polycistronic vector comprises an expression cassette that contains a nucleotide sequence encoding a CD19 CAR as set forth in SEQ ID NO:116 or is at least 80% identical (e.g., at least 80%, at least 85%, at least 90%, at least 95%, at least 96%, at least 97%, at least 98%, at least 99%, or 100% identical) to the nucleotide sequence set forth in SEQ ID NO:116 (see Table 7). The encoded CD19 CAR has a corresponding amino acid sequence set forth in SEQ ID NO:117 or is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:117, with the following components: CD8α signal peptide, FMC63 scFv ($V_L$-Whitlow linker-$V_H$), CD8α hinge domain, CD8α transmembrane domain, 4-1BB costimulatory domain, and CD3ζ signaling domain.

In some embodiments, the polycistronic vector comprises an expression cassette that contains a nucleotide sequence encoding a commercially available embodiment of CD19

CAR. Non-limiting examples of commercially available embodiments of CD19 CARs expressed and/or encoded by T cells include tisagenlecleucel, lisocabtagene maraleucel, axicabtagene ciloleucel, and brexucabtagene autoleucel.

In some embodiments, the polycistronic vector comprises an expression cassette that contains a nucleotide sequence encoding tisagenlecleucel or portions thereof. Tisagenlecleucel comprises a CD19 CAR with the following components: CD8α signal peptide, FMC63 scFv (V$_L$-3×G$_4$S linker-V$_H$), CD8α hinge domain, CD8α transmembrane domain, 4-1BB costimulatory domain, and CD3ζ signaling domain. The nucleotide and amino acid sequence of the CD19 CAR in tisagenlecleucel are provided in Table 7, with annotations of the sequences provided in Table 8.

In some embodiments, the polycistronic vector comprises an expression cassette that contains a nucleotide sequence encoding lisocabtagene maraleucel or portions thereof. Lisocabtagene maraleucel comprises a CD19 CAR with the following components: GMCSFR-α or CSF2RA signal peptide, FMC63 scFv (V$_L$-Whitlow linker-V$_H$), IgG4 hinge domain, CD28 transmembrane domain, 4-1BB costimulatory domain, and CD3ζ signaling domain. The nucleotide and amino acid sequence of the CD19 CAR in lisocabtagene maraleucel are provided in Table 7, with annotations of the sequences provided in Table 9.

In some embodiments, the polycistronic vector comprises an expression cassette that contains a nucleotide sequence encoding axicabtagene ciloleucel or portions thereof. Axicabtagene ciloleucel comprises a CD19 CAR with the following components: GMCSFR-α or CSF2RA signal peptide, FMC63 scFv (V$_L$-Whitlow linker-V$_H$), CD28 hinge domain, CD28 transmembrane domain, CD28 costimulatory domain, and CD3ζ signaling domain. The nucleotide and amino acid sequence of the CD19 CAR in axicabtagene ciloleucel are provided in Table 7, with annotations of the sequences provided in Table 10.

In some embodiments, the polycistronic vector comprises an expression cassette that contains a nucleotide sequence encoding brexucabtagene autoleucel or portions thereof. Brexucabtagene autoleucel comprises a CD19 CAR with the following components: GMCSFR-α signal peptide, FMC63 scFv, CD28 hinge domain, CD28 transmembrane domain, CD28 costimulatory domain, and CD3ζ signaling domain.

In some embodiments, the polycistronic vector comprises an expression cassette that contains a nucleotide sequence encoding a CD19 CAR as set forth in SEQ ID NO: 31, 33, or 35, or is at least 80% identical (e.g., at least 80%, at least 85%, at least 90%, at least 95%, at least 96%, at least 97%, at least 98%, at least 99%, or 100% identical) to the nucleotide sequence set forth in SEQ ID NO: 31, 33, or 35. The encoded CD19 CAR has a corresponding amino acid sequence set forth in SEQ ID NO: 32, 34, or 36, respectively, or is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 32, 34, or 36, respectively.

TABLE 7

Exemplary sequences of CD19 CARs

| SEQ ID NO: | Sequence | Description |
|---|---|---|
| 116 | atggcctta ccagtgaccgccttgctcctgccgctggccttgctgct ccacgccgccaggccggacatccagatgacacagactacatcctc cctgtctgcctctctgggagacagagtcaccatcagttgcagggca agtcaggacattagtaaatatttaaattggtatcagcagaaaccagat ggaactgttaaactcctgatctaccatacatcaagattacactcagg agtcccatcaaggttcagtggcagtgggtctggaacagattattctc tcaccattagcaacctggagcaagaagatattgccacttacttttgcc aacagggtaatacgcttccgtacacgttcggaggggggaccaagc tggagatcacaggctccacctctggatccggcaagcccggatctg gcgagggatccaccaagggcgaggtgaaactgcaggagtcagg acctggcctggtggcgccctcacagagcctgtccgtcacatgcact gtctcagggtctcattacccgactatggtgtaagctggattcgcca gcctccacgaaagggtctggagtggctgggagtaatatgggtag tgaaaccacatactataattcagctctcaaatccagactgaccatcat caaggacaactccaagagccaagtttttcttaaaatgaacagtctgc aaactgatgacacagccatttactactgtgccaaacattattactacg gtggtagctatgctatggactactggggccaaggaacctcagtcac cgtctcctcaaccacgacgccagcgccgcgaccaccaacaccgg cgcccaccatcgcgtcgcagccctgtcctgcgcccagaggcgt gccggccagaggaggggggcgcagtgcacacgaggggggctgg acttcgcctgtgatatctacatctgggcgccettggccgggacttgt ggggtccttctcctgtcactggttatcacccttttactgcaaacggg c agaaagaaactcctgtatattcaaacaaccatttatgagaccagta caaactactcaagaggaagatggctgtagctgccgatttccagaag aagaagaaggaggatgtgaactgagagtgaagttcagcaggagc gcagacgccccgcgtaccagcagggccagaaccagctctataa cgagctcaatctaggacgaagagaggagtacgatgttttggacaa gagacgtggccgggaccctgagatgggggaaagccgagaag gaagaaccctcaggaaggcctgtacaatgaactgcagaaagataa gatggcggaggcctacagtgagattgggatgaaaggcgagcgcc ggaggggcaaggggcacgatggccttaccagggtctcagtaca gccaccaaggacacctacgacgccttcacatgcaggccctgccc cctcgc | Exemplary CD19 CAR nucleotide sequence |
| 117 | MALPVTALLLPLALLLHAARPDIQMTQTTS SLSASLGDRVTISCRASQDISKYLNWYQQK PDGTVKLLIYHTSRLHSGVPSRFSGSGSGT DYSLTISNLEQEDIATYFCQQGNTLPYTFG GGTKLEITGSTSGSGKPGSGEGSTKGEVKL | Exemplary CD19 CAR amino acid sequence |

TABLE 7-continued

Exemplary sequences of CD19 CARs

| SEQ ID NO: | Sequence | Description |
|---|---|---|
| | QESGPGLVAPSQSLSVTCTVSGVSLPDYGV<br>SWIRQPPRKGLEWLGVIWGSETTYYNSAL<br>KSRLTIIKDNSKSQVFLKMNSLQTDDTAIY<br>YCAKHYYYGGSYAMDYWGQGTSVTVSST<br>TTPAPRPPTPAPTIASQPLSLRPEACRPAAG<br>GAVHTRGLDFACDIYIWAPLAGTCGVLLLS<br>LVITLYCKRGRKKLLYIFKQPFMRPVQTTQ<br>EEDGCSCRFPEEEEGGCELRVKFSRSADAP<br>AYQQGQNQLYNELNLGRREEYDVLDKRR<br>GRDPEMGGKPRRKNPQEGLYNELQKDKM<br>AEAYSEIGMKGERRRGKGHDGLYQGLSTA<br>TKDTYDALHMQALPPR | |
| 31 | atggccttaccagtgaccgccttgctcctgccgctggccttgctgct<br>ccacgccgccaggccggacatccagatgacacagactacatcctc<br>cctgtctgcctctctgggagacagagtcaccatcagttgcaggca<br>agtcaggacattagtaaatatttaaattggtatcagcagaaaccagat<br>ggaactgttaaactcctgatctaccatacatcaagattacactcagg<br>agtcccatcaaggttcagtggcagtgggtctggaacagattattctc<br>tcaccattagcaacctggagcaagaagatattgccacttacttttgcc<br>aacagggtaatacgcttccgtacacgttcggaggggggaccaagc<br>tggagatcacaggtggcggtggctcgggcggtggtgggtcgggt<br>ggcggcggatctgaggtgaaactgcaggagtcaggacctggcct<br>ggtggcgccctcacagagcctgtccgtcacatgcactgtctcagg<br>ggtctcattacccgactatggtgtaagctggattcgccagcctccac<br>gaaagggtctggagtggctgggagtaatatggggtagtgaaacca<br>catactataattcagctctcaaatccagactgaccatcatcaaggac<br>aactccaagagccaagttttcttaaaaatgaacagtctgcaaactga<br>tgacacagccatttactactgtgccaaacattattactacggtggtag<br>ctatgctatggactactggggccaaggaacctcagtcaccgtctcct<br>caaccacgacgccagcgccgcgaccaccaacaccggcgcccac<br>catcgcgtcgcagccctgtccctgcgcccagaggcgtgccggc<br>cagcggcgggggcgcagtgcacacgagggggctggacttcgc<br>ctgtgatatctacatctgggcgccttggccggacttgtgggtcc<br>ttctctgtcactggttatcaccattactgcaaacggggcagaaag<br>aaactcctgtatatattcaaacaaccatttatgagaccagtacaaact<br>actcaagaggaagatggctgtagctgccgatttccagaagaagaa<br>gaaggaggatgtgaactgagagtgaagttcagcaggagcgcaa<br>cgccccgcgtacaagcagggccagaaccagctctataacgagc<br>tcaatctaggacgaagagaggagtacgatgtttttggacaagagac<br>gtggccgggaccctgagatgggggaaagccgagaaggaaga<br>accctcaggaaggcctgtacaatgaactgcagaaagataagatgg<br>cggaggcctacagtgagattgggatgaaaggcgagcgccggag<br>gggcaaggggcacgatggcctttaccagggtctcagtacagccac<br>caaggacacctacgacgcccttcacatgcaggccctgccccctcg<br>c | Tisagenlecleucel<br>CD19 CAR<br>nucleotide<br>sequence |
| 32 | MALPVTALLLPLALLLHAARPDIQMTQTTS<br>SLSASLGDRVTISCRASQDISKYLNWYQQK<br>PDGTVKLLIYHTSRLHSGVPSRFSGSGSGT<br>DYSLTISNLEQEDIATYFCQQGNTLPYTFG<br>GGTKLEITGGGGSGGGGSGGGGSEVKLQE<br>SGPGLVAPSQSLSVTCTVSGVSLPDYGVSW<br>IRQPPRKGLEWLGVIWGSETTYYNSALKSR<br>LTIIKDNSKSQVFLKMNSLQTDDTAIYYCA<br>KHYYYGGSYAMDYWGQGTSVTVSSTTTP<br>APRPPTPAPTIASQPLSLRPEACRPAAGGAV<br>HTRGLDFACDIYIWAPLAGTCGVLLLSLVI<br>TLYCKRGRKKLLYIFKQPFMRPVQTTQEED<br>GCSCRFPEEEEGGCELRVKFSRSADAPAYK<br>QGQNQLYNELNLGRREEYDVLDKRRGRD<br>PEMGGKPRRKNPQEGLYNELQKDKMAEA<br>YSEIGMKGERRRGKGHDGLYQGLSTATKD<br>TYDALHMQALPPR | Tisagenlecleucel<br>CD19 CAR amino<br>acid sequence |
| 33 | atgctgctgctggtgaccagcctgctgctgtgcgagctgccccacc<br>ccgcctttctgctgatccccgacatccagatgacccagaccacctc<br>cagcctgagcgccagcctgggcgaccgggtgaccatcagctgcc<br>gggccagccaggacatcagcaagtacctgaactggtatcagcag<br>aagcccgacggcaccgtcaagctgctgatctaccacaccagccg<br>gctgcacagcggcgtgcccagccggtttagcggcagcggctccg<br>gcaccgactacagcctgaccatctccaacctggaacaggaagata<br>tcgccacctacttttgccagcagggcaacacactgccctacacctt<br>tggcggcggaacaaagctggaaatcaccggcagcacctccggca<br>gcggcaagcctggcagcggcgagggcagcaccaagggcgagg<br>tgaagctgcaggaaagcggccctggcctggtggccccagcag | Lisocabtagene<br>maraleucel CD19<br>CAR nucleotide<br>sequence |

TABLE 7-continued

Exemplary sequences of CD19 CARs

| SEQ ID NO: | Sequence | Description |
|---|---|---|
| | agcctgagcgtgacctgcaccgtgagcggcgtgagcctgcccga<br>ctacggcgtgagctggatccggcagcccccaggaagggctgg<br>aatggctgggcgtgatctggggcagcgagaccacctactacaaca<br>gcgccctgaagagccggctgaccatcatcaaggacaacagcaag<br>agccaggtgttcctgaagatgaacagcctgcagaccgacgacacc<br>gccatctactactgcgccaagcactactactacggcggcagctacg<br>ccatggactactggggccagggcaccagcgtgaccgtgagcagc<br>gaatctaagtacggaccgccctgccccccttgccctatgttctgggt<br>gctggtggtggtcggaggcgtgctggcctgctacagcctgctggt<br>caccgtggccttcatcatctttgggtgaaacggggcagaaagaaa<br>ctcctgtatatattcaaacaaccatttatgagaccagtacaaactactc<br>aagaggaagatggctgtagctgccgatttccagaagaagaagaag<br>gaggatgtgaactgcgggtgaagttcagcagaagcgccgacgcc<br>cctgcctaccagcagggccagaatcagctgtacaacgagctgaac<br>ctgggcagaagggaagagtacgacgtcctggataagcggagag<br>gccgggaccctgagatgggcggcaagcctcggcggaagaaccc<br>ccaggaaggcctgtataacgaactgcagaaagacaagatggccg<br>aggcctacagcgagatcggcatgaagggcgagcggaggcggg<br>gcaagggccacgacggcctgtatcagggcctgtccaccgccacc<br>aaggatacctacgacgccctgcacatgcaggccctgccccaag<br>g | |
| 34 | MLLLVTSLLLCELPHPAFLLIPDIQMTQTTS<br>SLSASLGDRVTISCRASQDISKYLNWYQQK<br>PDGTVKLLIYHTSRLHSGVPSRFSGSGSGT<br>DYSLTISNLEQEDIATYFCQQGNTLPYTFG<br>GGTKLEITGSTSGSGKPGSGEGSTKGEVKL<br>QESGPGLVAPSQSLSVTCTVSGVSLPDYGV<br>SWIRQPPRKGLEWLGVIWGSETTYYNSAL<br>KSRLTIIKDNSKSQVFLKMNSLQTDDTAIY<br>YCAKHYYYGGSYAMDYWGQGTSVTVSSE<br>SKYGPPCPPCPMFWVLVVVGGVLACYSLL<br>VTVAFIIFWVKRGRKKLLYIFKQPFMRPVQ<br>TTQEEDGCSCRFPEEEEGGCELRVKFSRSA<br>DAPAYQQGQNQLYNELNLGRREEYDVLD<br>KRRGRDPEMGGKPRRKNPQEGLYNELQK<br>DKMAEAYSEIGMKGERRRGKGHDGLYQG<br>LSTATKDTYDALHMQALPPR | Lisocabtagene<br>maraleucel CD19<br>CAR amino acid<br>sequence |
| 35 | atgcttctcctggtgacaagccttctgctctgtgagttaccacaccca<br>gcattcctcctgatcccagacatccagatgacacagactacatcctc<br>cctgtctgcctctctgggagacagagtcaccatcagttgcaggca<br>agtcaggacattagtaaatatttaaattggtatcagcagaaaccagat<br>ggaactgttaaactcctgatctaccatacatcaagattacactcagg<br>agtcccatcaaggttcagtggcagtgggtctggaacagattattctc<br>tcaccattagcaacctggagcaagaagatattgccacttacttttgcc<br>aacagggtaatacgcttccgtacacgttcggaggggggactaagtt<br>ggaaataacaggctccacctctggatccggcaagcccggatctgg<br>cgagggatccaccaagggcgaggtgaaactgcaggagtcagga<br>cctggcctggtggcgccctcacagagcctgtccgtcacatgcactg<br>tctcaggggtctcattacccgactatggtgtaagctggattcgccag<br>cctccacgaaagggtctggagtggctgggagtaatatggggtagt<br>gaaaccacatactataattcagctctcaaatccagactgaccatcatc<br>aaggacaactccaagagccaagtificttaaaaatgaacagtctgca<br>aactgatgacacagccatttactactgtgccaaacattattactacgg<br>tggtagctatgctatggactactgggtcaaggaacctcagtcacc<br>gtctcctcagcggccgcaattgaagttatgtatcctcctccttaccta<br>gacaatgagaagagcaatggaaccattatccatgtgaaagggaaa<br>cacctttgtccaagtcccctatttcccggaccttctaagccttttggg<br>tgctggtggtggttgggggagtcctggcttgctatagcttgctagta<br>acagtggcctttattattttctgggtgaggagtaagaggagcaggct<br>cctgcacagtgactacatgaacatgactccccgcgccccgggcc<br>cacccgcaagcattaccagccctatgccccaccacgcgacttcgc<br>agcctatcgctccagagtgaagttcagcaggagcgcagacgccc<br>ccgcgtaccagcagggccagaaccagctctataacgagctcaatc<br>taggacaagagaggagtacgatgttttggacaagagacgtggcc<br>gggaccctgagatgggggaaagccgagaaggaagaaccctca<br>ggaaggcctgtacaatgaactgcagaaagataagatggcggagg<br>cctacagtgagattgggatgaaaggcgagcgccggaggggcaa<br>ggggcacgatggccttaccagggtctcagtacagccaccaagga<br>cacctacgacgcccttcacatgcaggccctgccccctcgc | Axicabtagene<br>ciloleucel CD19<br>CAR nucleotide<br>sequence |

TABLE 7-continued

Exemplary sequences of CD19 CARs

| SEQ ID NO: | Sequence | Description |
|---|---|---|
| 36 | MLLLVTSLLLCELPHPAFLLIPDIQMTQTTS SLSASLGDRVTISCRASQDISKYLNWYQQK PDGTVKLLIYHTSRLHSGVPSRFSGSGSGT DYSLTISNLEQEDIATYFCQQGNTLPYTFG GGTKLEITGSTSGSGKPGSGEGSTKGEVKL QESGPGLVAPSQSLSVTCTVSGVSLPDYGV SWIRQPPRKGLEWLGVIWGSETTYYNSAL KSRLTIIKDNSKSQVFLKMNSLQTDDTAIY YCAKHYYYGGSYAMDYWGQGTSVTVSSA AAIEVMYPPPYLDNEKSNGTIIHVKGKHLC PSPLFPGPSKPFWVLVVVGGVLACYSLLVT VAFIIFWVRSKRSRLLHSDYMNMTPRRPGP TRKHYQPYAPPRDFAAYRSRVKFSRSADA PAYQQGQNQLYNELNLGRREEYDVLDKR RGRDPEMGGKPRRKNPQEGLYNELQKDK MAEAYSEIGMKGERRRGKGHDGLYQGLS TATKDTYDALHMQALPPR | Axicabtagene ciloleucel CD19 CAR amino acid sequence |

TABLE 8

Annotation of tisagenlecleucel CD19 CAR sequences

| Feature | Nucleotide Sequence Position | Amino Acid Sequence Position |
|---|---|---|
| CD8α signal peptide | 1-63 | 1-21 |
| FMC63 scFv (V$_L$-3xG$_4$S linker-V$_H$) | 64-789 | 22-263 |
| CD8α hinge domain | 790-924 | 264-308 |
| CD8α transmembrane domain | 925-996 | 309-332 |
| 4-1BB costimulatory domain | 997-1122 | 333-374 |
| CD3ζ signaling domain | 1123-1458 | 375-486 |

TABLE 9

Annotation of lisocabtagene maraleucel CD19 CAR sequences

| Feature | Nucleotide Sequence Position | Amino Acid Sequence Position |
|---|---|---|
| GMCSFR-α signal peptide | 1-66 | 1-22 |
| FMC63 scFv (V$_L$-Whitlow linker-V$_H$) | 67-801 | 23-267 |
| IgG4 hinge domain | 802-837 | 268-279 |
| CD28 transmembrane domain | 838-921 | 280-307 |
| 4-1BB costimulatory domain | 922-1047 | 308-349 |
| CD3ζ signaling domain | 1048-1383 | 350-461 |

TABLE 10

Annotation of axicabtagene ciloleucel CD19 CAR sequences

| Feature | Nucleotide Sequence Position | Amino Acid Sequence Position |
|---|---|---|
| CSF2RA signal peptide | 1-66 | 1-22 |
| FMC63 scFv (V$_L$-Whitlow linker-V$_H$) | 67-801 | 23-267 |
| CD28 hinge domain | 802-927 | 268-309 |
| CD28 transmembrane domain | 928-1008 | 310-336 |
| CD28 costimulatory domain | 1009-1131 | 337-377 |
| CD3ζ signaling domain | 1132-1467 | 378-489 |

In some embodiments, the polycistronic vector comprises an expression cassette that contains a nucleotide sequence encoding CD19 CAR as set forth in SEQ ID NO: 31, 33, or 35, or at least 80% identical (e.g., at least 80%, at least 85%, at least 90%, at least 95%, at least 96%, at least 97%, at least 98%, at least 99%, or 100% identical) to the nucleotide sequence set forth in SEQ ID NO: 31, 33, or 35. The encoded CD19 CAR has a corresponding amino acid sequence set forth in SEQ ID NO: 32, 34, or 36, respectively, is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 32, 34, or 36, respectively.

CD20 CAR

In some embodiments, the CAR is a CD20 CAR ("CD20-CAR"), and in these embodiments, the polycistronic vector comprises an expression cassette that contains a nucleotide sequence encoding a CD20 CAR. CD20 is an antigen found on the surface of B cells as early at the pro-B phase and progressively at increasing levels until B cell maturity, as well as on the cells of most B-cell neoplasms. CD20 positive cells are also sometimes found in cases of Hodgkins disease, myeloma, and thymoma. In some embodiments, the CD20 CAR may comprise a signal peptide, an extracellular binding domain that specifically binds CD20, a hinge domain, a transmembrane domain, an intracellular costimulatory domain, and/or an intracellular signaling domain in tandem.

In some embodiments, the signal peptide of the CD20 CAR comprises a CD8α signal peptide. In some embodiments, the CD8α signal peptide comprises or consists of an amino acid sequence set forth in SEQ ID NO:6 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:6. In some embodiments, the signal peptide comprises an IgK signal peptide. In some embodiments, the IgK signal peptide comprises or consists of an amino acid sequence set forth in SEQ ID NO:7 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:7. In some embodiments, the signal peptide comprises a GMCSFR-α or CSF2RA signal peptide. In some embodiments, the GMCSFR-α or CSF2RA signal peptide comprises or consists of an amino acid sequence set forth in SEQ ID NO:8 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:8.

In some embodiments, the extracellular binding domain of the CD20 CAR is specific to CD20, for example, human CD20. The extracellular binding domain of the CD20 CAR can be codon-optimized for expression in a host cell or to have variant sequences to increase functions of the extracellular binding domain. In some embodiments, the extracellular binding domain comprises an immunogenically active portion of an immunoglobulin molecule, for example, an scFv.

In some embodiments, the extracellular binding domain of the CD20 CAR is derived from an antibody specific to CD20, including, for example, Leu16, IF5, 1.5.3, rituximab, obinutuzumab, ibritumomab, ofatumumab, tositumumab, odronextamab, veltuzumab, ublituximab, and ocrelizumab. In any of these embodiments, the extracellular binding domain of the CD20 CAR can comprise or consist of the $V_H$, the $V_L$, and/or one or more CDRs of any of the antibodies.

In some embodiments, the extracellular binding domain of the CD20 CAR comprises an scFv derived from the Leu16 monoclonal antibody, which comprises the heavy chain variable region ($V_H$) and the light chain variable region ($V_L$) of Leu16 connected by a linker. See Wu et al., Protein Engineering. 14(12):1025-1033 (2001). In some embodiments, the linker is a 3×G$_4$S linker. In other embodiments, the linker is a Whitlow linker as described herein. In some embodiments, the amino acid sequences of different portions of the entire Leu16-derived scFv (also referred to as Leu16 scFv) and its different portions are provided in Table 11 below. In some embodiments, the CD20-specific scFv comprises or consists of an amino acid sequence set forth in SEQ ID NO:37, 38, or 42, or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:37, 38, or 42. In some embodiments, the CD20-specific scFv may comprise one or more CDRs having amino acid sequences set forth in SEQ ID NOs: 39-41, 43 and 44. In some embodiments, the CD20-specific scFv may comprise a light chain with one or more CDRs having amino acid sequences set forth in SEQ ID NOs: 39-41. In some embodiments, the CD20-specific scFv may comprise a heavy chain with one or more CDRs having amino acid sequences set forth in SEQ ID NOs: 43-44. In any of these embodiments, the CD20-specific scFv may comprise one or more CDRs comprising one or more amino acid substitutions, or comprising a sequence that is at least 80% identical (e.g., at least 80%, at least 85%, at least 90%, at least 95%, at least 96%, at least 97%, at least 98%, at least 99%, or 100% identical), to any of the sequences identified. In some embodiments, the extracellular binding domain of the CD20 CAR comprises or consists of the one or more CDRs as described herein.

TABLE 11

Exemplary sequences of anti-CD20 scFv and components

| SEQ ID NO: | Amino Acid Sequence | Description |
|---|---|---|
| 37 | DIVLTQSPAILSASPGEKVTMTCRASSSVNYMDWYQKKPGSSPKPWIYATSNLASGVPARFSGSGSGTSYSLTISRVEAEDAATYYCQQWSFNPPTFGGGTKLEIKGSTSGSGKPGSGEGSTKGEVQLQQSGAELVKPGASVKMSCKASGYTFTSYNMHWVKQTPGQGLEWIGAIYPGNGDTSYNQKFKGKATLTADKSSSTAYMQLSSLTSEDSADYYCARSNYYGSSYWFFDVWGAGTTVTVSS | Anti-CD20 Leu16 scFv entire sequence, with Whitlow linker |
| 38 | DIVLTQSPAILSASPGEKVTMTCRASSSVNYMDWYQKKPGSSPKPWIYATSNLASGVPARFSGSGSGTSYSLTISRVEAEDAATYYCQQWSFNPPTFGGGTKLEIK | Anti-CD20 Leu16 scFv light chain variable region |
| 39 | RASSSVNYMD | Anti-CD20 Leu16 scFv light chain CDR1 |
| 40 | ATSNLAS | Anti-CD20 Leu16 scFv light chain CDR2 |
| 41 | QQWSFNPPT | Anti-CD20 Leu16 scFv light chain CDR3 |

TABLE 11-continued

Exemplary sequences of anti-CD20 scFv and components

| SEQ ID NO: | Amino Acid Sequence | Description |
|---|---|---|
| 42 | EVQLQQSGAELVKPGASVKMSCKA SGYTFTSYNMHWVKQTPGQGLEWI GAIYPGNGDTSYNQKFKGKATLTA DKSSSTAYMQLSSLTSEDSADYYCA RSNYYGSSYWFFDVWGAGTTVTVS S | Anti-CD20 Leu16 scFv heavy chain |
| 43 | SYNMH | Anti-CD20 Leu16 scFv heavy chain CDR1 |
| 44 | AIYPGNGDTSYNQKFKG | Anti-CD20 Leu16 scFv heavy chain CDR2 |

In some embodiments, the hinge domain of the CD20 CAR comprises a CD8α hinge domain, for example, a human CD8α hinge domain. In some embodiments, the CD8α hinge domain comprises or consists of an amino acid sequence set forth in SEQ ID NO:9 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:9. In some embodiments, the hinge domain comprises a CD28 hinge domain, for example, a human CD28 hinge domain. In some embodiments, the CD28 hinge domain comprises or consists of an amino acid sequence set forth in SEQ ID NO: 10 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 10. In some embodiments, the hinge domain comprises an IgG4 hinge domain, for example, a human IgG4 hinge domain. In some embodiments, the IgG4 hinge domain comprises or consists of an amino acid sequence set forth in SEQ ID NO:11 or SEQ ID NO: 12, or an amino acid sequence that is at least 80% identical (e.g., at least 80%, at least 85%, at least 90%, at least 95% at least 96%, at least 97% at least 98%, at least 99% or 100% identical) to the amino acid sequence set forth in of SEQ ID NO:11 or SEQ ID NO: 12. In some embodiments, the hinge domain comprises a IgG4 hinge-Ch2-Ch3 domain, for example, a human IgG4 hinge-Ch2-Ch3 domain. In some embodiments, the IgG4 hinge-Ch2-Ch3 domain comprises or consists of an amino acid sequence set forth in SEQ ID NO:13 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:13.

In some embodiments, the transmembrane domain of the CD20 CAR comprises a CD8α transmembrane domain, for example, a human CD8α transmembrane domain. In some embodiments, the CD8α transmembrane domain comprises or consists of an amino acid sequence set forth in SEQ ID NO:14 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO:14. In some embodiments, the transmembrane domain comprises a CD28 transmembrane domain, for example, a human CD28 transmembrane domain. In some embodiments, the CD28 transmembrane domain comprises or consists of an amino acid sequence set forth in SEQ ID NO:15 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO:15.

In some embodiments, the intracellular costimulatory domain of the CD20 CAR comprises a 4-1BB costimulatory domain, for example, a human 4-1BB costimulatory domain. In some embodiments, the 4-1BB costimulatory domain comprises or consists of an amino acid sequence set forth in SEQ ID NO:16 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO:16. In some embodiments, the intracellular costimulatory domain comprises a CD28 costimulatory domain, for example, a human CD28 costimulatory domain. In some embodiments, the CD28 costimulatory domain comprises or consists of an amino acid sequence set forth in SEQ ID NO:17 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO:17.

In some embodiments, the intracellular signaling domain of the CD20 CAR comprises a CD3 zeta (ζ) signaling domain, for example, a human CD3ζ signaling domain. In some embodiments, the CD3ζ signaling domain comprises or consists of an amino acid sequence set forth in SEQ ID NO:18 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO:18.

In some embodiments, the polycistronic vector comprises an expression cassette that contains a nucleotide sequence encoding a CD20 CAR, including, for example, a CD20 CAR comprising the CD20-specific scFv having sequences set forth in SEQ ID NO:37, the CD8α hinge domain of SEQ ID NO:9, the CD8α transmembrane domain of SEQ ID NO:14, the 4-1BB costimulatory domain of SEQ ID NO:16, the CD3ζ signaling domain of SEQ ID NO:18, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof.

In some embodiments, the polycistronic vector comprises an expression cassette that contains a nucleotide sequence encoding a CD20 CAR, including, for example, a CD20 CAR comprising the CD20-specific scFv having sequences set forth in SEQ ID NO:37, the CD28 hinge domain of SEQ ID NO:10, the CD8α transmembrane domain of SEQ ID NO:14, the 4-1BB costimulatory domain of SEQ ID NO:16, the CD3ζ signaling domain of SEQ ID NO:18, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof.

In some embodiments, the polycistronic vector comprises an expression cassette that contains a nucleotide sequence encoding a CD20 CAR, including, for example, a CD20 CAR comprising the CD20-specific scFv having sequences set forth in SEQ ID NO:37, the IgG4 hinge domain of SEQ ID NO:11 or SEQ ID NO:12, the CD8α transmembrane domain of SEQ ID NO:14, the 4-1BB costimulatory domain of SEQ ID NO:16, the CD3ζ signaling domain of SEQ ID NO:18, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof.

In some embodiments, the polycistronic vector comprises an expression cassette that contains a nucleotide sequence encoding a CD20 CAR, including, for example, a CD20 CAR comprising the CD20-specific scFv having sequences set forth in SEQ ID NO:37, the CD8α hinge domain of SEQ ID NO:9, the CD28 transmembrane domain of SEQ ID NO:15, the 4-1BB costimulatory domain of SEQ ID NO:16, the CD3ζ signaling domain of SEQ ID NO:18, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof.

In some embodiments, the polycistronic vector comprises an expression cassette that contains a nucleotide sequence encoding a CD20 CAR, including, for example, a CD20 CAR comprising the CD20-specific scFv having sequences set forth in SEQ ID NO:37, the CD28 hinge domain of SEQ ID NO:10, the CD28 transmembrane domain of SEQ ID NO:15, the 4-1BB costimulatory domain of SEQ ID NO:16, the CD3ζ signaling domain of SEQ ID NO:18, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof.

In some embodiments, the polycistronic vector comprises an expression cassette that contains a nucleotide sequence encoding a CD20 CAR, including, for example, a CD20 CAR comprising the CD20-specific scFv having sequences set forth in SEQ ID NO:37, the IgG4 hinge domain of SEQ ID NO:11 or SEQ ID NO:1, the CD28 transmembrane domain of SEQ ID NO:15, the 4-1BB costimulatory domain of SEQ ID NO:16, the CD3ζ signaling domain of SEQ ID NO:18, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof. CD22 CAR In some embodiments, the CAR is a CD22 CAR ("CD22-CAR"), and in these embodiments, the polycistronic vector comprises an expression cassette that contains a nucleotide sequence encoding a CD22 CAR. CD22, which is a transmembrane protein found mostly on the surface of mature B cells that functions as an inhibitory receptor for B cell receptor (BCR) signaling. CD22 is expressed in 60-70% of B cell lymphomas and leukemias (e.g., B-chronic lymphocytic leukemia, hairy cell leukemia, acute lymphocytic leukemia (ALL), and Burkitt's lymphoma) and is not present on the cell surface in early stages of B cell development or on stem cells. In some embodiments, the CD22 CAR may comprise a signal peptide, an extracellular binding domain that specifically binds CD22, a hinge domain, a transmembrane domain, an intracellular costimulatory domain, and/or an intracellular signaling domain in tandem.

In some embodiments, the signal peptide of the CD22 CAR comprises a CD8α signal peptide. In some embodiments, the CD8α signal peptide comprises or consists of an amino acid sequence set forth in SEQ ID NO:6 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:6. In some embodiments, the signal peptide comprises an IgK signal peptide. In some embodiments, the IgK signal peptide comprises or consists of an amino acid sequence set forth in SEQ ID NO:7 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:7. In some embodiments, the signal peptide comprises a GMCSFR-α or CSF2RA signal peptide. In some embodiments, the GMCSFR-α or CSF2RA signal peptide comprises or consists of an amino acid sequence set forth in SEQ ID NO:8 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:8.

In some embodiments, the extracellular binding domain of the CD22 CAR is specific to CD22, for example, human CD22. The extracellular binding domain of the CD22 CAR can be codon-optimized for expression in a host cell or to have variant sequences to increase functions of the extracellular binding domain. In some embodiments, the extracellular binding domain comprises an immunogenically active portion of an immunoglobulin molecule, for example, an scFv.

In some embodiments, the extracellular binding domain of the CD22 CAR is derived from an antibody specific to CD22, including, for example, SM03, inotuzumab, epratuzumab, moxetumomab, and pinatuzumab. In any of these embodiments, the extracellular binding domain of the CD22 CAR can comprise or consist of the $V_H$, the $V_L$, and/or one or more CDRs of any of the antibodies.

In some embodiments, the extracellular binding domain of the CD22 CAR comprises an scFv derived from the m971 monoclonal antibody (m971), which comprises the heavy chain variable region ($V_H$) and the light chain variable region ($V_L$) of m971 connected by a linker. In some embodiments, the linker is a 3×G$_4$S linker. In other embodiments, the Whitlow linker may be used instead. In some embodiments, the amino acid sequences of the entire m971-derived scFv (also referred to as m971 scFv) and its different portions are provided in Table 12 below. In some embodiments, the CD22-specific scFv comprises or consists of an amino acid sequence set forth in SEQ ID NO:45, 46, or 50, or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:45, 46, or 50. In some embodiments, the CD22-specific scFv may comprise one or more CDRs having amino acid sequences set forth in SEQ ID NOs: 47-49 and 51-53. In some embodiments, the CD22-specific scFv may comprise a heavy chain with one or more CDRs having amino acid sequences set forth in SEQ ID NOs: 47-49. In some embodiments, the CD22-specific scFv may comprise a light chain with one or more CDRs having amino acid sequences set forth in SEQ ID NOs: 51-53. In any of these embodiments, the CD22-specific scFv may comprise one or more CDRs comprising one or more amino acid substitutions, or comprising a sequence that is at least 80% identical (e.g., at least 80%, at least 85%, at least 90%, at least 95%, at least 96%, at least 97%, at least 98%, at least 99%, or 100% identical), to any of the sequences identified. In some embodiments, the extracellular binding domain of the CD22 CAR comprises or consists of the one or more CDRs as described herein.

In some embodiments, the extracellular binding domain of the CD22 CAR comprises an scFv derived from m971-L7, which is an affinity matured variant of m971 with significantly improved CD22 binding affinity compared to the parental antibody m971 (improved from about 2 nM to less than 50 pM). In some embodiments, the scFv derived from m971-L7 comprises the $V_H$ and the $V_L$ of m971-L7 connected by a 3×G$_4$S linker. In other embodiments, the Whitlow linker may be used instead. In some embodiments, the amino acid sequences of the entire m971-L7-derived scFv (also referred to as m971-L7 scFv) and its different portions are provided in Table 12 below. In some embodiments, the CD22-specific scFv comprises or consists of an amino acid sequence set forth in SEQ ID NO:54, 55, or 59, or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:54, 55, or 59. In some embodiments, the CD22-specific scFv may comprise one or more CDRs having amino acid sequences set forth in SEQ ID NOs: 56-58 and 60-62. In some embodiments, the CD22-specific scFv may comprise a heavy chain with one or more CDRs having amino acid sequences set forth in SEQ ID NOs: 56-58. In some embodiments, the CD22-specific scFv may comprise a light chain with one or more CDRs having amino acid sequences set forth in SEQ ID NOs: 60-62. In any of these embodiments, the CD22-specific scFv may comprise one or more CDRs comprising one or more amino acid substitutions, or comprising a sequence that is at least 8000 identical (e.g., at least 80%, at least 85%, at least 90%, at least 95%, at least 96%, at least 97%, at least 98%, at least 99%, or 100% identical), to any of the sequences identified. In some embodiments, the extracellular binding domain of the CD22 CAR comprises or consists of the one or more CDRs as described herein.

TABLE 12

Exemplary sequences of anti-CD22 scFv and components

| SEQ ID NO: | Amino Acid Sequence | Description |
|---|---|---|
| 45 | QVQLQQSGPGLVKPSQTLSLTCAISG DSVSSNSAAWNWIRQSPSRGLEWL GRTYYRSKWYNDYAVSVKSRITINP DTSKNQFSLQLNSVTPEDTAVYYCA REVTGDLEDAFDIWGQGTMVTVSS GGGGSGGGGSGGGGSDIQMTQSPSS LSASVGDRVTITCRASQTIWSYLNW YQQRPGKAPNLLIYAASSLQSGVPS RFSGRGSGTDFTLTISSLQAEDFATY YCQQSYSIPQTFGQGTKLEIK | Anti-CD22 m971 scFv entire sequence, with 3xG$_4$S linker |
| 46 | QVQLQQSGPGLVKPSQTLSLTCAISG DSVSSNSAAWNWIRQSPSRGLEWL GRTYYRSKWYNDYAVSVKSRITINP DTSKNQFSLQLNSVTPEDTAVYYCA REVTGDLEDAFDIWGQGTMVTVSS | Anti-CD22 m971 scFv heavy chain variable region |
| 47 | GDSVSSNSAA | Anti-CD22 m971 scFv heavy chain CDR1 |
| 48 | TYYRSKWYN | Anti-CD22 m971 scFv heavy chain CDR2 |
| 49 | AREVTGDLEDAFDI | Anti-CD22 m971 scFv heavy chain CDR3 |
| 50 | DIQMTQSPSSLSASVGDRVTITCRAS QTIWSYLNWYQQRPGKAPNLLIYA ASSLQSGVPSRFSGRGSGTDFTLTISS LQAEDFATYYCQQSYSIPQTFGQGT KLEIK | Anti-CD22 m971 scFv light chain |
| 51 | QTIWSY | Anti-CD22 m971 scFv light chain CDR1 |
| 52 | AAS | Anti-CD22 m971 scFv light chain CDR2 |
| 53 | QQSYSIPQT | Anti-CD22 m971 scFv light chain CDR3 |
| 54 | QVQLQQSGPGMVKPSQTLSLTCAIS GDSVSSNSVAWNWIRQSPSRGLEW LGRTYYRSTWYNDYAVSMKSRITIN PDTNKNQFSLQLNSVTPEDTAVYYC | Anti-CD22 m971-L7 scFv entire sequence, with 3xG$_4$S linker |

TABLE 12-continued

Exemplary sequences of anti-CD22 scFv and components

| SEQ ID NO: | Amino Acid Sequence | Description |
|---|---|---|
| | AREVTGDLEDAFDIWGQGTMVTVS SGGGGSGGGGSGGGGSDIQMIQSPS SLSASVGDRVTITCRASQTIWSYLN WYRQRPGEAPNLLIYAASSLQSGVP SRFSGRGSGTDFTLTISSLQAEDFAT YYCQQSYSIPQTFGQGTKLEIK | |
| 55 | QVQLQQSGPGMVKPSQTLSLTCAIS GDSVSSNSVAWNWIRQSPSRGLEW LGRTYYRSTWYNDYAVSMKSRITIN PDTNKNQFSLQLNSVTPEDTAVYYC AREVTGDLEDAFDIWGQGTMVTVS S | Anti-CD22 m971-L7 scFv heavy chain variable region |
| 56 | GDSVSSNSVA | Anti-CD22 m971-L7 scFv heavy chain CDR1 |
| 57 | TYYRSTWYN | Anti-CD22 m971-L7 scFv heavy chain CDR2 |
| 58 | AREVTGDLEDAFDI | Anti-CD22 m971-L7 scFv heavy chain CDR3 |
| 59 | DIQMIQSPSSLSASVGDRVTITCRAS QTIWSYLNWYRQRPGEAPNLLIYAA SSLQSGVPSRFSGRGSGTDFTLTISSL QAEDFATYYCQQSYSIPQTFGQGTK LEIK | Anti-CD22 m971-L7 scFv light chain variable region |
| 60 | QTIWSY | Anti-CD22 m971-L7 scFv light chain CDR1 |
| 61 | AAS | Anti-CD22 m971-L7 scFv light chain CDR2 |
| 62 | QQSYSIPQT | Anti-CD22 m971-L7 scFv light chain CDR3 |

In some embodiments, the extracellular binding domain of the CD22 CAR comprises immunotoxins HA22 or BL22. Immunotoxins BL22 and HA22 are therapeutic agents that comprise an scFv specific for CD22 fused to a bacterial toxin, and thus can bind to the surface of the cancer cells that express CD22 and kill the cancer cells. BL22 comprises a dsFv of an anti-CD22 antibody, RFB4, fused to a 38-kDa truncated form of *Pseudomonas* exotoxin A (Bang et al., Clin. Cancer Res., 11:1545-50 (2005)). HA22 (CAT8015, moxetumomab pasudotox) is a mutated, higher affinity version of BL22 (Ho et al., J. Biol. Chem., 280(1): 607-17 (2005)). Suitable sequences of antigen binding domains of HA22 and BL22 specific to CD22 are disclosed in, for example, U.S. Pat. Nos. 7,541,034; 7,355,012; and 7,982, 011, which are hereby incorporated by reference in their entirety.

In some embodiments, the hinge domain of the CD22 CAR comprises a CD8α hinge domain, for example, a human CD8α hinge domain. In some embodiments, the CD8α hinge domain comprises or consists of an amino acid sequence set forth in SEQ ID NO:9 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:9. In some embodiments, the hinge domain comprises a CD28 hinge domain, for example, a human CD28 hinge domain. In some embodiments, the CD28 hinge domain comprises or consists of an amino acid sequence set forth in SEQ ID NO:10 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:10. In some embodiments, the hinge domain comprises an IgG4 hinge domain, for example, a human IgG4 hinge domain. In some embodiments, the IgG4 hinge domain comprises or consists of an amino acid sequence set forth in SEQ ID NO:11 or SEQ ID NO:12, or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:11 or SEQ ID NO:12. In some embodiments, the hinge domain comprises a IgG4 hinge-Ch2-Ch3 domain, for example, a human IgG4 hinge-Ch2-Ch3 domain. In some embodiments, the IgG4 hinge-Ch2-Ch3 domain comprises or consists of an amino acid sequence set forth in SEQ ID NO:13 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:13.

In some embodiments, the transmembrane domain of the CD22 CAR comprises a CD8α transmembrane domain, for example, a human CD8α transmembrane domain. In some embodiments, the CD8α transmembrane domain comprises or consists of an amino acid sequence set forth in SEQ ID NO:14 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO:14. In some embodiments, the transmembrane domain comprises a CD28 transmembrane domain, for example, a human CD28 transmembrane domain. In some embodiments, the CD28 transmembrane domain comprises or consists of an amino acid sequence set forth in SEQ ID NO:15 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO:15.

In some embodiments, the intracellular costimulatory domain of the CD22 CAR comprises a 4-1BB costimulatory domain, for example, a human 4-1BB costimulatory domain. In some embodiments, the 4-1BB costimulatory domain comprises or consists of an amino acid sequence set forth in SEQ ID NO:16 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO:16. In some embodiments, the intracellular costimulatory domain comprises a CD28 costimulatory domain, for example, a human CD28 costimulatory domain. In some embodiments, the CD28 costimulatory domain comprises or consists of an amino acid sequence set forth in SEQ ID NO:17 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO:17.

In some embodiments, the intracellular signaling domain of the CD22 CAR comprises a CD3 zeta (ζ) signaling domain, for example, a human CD3ζ signaling domain. In some embodiments, the CD3ζ signaling domain comprises or consists of an amino acid sequence set forth in SEQ ID NO:18 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO:18.

In some embodiments, the polycistronic vector comprises an expression cassette that contains a nucleotide sequence encoding a CD22 CAR, including, for example, a CD22 CAR comprising the CD22-specific scFv having sequences set forth in SEQ ID NO:45 or SEQ ID NO:54, the CD8α hinge domain of SEQ ID NO:9, the CD8α transmembrane domain of SEQ ID NO:14, the 4-1BB costimulatory domain of SEQ ID NO:16, the CD3ζ signaling domain of SEQ ID NO:18, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof.

In some embodiments, the polycistronic vector comprises an expression cassette that contains a nucleotide sequence encoding a CD22 CAR, including, for example, a CD22 CAR comprising the CD22-specific scFv having sequences set forth in SEQ ID NO:45 or SEQ ID NO:54, the CD28 hinge domain of SEQ ID NO:10, the CD8α transmembrane domain of SEQ ID NO:14, the 4-1BB costimulatory domain of SEQ ID NO:16, the CD3ζ signaling domain of SEQ ID NO:18, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof.

In some embodiments, the polycistronic vector comprises an expression cassette that contains a nucleotide sequence encoding a CD22 CAR, including, for example, a CD22 CAR comprising the CD22-specific scFv having sequences set forth in SEQ ID NO:45 or SEQ ID NO:54, the IgG4 hinge domain of SEQ ID NO:11 or SEQ ID NO:12, the CD8α transmembrane domain of SEQ ID NO:14, the 4-1BB costimulatory domain of SEQ ID NO:16, the CD3ζ signaling domain of SEQ ID NO:18, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof.

In some embodiments, the polycistronic vector comprises an expression cassette that contains a nucleotide sequence encoding a CD22 CAR, including, for example, a CD22 CAR comprising the CD22-specific scFv having sequences set forth in SEQ ID NO:45 or SEQ ID NO:54, the CD8α hinge domain of SEQ ID NO:9, the CD28 transmembrane domain of SEQ ID NO:15, the 4-1BB costimulatory domain of SEQ ID NO:16, the CD3ζ signaling domain of SEQ ID NO:18, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof.

In some embodiments, the polycistronic vector comprises an expression cassette that contains a nucleotide sequence encoding a CD22 CAR, including, for example, a CD22 CAR comprising the CD22-specific scFv having sequences set forth in SEQ ID NO:45 or SEQ ID NO:54, the CD28 hinge domain of SEQ ID NO:10, the CD28 transmembrane domain of SEQ ID NO:15, the 4-1BB costimulatory domain of SEQ ID NO:16, the CD3ζ signaling domain of SEQ ID NO:18, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof.

In some embodiments, the polycistronic vector comprises an expression cassette that contains a nucleotide sequence encoding a CD22 CAR, including, for example, a CD22 CAR comprising the CD22-specific scFv having sequences set forth in SEQ ID NO:45 or SEQ ID NO:54, the IgG4 hinge domain of SEQ ID NO:11 or SEQ ID NO:12, the CD28 transmembrane domain of SEQ ID NO:15, the 4-1BB costimulatory domain of SEQ ID NO:16, the CD3ζ signaling domain of SEQ ID NO:18, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof.

BCMA CAR

In some embodiments, the CAR is a BCMA CAR ("BCMA-CAR"), and in these embodiments, the polycistronic vector comprises an expression cassette that contains a nucleotide sequence encoding a BCMA CAR. BCMA is a tumor necrosis family receptor (TNFR) member expressed on cells of the B cell lineage, with the highest expression on terminally differentiated B cells or mature B lymphocytes. BCMA is involved in mediating the survival of plasma cells for maintaining long-term humoral immunity. The expression of BCMA has been recently linked to a number of cancers, such as multiple myeloma, Hodgkin's and non-Hodgkin's lymphoma, various leukemias, and glioblastoma. In some embodiments, the BCMA CAR may comprise a signal peptide, an extracellular binding domain that specifically binds BCMA, a hinge domain, a transmembrane domain, an intracellular costimulatory domain, and/or an intracellular signaling domain in tandem.

In some embodiments, the signal peptide of the BCMA CAR comprises a CD8α signal peptide. In some embodiments, the CD8α signal peptide comprises or consists of an amino acid sequence set forth in SEQ ID NO:6 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:6. In some embodiments, the signal peptide comprises an IgK signal peptide. In some embodiments, the IgK signal peptide comprises or consists of an amino acid sequence set forth in SEQ ID NO:7 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:7. In some embodiments, the signal peptide comprises a GMCSFR-α or CSF2RA signal peptide. In some embodiments, the GMCSFR-α or CSF2RA signal peptide comprises or consists of an amino acid sequence set forth in SEQ ID NO:8 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:8.

In some embodiments, the extracellular binding domain of the BCMA CAR is specific to BCMA, for example, human BCMA. The extracellular binding domain of the BCMA CAR can be codon-optimized for expression in a host cell or to have variant sequences to increase functions of the extracellular binding domain.

In some embodiments, the extracellular binding domain comprises an immunogenically active portion of an immunoglobulin molecule, for example, an scFv. In some embodiments, the extracellular binding domain of the BCMA CAR is derived from an antibody specific to BCMA, including, for example, belantamab, erlanatamab, teclistamab, LCAR-B38M, and ciltacabtagene. In any of these embodiments, the extracellular binding domain of the BCMA CAR can comprise or consist of the $V_H$, the $V_L$, and/or one or more CDRs of any of the antibodies.

In some embodiments, the extracellular binding domain of the BCMA CAR comprises an scFv derived from C11D5.3, a murine monoclonal antibody as described in Carpenter et al., Clin. Cancer Res. 19(8):2048-2060 (2013). See also PCT Application Publication No. WO2010/104949. The C11D5.3-derived scFv may comprise the heavy chain variable region ($V_H$) and the light chain variable region ($V_L$) of C11D5.3 connected by the Whitlow linker, the amino acid sequences of which is provided in Table 13 below. In some embodiments, the BCMA-specific extracellular binding domain comprises or consists of an amino acid sequence set forth in SEQ ID NO:63, 64, or 68, or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:63, 64, or 68. In some embodiments, the BCMA-specific extracellular binding domain may comprise one or more CDRs having amino acid sequences set forth in SEQ ID NOs: 65-67 and 69-71. In some embodiments, the BCMA-specific extracellular binding domain may comprise a light chain with one or more CDRs having amino acid sequences set forth in SEQ ID NOs: 65-67. In some embodiments, the BCMA-specific extracellular binding domain may comprise a heavy chain with one or more CDRs having amino acid sequences set forth in SEQ ID NOs: 69-71. In any of these embodiments, the BCMA-specific scFv may comprise one or more CDRs comprising one or more amino acid substitutions, or comprising a sequence that is at least 80% identical (e.g., at least 80%, at least 85%, at least 90%, at least 95%, at least 96%, at least 97%, at least 98%, at least 99%, or 100% identical), to any of the sequences identified. In some embodiments, the extracellular binding domain of the BCMA CAR comprises or consists of the one or more CDRs as described herein.

In some embodiments, the extracellular binding domain of the BCMA CAR comprises an scFv derived from another murine monoclonal antibody, C12A3.2, as described in Carpenter et al., Clin. Cancer Res. 19(8):2048-2060 (2013) and PCT Application Publication No. WO2010/104949, the amino acid sequence of which is also provided in Table 13 below. In some embodiments, the BCMA-specific extracellular binding domain comprises or consists of an amino acid sequence set forth in SEQ ID NO:72, 73, or 77, or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:72, 73, or 77. In some embodiments, the BCMA-specific extracellular binding domain may comprise one or more CDRs having amino acid sequences set forth in SEQ ID NOs: 74-76 and 78-80. In some embodiments, the BCMA-specific extracellular binding domain may comprise a light chain with one or more CDRs having amino acid sequences set forth in SEQ ID NOs: 74-76. In some embodiments, the BCMA-specific extracellular binding domain may comprise a heavy chain with one or more CDRs having amino acid sequences set forth in SEQ ID NOs: 78-80. In any of these embodiments, the BCMA-specific scFv may comprise one or more CDRs comprising one or more amino acid substitutions, or comprising a sequence that is at least 80% identical (e.g., at least 80%, at least 85%, at least 90%, at least 95%, at least 96%, at least 97%, at least 98%, at least 99%, or 100% identical), to any of the sequences identified. In some embodiments, the extracellular binding domain of the BCMA CAR comprises or consists of the one or more CDRs as described herein.

In some embodiments, the extracellular binding domain of the BCMA CAR comprises a murine monoclonal antibody with high specificity to human BCMA, referred to as BB2121 in Friedman et al., Hum. Gene Ther. 29(5):585-601 (2018)). See also, PCT Application Publication No. WO2012163805.

In some embodiments, the extracellular binding domain of the BCMA CAR comprises single variable fragments of two heavy chains (VHH) that can bind to two epitopes of BCMA as described in Zhao et al., J. Hematol. Oncol. 11(1):141 (2018), also referred to as LCAR-B38M. See also, PCT Application Publication No. WO2018/028647.

In some embodiments, the extracellular binding domain of the BCMA CAR comprises a fully human heavy-chain variable domain (FHVH) as described in Lam et al., Nat. Commun. 11(1):283 (2020), also referred to as FHVH33. See also, PCT Application Publication No. WO2019/006072. The amino acid sequences of FHVH33 and its CDRs are provided in Table 13 below. In some embodiments, the BCMA-specific extracellular binding domain comprises or consists of an amino acid sequence set forth in SEQ ID NO:81 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:81. In some embodiments, the BCMA-specific extracellular binding domain may comprise one or more CDRs having amino acid sequences set forth in SEQ ID NOs: 82-84. In any of these embodiments, the BCMA-specific extracellular binding domain may comprise one or more CDRs comprising one or more amino acid substitutions, or comprising a sequence that is at least 80% identical (e.g., at least 80%, at least 85%, at least 90%, at least 95%, at least 96%, at least 97%, at least 98%, at least 99%, or 100% identical), to any of the sequences identified. In some embodiments, the extracellular binding domain of the BCMA CAR comprises or consists of the one or more CDRs as described herein.

In some embodiments, the extracellular binding domain of the BCMA CAR comprises an scFv derived from CT103A (or CAR0085) as described in U.S. Pat. No. 11,026,975 B2, the amino acid sequence of which is provided in Table 13 below. In some embodiments, the BCMA-specific extracellular binding domain comprises or consists of an amino acid sequence set forth in SEQ ID NO:118, 119, or 123, or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 118, 119, or 123. In some embodiments, the BCMA-specific extracellular binding domain may comprise one or more CDRs having amino acid sequences set forth in SEQ ID NOs: 120-122 and 124-126. In some embodiments, the BCMA-specific extracellular binding domain may comprise a light chain with one or more CDRs having amino acid sequences set forth in SEQ ID NOs: 120-122. In some embodiments, the BCMA-specific extracellular binding domain may comprise a heavy chain with one or more CDRs having amino acid sequences set forth in SEQ ID NOs: 124-126. In any of these embodiments, the BCMA-specific scFv may comprise one or more CDRs comprising one or more amino acid substitutions, or comprising a sequence that is at least 80% identical (e.g., at least 80%, at least 85%, at least 90%, at least 95%, at least 96%, at least 97%, at least 98%, at least 99%, or 100% identical), to any of the sequences identified. In some embodiments, the extracellular binding domain of the BCMA CAR comprises or consists of the one or more CDRs as described herein.

Additionally, CARs and binders directed to BCMA have been described in U.S. Application Publication Nos. 2020/0246381 A1 and 2020/0339699 A1, the entire contents of each of which are incorporated by reference herein.

TABLE 13

Exemplary sequences of anti-BCMA binder and components

| SEQ ID NO: | Amino Acid Sequence | Description |
|---|---|---|
| 63 | DIVLTQSPASLAMSLGKRATISCRAS ESVSVIGAHLIHWYQQKPGQPPKLLI YLASNLETGVPARFSGSGSGTDFTLT IDPVEEDDVAIYSCLQSRIFPRTFGG GTKLEIKGSTSGSGKPGSGEGSTKG QIQLVQSGPELKKPGETVKISCKASG YTFTDYSINWVKRAPGKGLKWMG WINTETREPAYAYDFRGRFAFSLETS ASTAYLQINNLKYEDTATYFCALDY SYAMDYWGQGTSVTVSS | Anti-BCMA C11D5.3 scFv entire sequence, with Whitlow linker |
| 64 | DIVLTQSPASLAMSLGKRATISCRAS ESVSVIGAHLIHWYQQKPGQPPKLLI YLASNLETGVPARFSGSGSGTDFTLT IDPVEEDDVAIYSCLQSRIFPRTFGG GTKLEIK | Anti-BCMA C11D5.3 scFv light chain variable region |
| 65 | RASESVSVIGAHLIH | Anti-BCMA C11D5.3 scFv light chain CDR1 |
| 66 | LASNLET | Anti-BCMA C11D5.3 scFv light chain CDR2 |
| 67 | LQSRIFPRT | Anti-BCMA C11D5.3 scFv light chain CDR3 |
| 68 | QIQLVQSGPELKKPGETVKISCKASG YTFTDYSINWVKRAPGKGLKWMG WINTETREPAYAYDFRGRFAFSLETS ASTAYLQINNLKYEDTATYFCALDY SYAMDYWGQGTSVTVSS | Anti-BCMA C11D5.3 scFv heavy chain variable region |
| 69 | DYSIN | Anti-BCMA C11D5.3 scFv heavy chain CDR1 |
| 70 | WINTETREPAYAYDFRG | Anti-BCMA C11D5.3 scFv heavy chain CDR2 |
| 71 | DYSYAMDY | Anti-BCMA C11D5.3 scFv heavy chain CDR3 |
| 72 | DIVLTQSPPSLAMSLGKRATISCRAS ESVTILGSHLIYWYQQKPGQPPTLLI QLASNVQTGVPARFSGSGSRTDFTL TIDPVEEDDVAVYYCLQSRTIPRTFG GGTKLEIKGSTSGSGKPGSGEGSTK | Anti-BCMA C12A3.2 scFv entire sequence, with Whitlow linker |

TABLE 13-continued

Exemplary sequences of anti-BCMA binder and components

| SEQ ID NO: | Amino Acid Sequence | Description |
|---|---|---|
| | GQIQLVQSGPELKKPGETVKISCKAS GYTFRHYSMNWVKQAPGKGLKWM GRINTESGVPIYADDFKGRFAFSVET SASTAYLVINNLKDEDTASYFCSND YLYSLDFWGQGTALTVSS | |
| 73 | DIVLTQSPPSLAMSLGKRATISCRAS ESVTILGSHLIYWYQQKPGQPPTLLI QLASNVQTGVPARFSGSGSRTDFTL TIDPVEEDDVAVYYCLQSRTIPRTFG GGTKLEIK | Anti-BCMA C12A3.2 scFv light chain variable region |
| 74 | RASESVTILGSHLIY | Anti-BCMA C12A3.2 scFv light chain CDR1 |
| 75 | LASNVQT | Anti-BCMA C12A3.2 scFv light chain CDR2 |
| 76 | LQSRTIPRT | Anti-BCMA C12A3.2 scFv light chain CDR3 |
| 77 | QIQLVQSGPELKKPGETVKISCKASG YTFRHYSMNWVKQAPGKGLKWMG RINTESGVPIYADDFKGRFAFSVETS ASTAYLVINNLKDEDTASYFCSNDY LYSLDFWGQGTALTVSS | Anti-BCMA C12A3.2 scFv heavy chain variable region |
| 78 | HYSMN | Anti-BCMA C12A3.2 scFv heavy chain CDR1 |
| 79 | RINTESGVPIYADDFKG | Anti-BCMA C12A3.2 scFv heavy chain CDR2 |
| 80 | DYLYSLDF | Anti-BCMA C12A3.2 scFv heavy chain CDR3 |
| 81 | EVQLLESGGGLVQPGGSLRLSCAAS GFTFSSYAMSWVRQAPGKGLEWVS SISGSGDYIYYADSVKGRFTISRDISK NTLYLQMNSLRAEDTAVYYCAKEG TGANSSLADYRGQGTLVTVSS | Anti-BCMA FHVH33 entire sequence |
| 82 | GFTFSSYA | Anti-BCMA FHVH33 CDR1 |
| 83 | ISGSGDYI | Anti-BCMA FHVH33 CDR2 |
| 84 | AKEGTGANSSLADY | Anti-BCMA FHVH33 CDR3 |
| 118 | DIQMTQSPSSLSASVGDRVTITCRAS QSISSYLNWYQQKPGKAPKLLIYAA SSLQSGVPSRFSGSGSGTDFTLTISSL QPEDFATYYCQQKYDLLTFGGGTK VEIKGSTSGSGKPGSGEGSTKGQLQ LQESGPGLVKPSETLSLTCTVSGGSI SSSSYYWGWIRQPPGKGLEWIGSIY SGSTYYNPSLKSRVTISVDTSKNQFS LKLSSVTAADTAVYYCARDRGDTIL DVWGQGTMVTVSS | Anti-BCMA CT103A scFv entire sequence, with Whitlow linker |
| 119 | DIQMTQSPSSLSASVGDRVTITCRAS QSISSYLNWYQQKPGKAPKLLIYAA SSLQSGVPSRFSGSGSGTDFTLTISSL QPEDFATYYCQQKYDLLTFGGGTK VEIK | Anti-BCMA CT103A scFv light chain variable region |
| 120 | QSISSY | Anti-BCMA CT103A scFv light chain CDR1 |
| 121 | AAS | Anti-BCMA CT103A scFv light chain CDR2 |
| 122 | QQKYDLLT | Anti-BCMA CT103A scFv light chain CDR3 |

TABLE 13-continued

Exemplary sequences of anti-BCMA binder and components

| SEQ ID NO: | Amino Acid Sequence | Description |
| --- | --- | --- |
| 123 | QLQLQESGPGLVKPSETLSLTCTVSG GSISSSSYYWGWIRQPPGKGLEWIGS ISYSGSTYYNPSLKSRVTISVDTSKN QFSLKLSSVTAADTAVYYCARDRG DTILDVWGQGTMVTVSS | Anti-BCMA CT103A scFv heavy chain variable region |
| 124 | GGSISSSSYY | Anti-BCMA CT103A scFv heavy chain CDR1 |
| 125 | ISYSGST | Anti-BCMA CT103A scFv heavy chain CDR2 |
| 126 | ARDRGDTILDV | Anti-BCMA CT103A scFv heavy chain CDR3 |

In some embodiments, the hinge domain of the BCMA CAR comprises a CD8α hinge domain, for example, a human CD8α hinge domain. In some embodiments, the CD8α hinge domain comprises or consists of an amino acid sequence set forth in SEQ ID NO:9 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:9. In some embodiments, the hinge domain comprises a CD28 hinge domain, for example, a human CD28 hinge domain. In some embodiments, the CD28 hinge domain comprises or consists of an amino acid sequence set forth in SEQ ID NO: 10 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO: 10. In some embodiments, the hinge domain comprises an IgG4 hinge domain, for example, a human IgG4 hinge domain. In some embodiments, the IgG4 hinge domain comprises or consists of an amino acid sequence set forth in SEQ ID NO:11 or SEQ ID NO: 12, or an amino acid sequence that is at least 80% identical (e.g., at least 80%, at least 85%, at least 90%, at least 95% at least 96%, at least 97% at least 98%, at least 99%, or 100% identical) to the amino acid sequence set forth in of SEQ ID NO:11 or SEQ ID NO:12. In some embodiments, the hinge domain comprises a IgG4 hinge-Ch2-Ch3 domain, for example, a human IgG4 hinge-Ch2-Ch3 domain. In some embodiments, the IgG4 hinge-Ch2-Ch3 domain comprises or consists of an amino acid sequence set forth in SEQ ID NO:13 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:13.

In some embodiments, the transmembrane domain of the BCMA CAR comprises a CD8α transmembrane domain, for example, a human CD8α transmembrane domain. In some embodiments, the CD8α transmembrane domain comprises or consists of an amino acid sequence set forth in SEQ ID NO:14 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO:14. In some embodiments, the transmembrane domain comprises a CD28 transmembrane domain, for example, a human CD28 transmembrane domain. In some embodiments, the CD28 transmembrane domain comprises or consists of an amino acid sequence set forth in SEQ ID NO:15 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO:15.

In some embodiments, the intracellular costimulatory domain of the BCMA CAR comprises a 4-1BB costimulatory domain, for example, a human 4-1BB costimulatory domain. In some embodiments, the 4-1BB costimulatory domain comprises or consists of an amino acid sequence set forth in SEQ ID NO:16 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO:16. In some embodiments, the intracellular costimulatory domain comprises a CD28 costimulatory domain, for example, a human CD28 costimulatory domain. In some embodiments, the CD28 costimulatory domain comprises or consists of an amino acid sequence set forth in SEQ ID NO:17 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO:17.

In some embodiments, the intracellular signaling domain of the BCMA CAR comprises a CD3 zeta (ζ) signaling domain, for example, a human CD3ζ signaling domain. In some embodiments, the CD3ζ signaling domain comprises or consists of an amino acid sequence set forth in SEQ ID NO:18 or an amino acid sequence that is at least 80% identical (e.g., at least 80%, at least 85%, at least 90%, at least 95%, at least 96%, at least 97%, at least 98%, at least 99%, or 100% identical) to the amino acid sequence set forth in SEQ ID NO:18.

In some embodiments, the polycistronic vector comprises an expression cassette that contains a nucleotide sequence encoding a BCMA CAR, including, for example, a BCMA CAR comprising any of the BCMA-specific extracellular binding domains as described, the CD8α hinge domain of SEQ ID NO:9, the CD8α transmembrane domain of SEQ ID NO:14, the 4-1BB costimulatory domain of SEQ ID NO:16, the CD3ζ signaling domain of SEQ ID NO:18, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof. In any of these embodiments, the BCMA CAR may additionally comprise a signal peptide (e.g., a CD8α signal peptide) as described.

In some embodiments, the polycistronic vector comprises an expression cassette that contains a nucleotide sequence encoding a BCMA CAR, including, for example, a BCMA CAR comprising any of the BCMA-specific extracellular binding domains as described, the CD8α hinge domain of SEQ ID NO:9, the CD8α transmembrane domain of SEQ ID NO:14, the CD28 costimulatory domain of SEQ ID NO:17, the CD3ζ signaling domain of SEQ ID NO:18, and/or variants (i.e., having a sequence that is at least 80% identical, for example, at least 80%, at least 85%, at least 90%, at least 95%, at least 96%, at least 97%, at least 98%, or at least 99 identical to the disclosed sequence) thereof. In any of these embodiments, the BCMA CAR may additionally comprise a signal peptide as described.

In some embodiments, the polycistronic vector comprises an expression cassette that contains a nucleotide sequence encoding a BCMA CAR as set forth in SEQ ID NO:127 or is at least 80% identical (e.g., at least 80%, at least 85%, at least 90%, at least 95%, at least 96%, at least 97%, at least 98%, at least 99%, or 100% identical) to the nucleotide sequence set forth in SEQ ID NO:127 (see Table 14). The encoded BCMA CAR has a corresponding amino acid sequence set forth in SEQ ID NO:128 or is at least 80% identical (e.g., at least 80%, at least 85%, at least 90%, at least 95%, at least 96%, at least 97%, at least 98%, at least 99%, or 100% identical) to the amino acid sequence set forth in of SEQ ID NO:128, with the following components: CD8α signal peptide, CT103A scFv ($V_L$-Whitlow linker-$V_H$), CD8α hinge domain, CD8α transmembrane domain, 4-1BB costimulatory domain, and CD3 signaling domain.

In some embodiments, the polycistronic vector comprises an expression cassette that contains a nucleotide sequence encoding a commercially available embodiment of BCMA CAR, including, for example, idecabtagene vicleucel (ide-cel, also called bb2121). In some embodiments, the polycistronic vector comprises an expression cassette that contains a nucleotide sequence encoding idecabtagene vicleucel or portions thereof. Idecabtagene vicleucel comprises a BCMA CAR with the following components: the BB2121 binder, CD8α hinge domain, CD8α transmembrane domain, 4-1BB costimulatory domain, and CD3 signaling domain.

TABLE 14

Exemplary sequences of BCMA CARs

| SEQ ID NO: | Sequence | Description |
| --- | --- | --- |
| 127 | atggccttaccagtgaccgccttgctcctgccgctggccttgctgc tccacgccgccaggccggacatccagatgacccagtctccatcct ccctgtctgcatctgtaggagacagagtcaccatcacttgccggg caagtcagagcattagcagctatttaaattggtatcagcagaaacc agggaaagcccctaagctcctgatctatgctgcatccagtttgcaa agtggggtcccatcaaggttcagtggcagtggatctgggacagat ttcactctcaccatcagcagtctgcaacctgaagatttttgcaacttac tactgtcagcaaaaatacgacctcctcacttttggcggagggacca aggttgagatcaaaggcagcaccagcggctccggcaagcctgg ctctggcgagggcagcacaaagggacagctgcagctgcagga gtcgggcccaggactggtgaagccttcggagaccctgtccctca cctgcactgtctctggtggctccatcagcagtagtagttactactgg ggctggatccgccagcccccagggaaggggctggagtggattg ggagtatctcctatagtgggagcacctactacaacccgtccctcaa gagtcgagtcaccatatccgtagacacgtccaagaaccagttctc cctgaagctgagttctgtgaccgccgcagacacggcggtgtacta ctgcgccagagatcgtggagacaccatactagacgtatggggtc agggtacaatggtcaccgtcagctcattcgtgcccgtgttcctgcc cgccaaacctaccaccaccccctgcccctagacctcccacccag cccccaacaatcgccagccagcctctgtctctgcggcccgaagcct gtagacctgctgccggcggagccgtgcacaccagaggcctgga cttcgcctgcgacatctacatctgggcccctctggccggcacctgt ggcgtgctgctgctgagcctggtgatcaccctgtactgcaaccac cggaacaaacggggcagaaagaaactcctgtatatattcaaacaa ccatttatgagaccagtacaaactactcaagaggaagatggctgta gctgccgatttccagaagaagaagaaggaggatgtgaactgaga gtgaagttcagcagatccgccgacgcccctgcctaccagcaggg acagaaccagctgtacaacgagctgaacctgggcagacgggaa gagtacgacgtgctggacaagcggagaggccgggaccccgag atgggcggaaagcccagacggaagaaccccccaggaaggcctg tataacgaactgcagaaagacaagatggccgaggcctacagcg agatcggcatgaagggcgagcggaggcgcggcaagggccac gatggcctgtaccagggcctgagcaccgccaccaaggacacct acgacgccctgcacatgcaggccctgcccccccaga | Exemplary BCMA CAR nucleotide sequence |
| 128 | MALPVTALLLPLALLLHAARPDIQMTQSP SSLSASVGDRVTITCRASQSISSYLNWYQQ KPGKAPKLLIYAASSLQSGVPSRFSGSGSG TDFTLTISSLQPEDFATYYCQQKYDLLTFG GGTKVEIKGSTSGSGKPGSGEGSTKGQLQ LQESGPGLVKPSETLSLTCTVSGGSISSSSY YWGWIRQPPGKGLEWIGSISYSGSTYYNP SLKSRVTISVDTSKNQFSLKLSSVTAADTA VYYCARDRGDTILDVWGQGTMVTVSSFV PVFLPAKPTTTPAPRPPTPAPTIASQPLSLR PEACRPAAGGAVHTRGLDFACDIYIWAPL AGTCGVLLLSLVITLYCNHRNKRGRKKLL | Exemplary BCMA CAR amino acid sequence |

TABLE 14-continued

Exemplary sequences of BCMA CARs

| SEQ ID NO: | Sequence | Description |
|---|---|---|
| | YIFKQPFMRPVQTTQEEDGCSCRFPEEEEG<br>GCELRVKFSRSADAPAYQQGQNQLYNEL<br>NLGRREEYDVLDKRRGRDPEMGGKPRRK<br>NPQEGLYNELQKDKMAEAYSEIGMKGER<br>RRGKGHDGLYQGLSTATKDTYDALHMQ<br>ALPPR | |

O. Characteristics of Hypoimmunogenic Cells

In some embodiments, the population of hypoimmunogenic stem cells retains pluripotency as compared to a control stem cell (e.g., a wild-type stem cell or immunogenic stem cell). In some embodiments, the population of hypoimmunogenic stem cells retains differentiation potential as compared to a control stem cell (e.g., a wild-type stem cell or immunogenic stem cell).

In some embodiments, the administered population of hypoimmunogenic cells such as hypoimmunogenic CAR-T cells elicits a decreased or lower level of immune activation in the subject or patient. In some instances, the level of immune activation elicited by the cells is at least 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% lower compared to the level of immune activation produced by the administration of immunogenic cells. In some embodiments, the administered population of hypoimmunogenic cells fails to elicit immune activation in the subject or patient.

In some embodiments, the administered population of hypoimmunogenic cells such as hypoimmunogenic CAR-T cells elicits a decreased or lower level of T cell response in the subject or patient. In some instances, the level of T cell response elicited by the cells is at least 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% lower compared to the level of T cell response produced by the administration of immunogenic cells. In some embodiments, the administered population of hypoimmunogenic cells fails to elicit a T cell response to the cells in the subject or patient.

In some embodiments, the administered population of hypoimmunogenic cells such as hypoimmunogenic CAR-T cells elicits a decreased or lower level of NK cell response in the subject or patient. In some instances, the level of NK cell response elicited by the cells is at least 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% lower compared to the level of NK cell response produced by the administration of immunogenic cells. In some embodiments, the administered population of hypoimmunogenic cells fails to elicit an NK cell response to the cells in the subject or patient.

In some embodiments, the administered population of hypoimmunogenic cells such as hypoimmunogenic CAR-T cells elicits a decreased or lower level of macrophage engulfment in the subject or patient. In some instances, the level of NK cell response elicited by the cells is at least 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% lower compared to the level of macrophage engulfment produced by the administration of immunogenic cells. In some embodiments, the administered population of hypoimmunogenic cells fails to elicit macrophage engulfment of the cells in the subject or patient.

In some embodiments, the administered population of hypoimmunogenic cells such as hypoimmunogenic CAR-T cells elicits a decreased or lower level of systemic TH1 activation in the subject or patient. In some instances, the level of systemic TH1 activation elicited by the cells is at least 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% lower compared to the level of systemic TH1 activation produced by the administration of immunogenic cells. In some embodiments, the administered population of hypoimmunogenic cells fails to elicit systemic TH1 activation in the subject or patient.

In some embodiments, the administered population of hypoimmunogenic cells such as hypoimmunogenic CAR-T cells elicits a decreased or lower level of NK cell killing in the subject or patient. In some instances, the level of NK cell killing elicited by the cells is at least 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% lower compared to the level of NK cell killing produced by the administration of immunogenic cells. In some embodiments, the administered population of hypoimmunogenic cells fails to elicit NK cell killing in the subject or patient.

In some embodiments, the administered population of hypoimmunogenic cells such as hypoimmunogenic CAR-T cells elicits a decreased or lower level of immune activation of peripheral blood mononuclear cells (PBMCs) in the subject or patient. In some instances, the level of immune activation of PBMCs elicited by the cells is at least 5%, 10%, 15%, 20%, 25%, 30%, 35%0, 40%, 45%, 50%, 55%, 60%, 65%, 70%, 75%, 80%, 85%, 90%, 91%, 92%, 93%, 94%, 95%, 96%, 97%, 98%, or 99% lower compared to the level of immune activation of PBMCs produced by the administration of immunogenic cells. In some embodiments, the administered population of hypoimmunogenic cells fails to elicit immune activation of PBMCs in the subject or patient.

In some embodiments, the administered population of hypoimmunogenic cells such as hypoimmunogenic CAR-T cells elicits a decreased or lower level of donor-specific IgG antibodies in the subject or patient. In some instances, the level of donor-specific IgG antibodies elicited by the cells is at least 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% lower compared to the level of donor-specific IgG antibodies produced by the administration of immunogenic cells. In some embodiments, the administered population of hypoimmunogenic cells fails to elicit donor-specific IgG antibodies in the subject or patient.

In some embodiments, the administered population of hypoimmunogenic cells such as hypoimmunogenic CAR-T cells elicits a decreased or lower level of donor-specific IgM antibodies in the subject or patient. In some instances, the level of donor-specific IgM antibodies elicited by the cells is at least 5%, 10%, 15%, 20%, 25%, 30%, 35%, 40%, 45% 50%, 55%, 60%, 65%, 70%, 75%, 80%, 85%, 90%, 91%, 92%, 93%, 94%, 95%, 96%, 97%, 98%, or 99% lower compared to the level of donor-specific IgM antibodies produced by the administration of immunogenic cells. In some embodiments, the administered population of hypoimmunogenic cells fails to elicit donor-specific IgM antibodies in the subject or patient.

In some embodiments, the administered population of hypoimmunogenic cells such as hypoimmunogenic CAR-T cells elicits a decreased or lower level of IgM and IgG antibody production in the subject or patient. In some instances, the level of IgM and IgG antibody production elicited by the cells is at least 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% lower compared to the level of IgM and IgG antibody production produced by the administration of immunogenic cells. In some embodiments, the administered population of hypoimmunogenic cells fails to elicit IgM and IgG antibody production in the subject or patient.

In some embodiments, the administered population of hypoimmunogenic cells such as hypoimmunogenic CAR-T cells elicits a decreased or lower level of cytotoxic T cell killing in the subject or patient. In some instances, the level of cytotoxic T cell killing elicited by the cells is at least 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% lower compared to the level of cytotoxic T cell killing produced by the administration of immunogenic cells. In some embodiments, the administered population of hypoimmunogenic cells fails to elicit cytotoxic T cell killing in the subject or patient.

In some embodiments, the administered population of hypoimmunogenic cells such as hypoimmunogenic CAR-T cells elicits a decreased or lower level of complement-dependent cytotoxicity (CDC) in the subject or patient. In some instances, the level of CDC elicited by the cells is at least 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% lower compared to the level of CDC produced by the administration of immunogenic cells. In some embodiments, the administered population of hypoimmunogenic cells fails to elicit CDC in the subject or patient.

P. Therapeutic Cells from Primary T Cells

Provided herein are hypoimmunogenic cells including, but not limited to, primary T cells that evade immune recognition. In some embodiments, the hypoimmunogenic cells are produced (e.g., generated, cultured, or derived) from T cells such as primary T cells. In some instances, primary T cells are obtained (e.g., harvested, extracted, removed, or taken) from a subject or an individual. In some embodiments, primary T cells are produced from a pool of T cells such that the T cells are from one or more subjects (e.g., one or more human including one or more healthy humans). In some embodiments, the pool of primary T cells is from 1-100, 1-50, 1-20, 1-10, 1 or more, 2 or more, 3 or more, 4 or more, 5 or more, 10 or more, 20 or more, 30 or more, 40 or more, 50 or more, or 100 or more subjects. In some embodiments, the donor subject is different from the patient (e.g., the recipient that is administered the therapeutic cells). In some embodiments, the pool of T cells do not include cells from the patient. In some embodiments, one or more of the donor subjects from which the pool of T cells is obtained are different from the patient.

In some embodiments, the hypoimmunogenic cells do not activate an innate and/or an adaptive immune response in the patient (e.g., recipient upon administration). Provided are methods of treating a disorder by administering a population of hypoimmunogenic cells to a subject (e.g., recipient) or patient in need thereof. In some embodiments, the hypoimmunogenic cells described herein comprise T cells engineered (e.g., are modified) to express a chimeric antigen receptor including but not limited to a chimeric antigen receptor described herein. In some instances, the T cells are populations or subpopulations of primary T cells from one or more individuals. In some embodiments, the T cells described herein such as the engineered or modified T cells comprise reduced expression of an endogenous T cell receptor.

In some embodiments, the present disclosure is directed to hypoimmunogenic primary T cells that overexpress CD47 and CARs, and have reduced expression or lack expression of MHC class I and/or MHC class II human leukocyte antigens and have reduced expression or lack expression of TCR complex molecules. The cells outlined herein overexpress CD47 and CARs and evade immune recognition. In some embodiments, the primary T cells display reduced levels or activity of MHC class I antigens, MHC class II antigens, and/or TCR complex molecules. In certain embodiments, primary T cells overexpress CD47 and CARs and harbor a genomic modification in the B2M gene. In some embodiments, T cells overexpress CD47 and CARs and harbor a genomic modification in the CIITA gene. In some embodiments, primary T cells overexpress CD47 and CARs and harbor a genomic modification in the TRAC gene. In some embodiments, primary T cells overexpress CD47 and CARs and harbor a genomic modification in the TRB gene. In some embodiments, T cells overexpress CD47 and CARs and harbor genomic modifications in one or more of the following genes: the B2M, CIITA, TRAC and TRB genes.

Exemplary T cells of the present disclosure are selected from the group consisting of cytotoxic T cells, helper T cells, memory T cells, central memory T cells, effector memory T cells, effector memory RA T cells, regulatory T cells, tissue infiltrating lymphocytes, and combinations thereof. In certain embodiments, the T cells express CCR7, CD27, CD28, and CD45RA. In some embodiments, the central T cells express CCR7, CD27, CD28, and CD45RO. In other embodiments, the effector memory T cells express PD-1, CD27, CD28, and CD45RO. In other embodiments, the effector memory RA T cells express PD-1, CD57, and CD45RA.

In some embodiments, the T cell is a modified (e.g., an engineered) T cell. In some cases, the modified T cell comprise a modification causing the cell to express at least one chimeric antigen receptor that specifically binds to an antigen or epitope of interest expressed on the surface of at least one of a damaged cell, a dysplastic cell, an infected cell, an immunogenic cell, an inflamed cell, a malignant cell, a metaplastic cell, a mutant cell, and combinations thereof. In other cases, the modified T cell comprise a modification causing the cell to express at least one protein that modulates a biological effect of interest in an adjacent cell, tissue, or organ when the cell is in proximity to the adjacent cell, tissue, or organ. Useful modifications to primary T cells are described in detail in US2016/0348073 and WO2020/018620, the disclosures of which are incorporated herein in their entireties.

In some embodiments, the hypoimmunogenic cells described herein comprise T cells that are engineered (e.g., are modified) to express a chimeric antigen receptor including but not limited to a chimeric antigen receptor described herein. In some instances, the T cells are populations or subpopulations of primary T cells from one or more individuals. In some embodiments, the T cells described herein such as the engineered or modified T cells include reduced expression of an endogenous T cell receptor. In some embodiments, the T cells described herein such as the engineered or modified T cells include reduced expression of cytotoxic T-lymphocyte-associated protein 4 (CTLA-4). In other embodiments, the T cells described herein such as the engineered or modified T cells include reduced expression of programmed cell death (PD-1). In certain embodiments, the T cells described herein such as the engineered or modified T cells include reduced expression of CTLA-4 and PD-1. Methods of reducing or eliminating expression of CTLA-4, PD-1 and both CTLA-4 and PD-1 can include any recognized by those skilled in the art, such as but not limited to, genetic modification technologies that utilize rare-cutting endonucleases and RNA silencing or RNA interference technologies. Non-limiting examples of a rare-cutting endonuclease include any Cas protein, TALEN, zinc finger nuclease, meganuclease, and homing endonuclease. In some embodiments, an exogenous nucleic acid encoding a polypeptide as disclosed herein (e.g., a chimeric antigen receptor, CD47, or another tolerogenic factor disclosed herein) is inserted at a CTLA-4 and/or PD-1 gene locus. In some embodiments, the exogenous polynucleotide is inserted into at least one allele of the cell using viral transduction, for example, with a vector. In some embodiments, the vector is a pseudotyped, self-inactivating lentiviral vector that carries the exogenous polynucleotide. In some embodiments, the vector is a self-inactivating lentiviral vector pseudotyped with a vesicular stomatitis VSV-G envelope, and which carries the exogenous polynucleotide. In some embodiments, the exogenous polynucleotide is inserted into at least one allele of the cell using viral transduction. In some embodiments, the exogenous polynucleotide is inserted into at least one allele of the cell using a lentivirus based viral vector.

In some embodiments, the T cells described herein such as the engineered or modified T cells include enhanced expression of PD-L1.

In some embodiments, the hypoimmunogenic T cell includes a polynucleotide encoding a CAR, wherein the polynucleotide is inserted in a genomic locus. In some embodiments, the polynucleotide encoding the CAR is randomly integrated into the genome of the cell. In some embodiments, the polynucleotide encoding the CAR is randomly integrated into the genome of the cell via viral vector transduction. In some embodiments, the polynucleotide encoding the CAR is randomly integrated into the genome of the cell via lentiviral vector transduction. In some embodiments, the polynucleotide is inserted into a safe harbor or target locus, such as but not limited to, an AAVS1, CCR5, CLYBL, ROSA26, SHS231, F3 (also known as CD142), MICA, MICB, LRP1 (also known as CD91), HMGB1, ABO, RHD, FUT1, or KDM5D gene locus. In some embodiments, the polynucleotide is inserted in a B2M, CIITA, TRAC, TRB, PD-1 or CTLA-4 gene.

In some embodiments, the hypoimmunogenic T cell includes a polynucleotide encoding a CAR that is expressed in a cell using an expression vector. In some embodiments, the CAR is introduced to the cell using a viral expression vector that mediates integration of the CAR sequence into the genome of the cell. For example, the expression vector for expressing the CAR in a cell comprises a polynucleotide sequence encoding the CAR. The expression vector can be an inducible expression vector. The expression vector can be a viral vector, such as but not limited to, a lentiviral vector.

Hypoimmunogenic T cells provided herein are useful for the treatment of suitable cancers including, but not limited to, B cell acute lymphoblastic leukemia (B-ALL), diffuse large B-cell lymphoma, liver cancer, pancreatic cancer, breast cancer, ovarian cancer, colorectal cancer, lung cancer, non-small cell lung cancer, acute myeloid lymphoid leukemia, multiple myeloma, gastric cancer, gastric adenocarcinoma, pancreatic adenocarcinoma, glioblastoma, neuroblastoma, lung squamous cell carcinoma, hepatocellular carcinoma, and bladder cancer.

Q. Therapeutic Cells Differentiated from Hypoimmunogenic Pluripotent Stem Cells

Provided herein are hypoimmunogenic cells including, cells derived from pluripotent stem cells, that evade immune recognition. In some embodiments, the cells do not activate an innate and/or an adaptive immune response in the patient or subject (e.g., recipient upon administration). Provided are methods of treating a disorder comprising repeat dosing of a population of hypoimmunogenic cells to a recipient subject in need thereof.

In some embodiments, the pluripotent stem cell and any cell differentiated from such a pluripotent stem cell is modified to exhibit reduced expression of MHC class I human leukocyte antigens. In other embodiments, the pluripotent stem cell and any cell differentiated from such a pluripotent stem cell is modified to exhibit reduced expression of MHC class II human leukocyte antigens. In certain embodiments, the pluripotent stem cell and any cell differentiated from such a pluripotent stem cell is modified to exhibit reduced expression of TCR complexes. In some embodiments, the pluripotent stem cell and any cell differentiated from such a pluripotent stem cell is modified to exhibit reduced expression of MHC class I and II human leukocyte antigens. In some embodiments, the pluripotent stem cell and any cell differentiated from such a pluripotent stem cell is modified to exhibit reduced expression of MHC class I and II human leukocyte antigens and TCR complexes.

In some embodiments, the pluripotent stem cell and any cell differentiated from such a pluripotent stem cell is modified to exhibit reduced expression of MHC class I and/or II human leukocyte antigens and exhibit increased CD47 expression. In some instances, the cell overexpresses CD47 by harboring one or more CD47 transgenes. In some embodiments, the pluripotent stem cell and any cell differentiated from such a pluripotent stem cell is modified to exhibit reduced expression of MHC class I and II human leukocyte antigens and exhibit increased CD47 expression. In some embodiments, the pluripotent stem cell and any cell differentiated from such a pluripotent stem cell is modified to exhibit reduced expression of MHC class I and II human leukocyte antigens and TCR complexes and exhibit increased CD47 expression.

In some embodiments, the pluripotent stem cell and any cell differentiated from such a pluripotent stem cell is modified to exhibit reduced expression of MHC class I and/or II human leukocyte antigens, to exhibit increased CD47 expression, and to exogenously express a chimeric antigen receptor. In some instances, the cell overexpresses CD47 polypeptides by harboring one or more CD47 transgenes. In some instances, the cell overexpresses CAR polypeptides by harboring one or more CAR transgenes. In some embodiments, the pluripotent stem cell and any cell differentiated from such a pluripotent stem cell is modified to exhibit reduced expression of MHC class I and II human leukocyte antigens, exhibit increased CD47 expression, and to exogenously express a chimeric antigen receptor. In some embodiments, the pluripotent stem cell and any cell differentiated from such a pluripotent stem cell is modified to exhibit reduced expression of MHC class I and II human leukocyte antigens and TCR complexes, to exhibit increased CD47 expression, and to exogenously express a chimeric antigen receptor.

Such pluripotent stem cells are hypoimmunogenic stem cells. Such differentiated cells are hypoimmunogenic cells.

Any of the pluripotent stem cells described herein can be differentiated into any cells of an organism and tissue. In some embodiments, the cells exhibit reduced expression of MHC class I and/or II human leukocyte antigens and reduced expression of TCR complexes. In some instances, expression of MHC class I and/or II human leukocyte antigens is reduced compared to unmodified or wild-type cell of the same cell type. In some instances, expression of TCR complexes is reduced compared to unmodified or wild-type cell of the same cell type. In some embodiments, the cells exhibit increased CD47 expression. In some instances, expression of CD47 is increased in cells encompassed by the present disclosure as compared to unmodified or wild-type cells of the same cell type. In some embodiments, the cells exhibit exogenous CAR expression. Methods for reducing levels of MHC class I and/or II human leukocyte antigens and TCR complexes and increasing the expression of CD47 and CARs are described herein.

In some embodiments, the cells used in the methods described herein evade immune recognition and responses when administered to a patient (e.g., recipient subject). The cells can evade killing by immune cells in vitro and in vivo. In some embodiments, the cells evade killing by macrophages and NK cells. In some embodiments, the cells are ignored by immune cells or a subject's immune system. In other words, the cells administered in accordance with the methods described herein are not detectable by immune cells of the immune system. In some embodiments, the cells are cloaked and therefore avoid immune rejection.

Methods of determining whether a pluripotent stem cell and any cell differentiated from such a pluripotent stem cell evades immune recognition include, but are not limited to, IFN-γ Elispot assays, microglia killing assays, cell engraftment animal models, cytokine release assays, ELISAs, killing assays using bioluminescence imaging or chromium release assay or a real-time, quantitative microelectronic biosensor system for cell analysis (xCELLigence® RTCA system, Agilent), mixed-lymphocyte reactions, immunofluorescence analysis, etc.

Therapeutic cells outlined herein are useful to treat a disorder such as, but not limited to, a cancer, a genetic disorder, a chronic infectious disease, an autoimmune disorder, a neurological disorder, and the like.

1. T Lymphocytes Differentiated from Hypoimmunogenic Pluripotent Cells

Provided herein, T lymphocytes (T cells, including primary T cells) are derived from the HIP cells described herein (e.g., hypoimmunogenic iPSCs). Methods for generating T cells, including CAR-T cells, from pluripotent stem cells (e.g., iPSCs) are described, for example, in Iriguchi et al., Nature Communications 12, 430 (2021); Themeli et al., Cell Stem Cell, 16(4):357-366 (2015); Themeli et al., Nature Biotechnology 31:928-933 (2013).

T lymphocyte derived hypoimmunogenic cells include, but are not limited to, primary T cells that evade immune recognition. In some embodiments, the hypoimmunogenic cells are produced (e.g., generated, cultured, or derived) from T cells such as primary T cells. In some instances, primary T cells are obtained (e.g., harvested, extracted, removed, or taken) from a subject or an individual. In some embodiments, primary T cells are produced from a pool of T cells such that the T cells are from one or more subjects (e.g., one or more human including one or more healthy humans). In some embodiments, the pool of primary T cells is from 1-100, 1-50, 1-20, 1-10, 1 or more, 2 or more, 3 or more, 4 or more, 5 or more, 10 or more, 20 or more, 30 or more, 40 or more, 50 or more, or 100 or more subjects. In some embodiments, the donor subject is different from the patient (e.g., the recipient that is administered the therapeutic cells). In some embodiments, the pool of T cells does not include cells from the patient. In some embodiments, one or more of the donor subjects from which the pool of T cells is obtained are different from the patient.

In some embodiments, the hypoimmunogenic cells do not activate an immune response in the patient (e.g., recipient upon administration). Provided are methods of treating a disorder by administering a population of hypoimmunogenic cells to a subject (e.g., recipient) or patient in need thereof. In some embodiments, the hypoimmunogenic cells described herein comprise T cells engineered (e.g., are modified) to express a chimeric antigen receptor including but not limited to a chimeric antigen receptor described herein. In some instances, the T cells are populations or subpopulations of primary T cells from one or more individuals. In some embodiments, the T cells described herein such as the engineered or modified T cells comprise reduced expression of an endogenous T cell receptor.

In some embodiments, the HIP-derived T cell includes a chimeric antigen receptor (CAR). Any suitable CAR can be included in the hyHIP-derived T cell, including the CARs described herein. In some embodiments, the hypoimmunogenic induced pluripotent stem cell-derived T cell includes a polynucleotide encoding a CAR, wherein the polynucleotide is inserted in a genomic locus. In some embodiments, the polynucleotide is inserted into a safe harbor or target locus. In some embodiments, the polynucleotide is inserted in a B2M, CIITA, TRAC, TRB, PD-1 or CTLA-4 gene. Any suitable method can be used to insert the CAR into the genomic locus of the hypoimmunogenic cell including the gene editing methods described herein (e.g., a CRISPR/Cas system).

HIP-derived T cells provided herein are useful for the treatment of suitable cancers including, but not limited to, B cell acute lymphoblastic leukemia (B-ALL), diffuse large B-cell lymphoma, liver cancer, pancreatic cancer, breast cancer, ovarian cancer, colorectal cancer, lung cancer, non-small cell lung cancer, acute myeloid lymphoid leukemia, multiple myeloma, gastric cancer, gastric adenocarcinoma, pancreatic adenocarcinoma, glioblastoma, neuroblastoma, lung squamous cell carcinoma, hepatocellular carcinoma, and bladder cancer.

2. NK Cells Derived from Hypoimmunogenic Pluripotent Cells

Provided herein, natural killer (NK) cells are derived from the HIP cells described herein (e.g., hypoimmunogenic iPSCs).

NK cells (also defined as 'large granular lymphocytes') represent a cell lineage differentiated from the common lymphoid progenitor (which also gives rise to B lymphocytes and T lymphocytes). Unlike T-cells, NK cells do not naturally comprise CD3 at the plasma membrane. Importantly, NK cells do not express a TCR and typically also lack other antigen-specific cell surface receptors (as well as TCRs and CD3, they also do not express immunoglobulin B-cell receptors, and instead typically express CD16 and CD56). NK cell cytotoxic activity does not require sensitization but is enhanced by activation with a variety of cytokines including IL-2. NK cells are generally thought to lack appropriate or complete signaling pathways necessary for antigen-receptor-mediated signaling, and thus are not thought to be capable of antigen receptor-dependent signaling, activation and expansion. NK cells are cytotoxic, and balance activating and inhibitory receptor signaling to modulate their cytotoxic activity. For instance, NK cells expressing CD16 may bind to the Fc domain of antibodies bound to an infected cell, resulting in NK cell activation. By contrast, activity is reduced against cells expressing high levels of MHC class I proteins. On contact with a target cell NK cells release proteins such as perforin, and enzymes such as proteases (granzymes). Perforin can form pores in the cell membrane of a target cell, inducing apoptosis or cell lysis.

There are a number of techniques that can be used to generate NK cells, including CAR-NK-cells, from pluripotent stem cells (e.g., iPSC); see, for example, Zhu et al., *Methods Mol Biol.* 2019; 2048:107-119; Knorr et al., *Stem Cells Transl Med.* 2013 2(4):274-83. doi: 10.5966/sctm.2012-0084; Zeng et al., *Stem Cell Reports.* 2017 Dec. 12; 9(6):1796-1812; Ni et al., *Methods Mol Biol.* 2013; 1029:33-41; Bernareggi et al., *Exp Hematol.* 2019 71:13-23; Shankar et al., *Stem Cell Res Ther.* 2020; 11(1):234, all of which are incorporated herein by reference in their entirety and specifically for the methodologies and reagents for differentiation. Differentiation can be assayed as is known in the art, generally by evaluating the presence of NK cell associated and/or specific markers, including, but not limited to, CD56, KIRs, CD16, NKp44, NKp46, NKG2D, TRAIL, CD122, CD27, CD244, NK1.1, NKG2A/C, NCR1, Ly49, CD49b, CD11b, KLRG1, CD43, CD62L, and/or CD226.

In some embodiments, the hypoimmunogenic pluripotent cells are differentiated into hepatocytes to address loss of the hepatocyte functioning or cirrhosis of the liver. There are a number of techniques that can be used to differentiate HIP cells into hepatocytes; see for example, Pettinato et al., doi: 10.1038/spre32888, Snykers et al., *Methods Mol Biol.,* 2011 698:305-314, Si-Tayeb et al., *Hepatology,* 2010, 51:297-305 and Asgari et al., *Stem Cell Rev.,* 2013, 9(4):493-504, all of which are incorporated herein by reference in their entirety and specifically for the methodologies and reagents for differentiation. Differentiation can be assayed as is known in the art, generally by evaluating the presence of hepatocyte associated and/or specific markers, including, but not limited to, albumin, alpha fetoprotein, and fibrinogen. Differentiation can also be measured functionally, such as the metabolization of ammonia, LDL storage and uptake, ICG uptake and release, and glycogen storage.

In some embodiments, the NK cells do not activate an innate and/or an adaptive immune response in the patient (e.g., recipient upon administration). Provided are methods of treating a disorder by administering a population of NK cells to a subject (e.g., recipient) or patient in need thereof. In some embodiments, the NK cells described herein comprise NK cells engineered (e.g., are modified) to express a chimeric antigen receptor including but not limited to a chimeric antigen receptor described herein. Any suitable CAR can be included in the NK cells, including the CARs described herein. In some embodiments, the NK cell includes a polynucleotide encoding a CAR, wherein the polynucleotide is inserted in a genomic locus. In some embodiments, the polynucleotide is inserted into a safe harbor or a target locus. In some embodiments, the polynucleotide is inserted in a B2M, CIITA, PD1 or CTLA4 gene. Any suitable method can be used to insert the CAR into the genomic locus of the NK cell including the gene editing methods described herein (e.g., a CRISPR/Cas system).

R. Methods of Genetic Modifications

In some embodiments, a vector herein is a nucleic acid molecule capable transferring or transporting another nucleic acid molecule, including into the cell or into genome of a cell. The transferred nucleic acid is generally linked to, e.g., inserted into, the vector nucleic acid molecule. A vector may include sequences that direct autonomous replication in a cell or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., replication defective retroviruses and lentiviruses. Non-viral vectors may require a delivery vehicle to facilitate entry of the nucleic acid molecule into a cell.

A viral vector can comprise a nucleic acid molecule that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s). A viral vector can comprise, e.g., a virus or viral particle capable of transferring a nucleic acid into a cell, or to the transferred nucleic acid (e.g., as naked DNA). Viral vectors and transfer plasmids can comprise structural and/or functional genetic elements that are primarily derived from a virus. A retroviral vector can comprise a viral vector or plasmid containing structural and functional genetic elements, or portions thereof, that are primarily derived from a retrovirus.

In some vectors described herein, at least part of one or more protein coding regions that contribute to or are essential for replication may be absent compared to the corresponding wild-type virus. This makes the viral vector replication-defective. In some embodiments, the vector is capable of transducing a target non-dividing host cell and/or integrating its genome into a host genome.

In some embodiments, the retroviral nucleic acid comprises one or more of (e.g., all of): a 5' promoter (e.g., to control expression of the entire packaged RNA), a 5' LTR (e.g., that includes R (polyadenylation tail signal) and/or U5 which includes a primer activation signal), a primer binding site, a psi packaging signal, a RRE element for nuclear export, a promoter directly upstream of the transgene to control transgene expression, a transgene (or other exogenous agent element), a polypurine tract, and a 3' LTR (e.g., that includes a mutated U3, a R, and U5). In some embodiments, the retroviral nucleic acid further comprises one or more of a cPPT, a WPRE, and/or an insulator element.

A retrovirus typically replicates by reverse transcription of its genomic RNA into a linear double-stranded DNA copy and subsequently covalently integrates its genomic DNA into a host genome. The structure of a wild-type retrovirus genome often comprises a 5' long terminal repeat (LTR) and a 3' LTR, between or within which are located a packaging signal to enable the genome to be packaged, a primer binding site, integration sites to enable integration into a host cell genome and gag, pol and env genes encoding the packaging components which promote the assembly of viral particles. More complex retroviruses have additional features, such as rev and RRE sequences in HIV, which enable the efficient export of RNA transcripts of the integrated provirus from the nucleus to the cytoplasm of an infected target cell. In the provirus, the viral genes are flanked at both ends by regions called long terminal repeats (LTRs). The LTRs are involved in proviral integration and transcription. LTRs also serve as enhancer-promoter sequences and can control the expression of the viral genes. Encapsidation of the retroviral RNAs occurs by virtue of a psi sequence located at the 5' end of the viral genome.

The LTRs themselves are typically similar (e.g., identical) sequences that can be divided into three elements, which are called U3, R and U5. U3 is derived from the sequence unique to the 3' end of the RNA. R is derived from a sequence repeated at both ends of the RNA and U5 is derived from the sequence unique to the 5' end of the RNA. The sizes of the three elements can vary considerably among different retroviruses.

For the viral genome, the site of transcription initiation is typically at the boundary between U3 and R in one LTR and the site of poly (A) addition (termination) is at the boundary between R and U5 in the other LTR. U3 contains most of the transcriptional control elements of the provirus, which include the promoter and multiple enhancer sequences responsive to cellular and in some cases, viral transcriptional activator proteins. Some retroviruses comprise any one or more of the following genes that code for proteins that are involved in the regulation of gene expression: tot, rev, tax and rex.

With regard to the structural genes gag, pol and env themselves, gag encodes the internal structural protein of the virus. Gag protein is proteolytically processed into the mature proteins MA (matrix), CA (capsid) and NC (nucleocapsid). The pol gene encodes the reverse transcriptase (RT), which contains DNA polymerase, associated RNase H and integrase (IN), which mediate replication of the genome. The env gene encodes the surface (SU) glycoprotein and the transmembrane (TM) protein of the virion, which form a complex that interacts specifically with cellular receptor proteins. This interaction promotes infection, e.g., by fusion of the viral membrane with the cell membrane.

In a replication-defective retroviral vector genome gag, pol and env may be absent or not functional. The R regions at both ends of the RNA are typically repeated sequences. U5 and U3 represent unique sequences at the 5' and 3' ends of the RNA genome respectively. Retroviruses may also contain additional genes which code for proteins other than gag, pol and env. Examples of additional genes include (in HIV), one or more of vif, vpr, vpx, vpu, tat, rev and nef. EIAV has (amongst others) the additional gene S2.

Illustrative retroviruses suitable for use in particular embodiments, include, but are not limited to: Moloney murine leukemia virus (M-MuLV), Moloney murine sarcoma virus (MoMSV), Harvey murine sarcoma virus (Ha-MuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus.

In some embodiments the retrovirus is a Gammretrovirus. In some embodiments the retrovirus is an Epsilonretrovirus. In some embodiments the retrovirus is an Alpharetrovirus. In some embodiments the retrovirus is a Betaretro virus. In some embodiments the retrovirus is a Deltaretro virus. In some embodiments the retrovirus is a Spumaretrovirus. In some embodiments the retrovirus is an endogenous retrovirus. In some embodiments the retrovirus is a lentivirus.

In some embodiments, a retroviral or lentivirus vector further comprises one or more insulator elements, e.g., an insulator element described herein. In various embodiments, the vectors comprise a promoter operably linked to a polynucleotide encoding an exogenous agent. The vectors may have one or more LTRs, wherein either LTR comprises one or more modifications, such as one or more nucleotide substitutions, additions, or deletions. The vectors may further comprise one of more accessory elements to increase transduction efficiency (e.g., a cPPT/FLAP), viral packaging (e.g., a Psi (Y) packaging signal, RRE), and/or other elements that increase exogenous gene expression (e.g., poly (A) sequences), and may optionally comprise a WPRE or HPRE. In some embodiments, a lentiviral nucleic acid comprises one or more of, e.g., all of, e.g., from 5' to 3', a promoter (e.g., CMV), an R sequence (e.g., comprising TAR), a U5 sequence (e.g., for integration), a PBS sequence (e.g., for reverse transcription), a DIS sequence (e.g., for genome dimerization), a psi packaging signal, a partial gag sequence, an RRE sequence (e.g., for nuclear export), a cPPT sequence (e.g., for nuclear import), a promoter to drive expression of the exogenous agent, a gene encoding the exogenous agent, a WPRE sequence (e.g., for efficient transgene expression), a PPT sequence (e.g., for reverse transcription), an R sequence (e.g., for polyadenylation and termination), and a U5 signal (e.g., for integration).

Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In some embodiments, HIV based vector backbones (i.e., HIV cis-acting sequence elements) are used. A lentivirus vector can comprise a viral vector or plasmid containing structural and functional genetic elements, or portions thereof, including LTRs that are primarily derived from a lentivirus.

In embodiments, a lentivirus vector (e.g., lentiviral expression vector) may comprise a lentiviral transfer plasmid (e.g., as naked DNA) or an infectious lentiviral particle. With respect to elements such as cloning sites, promoters, regulatory elements, heterologous nucleic acids, etc., it is to be understood that the sequences of these elements can be present in RNA form in lentiviral particles and can be present in DNA form in DNA plasmids.

In embodiments, a lentivirus vector is a vector with sufficient retroviral genetic information to allow packaging of an RNA genome, in the presence of packaging components, into a viral particle capable of infecting a target cell. Infection of the target cell can comprise reverse transcription and integration into the target cell genome. The RLV typically carries non-viral coding sequences which are to be delivered by the vector to the target cell. In embodiments, an RLV is incapable of independent replication to produce infectious retroviral particles within the target cell. Usually the RLV lacks a functional gag-pol and/or env gene and/or other genes involved in replication. The vector may be configured as a split-intron vector, e.g., as described in PCT patent application WO 99/15683, which is herein incorporated by reference in its entirety.

In some embodiments, the lentivirus vector comprises a minimal viral genome, e.g., the viral vector has been manipulated so as to remove the non-essential elements and to retain the essential elements in order to provide the required functionality to infect, transduce and deliver a nucleotide sequence of interest to a target host cell, e.g., as described in WO 98/17815, which is herein incorporated by reference in its entirety.

A minimal lentiviral genome may comprise, e.g., (5')R-U5-one or more first nucleotide sequences-U3-R(3') However, the plasmid vector used to produce the lentiviral genome within a source cell can also include transcriptional regulatory control sequences operably linked to the lentiviral genome to direct transcription of the genome in a source cell. These regulatory sequences may comprise the natural sequences associated with the transcribed retroviral sequence, e.g., the 5' U3 region, or they may comprise a heterologous promoter such as another viral promoter, for example the CMV promoter. Some lentiviral genomes comprise additional sequences to promote efficient virus production. For example, in the case of HIV, rev and RRE sequences may be included.

In some embodiments, the rare-cutting endonuclease is introduced into a cell containing the target polynucleotide sequence in the form of a nucleic acid encoding a rare-cutting endonuclease. The process of introducing the nucleic acids into cells can be achieved by any suitable technique. Suitable techniques include calcium phosphate or lipid-mediated transfection, electroporation, and transduction or infection using a viral vector. In some embodiments, the nucleic acid comprises DNA. In some embodiments, the nucleic acid comprises a modified DNA, as described herein. In some embodiments, the nucleic acid comprises mRNA. In some embodiments, the nucleic acid comprises a modified mRNA, as described herein (e.g., a synthetic, modified mRNA).

The present disclosure contemplates altering target polynucleotide sequences in any manner which is available to the skilled artisan utilizing a gene editing system (e.g., CRISPR/Cas) of the present disclosure. Any CRISPR/Cas system that is capable of altering a target polynucleotide sequence in a cell can be used. Such CRISPR-Cas systems can employ a variety of Cas proteins (Haft et al. PLoS Comput Biol. 2005; 1(6)e60). The molecular machinery of such Cas proteins that allows the CRISPR/Cas system to alter target polynucleotide sequences in cells include RNA binding proteins, endo- and exo-nucleases, helicases, and polymerases. In some embodiments, the CRISPR/Cas system is a CRISPR type I system. In some embodiments, the CRISPR/Cas system is a CRISPR type II system. In some embodiments, the CRISPR/Cas system is a CRISPR type V system.

The CRISPR/Cas systems of the present disclosure can be used to alter any target polynucleotide sequence in a cell. Those skilled in the art will readily appreciate that desirable target polynucleotide sequences to be altered in any particular cell may correspond to any genomic sequence for which expression of the genomic sequence is associated with a disorder or otherwise facilitates entry of a pathogen into the cell. For example, a desirable target polynucleotide sequence to alter in a cell may be a polynucleotide sequence corresponding to a genomic sequence which contains a disease associated single polynucleotide polymorphism. In such example, the CRISPR/Cas systems of the present disclosure can be used to correct the disease associated SNP in a cell by replacing it with a wild-type allele. As another example, a polynucleotide sequence of a target gene which is responsible for entry or proliferation of a pathogen into a cell may be a suitable target for deletion or insertion to disrupt the function of the target gene to prevent the pathogen from entering the cell or proliferating inside the cell.

In some embodiments, the target polynucleotide sequence is a genomic sequence. In some embodiments, the target polynucleotide sequence is a human genomic sequence. In some embodiments, the target polynucleotide sequence is a mammalian genomic sequence. In some embodiments, the target polynucleotide sequence is a vertebrate genomic sequence.

In some embodiments, a CRISPR/Cas system of the present disclosure includes a Cas protein and at least one to two ribonucleic acids that are capable of directing the Cas protein to and hybridizing to a target motif of a target polynucleotide sequence. As used herein, "protein" and "polypeptide" are used interchangeably to refer to a series of amino acid residues joined by peptide bonds (i.e., a polymer of amino acids) and include modified amino acids (e.g., phosphorylated, glycated, glycosylated, etc.) and amino acid analogs. Exemplary polypeptides or proteins include gene products, naturally occurring proteins, homologs, paralogs, fragments and other equivalents, variants, and analogs of the above.

In some embodiments, a Cas protein comprises one or more amino acid substitutions or modifications. In some embodiments, the one or more amino acid substitutions comprises a conservative amino acid substitution. In some instances, substitutions and/or modifications can prevent or reduce proteolytic degradation and/or extend the half-life of the polypeptide in a cell. In some embodiments, the Cas protein can comprise a peptide bond replacement (e.g., urea, thiourea, carbamate, sulfonyl urea, etc.). In some embodiments, the Cas protein can comprise a naturally occurring amino acid. In some embodiments, the Cas protein can comprise an alternative amino acid (e.g., D-amino acids, beta-amino acids, homocysteine, phosphoserine, etc.). In some embodiments, a Cas protein can comprise a modification to include a moiety (e.g., PEGylation, glycosylation, lipidation, acetylation, end-capping, etc.).

In some embodiments, a Cas protein comprises a core Cas protein, isoform thereof, or any Cas-like protein with similar function or activity of any Cas protein or isoform thereof. In some embodiments, a Cas protein comprises a core Cas protein. Exemplary Cas core proteins include, but are not limited to Cas1, Cas2, Cas3, Cas4, Cas5, Cas6, Cas7, Cas8 and Cas9. In some embodiments, a Cas protein comprises type V Cas protein. In some embodiments, a Cas protein comprises a Cas protein of an *E. coli* subtype (also known as CASS2). Exemplary Cas proteins of the *E. Coli* subtype include, but are not limited to Cse1, Cse2, Cse3, Cse4, and Cas5e. In some embodiments, a Cas protein comprises a Cas protein of the Ypest subtype (also known as CASS3). Exemplary Cas proteins of the Ypest subtype include, but are not limited to Csy1, Csy2, Csy3, and Csy4. In some embodiments, a Cas protein comprises a Cas protein of the Nmeni subtype (also known as CASS4). Exemplary Cas proteins of the Nmeni subtype include, but are not limited to Csn1 and Csn2. In some embodiments, a Cas protein comprises a Cas protein of the Dvulg subtype (also known as CASS1). Exemplary Cas proteins of the Dvulg subtype include Csd1, Csd2, and Cas5d. In some embodiments, a Cas protein comprises a Cas protein of the Tneap subtype (also known as CASS7). Exemplary Cas proteins of the Tneap subtype include, but are not limited to, Cst1, Cst2, Cas5t. In some embodiments, a Cas protein comprises a Cas protein of the Hmari subtype. Exemplary Cas proteins of the Hmari subtype include, but are not limited to Csh1, Csh2, and Cas5h.

In some embodiments, a Cas protein comprises a Cas protein of the Apern subtype (also known as CASS5). Exemplary Cas proteins of the Apern subtype include, but are not limited to Csa1, Csa2, Csa3, Csa4, Csa5, and Cas5a. In some embodiments, a Cas protein comprises a Cas protein of the Mtube subtype (also known as CASS6). Exemplary Cas proteins of the Mtube subtype include, but are not limited to Csm1, Csm2, Csm3, Csm4, and Csm5. In some embodiments, a Cas protein comprises a RAMP module Cas protein. Exemplary RAMP module Cas proteins include, but are not limited to, Cmr1, Cmr2, Cmr3, Cmr4, Cmr5, and Cmr6. See, e.g., Klompe et al., Nature 571, 219-225 (2019); Strecker et al., Science 365, 48-53 (2019). Examples of Cas proteins include, but are not limited to: Cas3, Cas8a, Cas5, Cas8b, Cas8c, Cas10d, Cse1, Cse2, Csy1, Csy2, Csy3, and/or GSU0054. In some embodiments, a Cas protein comprises Cas3, Cas8a, Cas5, Cas8b, Cas8c, Cas10d, Cse1, Cse2, Csy1, Csy2, Csy3, and/or GSU0054. Examples of Cas proteins include, but are not limited to: Cas9, Csn2, and/or Cas4. In some embodiments, a Cas protein comprises Cas9, Csn2, and/or Cas4. In some embodiments, Examples of Cas proteins include, but are not limited to: Cas10, Csm2, Cmr5, Cas10, Csx11, and/or Csx10. In some embodiments, a Cas protein comprises a Cas10, Csm2, Cmr5, Cas10, Csx11, and/or Csx10. In some embodiments, examples of Cas proteins include, but are not limited to: Csf1. In some embodiments, a Cas protein comprises Csf1. In some embodiments, examples of Cas proteins include, but are not limited to: Cas12a, Cas12b, Cas12c, C2c4, C2c8, C2c5, C2c10, and C2c9; as well as CasX (Cas12e) and CasY (Cas12d). Also see, e.g., Koonin et al., Curr Opin Microbiol. 2017; 37:67-78: "Diversity, classification and evolution of CRISPR-Cas systems." In some embodiments, a Cas protein comprises Cas12a, Cas12b, Cas12c, Cas12d, Cas12e, Cas12d, and/or Cas12e. In some embodiments, a Cas protein comprises Cas13, Cas13a, C2c2, Cas13b, Cas13c, and/or Cas13d. In some embodiments, the CRISPR/Cas system comprises a Cas effector protein selected from the group consisting of: a) Cas3, Cas8a, Cas5, Cas8b, Cas8c, Cas10d, Cse1, Cse2, Csy1, Csy2, Csy3, and GSU0054; b) Cas9, Csn2, and Cas4; c) Cas10, Csm2, Cmr5, Cas10, Csx11, and Csx10; d) Csf1; e) Cas12a, Cas12b, Cas12c, C2c4, C2c8, C2c5, C2c10, C2c9, CasX (Cas12e), and CasY (Cas12d); and f) Cas13, Cas13a, C2c2, Cas13b, Cas13c, and Cas13d.

In some embodiments, a Cas protein comprises any one of the Cas proteins described herein or a functional portion thereof. As used herein, "functional portion" refers to a portion of a peptide which retains its ability to complex with at least one ribonucleic acid (e.g., guide RNA (gRNA)) and cleave a target polynucleotide sequence. In some embodiments, the functional portion comprises a combination of operably linked Cas9 protein functional domains selected from the group consisting of a DNA binding domain, at least one RNA binding domain, a helicase domain, and an endonuclease domain. In some embodiments, the functional portion comprises a combination of operably linked Cas12a (also known as Cpf1) protein functional domains selected from the group consisting of a DNA binding domain, at least one RNA binding domain, a helicase domain, and an endonuclease domain. In some embodiments, the functional domains form a complex. In some embodiments, a functional portion of the Cas9 protein comprises a functional portion of a RuvC-like domain. In some embodiments, a functional portion of the Cas9 protein comprises a functional portion of the HNH nuclease domain. In some embodiments, a functional portion of the Cas12a protein comprises a functional portion of a RuvC-like domain.

In some embodiments, exogenous Cas protein can be introduced into the cell in polypeptide form. In certain embodiments, Cas proteins can be conjugated to or fused to a cell-penetrating polypeptide or cell-penetrating peptide. As used herein, "cell-penetrating polypeptide" and "cell-penetrating peptide" refers to a polypeptide or peptide, respectively, which facilitates the uptake of molecule into a cell. The cell-penetrating polypeptides can contain a detectable label.

In many embodiments, Cas proteins can be conjugated to or fused to a charged protein (e.g., that carries a positive, negative or overall neutral electric charge). Such linkage may be covalent. In some embodiments, the Cas protein can be fused to a superpositively charged GFP to significantly increase the ability of the Cas protein to penetrate a cell (Cronican et al. ACS Chem Biol. 2010; 5(8):747-52). In certain embodiments, the Cas protein can be fused to a protein transduction domain (PTD) to facilitate its entry into a cell. Exemplary PTDs include Tat, oligoarginine, and penetratin. In some embodiments, the Cas9 protein comprises a Cas9 polypeptide fused to a cell-penetrating peptide. In some embodiments, the Cas9 protein comprises a Cas9 polypeptide fused to a PTD. In some embodiments, the Cas9 protein comprises a Cas9 polypeptide fused to a tat domain. In some embodiments, the Cas9 protein comprises a Cas9 polypeptide fused to an oligoarginine domain. In some embodiments, the Cas9 protein comprises a Cas9 polypeptide fused to a penetratin domain. In some embodiments, the Cas9 protein comprises a Cas9 polypeptide fused to a superpositively charged GFP. In some embodiments, the Cas12a protein comprises a Cas12a polypeptide fused to a cell-penetrating peptide. In some embodiments, the Cas12a protein comprises a Cas12a polypeptide fused to a PTD. In some embodiments, the Cas12a protein comprises a Cas12a polypeptide fused to a tat domain. In some embodiments, the Cas12a protein comprises a Cas12a polypeptide fused to an oligoarginine domain. In some embodiments, the Cas12a protein comprises a Cas12a polypeptide fused to a penetratin domain. In some embodiments, the Cas12a protein comprises a Cas12a polypeptide fused to a superpositively charged GFP.

In some embodiments, the Cas protein can be introduced into a cell containing the target polynucleotide sequence in the form of a nucleic acid encoding the Cas protein. The process of introducing the nucleic acids into cells can be achieved by any suitable technique. Suitable techniques include calcium phosphate or lipid-mediated transfection, electroporation, and transduction or infection using a viral vector. In some embodiments, the nucleic acid comprises DNA. In some embodiments, the nucleic acid comprises a modified DNA, as described herein. In some embodiments, the nucleic acid comprises mRNA. In some embodiments, the nucleic acid comprises a modified mRNA, as described herein (e.g., a synthetic, modified mRNA).

In some embodiments, the Cas protein is complexed with one to two ribonucleic acids. In some embodiments, the Cas protein is complexed with two ribonucleic acids. In some embodiments, the Cas protein is complexed with one ribonucleic acid. In some embodiments, the Cas protein is encoded by a modified nucleic acid, as described herein (e.g., a synthetic, modified mRNA).

The methods of the present disclosure contemplate the use of any ribonucleic acid that is capable of directing a Cas protein to and hybridizing to a target motif of a target polynucleotide sequence. In some embodiments, at least one of the ribonucleic acids comprises tracrRNA. In some embodiments, at least one of the ribonucleic acids comprises CRISPR RNA (crRNA). In some embodiments, a single ribonucleic acid comprises a guide RNA that directs the Cas protein to and hybridizes to a target motif of the target polynucleotide sequence in a cell. In some embodiments, at least one of the ribonucleic acids comprises a guide RNA that directs the Cas protein to and hybridizes to a target motif of the target polynucleotide sequence in a cell. In some embodiments, both of the one to two ribonucleic acids comprise a guide RNA that directs the Cas protein to and hybridizes to a target motif of the target polynucleotide sequence in a cell. The ribonucleic acids of the present disclosure can be selected to hybridize to a variety of different target motifs, depending on the particular CRISPR/Cas system employed, and the sequence of the target polynucleotide, as will be appreciated by those skilled in the art. The one to two ribonucleic acids can also be selected to minimize hybridization with nucleic acid sequences other than the target polynucleotide sequence. In some embodiments, the one to two ribonucleic acids hybridize to a target motif that contains at least two mismatches when compared with all other genomic nucleotide sequences in the cell. In some embodiments, the one to two ribonucleic acids hybridize to a target motif that contains at least one mismatch when compared with all other genomic nucleotide sequences in the cell. In some embodiments, the one to two ribonucleic acids are designed to hybridize to a target motif immediately adjacent to a deoxyribonucleic acid motif recognized by the Cas protein. In some embodiments, each of the one to two ribonucleic acids are designed to hybridize to target motifs immediately adjacent to deoxyribonucleic acid motifs recognized by the Cas protein which flank a mutant allele located between the target motifs.

In some embodiments, each of the one to two ribonucleic acids comprises guide RNAs that directs the Cas protein to and hybridizes to a target motif of the target polynucleotide sequence in a cell.

In some embodiments, one or two ribonucleic acids (e.g., guide RNAs) are complementary to and/or hybridize to sequences on the same strand of a target polynucleotide sequence. In some embodiments, one or two ribonucleic acids (e.g., guide RNAs) are complementary to and/or hybridize to sequences on the opposite strands of a target polynucleotide sequence. In some embodiments, the one or two ribonucleic acids (e.g., guide RNAs) are not complementary to and/or do not hybridize to sequences on the opposite strands of a target polynucleotide sequence. In some embodiments, the one or two ribonucleic acids (e.g., guide RNAs) are complementary to and/or hybridize to overlapping target motifs of a target polynucleotide sequence. In some embodiments, the one or two ribonucleic acids (e.g., guide RNAs) are complementary to and/or hybridize to offset target motifs of a target polynucleotide sequence.

In some embodiments, nucleic acids encoding Cas protein and nucleic acids encoding the at least one to two ribonucleic acids are introduced into a cell via viral transduction (e.g., lentiviral transduction). In some embodiments, the Cas protein is complexed with 1-2 ribonucleic acids. In some embodiments, the Cas protein is complexed with two ribonucleic acids. In some embodiments, the Cas protein is complexed with one ribonucleic acid. In some embodiments, the Cas protein is encoded by a modified nucleic acid, as described herein (e.g., a synthetic, modified mRNA).

Exemplary gRNA sequences useful for CRISPR/Cas-based targeting of genes described herein are provided in Table 15. The sequences can be found in WO2016183041 filed May 9, 2016, the disclosure including the Tables, Appendices, and Sequence Listing is incorporated herein by reference in its entirety.

TABLE 15

Exemplary gRNA sequences useful for targeting genes

| Gene Name | SEQ ID NO: | WO2016183041 |
|---|---|---|
| HLA-A | SEQ ID NOs: 2-1418 | Table 8, Appendix 1 |
| HLA-B | SEQ ID NOs: 1419-3277 | Table 9, Appendix 2 |
| HLA-C | SEQ ID NOS: 3278-5183 | Table 10, Appendix 3 |
| RFX-ANK | SEQ ID NOs: 95636-102318 | Table 11, Appendix 4 |
| NFY-A | SEQ ID NOs: 102319-121796 | Table 13, Appendix 6 |
| RFX5 | SEQ ID NOs: 85645-90115 | Table 16, Appendix 9 |
| RFX-AP | SEQ ID NOs: 90116-95635 | Table 17, Appendix 10 |
| NFY-B | SEQ ID NOs: 121797-135112 | Table 20, Appendix 13 |
| NFY-C | SEQ ID NOs: 135113-176601 | Table 22, Appendix 15 |
| IRF1 | SEQ ID NOs: 176602-182813 | Table 23, Appendix 16 |
| TAP1 | SEQ ID NOs: 182814-188371 | Table 24, Appendix 17 |
| CIITA | SEQ ID NOS: 5184-36352 | Table 12, Appendix 5 |
| B2M | SEQ ID NOS: 81240-85644 | Table 15, Appendix 8 |
| NLRC5 | SEQ ID NOS: 36353-81239 | Table 14, Appendix 7 |
| CD47 | SEQ ID NOS: 200784-231885 | Table 29, Appendix 22 |

TABLE 15-continued

Exemplary gRNA sequences useful for targeting genes

| | | |
|---|---|---|
| HLA-E | SEQ ID NOS: 189859-193183 | Table 19, Appendix 12 |
| HLA-F | SEQ ID NOS: 688808-699754 | Table 45, Appendix 38 |
| HLA-G | SEQ ID NOS: 188372-189858 | Table 18, Appendix 11 |
| PD-L1 | SEQ ID NOS: 193184-200783 | Table 21, Appendix 14 |

| Gene Name | SEQ ID NO: | US20160348073 |
|---|---|---|
| TRAC | SEQ ID NOS: 532-609 and 9102-9797 | |
| TRB (also TCRB and TRBC) | SEQ ID NOS: 610-765 and 9798-10532 | |

Other exemplary gRNA sequences useful for CRISPR/Cas-based targeting of genes described herein are provided in U.S. Provisional Patent Application No. 63/190,685, filed May 19, 2021, and in U.S. Provisional Patent Application No. 63/221,887, filed Jul. 14, 2021, the disclosures of which, including the Tables, Appendices, and Sequence Listings, are incorporated herein by reference in their entireties.

In some embodiments, the cells of the technology are made using Transcription Activator-Like Effector Nucleases (TALEN) methodologies.

By a "TALE-nuclease" (TALEN) is intended a fusion protein consisting of a nucleic acid-binding domain typically derived from a Transcription Activator Like Effector (TALE) and one nuclease catalytic domain to cleave a nucleic acid target sequence. The catalytic domain is preferably a nuclease domain and more preferably a domain having endonuclease activity, like for instance I-TevI, ColE7, NucA and Fok-I. In numerous embodiments, the TALE domain can be fused to a meganuclease like for instance I-CreI and I-OnuI or functional variant thereof. In a more preferred embodiment, said nuclease is a monomeric TALE-Nuclease. A monomeric TALE-Nuclease is a TALE-Nuclease that does not require dimerization for specific recognition and cleavage, such as the fusions of engineered TAL repeats with the catalytic domain of I-TevI described in WO2012138927. Transcription Activator like Effector (TALE) are proteins from the bacterial species *Xanthomonas* comprise a plurality of repeated sequences, each repeat comprising di-residues in position 12 and 13 (RVD) that are specific to each nucleotide base of the nucleic acid targeted sequence. Binding domains with similar modular base-per-base nucleic acid binding properties (MBBBD) can also be derived from new modular proteins recently discovered by the applicant in a different bacterial species. The new modular proteins have the advantage of displaying more sequence variability than TAL repeats. Preferably, RVDs associated with recognition of the different nucleotides are HD for recognizing C, NG for recognizing T, NI for recognizing A, NN for recognizing G or A, NS for recognizing A, C, G or T, HG for recognizing T, IG for recognizing T, NK for recognizing G, HA for recognizing C, ND for recognizing C, HI for recognizing C, HN for recognizing G, NA for recognizing G, SN for recognizing G or A and YG for recognizing T, TL for recognizing A, VT for recognizing A or G and SW for recognizing A. In another embodiment, critical amino acids 12 and 13 can be mutated towards other amino acid residues in order to modulate their specificity towards nucleotides A, T, C and G and in particular to enhance this specificity. TALEN kits are sold commercially.

In some embodiments, the cells are manipulated using zinc finger nuclease (ZFN). A "zinc finger binding protein" is a protein or polypeptide that binds DNA, RNA and/or protein, preferably in a sequence-specific manner, as a result of stabilization of protein structure through coordination of a zinc ion. The term zinc finger binding protein is often abbreviated as zinc finger protein or ZFP. The individual DNA binding domains are typically referred to as "fingers." A ZFP has least one finger, typically two fingers, three fingers, or six fingers. Each finger binds from two to four base pairs of DNA, typically three or four base pairs of DNA. A ZFP binds to a nucleic acid sequence called a target site or target segment. Each finger typically comprises an approximately 30 amino acid, zinc-chelating, DNA-binding subdomain. Studies have demonstrated that a single zinc finger of this class consists of an alpha helix containing the two invariant histidine residues co-ordinated with zinc along with the two cysteine residues of a single beta turn (see, e.g., Berg & Shi, Science 271:1081-1085 (1996)).

In some embodiments, the cells of the present disclosure are made using a homing endonuclease. Such homing endonucleases are well-known to the art (Stoddard 2005). Homing endonucleases recognize a DNA target sequence and generate a single- or double-strand break. Homing endonucleases are highly specific, recognizing DNA target sites ranging from 12 to 45 base pairs (bp) in length, usually ranging from 14 to 40 bp in length. The homing endonuclease according to the technology may for example correspond to a LAGLIDADG endonuclease, to a HNH endonuclease, or to a GIY-YIG endonuclease. Preferred homing endonuclease according to the present disclosure can be an I-CreI variant.

In some embodiments, the cells of the technology are made using a meganuclease. Meganucleases are by definition sequence-specific endonucleases recognizing large sequences (Chevalier, B. S. and B. L. Stoddard, Nucleic Acids Res., 2001, 29, 3757-3774). They can cleave unique sites in living cells, thereby enhancing gene targeting by 1000-fold or more in the vicinity of the cleavage site (Puchta et al., Nucleic Acids Res., 1993, 21, 5034-5040; Rouet et al., Mol. Cell. Biol., 1994, 14, 8096-8106; Choulika et al., Mol. Cell. Biol., 1995, 15, 1968-1973; Puchta et al., Proc. Natl. Acad. Sci. USA, 1996, 93, 5055-5060; Sargent et al., Mol. Cell. Biol., 1997, 17, 267-77; Donoho et al., Mol. Cell. Biol, 1998, 18, 4070-4078; Elliott et al., Mol. Cell. Biol., 1998, 18, 93-101; Cohen-Tannoudji et al., Mol. Cell. Biol., 1998, 18, 1444-1448).

In some embodiments, the cells of the technology are made using RNA silencing or RNA interference (RNAi) to knock down (e.g., decrease, eliminate, or inhibit) the expression of a polypeptide such as a tolerogenic factor. Useful RNAi methods include those that utilize synthetic RNAi molecules, short interfering RNAs (siRNAs), PIWI-interacting NRAs (piRNAs), short hairpin RNAs (shRNAs), microRNAs (miRNAs), and other transient knock down methods recognized by those skilled in the art. Reagents for RNAi including sequence specific shRNAs, siRNA, miR-NAs and the like are commercially available. For instance, CIITA can be knocked down in a pluripotent stem cell by introducing a CIITA siRNA or transducing a CIITA shRNA-expressing virus into the cell. In some embodiments, RNA interference is employed to reduce or inhibit the expression of at least one selected from the group consisting of CIITA, B2M, NLRC5, TCR-alpha, and TCR-beta.

In some embodiments, the cells provided herein are genetically modified to reduce expression of one or more immune factors (including target polypeptides) to create immune-privileged or hypoimmunogenic cells. In certain embodiments, the cells (e.g., stem cells, induced pluripotent stem cells, differentiated cells, hematopoietic stem cells, primary T cells and CAR-T cells) disclosed herein comprise one or more genetic modifications to reduce expression of one or more target polynucleotides. Non-limiting examples of such target polynucleotides and polypeptides include CIITA, B2M, NLRC5, CTLA-4, PD-1, HLA-A, HLA-BM, HLA-C, RFX-ANK, NFY-A, RFX5, RFX-AP, NFY-B, NFY-C, IRF1, and TAP1.

In some embodiments, the genetic modification occurs using a CRISPR/Cas system. By modulating (e.g., reducing or deleting) expression of one or a plurality of the target polynucleotides, such cells exhibit decreased immune activation when engrafted into a recipient subject. In some embodiments, the cell is considered hypoimmunogenic, e.g., in a recipient subject or patient upon administration.

I. Gene Editing Systems

In some embodiments, the methods for genetically modifying cells to knock out, knock down, or otherwise modify one or more genes comprise using a site-directed nuclease, including, for example, zinc finger nucleases (ZFNs), transcription activator-like effector nucleases (TALENs), meganucleases, transposases, and clustered regularly interspaced short palindromic repeat (CRISPR)/Cas systems, as well as nickase systems, base editing systems, prime editing systems, and gene writing systems known in the art.

i. ZFNs

ZFNs are fusion proteins comprising an array of site-specific DNA binding domains adapted from zinc finger-containing transcription factors attached to the endonuclease domain of the bacterial FokI restriction enzyme. A ZFN may have one or more (e.g., 1, 2, 3, 4, 5, 6, 7, 8, 9, 10, or more) of the DNA binding domains or zinc finger domains. See, e.g., Carroll et al., *Genetics Society of America* (2011) 188:773-782; Kim et al., *Proc. Natl. Acad. Sci. USA* (1996) 93:1156-1160. Each zinc finger domain is a small protein structural motif stabilized by one or more zinc ions and usually recognizes a 3- to 4-bp DNA sequence. Tandem domains can thus potentially bind to an extended nucleotide sequence that is unique within a cell's genome.

Various zinc fingers of known specificity can be combined to produce multi-finger polypeptides which recognize about 6, 9, 12, 15, or 18-bp sequences. Various selection and modular assembly techniques are available to generate zinc fingers (and combinations thereof) recognizing specific sequences, including phage display, yeast one-hybrid systems, bacterial one-hybrid and two-hybrid systems, and mammalian cells. Zinc fingers can be engineered to bind a predetermined nucleic acid sequence. Criteria to engineer a zinc finger to bind to a predetermined nucleic acid sequence are known in the art. See, e.g., Sera et al., *Biochemistry* (2002) 41:7074-7081; Liu et al., *Bioinformatics* (2008) 24:1850-1857.

ZFNs containing FokI nuclease domains or other dimeric nuclease domains function as a dimer. Thus, a pair of ZFNs are required to target non-palindromic DNA sites. The two individual ZFNs must bind opposite strands of the DNA with their nucleases properly spaced apart. See Bitinaite et al., *Proc. Natl. Acad. Sci. USA* (1998) 95:10570-10575. To cleave a specific site in the genome, a pair of ZFNs are designed to recognize two sequences flanking the site, one on the forward strand and the other on the reverse strand. Upon binding of the ZFNs on either side of the site, the nuclease domains dimerize and cleave the DNA at the site, generating a DSB with 5' overhangs. HDR can then be utilized to introduce a specific mutation, with the help of a repair template containing the desired mutation flanked by homology arms. The repair template is usually an exogenous double-stranded DNA vector introduced to the cell. See Miller et al., *Nat. Biotechnol.* (2011) 29:143-148; Hockemeyer et al., *Nat. Biotechnol.* (2011) 29:731-734.

ii. TALENs

TALENs are another example of an artificial nuclease which can be used to edit a target gene. TALENs are derived from DNA binding domains termed TALE repeats, which usually comprise tandem arrays with 10 to 30 repeats that bind and recognize extended DNA sequences. Each repeat is 33 to 35 amino acids in length, with two adjacent amino acids (termed the repeat-variable di-residue, or RVD) conferring specificity for one of the four DNA base pairs. Thus, there is a one-to-one correspondence between the repeats and the base pairs in the target DNA sequences.

TALENs are produced artificially by fusing one or more TALE DNA binding domains (e.g., 1, 2, 3, 4, 5, 6, 7, 8, 9, 10 or more) to a nuclease domain, for example, a FokI endonuclease domain. See Zhang, *Nature Biotech.* (2011) 29:149-153. Several mutations to FokI have been made for its use in TALENs; these, for example, improve cleavage specificity or activity. See Cermak et al., *Nucl. Acids Res.* (2011) 39:e82; Miller et al., *Nature Biotech.* (2011) 29:143-148; Hockemeyer et al., *Nature Biotech.* (2011) 29:731-734; Wood et al., *Science* (2011) 333:307; Doyon et al., *Nature Methods* (2010) 8:74-79; Szczepek et al., *Nature Biotech* (2007) 25:786-793; Guo et al., *J. Mol. Biol.* (2010) 200:96. The FokI domain functions as a dimer, requiring two constructs with unique DNA binding domains for sites in the target genome with proper orientation and spacing. Both the number of amino acid residues between the TALE DNA binding domain and the FokI nuclease domain and the number of bases between the two individual TALEN binding sites appear to be important parameters for achieving high levels of activity. Miller et al., *Nature Biotech.* (2011) 29:143-148.

By combining engineered TALE repeats with a nuclease domain, a site-specific nuclease can be produced specific to any desired DNA sequence. Similar to ZFNs, TALENs can be introduced into a cell to generate DSBs at a desired target site in the genome, and so can be used to knock out genes or knock in mutations in similar, HDR-mediated pathways. See Boch, *Nature Biotech.* (2011) 29:135-136; Boch et al., *Science* (2009) 326:1509-1512; Moscou et al., *Science* (2009) 326:3501.

iii. Meganucleases

Meganucleases are enzymes in the endonuclease family which are characterized by their capacity to recognize and cut large DNA sequences (from 14 to 40 base pairs). Meganucleases are grouped into families based on their structural motifs which affect nuclease activity and/or DNA recognition. The most widespread and best known meganucleases are the proteins in the LAGLIDADG family, which owe their name to a conserved amino acid sequence. See Chevalier et al., *Nucleic Acids Res.* (2001) 29(18): 3757-3774. On the other hand, the GIY-YIG family members have a GIY-YIG module, which is 70-100 residues long and includes four or five conserved sequence motifs with four invariant residues, two of which are required for activity. See Van Roey et al., *Nature Struct. Biol.* (2002) 9:806-811. The His-Cys family meganucleases are characterized by a highly conserved series of histidines and cysteines over a region encompassing several hundred amino acid residues. See Chevalier et al., *Nucleic Acids Res.* (2001) 29(18):3757-3774. Members of the NHN family are defined by motifs containing two pairs of conserved histidines surrounded by asparagine residues. See Chevalier et al., *Nucleic Acids Res.* (2001) 29(18):3757-3774.

Because the chance of identifying a natural meganuclease for a particular target DNA sequence is low due to the high specificity requirement, various methods including mutagenesis and high throughput screening methods have been used to create meganuclease variants that recognize unique sequences. Strategies for engineering a meganuclease with altered DNA-binding specificity, e.g., to bind to a predetermined nucleic acid sequence are known in the art. See, e.g., Chevalier et al., *Mol. Cell.* (2002) 10:895-905; Epinat et al., *Nucleic Acids Res* (2003) 31:2952-2962; Silva et al., *J Mol. Biol.* (2006) 361:744-754; Seligman et al., *Nucleic Acids Res* (2002) 30:3870-3879; Sussman et al., *J Mol Biol* (2004) 342:31-41; Doyon et al., *J Am Chem Soc* (2006) 128:2477-2484; Chen et al., *Protein Eng Des Sel* (2009) 22:249-256; Arnould et al., *J Mol Biol.* (2006) 355:443-458; Smith et al., *Nucleic Acids Res.* (2006) 363(2):283-294.

Like ZFNs and TALENs, Meganucleases can create DSBs in the genomic DNA, which can create a frame-shift mutation if improperly repaired, e.g., via NHEJ, leading to a decrease in the expression of a target gene in a cell. Alternatively, foreign DNA can be introduced into the cell along with the meganuclease. Depending on the sequences of the foreign DNA and chromosomal sequence, this process can be used to modify the target gene. See Silva et al., *Current Gene Therapy* (2011) 11:11-27.

iv. Transposases

Transposases are enzymes that bind to the end of a transposon and catalyze its movement to another part of the genome by a cut and paste mechanism or a replicative transposition mechanism. By linking transposases to other systems such as the CRISPER/Cas system, new gene editing tools can be developed to enable site specific insertions or manipulations of the genomic DNA. There are two known DNA integration methods using transposons which use a catalytically inactive Cas effector protein and Tn7-like transposons. The transposase-dependent DNA integration does not provoke DSBs in the genome, which may guarantee safer and more specific DNA integration.

v. CRISPR Cas Systems

The CRISPR system was originally discovered in prokaryotic organisms (e.g., bacteria and archaea) as a system involved in defense against invading phages and plasmids that provides a form of acquired immunity. Now it has been adapted and used as a popular gene editing tool in research and clinical applications.

CRISPR/Cas systems generally comprise at least two components: one or more guide RNAs (gRNAs) and a Cas protein. The Cas protein is a nuclease that introduces a DSB into the target site. CRISPR-Cas systems fall into two major classes: class 1 systems use a complex of multiple Cas proteins to degrade nucleic acids; class 2 systems use a single large Cas protein for the same purpose. Class 1 is divided into types I, III, and IV; class 2 is divided into types II, V, and VI. Different Cas proteins adapted for gene editing applications include, but are not limited to, Cas3, Cas4, Cas5, Cas8a, Cas8b, Cas8c, Cas9, Cas10, Cas12, Cas12a (Cpf1), Cas12b (C2c1), Cas12c (C2c3), Cas12d (CasY), Cas12e (CasX), Cas12f (C2c10), Cas12g, Cas12h, Cas12i, Cas12k (C2c5), Cas13, Cas13a (C2c2), Cas13b, Cas13c, Cas13d, C2c4, C2c8, C2c9, Cmr5, Cse1, Cse2, Csf1, Csm2, Csn2, Csx10, Csx11, Csy1, Csy2, Csy3, and Mad7. The most widely used Cas9 is described herein as illustrative. These Cas proteins may be originated from different source species. For example, Cas9 can be derived from *S. pyogenes* or *S. aureus*.

In the original microbial genome, the type II CRISPR system incorporates sequences from invading DNA between CRISPR repeat sequences encoded as arrays within the host genome. Transcripts from the CRISPR repeat arrays are processed into CRISPR RNAs (crRNAs) each harboring a variable sequence transcribed from the invading DNA, known as the "protospacer" sequence, as well as part of the CRISPR repeat. Each crRNA hybridizes with a second transactivating CRISPR RNA (tracrRNA), and these two RNAs form a complex with the Cas9 nuclease. The protospacer-encoded portion of the crRNA directs the Cas9 complex to cleave complementary target DNA sequences, provided that they are adjacent to short sequences known as "protospacer adjacent motifs" (PAMs).

Since its discovery, the CRISPR system has been adapted for inducing sequence specific DSBs and targeted genome editing in a wide range of cells and organisms spanning from bacteria to eukaryotic cells including human cells. In its use in gene editing applications, artificially designed, synthetic gRNAs have replaced the original crRNA:tracrRNA complex. For example, the gRNAs can be single guide RNAs (sgRNAs) composed of a crRNA, a tetraloop, and a tracrRNA. The crRNA usually comprises a complementary region (also called a spacer, usually about 20 nucleotides in length) that is user-designed to recognize a target DNA of interest. The tracrRNA sequence comprises a scaffold region for Cas nuclease binding. The crRNA sequence and the tracrRNA sequence are linked by the tetraloop and each have a short repeat sequence for hybridization with each other, thus generating a chimeric sgRNA. One can change the genomic target of the Cas nuclease by simply changing the spacer or complementary region sequence present in the gRNA. The complementary region will direct the Cas nuclease to the target DNA site through standard RNA-DNA complementary base pairing rules.

In order for the Cas nuclease to function, there must be a PAM immediately downstream of the target sequence in the genomic DNA. Recognition of the PAM by the Cas protein is thought to destabilize the adjacent genomic sequence, allowing interrogation of the sequence by the gRNA and resulting in gRNA-DNA pairing when a matching sequence is present. The specific sequence of PAM varies depending on the species of the Cas gene. For example, the most commonly used Cas9 nuclease derived from *S. pyogenes* recognizes a PAM sequence of 5'-NGG-3' or, at less efficient rates, 5'-NAG-3', where "N" can be any nucleotide. Other Cas nuclease variants with alternative PAMs have also been characterized and successfully used for genome editing, which are summarized in Table 16 below.

TABLE 16

Exemplary Cas nuclease variants and their PAM sequences

| CRISPR Nuclease | Source Organism | PAM Sequence (5'→ 3') |
| --- | --- | --- |
| SpCas9 | Streptococcus pyogenes | NGG or NAG |
| SaCas9 | Staphylococcus aureus | NGRRT or NGRRN |
| NmeCas9 | Neisseria meningitidis | NNNNGATT |
| CjCas9 | Campylobacter jejuni | NNNNRYAC |
| StCas9 | Streptococcus thermophilus | NNAGAAW |
| TdCas9 | Treponema denticola | NAAAAC |
| LbCas12a (Cpf1) | Lachnospiraceae bacterium | TTTV |
| AsCas12a (Cpf1) | Acidaminococcus sp. | TTTV |
| AacCas12b | Alicyclobacillus acidiphilus | TTN |
| BhCas12b v4 | Bacillus hisashii | ATTN, TTTN, or GTTN |

R = A or G; Y = C or T; W = A or T; V = A or C or G; N = any base

In some embodiments, Cas nucleases may comprise one or more mutations to alter their activity, specificity, recognition, and/or other characteristics. For example, the Cas nuclease may have one or more mutations that alter its fidelity to mitigate off-target effects (e.g., eSpCas9, SpCas9-HF1, HypaSpCas9, HeFSpCas9, and evoSpCas9 high-fidelity variants of SpCas9). For another example, the Cas nuclease may have one or more mutations that alter its PAM specificity.

6. Nickases

Nuclease domains of the Cas, in particular the Cas9, nuclease can be mutated independently to generate enzymes referred to as DNA "nickases". Nickases are capable of introducing a single-strand cut with the same specificity as a regular CRISPR/Cas nuclease system, including for example CRISPR/Cas9. Nickases can be employed to generate double-strand breaks which can find use in gene editing systems (Mali et al., Nat Biotech, 31(9):833-838 (2013); Mali et al. Nature Methods, 10:957-963 (2013); Mali et al., Science, 339(6121):823-826 (2013)). In some instances, when two Cas nickases are used, long overhangs are produced on each of the cleaved ends instead of blunt ends which allows for additional control over precise gene integration and insertion (Mali et al., Nat Biotech, 31(9): 833-838 (2013); Mali et al. Nature Methods, 10:957-963 (2013); Mali et al., Science, 339(6121):823-826 (2013)). As both nicking Cas enzymes must effectively nick their target DNA, paired nickases can have lower off-target effects compared to the double-strand-cleaving Cas-based systems (Ran et al., Cell, 155(2):479-480(2013); Mali et al., Nat Biotech, 31(9):833-838 (2013); Mali et al. Nature Methods, 10:957-963 (2013); Mali et al., Science, 339(6121):823-826 (2013)).

S. Methods of Recombinant Expression of Tolerogenic Factors and/or Chimeric Antigen Receptors For all of these technologies, well-known recombinant techniques are used, to generate recombinant nucleic acids as outlined herein. In certain embodiments, the recombinant nucleic acids encoding a tolerogenic factor or a chimeric antigen receptor may be operably linked to one or more regulatory nucleotide sequences in an expression construct. Regulatory nucleotide sequences will generally be appropriate for the host cell and recipient subject to be treated. Numerous types of appropriate expression vectors and suitable regulatory sequences are known in the art for a variety of host cells. Typically, the one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are also contemplated. The promoters may be either naturally occurring promoters, hybrid promoters that combine elements of more than one promoter, or synthetic promoters. An expression construct may be present in a cell on an episome, such as a plasmid, or the expression construct may be inserted in a chromosome such as in a gene locus. In some embodiment, the expression vector includes a selectable marker gene to allow the selection of transformed host cells. Some embodiments, include an expression vector comprising a nucleotide sequence encoding a variant polypeptide operably linked to at least one regulatory sequence. Regulatory sequence for use herein include promoters, enhancers, and other expression control elements. In some embodiments, an expression vector is designed for the choice of the host cell to be transformed, the particular variant polypeptide desired to be expressed, the vector's copy number, the ability to control that copy number, and/or the expression of any other protein encoded by the vector, such as antibiotic markers.

Examples of suitable mammalian promoters include, for example, promoters from the following genes: elongation factor 1 alpha (EF1α) promoter, CAG promoter, ubiquitin/ S27a promoter of the hamster (WO 97/15664), Simian vacuolating virus 40 (SV40) early promoter, adenovirus major late promoter, mouse metallothionein-I promoter, the long terminal repeat region of Rous Sarcoma Virus (RSV), mouse mammary tumor virus promoter (MMTV), Moloney murine leukemia virus Long Terminal repeat region, and the early promoter of human Cytomegalovirus (CMV). Examples of other heterologous mammalian promoters are the actin, immunoglobulin or heat shock promoter(s). In additional embodiments, promoters for use in mammalian host cells can be obtained from the genomes of viruses such as polyoma virus, fowlpox virus (UK 2,211,504 published 5 Jul. 1989), bovine papilloma virus, avian sarcoma virus, cytomegalovirus, a retrovirus, hepatitis-B virus and Simian Virus 40 (SV40). In further embodiments, heterologous mammalian promoters are used. Examples include the actin promoter, an immunoglobulin promoter, and heat-shock promoters. The early and late promoters of SV40 are conveniently obtained as an SV40 restriction fragment which also contains the SV40 viral origin of replication (Fiers et al., Nature 273: 113-120 (1978)). The immediate early promoter of the human cytomegalovirus is conveniently obtained as a HindIII restriction enzyme fragment (Greenaway et al., Gene 18: 355-360 (1982)). The foregoing references are incorporated by reference in their entirety.

In some embodiments, the expression vector is a bicistronic or multicistronic expression vector. Bicistronic or multicistronic expression vectors may include (1) multiple promoters fused to each of the open reading frames; (2) insertion of splicing signals between genes; (3) fusion of genes whose expressions are driven by a single promoter; and (4) insertion of proteolytic cleavage sites between genes (self-cleavage peptide) or insertion of internal ribosomal entry sites (IRESs) between genes.

The process of introducing the polynucleotides described herein into cells can be achieved by any suitable technique. Suitable techniques include calcium phosphate or lipid-mediated transfection, electroporation, fusogens, and transduction or infection using a viral vector. In some embodiments, the polynucleotides are introduced into a cell via viral transduction (e.g., AAV transduction, lentiviral transduction) or otherwise delivered on a viral vector (e.g., fusogen-mediated delivery). In some embodiments, the polynucleotides are introduced into a cell via a fusogen-mediated delivery or a transposase system selected from the group consisting of conditional or inducible transposases, conditional or inducible PiggyBac transposons, conditional or inducible Sleeping Beauty (SB11) transposons, conditional or inducible Mos1 transposons, and conditional or inducible Tol2 transposons.

In some embodiments, the cells provided herein are genetically modified to include one or more exogenous polynucleotides inserted into one or more genomic loci of the hypoimmunogenic cell. In some embodiments, the exogenous polynucleotide encodes a protein of interest, e.g., a chimeric antigen receptor. Any suitable method can be used to insert the exogenous polynucleotide into the genomic locus of the hypoimmunogenic cell including the gene editing methods described herein (e.g., a CRISPR/Cas system). In some embodiments, the exogenous polynucleotide is inserted into at least one allele of the cell using viral transduction, for example, with a vector. In some embodiments, the vector is a pseudotyped, self-inactivating lentiviral vector that carries the exogenous polynucleotide. In some embodiments, the vector is a self-inactivating lentiviral vector pseudotyped with a vesicular stomatitis VSV-G envelope, and which carries the exogenous polynucleotide. In some embodiments, the exogenous polynucleotide is inserted into at least one allele of the cell using viral transduction. In some embodiments, the exogenous polynucleotide is inserted into at least one allele of the cell using a lentivirus based viral vector.

Unlike certain methods of introducing the polynucleotides described herein into cells which generally involve activating cells, such as activating T cells (e.g., CD8+ T cells), suitable techniques can be utilized to introduce polynucleotides into non-activated T cells. Suitable techniques include, but are not limited to, activation of T cells, such as CD8+ T cells, with one or more antibodies which bind to CD3, CD8, and/or CD28, or fragments or portions thereof (e.g., scFv and VHH) that may or may not be bound to beads. Surprisingly, fusogen-mediated introduction of polynucleotides into T cells is performed in non-activated T cells (e.g., CD8+ T cells) that have not been previously contacted with one or more activating antibodies or fragments or portions thereof (e.g., CD3, CD8, and/or CD28). In some embodiments, fusogen-mediated introduction of polynucleotides into T cells is performed in vivo (e.g., after the T cells have been administered to a subject). In other embodiments, fusogen-mediated introduction of polynucleotides into T cells is performed in vitro (e.g., before the T cells are been administered to a subject).

Provided herein are non-activated T cells comprising reduced expression of HLA-A, HLA-B, HLA-C, HLA-DP, HLA-DQ, HLA-DR, B2M, CIITA, TCR-alpha, and/or TCR-beta relative to a wild-type T cell, wherein the non-activated T cell further comprises a first exogenous polynucleotide encoding a chimeric antigen receptor (CAR).

In some embodiments, the non-activated T cell has not been treated with an anti-CD3 antibody, an anti-CD28 antibody, a T cell activating cytokine, or a soluble T cell costimulatory molecule. In some embodiments, the non-activated T cell does not express activation markers. In some embodiments, the non-activated T cell expresses CD3 and CD28, and wherein the CD3 and/or CD28 are inactive.

In some embodiments, the anti-CD3 antibody is OKT3. In some embodiments, the anti-CD28 antibody is CD28.2. In some embodiments, the T cell activating cytokine is selected from the group of T cell activating cytokines consisting of IL-2, IL-7, IL-15, and IL-21. In some embodiments, the soluble T cell costimulatory molecule is selected from the group of soluble T cell costimulatory molecules consisting of an anti-CD28 antibody, an anti-CD80 antibody, an anti-CD86 antibody, an anti-CD137L antibody, and an anti-ICOS-L antibody.

In some embodiments, the non-activated T cell is a primary T cell. In other embodiments, the non-activated T cell is differentiated from the hypoimmunogenic cells of the present disclosure. In some embodiments, the T cell is a CD8+ T cell.

In some embodiments, the first exogenous polynucleotide encodes a CAR is selected from the group consisting of a CD19-specific CAR and a CD22-specific CAR.

In some embodiments, the first and/or second exogenous polynucleotide is carried by a viral vector, including a lentiviral vector. In some embodiments, the first and/or second exogenous polynucleotide is carried by a lentiviral vector that comprises a CD8 binding agent. In some embodiments, the first and/or second exogenous polynucleotide is introduced into the cells using fusogen-mediated delivery or a transposase system selected from the group consisting of conditional or inducible transposases, conditional or inducible PiggyBac transposons, conditional or inducible Sleeping Beauty (SB11) transposons, conditional or inducible Mos1 transposons, and conditional or inducible Tol2 transposons.

In some embodiments, the non-activated T cell further comprises a second exogenous polynucleotide encoding CD47. In some embodiments, the first and/or second exogenous polynucleotides are inserted into a specific locus of at least one allele of the T cell. In some embodiments, the specific locus is selected from the group consisting of a safe harbor or target locus, a target locus, a B2M locus, a CIITA locus, a TRAC locus, and a TRB locus. In some embodiments, the second exogenous polynucleotide encoding CD47 is inserted into the specific locus selected from the group consisting of a safe harbor or target locus, a target locus, a B2M locus, a CIITA locus, a TRAC locus and a TRB locus. In some embodiments, the first exogenous polynucleotide encoding the CAR is inserted into the specific locus selected from the group consisting of a safe harbor or target locus, a target locus, a B2M locus, a CIITA locus, a TRAC locus and a TRB locus. In some embodiments, the second exogenous polynucleotide encoding CD47 and the first exogenous polynucleotide encoding the CAR are inserted into different loci. In some embodiments, the second exogenous polynucleotide encoding CD47 and the first exogenous polynucleotide encoding the CAR are inserted into the same locus. In some embodiments, the second exogenous polynucleotide encoding CD47 and the first exogenous polynucleotide encoding the CAR are inserted into the B2M locus. In some embodiments, the second exogenous polynucleotide encoding CD47 and the first exogenous polynucleotide encoding the CAR are inserted into the CIITA locus. In some embodiments, the second exogenous polynucleotide encoding CD47 and the first exogenous polynucleotide encoding the CAR are inserted into the TRAC locus. In some embodiments, the second exogenous polynucleotide encoding CD47 and the first exogenous polynucleotide encoding the CAR are inserted into the TRB locus. In some embodiments, the second exogenous polynucleotide encoding CD47 and the first exogenous polynucleotide encoding the CAR are inserted into the safe harbor or target locus. In some embodiments, the safe harbor or target locus is selected from the group consisting of a CCR5 gene locus, a CXCR4 gene locus, a PPP1R12C gene locus, an albumin gene locus, a SHS231 gene locus, a CLYBL gene locus, a Rosa gene locus, an F3 (CD142) gene locus, a MICA gene locus, a MICB gene locus, a LRP1 (CD91) gene locus, a HMGB1 gene locus, an ABO gene locus, an RHD gene locus, a FUT1 locus, and a KDM5D gene locus.

In some embodiments, the non-activated T cell does not express HLA-A, HLA-B, and/or HLA-C antigens. In some embodiments, the non-activated T cell does not express B2M. In some embodiments, the non-activated T cell does not express HLA-DP, HLA-DQ, and/or HLA-DR antigens. In some embodiments, the non-activated T cell does not express CIITA. In some embodiments, the non-activated T cell does not express TCR-alpha. In some embodiments, the non-activated T cell does not express TCR-beta. In some embodiments, the non-activated T cell does not express TCR-alpha and TCR-beta.

In some embodiments, the non-activated T cell is a $B2M^{indel/indel}$, $CIITA^{indel/indel}$, $TRAC^{indel/indel}$ cell comprising second exogenous polynucleotide encoding CD47 and/or the first exogenous polynucleotide encoding CAR inserted into the TRAC locus. In some embodiments, the non-activated T cell is a $B2M^{indel/indel}$, $CIITA^{indel/indel}$, $TRAC^{indel/indel}$ cell comprising the second exogenous polynucleotide encoding CD47 and the first exogenous polynucleotide encoding CAR inserted into the TRAC locus. In some embodiments, the non-activated T cell is a $B2M^{indel/indel}$, $CIITA^{indel/indel}$, $TRAC^{indel/indel}$ cell comprising second exogenous polynucleotide encoding CD47 and/or the first exogenous polynucleotide encoding CAR inserted into the TRB locus. In some embodiments, the non-activated T cell is a $B2M^{indel/indel}$, $CIITA^{indel/indel}$, $TRAC^{indel/indel}$ cell comprising the second exogenous polynucleotide encoding CD47 and the first exogenous polynucleotide encoding CAR inserted into the TRB locus. In some embodiments, the non-activated T cell is a $B2M^{indel/indel}$, $CIITA^{indel/indel}$, $TRAC^{indel/indel}$ cell comprising second exogenous polynucleotide encoding CD47 and/or the first exogenous polynucleotide encoding CAR inserted into the B2M locus. In some embodiments, the non-activated T cell is a $B2M^{indel/indel}$, $CIITA^{indel/indel}$, $TRAC^{indel/indel}$ cell comprising the second exogenous polynucleotide encoding CD47 and the first exogenous polynucleotide encoding CAR inserted into a B2M locus. In some embodiments, the non-activated T cell is a $B2M^{indel/indel}$, $CIITA^{indel/indel}$, $TRAC^{indel/indel}$ cell comprising second exogenous polynucleotide encoding CD47 and/or the first exogenous polynucleotide encoding CAR inserted into the CIITA locus. In some embodiments, the non-activated T cell is a $B2M^{indel/indel}$, $CIITA^{indel/indel}$, $TRAC^{indel/indel}$ cell comprising the second exogenous polynucleotide encoding CD47 and the first exogenous polynucleotide encoding CAR inserted into a CIITA locus.

In some embodiments, the non-activated T cell is a $B2M^{indel/indel}$, $CIITA^{indel/indel}$, $TRB^{indel/indel}$ cell comprising second exogenous polynucleotide encoding CD47 and/or the first exogenous polynucleotide encoding CAR inserted into the TRAC locus. In some embodiments, the non-activated T cell is a $B2M^{indel/indel}$, $CIITA^{indel/indel}$, $TRB^{indel/indel}$ cell comprising the second exogenous polynucleotide encoding CD47 and the first exogenous polynucleotide encoding CAR inserted into the TRAC locus. In some embodiments, the non-activated T cell is a $B2M^{indel/indel}$, $CIITA^{indel/indel}$, $TRB^{indel/indel}$ cell comprising second exogenous polynucleotide encoding CD47 and/or the first exogenous polynucleotide encoding CAR inserted into the TRB locus. In some embodiments, the non-activated T cell is a $B2M^{indel/indel}$, $CIITA^{indel/indel}$, $TRB^{indel/indel}$ cell comprising the second exogenous polynucleotide encoding CD47 and the first exogenous polynucleotide encoding CAR inserted into the TRB locus. In some embodiments, the non-activated T cell is a $B2M^{indel/indel}$, $CIITA^{indel/indel}$, $TRB^{indel/indel}$ cell comprising second exogenous polynucleotide encoding CD47 and/or the first exogenous polynucleotide encoding CAR inserted into the B2M locus. In some embodiments, the non-activated T cell is a $B2M^{indel/indel}$, $CIITA^{indel/indel}$, $TRB^{indel/indel}$ cell comprising the second exogenous polynucleotide encoding CD47 and the first exogenous polynucleotide encoding CAR inserted into a B2M locus. In some embodiments, the non-activated T cell is a $B2M^{indel/indel}$, $CIITA^{indel/indel}$, $TRB^{indel/indel}$ cell comprising second exogenous polynucleotide encoding CD47 and/or the first exogenous polynucleotide encoding CAR inserted into the CIITA locus. In some embodiments, the non-activated T cell is a $B2M^{indel/indel}$, $CIITA^{indel/indel}$, $TRB^{indel/indel}$ cell comprising the second exogenous polynucleotide encoding CD47 and the first exogenous polynucleotide encoding CAR inserted into a CIITA locus.

Provided herein are engineered T cells comprising reduced expression of HLA-A, HLA-B, HLA-C, HLA-DP, HLA-DQ, HLA-DR, B2M, CIITA, TCR-alpha, and/or TCR-beta relative to a wild-type T cell, wherein the engineered T cell further comprises a first exogenous polynucleotide encoding a chimeric antigen receptor (CAR) carried by a viral vector, including a lentiviral vector. Provided herein are engineered T cells comprising reduced expression of HLA-A, HLA-B, HLA-C, HLA-DP, HLA-DQ, HLA-DR, B2M, CIITA, TCR-alpha, and/or TCR-beta relative to a wild-type T cell, wherein the engineered T cell further comprises a first exogenous polynucleotide encoding a chimeric antigen receptor (CAR) carried by a lentiviral vector that comprises a CD8 binding agent.

In some embodiments, the engineered T cell is a primary T cell. In other embodiments, the engineered T cell is differentiated from the hypoimmunogenic cell of the present disclosure. In some embodiments, the T cell is a CD8⁺ T cell. In some embodiments, the T cell is a CD4⁺ T cell.

In some embodiments, the engineered T cell does not express activation markers. In some embodiments, the engineered T cell expresses CD3 and CD28, and wherein the CD3 and/or CD28 are inactive.

In some embodiments, the engineered T cell has not been treated with an anti-CD3 antibody, an anti-CD28 antibody, a T cell activating cytokine, or a soluble T cell costimulatory molecule. In some embodiments, the anti-CD3 antibody is OKT3, wherein the anti-CD28 antibody is CD28.2, wherein the T cell activating cytokine is selected from the group of T cell activating cytokines consisting of IL-2, IL-7, IL-15, and IL-21, and wherein soluble T cell costimulatory molecule is selected from the group of soluble T cell costimulatory molecules consisting of an anti-CD28 antibody, an anti-CD80 antibody, an anti-CD86 antibody, an anti-CD137L antibody, and an anti-ICOS-L antibody. In some embodiments, the engineered T cell has not been treated with one or more T cell activating cytokines selected from the group consisting of IL-2, IL-7, IL-15, and IL-21. In some instances, the cytokine is IL-2. In some embodiments, the one or more cytokines is IL-2 and another selected from the group consisting of IL-7, IL-15, and IL-21.

In some embodiments, the engineered T cell further comprises a second exogenous polynucleotide encoding CD47. In some embodiments, the first and/or second exogenous polynucleotides are inserted into a specific locus of at least one allele of the T cell. In some embodiments, the specific locus is selected from the group consisting of a safe harbor or target locus, a target locus, a B2M locus, a CIITA locus, a TRAC locus, and a TRB locus. In some embodiments, the second exogenous polynucleotide encoding CD47 is inserted into the specific locus selected from the group consisting of a safe harbor or target locus, a target locus, a B2M locus, a CIITA locus, a TRAC locus and a TRB locus. In some embodiments, the first exogenous polynucleotide encoding the CAR is inserted into the specific locus selected from the group consisting of a safe harbor or target locus, a target locus, a B2M locus, a CIITA locus, a TRAC locus and a TRB locus. In some embodiments, the second exogenous polynucleotide encoding CD47 and the first exogenous polynucleotide encoding the CAR are inserted into different loci. In some embodiments, the second exogenous polynucleotide encoding CD47 and the first exogenous polynucleotide encoding the CAR are inserted into the same locus. In some embodiments, the second exogenous polynucleotide encoding CD47 and the first exogenous polynucleotide encoding the CAR are inserted into the B2M locus, the CIITA locus, the TRAC locus, the TRB locus, or the safe harbor or target locus. In some embodiments, the safe harbor or target locus is selected from the group consisting of a CCR5 gene locus, a CXCR4 gene locus, a PPP1R12C gene locus, an albumin gene locus, a SHS231 gene locus, a CLYBL gene locus, a Rosa gene locus, an F3 (CD142) gene locus, a MICA gene locus, a MICB gene locus, a LRP1 (CD91) gene locus, a HMGB1 gene locus, an ABO gene locus, an RHD gene locus, a FUT1 locus, and a KDM5D gene locus.

In some embodiments, the CAR is selected from the group consisting of a CD19-specific CAR and a CD22-specific CAR. In some embodiments, the CAR is a CD19-specific CAR. In some embodiments, the CAR is a CD22-specific CAR. In some embodiments, the CAR comprises an antigen binding domain that binds to any one selected from the group consisting of CD19, CD22, CD38, CD123, CD138, and BCMA.

In some embodiments, the engineered T cell does not express HLA-A, HLA-B, and/or HLA-C antigens, wherein the engineered T cell does not express B2M, wherein the engineered T cell does not express HLA-DP, HLA-DQ, and/or HLA-DR antigens, wherein the engineered T cell does not express CIITA, and/or wherein the engineered T cell does not express TCR-alpha and TCR-beta.

In some embodiments, the engineered T cell is a $B2M^{indel/indel}$, $CIITA^{indel/indel}$, $TRAC^{indel/indel}$ cell comprising the second exogenous polynucleotide encoding CD47 and/or the first exogenous polynucleotide encoding CAR inserted into the TRAC locus, into the TRB locus, into the B2M locus, or into the CIITA locus. In some embodiments, the engineered T cell is a $B2M^{indel/indel}$, $CIITA^{indel/indel}$, $TRB^{indel/indel}$ cell comprising the second exogenous polynucleotide encoding CD47 and/or the first exogenous polynucleotide encoding CAR inserted into the TRAC locus, into the TRB locus, into the B2M locus, or into the CIITA locus.

In some embodiments, the non-activated T cell and/or the engineered T cell of the present disclosure are in a subject. In other embodiments, the non-activated T cell and/or the engineered T cell of the present disclosure are in vitro.

In some embodiments, the non-activated T cell and/or the engineered T cell of the present disclosure express a CD8 binding agent. In some embodiments, the CD8 binding agent is an anti-CD8 antibody. In some embodiments, the anti-CD8 antibody is selected from the group consisting of a mouse anti-CD8 antibody, a rabbit anti-CD8 antibody, a human anti-CD8 antibody, a humanized anti-CD8 antibody, a camelid (e.g., llama, alpaca, camel) anti-CD8 antibody, and a fragment thereof. In some embodiments, the fragment thereof is an scFv or a VHH. In some embodiments, the CD8 binding agent binds to a CD8 alpha chain and/or a CD8 beta chain.

In some embodiments, the CD8 binding agent is fused to a transmembrane domain incorporated in the viral envelope. In some embodiments, the lentivirus vector is pseudotyped with a viral fusion protein. In some embodiments, the viral fusion protein comprises one or more modifications to reduce binding to its native receptor.

In some embodiments, the viral fusion protein is fused to the CD8 binding agent. In some embodiments, the viral fusion protein comprises Nipah virus F glycoprotein and Nipah virus G glycoprotein fused to the CD8 binding agent. In some embodiments, the lentivirus vector does not comprise a T cell activating molecule or a T cell costimulatory molecule. In some embodiments, the lentivirus vector encodes the first exogenous polynucleotide and/or the second exogenous polynucleotide.

In some embodiments, following transfer into a first subject, the non-activated T cell or the engineered T cell exhibits one or more responses selected from the group consisting of (a) a T cell response, (b) an NK cell response, and (c) a macrophage response, that are reduced as compared to a wild-type cell following transfer into a second subject. In some embodiments, the first subject and the second subject are different subjects. In some embodiments, the macrophage response is engulfment.

In some embodiments, following transfer into a subject, the non-activated T cell or the engineered T cell exhibits one or more selected from the group consisting of (a) reduced TH1 activation in the subject, (b) reduced NK cell killing in the subject, and (c) reduced killing by whole PBMCs in the subject, as compared to a wild-type cell following transfer into the subject.

In some embodiments, following transfer into a subject, the non-activated T cell or the engineered T cell elicits one or more selected from the group consisting of (a) reduced donor specific antibodies in the subject, (b) reduced IgM or IgG antibodies in the subject, and (c) reduced complement-dependent cytotoxicity (CDC) in a subject, as compared to a wild-type cell following transfer into the subject.

In some embodiments, the non-activated T cell or the engineered T cell is transduced with a lentivirus vector comprising a CD8 binding agent within the subject. In some embodiments, the lentivirus vector carries a gene encoding the CAR and/or CD47.

In some embodiments, the gene encoding the CAR and/or CD47 is introduced into the cells using fusogen-mediated delivery, a transposase system selected from the group consisting of transposases, PiggyBac transposons, Sleeping Beauty (SB11) transposons, Mos1 transposons, and Tol2 transposons, or a viral vector, including a lentiviral vector.

Provided herein are pharmaceutical compositions comprising a population of the non-activated T cells and/or the engineered T cells of the present disclosure and a pharmaceutically acceptable additive, carrier, diluent or excipient.

Provided herein are methods comprising administering to a subject a composition comprising a population of the non-activated T cells and/or the engineered T cells of the present disclosure, or one or more the pharmaceutical compositions of the present disclosure.

In some embodiments, the subject is not administered a T cell activating treatment before, after, and/or concurrently with administration of the composition. In some embodiments, the T cell activating treatment comprises lymphodepletion.

Provided herein are methods of treating a subject suffering from cancer, comprising administering to a subject a composition comprising a population of the non-activated T cells and/or the engineered T cells of the present disclosure, or one or more the pharmaceutical compositions of the present disclosure, wherein the subject is not administered a T cell activating treatment before, after, and/or concurrently with administration of the composition. In some embodiments, the T cell activating treatment comprises lymphodepletion.

Provided herein are methods for expanding T cells capable of recognizing and killing tumor cells in a subject in need thereof within the subject, comprising administering to a subject a composition comprising a population of the non-activated T cells and/or the engineered T cells of the present disclosure, or one or more the pharmaceutical compositions of the present disclosure, wherein the subject is not administered a T cell activating treatment before, after, and/or concurrently with administration of the composition. In some embodiments, the T cell activating treatment comprises lymphodepletion.

Provided herein are dosage regimens for treating a condition, disease or disorder in a subject comprising administration of a pharmaceutical composition comprising a population of the non-activated T cells and/or the engineered T cells of the present disclosure, or one or more the pharmaceutical compositions of the present disclosure, and a pharmaceutically acceptable additive, carrier, diluent or excipient, wherein the pharmaceutical composition is administered in about 1-3 therapeutically effective doses. Provided herein are dosage regimens for treating a condition, disease or disorder in a subject comprising administration of a pharmaceutical composition comprising a population of the non-activated T cells and/or the engineered T cells of the present disclosure, or one or more the pharmaceutical compositions of the present disclosure, and a pharmaceutically acceptable additive, carrier, diluent or excipient, wherein the pharmaceutical composition is administered in about 1-3 clinically effective doses.

Once altered, the presence of expression of any of the molecule described herein can be assayed using known techniques, such as Western blots, ELISA assays, FACS assays, other immunoassays, reverse transcriptase polymerase chain reactions (RT-PCR), and the like.

T. Generation of Induced Pluripotent Stem Cells

The technology provides methods of producing hypoimmunogenic pluripotent cells. In some embodiments, the method comprises generating pluripotent stem cells. The generation of mouse and human pluripotent stem cells (generally referred to as iPSCs; miPSCs for murine cells or hiPSCs for human cells) is generally known in the art. As will be appreciated by those in the art, there are a variety of different methods for the generation of iPCSs. The original induction was done from mouse embryonic or adult fibroblasts using the viral introduction of four transcription factors, Oct3/4, Sox2, c-Myc and Klf4; see Takahashi and Yamanaka Cell 126:663-676 (2006), hereby incorporated by reference in its entirety and specifically for the techniques outlined therein. Since then, a number of methods have been developed; see Seki et al, World J. Stem Cells 7(1): 116-125 (2015) for a review, and Lakshmipathy and Vermuri, editors, Methods in Molecular Biology: Pluripotent Stem Cells, Methods and Protocols, Springer 2013, both of which are hereby expressly incorporated by reference in their entirety, and in particular for the methods for generating hiPSCs (see for example Chapter 3 of the latter reference).

Generally, iPSCs are generated by the transient expression of one or more reprogramming factors" in the host cell, usually introduced using episomal vectors. Under these conditions, small amounts of the cells are induced to become iPSCs (in general, the efficiency of this step is low, as no selection markers are used). Once the cells are "reprogrammed", and become pluripotent, they lose the episomal vector(s) and produce the factors using the endogenous genes.

As is also appreciated by those of skill in the art, the number of reprogramming factors that can be used or are used can vary. Commonly, when fewer reprogramming factors are used, the efficiency of the transformation of the cells to a pluripotent state goes down, as well as the "pluripotency", e.g., fewer reprogramming factors may result in cells that are not fully pluripotent but may only be able to differentiate into fewer cell types.

In some embodiments, a single reprogramming factor, OCT4, is used. In other embodiments, two reprogramming factors, OCT4 and KLF4, are used. In other embodiments, three reprogramming factors, OCT4, KLF4 and SOX2, are used. In other embodiments, four reprogramming factors, OCT4, KLF4, SOX2 and c-Myc, are used. In other embodiments, 5, 6 or 7 reprogramming factors can be used selected from SOKMNLT; SOX2, OCT4 (POU5F1), KLF4, MYC, NANOG, LIN28, and SV40L T antigen. In general, these reprogramming factor genes are provided on episomal vectors such as are known in the art and commercially available.

In general, as is known in the art, iPSCs are made from non-pluripotent cells such as, but not limited to, blood cells, fibroblasts, etc., by transiently expressing the reprogramming factors as described herein.

U. Assays for Hypoimmunogenicity Phenotypes and Retention of Pluripotency

Once the hypoimmunogenic cells have been generated, they may be assayed for their hypoimmunogenicity and/or retention of pluripotency as is described in WO2016183041 and WO2018132783.

Figure 13:
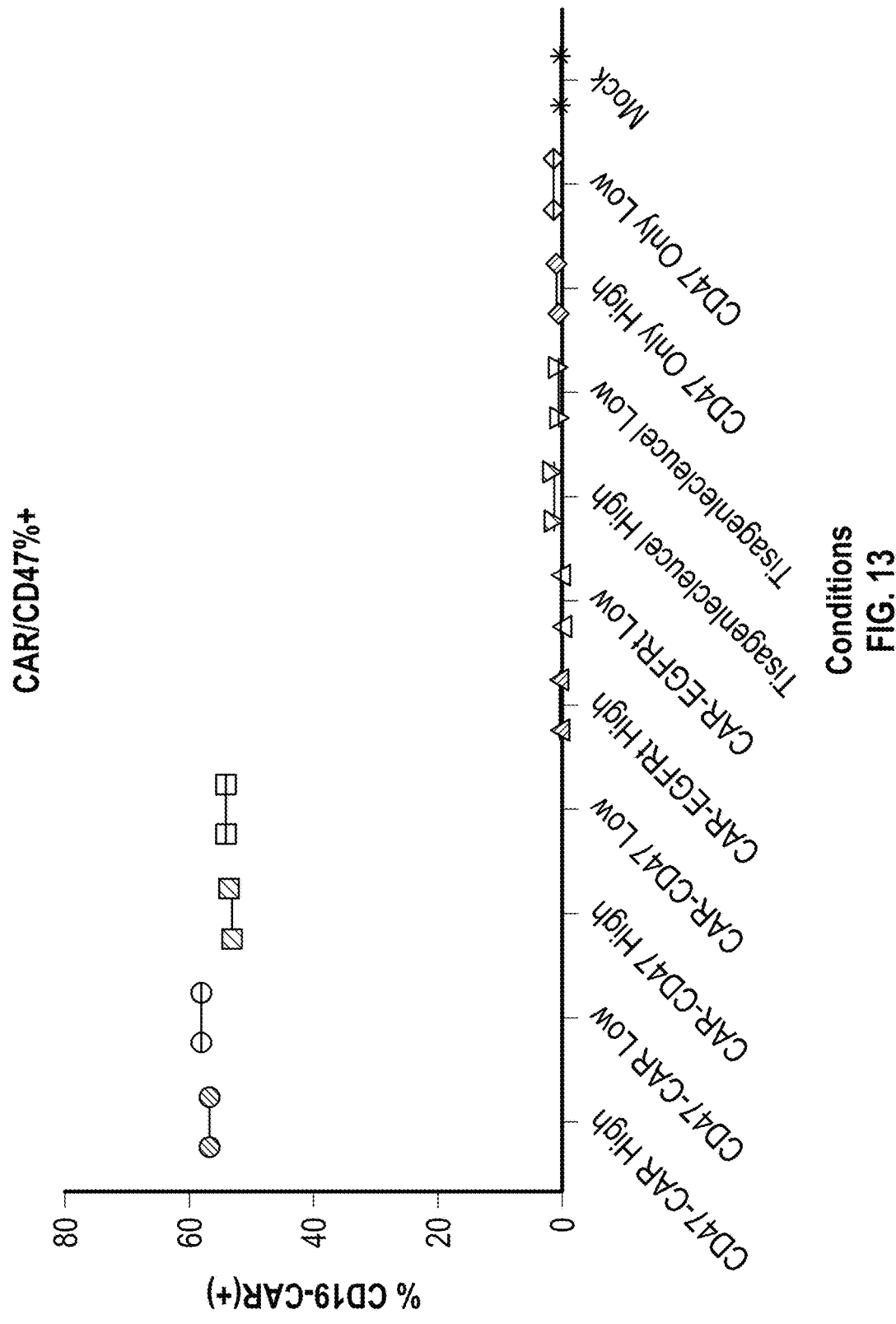
FIG. 13 shows the frequency of both an exemplary CD19-specific CAR and CD47 molecules in hypoimmunogenic CD19-specific CAR-CD47 T cells and control T cells (CD19-specific CAR-EGFRt T cells, tisagenlecleucel biosimilar/surrogate cells, CD47 expressing T cells, and mock T cells).
Figure 14:
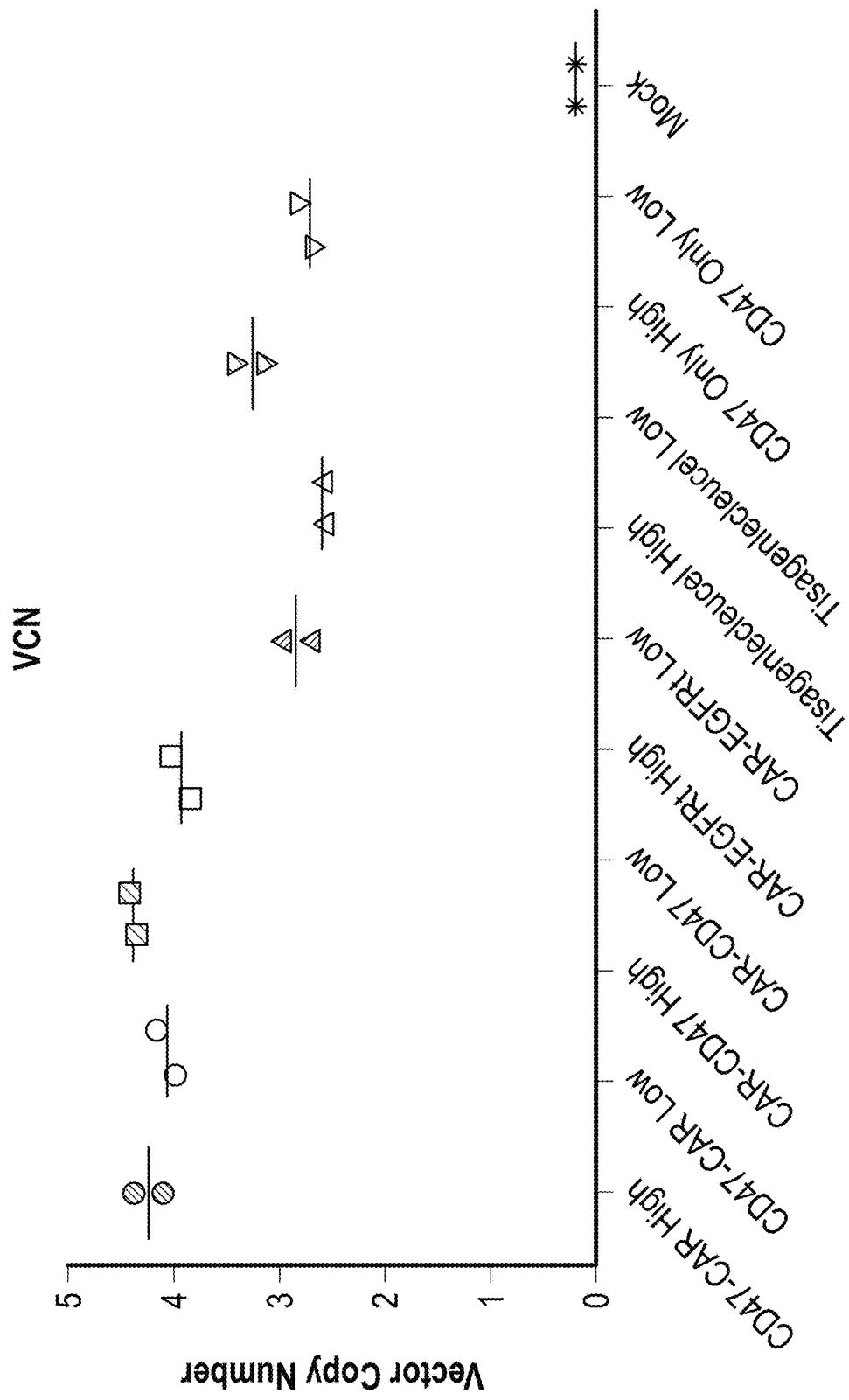
FIG. 14 depicts the vector copy number in hypoimmunogenic CD19-specific CAR-CD47 T cells and control T cells (CD19-specific CAR-EGFRt T cells, tisagenlecleucel biosimilar/surrogate cells, and mock T cells) on day 8 post-activation.
Figure 15:
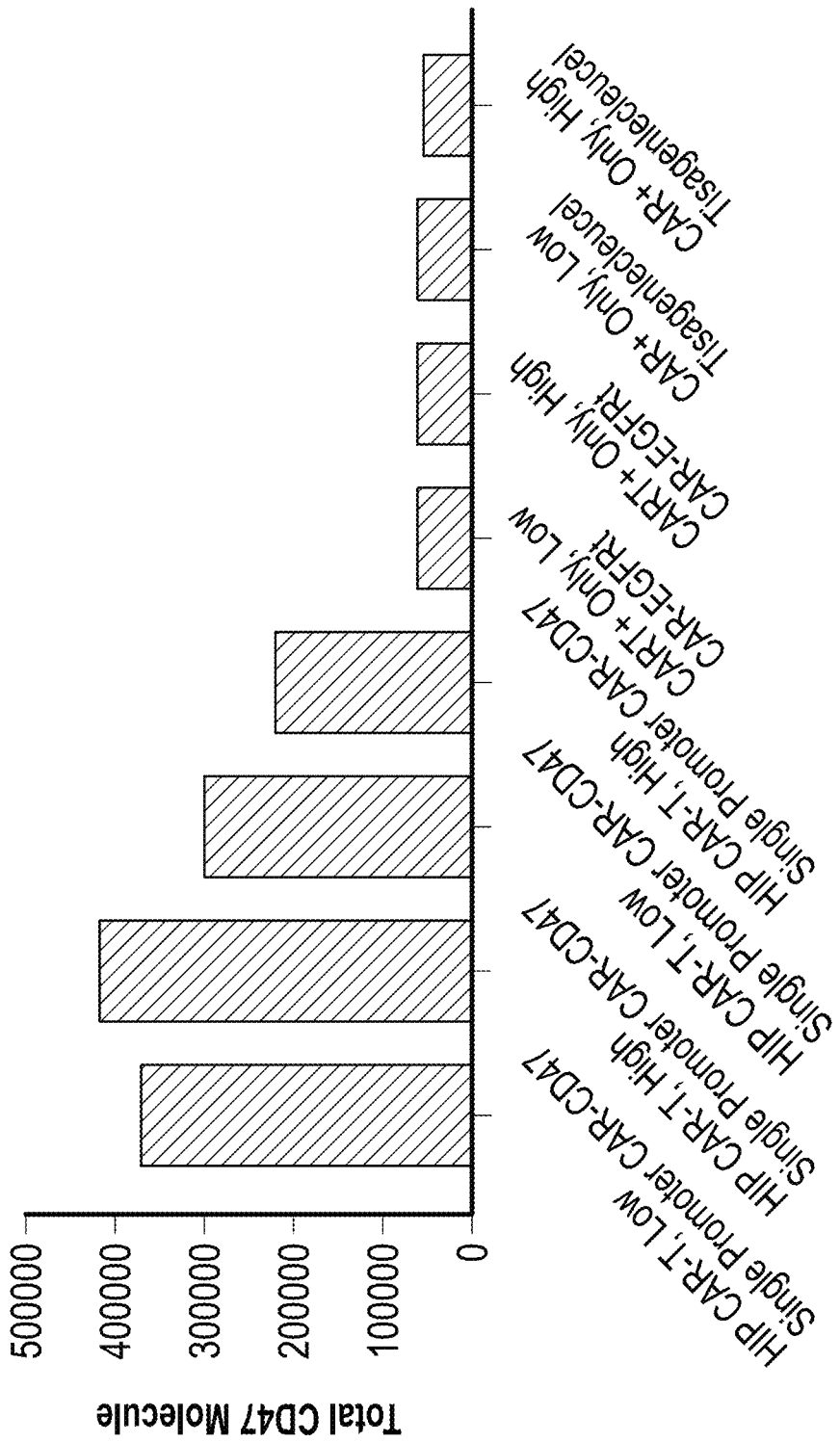
FIG. 15 depicts the expression of CD47 molecules in hypoimmunogenic CD19-specific CAR-CD47 T cells using a method for flow cytometric estimation of antibodies per cell (e.g., QuantiBRITE™, BD Biosciences). In this assay, exogenous CD47 expression is above 200,000 molecules per cell.
Figure 16A:
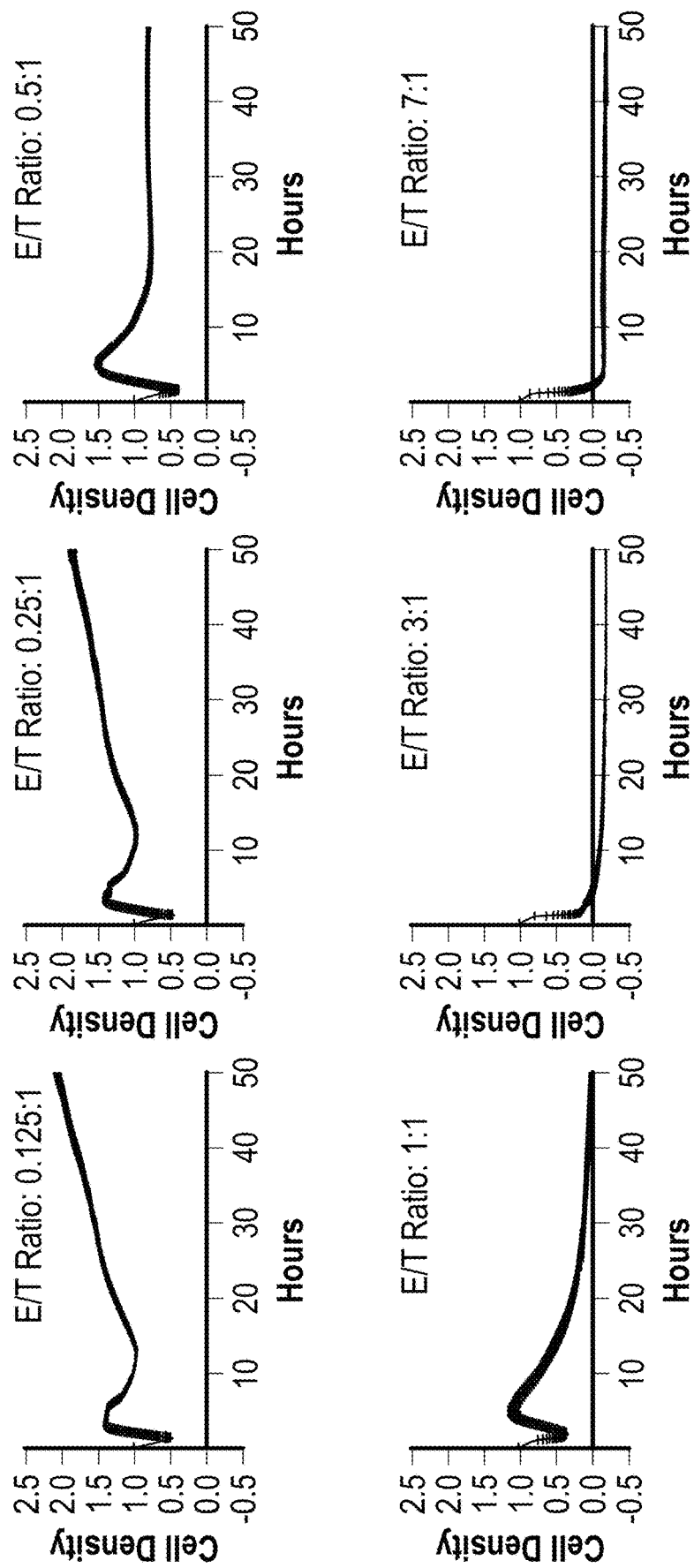
FIGS. 16A-D, 17A-D-18A-C show that the presence of the triple gene inactivation of the TRAC, B2M and CIITA genes and overexpression of CD47 proteins did not affect activity of an exemplary CD19-specific CAR in the hypoimmunogenic CD19-specific CAR-CD47 T cells described herein.
Figure 16B:
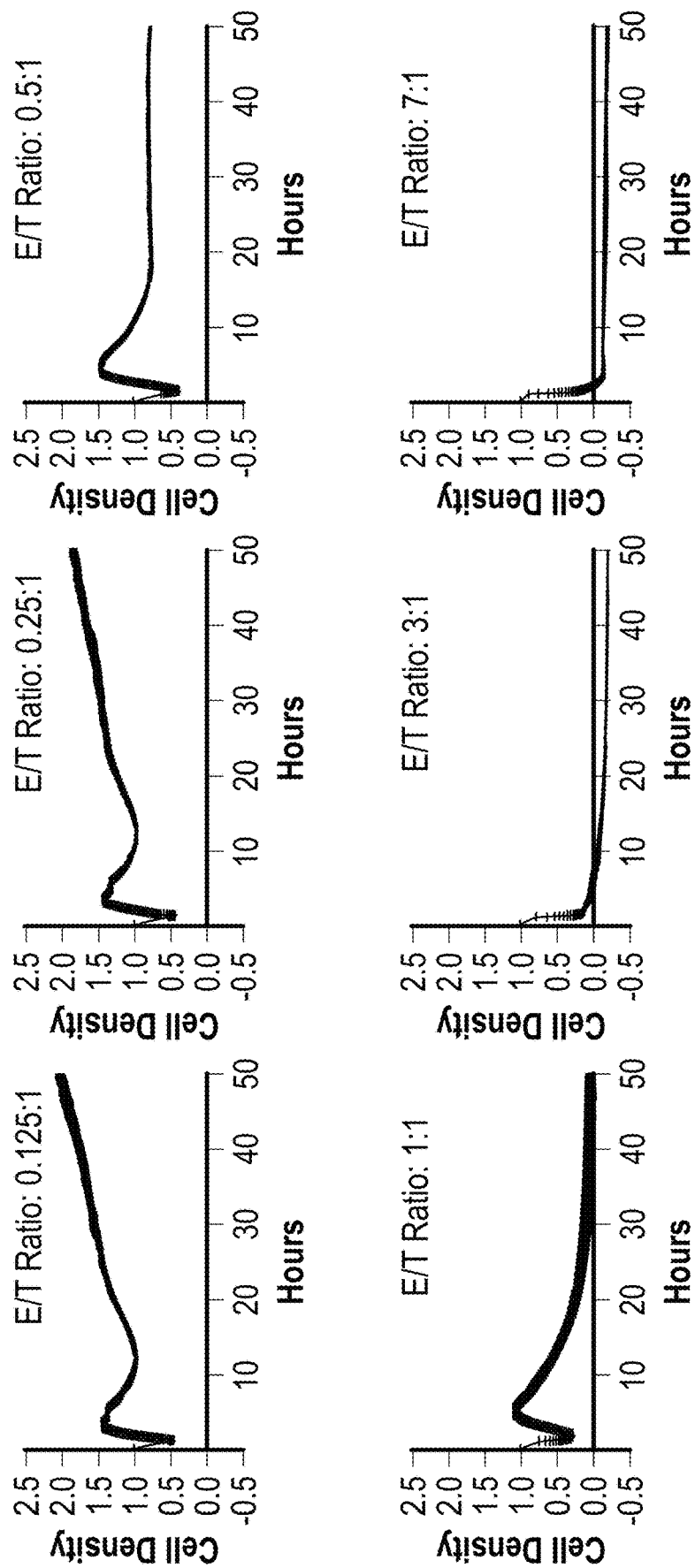
Figure 16C:
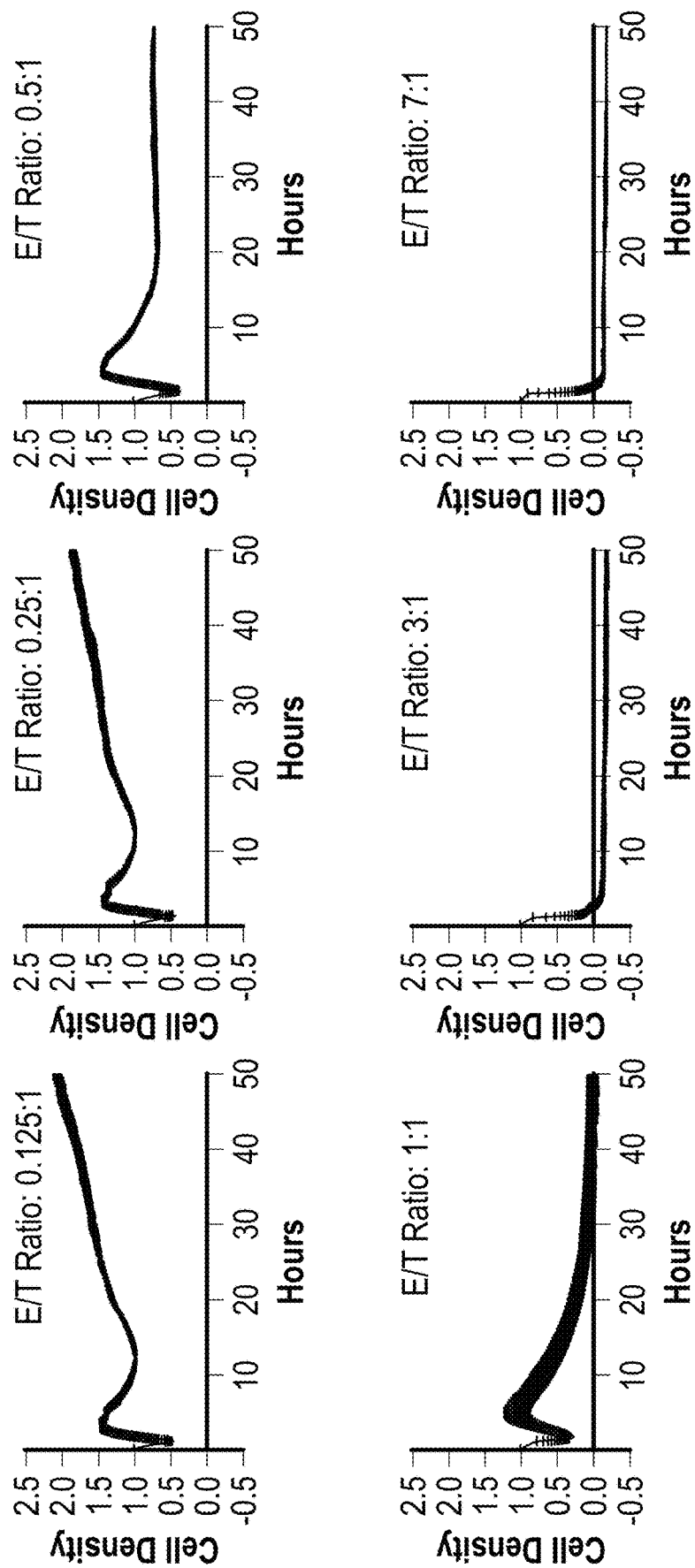
Figure 16D:
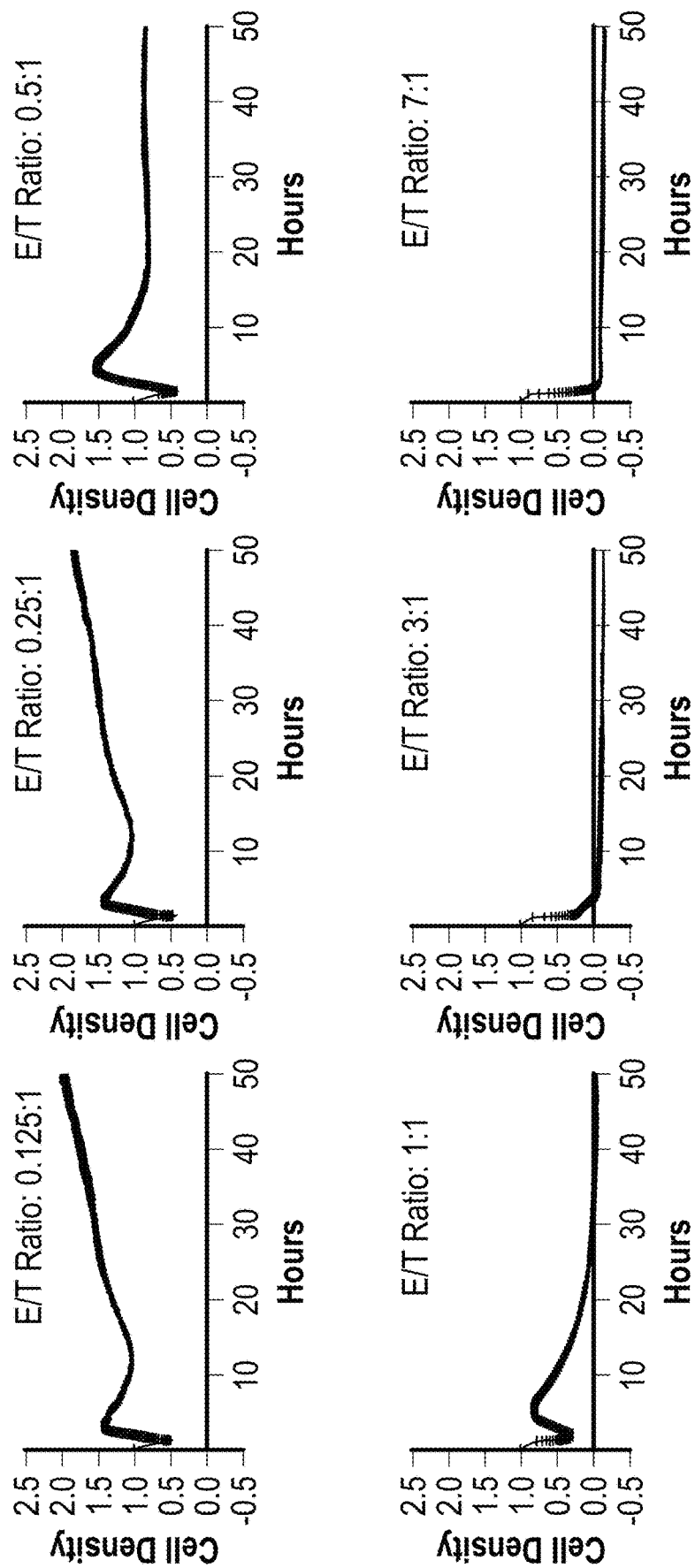
Figure 17A:
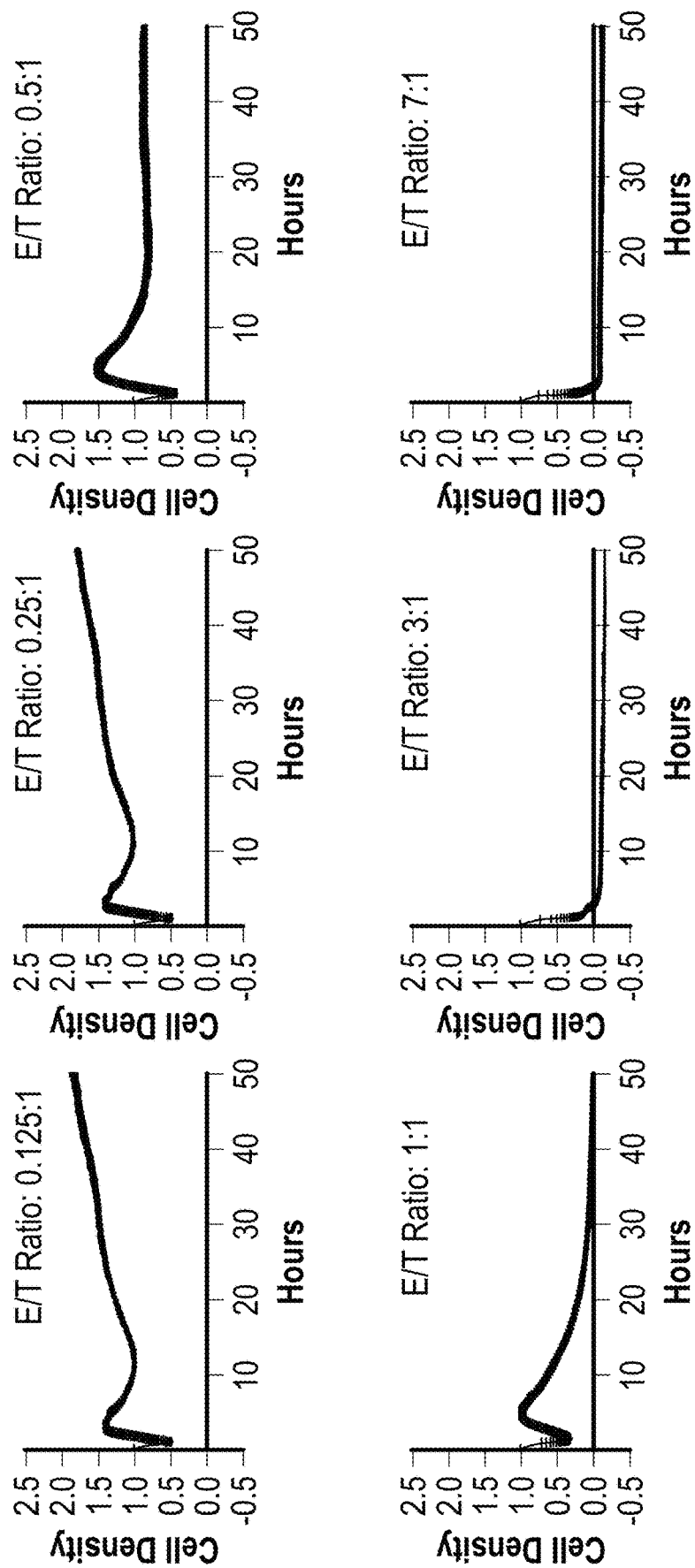
Figure 17B:
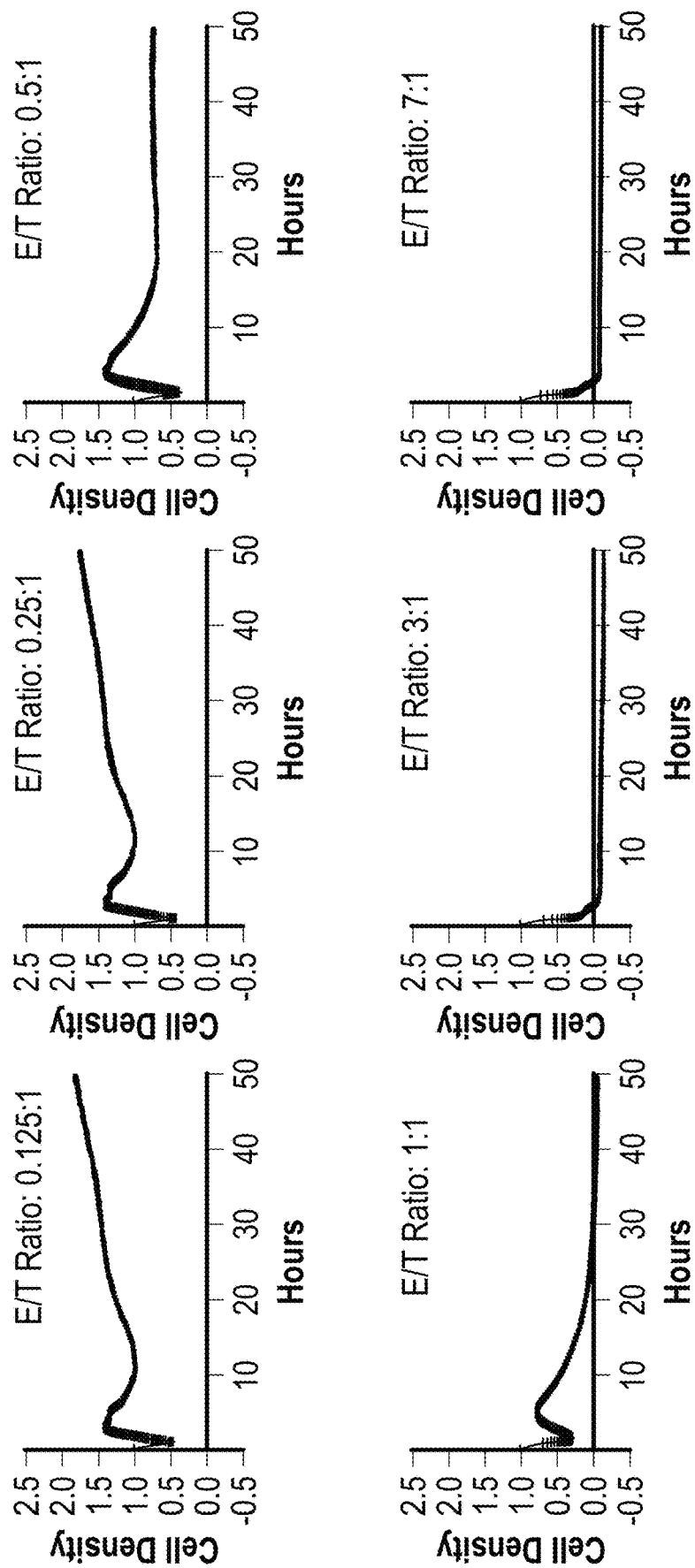
Figure 17C:
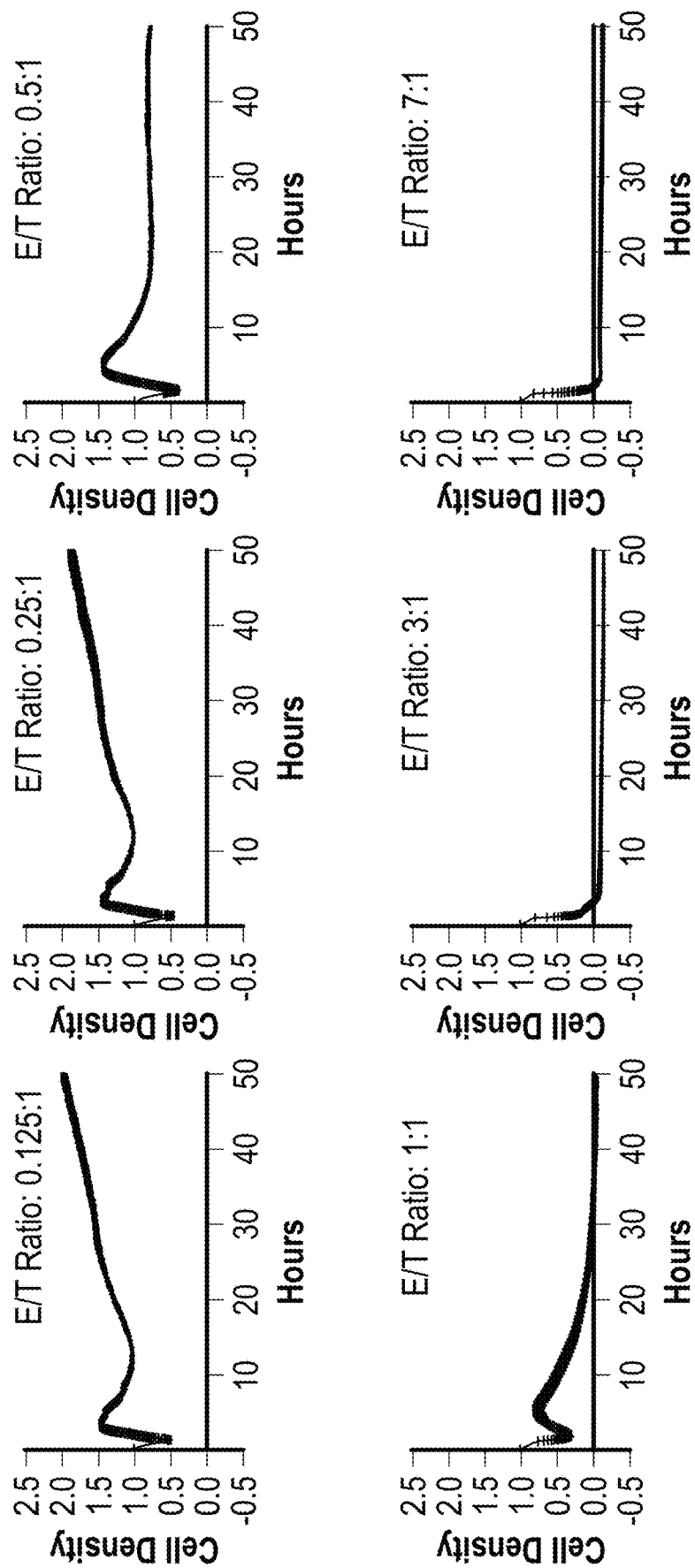
Figure 17D:
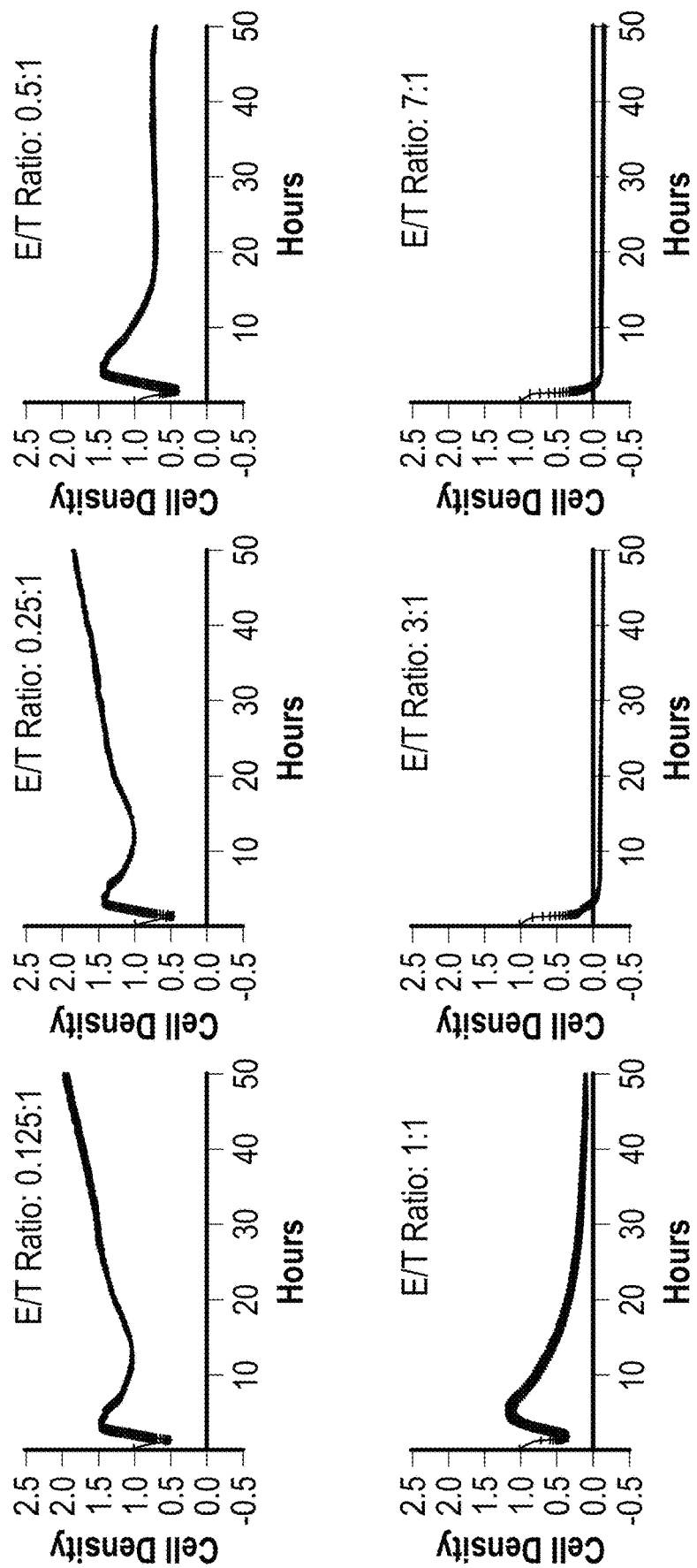
Figure 18A:
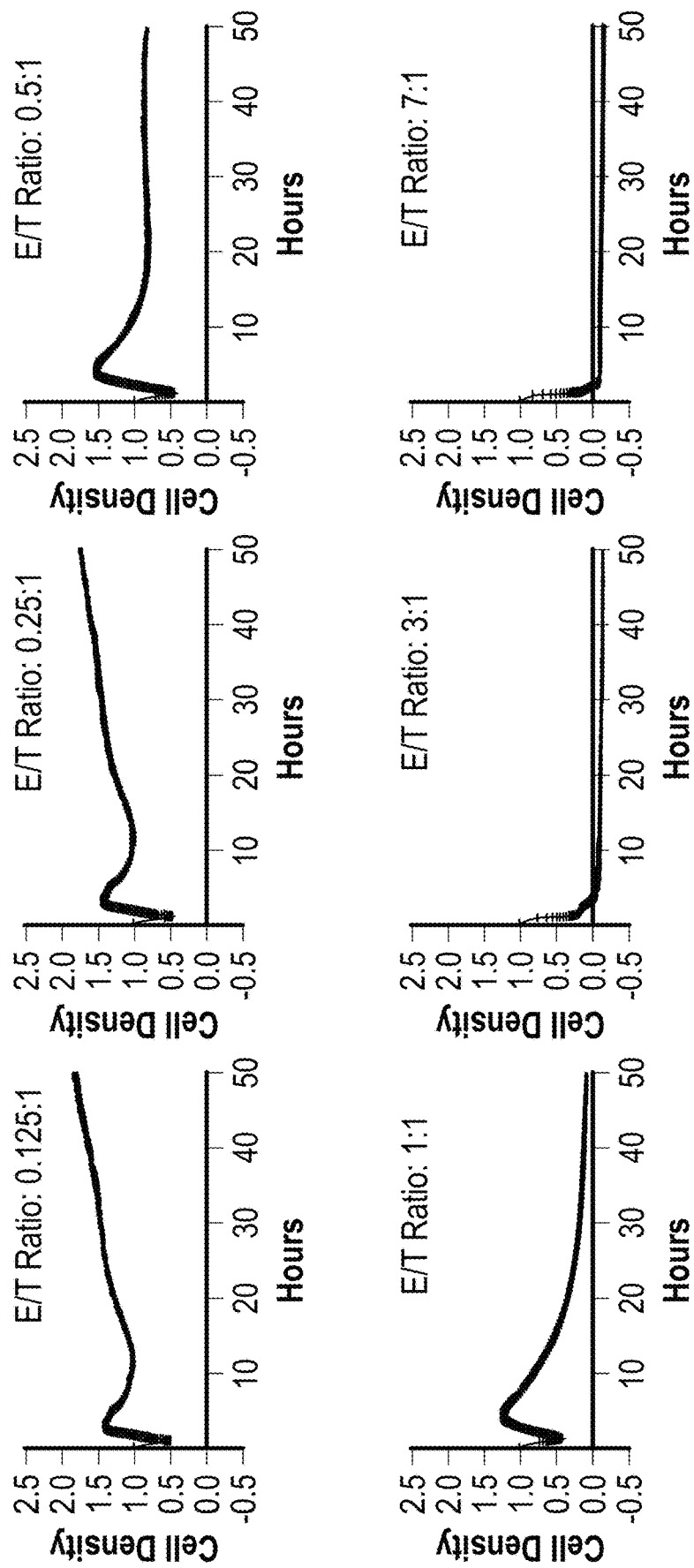
Figure 18B:
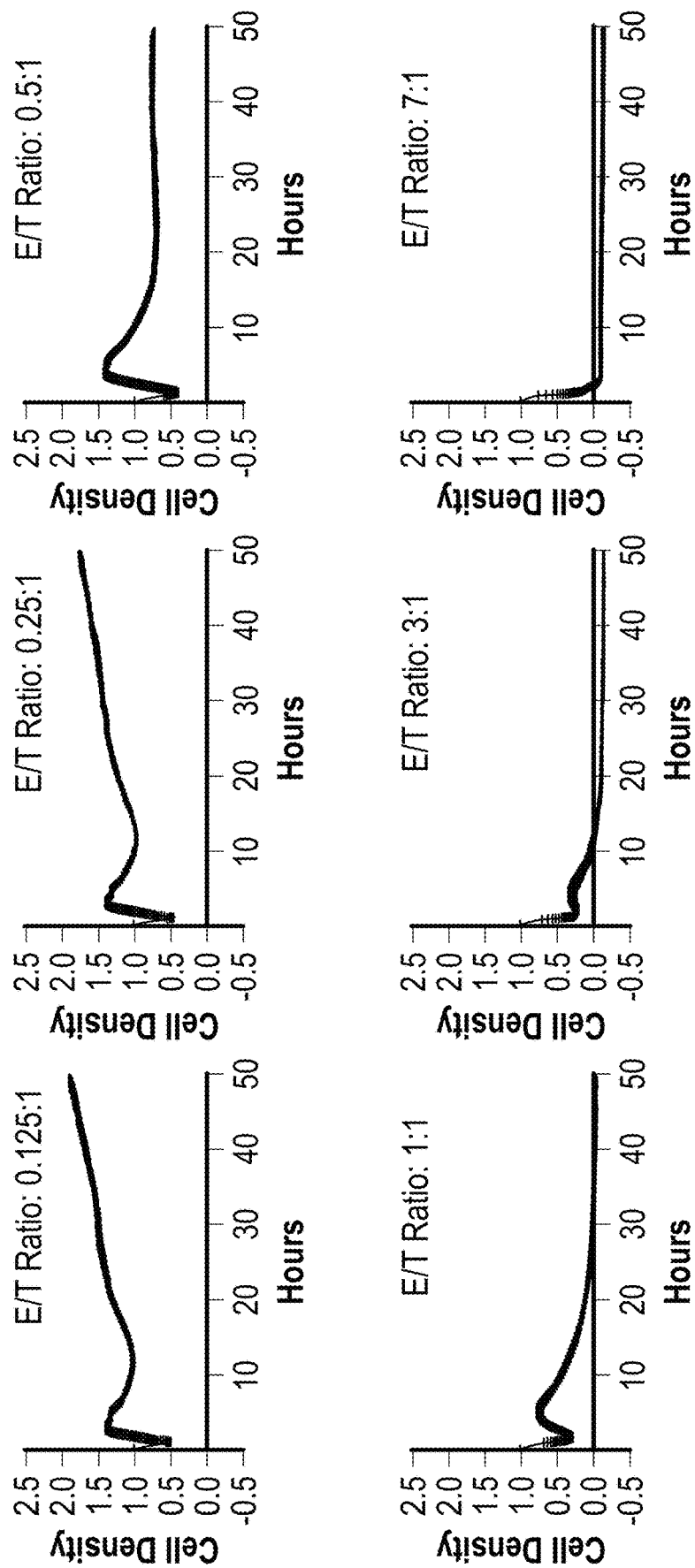
Figure 18C:
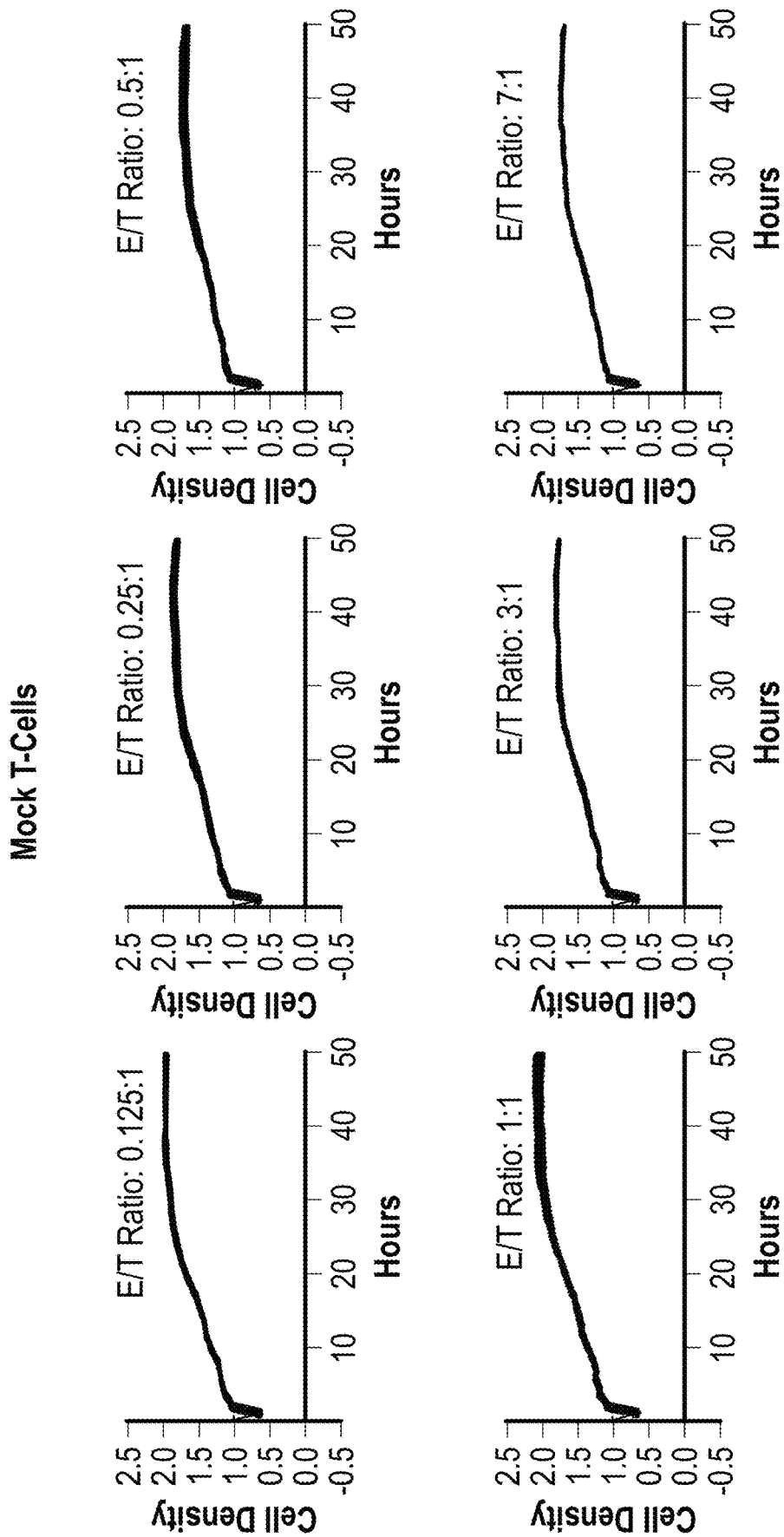
Figure 19:
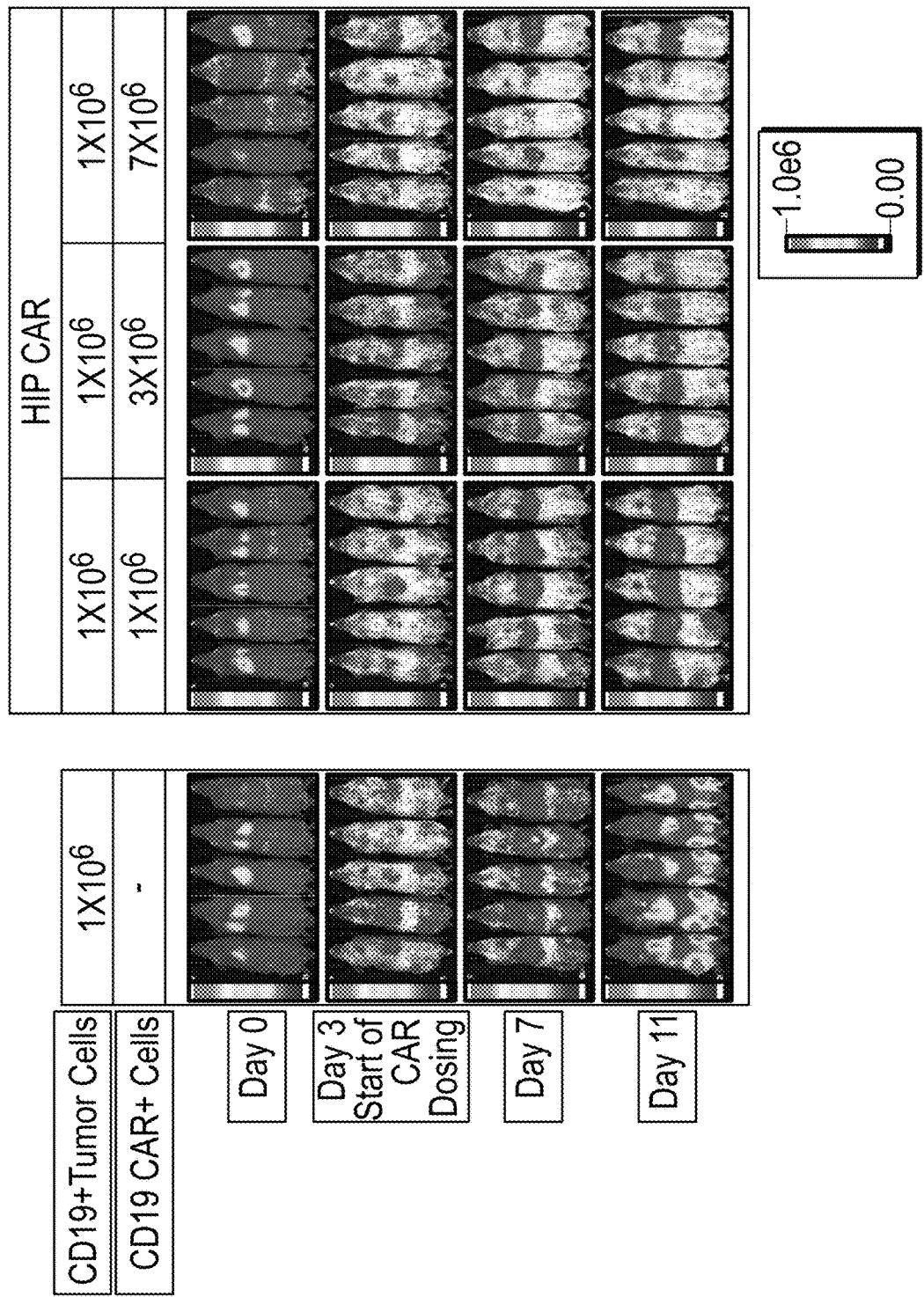
FIGS. 19-22 provide the efficacy of the hypoimmunogenic CD19-specific CAR-CD47 T cells described herein in a mouse model with CD19+ tumor cells. Whole animal scans show killing of tumor cells by such hypoimmunogenic CD19-specific CAR-T cells. The killing activity appeared to be in a dose-dependent manner.
Figure 20:
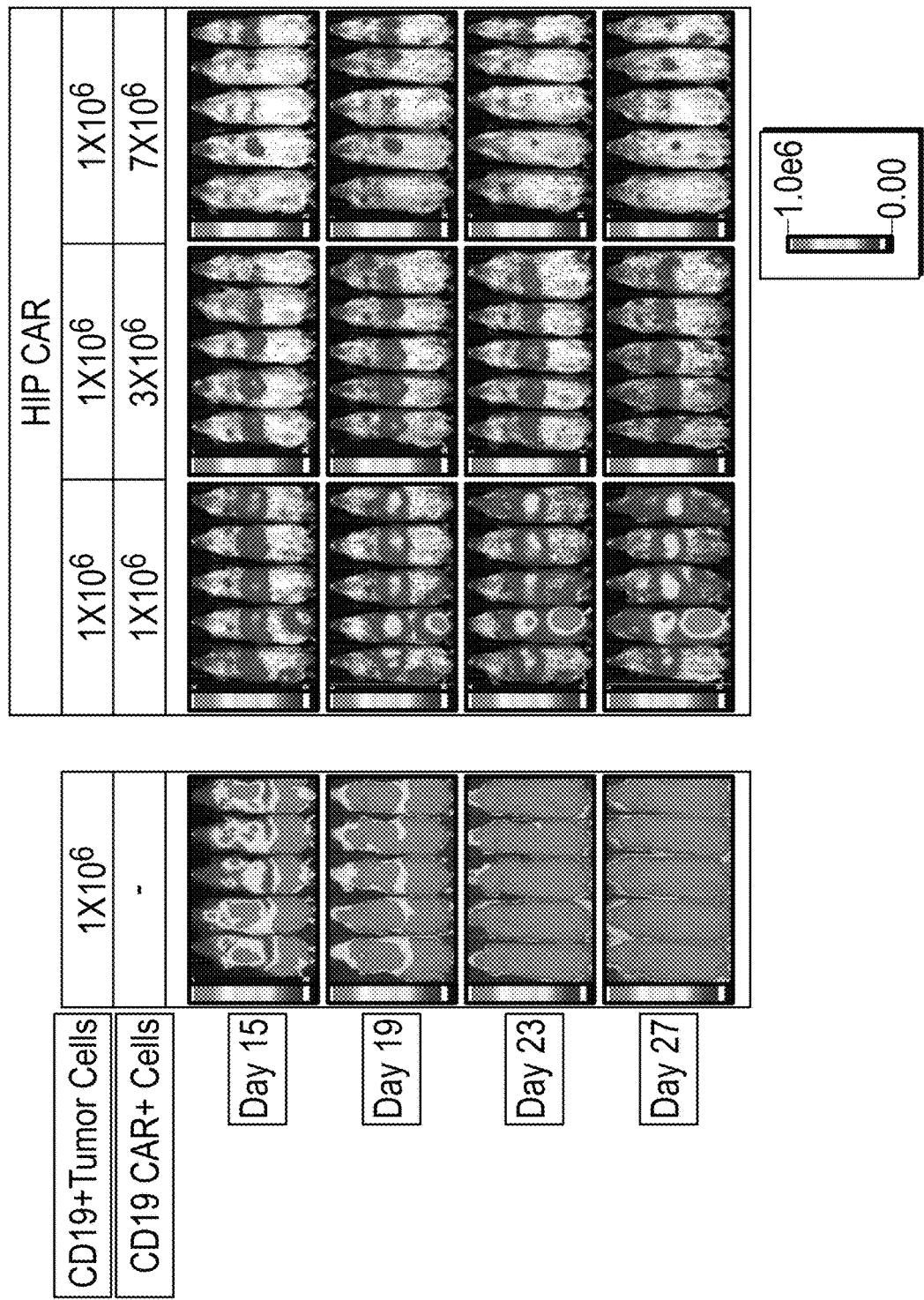

In some embodiments, hypoimmunogenicity is assayed using a number of techniques as exemplified in FIG. 13 and FIG. 15 of WO2018132783. These techniques include transplantation into allogeneic hosts and monitoring for hypoimmunogenic pluripotent cell growth (e.g., teratomas) that escape the host immune system. In some instances, hypoimmunogenic pluripotent cell derivatives are transduced to express luciferase and can then followed using bioluminescence imaging. Similarly, the T cell and/or B cell response of the host animal to such cells are tested to confirm that the cells do not cause an immune reaction in the host animal. T cell responses can be assessed by Elispot, ELISA, FACS, PCR, or mass cytometry (CYTOF). B cell responses or antibody responses are assessed using FACS or Luminex. Additionally or alternatively, the cells may be assayed for their ability to avoid innate immune responses, e.g., NK cell killing, as is generally shown in FIGS. 14 and 15 of WO2018132783.

In some embodiments, the immunogenicity of the cells is evaluated using T cell immunoassays such as T cell proliferation assays, T cell activation assays, and T cell killing assays recognized by those skilled in the art. In some cases, the T cell proliferation assay includes pretreating the cells with interferon-gamma and coculturing the cells with labelled T cells and assaying the presence of the T cell population (or the proliferating T cell population) after a preselected amount of time. In some cases, the T cell activation assay includes coculturing T cells with the cells outlined herein and determining the expression levels of T cell activation markers in the T cells.

In vivo assays can be performed to assess the immunogenicity of the cells outlined herein. In some embodiments, the survival and immunogenicity of hypoimmunogenic cells is determined using an allogenic humanized immunodeficient mouse model. In some instances, the hypoimmunogenic pluripotent stem cells are transplanted into an allogenic humanized NSG-SGM3 mouse and assayed for cell rejection, cell survival, and teratoma formation. In some instances, grafted hypoimmunogenic pluripotent stem cells or differentiated cells thereof display long-term survival in the mouse model.

Additional techniques for determining immunogenicity including hypoimmunogenicity of the cells are described in, for example, Deuse et al., Nature Biotechnology, 2019, 37, 252-258 and Han et al., Proc Natl Acad Sci USA, 2019, 116(21), 10441-10446, the disclosures including the figures, figure legends, and description of methods are incorporated herein by reference in their entirety.

Figure 29:
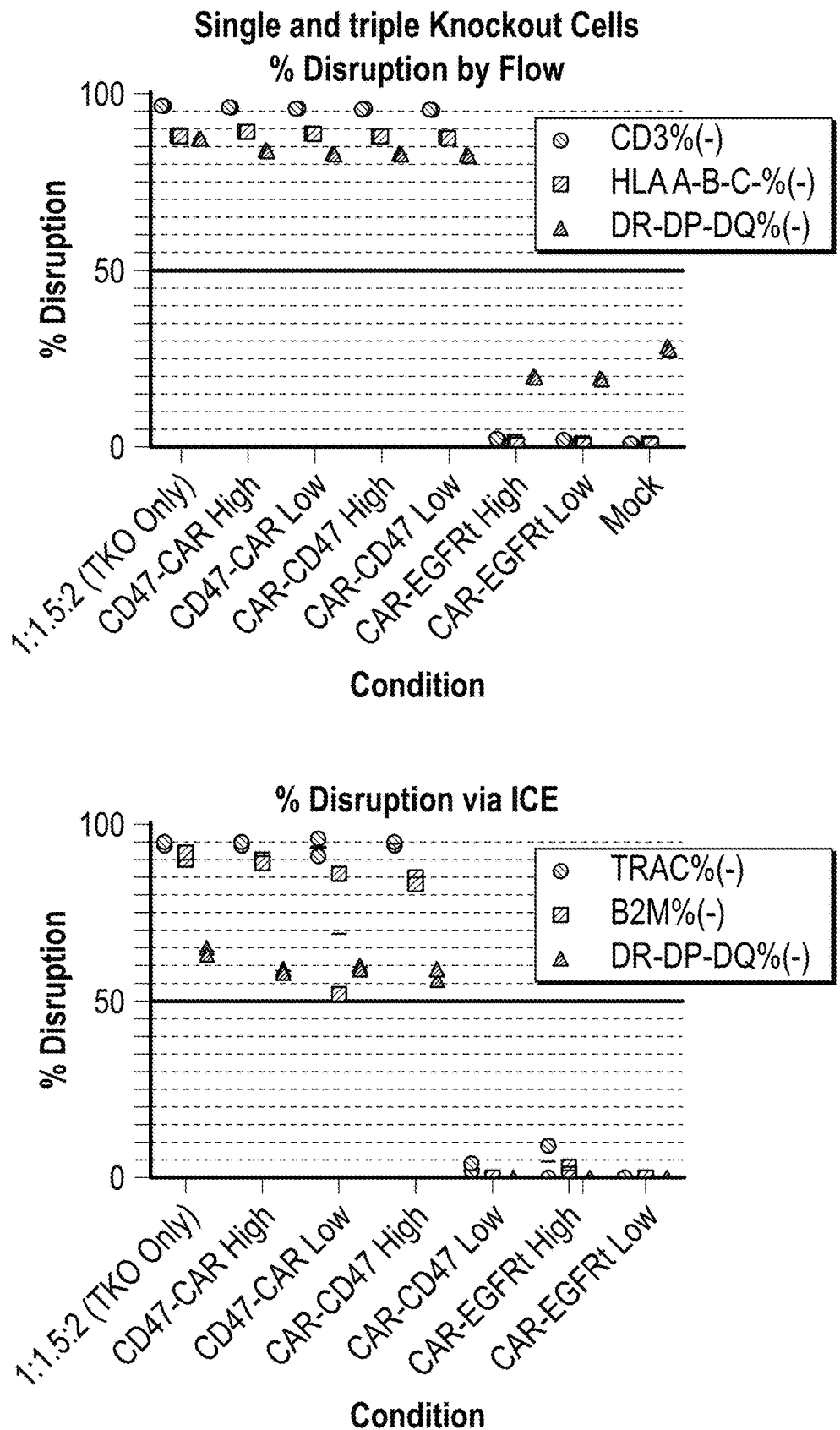
FIG. 29 depicts the expression of CD3, B2M, TRAC, HLA-DR/HLA-DP/HLA-DQ, and HLA-A/HLA-B/HLA-C as determined by FACS and ICE in hypoimmunogenic CD19-specific CAR-CD47 T cells, CD19-specific CAR-EGFRt T cells, and mock T cells.

Similarly, the retention of pluripotency is tested in a number of ways. In some embodiments, pluripotency is assayed by the expression of certain pluripotency-specific factors as generally described herein and shown in FIG. 29 of WO2018132783. Additionally or alternatively, the pluripotent cells are differentiated into one or more cell types as an indication of pluripotency.

As will be appreciated by those in the art, the successful reduction of the MHC I function (HLA I when the cells are derived from human cells) in the pluripotent cells can be measured using techniques known in the art and as described below; for example, FACS techniques using labeled antibodies that bind the HLA complex; for example, using commercially available HLA-A, HLA-B, and HLA-C antibodies that bind to the alpha chain of the human major histocompatibility HLA Class I antigens.

In addition, the cells can be tested to confirm that the HLA I complex is not expressed on the cell surface. This may be assayed by FACS analysis using antibodies to one or more HLA cell surface components as discussed above.

The successful reduction of the MHC II function (HLA II when the cells are derived from human cells) in the pluripotent cells or their derivatives can be measured using techniques known in the art such as Western blotting using antibodies to the protein, FACS techniques, RT-PCR techniques, etc.

Figure 21:
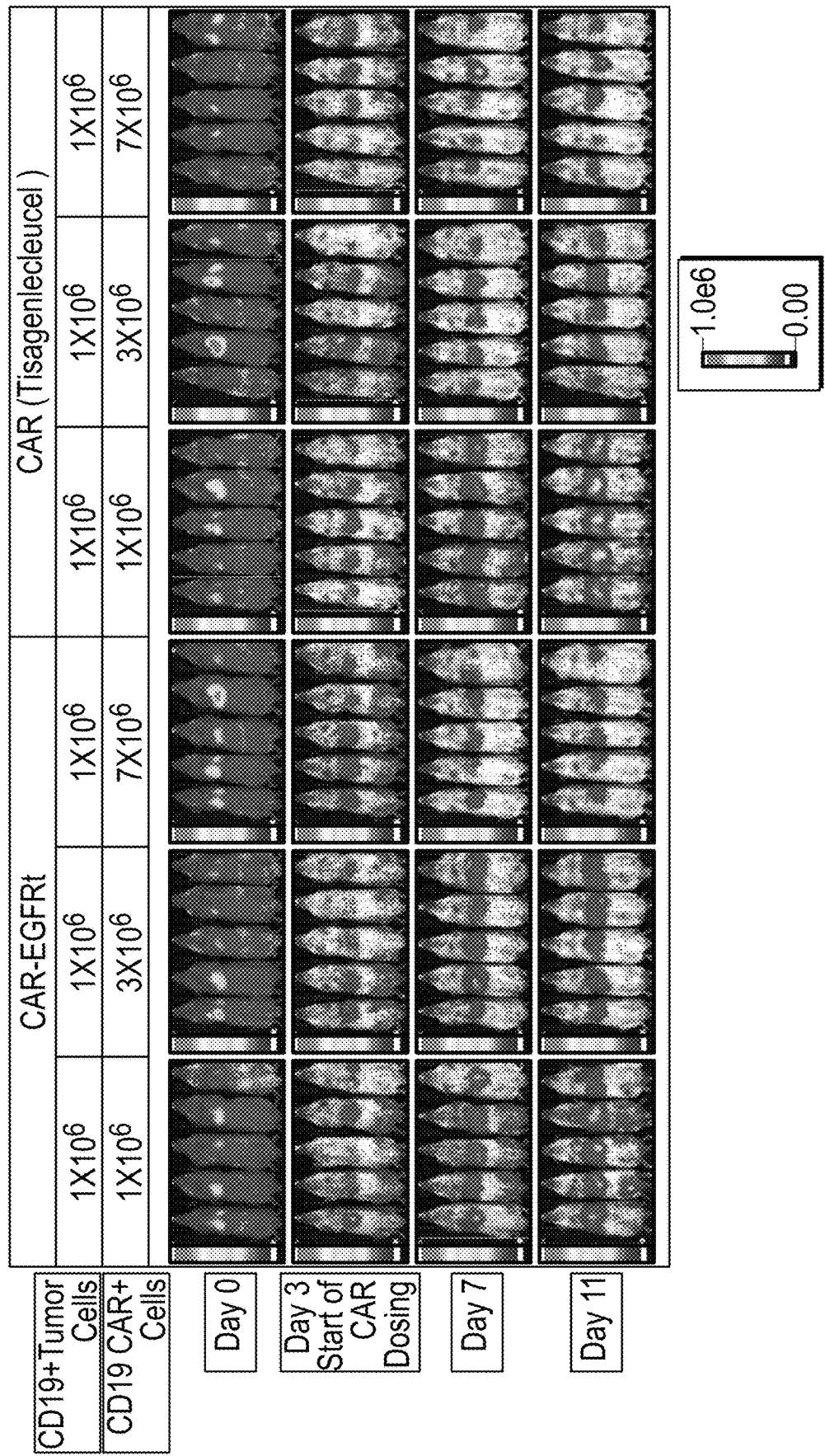
Figure 22:
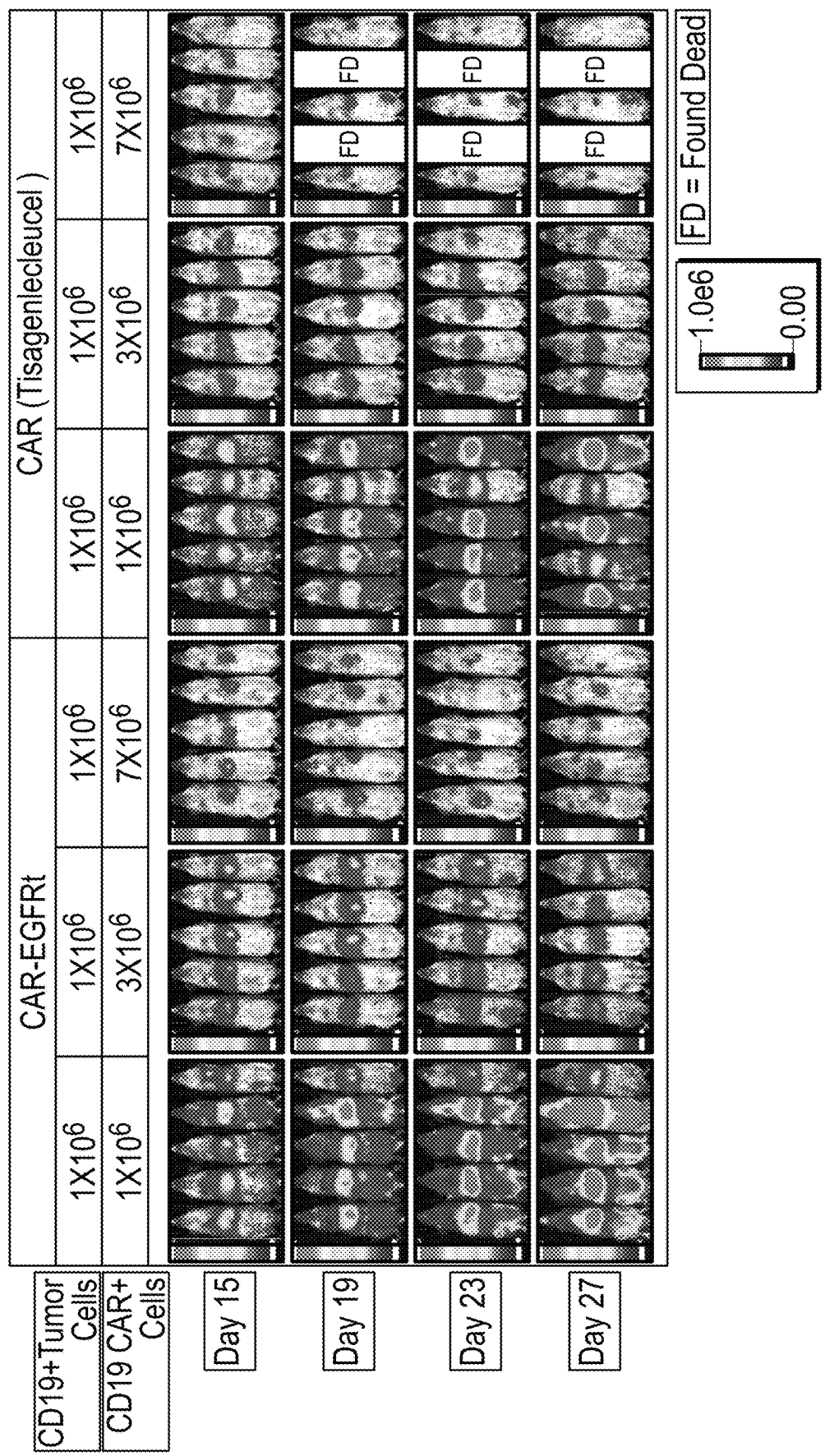
Figure 23:
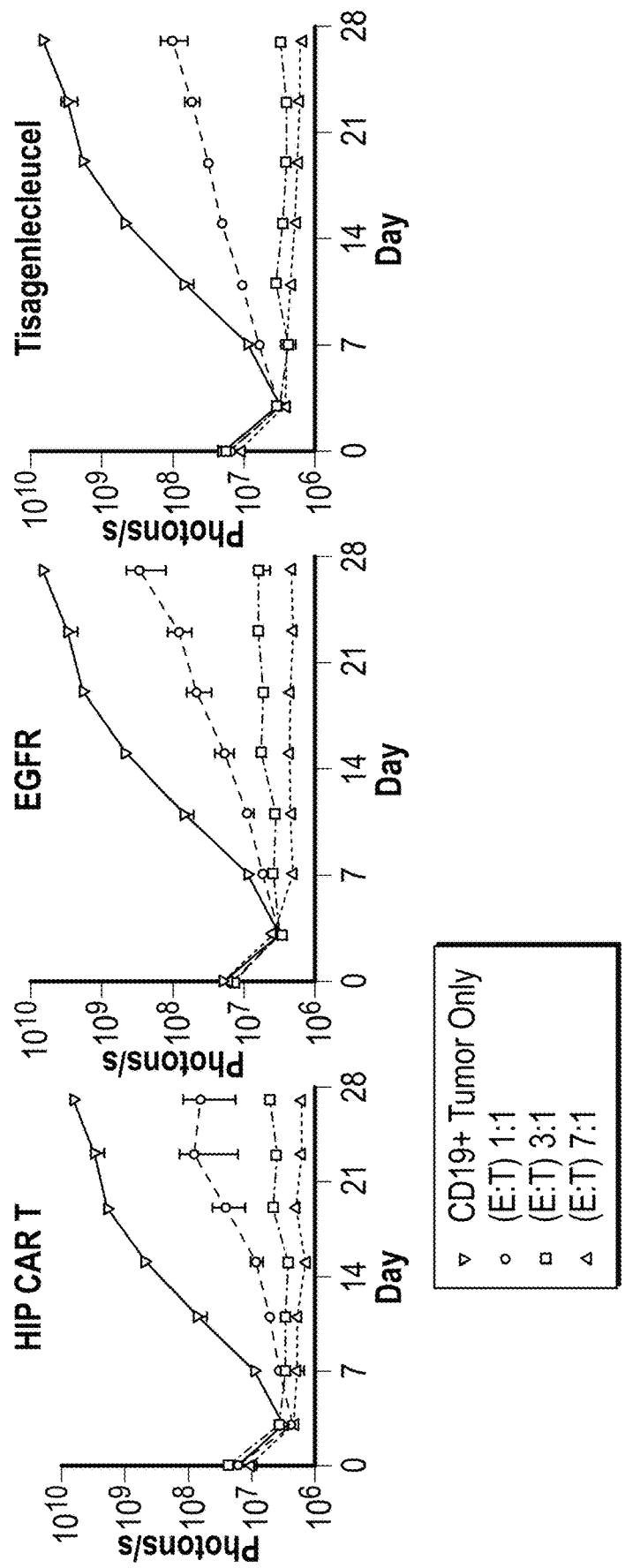
FIG. 23 shows the efficacy of the hypoimmunogenic CD19-specific CAR-CD47 T cells at varying effector:tumor cell ratios over a range of 0 to 28 days.
Figure 24:
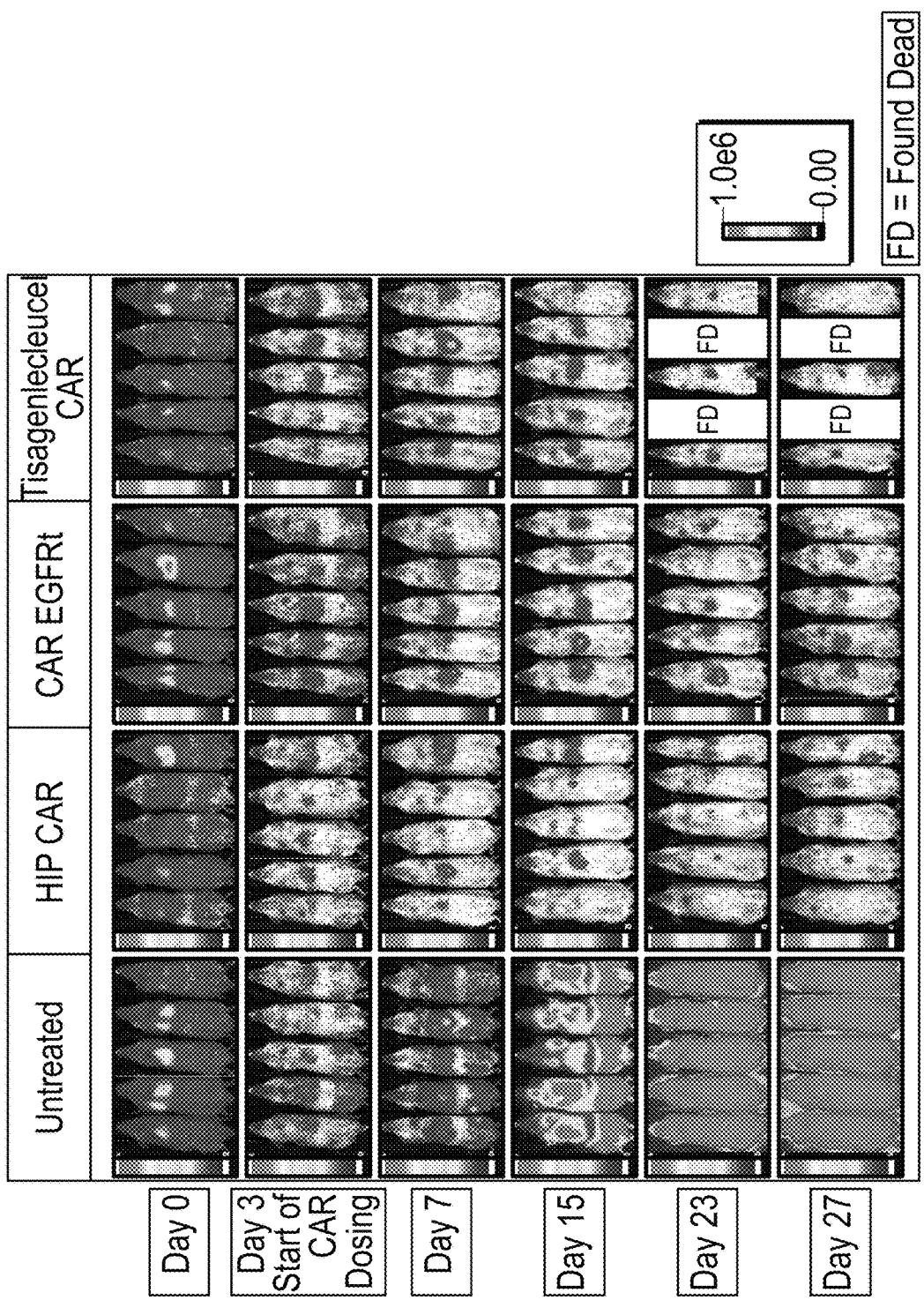
FIG. 24 shows whole animal scans depicting killing of tumor cells by hypoimmunogenic CD19-specific CAR-CD47 T cells over range of 27 days. The effector:tumor cell ratio used was 7:1.
Figure 26:
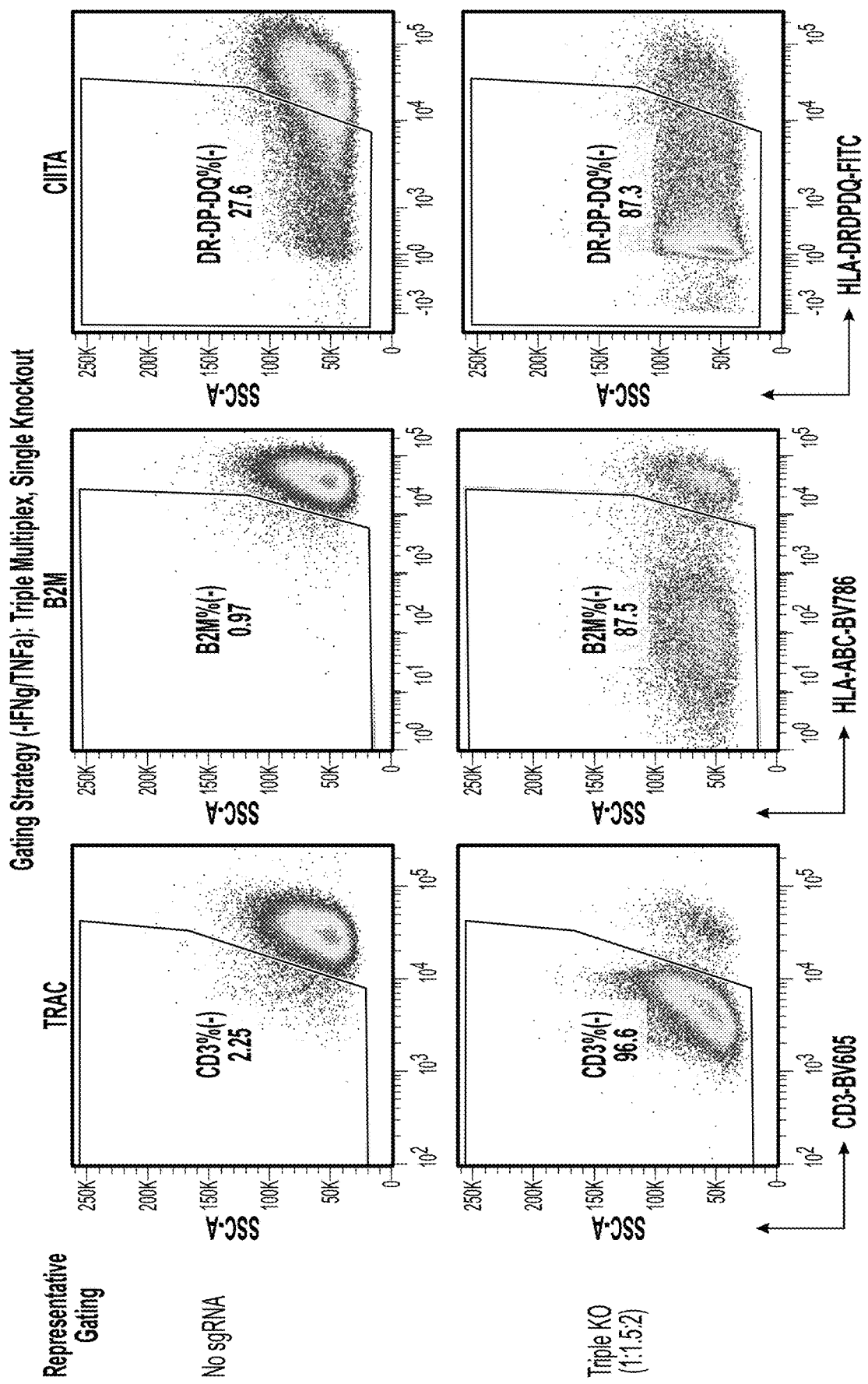
FIG. 26 and FIG. 27 depict FACS analysis of the exemplary hypoimmunogenic CD19-specific CAR-CD47 T cells and the absence of CD3, B2M, HLA-DR/ILA-DP/HLA-DQ, and HLA-A/HLA-B/HLA-C expression.
Figure 27:
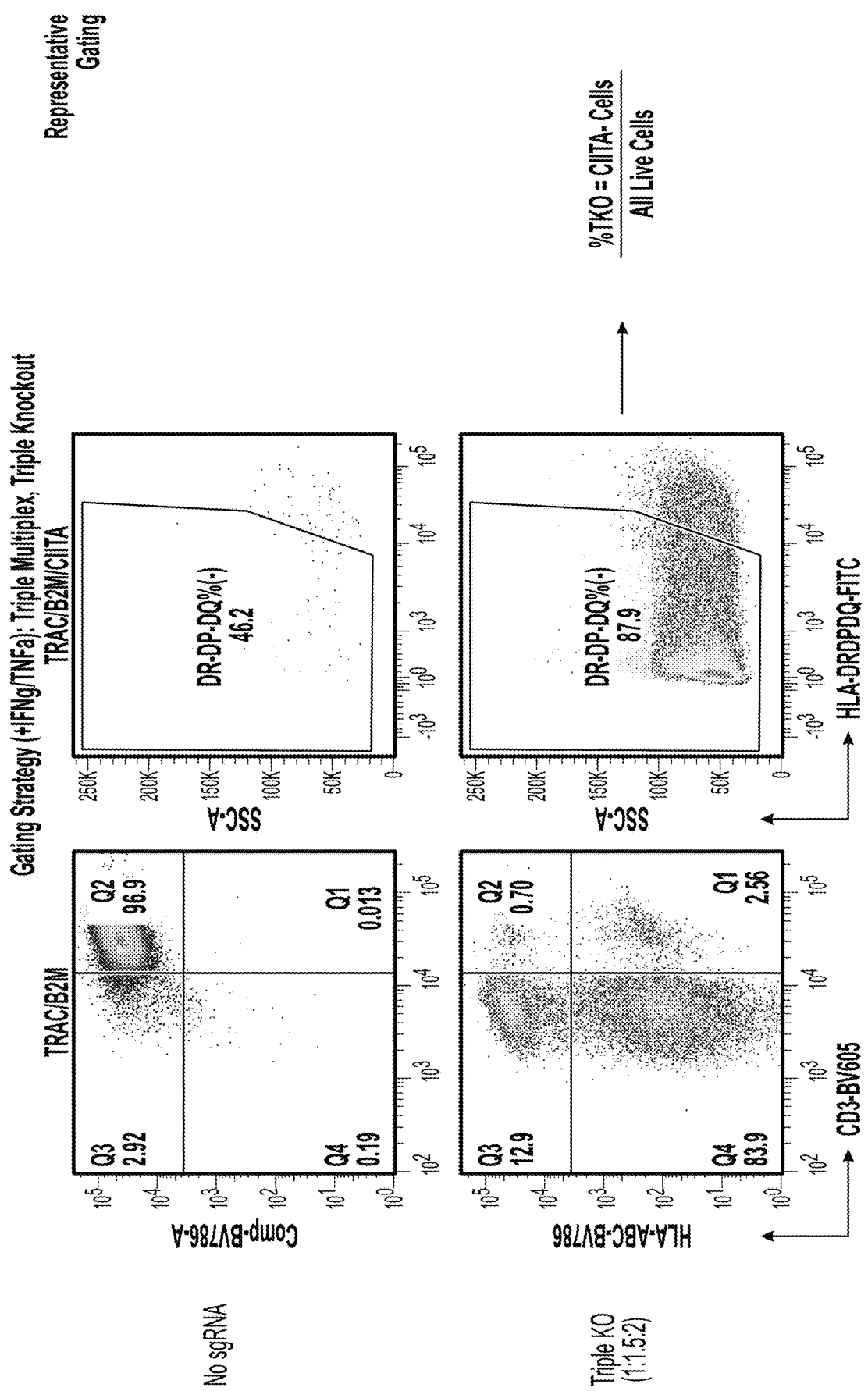
Figure 28:
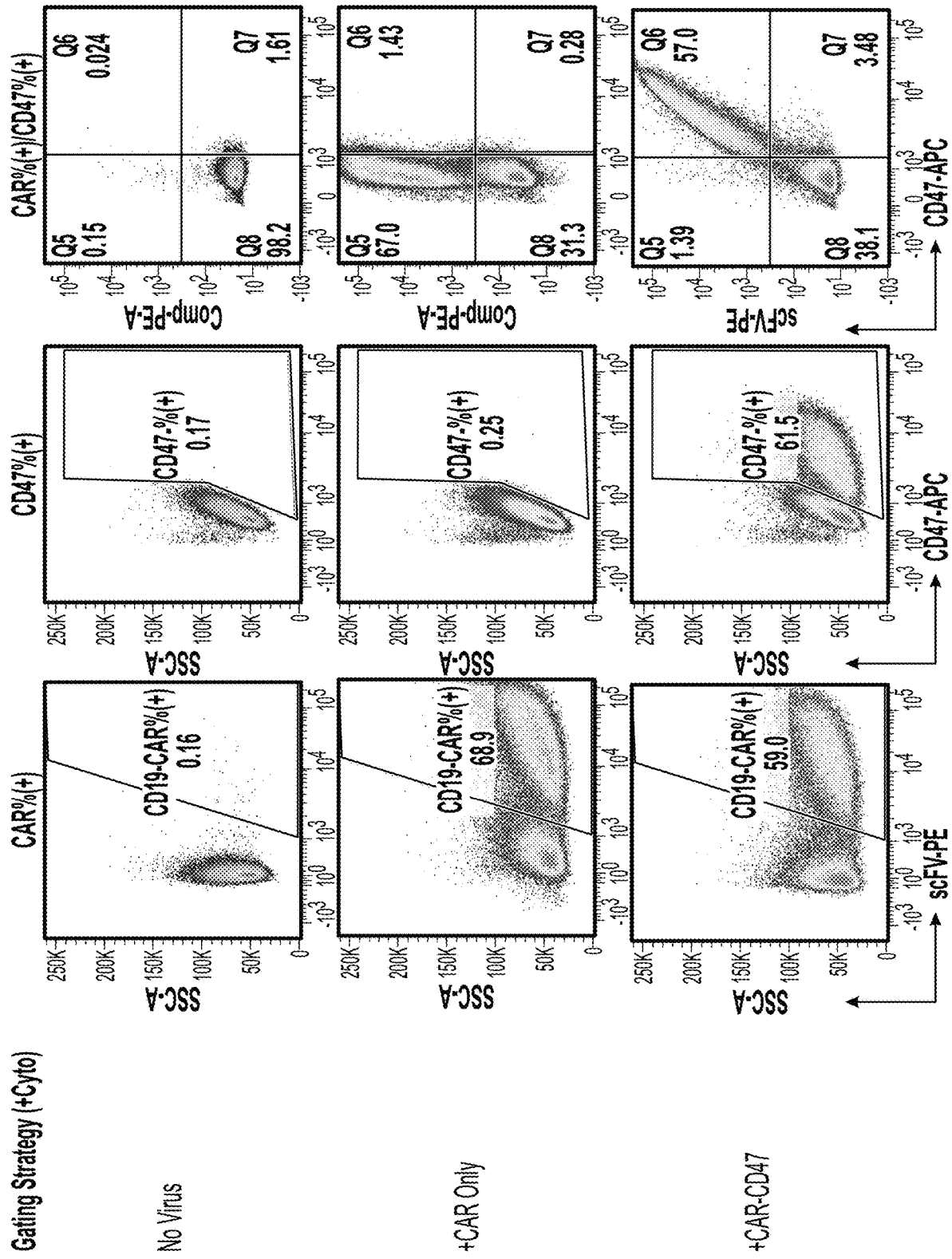
FIG. 28 shows FACS analysis of the expression of CD47 and CD19-CAR in hypoimmunogenic CD19-specific CAR-CD47 T cells.

In addition, the cells can be tested to confirm that the HLA II complex is not expressed on the cell surface. Again, this assay is done as is known in the art (See FIG. 21 of WO2018132783, for example) and generally is done using either Western Blots or FACS analysis based on commercial antibodies that bind to human HLA Class II HLA-DR, DP and most DQ antigens.

In addition to the reduction of HLA I and II (or MHC I and II), the hypoimmunogenic cells of the technology have a reduced susceptibility to macrophage phagocytosis and NK cell killing. The resulting hypoimmunogenic cells "escape" the immune macrophage and innate pathways due to reduction or lack of the TCR complex and the expression of one or more CD47 transgenes.

V. Exogenous Polynucleotides

In some embodiments, the hypoimmunogenic cells provided herein are genetically modified to include one or more exogenous polynucleotides inserted into one or more genomic loci of the hypoimmunogenic cell. In some embodiments, the exogenous polynucleotide encodes a protein of interest, e.g., a chimeric antigen receptor. Any suitable method can be used to insert the exogenous polynucleotide into the genomic locus of the hypoimmunogenic cell including the gene editing methods described herein (e.g., a CRISPR/Cas system). In some embodiments, the one or more exogenous polynucleotides are inserted into at least one allele of the cell using viral transduction, for example, with a vector. In some embodiments, the vector is a pseudotyped, self-inactivating lentiviral vector that carries the one or more exogenous polynucleotides. In some embodiments, the vector is a self-inactivating lentiviral vector pseudotyped with a vesicular stomatitis VSV-G envelope, and which carries the one or more exogenous polynucleotides. In some embodiments, the one or more exogenous polynucleotides are inserted into at least one allele of the cell using viral transduction. In some embodiments, the one or more exogenous polynucleotide are inserted into at least one allele of the cell using a lentivirus based viral vector.

The exogenous polynucleotide can be inserted into any suitable genomic loci of the hypoimmunogenic cell. In some embodiments, the exogenous polynucleotide is inserted into a safe harbor or target locus as described herein. Suitable safe harbor and target loci include, but are not limited to, a CCR5 gene, a CXCR4 gene, a PPPR12C (also known as AAVS1) gene, an albumin gene, a SH231 locus, a CLYBL gene, a Rosa gene (e.g., ROnA26), an F3 gene (also known as CD142), a MICA gene, a MICB gene, a LRP1 gene (also known as CD91), a HMNGB1 gene, an ABO gene, a RRD gene, a FUT1 gene, a PDGFRa gene, an OLIG2 gene, a GFAP gene, and a KDM5D gene (also known as HY). In some embodiments, the exogenous polynucleotide is interested into an intron, exon, or coding sequence region of the safe harbor or target gene locus. In some embodiments, the exogenous polynucleotide is inserted into an endogenous gene wherein the insertion causes silencing or reduced expression of the endogenous gene. In some embodiments, the polynucleotide is inserted in a B32M, CIITA, TRAC, TRB, PD-1 or CTLA-4 gene locus. Exemplary genomic loci for insertion of an exogenous polynucleotide are depicted in Table 17.

TABLE 17

Exemplary genomic loci for insertion of exogenous polynucleotides

| Number | species | Name | Ensembl ID | Target region for cleavage | Also known as |
|---|---|---|---|---|---|
| 1 | human | B2M | ENSG00000166710 | CDS | |
| 2 | human | CIITA | ENSG00000179583 | CDS | |
| 3 | human | TRAC | ENSG00000277734 | CDS | |
| 4 | human | PPP1R12C | ENSG00000125503 | Intron 1 and 2 | AAVS1 |
| 5 | human | CLYBL | ENSG00000125246 | Intron 2 | |
| 6 | human | CCR5 | ENSG00000160791 | Exons 1-3, introns 1-2, and CDS | |
| 7 | human | THUMPD3-AS1 | ENSG00000206573 | Intron 1 | ROSA26 |
| 8 | human | Ch-4:58,976,613 | | 500 bp window | SHS231 |
| 9 | human | F3 | ENSG00000117525 | CDS | CD142 |
| 10 | human | MICA | ENSG00000204520 | CDS | |
| 11 | human | MICB | ENSG00000204516 | CDS | |
| 12 | human | LRP1 | ENSG00000123384 | CDS | |
| 13 | human | HMGB1 | ENSG00000189403 | CDS | |
| 14 | human | ABO | ENSG00000175164 | CDS | |
| 15 | human | RHD | ENSG00000187010 | CDS | |
| 16 | human | FUT1 | ENSG00000174951 | CDS | |
| 17 | human | KDM5D | ENSG00000012817 | CDS | HY |

TABLE 18

Non-limiting examples of Cas9 guide RNAs

| Gene | SEQ ID NO: | guide sequence | PAM | Target site | gRNA cut location |
|---|---|---|---|---|---|
| ABO | 1 | UCUCUCCAUGUGCAGUAGGA | AGG | Exon 7 | chr9: 133, 257, 541 |
| FUT1 | 2 | CUGGAUGUCGGAGGAGUACG | CGG | Exon 4 | chr19: 48, 750, 822 |
| RH | 3 | GUCUCCGGAAACUCGAGGUG | AGG | Exon 2 | chr1: 25, 284, 622 |
| F3 (CD142) | 4 | ACAGUGUAGACUUGAUUGAC | GGG | Exon 2 | chr1: 94, 540, 281 |
| B2M | 5 | CGUGAGUAAACCUGAAUCUU | TGG | Exon 2 | chr15: 44, 715, 434 |
| CIITA | 6 | GAUAUUGGCAUAAGCCUCCC | TGG | Exon 3 | chr16: 10, 895, 747 |

TABLE 18-continued

Non-limiting examples of Cas9 guide RNAs

| Gene | SEQ ID NO: | guide sequence | PAM | Target site | gRNA cut location |
|---|---|---|---|---|---|
| TRAC | 7 | AGAGUCUCUCAGCUGGUACA | CGG | Exon 1 | chr14: 22, 5547, 533 |

For the Cas9 guides, the spacer sequence for all Cas9 guides is provided in Table 19, with description that the 20 nt guide sequence corresponds to a unique guide sequence and can be any of those described herein, including for example those listed in Table 18.

TABLE 19

Cas9 guide RNAs

| Description | SEQ ID NO: | Sequence |
|---|---|---|
| 20 nt guide sequence* | 8 | NNNNNNNNNNNNNNNNNNNN |
| 12 nt crRNA repeat sequence | 9 | GUUUUAGAGCUA |
| 4 nt tetraloop sequence | 10 | GAAA |
| 64 nt tracrRNA sequence | 11 | UAGCAAGUUAAAAUAAGGCUAGUCCGUUAUCAACU UGAAAAAGUGGCACCGAGUCGGUGCUUU |
| Exemplary full sequence | 12 | NNNNNNNNNNNNNNNNNNNNGUUUUAGAGCUAGAA AUAGCAAGUUAAAAUAAGGCUAGUCCGUUAUCAAC UUGAAAAAGUGGCACCGAGUCGGUGCUUU |

In some embodiments, the hypoimmunogenic cel that includes the exogenous polynucleotide is derived from a hypoimmunogenic induced pluripotent cell (HIP), for example, as described herein. Such hypoimmunogenic cells include, for example, T cells and NIK cells. In some embodiments, the hypoimmunogenic cell that includes the exogenous polynucleotide is a T cell (e.g., a primary T cell), or an NK cell.

In some embodiments, the exogenous polynucleotide encodes an exogenous CD47 polypeptide (e.g., a human CD47 polypeptide) and the exogenous polypeptide is inserted into the genome of the cell using a gene therapy vector. In some embodiments, the exogenous polynucleotide encodes an exogenous CD47 polypeptide (e.g., a human CD47 polypeptide) and the exogenous polypeptide is inserted into a safe harbor or target gene loci or a safe harbor or target site as disclosed herein or a genomic locus that causes silencing or reduced expression of the endogenous gene. In some embodiments, the polynucleotide is inserted in a B2M, CIITA, TRAC, TRB, PD1 or CTLA4 gene locus.

In some embodiments, the hypoimmunogenic cell that includes the exogenous polynucleotide is a primary T cell or a T cell derived from a hypoimmunogenic pluripotent cell (e.g., a hypoimmunogenic iPSC). In exemplary embodiments, the exogenous polynucleotide is a chimeric antigen receptor (e.g., any of the CARs described herein). In some embodiments, the exogenous polynucleotide is operably linked to a promoter for expression of the exogenous polynucleotide in the hypoimmunogenic cell.

W. Pharmaceutically Acceptable Carriers

In some embodiments, the pharmaceutical composition provided herein further include a pharmaceutically acceptable carrier. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); salts such as sodium chloride; and/or non-ionic surfactants such as polysorbates (TWEEN™) poloxamers (PLURONICS™) or polyethylene glycol (PEG). In some embodiments, the pharmaceutical composition includes a pharmaceutically acceptable buffer (e.g., neutral buffer saline or phosphate buffered saline).

In some embodiments, the pharmaceutical composition includes one or more electrolyte base solutions selected from the group consisting of lactated CryoStor®, Ringer's solution, PlasmaLyte-A™, Iscove's Modified Dulbecco's Medium, Normosol-R™, Veen-D™, Polysal® and Hank's Balanced Salt Solution (containing no phenol red). These base solutions closely approximate the composition of extracellular mammalian physiological fluids.

In some embodiments, the pharmaceutical composition includes one or more cryoprotective agents selected from the group consisting of arabinogalactan, glycerol, polyvinylpyrrolidone (PVP), dextrose, dextran, trehalose, sucrose, raffinose, hydroxyethyl starch (HES), propylene glycol, human serum albumin (HSA), and dimethylsulfoxide (DMSO). In some embodiments, the pharmaceutically acceptable buffer is neutral buffer saline or phosphate buffered saline. In some embodiments, pharmaceutical compositions provided herein include one or more of CryoStor® CSB, Plasma-Lyte-A™, HSA, DMSO, and trehalose.

CryoStor® is an intracellular-like optimized solution containing osmotic/oncotic agents, free radical scavengers, and energy sources to minimize apoptosis, minimize ischemia/reperfusion injury and maximize the post-thaw recovery of the greatest numbers of viable, functional cells. CryoStor® is serum- and protein-free, and non-immunogenic. CryoStor® is cGMP-manufactured from raw materials of USPgrade or higher. CryoStor® is a family of solutions pre-formulated with 0%, 2%, 5% or 10% DMSO. CryoStor® CSB is a DMSO-free version of CryoStor®. In some embodiments, the pharmaceutical composition includes a base solution of CryoStor® CSB at a concentration of about 0-100%, 5-95%, 10-90%, 15-85%, 20-80%, 30-80%, 40-80%, 50-80%, 60-80%, 70-80%, 25-75%, 30-70%, 35-65%, 40-60%, or 45-55% w/w. In some embodiments, the pharmaceutical composition includes a base solution of CryoStor® CSB at a concentration of about 0%, 5%, 10%, 15%, 20%, 25%, 30%, 35%, 40%, 45%, 50%, 55%, 60%, 65%, 70%, 75%, 80%, 85%, 90%, 95%, or 100% w/w.

PlasmaLyte-A™ is a non-polymeric plasma expander and contains essential salts and nutrients similar to those found in culture medium but does not contain additional constituents found in tissue culture medium which are not approved for human infusion, e.g., phenol red, or are unavailable in U.S.P. grade. PlasmaLyte-A™ contains about 140 mEq/liter of sodium (Na), about 5 mEq/liter of potassium (K), about 3 mEq/liter of magnesium (Mg), about 98 mEq/liter of chloride (Cl), about 27 mEq/liter of acetate, and about 23 mEq/liter of gluconate. (PlasmaLyte-A™ is commercially available from Baxter, Hyland Division, Glendale Calif., product No. 2B2543). In some embodiments, the pharmaceutical composition includes a base solution of Plasma-Lyte-A™ at a concentration of about 0-100%, 5-95%, 10-90%, 15-85%, 15-80%, 15-75%, 15-70%, 15-65%, 15-60%, 15-55%, 15-50%, 15-45%, 15-40%, 15-35%, 15-30%, 15-25%, 20-80%, 20-75%, 20-70%, 20-65%, 20-60%, 20-55%, 20-50%, 20-45%, 20-40%, 20-35%, 20-30%, 25-75%, 30-70%, 35-65%, 40-60%, or 45-55% w/w. In some embodiments, the pharmaceutical composition includes a base solution of PlasmaLyte-A™ at a concentration of about 0%, 5%, 10%, 15%, 20%, 25%, 30%, 35%, 40%, 45%, 50%, 55%, 60%, 65%, 70%, 75%, 80%, 85%, 90%, 95%, or 100% w/w.

In some embodiments, the pharmaceutical composition includes human serum albumin (HSA) at a concentration of about 0-10%, 0.3-9.3%, 0.3-8.3%, 0.3-7.3%, 0.3-6.3%, 0.3-5.3%, 0.3-4.3%, 0.3-3.3%, 0.3-2.3%, 0.3-1.3%, 0.6-8.3%, 0.9-7.3%, 1.2-6.3%, 1.5-5.3%, 1.8-4.3%, or 2.1-3.3% w/v. In some embodiments, the pharmaceutical composition includes HSA at a concentration of about 0%, 0.3%, 0.6%, 0.9%, 1.2%, 1.5%, 1.8%, 2.1%, 2.4%, 2.7%, 3.0%, 3.3%, 3.6%, 3.9%, 4.3%, 4.6%, 4.9%, 5.3%, 5.6%, 5.9%, 6.3%, 6.6%, 6.9%, 7.3%, 7.6%, 7.9%, 8.3%, 8.6%, 8.9%, 9.3%, 9.6%, 9.9%, or 10% w/v.

In some embodiments, the pharmaceutical composition includes dimethylsulfoxide (DMSO) at a concentration of about 0-10%, 0.5-9.5%, 1-9%, 1.5-8.5%, 2-8%, 3-8%, 4-8%, 5-8%, 6-8%, 7-8%, 2.5-7.5%, 3-7%, 3.5-6.5%, 4-6%, or 4.5-5.5% v/v. In some embodiments, the pharmaceutical composition includes HSA at a concentration of about 0%, 0.25%, 0.5%, 0.75%, 1.0%, 1.25%, 1.5%, 1.75%, 2.0%, 2.25%, 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0%, 8.25%, 8.5%, 8.75%, 9.0%, 9.25%, 9.5%, 9.75%, or 10.0% v/v.

In some embodiments, the pharmaceutical composition includes trehalose at a concentration of about 0-500 mM, 50-450 mM, 100-400 mM, 150-350 mM, or 200-300 mM. In some embodiments, the pharmaceutical composition includes trehalose at a concentration of about 0 mM, 10 mM, 20 mM, 30 mM, 40 mM, 50 mM, 60 mM, 70 mM, 80 mM, 90 mM, 100 mM, 125 mM, 150 mM, 175 mM, 200 mM, 225 mM, 250 mM, 275 mM, 300 mM, 325 mM, 350 mM, 375 mM, 400 mM, 425 mM, 450 mM, 475 mM, or 500 mM.

Exemplary pharmaceutical composition components are shown in Table 20.

TABLE 20

Exemplary pharmaceutical composition components.

| Formulation | Base Solution | c[DMSO] | Additional c[HSA]* | c[trehalose] |
|---|---|---|---|---|
| A | 75% CroStor ® | 7.5% | 0.3% | |
| B | CSB + 25% | 3.75% | 0.3% | |
| C | PlasmaLyte | | 5.3% | |
| D | A ™ + 1.2% HSA | | 0.3% | 250 mM |
| E | 100% | 7.5% | 0.3% | |
| F | PlasmaLyte | 7.5% | 5.3% | |
| G | A ™ + 1.2% HSA | 7.5% | 5.3% | 250 mM |

*Additional HSA in addition to PlasmaLyte.

In some embodiments, the pharmaceutical composition comprises hypoimmunogenic cells described herein and a pharmaceutically acceptable carrier comprising 31.25% (v/v) Plasma-Lyte A, 31.25% (v/v) of 5% dextrose/0.45% sodium chloride, 10% dextran 40 (LMD)/5% dextrose, 20% (v/v) of 25% human serum albumin (HSA), and 7.5% (v/v) dimethylsulfoxide (DMSO).

X. Formulations and Dosage Regimens

Any therapeutically effective amount of cells described herein can be included in the pharmaceutical composition, depending on the indication being treated. Non-limiting examples of the cells include primary T cells, T cells differentiated from hypoimmunogenic induced pluripotent stem cells, and other cells differentiated from hypoimmunogenic induced pluripotent stem cells described herein. In some embodiments, the pharmaceutical composition includes at least about $1\times10^2$, $5\times10^2$, $1\times10^3$, $5\times10^3$, $1\times10^4$, $5\times10^4$, $1\times10^5$, $5\times10^5$, $1\times10^6$, $5\times10^6$, $1\times10^7$, $5\times10^7$, $1\times10^8$, $5\times10^9$, $1\times10^9$, $5\times10^9$, $1\times10^{10}$, or $5\times10^{10}$ cells. In some embodiments, the pharmaceutical composition includes up to about $1\times10^2$, $5\times10^2$, $1\times10^3$, $5\times10^3$, $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, $1\times10^{10}$, or $5\times10^{10}$ cells. In some embodiments, the pharmaceutical composition includes up to about $6.0\times10^8$ cells. In some embodiments, the pharmaceutical composition includes up to about $8.0\times10^8$ cells. In some embodiments, the pharmaceutical composition includes at least about $1\times10^2$-$5\times10^2$, $5\times10^2$-$1\times10^3$, $1\times10^3$-$5\times10^3$, $5\times10^3$-$1\times10^4$, $1\times10^4$-$5\times10^4$, $5\times10^4$-$1\times10^5$, $1\times10^5$-$5\times10^5$, $5\times10^5$-$1\times$ $10^6$, $1 \times 10^6$-$5 \times 10^6$, $5 \times 10^6$-$1 \times 10^7$, $1 \times 10^7$-$5 \times 10^7$, $5 \times 10^7$-$1 \times 10^8$, $1 \times 10^8$-$5 \times 10^8$, $5 \times 10^8$-$1 \times 10^9$, $1 \times 10^9$-$5 \times 10^9$, $5 \times 10^9$-$1 \times 10^{10}$, or $1 \times 10^{10}$-$5 \times 10^{10}$ cells. In exemplary embodiments, the pharmaceutical composition includes from about $1.0 \times 10^6$ to about $2.5 \times 10^8$ cells. In certain embodiments, the pharmaceutical composition includes from about $2.0 \times 10^6$ to about $2.0 \times 10^8$ cells, such as but not limited to, primary T cells, T cells differentiated from hypoimmunogenic induced pluripotent stem cells.

In some embodiments, the pharmaceutical composition has a volume of at least 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, or 500 ml. In exemplary embodiments, the pharmaceutical composition has a volume of up to about 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, or 500 ml. In exemplary embodiments, the pharmaceutical composition has a volume of about 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, or 500 ml. In some embodiments, the pharmaceutical composition has a volume of from about 1-50 ml, 50-100 ml, 100-150 ml, 150-200 ml, 200-250 ml, 250-300 ml, 300-350 ml, 350-400 ml, 400-450 ml, or 450-500 ml. In some embodiments, the pharmaceutical composition has a volume of from about 1-50 ml, 50-100 ml, 100-150 ml, 150-200 ml, 200-250 ml, 250-300 ml, 300-350 ml, 350-400 ml, 400-450 ml, or 450-500 ml. In some embodiments, the pharmaceutical composition has a volume of from about 1-10 ml, 10-20 ml, 20-30 ml, 30-40 ml, 40-50 ml, 50-60 ml, 60-70 ml, 70-80 ml, 70-80 ml, 80-90 ml, or 90-100 ml. In some embodiments, the pharmaceutical composition has a volume that ranges from about 5 ml to about 80 ml. In exemplary embodiments, the pharmaceutical composition has a volume that ranges from about 10 ml to about 70 ml. In certain embodiments, the pharmaceutical composition has a volume that ranges from about 10 ml to about 50 ml.

The specific amount/dosage regimen will vary depending on the weight, gender, age and health of the individual; the formulation, the biochemical nature, bioactivity, bioavailability and the side effects of the cells and the number and identity of the cells in the complete therapeutic regimen.

In some embodiments, a therapeutically effective dose or a clinically effective dose of the pharmaceutical composition includes about $1.0 \times 10^5$ to about $2.5 \times 10^8$ cells at a volume of about 10 ml to 50 ml and the pharmaceutical composition is administered as a single therapeutically effective dose or clinically effective dose. In some cases, the therapeutically effective dose or clinically effective dose includes about $1.0 \times 10^5$ to about $2.5 \times 10^8$ primary T cells described herein at a volume of about 10 ml to 50 ml. In some cases, the therapeutically effective dose or clinically effective dose includes about $1.0 \times 10^5$ to about $2.5 \times 10^8$ primary T cells that have been described above at a volume of about 10 ml to 50 ml. In various cases, the therapeutically effective dose or clinically effective dose includes about $1.0 \times 10^5$ to about $2.5 \times 10^8$ T cells differentiated from hypoimmunogenic induced pluripotent stem cells described herein at a volume of about 10 ml to 50 ml. In some embodiments, the therapeutically effective dose or clinically effective dose is $1.0 \times 10^5$, $1.1 \times 10^5$, $1.2 \times 10^5$, $1.3 \times 10^5$, $1.4 \times 10^5$, $1.5 \times 10^5$, $1.6 \times 10^5$, $1.7 \times 10^5$, $1.8 \times 10^5$, $1.9 \times 10^5$, $2.0 \times 10^5$, $2.1 \times 10^5$, $2.2 \times 10^5$, $2.3 \times 10^5$, $2.4 \times 10^5$, $2.5 \times 10^5$, $1.0 \times 10^6$, $1.1 \times 10^6$, $1.2 \times 10^6$, $1.3 \times 10^6$, $1.4 \times 10^6$, $1.5 \times 10^6$, $1.6 \times 10^6$, $1.7 \times 10^6$, $1.8 \times 10^6$, $1.9 \times 10^6$, $2.0 \times 10^6$, $2.1 \times 10^6$, $2.2 \times 10^6$, $2.3 \times 10^6$, $2.4 \times 10^6$, $2.5 \times 10^6$, $1.0 \times 10^7$, $1.1 \times 10^7$, $1.2 \times 10^7$, $1.3 \times 10^7$, $1.4 \times 10^7$, $1.5 \times 10^7$, $1.6 \times 10^7$, $1.7 \times 10^7$, $1.8 \times 10^7$, $1.9 \times 10^7$, $2.0 \times 10^7$, $2.1 \times 10^7$, $2.2 \times 10^7$, $2.3 \times 10^7$, $2.4 \times 10^7$, $2.5 \times 10^7$, $1.0 \times 10^8$, $1.1 \times 10^8$, $1.2 \times 10^8$, $1.3 \times 10^8$, $1.4 \times 10^8$, $1.5 \times 10^8$, $1.6 \times 10^8$, $1.7 \times 10^8$, $1.8 \times 10^8$, $1.9 \times 10^8$, $2.0 \times 10^8$, $2.1 \times 10^8$, $2.2 \times 10^8$, $2.3 \times 10^8$, $2.4 \times 10^8$, or $2.5 \times 10^8$ T cells differentiated from hypoimmunogenic induced pluripotent stem cells described herein at a volume of about 10 ml to 50 ml. In other cases, the therapeutically effective dose or clinically effective dose is at a range that is lower than about $1.0 \times 10^5$ to about $2.5 \times 10^8$ T cells, including primary T cells or T cells differentiated from hypoimmunogenic induced pluripotent stem cells. In yet other cases, the therapeutically effective dose or clinically effective dose is at a range that is higher than about $1.0 \times 10^5$ to about $2.5 \times 10^8$ T cells, including primary T cells and T cells differentiated from hypoimmunogenic induced pluripotent stem cells.

In some embodiments, the pharmaceutical composition is administered as a single therapeutically effective dose or clinically effective dose of from about $1.0 \times 10^5$ to about $1.0 \times 10^7$ cells (such as primary T cells and T cells differentiated from hypoimmunogenic induced pluripotent stem cells) per kg body weight for subjects 50 kg or less. In some embodiments, the pharmaceutical composition is administered as a single therapeutically effective dose or clinically effective dose of from about $0.5 \times 10^5$ to about $1.0 \times 10^7$, about $1.0 \times 10^5$ to about $1.0 \times 10^7$, about $1.0 \times 10^5$ to about $1.0 \times 10^7$, about $5.0 \times 10^5$ to about $1 \times 10^7$, about $1.0 \times 10^6$ to about $1 \times 10^7$, about $5.0 \times 10^6$ to about $1.0 \times 10^7$, about $1.0 \times 10^5$ to about $5.0 \times 10^6$, about $1.0 \times 10^5$ to about $1.0 \times 10^6$, about $1.0 \times 10^5$ to about $5.0 \times 10^5$, about $1.0 \times 10^5$ to about $5.0 \times 10^6$, about $2.0 \times 10^5$ to about $5.0 \times 10^6$, about $3.0 \times 10^5$ to about $5.0 \times 10^6$, about $4.0 \times 10^5$ to about $5.0 \times 10^6$, about $5.0 \times 10^5$ to about $5.0 \times 10^6$, about $6.0 \times 10^5$ to about $5.0 \times 10^6$, about $7.0 \times 10^5$ to about $5.0 \times 10^6$, about $8.0 \times 10^5$ to about $5.0 \times 10^6$, or about $9.0 \times 10^5$ to about $5.0 \times 10^6$ cells per kg body weight for subjects 50 kg or less. In some embodiments, the therapeutically effective dose or clinically effective dose is $0.5 \times 10^5$, $0.6 \times 10^5$, $0.7 \times 10^5$, $0.8 \times 10^5$, $0.9 \times 10^5$, $1.0 \times 10^5$, $1.1 \times 10^5$, $1.2 \times 10^5$, $1.3 \times 10^5$, $1.4 \times 10^5$, $1.5 \times 10^5$, $1.6 \times 10^5$, $1.7 \times 10^5$, $1.8 \times 10^5$, $1.9 \times 10^5$, $2.0 \times 10^5$, $2.1 \times 10^5$, $2.2 \times 10^5$, $2.3 \times 10^5$, $2.4 \times 10^5$, $2.5 \times 10^5$, $2.6 \times 10^5$, $2.7 \times 10^5$, $2.8 \times 10^5$, $2.9 \times 10^5$, $3.0 \times 10^5$, $3.1 \times 10^5$, $3.2 \times 10^5$, $3.3 \times 10^5$, $3.4 \times 10^5$, $3.5 \times 10^5$, $3.6 \times 10^5$, $3.7 \times 10^5$, $3.8 \times 10^5$, $3.9 \times 10^5$, $4.0 \times 10^5$, $4.1 \times 10^5$, $4.2 \times 10^5$, $4.3 \times 10^5$, $4.4 \times 10^5$, $4.5 \times 10^5$, $4.6 \times 10^5$, $4.7 \times 10^5$, $2.1 \times 10^5$, $4.9 \times 10^5$, $5.0 \times 10^5$, $0.5 \times 10^6$, $0.6 \times 10^6$, $0.7 \times 10^6$, $0.8 \times 10^6$, $0.9 \times 10^6$, $1.0 \times 10^6$, $1.1 \times 10^6$, $1.2 \times 10^6$, $1.3 \times 10^6$, $1.4 \times 10^6$, $1.5 \times 10^6$, $1.6 \times 10^6$, $1.7 \times 10^6$, $1.8 \times 10^6$, $1.9 \times 10^6$, $2.0 \times 10^6$, $2.1 \times 10^6$, $2.2 \times 10^6$, $2.3 \times 10^6$, $2.4 \times 10^6$, $2.5 \times 10^6$, $2.6 \times 10^6$, $2.7 \times 10^6$, $2.8 \times 10^6$, $2.9 \times 10^6$, $3.0 \times 10^6$, $3.1 \times 10^6$, $3.2 \times 10^6$, $3.3 \times 10^6$, $3.4 \times 10^6$, $3.5 \times 10^6$, $3.6 \times 10^6$, $3.7 \times 10^6$, $3.8 \times 10^6$, $3.9 \times 10^6$, $4.0 \times 10^6$, $4.1 \times 10^6$, $4.2 \times 10^6$, $4.3 \times 10^6$, $4.4 \times 10^6$, $4.5 \times 10^6$, $4.6 \times 10^6$, $4.7 \times 10^6$, $4.8 \times 10^6$, $4.9 \times 10^6$, $5.0 \times 10^6$, $5.1 \times 10^6$, $5.2 \times 10^6$, $5.3 \times 10^6$, $5.4 \times 10^6$, $5.5 \times 10^6$, $5.6 \times 10^6$, $5.7 \times 10^6$, $5.8 \times 10^6$, $5.9 \times 10^6$, $6.0 \times 10^6$, $6.1 \times 10^6$, $6.2 \times 10^6$, $6.3 \times 10^6$, $6.4 \times 10^6$, $6.5 \times 10^6$, $6.6 \times 10^6$, $6.7 \times 10^6$, $6.8 \times 10^6$, $6.9 \times 10^6$, $7.0 \times 10^6$, $7.1 \times 10^6$, $7.2 \times 10^6$, $7.3 \times 10^6$, $7.4 \times 10^6$, $7.5 \times 10^6$, $7.6 \times 10^6$, $7.7 \times 10^6$, $7.8 \times 10^6$, $7.9 \times 10^6$, $8.0 \times 10^6$, $8.1 \times 10^6$, $8.2 \times 10^6$, $8.3 \times 10^6$, $8.4 \times 10^6$, $8.5 \times 10^6$, $8.6 \times 10^6$, $8.7 \times 10^6$, $8.8 \times 10^6$, $8.9 \times 10^6$, $9.0 \times 10^6$, $9.1 \times 10^6$, $9.2 \times 10^6$, $9.3 \times 10^6$, $9.4 \times 10^6$, $9.5 \times 10^6$, $9.6 \times 10^6$, $9.7 \times 10^6$, $9.8 \times 10^6$, $9.9 \times 10^6$, $0.5 \times 10^7$, $0.6 \times 10^7$, $0.7 \times 10^7$, $0.8 \times 10^7$, $0.9 \times 10^7$, or $1.0 \times 10^7$ cells per kg body weight for subjects 50 kg or less. In some embodiments, the therapeutically effective dose or clinically effective dose is from about $0.2 \times 10^6$ to about $5.0 \times 10^6$ cells per kg body weight for subjects 50 kg or less. In certain embodiments, the therapeutically effective dose or clinically effective dose is at a range that is lower than from about $0.2 \times 10^6$ to about $5.0 \times 10^6$ cells per kg body weight for subjects 50 kg or less. or clinically effective dose In exemplary embodiments, the single therapeutically effective dose or clinically effective dose is at a volume of about 10 ml to 50 ml. In some embodiments, the therapeutically effective dose or clinically effective dose is administered intravenously.

In exemplary embodiments, the cells are administered in a single therapeutically effective dose of from about $1.0 \times 10^6$ to about $5.0 \times 10^8$ cells (such as primary T cells and T cells differentiated from hypoimmunogenic induced pluripotent stem cells) for subjects above 50 kg. In some embodiments, the pharmaceutical composition is administered as a single therapeutically effective dose or clinically effective dose of from about $0.5 \times 10^6$ to about $1.0 \times 10^9$, about $1.0 \times 10^6$ to about $1.0 \times 10^9$, about $1.0 \times 10^6$ to about $1.0 \times 10^9$, about $5.0 \times 10^6$ to about $1.0 \times 10^9$, about $1.0 \times 10^7$ to about $1.0 \times 10^9$, about $5.0 \times 10^7$ to about $1.0 \times 10^9$, about $1.0 \times 10^6$ to about $5.0 \times 10^7$, about $1.0 \times 10^6$ to about $1.0 \times 10^7$, about $1.0 \times 10^6$ to about $5.0 \times 10^7$, about $1.0 \times 10^7$ to about $5.0 \times 10^8$, about $2.0 \times 10^7$ to about $5.0 \times 10^8$, about $3.0 \times 10^7$ to about $5.0 \times 10^8$, about $4.0 \times 10^7$ to about $5.0 \times 10^8$, about $5.0 \times 10^7$ to about $5.0 \times 10^8$, about $6.0 \times 10^7$ to about $5.0 \times 10^8$, about $7.0 \times 10^7$ to about $5.0 \times 10^8$, about $8.0 \times 10^7$ to about $5.0 \times 10^{'}$, or about $9.0 \times 10^7$ to about $5.0 \times 10^8$ cells per kg body weight for subjects 50 kg or less. In some embodiments, the therapeutically effective dose or clinically effective dose is $1.0 \times 10^6$, $1.1 \times 10^6$, $1.2 \times 10^6$, $1.3 \times 10^6$, $1.4 \times 10^6$, $1.5 \times 10^6$, $1.6 \times 10^6$, $1.7 \times 10^6$, $1.8 \times 10^6$, $1.9 \times 10^6$, $2.0 \times 10^6$, $2.1 \times 10^6$, $2.2 \times 10^6$, $2.3 \times 10^6$, $2.4 \times 10^6$, $2.5 \times 10^6$, $2.6 \times 10^6$, $2.7 \times 10^6$, $2.8 \times 10^6$, $2.9 \times 10^6$, $3.0 \times 10^6$, $3.1 \times 10^6$, $3.2 \times 10^6$, $3.3 \times 10^6$, $3.4 \times 10^6$, $3.5 \times 10^6$, $3.6 \times 10^6$, $3.7 \times 10^6$, $3.8 \times 10^6$, $3.9 \times 10^6$, $4.0 \times 10^6$, $4.1 \times 10^6$, $4.2 \times 10^6$, $4.3 \times 10^6$, $4.4 \times 10^6$, $4.5 \times 10^6$, $4.6 \times 10^6$, $4.7 \times 10^6$, $4.8 \times 10^6$, $4.9 \times 10^6$, $5.0 \times 10^6$, $5.1 \times 10^6$, $5.2 \times 10^6$, $5.3 \times 10^6$, $5.4 \times 10^6$, $5.5 \times 10^6$, $5.6 \times 10^6$, $5.7 \times 10^6$, $5.8 \times 10^6$, $5.9 \times 10^6$, $6.0 \times 10^6$, $6.1 \times 10^6$, $6.2 \times 10^6$, $6.3 \times 10^6$, $6.4 \times 10^6$, $6.5 \times 10^6$, $6.6 \times 10^6$, $6.7 \times 10^6$, $6.8 \times 10^6$, $6.9 \times 10^6$, $7.0 \times 10^6$, $7.1 \times 10^6$, $7.2 \times 10^6$, $7.3 \times 10^6$, $7.4 \times 10^6$, $7.5 \times 10^6$, $7.6 \times 10^6$, $7.7 \times 10^6$, $7.8 \times 10^6$, $7.9 \times 10^6$, $8.0 \times 10^6$, $8.1 \times 10^6$, $8.2 \times 10^6$, $8.3 \times 10^6$, $8.4 \times 10^6$, $8.5 \times 10^6$, $8.6 \times 10^6$, $8.7 \times 10^6$, $8.8 \times 10^6$, $8.9 \times 10^6$, $9.0 \times 10^6$, $9.1 \times 10^6$, $9.2 \times 10^6$, $9.3 \times 10^6$, $9.4 \times 10^6$, $9.5 \times 10^6$, $9.6 \times 10^6$, $9.7 \times 10^6$, $9.8 \times 10^6$, $9.9 \times 10^6$, $1.0 \times 10^7$, $1.1 \times 10^7$, $1.2 \times 10^7$, $1.3 \times 10^7$, $1.4 \times 10^7$, $1.5 \times 10^7$, $1.6 \times 10^7$, $1.7 \times 10^7$, $1.8 \times 10^7$, $1.9 \times 10^7$, $2.0 \times 10^7$, $2.1 \times 10^7$, $2.2 \times 10^7$, $2.3 \times 10^7$, $2.4 \times 10^7$, $2.5 \times 10^7$, $2.6 \times 10^7$, $2.7 \times 10^7$, $2.8 \times 10^7$, $2.9 \times 10^7$, $3.0 \times 10^7$, $3.1 \times 10^7$, $3.2 \times 10^7$, $3.3 \times 10^7$, $3.4 \times 10^7$, $3.5 \times 10^7$, $3.6 \times 10^7$, $3.7 \times 10^7$, $3.8 \times 10^7$, $3.9 \times 10^7$, $4.0 \times 10^7$, $4.1 \times 10^7$, $4.2 \times 10^7$, $4.3 \times 10^7$, $4.4 \times 10^7$, $4.5 \times 10^7$, $4.6 \times 10^7$, $4.7 \times 10^7$, $4.8 \times 10^7$, $4.9 \times 10^7$, $5.0 \times 10^7$, $5.1 \times 10^7$, $5.2 \times 10^7$, $5.3 \times 10^7$, $5.4 \times 10^7$, $5.5 \times 10^7$, $5.6 \times 10^7$, $5.7 \times 10^7$, $5.8 \times 10^7$, $5.9 \times 10^7$, $6.0 \times 10^7$, $6.1 \times 10^7$, $6.2 \times 10^7$, $6.3 \times 10^7$, $6.4 \times 10^7$, $6.5 \times 10^7$, $6.6 \times 10^7$, $6.7 \times 10^7$, $6.8 \times 10^7$, $6.9 \times 10^7$, $7.0 \times 10^7$, $7.1 \times 10^7$, $7.2 \times 10^7$, $7.3 \times 10^7$, $7.4 \times 10^7$, $7.5 \times 10^7$, $7.6 \times 10^7$, $7.7 \times 10^7$, $7.8 \times 10^7$, $7.9 \times 10^7$, $8.0 \times 10^7$, $8.1 \times 10^7$, $8.2 \times 10^7$, $8.3 \times 10^7$, $8.4 \times 10^7$, $8.5 \times 10^7$, $8.6 \times 10^7$, $8.7 \times 10^7$, $8.8 \times 10^7$, $8.9 \times 10^7$, $9.0 \times 10^7$, $9.1 \times 10^7$, $9.2 \times 10^7$, $9.3 \times 10^7$, $9.4 \times 10^7$, $9.5 \times 10^7$, $9.6 \times 10^7$, $9.7 \times 10^7$, $9.8 \times 10^7$, $9.9 \times 10^7$, $1.0 \times 10^8$, $1.1 \times 10^8$, $1.2 \times 10^8$, $1.3 \times 10^8$, $1.4 \times 10^8$, $1.5 \times 10^8$, $1.6 \times 10^8$, $1.7 \times 10^8$, $1.8 \times 10^8$, $1.9 \times 10^8$, $2.0 \times 10^8$, $2.1 \times 10^{'}$, $2.2 \times 10^{'}$, $2.3 \times 10^{'}$, $2.4 \times 10^{'}$, $2.5 \times 10^{'}$, $2.6 \times 10^{'}$, $2.7 \times 10^{'}$, $2.8 \times 10^{'}$, $2.9 \times 10^{'}$, $3.0 \times 10^{'}$, $3.1 \times 10^8$, $3.2 \times 10^8$, $3.3 \times 10^8$, $3.4 \times 10^8$, $3.5 \times 10^8$, $3.6 \times 10^8$, $3.7 \times 10^8$, $3.8 \times 10^8$, $3.9 \times 10^8$, $4.0 \times 10^8$, $4.1 \times 10^8$, $4.2 \times 10^8$, $4.3 \times 10^8$, $4.4 \times 10^8$, $4.5 \times 10^8$, $4.6 \times 10^8$, $4.7 \times 10^8$, $4.8 \times 10^8$, $4.9 \times 10^8$, or $5.0 \times 10^8$ cells per kg body weight for subjects 50 kg or less. In certain embodiments, the cells are administered in a single therapeutically effective dose or clinically effective dose of about $1.0 \times 10^7$ to about $2.5 \times 10^8$ cells for subjects above 50 kg. In some embodiments, the cells are administered in a single therapeutically effective dose or clinically effective dose of a range that is less than about $1.0 \times 10^7$ to about $2.5 \times 10^8$ cells for subjects above 50 kg. In some embodiments, the cells are administered in a single therapeutically effective dose or clinically effective dose of a range that is higher than about $1.0 \times 10^7$ to about $2.5 \times 10^8$ cells for subjects above 50 kg. In some embodiments, the dose is administered intravenously. In exemplary embodiments, the single therapeutically effective dose or clinically effective dose is at a volume of about 10 ml to 50 ml. In some embodiments, the therapeutically effective dose or clinically effective dose is administered intravenously.

In exemplary embodiments, the therapeutically effective dose or clinically effective dose is administered intravenously at a rate of about 1 to 50 ml per minute, 1 to 40 ml per minute, 1 to 30 ml per minute, 1 to 20 ml per minute, 10 to 20 ml per minute, 10 to 30 ml per minute, 10 to 40 ml per minute, 10 to 50 ml per minute, 20 to 50 ml per minute, 30 to 50 ml per minute, 40 to 50 ml per minute. In numerous embodiments, the pharmaceutical composition is stored in one or more infusion bags for intravenous administration. In some embodiments, the dose is administered completely at no more than 10 minutes, 15 minutes, 20 minutes, 25 minutes, 30 minutes, 35 minutes, 40 minutes, 45 minutes, 50 minutes, 55 minutes, 60 minutes, 70 minutes, 80 minutes, 90 minutes, 120 minutes, 150 minutes, 180 minutes, 240 minutes, or 300 minutes.

In some embodiments, a single therapeutically effective dose or clinically effective dose of the pharmaceutical composition is present in a single infusion bag. In other embodiments, a single therapeutically effective dose or clinically effective dose of the pharmaceutical composition is divided into 2, 3, 4 or 5 separate infusion bags.

In some embodiments, the cells described herein are administered in a plurality of doses such as 2, 3, 4, 5, 6 or more doses, wherein the plurality of doses together constitute a therapeutically effective dose or clinically effective dose regimen. In some embodiments, each dose of the plurality of doses is administered to the subject ranging from 1 to 24 hours apart. In some instances, a subsequent dose is administered from about 1 hour to about 24 hours (e.g., about 1, 2, 3, 4, 5, 6, 7, 8, 9, 10, 11, 12, 13, 14, 15, 16, 17, 18, 19, 20, 21, 22, 23 or about 24 hours) after an initial or preceding dose. In some embodiments, each dose of the plurality of doses is administered to the subject ranging from about 1 day to 28 days apart. In some instances, a subsequent dose is administered from about 1 day to about 28 days (e.g., about 1, 2, 3, 4, 5, 6, 7, 8, 9, 10, 11, 12, 13, 14, 15, 16, 17, 18, 19, 20, 21, 22, 23, 24, 25, 26, 27, or about 28 days) after an initial or preceding dose. In certain embodiments, each dose of the plurality of doses is administered to the subject ranging from 1 week to about 6 weeks apart. In certain instances, a subsequent dose is administered from about 1 week to about 6 weeks (e.g., about 1, 2, 3, 4, 5, or 6 weeks) after an initial or preceding dose. In several embodiments, each dose of the plurality of doses is administered to the subject ranging from about 1 month to about 12 months apart. In several instances, a subsequent dose is administered from about 1 month to about 12 months (e.g., about 1, 2, 3, 4, 5, 6, 7, 8, 9, 10, 11, or 12 months) after an initial or preceding dose.

In some embodiments, a subject is administered a first dosage regimen at a first timepoint, and then subsequently administered a second dosage regimen at a second timepoint. In some embodiments, the first dosage regimen is the same as the second dosage regimen. In other embodiments, the first dosage regimen is different than the second dosage regimen. In some instances, the number of cells in the first dosage regimen and the second dosage regimen are the same. In some instances, the number of cells in the first dosage regimen and the second dosage regimen are different. In some cases, the number of doses of the first dosage regimen and the second dosage regimen are the same. In some cases, the number of doses of the first dosage regimen and the second dosage regimen are different.

In some embodiments, the first dosage regimen includes hypoimmune (HIP) T cells or primary T cells expressing a first CAR and the second dosage regimen includes hypoimmune (HIP) T cells or primary T cells expressing a second CAR such that the first CAR and the second CAR are different. For instance, the first CAR and second CAR bind different target antigens. In some cases, the first CAR includes an scFv that binds an antigen and the second CAR includes an scFv that binds a different antigen. In some embodiments, the first dosage regimen includes hypoimmune (HIP) T cell or primary T cells expressing a first CAR and the second dosage regimen includes hypoimmune (HIP) T cell or primary T cells expressing a second CAR such that the first CAR and the second CAR are the same. The first dosage regimen can be administered to the subject at least 1 month, 2 months, 3 months, 4 months, 5 months, 6 months, 7 months, 8 months, 9 months, 10 months, 11 months, 12 months, 1-3 months, 1-6 months, 4-6 months, 3-9 months, 3-12 months, or more months apart from the second dosage regimen. In some embodiments, a subject is administered a plurality of dosage regimens during the course of a disease (e.g., cancer) and at least two of the dosage regimens comprise the same type of hypoimmune (HIP) T cells or primary T cells described herein. In other embodiments, at least two of the plurality of dosage regimens comprise different types of hypoimmune (HIP) T cells or primary T cells described herein.

In some embodiments, the CD19 specific (CD19) CAR-T cells described herein are administered to a subject at a dose of about $50 \times 10^6$ to about $110 \times 10^6$ (e.g., $50 \times 10^6$, $51 \times 10^6$, $52 \times 10^6$, $53 \times 10^6$, $54 \times 10^6$, $55 \times 10^6$, $56 \times 10^6$, $57 \times 10^6$, $58 \times 10^6$, $59 \times 10^6$, $60 \times 10^6$, $61 \times 10^6$, $62 \times 10^6$, $63 \times 10^6$, $64 \times 10^6$, $65 \times 10^6$, $66 \times 10^6$, $67 \times 10^6$, $68 \times 10^6$, $69 \times 10^6$, $70 \times 10^6$, $71 \times 10^6$, $72 \times 10^6$, $73 \times 10^6$, $74 \times 10^6$, $75 \times 10^6$, $76 \times 10^6$, $77 \times 10^6$, $78 \times 10^6$, $79 \times 10^6$, $80 \times 10^6$, $81 \times 10^6$, $82 \times 10^6$, $83 \times 10^6$, $84 \times 10^6$, $85 \times 10^6$, $86 \times 10^6$, $87 \times 10^6$, $88 \times 10^6$, $89 \times 10^6$, $90 \times 10^6$, $91 \times 10^6$, $92 \times 10^6$, $93 \times 10^6$, $94 \times 10^6$, $95 \times 10^6$, $96 \times 10^6$, $97 \times 10^6$, $98 \times 10^6$, $99 \times 10^6$, $100 \times 10^6$, $101 \times 10^6$, $102 \times 10^6$, $103 \times 10^6$, $104 \times 10^6$, $105 \times 10^6$, $106 \times 10^6$, $107 \times 10^6$, $108 \times 10^6$, $109 \times 10^6$, or $110 \times 10^6$) viable CD19 specific CAR-T cells. In some embodiments, the dose is a therapeutically effective amount of viable CD19 specific CAR-T cells. In other embodiments, the dose is a clinically effective amount of viable CD19 specific CAR-T cells. In some embodiments, the viable CD19 specific CAR-T cells include CD19 specific CAR expressing CD4+ T cells and CD19 specific CAR expressing CD8+ T cells at a ratio of about 1:1. In some embodiments, the CD19 specific CAR of the cells is lisocabtagene maraleucel (BREYANZI®), a structural equivalent thereof, or a functional equivalent thereof.

In some embodiments, a subject is administered about $50 \times 10^6$ to about $110 \times 10^6$ (e.g., $50 \times 10^6$, $51 \times 10^6$, $52 \times 10^6$, $53 \times 10^6$, $54 \times 10^6$, $55 \times 10^6$, $56 \times 10^6$, $57 \times 10^6$, $58 \times 10^6$, $59 \times 10^6$, $60 \times 10^6$, $61 \times 10^6$, $62 \times 10^6$, $63 \times 10^6$, $64 \times 10^6$, $65 \times 10^6$, $66 \times 10^6$, $67 \times 10^6$, $68 \times 10^6$, $69 \times 10^6$, $70 \times 10^6$, $71 \times 10^6$, $72 \times 10^6$, $73 \times 10^6$, $74 \times 10^6$, $75 \times 10^6$, $76 \times 10^6$, $77 \times 10^6$, $78 \times 10^6$, $79 \times 10^6$, $80 \times 10^6$, $81 \times 10^6$, $82 \times 10^6$, $83 \times 10^6$, $84 \times 10^6$, $85 \times 10^6$, $86 \times 10^6$, $87 \times 10^6$, $88 \times 10^6$, $89 \times 10^6$, $90 \times 10^6$, $91 \times 10^6$, $92 \times 10^6$, $93 \times 10^6$, $94 \times 10^6$, $95 \times 10^6$, $96 \times 10^6$, $97 \times 10^6$, $98 \times 10^6$, $99 \times 10^6$, $100 \times 10^6$, $101 \times 10^6$, $102 \times 10^6$, $103 \times 10^6$, $104 \times 10^6$, $105 \times 10^6$, $106 \times 10^6$, $107 \times 10^6$, $108 \times 10^6$, $109 \times 10^6$, or $110 \times 10^6$) viable CD19 specific CAR-T cells described herein. In some embodiments, the dose is a therapeutically effective amount of viable CD19 specific CAR-T cells. In other embodiments, the dose is a clinically effective amount of viable CD19 specific CAR-T cells. In some instances, 50% of the viable CD19 specific CAR-T cells are CD19 specific CAR expressing CD4+ T cells and 50% of the viable CD19 specific CAR-T cells are CD19 specific CAR expressing CD8+ T cells. In some embodiments, the CD19 specific CAR of the cells is lisocabtagene maraleucel (BREYANZI®), a structural equivalent thereof, or a functional equivalent thereof.

In some embodiments, the CD19 specific CAR-T cells described herein are administered to a subject at a dose of about $2 \times 10^6$ per kg of body weight. In some embodiments, a maximum dose administered is about $2 \times 10^8$ viable CD19 specific CAR-T cells. In some embodiments, the dose is a therapeutically effective amount of viable CD19 specific CAR-T cells. In other embodiments, the dose is a clinically effective amount of viable CD19 specific CAR-T cells. In some embodiments, the CD19 specific CAR of the cells is the same CD19 specific CAR as axicabtagene ciloleucel (YESCARTA®), a structural equivalent thereof, or a functional equivalent thereof.

In some embodiments, the CD19 specific CAR-T cells described herein are administered to a subject at a dose of about $2 \times 10^6$ per kg of body weight. In some embodiments, a maximum dose of about $2 \times 10^8$ viable CD19 specific CAR-T cells is administered to a patient of about 100 kg of body weight and above. In some embodiments, the dose is a therapeutically effective amount of viable CD19 specific CAR-T cells. In other embodiments, the dose is a clinically effective amount of viable CD19 specific CAR-T cells. In some embodiments, the CD19 specific CAR of the cells is the same CD19 specific CAR as brexucabtagene autoleucel (TECARTUS®), a structural equivalent thereof, or a functional equivalent thereof.

In some embodiments, the CD19 specific CAR-T cells described herein are administered to a subject at a dose of up to about $2 \times 10^8$ viable CD19 specific CAR-T cells. In some embodiments, a subject is administered from about $0.2 \times 10^6$ to about $5.0 \times 10^6$ (e.g., about $0.2 \times 10^6$, $0.4 \times 10^6$, $0.5 \times 10^6$, $0.6 \times 10^6$, $0.8 \times 10^6$, $0.9 \times 10^6$, $1.0 \times 10^6$, $1.2 \times 10^6$, $1.4 \times 10^6$, $1.5 \times 10^6$, $1.6 \times 10^6$, $1.8 \times 10^6$, $1.9 \times 10^6$, $2.0 \times 10^6$, $2.2 \times 10^6$, $2.4 \times 10^6$, $2.5 \times 10^6$, $2.6 \times 10^6$, $2.8 \times 10^6$, $2.9 \times 10^6$, $3.0 \times 10^6$, $3.2 \times 10^6$, $3.4 \times 10^6$, $3.5 \times 10^6$, $3.6 \times 10^6$, $3.8 \times 10^6$, $3.9 \times 10^6$, $4.0 \times 10^6$, $4.2 \times 10^6$, $4.4 \times 10^6$, $4.5 \times 10^6$, $4.6 \times 10^6$, $4.8 \times 10^6$, $4.9 \times 10^6$, or $5.0 \times 10^6$) viable CD19 specific CAR-T cells per kg of body weight for a subject with a body weight of about 50 kg or less. In some embodiments, a subject is administered from about $0.1 \times 10^8$ to about $2.5 \times 10^8$ (e.g., about $0.1 \times 10^6$, $0.2 \times 10^6$, $0.4 \times 10^6$, $0.5 \times 10^6$, $0.6 \times 10^6$, $0.8 \times 10^6$, $0.9 \times 10^6$, $1.0 \times 10^6$, $1.2 \times 10^6$, $1.4 \times 10^6$, $1.5 \times 10^6$, $1.6 \times 10^6$, $1.8 \times 10^6$, $1.9 \times 10^6$, $2.0 \times 10^6$, $2.2 \times 10^6$, $2.4 \times 10^6$, or $2.5 \times 10^6$) viable CD19 specific CAR-T cells for a subject with a body weight of greater than about 50 kg. In some embodiments, a subject is administered from about $0.6 \times 10^8$ to about $6.0 \times 10^8$ (e.g., about $0.6 \times 10^8$, $0.8 \times 10^8$, $0.9 \times 10^8$, $1.0 \times 10^8$, $1.2 \times 10^8$, $1.4 \times 10^8$, $1.5 \times 10^8$, $1.6 \times 10^8$, $1.8 \times 10^8$, $1.9 \times 10^8$, $2.0 \times 10^8$, $2.2 \times 10^8$, $2.4 \times 10^8$, $2.5 \times 10^8$, $2.6 \times 10^8$, $2.8 \times 10^8$, $2.9 \times 10^{81}$, $3.0 \times 10^8$, $3.2 \times 10^8$, $3.4 \times 10^8$, $3.5 \times 10^8$, $3.6 \times 10^8$, $3.8 \times 10^8$, $3.9 \times 10^8$, $4.0 \times 10^8$, $4.2 \times 10^8$, $4.4 \times 10^8$, $4.5 \times 10^8$, $4.6 \times 10^8$, $4.8 \times 10^8$, $4.9 \times 10^8$, $5.0 \times 10^8$, $5.2 \times 10^8$, $5.4 \times 10^8$, $5.5 \times 10^8$, $5.6 \times 10^8$, $5.8 \times 10^8$, $5.9 \times 10^8$, or $6.0 \times 10^8$) viable CD19 specific CAR-T cells. In some embodiments, the dose is a therapeutically effective amount of viable CD19 specific CAR-T cells. In other embodiments, the dose is a clinically effective amount of viable CD19 specific CAR-T cells. In some embodiments, the CD19 specific CAR of the cells is the same CD19 specific CAR as tisagenlecleucel (KYMRIAH®), a structural equivalent thereof, or a functional equivalent thereof.

In some embodiments, a single dose of any of the CD19 specific CAR-T cells described herein includes about $50\times10^6$ to about $110\times10^6$ (e.g., $50\times10^6$, $51\times10^6$, $52\times10^6$, $53\times10^6$, $54\times10^6$, $55\times10^6$, $56\times10^6$, $57\times10^6$, $58\times10^6$, $59\times10^6$, $60\times10^6$, $61\times10^6$, $62\times10^6$, $63\times10^6$, $64\times10^6$, $65\times10^6$, $66\times10^6$, $67\times10^6$, $68\times10^6$, $69\times10^6$, $70\times10^6$, $71\times10^6$, $72\times10^6$, $73\times10^6$, $74\times10^6$, $75\times10^6$, $76\times10^6$, $77\times10^6$, $78\times10^6$, $79\times10^6$, $80\times10^6$, $81\times10^6$, $82\times10^6$, $83\times10^6$, $84\times10^6$, $85\times10^6$, $86\times10^6$, $87\times10^6$, $88\times10^6$, $89\times10^6$, $90\times10^6$, $91\times10^6$, $92\times10^6$, $93\times10^6$, $94\times10^6$, $95\times10^6$, $96\times10^6$, $97\times10^6$, $98\times10^6$, $99\times10^6$, $100\times10^6$, $101\times10^6$, $102\times10^6$, $103\times10^6$, $104\times10^6$, $105\times10^6$, $106\times10^6$, $107\times10^6$, $108\times10^6$, $109\times10^6$, or $110\times10^6$) viable CD19 specific CAR-T cells. In some embodiments, the dose is a therapeutically effective amount of viable CD19 specific CAR-T cells. In other embodiments, the dose is a clinically effective amount of viable CD19 specific CAR-T cells. In some embodiments, the viable CD19 specific CAR-T cells include CD19 specific CAR expressing CD4+ T cells and CD19 specific CAR expressing CD8+ T cells at a ratio of about 1:1. In some embodiments, the CD19 specific CAR is the same CD19 specific CAR as lisocabtagene maraleucel (BREYANZI®), a structural equivalent thereof, or a functional equivalent thereof.

In some embodiments, a single dose of any of the CD19 specific CAR-T cells described herein includes about $2\times10^8$ viable CD19 specific CAR-T cells. In some embodiments, a single infusion bag of any of the CD19 specific CAR-T cells described herein includes about $2\times10^8$ viable CD19 specific CAR-T cells in a cell suspension of about 68 mL. In some embodiments, the CD19 specific CAR is the same CD19 specific CAR as axicabtagene ciloleucel (YESCARTA®), a structural equivalent thereof, or a functional equivalent thereof.

In some embodiments, a single dose of any of the CD19 specific CAR-T cells described herein includes about $2\times10^8$ viable CD19 specific CAR-T cells. In some embodiments, a single infusion bag of any of the CD19 specific CAR-T cells described herein includes about $2\times10^8$ viable CD19 specific CAR-T cells in a cell suspension of about 68 mL. In some embodiments, the CD19 specific CAR is the same CD19 specific CAR as brexucabtagene autoleucel (TECARTUS®), a structural equivalent thereof, or a functional equivalent thereof.

In some embodiments, a single dose of any of the CD19 specific CAR-T cells described herein includes about $0.2\times10^6$ to about $5.0\times10^6$ (e.g., about $0.2\times10^6$, $0.3\times10^6$, $0.4\times10^6$, $0.5\times10^6$, $0.6\times10^6$, $0.7\times10^6$, $0.8\times10^6$, $0.9\times10^6$, $1.0\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$, $2.0\times10^6$, $2.1\times10^6$, $2.2\times10^6$, $2.3\times10^6$, $2.4\times10^6$, $2.5\times10^6$, $2.6\times10^6$, $2.7\times10^6$, $2.8\times10^6$, $2.9\times10^6$, $3.0\times10^6$, $3.1\times10^6$, $3.2\times10^6$, $3.3\times10^6$, $3.4\times10^6$, $3.5\times10^6$, $3.6\times10^6$, $3.7\times10^6$, $3.8\times10^6$, $3.9\times10^6$, $4.0\times10^6$, $4.1\times10^6$, $4.2\times10^6$, $4.3\times10^6$, $4.4\times10^6$, $4.5\times10^6$, $4.6\times10^6$, $4.7\times10^6$, $4.8\times10^6$, $4.9\times10^6$, or $5.0\times10^6$) viable CD19 specific CAR-T cells per kg of body weight for a subject with a body weight of 50 kg or less. In some embodiments, a single dose of any of the CD19 specific CAR-T cells described herein includes about $0.1\times10^8$ to about $2.5\times10^8$ (e.g., about $0.1\times10^6$, $0.2\times10^6$, $0.3\times10^6$, $0.4\times10^6$, $0.5\times10^6$, $0.6\times10^6$, $0.7\times10^6$, $0.8\times10^6$, $0.9\times10^6$, $1.0\times10^6$, $1.1\times10^6$, $1.2\times10^6$, $1.3\times10^6$, $1.4\times10^6$, $1.5\times10^6$, $1.6\times10^6$, $1.7\times10^6$, $1.8\times10^6$, $1.9\times10^6$, $2.0\times10^6$, $2.1\times10^6$, $2.2\times10^6$, $2.3\times10^6$, $2.4\times10^6$, or $2.5\times10^6$) viable CD19 specific CAR-T cells per kg of body weight for a subject with a body weight of more than 50 kg. In some embodiments, a single dose of any of the CD19 specific CAR-T cells described herein includes about $0.6\times10^8$ to about $6.0\times10^8$ (e.g., about $0.6\times10^8$, $0.7\times10^8$, $0.8\times10^8$, $0.9\times10^8$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.1\times10^8$, $3.2\times10^8$, $3.3\times10^8$, $3.4\times10^8$, $3.5\times10^8$, $3.6\times10^8$, $3.7\times10^8$, $3.8\times10^8$, $3.9\times10^8$, $4.0\times10^8$, $4.1\times10^8$, $4.2\times10^8$, $4.3\times10^8$, $4.4\times10^8$, $4.5\times10^8$, $4.6\times10^8$, $4.7\times10^8$, $4.8\times10^8$, $4.9\times10^8$, $5.0\times10^8$, $5.1\times10^8$, $5.2\times10^8$, $5.3\times10^8$, $5.4\times10^8$, $5.5\times10^8$, $5.6\times10^8$, $5.7\times10^8$, $5.8\times10^8$, $5.9\times10^8$, or $6.0\times10^8$) viable CD19 specific CAR-T cells. In some embodiments, a single infusion bag of any of the CD19 specific CAR-T cells described herein includes about $0.6\times10^8$ to about $6.0\times10^8$ (e.g., about $0.6\times10^8$, $0.7\times10^8$, $0.8\times10^8$, $0.9\times10^8$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.1\times10^8$, $3.2\times10^8$, $3.3\times10^8$, $3.4\times10^8$, $3.5\times10^8$, $3.6\times10^8$, $3.7\times10^8$, $3.8\times10^8$, $3.9\times10^8$, $4.0\times10^8$, $4.1\times10^8$, $4.2\times10^8$, $4.3\times10^8$, $4.4\times10^8$, $4.5\times10^8$, $4.6\times10^8$, $4.7\times10^8$, $4.8\times10^8$, $4.9\times10^8$, $5.0\times10^8$, $5.1\times10^8$, $5.2\times10^8$, $5.3\times10^8$, $5.4\times10^8$, $5.5\times10^8$, $5.6\times10^8$, $5.7\times10^8$, $5.8\times10^8$, $5.9\times10^8$, or $6.0\times10^8$) viable CD19 specific CAR-T cells in a cell suspension of from about 10 mL to about 50 mL. In some embodiments, the dose is a therapeutically effective amount of viable CD19 specific CAR-T cells. In other embodiments, the dose is a clinically effective amount of viable CD19 specific CAR-T cells. In some embodiments, the CD19 specific CAR of the cells is the same CD19 specific CAR as tisagenlecleucel (KYMRIAH®), a structural equivalent thereof, or a functional equivalent thereof.

Y. Methods for Administering Hypoimmunogenic Cells Including T Cells

As is described in further detail herein, provided herein are methods for treating a patient with a condition, disorder, or disorder through administration of hypoimmunogenic cells, particularly hypoimmunogenic T cells. As will be appreciated, for all the multiple embodiments described herein related to the timing and/or combinations of therapies, the administration of the cells is accomplished by a method or route which results in at least partial localization of the introduced cells at a desired site. The cells can be infused, implanted, or transplanted directly to the desired site, or alternatively be administered by any appropriate route which results in delivery to a desired location in the subject where at least a portion of the implanted cells or components of the cells remain viable.

Provided herein are methods for treating a patient with a condition, disorder, or disorder includes administration of a population of hypoimmunogenic cells (e.g., primary T cells, T cells differentiated from hypoimmunogenic induced pluripotent stem cells, or other cells differentiated from hypoimmunogenic induced pluripotent stem cells described herein) to a subject, e.g., a human patient. For instance, a population of hypoimmunogenic primary T cells such as, but limited to, CD3+ T cells, CD4+ T cells, CD8+ T cells, naïve T cells, regulatory T (Treg) cells, non-regulatory T cells, Th1 cells, Th2 cells, Th9 cells, Th17 cells, T-follicular helper (Tfh) cells, cytotoxic T lymphocytes (CTL), effector T (Teff) cells, central memory T (Tcm) cells, effector memory T (Tem) cells, effector memory T cells that express CD45RA (TEMRA cells), tissue-resident memory (Trm) cells, virtual memory T cells, innate memory T cells, memory stem cell (Tsc), γδ T cells, and any other subtype of T cell is administered to a patient to treat a condition, disorder, or disorder. In some embodiments, an immunosuppressive and/or immunomodulatory agent (such as, but not limited to a lymphodepletion agent) is not administered to the patient before the administration of the population of hypoimmunogenic cells. In some embodiments, an immunosuppressive and/or immunomodulatory agent is administered at least 1, 2, 3, 4, 5, 6, 7, 8, 9, 10, 11, 12, 13, 14 days or more before the administration of the cells. In some embodiments, an immunosuppressive and/or immunomodulatory agent is administered at least 1 week, 2 weeks, 3 weeks, 4 weeks, 5 weeks, 6 weeks, 7 weeks, 8 weeks, 9 weeks, 10 weeks or more before the administration of the cells. In numerous embodiments, an immunosuppressive and/or immunomodulatory agent is not administered to the patient after the administration of the cells, or is administered at least 1, 2, 3, 4, 5, 6, 7, 8, 9, 10, 11, 12, 13, 14 days or more after the administration of the cells. In some embodiments, an immunosuppressive and/or immunomodulatory agent is administered at least 1 week, 2 weeks, 3 weeks, 4 weeks, 5 weeks, 6 weeks, 7 weeks, 8 weeks, 9 weeks, 10 weeks or more after the administration of the cells. In some embodiments where an immunosuppressive and/or immunomodulatory agent is administered to the patient before or after the administration of the cells, the administration is at a lower dosage than would be required for cells with MHC I and/or MHC II expression and without exogenous expression of CD47.

Non-limiting examples of an immunosuppressive and/or immunomodulatory agent (such as, but not limited to a lymphodepletion agent) include cyclosporine, azathioprine, mycophenolic acid, mycophenolate mofetil, corticosteroids such as prednisone, methotrexate, gold salts, sulfasalazine, antimalarials, brequinar, leflunomide, mizoribine, 15-deoxyspergualine, 6-mercaptopurine, cyclophosphamide, rapamycin, tacrolimus (FK-506), OKT3, anti-thymocyte globulin, thymopentin, thymosin-α and similar agents. In some embodiments, the immunosuppressive and/or immunomodulatory agent is selected from a group of immunosuppressive antibodies consisting of antibodies binding to p75 of the IL-2 receptor, antibodies binding to, for instance, MHC, CD2, CD3, CD4, CD7, CD28, B7, CD40, CD45, IFN-gamma, TNF-alpha, IL-4, IL-5, IL-6R, IL-6, IGF, IGFR1, IL-7, IL-8, IL-10, CD11a, or CD58, and antibodies binding to any of their ligands. In some embodiments, such an immunosuppressive and/or immunomodulatory agent may be selected from soluble IL-15R, IL-10, B7 molecules (e.g., B7-1, B7-2, variants thereof, and fragments thereof), ICOS, and OX40, an inhibitor of a negative T cell regulator (such as an antibody against CTLA-4) and similar agents.

In some embodiments, where an immunosuppressive and/or immunomodulatory agent is administered to the patient before or after the administration of the cells, the administration is at a lower dosage than would be required for cells with MHC I and/or MHC II expression, TCR expression and without exogenous expression of CD47. In some embodiments, where an immunosuppressive and/or immunomodulatory agent is administered to the patient before or after the first administration of the cells, the administration is at a lower dosage than would be required for cells with MHC I and MHC II expression, TCR expression and without exogenous expression of CD47.

In some embodiments, the cells described are co-administered with a therapeutic agent that that binds to and/or interacts with one or more receptors selected from the group consisting of CD94, KIR2DL4, PD-1, an inhibitory NK cell receptor, and an activating NK receptor. In some instances, the therapeutic agent binds to a receptor on the surface of an NK cell, including one or more subpopulations of NK cells. In some embodiments, the therapeutic agent is selected from the group consisting of an antibody and fragments and variants thereof, an antibody mimetic, a small molecule, a blocking peptide, and a receptor antagonist.

For therapeutic application, cells prepared according to the disclosed methods can typically be supplied in the form of a pharmaceutical composition comprising an isotonic excipient, and are prepared under conditions that are sufficiently sterile for human administration. For general principles in medicinal formulation of cell compositions, see "Cell Therapy: Stem Cell Transplantation, Gene Therapy, and Cellular Immunotherapy," by Morstyn & Sheridan eds, Cambridge University Press, 1996; and "Hematopoietic Stem Cell Therapy," E. D. Ball, J. Lister & P. Law, Churchill Livingstone, 2000. The cells can be packaged in a device or container suitable for distribution or clinical use.

IV. EXAMPLES

Example 1: Generation of TRAC, B2M, and CIITA Triple Knockout, CD47 Transgenic CAR-T Cells (tKO/CD47 CAR-T Cells)

Described herein is an exemplary method for producing TRAC, B2M and CIITA triple knockout, CD47 transgenic CAR-T cells (HIP CD19-CAR-T cells). CD19-specific chimeric antigen receptors (CD19-CAR) were introduced in T cells using lentiviral expression technology and the TRAC, B2M and CIITA genes were inactivated using CRISPR/Cas9 technology.

Production of lentiviral vectors: HEK293LX grown in suspension cultures were transfected using standard chemical transfection complexes containing viral expression and transfer vectors harboring a control CAR or a test CAR, respectively. Cell cultures were harvested and clarified post transfection, followed by centrifugation for concentration. Lentiviral pelleted were resuspended to a final concentrate.

Culturing, transduction, and nucleofection of human pan T cells (including CD3-positive T cells): Pan T cells were thawed and activated the same day. After activation, the lentivirus concentrate was mixed with T cells in standard culture plates. In particular, T cells were mixed with media containing the lentiviral concentrate and then spinfected. Cells of the same condition were pooled at seeded on non-treated culture plates. Specifically, T cells were transduced with either (1) a control construct containing a CD47 transgene alone, (2) a control construct containing a CD19-CAR, or (3) a construct containing both a CD47 transgene and a CD19-CAR (also referred to as "CAR-CD47"). Post transduction, all transduced T cells were collected and pelleted in preparation for nucleofection of Cas9 ribonucleoproteins (RNPs) to generate TRAC, B2M, and CIITA triple knockout cells. RNPs for each target locus were complexed separately at a particular sgRNA:Cas9 ratio, followed by mixture of the three RNPs at specific amount per million cells. The RNP mixture was diluted in a solution, mixed with the cell pellet, and nucleofected under specific conditions. Nucleofected cells were seeded and cultured, and then cryopreserved post-activation in a cryopreservation media. See Table 21 for more information.

TABLE 21

Summary of Test Materials

| Cell Name | Editing |
|---|---|
| Unedited T cells | HLA$^+$ TCR$^+$ CD47wt |
| CD19-CAR-T cells | HLA$^+$ TCR$^+$ CD47wt CD19-CAR$^+$ EGFRt$^+$ |
| tKO CD19-CAR-T cells | HLA$^-$ TCR$^-$ CD47wt CD19-CAR$^+$ EGFRt |

TABLE 21-continued

Summary of Test Materials

| Cell Name | Editing |
|---|---|
| HIP CD19-CAR-T (tKO/CD47 CD19-CAR-T) | HLA⁻ TCR⁻ CD47++ CD19-CAR+ |

Abbreviations: HLA, human leukocyte antigen; TCR, T cell receptor; wt, wild-type; ⁻, negative; ++, overexpression; +, positive

Example 2: Creating Hypoimmunogenic CAR-T Cells to Evade Immune Recognition for Allogenic Therapies Off-the-shelf CAR-T cells could offer advantages over autologous strategies, including ease of manufacturing, quality control and avoidance of malignant contamination and T cell dysfunction. However, the vigorous host-versus-graft immune response against histoincompatible T cells prevents expansion and persistence of allogeneic CAR-T cells and mitigates the efficacy of this approach.

Described herein are engineered or modified human immune evasive CAR-T cells based, in part, on the hypoimmune editing platform described in WO2018132783. The inventors have taken advantage of the findings that T cells lose their immunogenicity when human leukocyte antigen (HLA) class I and II genes are inactivated and CD47 is over-expressed, and that the risk of graft-versus-host disease can be controlled via TCR knockout. Additionally, TCR knockout was performed to control the risk of graft-versus-host disease.

This example describes hypoimmunogenic CD19-specific CAR-T cells and the effect of exogenous CD47 expression on the activity of such cells compared to control CD19-specific CAR-T cells in in vitro tumor efficacy experiments. In the experiments, CD19+ tumor cells were used as the target cell and CAR-T cells such as the test and control CAR-T cells were used as the effector cell.

In the study, the test hypoimmunogenic CAR-T cells included (a) genome editing of the B2M, CIITA and TRAC genes and (b) transgenes containing a polynucleotide encoding a CD19-specific CAR and a polynucleotide encoding CD47. In some instances, the control CAR-T cell included a polynucleotide encoding a CD19-specific CAR. In certain instances, the control CAR-T cell included a T cell expressing the same CAR construct as tisagenlecleucel or a biosimilar/surrogate thereof.

When transplanted into allogeneic humanized mice, hypoimmunogenic HLA-I/II-negative, TCR-negative, CD47-positive, CD19-specific CAR-T cells evaded immune recognition by T and B cells compared to CD19-specific CAR-T cells generated from the same human donor. Innate immune cell assays showed that CD47 overexpression protects MHC-I/II deficient CAR-T cells from innate immune cell killing in vitro and in vivo. CD47 expression levels were analyzed using method for flow cytometric estimation of antibodies per cell to understand threshold levels for protection. The strategy described herein could additionally be used as a safety strategy for the hypoimmunogenic CAR-T cells.

Neither isolated CD47 overexpression nor all three hypoimmune edits or knockouts (B2M/CIITA/TRAC) showed any effect on the cytotoxic potential of CAR-T cells. Hypoimmunogenic CD19-specific CAR-T cells (e.g., B2M⁻/⁻, CIITA⁻/⁻, TRAC⁻/⁻ CD19-specific CAR-CD47 T cells) retained their antitumor activity in the CD19+ tumor model in vitro as well as in NSG mice across a range of tumor cell:CAR-T cell ratios. It does not appear that the introduction of the hypoimmune gene edits (e.g., B2M/CIITA/TRAC gene inactivation) changed their cytokine independent growth compared to immunogenic CAR-T cells. These findings show that hypoimmunogenic CD19-specific CAR-T cells are functionally immune evasive in allogeneic recipients with prolonged cytotoxic anti-tumor capacity and suggest they could provide universal immunotherapeutic options for cancer patients.

In summary, provided in this example and corresponding figures are hypoimmunogenic T cells with CD19-specific CAR activity (e.g., triple TRAC, B2M, CIITA knockout and both CD19-specific CAR and CD47 protein overexpression). Such hypoimmunogenic CAR-T cells are protected from innate immune cell killing, as demonstrated in in vitro assays. T cells exogenously expressing a construct containing the CD19-specific CAR and CD47 under the control of a single EF1α promoter (CAR-CD47 construct) showed similar activity as other comparable CD19-specific CAR-T cells, as shown in vitro and in vivo assays. Also, expression of the CAR-CD47 construct in T-lymphoblastic cell line (Mo) cells showed cytokine independent growth. The hypoimmunogenic CAR-T cells described herein were not rejected, as shown in vitro and in vivo experiments. The hypoimmunogenic CAR-T cells also showed a similar tumor killing activity to comparable immunogenic CAR-T cells in both in vitro and in vivo assays. The experimental data is provided in FIGS. 1-30.

Figure 31:
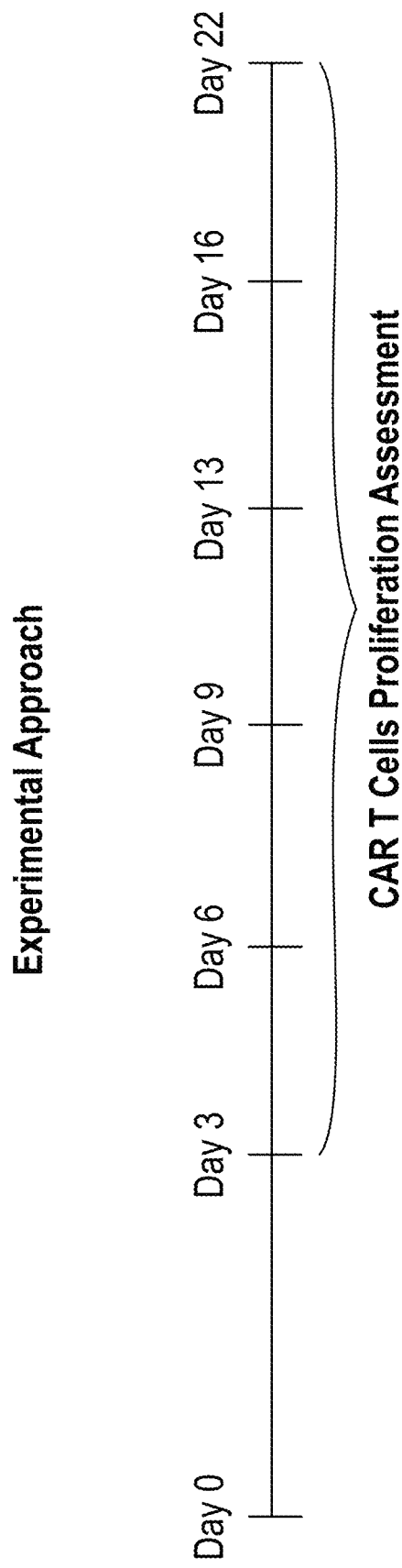
FIG. 31 provides a schematic diagram of the experimental approach of Example 3 for studying cytokine-independent proliferation of TRAC, B2M, and CIITA Triple Knockout CAR-T Cells expressing a CD47 transgene ($B2M^{-/-}$, $CIITA^{-/-}$, $TRAC^{-/-}$, CD47tg CD19-specific CAR-T cells, which are also known as tKO/CD47 CAR-T cells or as HIP CD19-CAR-T cells).

Example 3: Absence of Cytokine-Independent Proliferation of TRAC, B2M, and CIITA Triple Knockout CAR-T Cells On Day −1 the cells were resuspended in culture media supplemented with IL-2. The cells were stained with cell viability dyes to detect live and dead cells using a standard protocol known to those skilled in the art. The stained cells were then plated at a predetermined concentration and incubated at 37° C.; 5% CO2 overnight. On Day 0 the cells were cells were stained and then counted. The cells were resuspended at a pre-selected concentration in culture media without IL-2. The cells were split into two aliquots—sample #1 was supplemented with IL-2 and sample #2 was not supplemented with IL-2. The two samples were fed every three days such that sample #1 was fed with media supplemented with IL-2 and sample #2 was fed with media without IL-2 supplementation. On Day 19 both samples were cultured in media supplemented with IL-2. On Day 22 the samples were stained with cell viability dyes. The cells were counted and viability was evaluated using a standard cellometer to determine the number of live cells and dead cells. FIG. 31 provides a schematic diagram of the experimental approach.

Figure 32A:
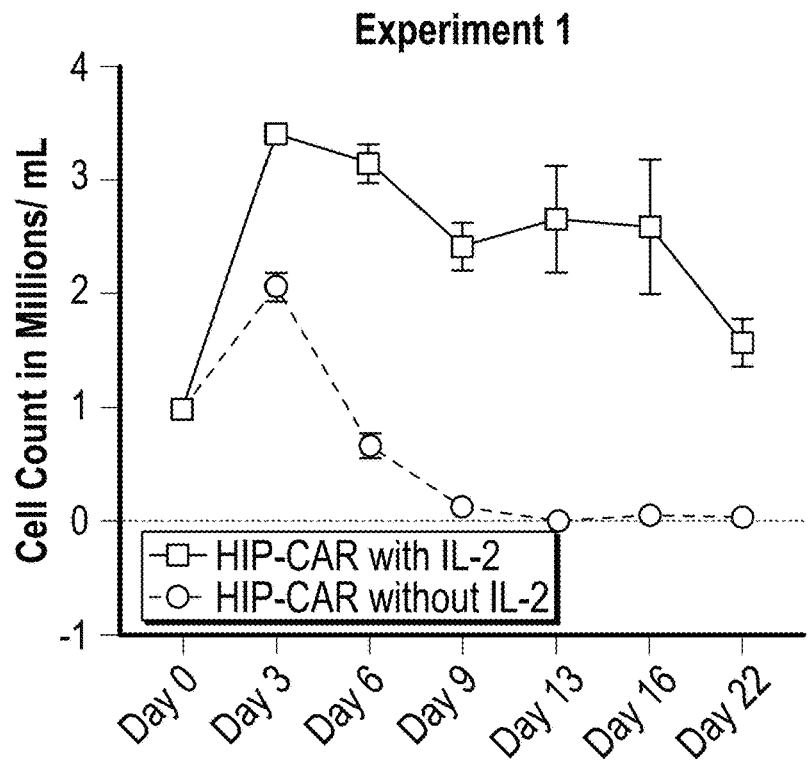
FIG. 32A and FIG. 32B depict graphs that illustrate the proliferation of the $B2M^{-/-}$, $CIITA^{-/-}$, $TRAC^{-/-}$, CD47tg CD19-specific CAR-T cells (tKO/CD47 CAR-T cells or HIP CD19-CAR-T cells) cultured either in media supplemented with IL-2 or without supplemented IL-2.
Figure 32B:
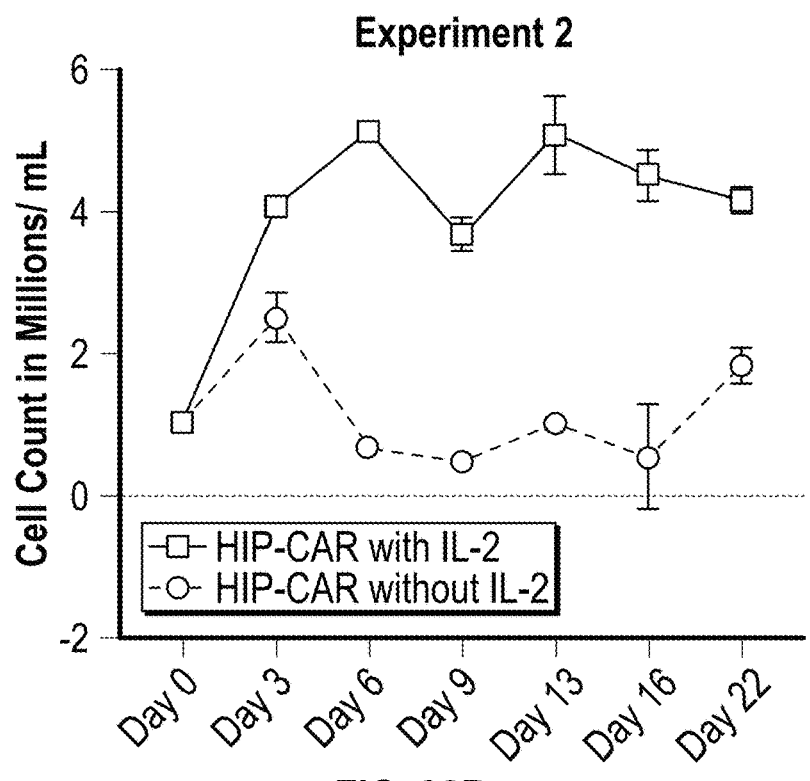

The results show that sample #1 cells (supplemented with IL-2) proliferated and sample #2 cells (not supplemented with IL-2) did not (FIG. 32A and FIG. 32B).

Figure 33:
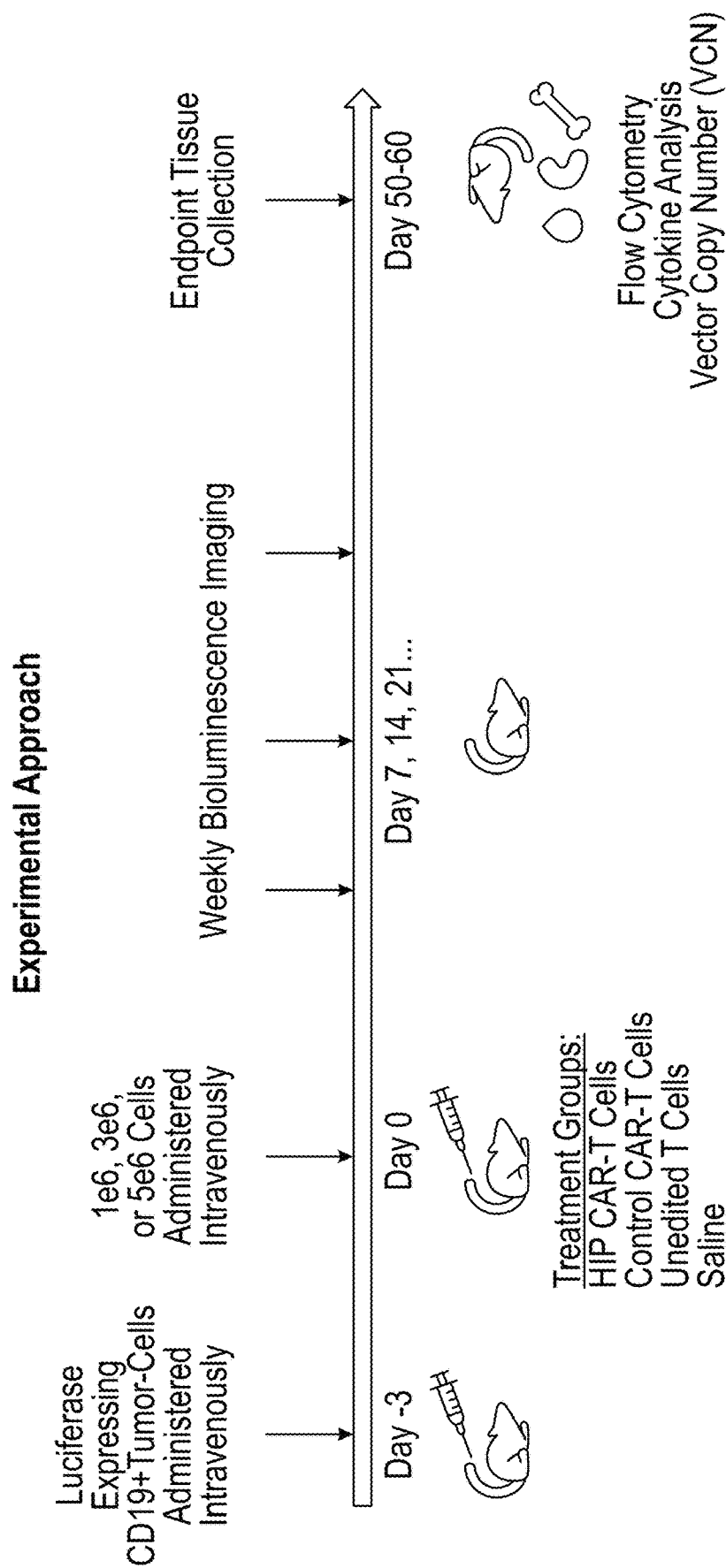
FIG. 33 provides a schematic diagram of the experimental approach of Example 4.

Example 4: tKO/CD47 CAR-T Cell Mediated Cytotoxicity of Nalm6 Tumor Cells in a Xenograft Mouse Model NSG mice xenografted with Nalm6-luc leukemia tumor cells were used for evaluating the cytotoxicity of hypoimmunogenic CAR-T cells (HLA−/TCR−/CD47tg CD19-specific CAR-T cells, also referred to as tKO/CD47 CAR-T cells or as HIP CD19-CAR-T cells) of the present disclosure against the tumor cells. The experimental approach used in the study is provided in FIG. 33.

Nalm6-luc cells were originally derived from a male acute B lymphoblastic leukemia (B-ALL) patient and have been modified to stably express luciferase and G418 resistance genes. Cells were cultured under semi-suspension culture conditions and passaged every 2-3 days. For in vivo injections, cells were collected while in log-phase of growth and washed in a standard buffer before administered to the recipient NSG mice.

tKO/CD47 CAR-T (HIP CD19-CAR-T) cells were thawed and cultured using standard T cell culture conditions. An aliquot of cells were reserved for post-thaw flow analysis of viability and CD19-specific CAR expression frequency. Viability and CAR expression was determined using flow cytometry. Dosing of the CAR-T cells was calculated based on the viability of the cells and frequency of CAR expression.

On day −3 NSG mice were intravenously (iv) injected with Nalm6-luc cells. The mice challenged with Nalm6 tumors were distributed into four treatment groups. Tumor load was determined over time in mice administered tKO/CD47 CAR-T (HIP CD19-CAR-T) cells and compared to mice administered either control CAR-T cells, unedited T cells or saline.

On day 0, a first group of mice was iv injected with tKO/CD47 CAR-T (HIP CD19-CAR-T) cells at three different doses—dose #1 of $1\times10^6$ tKO/CD47 CAR-T cells (HIP CD19-CAR-T), dose #2 of $3\times10^6$ tKO/CD47 CAR-T (HIP CD19-CAR-T) cells and dose #3 of $5\times10^6$ tKO/CD47 CAR-T (HIP CD19-CAR-T) cells. A second group of mice was iv injected with control CAR-T cells at three different doses—dose #1 of $1\times10^6$ control CAR-T cells, dose #2 of $3\times10^6$ control CAR-T cells and dose #3 of $5\times10^6$ control CAR-T cells. A third group of mice was iv injected with $5\times10^6$ unedited T cells. Finally, a fourth group of mice was iv injected with saline.

In vivo imaging to detect the tumor cells was performed weekly such as on day 7, 14, 21, 28, and the like over the course of the study. At the endpoint of the study, tissue samples from the mice will be collected and samples will undergo analysis such as but not limited, cytokine analysis and viral copy number (VCN).

Figure 34:
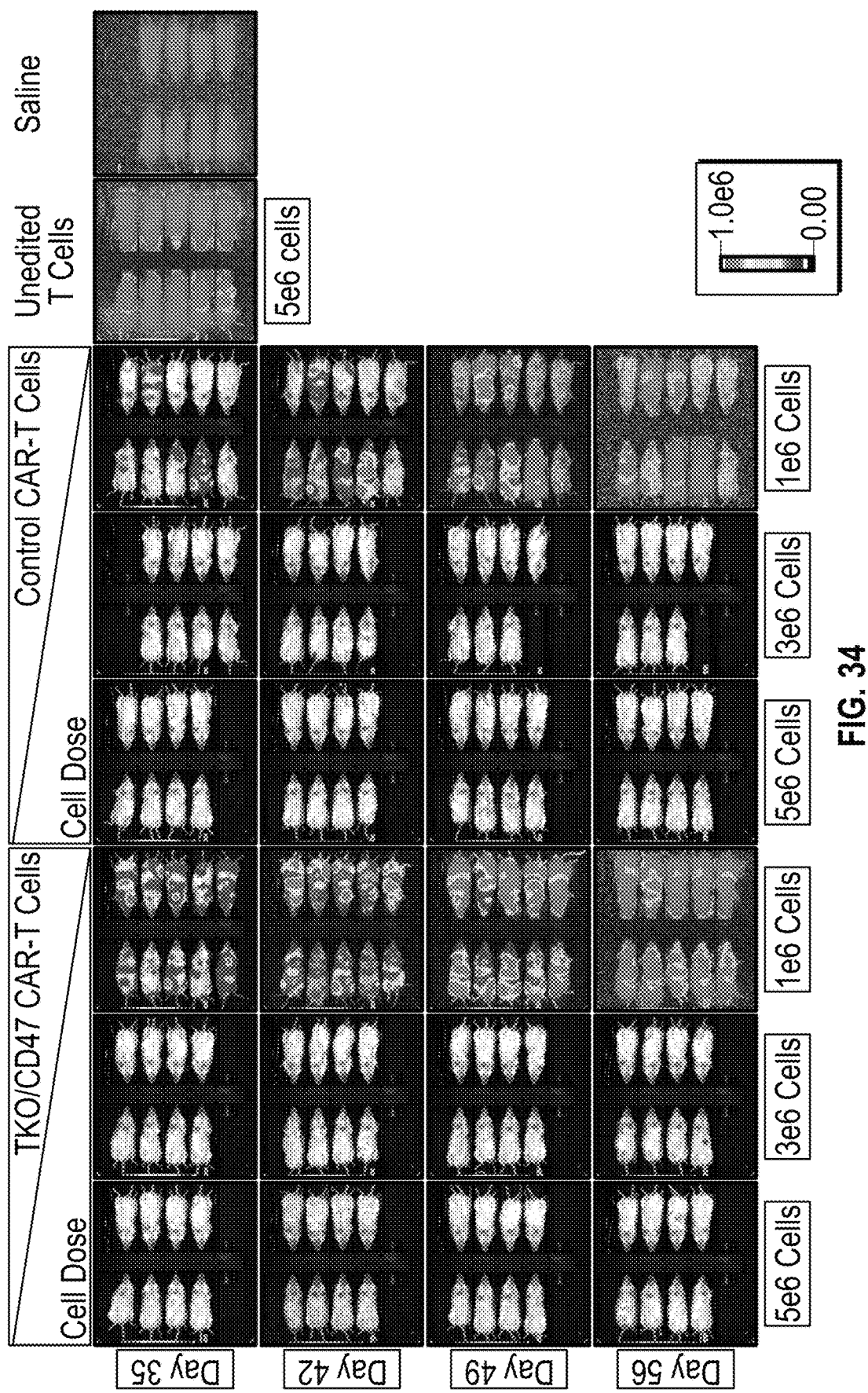
FIG. 34 shows in vivo bioluminescent images to detect Nalm6-luc tumor cells in xenografted mice. The mice were administered with either tKO/CD47 CAR-T cells (HIP CD19-CAR-T cells), control CAR-T cells (CD19-CAR-T cells), unedited T cells, or saline. The bioluminescence images show tumor progression at day 35, day 42, day 49 and day 56 of the study.
Figure 35:
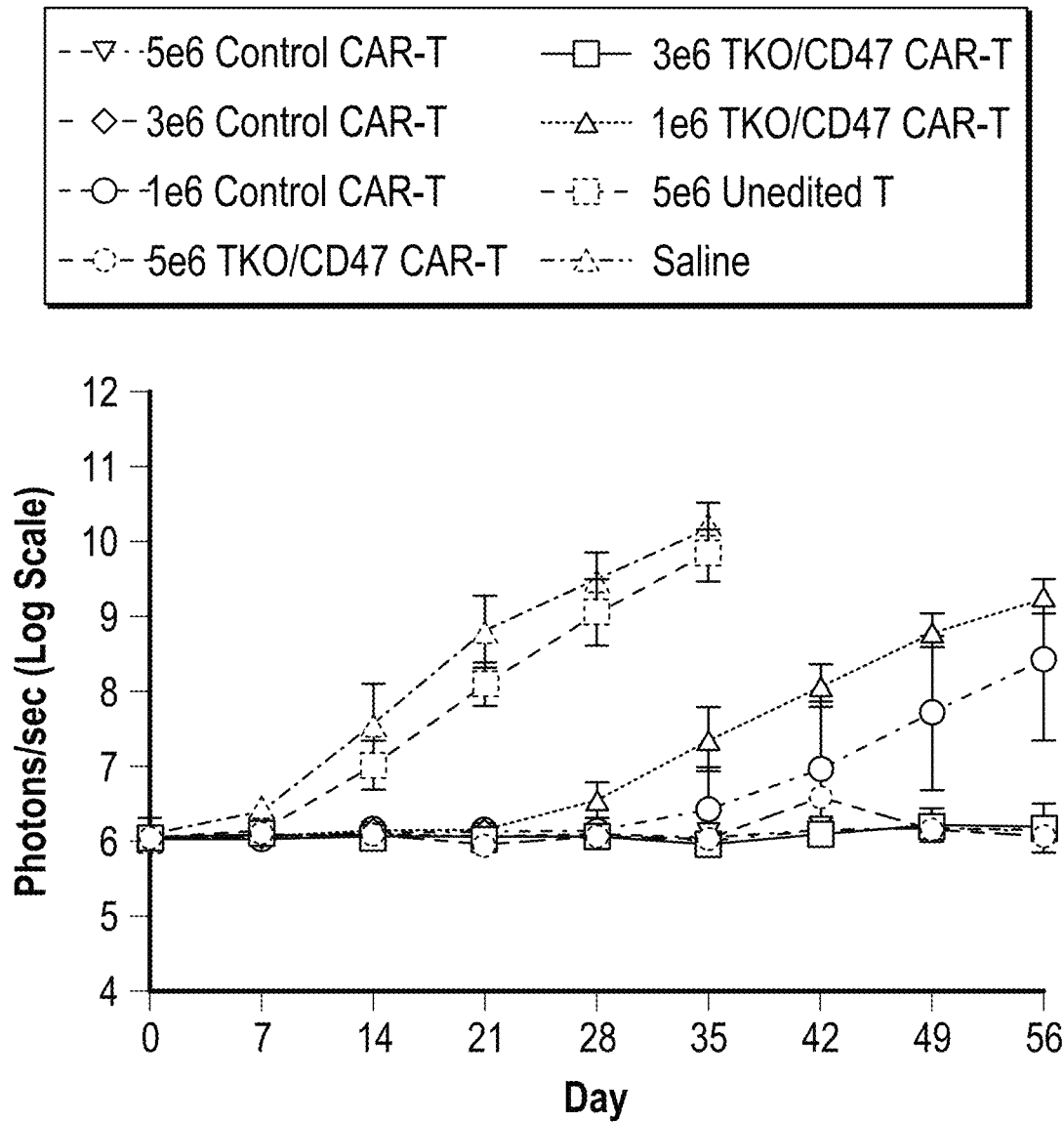
FIG. 35 provides a graph representing Nalm6-luc tumor cells detected in the xenografted mice. Images of Nalm6-luc bearing mice show delayed tumor growth in tKO/CD47 CAR-T cells (HIP CD19-CAR-T cells) treated mice when compared with control CAR-T (CD19-CAR-T) treated mice, unedited T cell-treated mice and saline-treated mice.
Figure 36:
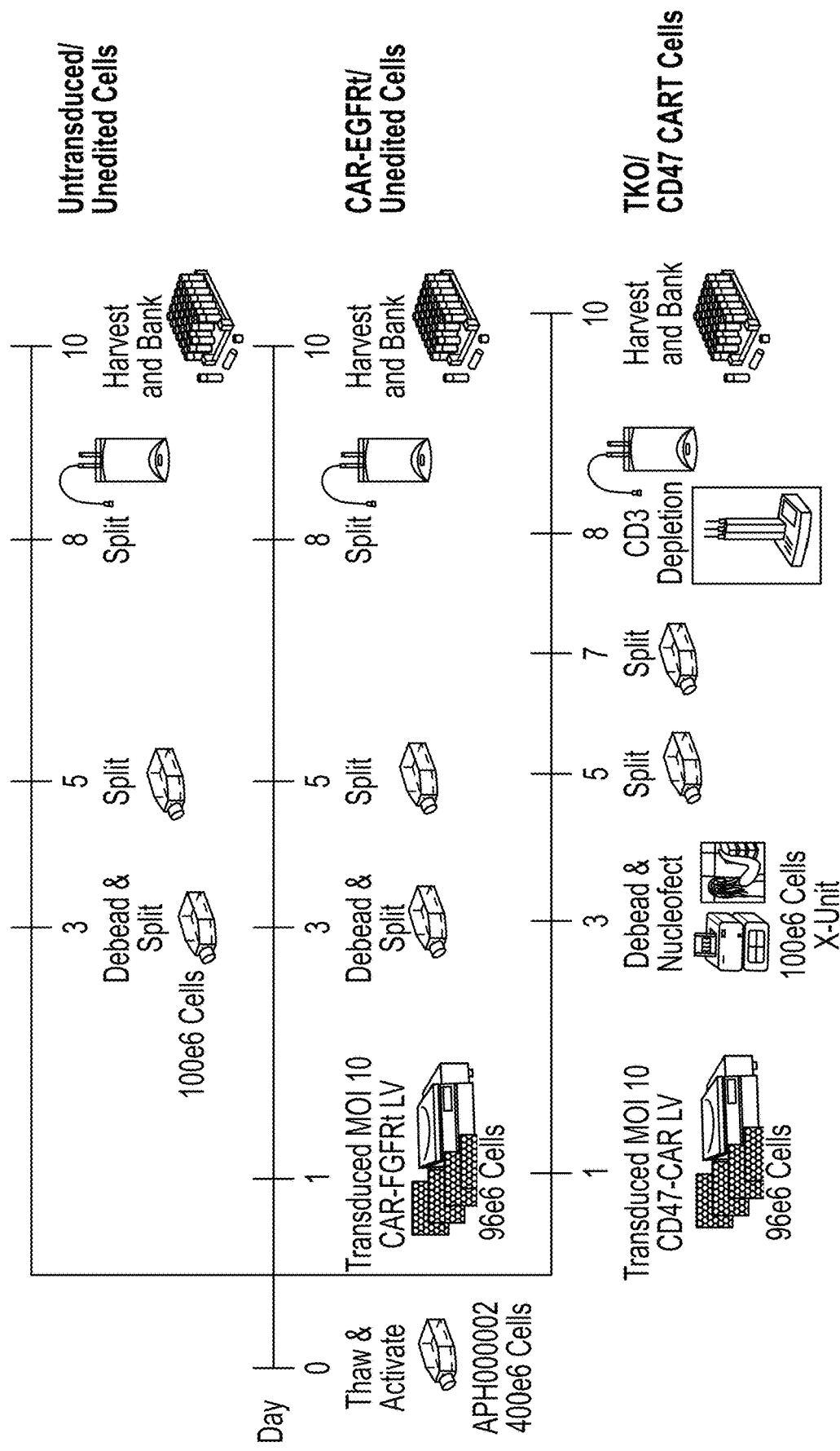
FIG. 36 shows a schematic diagram of an experimental approach for generating $B2M^{indel/indel}$, $CIITA^{indel/indel}$, $TRAC^{indel/indel}$, CD47tg T cells expressing a CD19-specific CAR, also referred to as tKO/CD47 CAR-T cells or HIP CD19-CAR-T cells. Such cells are CD47-CAR lentivirus transduced and gene edited T cells (bottom row; HIP CAR-T cells). The diagram also shows the generation of two types of control cells: untransduced and unedited cells (top row; unedited T cells) and CAR-EGFRt lentivirus transduced and unedited cells (middle row; control CAR-T cells).
Figure 37:
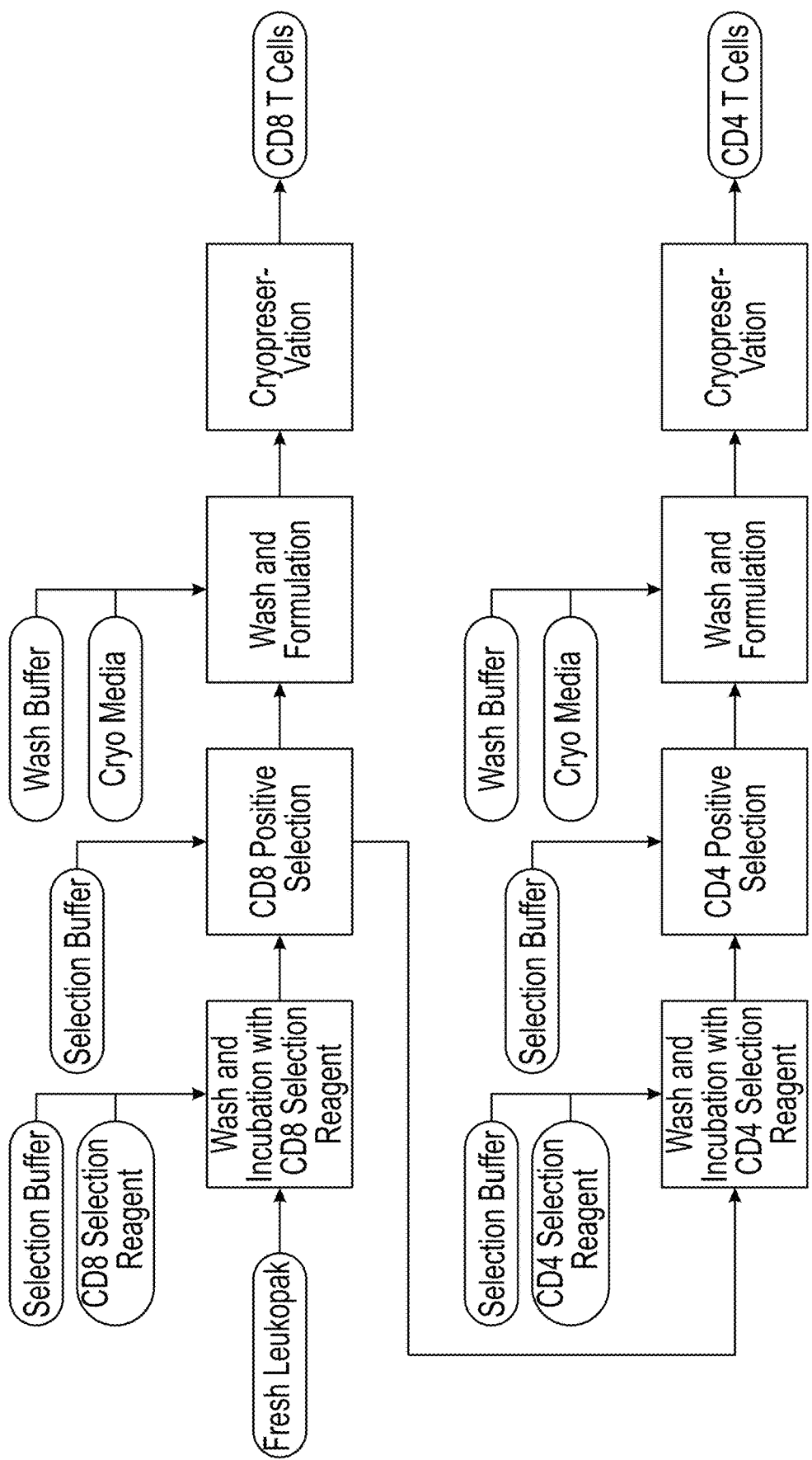
FIG. 37 shows a flow chart of an illustrative serial positive immunomagnetic cell selection strategy for isolating CD8 T cells and CD4 T cells from an enriched leukapheresis product collected from normal, healthy peripheral blood.
Figure 42A:
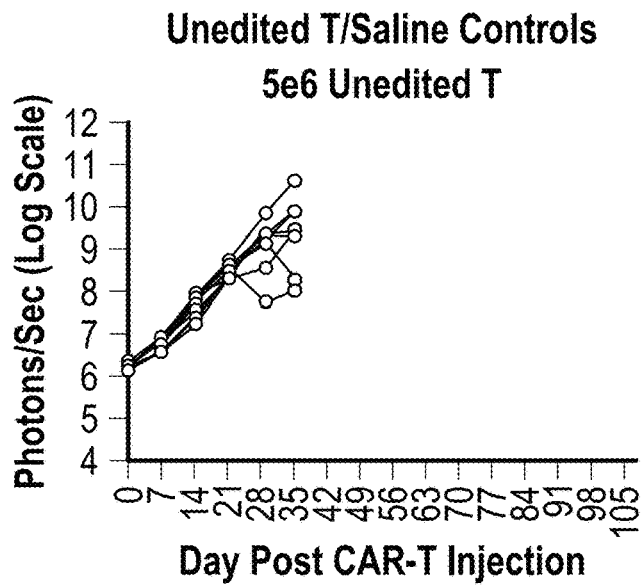
FIGS. 42A-J show the quantification of tumor burden over time for the study described in Example 9.
Figure 42B:
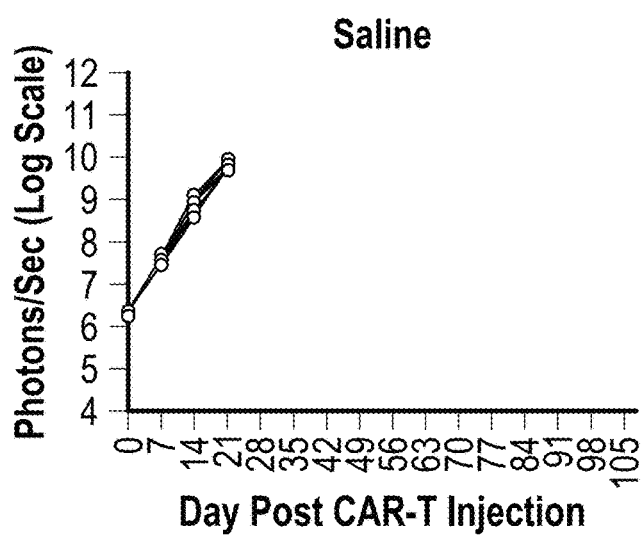
Figure 42C:
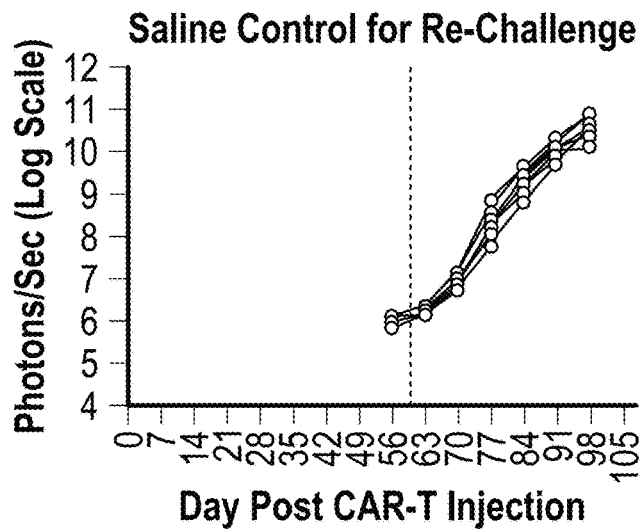
Figure 42D:
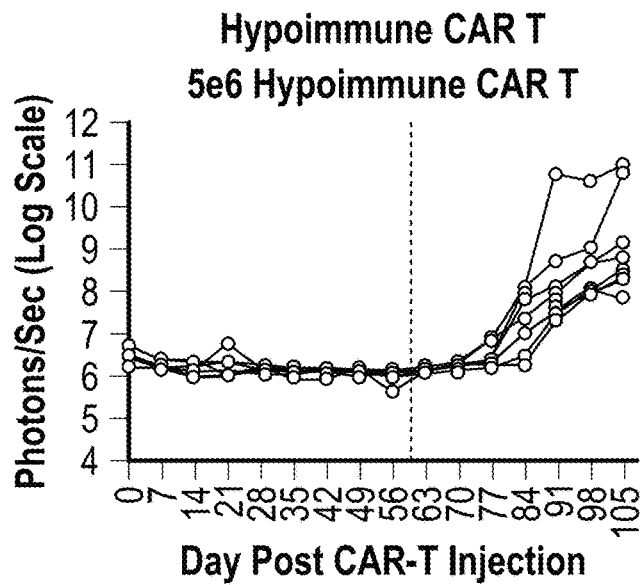
Figure 42E:
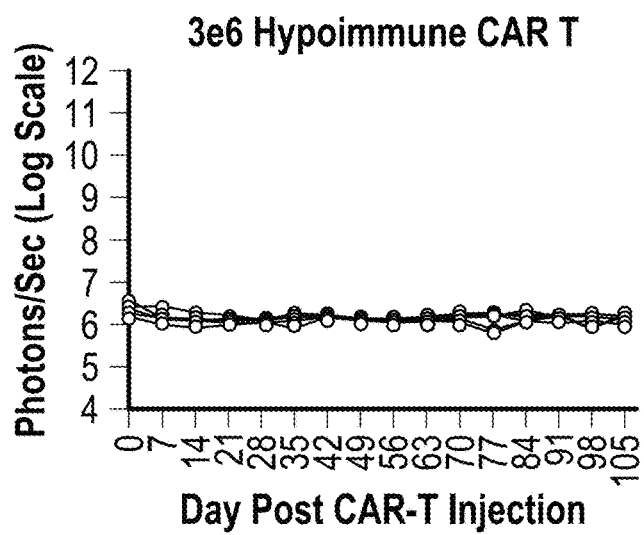
Figure 42F:
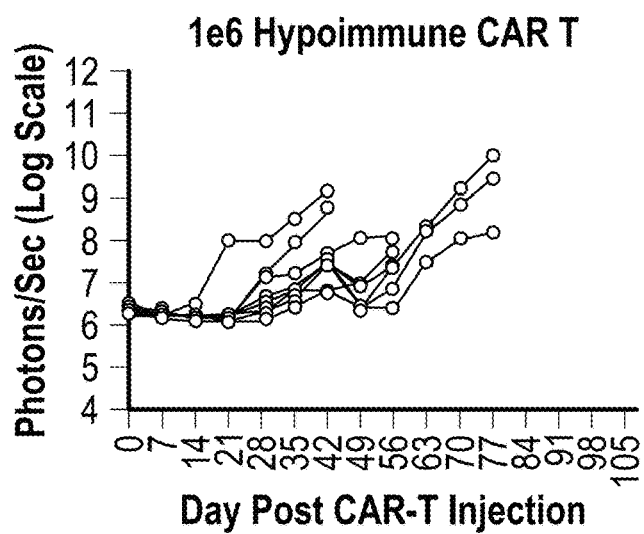
Figure 42G:
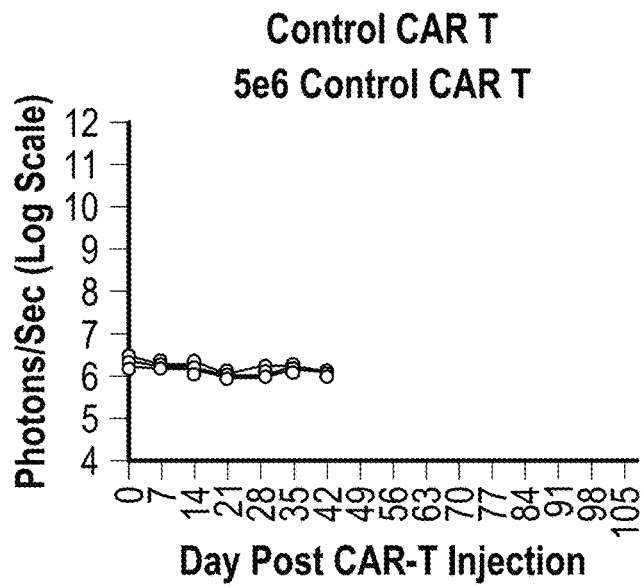
Figure 42H:
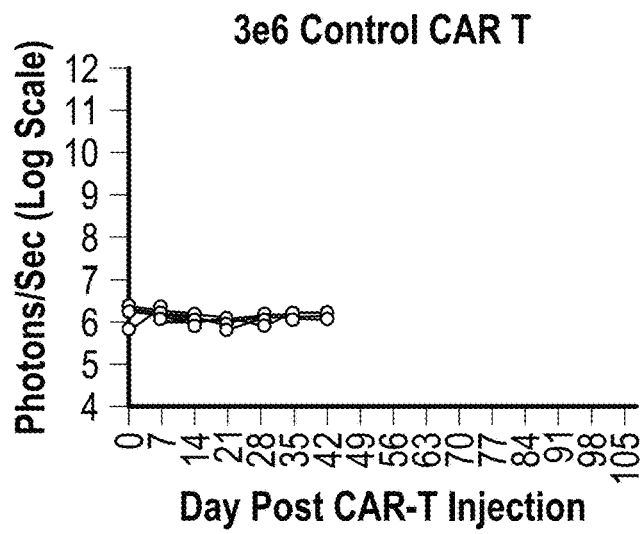
Figure 42I:
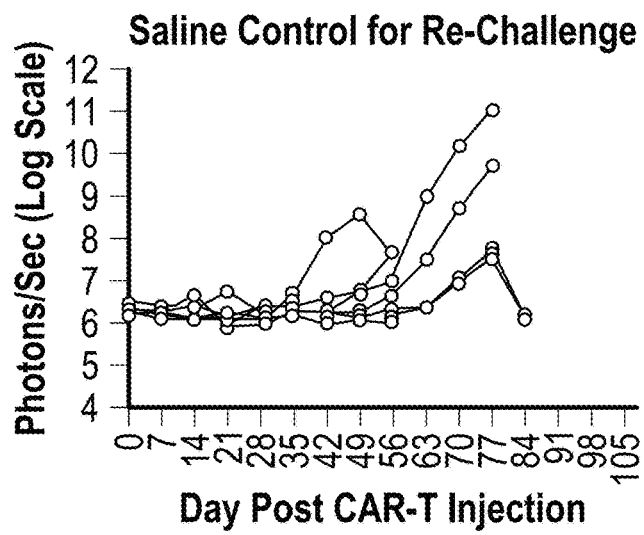
Figure 42J:
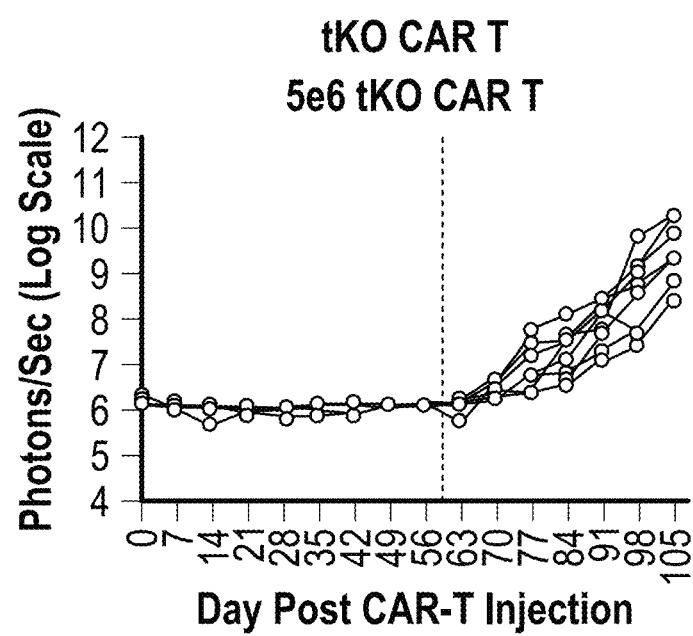
Figure 43A:
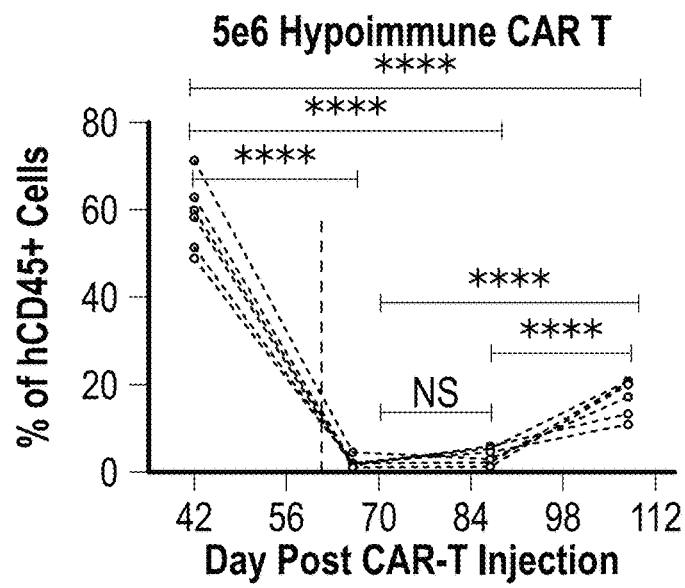
FIGS. 43A-H shows the HIP CD19-CAR-T cell frequencies and expression of CD47 in blood for the study described in Example 9. Specifically.
Figure 43B:
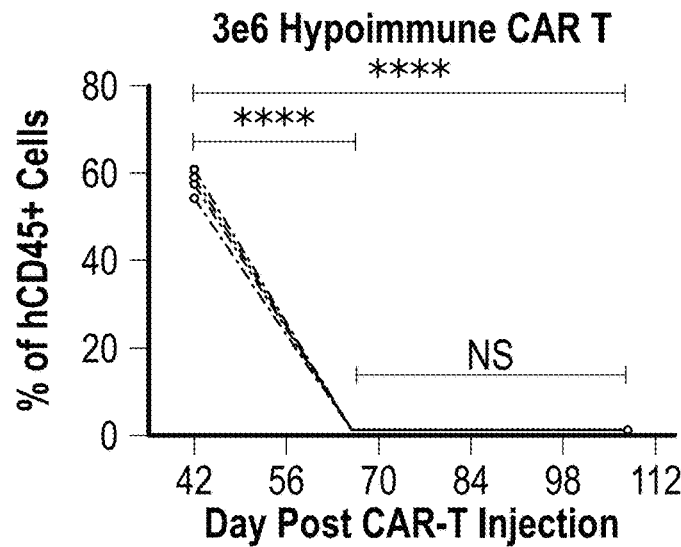
Figure 43C:
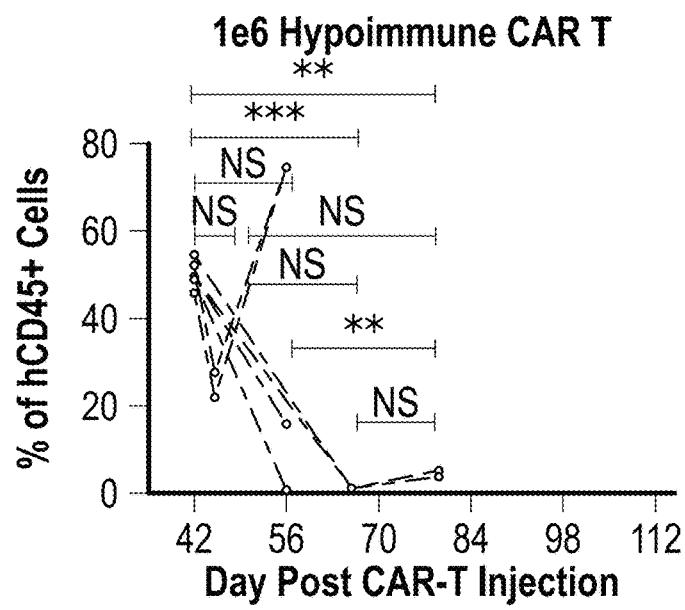
Figure 43D:
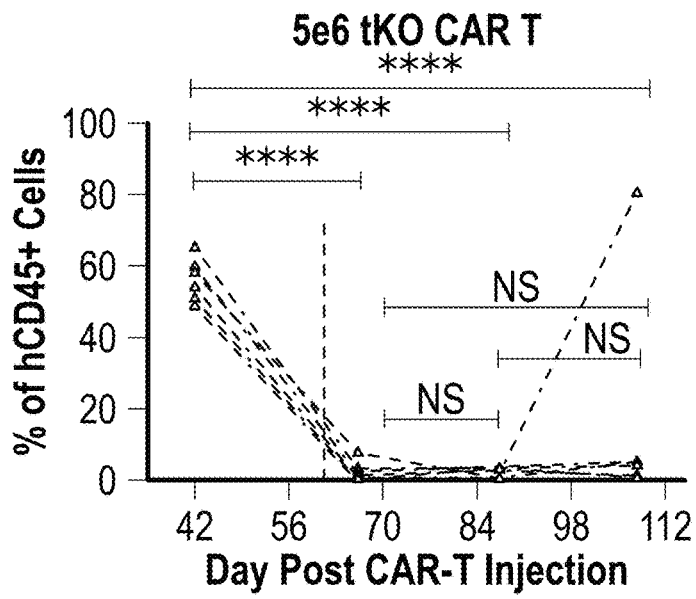
Figure 43E:
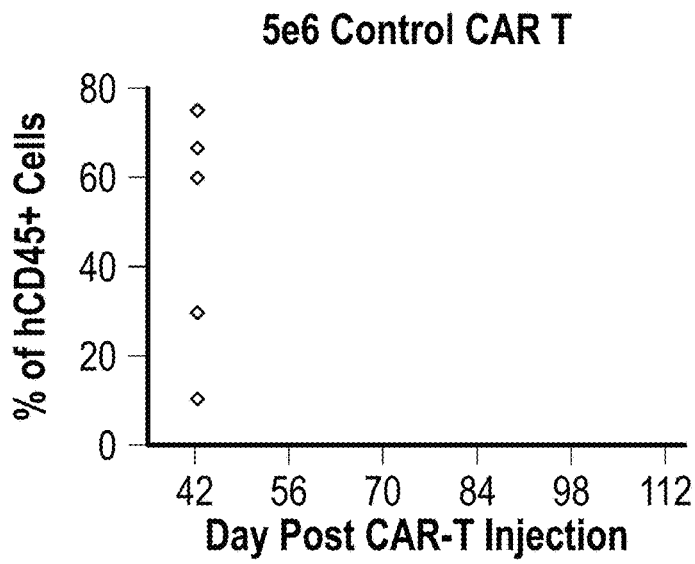
Figure 43F:
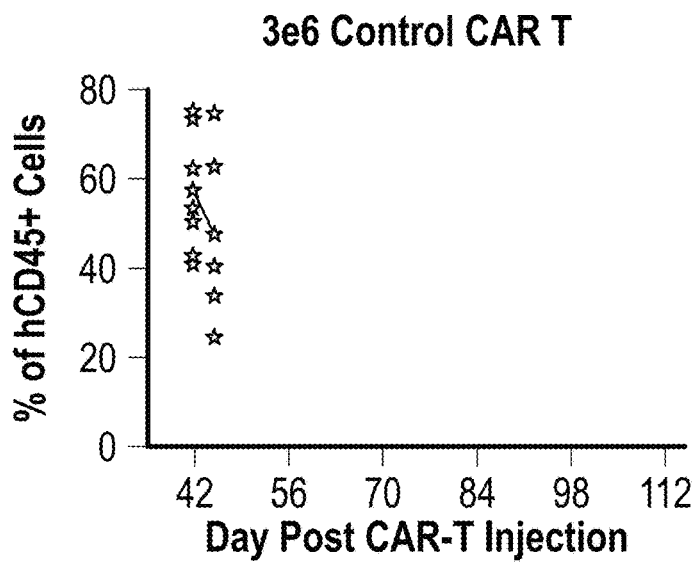
Figure 43G:
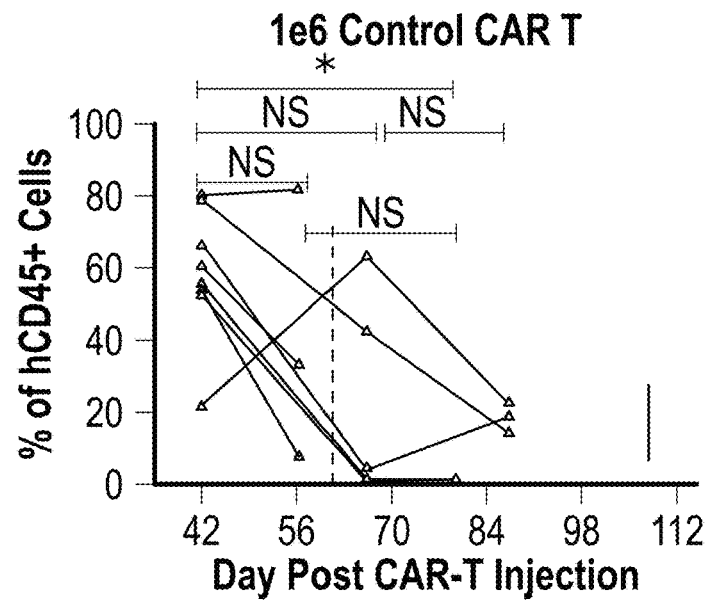
Figure 43H:
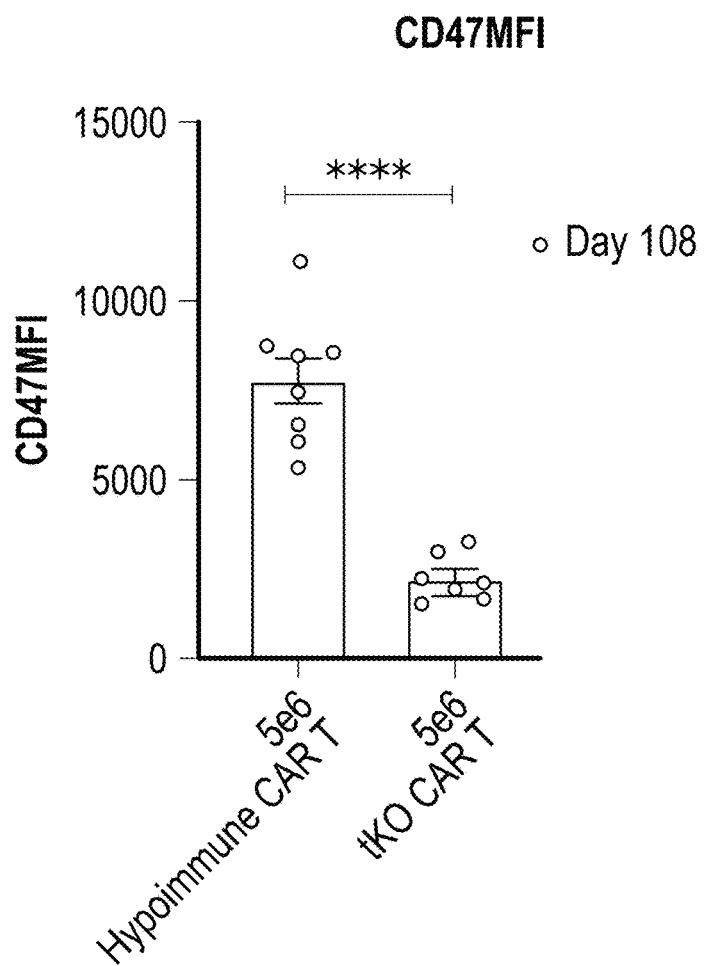

The images of Nalm6-bearing mice obtained after CAR-T cell therapy showed delayed tumor growth in tKO/CD47 CAR-T (HIP CD19-CAR-T) cells-treated mice when compared with control CAR-T treated mice, unedited T cell-treated mice and saline-treated mice (FIGS. 34 and 35).

Example 5: Method for Producing Hypoimmunogenic CAR-T Cells for Allogeneic Cell Therapy This example describes a method of generating hypoimmunogenic CAR-T cells ($B2M^{indel/indel}$, $CIITA^{indel/indel}$, $TRAC^{indel/indel}$, CD47tg T cells expressing a CD19-specific CAR-T cells, also referred to as tKO/CD47 CD19-CAR-T (HIP CD19-CAR-T) cells) from mononuclear cells and plasma (leukopak) obtained from healthy female donor who was less than 35 years old and had an O+ blood type. The CD4+ and CD8+ T cells from the healthy donor were isolated, separated and activated prior to lentiviral transduction of the CD4+ and CD8+ T cells with lentivirus carrying a CD47 transgenes and CD19-specific CARs. The transduced cells were then genetically modified to inactivate the B2M, CIITA and TRAC genes via CRISPR/Cas9, thereby producing tKO/CD47 CD19-CAR-T cells (HIP CD19-CAR-T).

Isolation of CD4+ and CD8+ T Cells

To isolate CD4+ and CD8+ T cells from the donor's mononuclear cells/plasma, a serial positive immunomagnetic cell selection strategy was utilized to isolated CD8+ T cells and CD4+ T cells. The CD8+ T cells were formulated with a cryopreservation media, aliquoted in cryopreservation vials, and frozen using a controlled-rate freezer. Separately, the CD4+ T cells were formulated with a cryopreservation media, aliquoted in cryopreservation vials, and frozen using a controlled-rate freezer.

Activation of CD4+ and CD8+ T Cells

Frozen aliquots of CD4+ and CD8+ cells were thawed, activated using CD3/CD28 beads and cultured under conditions for cell growth and expansion. Briefly, the CD4+ and CD8+ T cells were combined with CD3/CD28 (anti-CD3/anti-CD28) beads at a bead:cell ratio of about 3:1. The cell and bead mixture were seeded at a CD4:CD8 ratio of about 1:1 and cultured overnight in a culture media containing IL-2. The process described constituted day 0 of activation.

Lentiviral Vector Production

HEK293-derived cells for lentivirus production were cultured according to manufacturer's conditions. At Day 0 (transfection day) the cells were transfected with a transfection mixture containing lentiviral packaging plasmids and a pre-selected expression vector. At Day 1 after transfection, the cells were exposed to an additive such as sodium butyrate to improve viral protein production. At Day 1 after transfection, viral supernatant was collected, clarified, and then concentrated by ultra-high speed centrifugation. The resulting viral pellet was isolated and resuspended in a standard viral formulation buffer.

Lentiviral Transduction of CD4+ and CD8+ T Cells

On day 0, frozen aliquots of CD4+ and CD8+ cells were thawed, activated using CD3/CD28 beads and cultured under conditions for cell growth and expansion. Briefly, the CD4+ and CD8+ T cells were combined with CD3/CD28 (anti-CD3/anti-CD28) beads at a bead:cell ratio of about 3:1, seeded at a CD4:CD8 ratio of about 1:1 and cultured overnight in a culture media without cytokines. On the day after activation (day 1 post-activation), the activated CD4+ and CD8+ T cells were ready for lentiviral transduction and were divided into three experimental groups. Group 1 cells, considered the untransduced control T cells ("unedited control"), were allowed to proliferate under standard T cell culture conditions and were not transduced with a lentiviral vector. Group 2 cells, considered the transduced control CD19-CAR-EGFRt T cells ("control CAR-T"), were transduced with a lentiviral vector encoding a CD19-specific CAR and truncated EGFR. Group 3 cells, considered the transduced hypoimmunogenic CD19-CAR-T cells ("HIP CAR-T"), were transduced with a lentiviral vector encoding a bicistronic expression cassette for both CD47 transgenes and a CD19-specific CAR. For Group 2 and Group 3 cells, the cells were exposed to their respective concentrated lentiviral particles at a MOI of about 10, as calculated from a functional titer. The cells were transduced using a standard spinfection protocol and were allowed to recover in the incubator for about 2 days.

After recovery and on day 3 post-activation, the transduced cells (Group 2 and 3 cells) and control cells (Group 1 cells) were separately harvested and were subjected to a CD3/CD28 bead removal method. The resulting cells from each group were washed and resuspended in a culture media containing IL-2.

Gene Editing Lentiviral Transduced CD4+ and CD8+ T Cells

Ribonucleoproteins (RNPs) for the TRAC, B2M and CIITA genes were assembled such that the sgRNAs were precomplexed with recombinant Cas9. Briefly, synthetic modified sgRNAs were mixed with SPyFi Cas9 at a ratio such that Cas9 was in excess. Binary complex formation of gRNAs targeting TRAC, CIITA and B2M with Cas9 was carried out according to standard protocols recognized by those skilled in the art. The RNPs were combined for the triple knock-out nucleofection at a 1:1.5:2 ratio of TRAC-RNP:B2M-RNP:CIITA-RNP and nucleofected into the Group 3 cells. The cells were allowed to recover in the incubator for about 2 days.

Cells of Group 3, as well as those of Groups 1 and 2 were cultured and maintained using standard protocols known in the art.

Depletion of CD3+ T Cells from HIP CAR-T Cells

On day 8 post-activation, Group 3 "HIP CAR-T" cells were depleted of CD3 positive cells using a standard negative selection method known to those skilled in the art.

The collected CD3-negative HIP CAR-T cells were resuspended and cultured in culture media supplemented with IL-2. For cryopreservation, the cells were counted and suspended at a pre-selected concentration in a cryopreservation formulation. The cells were stored in liquid nitrogen for long-term storage.

Characterization of CD3-Depleted HIP CAR-T Cells

On day 10 post-activation cells from experimental Groups 1, 2 and 3 were prepared for flow cytometry analysis using standard protocols to determine the cell viability and expression of cell markers including CD3, CD4, CD8a, HLA-ABC, HLA-DR/DP/DQ, CD19-CAR and CD47. FIG. 38 provides a table of flow cytometry results for the HIP CAR-T cells, control CAR-T cells and unedited T cells produced from the method described.

Results

The data show that the HIP CAR-T cells included a significantly higher percentage of CD47 positive cells, CD47 positive and CAR positive cells, CD3 negative cells, HLA-ABC negative cells, HLA-DR/DP/DQ negative cells, and triple knockout cells compared to the control CAR-T cells and the unedited T cells. The HIP CAR-T cells contained similar percentages of CD4+ T cells and CD8+ T cells. The example describes an illustrative method for generating hypoimmunogenic CD19-specific CAR-T cells that are useful for allogeneic CAR-T therapies.

Example 6: Adaptive Immune Evasion by HIP CAR-T Cells in Humanized Mice

Humanized NSG-SGM3 mice were used as recipients for a CDC killing assay. Animals were randomly assigned to experimental groups. $1\times10^6$ CD19-CAR-T cells were injected intravenously into the tail vein, and blood serum was collected 7 days after injection.

CDC killing assays were performed on the XCelligence MP platform (Agilent Technologies, Santa Clara, CA). 96-well E-plates (Agilent Technologies) were coated with tumor coating solution (Agilent Technologies) and $4\times10^4$ target CD19-CAR-T cells or HIP CD19-CAR-T cells were plated in 100 µl Optimizer Media (including supplement, Thermo Fisher) with human IL-2. After the cell index reached 0.7, 50 µl serum samples were mixed with 50 µl human complement (Quidel, San Diego, CA) and added to the target cells. As killing control, cells were treated with 2% TritonX100 (data not shown). Data were standardized and analyzed with the RTCA software (Agilent Technologies).

As shown in FIGS. 39A-B, transplantation of non-hypoimmune edited CD19-CAR-T cells (T cells engineered to express a CAR but lacking any modifications to B2M, CIITA, or a CD47 transgene) into allogeneic humanized mice resulted in a significant T cell activation, whereas hypoimmune CD19-CAR-T cells (T cells engineered to express a CAR and a CD47 transgene, and engineered for reduced expression of B2M and CIITA) evaded immune recognition ($p<0.0001$).

As shown in FIGS. 39C-D, hypoimmune CD19-CAR-T cells were functionally immune evasive in allogeneic humanized mouse recipients, even after CAR sensitization. These data suggest that hypoimmune CD19-CAR-T cells can be used in sensitized patients and for redosing strategies.

Example 7: Generation of Exemplary HIP CD19-CAR-T Cells

HIP CD19-CAR-T cells were manufactured via an ex vivo process including two separate steps for genome modification of purified $CD8^+$ and $CD4^+$ T cells: a lentiviral transduction step to enable transgene expression of the anti-CD19 chimeric antigen receptor (CD19-CAR) and CD47 genes, and a genome editing step in which Cas enzyme is used to target three loci for knockout (TRAC, B2M, and CIITA). The lentiviral vector was pseudotyped with VSV-G and carried a bicistronic transgene containing both CD19-CAR and CD47 genes. The reagents used in the genome editing step comprise an mRNA which encodes the Cas nuclease, or a Cas protein, and three single guide RNAs (sgRNAs), each of which target one of the loci described above. Through (i) CD47 overexpression to block host innate immunity; (ii) reduced expression of MHC class I and class II HLAs to prevent host adaptive immunity and (iii) reduced expression of T cell receptor (TCR) to prevent graft-versus-host reaction, the HIP CD19-CAR-T cells were designed to evade the immune system of the host while mediating the durable killing of CD19-expressing tumor cells. Previously described experiments have demonstrated that these cells are able to hide from the immune system and avoid immune rejection. See, e.g., PCT/US21/45822, filed Aug. 12, 2021, and WO2021222285, incorporated herein by reference in their entireties.

Both in vitro and in vivo studies using HIP CD19-CAR-T cells have demonstrated the intended pharmacological activity of targeting and killing $CD19^+$ tumor cells (NALM-6) that is similar to CD19-CAR-T cells (transduction with a lentiviral vector to express CD19-CAR but no hypoimmune edits). HIP CD19-CAR-T cells lack a graft-versus-host response that is similar to triple knockout (tKO) CD19-CAR-T cells, and uniquely evade innate and adaptive host immune system responses when compared to standard or tKO CD19-CAR-T cells. See, e.g., PCT/US21/45822, filed Aug. 12, 2021, and WO2021222285, and FIGS. 39 and 41.

Example 8: In Vitro Assessment of the HIP CD19-CAR-T Cell Killing

The objective of this in vitro study was to test the killing activity of HIP CD19-CAR-T cells described herein.

Cells used in this study included (i) HIP CD19-CAR-T cells, (ii) CD19-CAR-T cells, and (iii) unedited T cells from the same donor. To evaluate killing activity, CD19-CAR-T and HIP CD19-CAR-T cells were thawed, rested overnight, and assessed by flow cytometry for CD19-CAR frequency.

CD19-CAR-T and HIP CD19-CAR-T cells were co-cultured for 18 hours with NALM-6 cells (target cells labeled with Cell Trace Violet, CTV) at different effector to target ratios (range 3:1 to 1:243, 3-fold dilution series). Unedited T cells were added to each E:T ratio to maintain the same total number of T cells in each condition. The co-culture of unedited T cells and NALM-6 cells (CTV-labeled) were used to normalize cell killing.

CD19-CAR-T cells and HIP CD19-CAR-T cells had a similar percentage (75%) of viable cells expressing a CD19-CAR (data not shown). When in co-culture with CD19+ NALM-6 tumor target cells, both CD19-CAR-T and HIP CD19-CAR-T cells showed dose-related activity with an effective dose 5000 ($ED_{50}$) of 1:20 effector to target ratio (E:T) (data not shown). These findings indicate that HIP CD19-CAR-T cells have similar expression of CD19-CAR and demonstrate similar activity to CD19-CAR-T cells.

Example 9: Single Intravenous Dose 108-Day Study of Anti-Tumor Activity of HIP CAR-T Cells in NALM-6-Luc Tumor Bearing Female NSG Mice The objective of this study was to demonstrate anti-tumor activity of Cas9 gene-edited HIP CD19-CAR-T cells in the CD19+ NALM-6-Luciferase tumor NSG mouse model of B-cell malignancy.

Table 22 summarizes this dose-ranging, longitudinal study that included a tumor rechallenge at Day 60 to evaluate the level of longer-term CD19-CAR-T cell activity.

TABLE 22

Study Groups

| Group | NALM-6-Luc cells/mouse Day −3 | Test Article | CD19-CAR+ cells/mouse | NALM-6-Luc cells/mouse Day 60 (Rechallenge) |
|---|---|---|---|---|
| A | $1 \times 10^6$ | HIP CD19-CAR-T | $5 \times 10^6$ | $1 \times 10^6$ |
| B | $1 \times 10^6$ | HIP CD19-CAR-T | $3 \times 10^6$ | NA |
| C | $1 \times 10^6$ | HIP CD19-CAR-T | $1 \times 10^6$ | NA |
| D | $1 \times 10^6$ | CD19-CAR-T | $5 \times 10^6$ | NA |
| E | $1 \times 10^6$ | CD19-CAR-T | $3 \times 10^6$ | NA |
| F | $1 \times 10^6$ | CD19-CAR-T | $1 \times 10^6$ | NA |
| G | $1 \times 10^6$ | tKO CD19-CAR-T | $5 \times 10^6$ | $1 \times 10^6$ |
| H | $1 \times 10^6$ | Unedited T | $5 \times 10^6$ | NA |
| I | $1 \times 10^6$ | Saline | NA | NA |
| J | NA | Saline | NA | $1 \times 10^6$ | n=8 for all groups. NA designates animals that were not re-challenged, or animals that were not in-life at the time of the designated bleed. Time of sacrifice varied from mouse-to-mouse.

Female NSG mice (n=8/group) were implanted with $1 \times 10^6$ NALM-6-Luc tumor cells intravenously on Day −3. Viability and CD19-CAR expression on T cells were evaluated to calculate total T cell numbers (intended number of CD19-CAR+ cell number/% viable, CD19-CAR+ cells). Unedited T cells were calculated based on frequency of viable cells. On Day 0, CD19-CAR-T cells were administered to mice. Animals in groups A and G ($5 \times 10^6$ HIP CD19-CAR-T cells/mouse and $5 \times 10^6$ tKO CD19-CAR-T cells/mouse, respectively) were re-challenged with an additional intravenous injection of $1 \times 10^6$ NALM-6-Luc cells on Day 60. A new cohort of naïve NSG mice (group J) was intravenously injected with $1 \times 10^6$ NALM-6-Luc cells to serve as an untreated control.

Immunophenotyping was performed on isolated PBMCs, spleen and bone marrow T cell populations. Bioluminescence imaging (BLI) was performed to monitor tumor burden on a weekly basis. Histopathology was performed on tissues collected at necropsy and histological changes were subjectively scored for severity of graft-versus-host response (GvHR), tumor burden and/or other microscopic changes.

Statistical analysis for flow cytometry data was performed with a one-way or two-way analysis of variance (ANOVA) and random coefficient models with a random effect for slope were used BLI data and for re-challenged mice.

Results-Tumor Burden. Saline-treated animals were euthanized on Day 21 due to moribundity from tumor burden (FIG. 42). Although two unedited T cell-treated mice had reduced tumor growth, the remaining unedited T cell-treated mice developed tumors and were sacrificed on Day 35. Two of eight mice in the $1 \times 10^6$ CD19-CAR-T cell/mouse group had tumor growth and were sacrificed on Day 35; the remaining six mice in the $1 \times 10^6$ CD19-CAR-T group were sacrificed on Day 42 due to GvHR. Animals treated with $1 \times 10^6$ HIP CD19-CAR-T cells showed tumor growth starting on Day 21. Mice dosed with $3 \times 10^6$ HIP CD19-CAR-T cells and mice dosed with either $5 \times 10^6$ HIP CD19-CAR-T or tKO CD19-CAR-T cells were tumor free until after NALM-6-Luc rechallenge (Day 60 (FIG. 42)).

Importantly, no HIP CD19-CAR-T or tKO CD19-CAR-T treated animals had symptoms of GvHR, whereas every mouse in the $5 \times 10^6$ and $3 \times 10^6$ CD19-CAR-T treatment groups developed GvHR symptoms that included significant weight loss, fur loss, and/or hunched posture.

On Day 60, the $5 \times 10^6$ HIP CD19-CAR-T and $5 \times 10^6$ tKO CD19-CAR-T-treated groups were re-challenged with $1 \times 10^6$ NALM-6-Luc cells. A new cohort of naïve NSG mice injected with $1 \times 10^6$ NALM-6-Luc cells and treated with saline were added to the study to serve as controls. The $5 \times 10^6$ HIP CD19-CAR-T and tKO CD19-CAR-T animals re-challenged with NALM-6-Luc cells displayed similar, significantly improved tumor suppression compared to the saline-treated mice over the 48-day period (FIG. 42). The study was terminated on Day 108 when all re-challenged mice had tumor resurgence.

Results—CD19-CAR-T and CD47 Expression Levels. Frequencies of CD19-CAR+ cells were evaluated from blood collected at interim bleeds between Days 42 and 108 and at time of sacrifice (FIG. 43). Since time of sacrifice was not pre-determined for any group, head-to-head comparisons were not possible at every timepoint. There was a significant decrease in CD19-CAR+ cell frequency in blood of all hypoimmune and tKO CD19-CAR-T treated mice, and in $1 \times 10^6$ CD19-CAR-T treated mice, between days 42 and 66 ($5 \times 10^6$ HIP CD19-CAR-T treated $p < 0.0001$, $3 \times 10^6$ HIP CD19-CAR-T treated $p < 0.0001$, $1 \times 10^6$ HIP CD19-CAR-T treated $p = 0.0015$; $5 \times 10^6$ tKO CD19-CAR-T treated $p < 0.0001$; $1 \times 10^6$ CD19-CAR-T treated $p = 0.0410$). The re-challenged $5 \times 10^6$ HIP CD19-CAR-T treated group had a significant increase in CD19-CAR+ cells between Days 66 and 108 ($p < 0.0001$), whereas the re-challenged $5 \times 10^6$ tKO CD19-CAR-T treated groups did not ($p = 0.4694$).

The CD47MFI was significantly higher on HIP CD19-CAR-T cells than on tKO CD19-CAR-T cells on Day 108 ($p < 0.0001$) (FIG. 43). CD47MFI could not be compared between hypoimmune versus CD19-CAR-T cells due to lack of sufficient same-day bleeds or sacrifice.

Results. Histopathological analyses were performed on lung, liver, and skin. GvHR characterized by perivascular, peribronchiolar and periadnexal mononuclear (lymphocytes and macrophages) infiltrates in the liver, lungs, and skin was observed in mice administered CD19-CAR-T cells or unedited CD19-CAR-T cells. GvHR was not evident in mice administered HIP CD19-CAR-T or tKO CD19-CAR-T at any dose. Infiltrates of tumor (NALM-6) cells within hepatic sinusoids and/or alveolar septa of lungs were observed in mice administered the lowest ($1 \times 10^6$) dose of HIP CD19-CAR-T cells and in all re-challenged mice. Two mice administered unedited CD19-CAR-T cells had infiltrates of NALM-6 tumor cells and GvHR concurrently in the liver. Abdominal masses from several mice treated with $5 \times 10^6$ HIP CD19-CAR-T cells, $1 \times 10^6$ CD19-CAR-T cells, or $5 \times 10^6$ tKO CD19-CAR-T cells corresponded to NALM-6 tumor cells that had replaced the normal ovarian architecture.

Conclusions. Administration of HIP CD19-CAR-T cells to NSG mice engrafted with CD19+ NALM-6-Luc tumor cells resulted in a dose-dependent reduction of systemic tumor burden without evidence of GvHR over a 108-day study period. CD19-CAR-T cells at the $3 \times 10^6$ and $5 \times 10^6$ doses also had reduced tumor burden, but also developed GvHR as confirmed by histopathological analysis. The high incidence of GvHR in CD19-CAR-T treated animals is likely due to TCR and MHC signaling, which did not occur in hypoimmune or tKO CD19-CAR-T cells. Furthermore, $5 \times 10^6$ HIP CD19-CAR-T and $5 \times 10^6$ tKO CD19-CAR-T cell/mouse treatments resulted in comparable tumor burden reduction, as well as a significant and similar suppression when rechallenged with tumor cells compared to saline treated controls. At study termination, CD19-CAR+ cells were still detectable in re-challenged animals, and CD47 expression was significantly higher on HIP CD19-CAR-T cells compared to tKO CD19-CAR-T cells.

Example 10: In Vitro Cytokine-Independent Proliferation of HIP CD19-CAR-T Cell

The objective of this study was to determine whether HIP CD19-CAR-T cells have the ability to proliferate in the absence of IL2 as an indicator of potential oncogenic transformation.

Figure 44:
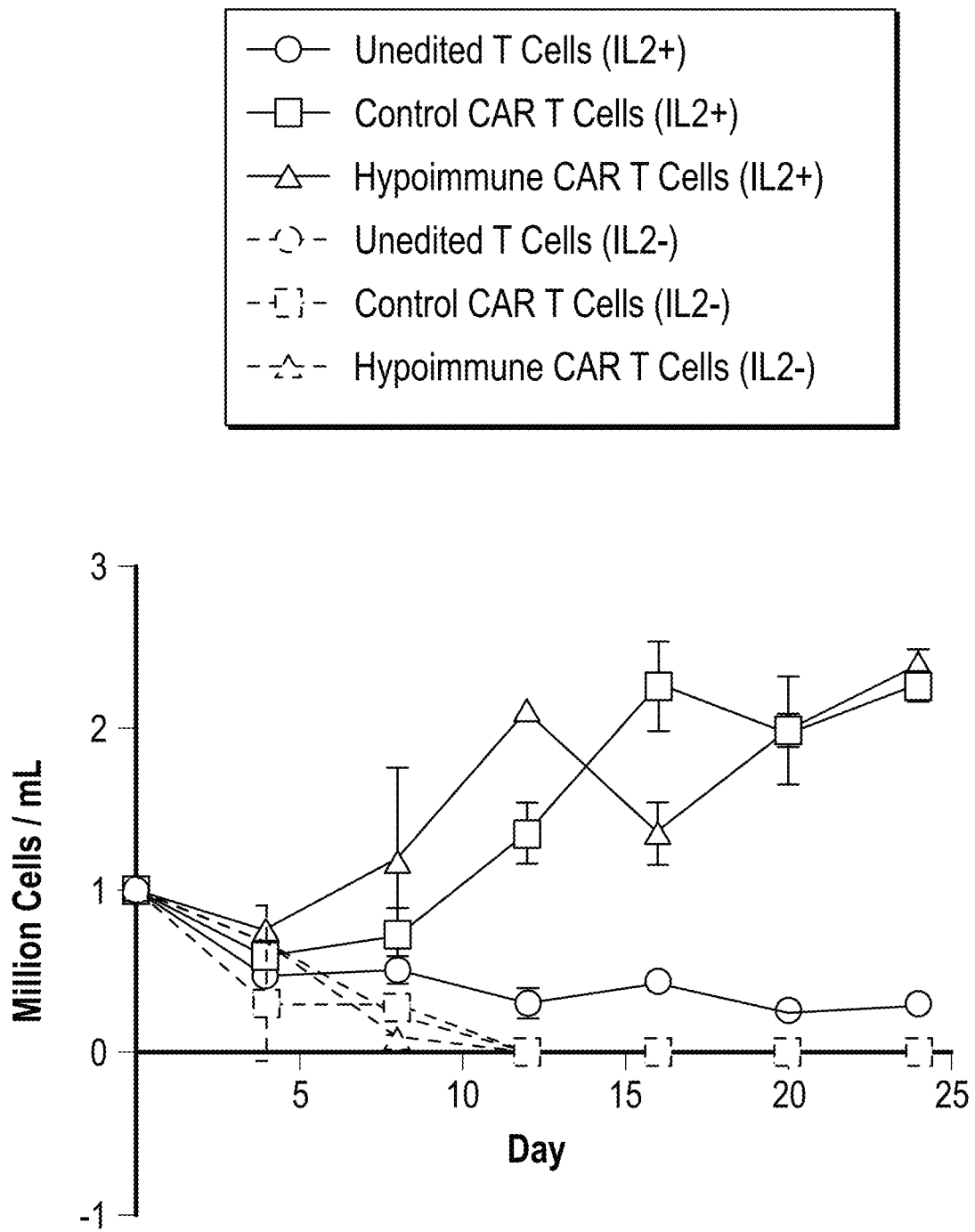
FIG. 44 shows exploratory autonomous growth assay cell count results for the study described in Example 10.

CD19-CAR-T (control) and HIP CD19-CAR-T cells cultured in the presence of IL2 showed a similar increased cell count compared to Day 0, suggesting comparable cell proliferation. CD19-CAR-T cells and HIP CD19-CAR-T cells cultured in absence of IL2 were comparable and showed minimal evidence of proliferation, reduced survival (decreased cell count) and eventually no viable cells were present by day 12 (FIG. 44).

The HIP CD19-CAR-T cells did not demonstrate proliferation in absence of IL2, suggesting the genomic modifications do not result in potential oncogenic transformation. Further, HIP CD19-CAR-T cells demonstrated similar behavior when compared to CD19-CAR-T cells in the presence or absence of IL2.

All headings and section designations are used for clarity and reference purposes only and are not to be considered limiting in any way. For example, those of skill in the art will appreciate the usefulness of combining various embodiments from different headings and sections as appropriate according to the spirit and scope of the technology described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

SEQUENCE LISTING

```
Sequence total quantity: 149
SEQ ID NO: 1             moltype = RNA  length = 20
FEATURE                  Location/Qualifiers
misc_feature             1..20
                         note = Synthetic guide sequence
source                   1..20
                         mol_type = other RNA
                         organism = synthetic construct
ncRNA                    1..20
                         ncRNA_class = guide_RNA
SEQUENCE: 1
tctctccatg tgcagtagga                                                    20

SEQ ID NO: 2             moltype = RNA  length = 20
FEATURE                  Location/Qualifiers
misc_feature             1..20
                         note = Synthetic guide sequence
source                   1..20
                         mol_type = other RNA
                         organism = synthetic construct
ncRNA                    1..20
                         ncRNA_class = guide_RNA
SEQUENCE: 2
ctggatgtcg gaggagtacg                                                    20

SEQ ID NO: 3             moltype = RNA  length = 20
FEATURE                  Location/Qualifiers
misc_feature             1..20
                         note = Synthetic guide sequence
source                   1..20
```

```
                         mol_type = other RNA
                         organism = synthetic construct
ncRNA                    1..20
                         ncRNA_class = guide_RNA
SEQUENCE: 3
gtctccggaa actcgaggtg                                                  20

SEQ ID NO: 4             moltype = RNA  length = 20
FEATURE                  Location/Qualifiers
misc_feature             1..20
                         note = Synthetic guide sequence
source                   1..20
                         mol_type = other RNA
                         organism = synthetic construct
ncRNA                    1..20
                         ncRNA_class = guide_RNA
SEQUENCE: 4
acagtgtaga cttgattgac                                                  20

SEQ ID NO: 5             moltype = RNA  length = 20
FEATURE                  Location/Qualifiers
misc_feature             1..20
                         note = Synthetic guide sequence
source                   1..20
                         mol_type = other RNA
                         organism = synthetic construct
ncRNA                    1..20
                         ncRNA_class = guide_RNA
SEQUENCE: 5
cgtgagtaaa cctgaatctt                                                  20

SEQ ID NO: 6             moltype = AA  length = 21
FEATURE                  Location/Qualifiers
REGION                   1..21
                         note = Synthetic peptide
source                   1..21
                         mol_type = protein
                         organism = synthetic construct
SEQUENCE: 6
MALPVTALLL PLALLLHAAR P                                                21

SEQ ID NO: 7             moltype = AA  length = 20
FEATURE                  Location/Qualifiers
REGION                   1..20
                         note = Synthetic peptide
source                   1..20
                         mol_type = protein
                         organism = synthetic construct
SEQUENCE: 7
METDTLLLWV LLLWVPGSTG                                                  20

SEQ ID NO: 8             moltype = AA  length = 22
FEATURE                  Location/Qualifiers
REGION                   1..22
                         note = Synthetic peptide
source                   1..22
                         mol_type = protein
                         organism = synthetic construct
SEQUENCE: 8
MLLLVTSLLL CELPHPAFLL IP                                               22

SEQ ID NO: 9             moltype = AA  length = 45
FEATURE                  Location/Qualifiers
REGION                   1..45
                         note = Synthetic hinge domain
source                   1..45
                         mol_type = protein
                         organism = synthetic construct
SEQUENCE: 9
TTTPAPRPPT PAPTIASQPL SLRPEACRPA AGGAVHTRGL DFACD                      45

SEQ ID NO: 10            moltype = AA  length = 39
FEATURE                  Location/Qualifiers
REGION                   1..39
                         note = Synthetic hinge domain
source                   1..39
                         mol_type = protein
                         organism = synthetic construct
SEQUENCE: 10
```

```
IEVMYPPPYL DNEKSNGTII HVKGKHLCPS PLFPGPSKP                                 39

SEQ ID NO: 11          moltype = AA   length = 12
FEATURE                Location/Qualifiers
REGION                 1..12
                       note = Synthetic hinge domain
source                 1..12
                       mol_type = protein
                       organism = synthetic construct
SEQUENCE: 11
ESKYGPPCPP CP                                                              12

SEQ ID NO: 12          moltype = AA   length = 12
FEATURE                Location/Qualifiers
REGION                 1..12
                       note = Synthetic hinge domain
source                 1..12
                       mol_type = protein
                       organism = synthetic construct
SEQUENCE: 12
ESKYGPPCPS CP                                                              12

SEQ ID NO: 13          moltype = AA   length = 229
FEATURE                Location/Qualifiers
REGION                 1..229
                       note = Synthetic hinge domain
source                 1..229
                       mol_type = protein
                       organism = synthetic construct
SEQUENCE: 13
ESKYGPPCPP CPAPEFLGGP SVFLFPPKPK DTLMISRTPE VTCVVVDVSQ EDPEVQFNWY           60
VDGVEVHNAK TKPREEQFNS TYRVVSVLTV LHQDWLNGKE YKCKVSNKGL PSSIEKTISK          120
AKGQPREPQV YTLPPSQEEM TKNQVSLTCL VKGFYPSDIA VEWESNGQPE NNYKTTPPVL          180
DSDGSFFLYS RLTVDKSRWQ EGNVFSCSVM HEALHNHYTQ KSLSLSLGK                      229

SEQ ID NO: 14          moltype = AA   length = 24
FEATURE                Location/Qualifiers
REGION                 1..24
                       note = Synthetic transmembrane domain
source                 1..24
                       mol_type = protein
                       organism = synthetic construct
SEQUENCE: 14
IYIWAPLAGT CGVLLLSLVI TLYC                                                 24

SEQ ID NO: 15          moltype = AA   length = 27
FEATURE                Location/Qualifiers
REGION                 1..27
                       note = Synthetic transmembrane domain
source                 1..27
                       mol_type = protein
                       organism = synthetic construct
SEQUENCE: 15
FWVLVVVGGV LACYSLLVTV AFIIFWV                                              27

SEQ ID NO: 16          moltype = AA   length = 42
FEATURE                Location/Qualifiers
REGION                 1..42
                       note = Synthetic costimulatory domain
source                 1..42
                       mol_type = protein
                       organism = synthetic construct
SEQUENCE: 16
KRGRKKLLYI FKQPFMRPVQ TTQEEDGCSC RFPEEEEGGC EL                             42

SEQ ID NO: 17          moltype = AA   length = 41
FEATURE                Location/Qualifiers
REGION                 1..41
                       note = Synthetic costimulatory domain
source                 1..41
                       mol_type = protein
                       organism = synthetic construct
SEQUENCE: 17
RSKRSRLLHS DYMNMTPRRP GPTRKHYQPY APPRDFAAYR S                              41

SEQ ID NO: 18          moltype = AA   length = 112
FEATURE                Location/Qualifiers
REGION                 1..112
                       note = Synthetic signaling domain
```

```
source                  1..112
                        mol_type = protein
                        organism = synthetic construct
SEQUENCE: 18
RVKFSRSADA PAYQQGQNQL YNELNLGRRE EYDVLDKRRG RDPEMGGKPR RKNPQEGLYN    60
ELQKDKMAEA YSEIGMKGER RRGKGHDGLY QGLSTATKDT YDALHMQALP PR           112

SEQ ID NO: 19           moltype = AA   length = 245
FEATURE                 Location/Qualifiers
REGION                  1..245
                        note = Synthetic amino acid
source                  1..245
                        mol_type = protein
                        organism = synthetic construct
SEQUENCE: 19
DIQMTQTTSS LSASLGDRVT ISCRASQDIS KYLNWYQQKP DGTVKLLIYH TSRLHSGVPS    60
RFSGSGSGTD YSLTISNLEQ EDIATYFCQQ GNTLPYTFGG GTKLEITGST SGSGKPGSGE   120
GSTKGEVKLQ ESGPGLVAPS QSLSVTCTVS GVSLPDYGVS WIRQPPRKGL EWLGVIWGSE   180
TTYYNSALKS RLTIIKDNSK SQVFLKMNSL QTDDTAIYYC AKHYYGGSY AMDYWGQGTS    240
VTVSS                                                              245

SEQ ID NO: 20           moltype = AA   length = 107
FEATURE                 Location/Qualifiers
REGION                  1..107
                        note = Synthetic amino acid
source                  1..107
                        mol_type = protein
                        organism = synthetic construct
SEQUENCE: 20
DIQMTQTTSS LSASLGDRVT ISCRASQDIS KYLNWYQQKP DGTVKLLIYH TSRLHSGVPS    60
RFSGSGSGTD YSLTISNLEQ EDIATYFCQQ GNTLPYTFGG GTKLEIT                107

SEQ ID NO: 21           moltype = AA   length = 6
FEATURE                 Location/Qualifiers
REGION                  1..6
                        note = Synthetic amino acid
source                  1..6
                        mol_type = protein
                        organism = synthetic construct
SEQUENCE: 21
QDISKY                                                               6

SEQ ID NO: 22           moltype =   length =
SEQUENCE: 22
000

SEQ ID NO: 23           moltype = AA   length = 9
FEATURE                 Location/Qualifiers
REGION                  1..9
                        note = Synthetic amino acid
source                  1..9
                        mol_type = protein
                        organism = synthetic construct
SEQUENCE: 23
QQGNTLPYT                                                            9

SEQ ID NO: 24           moltype = AA   length = 18
FEATURE                 Location/Qualifiers
REGION                  1..18
                        note = Synthetic amino acid linker
source                  1..18
                        mol_type = protein
                        organism = synthetic construct
SEQUENCE: 24
GSTSGSGKPG SGEGSTKG                                                  18

SEQ ID NO: 25           moltype = AA   length = 120
FEATURE                 Location/Qualifiers
REGION                  1..120
                        note = Synthetic amino acid
source                  1..120
                        mol_type = protein
                        organism = synthetic construct
SEQUENCE: 25
EVKLQESGPG LVAPSQSLSV TCTVSGVSLP DYGVSWIRQP PRKGLEWLGV IWGSETTYYN    60
SALKSRLTII KDNSKSQVFL KMNSLQTDDT AIYYCAKHYY YGGSYAMDYW GQGTSVTVSS   120

SEQ ID NO: 26           moltype = AA   length = 8
FEATURE                 Location/Qualifiers
```

```
REGION                   1..8
                         note = Synthetic amino acid
source                   1..8
                         mol_type = protein
                         organism = synthetic construct
SEQUENCE: 26
GVSLPDYG                                                                      8

SEQ ID NO: 27            moltype = AA   length = 7
FEATURE                  Location/Qualifiers
REGION                   1..7
                         note = Synthetic amino acid
source                   1..7
                         mol_type = protein
                         organism = synthetic construct
SEQUENCE: 27
IWGSETT                                                                       7

SEQ ID NO: 28            moltype = AA   length = 14
FEATURE                  Location/Qualifiers
REGION                   1..14
                         note = Synthetic amino acid
source                   1..14
                         mol_type = protein
                         organism = synthetic construct
SEQUENCE: 28
AKHYYYGGSY AMDY                                                              14

SEQ ID NO: 29            moltype = AA   length = 242
FEATURE                  Location/Qualifiers
REGION                   1..242
                         note = Synthetic amino acid
source                   1..242
                         mol_type = protein
                         organism = synthetic construct
SEQUENCE: 29
DIQMTQTTSS LSASLGDRVT ISCRASQDIS KYLNWYQQKP DGTVKLLIYH TSRLHSGVPS             60
RFSGSGSGTD YSLTISNLEQ EDIATYFCQQ GNTLPYTFGG GTKLEITGGG GSGGGGSGGG            120
GSEVKLQESG PGLVAPSQSL SVTCTVSGVS LPDYGSWIR QPPRKGLEWL GVIWGSETTY             180
YNSALKSRLT IIKDNSKSQV FLKMNSLQTD DTAIYYCAKH YYYGGSYAMD YWGQGTSVTV            240
SS                                                                          242

SEQ ID NO: 30            moltype = AA   length = 15
FEATURE                  Location/Qualifiers
REGION                   1..15
                         note = Synthetic amino acid linker
source                   1..15
                         mol_type = protein
                         organism = synthetic construct
SEQUENCE: 30
GGGGSGGGGS GGGGS                                                             15

SEQ ID NO: 31            moltype = DNA   length = 1458
FEATURE                  Location/Qualifiers
misc_feature             1..1458
                         note = Synthetic nucleotide sequence
source                   1..1458
                         mol_type = other DNA
                         organism = synthetic construct
SEQUENCE: 31
atggccttac cagtgaccgc cttgctcctg ccgctggcct tgctgctcca cgccgccagg            60
ccggacatcc agatgacaca gactacatcc tccctgtctg cctctctggg agacagagtc          120
accatcagtt gcagggcaag tcaggacatt agtaaatatt taaattggta tcagcagaaa          180
ccagatggaa ctgttaaact cctgatctac catacatcaa gattacactc aggagtccca          240
tcaaggttca gtggcagtgg gtctggaaca gattattctc tcaccattag caacctggag          300
caagaagata ttgccactta cttttgccaa caggtaata cgcttccgta cacgttcgga           360
ggggggacca agctggagat cacaggtggc ggtggctcgg gcggtggtgg gtcgggtggc          420
ggcggatctg aggtgaaact gcaggagtca ggacctggcc tggtggcgcc ctcacagagc          480
ctgtccgtca catgcactgt ctcagggtc tcattacccg actatggtgt aagctggatt           540
cgccagcctc cacgaaaggg tctggagtgg ctgggagtaa tatggggtag tgaaaccaca          600
tactataatt cagctctcaa atccagactg accatcatca aggacaactc caagagccaa          660
gttttcttaa aaatgaacag tctgcaaact gatgacacag ccatttacta ctgtgccaaa          720
cattattact acggtggtag ctatgctatg gactactggg gccaaggaac ctcagtcacc          780
gtctcctcag ccacgacgcc agcgccgcga ccaccaacac cggcgcccac catcgcgtc           840
cagcccctgt ccctgcgccc agaggcgtgc cggccagcgg cggggggcgc agtgcacacg          900
aggggctgg acttcgcctg tgatatctac atctgggcgc cctggccgg acttgtggg             960
gtccttctcc tgtcactggt tatcaccctt tactgcaaac ggggcagaaa gaaactcctg         1020
tatatattca acaaccatt tatgagacca gtacaaacta ctcaagagga agatggctgt          1080
agctgccgat tccagaaga agaagaagga ggatgtgaac tgagagtgaa gttcagcagg           1140
```

```
agcgcagacg ccccgcgta caagcagggc cagaaccagc tctataacga gctcaatcta  1200
ggacgaagag aggagtacga tgttttggac aagagacgtg gccgggaccc tgagatgggg  1260
ggaaagccga gaaggaagaa ccctcaggaa ggcctgtaca atgaactgca gaaagataag  1320
atggcggagc cctacagtga gattgggatg aaggcgagc gccggagggg caaggggcac  1380
gatggccttt accagggtct cagtacagcc accaaggaca cctacgacgc ccttcacatg  1440
caggccctgc cccctcgc                                                1458
```

| SEQ ID NO: 32 | moltype = AA length = 486 |
|---|---|
| FEATURE | Location/Qualifiers |
| REGION | 1..486 |
| | note = Synthetic amino acid |
| source | 1..486 |
| | mol_type = protein |
| | organism = synthetic construct |

```
SEQUENCE: 32
MALPVTALLL PLALLLHAAR PDIQMTQTTS SLSASLGDRV TISCRASQDI SKYLNWYQQK   60
PDGTVKLLIY HTSRLHSGVP SRFSGSGSGT DYSLTISNLE QEDIATYFCQ QGNTLPYTFG  120
GGTKLEITGG GGSGGGGSGG GGSEVKLQES GPGLVAPSQS LSVTCTVSGV SLPDYGVSWI  180
RQPPRKGLEW LGVIWGSETT YYNSALKSRL TIIKDNSKSQ VFLKMNSLQT DDTAIYYCAK  240
HYYYGGSYAM DYWGQGTSVT VSSTTTPAPR PPTPAPTIAS QPLSLRPEAC RPAAGGAVHT  300
RGLDFACDIY IWAPLAGTCG VLLLSLVITL YCKRGRKKLL YIFKQPFMRP VQTTQEEDGC  360
SCRFPEEEEG GCELRVKFSR SADAPAYKQG QNQLYNELNL GRREEYDVLD KRRGRDPEMG  420
GKPRRKNPQE GLYNELQKDK MAEAYSEIGM KGERRRGKGH DGLYQGLSTA TKDTYDALHM  480
QALPPR                                                             486
```

| SEQ ID NO: 33 | moltype = DNA length = 1383 |
|---|---|
| FEATURE | Location/Qualifiers |
| misc_feature | 1..1383 |
| | note = Synthetic nucleotide sequence |
| source | 1..1383 |
| | mol_type = other DNA |
| | organism = synthetic construct |

```
SEQUENCE: 33
atgctgctgc tggtgaccag cctgctgctg tgcgagctgc cccacccgc ctttctgctg   60
atccccgaca tccagatgac ccagaccacc tccagcctga cgccagcct gggcgaccgg  120
gtgaccatca gctgccgggc cagccaggac atcagcaagt acctgaactg gtatcagcag  180
aagcccgacg gcaccgtcaa gctgctgatc taccacacca gccggctgca cagcggcgtg  240
cccagccggt ttagcggcag cggctccggc accgactaca gcctgaccat ctccaacctg  300
gaacaggaag atatcgccac ctactttgc cagcagggca acactgcc ctacaccttt  360
ggcggcggaa caaagctgga aatcaccggc agcaccccg gcagcggcaa gcctggcagc  420
ggcgagggca gcaccaaggg cgaggtgaag ctgcaggaaa gcggcccctgg cctggtggcc  480
cccagccaga gcctgagcgt gacctgcacc gtgagcggcg tgagcctgcc cgactacggc  540
gtgagctgga tccggcagcc cccaggaag ggcctgaat ggctgggcgt gatctgggc  600
agcgagacca cctactacaa cagcgccctg aagagccggc tgaccatcat caaggacaac  660
agcaagagcc aggtgttcct gaagatgaac agcctgcaga ccgacgacac cgccatctac  720
tactgcgcca agcactacta ctacggcggc agctacgcca tggactactg gggccagggc  780
accagcgtga ccgtgagcag cgaatctaag tacggaccgc cctgcccccc ttgcccatg  840
ttctgggtgc tggtggtggt cggaggcgtg ctggcctgct acagcctgct ggtcaccgtg  900
gccttcatca tctttggt gaaacgggc agaaagaaac tcctgtatat attcaaacaa  960
ccatttatga ccagtaca aactactcaa gaggaagatg gctgtagctg ccgatttcca 1020
gaagaagaag aaggaggatg tgaactgcgg gtgaagttca gcagaagcgc cgacgcccct 1080
gcctaccagc agggcagaa tcagctgtac aacgagctga acctgggcag aagggaagag 1140
tacgacgtcc tggataagcg gagaggccgg accctgaga tgggcggcaa gcctcggcgg 1200
aagaaccccc aggaaggcct gtataacgaa ctgcagaaag acaagatggc cgaggcctac 1260
agcgagatcg gcatgaaggg cgagcggagg cggggcaagg gccacgacgg cctgtatcag 1320
ggcctgtcca ccgccaccaa ggatacctac gacgccctgc acatgcaggc cctgcccca 1380
agg                                                               1383
```

| SEQ ID NO: 34 | moltype = AA length = 461 |
|---|---|
| FEATURE | Location/Qualifiers |
| REGION | 1..461 |
| | note = Synthetic amino acid |
| source | 1..461 |
| | mol_type = protein |
| | organism = synthetic construct |

```
SEQUENCE: 34
MLLLVTSLLL CELPHPAFLL IPDIQMTQTT SSLSASLGDR VTISCRASQD ISKYLNWYQQ   60
KPDGTVKLLI YHTSRLHSGV PSRFSGSGSG TDYSLTISNL EQEDIATYFC QQGNTLPYTF  120
GGGTKLEITG STSGSGKPGS GEGSTKGEVK LQESGPGLVA PSQSLSVTCT VSGVSLPDYG  180
VSWIRQPPRK GLEWLGVIWG SETTYYNSAL KSRLTIIKDN SKSQVFLKMN SLQTDDTAIY  240
YCAKHYYYGG SYAMDYWGQG TSVTVSSESK YGPPCPPCPM FWVLVVVGGV LACYSLLVTV  300
AFIIFWVKRG RKKLLYIFKQ PFMRPVQTTQ EEDGCSCRFP EEEEGGCELR VKFSRSADAP  360
AYQQGQNQLY NELNLGRREE YDVLDKRRGR DPEMGGKPRR KNPQEGLYNE LQKDKMAEAY  420
SEIGMKGERR RGKHDGLYQ GLSTATKDTY DALHMQALPP R                      461
```

| SEQ ID NO: 35 | moltype = DNA length = 1467 |
|---|---|
| FEATURE | Location/Qualifiers |
| misc_feature | 1..1467 |
| | note = Synthetic nucleotide sequence |

```
source                  1..1467
                        mol_type = other DNA
                        organism = synthetic construct
SEQUENCE: 35
atgcttctcc tggtgacaag ccttctgctc tgtgagttac cacacccagc attcctcctg    60
atcccagaca tccagatgac acagactaca tcctccctgt ctgcctctct gggagacaga   120
gtcaccatca gttgcagggc aagtcaggac attagtaaat atttaaattg gtatcagcag   180
aaaccagatg gaactgttaa actcctgatc taccatacat caagattaca ctcaggagtc   240
ccatcaaggt tcagtggcag tgggtctgga acagattatc tctcaccat tagcaactg   300
gagcaagaag atattgccac ttacttttgc caacagggta tacgcttcc gtacacgttc   360
ggagggggga ctaagttgga aataacaggc tccacctctg gatccggcaa gcccggatct   420
ggcgaggat ccaccaaggg cgaggtgaaa ctgcaggagt caggacctgg cctggtggcg   480
ccctcacaga gcctgtccgt cacatgcact gtctcagggg tctcattacc cgactatggt   540
gtaagctgga ttcgccagcc tccacgaaag ggtctggagt ggctgggagt aatatgggat   600
agtgaaacca catactataa ttcagctctc aaatccagac tgaccatcat caaggacaac   660
tccaagagcc aagttttctt aaaaatgaac agtctgcaaa ctgatgacac agccatttac   720
tactgtgcca acattatta ctacggtggt agctatgcta tggactactg gggtcaagga   780
acctcagtca ccgtctcctc agcggccgca ttgaagtta tgtatcctcc tccttaccta   840
gacaatgaga agagcaatgg aaccattatc catgtgaaag gaaacacct ttgtccaagt   900
ccctatttc ccgaccttc taagcccttt gggtgctgg tggtggttgg gggagtcctg   960
gcttgctata gcttgctagt aacagtggcc tttattattt tctgggtgag gagtaagagg  1020
agcagctcc tgcacagtga ctacatgaac atgactcccc gccgcccgg gccccaccgc  1080
aagcattacc agcccatgc cccaccacg gacttcgcag cctatcgctc cagagtgaag  1140
ttcagcagga gcgcagacgc ccccgcgtac cagcagggcc agaaccagct ctataacgag  1200
ctcaatctag gacgaagaga ggagtacgat gttttggaca gagacgtgg ccgggaccct  1260
gagatggggg gaaagccgag aaggaagaac cctcaggaag gcctgtacaa tgaactgcag  1320
aaagataaga tggcggaggc ctacagtgag attgggatga aggcgagcg ccggagggcg  1380
aagggcacg atggccttta ccagggtctc agtacagcca ccaaggacac ctacgacgcc  1440
cttcacatgc aggccctgcc ccctcgc                                     1467

SEQ ID NO: 36           moltype = AA  length = 489
FEATURE                 Location/Qualifiers
REGION                  1..489
                        note = Synthetic amino acid
source                  1..489
                        mol_type = protein
                        organism = synthetic construct
SEQUENCE: 36
MLLLVTSLLL CELPHPAFLL IPDIQMTQTT SSLSASLGDR VTISCRASQD ISKYLNWYQQ    60
KPDGTVKLLI YHTSRLHSGV PSRFSGSGSG TDYSLTISNL EQEDIATYFC QQGNTLPYTF   120
GGGTKLEITG STSGSGKPGS GEGSTKGEVK LQESGPGLVA PSQSLSVTCT VSGVSLPDYG   180
VSWIRQPPRK GLEWLGVIWG SETTYYNSAL KSRLTIIKDN SKSQVFLKMN SLQTDDTAIY   240
YCAKHYYYGG SYAMDYWGQG TSVTVSSAAA IEVMYPPPYL DNEKSNGTII HVKGKHLCPS   300
PLFPGPSKPF WVLVVVGGVL ACYSLLVTVA FIIFWVRSKR SRLLHSDYMN MTPRRPGPTR   360
KHYQPYAPPR DFAAYRSRVK FSRSADAPAY QQGQNQLYNE LNLGRREEYD VLDKRRGRDP   420
EMGGKPRRKN PQEGLYNELQ KDKMAEAYSE IGMKGERRRG KGHDGLYQGL STATKDTYDA   480
LHMQALPPR                                                          489

SEQ ID NO: 37           moltype = AA  length = 246
FEATURE                 Location/Qualifiers
REGION                  1..246
                        note = Synthetic amino acid
source                  1..246
                        mol_type = protein
                        organism = synthetic construct
SEQUENCE: 37
DIVLTQSPAI LSASPGEKVT MTCRASSSVN YMDWYQKKPG SSPKPWIYAT SNLASGVPAR    60
FSGSGSGTSY SLTISRVEAE DAATYYCQQW SFNPPTFGGG TKLEIKGSTS GSGKPGSGEG   120
STKGEVQLQQ SGAELVKPGA SVKMSCKASG YTFTSYNMHW VKQTPGQGLE WIGAIYPGNG   180
DTSYNQKFKG KATLTADKSS STAYMQLSSL TSEDSADYYC ARSNYYGSSY WFFDVWGAGT   240
TVTVSS                                                             246

SEQ ID NO: 38           moltype = AA  length = 106
FEATURE                 Location/Qualifiers
REGION                  1..106
                        note = Synthetic amino acid
source                  1..106
                        mol_type = protein
                        organism = synthetic construct
SEQUENCE: 38
DIVLTQSPAI LSASPGEKVT MTCRASSSVN YMDWYQKKPG SSPKPWIYAT SNLASGVPAR    60
FSGSGSGTSY SLTISRVEAE DAATYYCQQW SFNPPTFGGG TKLEIK                 106

SEQ ID NO: 39           moltype = AA  length = 10
FEATURE                 Location/Qualifiers
REGION                  1..10
                        note = Synthetic amino acid
source                  1..10
                        mol_type = protein
```

-continued

```
                         organism = synthetic construct
SEQUENCE: 39
RASSSVNYMD                                                           10

SEQ ID NO: 40            moltype = AA  length = 7
FEATURE                  Location/Qualifiers
REGION                   1..7
                         note = Synthetic amino acid
source                   1..7
                         mol_type = protein
                         organism = synthetic construct
SEQUENCE: 40
ATSNLAS                                                              7

SEQ ID NO: 41            moltype = AA  length = 9
FEATURE                  Location/Qualifiers
REGION                   1..9
                         note = Synthetic amino acid
source                   1..9
                         mol_type = protein
                         organism = synthetic construct
SEQUENCE: 41
QQWSFNPPT                                                            9

SEQ ID NO: 42            moltype = AA  length = 122
FEATURE                  Location/Qualifiers
REGION                   1..122
                         note = Synthetic amino acid
source                   1..122
                         mol_type = protein
                         organism = synthetic construct
SEQUENCE: 42
EVQLQQSGAE LVKPGASVKM SCKASGYTFT SYNMHWVKQT PGQGLEWIGA IYPGNGDTSY     60
NQKFKGKATL TADKSSSTAY MQLSSLTSED SADYYCARSN YYGSSYWFFD VWGAGTTVTV    120
SS                                                                  122

SEQ ID NO: 43            moltype = AA  length = 5
FEATURE                  Location/Qualifiers
REGION                   1..5
                         note = Synthetic amino acid
source                   1..5
                         mol_type = protein
                         organism = synthetic construct
SEQUENCE: 43
SYNMH                                                                5

SEQ ID NO: 44            moltype = AA  length = 17
FEATURE                  Location/Qualifiers
REGION                   1..17
                         note = Synthetic amino acid
source                   1..17
                         mol_type = protein
                         organism = synthetic construct
SEQUENCE: 44
AIYPGNGDTS YNQKFKG                                                   17

SEQ ID NO: 45            moltype = AA  length = 246
FEATURE                  Location/Qualifiers
REGION                   1..246
                         note = Synthetic amino acid
source                   1..246
                         mol_type = protein
                         organism = synthetic construct
SEQUENCE: 45
QVQLQQSGPG LVKPSQTLSL TCAISGDSVS SNSAAWNWIR QSPSRGLEWL GRTYYRSKWY     60
NDYAVSVKSR ITINPDTSKN QFSLQLNSVT PEDTAVYYCA REVTGDLEDA FDIWGQGTMV    120
TVSSGGGGSG GGGSGGGGSD IQMTQSPSSL SASVGDRVTI TCRASQTIWS YLNWYQQRPG    180
KAPNLLIYAA SSLQSGVPSR FSGRGSGTDF TLTISSLQAE DFATYYCQQS YSIPQTFGQG    240
TKLEIK                                                              246

SEQ ID NO: 46            moltype = AA  length = 124
FEATURE                  Location/Qualifiers
REGION                   1..124
                         note = Synthetic amino acid
source                   1..124
                         mol_type = protein
                         organism = synthetic construct
SEQUENCE: 46
QVQLQQSGPG LVKPSQTLSL TCAISGDSVS SNSAAWNWIR QSPSRGLEWL GRTYYRSKWY     60
```

```
NDYAVSVKSR ITINPDTSKN QFSLQLNSVT PEDTAVYYCA REVTGDLEDA FDIWGQGTMV    120
TVSS                                                                124

SEQ ID NO: 47           moltype = AA  length = 10
FEATURE                 Location/Qualifiers
REGION                  1..10
                        note = Synthetic amino acid
source                  1..10
                        mol_type = protein
                        organism = synthetic construct
SEQUENCE: 47
GDSVSSNSAA                                                          10

SEQ ID NO: 48           moltype = AA  length = 9
FEATURE                 Location/Qualifiers
REGION                  1..9
                        note = Synthetic amino acid
source                  1..9
                        mol_type = protein
                        organism = synthetic construct
SEQUENCE: 48
TYYRSKWYN                                                           9

SEQ ID NO: 49           moltype = AA  length = 14
FEATURE                 Location/Qualifiers
REGION                  1..14
                        note = Synthetic amino acid
source                  1..14
                        mol_type = protein
                        organism = synthetic construct
SEQUENCE: 49
AREVTGDLED AFDI                                                     14

SEQ ID NO: 50           moltype = AA  length = 107
FEATURE                 Location/Qualifiers
REGION                  1..107
                        note = Synthetic amino acid
source                  1..107
                        mol_type = protein
                        organism = synthetic construct
SEQUENCE: 50
DIQMTQSPSS LSASVGDRVT ITCRASQTIW SYLNWYQQRP GKAPNLLIYA ASSLQSGVPS    60
RFSGRGSGTD FTLTISSLQA EDFATYYCQQ SYSIPQTFGQ GTKLEIK                  107

SEQ ID NO: 51           moltype = AA  length = 6
FEATURE                 Location/Qualifiers
REGION                  1..6
                        note = Synthetic amino acid
source                  1..6
                        mol_type = protein
                        organism = synthetic construct
SEQUENCE: 51
QTIWSY                                                              6

SEQ ID NO: 52           moltype =     length =
SEQUENCE: 52
000

SEQ ID NO: 53           moltype = AA  length = 9
FEATURE                 Location/Qualifiers
REGION                  1..9
                        note = Synthetic amino acid
source                  1..9
                        mol_type = protein
                        organism = synthetic construct
SEQUENCE: 53
QQSYSIPQT                                                           9

SEQ ID NO: 54           moltype = AA  length = 246
FEATURE                 Location/Qualifiers
REGION                  1..246
                        note = Synthetic amino acid
source                  1..246
                        mol_type = protein
                        organism = synthetic construct
SEQUENCE: 54
QVQLQQSGPG MVKPSQTLSL TCAISGDSVS SNSVAWNWIR QSPSRGLEWL GRTYYRSTWY    60
NDYAVSMKSR ITINPDTNKN QFSLQLNSVT PEDTAVYYCA REVTGDLEDA FDIWGQGTMV    120
TVSSGGGGSG GGGSGGGGSD IQMIQSPSSL SASVGDRVTI TCRASQTIWS YLNWYRQRPG    180
```

```
EAPNLLIYAA SSLQSGVPSR FSGRGSGTDF TLTISSLQAE DFATYYCQQS YSIPQTFGQG    240
TKLEIK                                                              246

SEQ ID NO: 55           moltype = AA  length = 124
FEATURE                 Location/Qualifiers
REGION                  1..124
                        note = Synthetic amino acid
source                  1..124
                        mol_type = protein
                        organism = synthetic construct
SEQUENCE: 55
QVQLQQSGPG MVKPSQTLSL TCAISGDSVS SNSVAWNWIR QSPSRGLEWL GRTYYRSTWY    60
NDYAVSMKSR ITINPDTNKN QFSLQLNSVT PEDTAVYYCA REVTGDLEDA FDIWGQGTMV   120
TVSS                                                                124

SEQ ID NO: 56           moltype = AA  length = 10
FEATURE                 Location/Qualifiers
REGION                  1..10
                        note = Synthetic amino acid
source                  1..10
                        mol_type = protein
                        organism = synthetic construct
SEQUENCE: 56
GDSVSSNSVA                                                          10

SEQ ID NO: 57           moltype = AA  length = 9
FEATURE                 Location/Qualifiers
REGION                  1..9
                        note = Synthetic amino acid
source                  1..9
                        mol_type = protein
                        organism = synthetic construct
SEQUENCE: 57
TYYRSTWYN                                                           9

SEQ ID NO: 58           moltype = AA  length = 14
FEATURE                 Location/Qualifiers
REGION                  1..14
                        note = Synthetic amino acid
source                  1..14
                        mol_type = protein
                        organism = synthetic construct
SEQUENCE: 58
AREVTGDLED AFDI                                                     14

SEQ ID NO: 59           moltype = AA  length = 107
FEATURE                 Location/Qualifiers
REGION                  1..107
                        note = Synthetic amino acid
source                  1..107
                        mol_type = protein
                        organism = synthetic construct
SEQUENCE: 59
DIQMIQSPSS LSASVGDRVT ITCRASQTIW SYLNWYRQRP GEAPNLLIYA ASSLQSGVPS    60
RFSGRGSGTD FTLTISSLQA EDFATYYCQQ SYSIPQTFGQ GTKLEIK                 107

SEQ ID NO: 60           moltype = AA  length = 6
FEATURE                 Location/Qualifiers
REGION                  1..6
                        note = Synthetic amino acid
source                  1..6
                        mol_type = protein
                        organism = synthetic construct
SEQUENCE: 60
QTIWSY                                                              6

SEQ ID NO: 61           moltype =     length =
SEQUENCE: 61
000

SEQ ID NO: 62           moltype = AA  length = 9
FEATURE                 Location/Qualifiers
REGION                  1..9
                        note = Synthetic amino acid
source                  1..9
                        mol_type = protein
                        organism = synthetic construct
SEQUENCE: 62
QQSYSIPQT                                                           9
```

```
SEQ ID NO: 63              moltype = AA   length = 246
FEATURE                    Location/Qualifiers
REGION                     1..246
                           note = Synthetic amino acid
source                     1..246
                           mol_type = protein
                           organism = synthetic construct
SEQUENCE: 63
DIVLTQSPAS LAMSLGKRAT ISCRASESVS VIGAHLIHWY QQKPGQPPKL LIYLASNLET    60
GVPARFSGSG SGTDFTLTID PVEEDDVAIY SCLQSRIFPR TFGGGTKLEI KGSTSGSGKP   120
GSGEGSTKGQ IQLVQSGPEL KKPGETVKIS CKASGYTFTD YSINWVKRAP GKGLKWMGWI   180
NTETREPAYA YDFRGRFAFS LETSASTAYL QINNLKYEDT ATYFCALDYS YAMDYWGQGT   240
SVTVSS                                                              246

SEQ ID NO: 64              moltype = AA   length = 111
FEATURE                    Location/Qualifiers
REGION                     1..111
                           note = Synthetic amino acid
source                     1..111
                           mol_type = protein
                           organism = synthetic construct
SEQUENCE: 64
DIVLTQSPAS LAMSLGKRAT ISCRASESVS VIGAHLIHWY QQKPGQPPKL LIYLASNLET    60
GVPARFSGSG SGTDFTLTID PVEEDDVAIY SCLQSRIFPR TFGGGTKLEI K            111

SEQ ID NO: 65              moltype = AA   length = 15
FEATURE                    Location/Qualifiers
REGION                     1..15
                           note = Synthetic amino acid
source                     1..15
                           mol_type = protein
                           organism = synthetic construct
SEQUENCE: 65
RASESVSVIG AHLIH                                                    15

SEQ ID NO: 66              moltype = AA   length = 7
FEATURE                    Location/Qualifiers
REGION                     1..7
                           note = Synthetic amino acid
source                     1..7
                           mol_type = protein
                           organism = synthetic construct
SEQUENCE: 66
LASNLET                                                             7

SEQ ID NO: 67              moltype = AA   length = 9
FEATURE                    Location/Qualifiers
REGION                     1..9
                           note = Synthetic amino acid
source                     1..9
                           mol_type = protein
                           organism = synthetic construct
SEQUENCE: 67
LQSRIFPRT                                                           9

SEQ ID NO: 68              moltype = AA   length = 117
FEATURE                    Location/Qualifiers
REGION                     1..117
                           note = Synthetic amino acid
source                     1..117
                           mol_type = protein
                           organism = synthetic construct
SEQUENCE: 68
QIQLVQSGPE LKKPGETVKI SCKASGYTFT DYSINWVKRA PGKGLKWMGW INTETREPAY    60
AYDFRGRFAF SLETSASTAY LQINNLKYED TATYFCALDY SYAMDYWGQG TSVTVSS      117

SEQ ID NO: 69              moltype = AA   length = 5
FEATURE                    Location/Qualifiers
REGION                     1..5
                           note = Synthetic amino acid
source                     1..5
                           mol_type = protein
                           organism = synthetic construct
SEQUENCE: 69
DYSIN                                                               5

SEQ ID NO: 70              moltype = AA   length = 17
FEATURE                    Location/Qualifiers
```

| | | |
|---|---|---|
| REGION | 1..17 | |
| | note = Synthetic amino acid | |
| source | 1..17 | |
| | mol_type = protein | |
| | organism = synthetic construct | |

SEQUENCE: 70
WINTETREPA YAYDFRG                                                      17

| | | |
|---|---|---|
| SEQ ID NO: 71 | moltype = AA   length = 8 | |
| FEATURE | Location/Qualifiers | |
| REGION | 1..8 | |
| | note = Synthetic amino acid | |
| source | 1..8 | |
| | mol_type = protein | |
| | organism = synthetic construct | |

SEQUENCE: 71
DYSYAMDY                                                                 8

| | | |
|---|---|---|
| SEQ ID NO: 72 | moltype = AA   length = 246 | |
| FEATURE | Location/Qualifiers | |
| REGION | 1..246 | |
| | note = Synthetic amino acid | |
| source | 1..246 | |
| | mol_type = protein | |
| | organism = synthetic construct | |

SEQUENCE: 72
DIVLTQSPPS LAMSLGKRAT ISCRASESVT ILGSHLIYWY QQKPGQPPTL LIQLASNVQT        60
GVPARFSGSG SRTDFTLTID PVEEDDVAVY YCLQSRTIPR TFGGGTKLEI KGSTSGSGKP       120
GSGEGSTKGQ IQLVQSGPEL KKPGETVKIS CKASGYTFRH YSMNWVKQAP GKGLKWMGRI       180
NTESGVPIYA DDFKGRFAFS VETSASTAYL VINNLKDEDT ASYFCSNDYL YSLDFWGQGT       240
ALTVSS                                                                 246

| | | |
|---|---|---|
| SEQ ID NO: 73 | moltype = AA   length = 111 | |
| FEATURE | Location/Qualifiers | |
| REGION | 1..111 | |
| | note = Synthetic amino acid | |
| source | 1..111 | |
| | mol_type = protein | |
| | organism = synthetic construct | |

SEQUENCE: 73
DIVLTQSPPS LAMSLGKRAT ISCRASESVT ILGSHLIYWY QQKPGQPPTL LIQLASNVQT        60
GVPARFSGSG SRTDFTLTID PVEEDDVAVY YCLQSRTIPR TFGGGTKLEI K                111

| | | |
|---|---|---|
| SEQ ID NO: 74 | moltype = AA   length = 15 | |
| FEATURE | Location/Qualifiers | |
| REGION | 1..15 | |
| | note = Synthetic amino acid | |
| source | 1..15 | |
| | mol_type = protein | |
| | organism = synthetic construct | |

SEQUENCE: 74
RASESVTILG SHLIY                                                        15

| | | |
|---|---|---|
| SEQ ID NO: 75 | moltype = AA   length = 7 | |
| FEATURE | Location/Qualifiers | |
| REGION | 1..7 | |
| | note = Synthetic amino acid | |
| source | 1..7 | |
| | mol_type = protein | |
| | organism = synthetic construct | |

SEQUENCE: 75
LASNVQT                                                                  7

| | | |
|---|---|---|
| SEQ ID NO: 76 | moltype = AA   length = 9 | |
| FEATURE | Location/Qualifiers | |
| REGION | 1..9 | |
| | note = Synthetic amino acid | |
| source | 1..9 | |
| | mol_type = protein | |
| | organism = synthetic construct | |

SEQUENCE: 76
LQSRTIPRT                                                                9

| | | |
|---|---|---|
| SEQ ID NO: 77 | moltype = AA   length = 117 | |
| FEATURE | Location/Qualifiers | |
| REGION | 1..117 | |
| | note = Synthetic amino acid | |
| source | 1..117 | |
| | mol_type = protein | |

```
                       organism = synthetic construct
SEQUENCE: 77
QIQLVQSGPE LKKPGETVKI SCKASGYTFR HYSMNWVKQA PGKGLKWMGR INTESGVPIY    60
ADDFKGRFAF SVETSASTAY LVINNLKDED TASYFCSNDY LYSLDFWGQG TALTVSS      117

SEQ ID NO: 78          moltype = AA  length = 5
FEATURE                Location/Qualifiers
REGION                 1..5
                       note = Synthetic amino acid
source                 1..5
                       mol_type = protein
                       organism = synthetic construct
SEQUENCE: 78
HYSMN                                                                 5

SEQ ID NO: 79          moltype = AA  length = 17
FEATURE                Location/Qualifiers
REGION                 1..17
                       note = Synthetic amino acid
source                 1..17
                       mol_type = protein
                       organism = synthetic construct
SEQUENCE: 79
RINTESGVPI YADDFKG                                                   17

SEQ ID NO: 80          moltype = AA  length = 8
FEATURE                Location/Qualifiers
REGION                 1..8
                       note = Synthetic amino acid
source                 1..8
                       mol_type = protein
                       organism = synthetic construct
SEQUENCE: 80
DYLYSLDF                                                              8

SEQ ID NO: 81          moltype = AA  length = 121
FEATURE                Location/Qualifiers
REGION                 1..121
                       note = Synthetic amino acid
source                 1..121
                       mol_type = protein
                       organism = synthetic construct
SEQUENCE: 81
EVQLLESGGG LVQPGGSLRL SCAASGFTFS SYAMSWVRQA PGKGLEWVSS ISGSGDYIYY    60
ADSVKGRFTI SRDISKNTLY LQMNSLRAED TAVYYCAKEG TGANSSLADY RGQGTLVTVS   120
S                                                                  121

SEQ ID NO: 82          moltype = AA  length = 8
FEATURE                Location/Qualifiers
REGION                 1..8
                       note = Synthetic amino acid
source                 1..8
                       mol_type = protein
                       organism = synthetic construct
SEQUENCE: 82
GFTFSSYA                                                              8

SEQ ID NO: 83          moltype = AA  length = 8
FEATURE                Location/Qualifiers
REGION                 1..8
                       note = Synthetic amino acid
source                 1..8
                       mol_type = protein
                       organism = synthetic construct
SEQUENCE: 83
ISGSGDYI                                                              8

SEQ ID NO: 84          moltype = AA  length = 14
FEATURE                Location/Qualifiers
REGION                 1..14
                       note = Synthetic amino acid
source                 1..14
                       mol_type = protein
                       organism = synthetic construct
SEQUENCE: 84
AKEGTGANSS LADY                                                      14

SEQ ID NO: 85          moltype =    length =
SEQUENCE: 85
```

```
SEQ ID NO: 86           moltype =    length =
SEQUENCE: 86
000

SEQ ID NO: 87           moltype =    length =
SEQUENCE: 87
000

SEQ ID NO: 88           moltype =    length =
SEQUENCE: 88
000

SEQ ID NO: 89           moltype =    length =
SEQUENCE: 89
000

SEQ ID NO: 90           moltype =    length =
SEQUENCE: 90
000

SEQ ID NO: 91           moltype =    length =
SEQUENCE: 91
000

SEQ ID NO: 92           moltype =    length =
SEQUENCE: 92
000

SEQ ID NO: 93           moltype =    length =
SEQUENCE: 93
000

SEQ ID NO: 94           moltype =    length =
SEQUENCE: 94
000

SEQ ID NO: 95           moltype =    length =
SEQUENCE: 95
000

SEQ ID NO: 96           moltype =    length =
SEQUENCE: 96
000

SEQ ID NO: 97           moltype =    length =
SEQUENCE: 97
000

SEQ ID NO: 98           moltype =    length =
SEQUENCE: 98
000

SEQ ID NO: 99           moltype =    length =
SEQUENCE: 99
000

SEQ ID NO: 100          moltype =    length =
SEQUENCE: 100
000

SEQ ID NO: 101          moltype =    length =
SEQUENCE: 101
000

SEQ ID NO: 102          moltype =    length =
SEQUENCE: 102
000

SEQ ID NO: 103          moltype =    length =
SEQUENCE: 103
000

SEQ ID NO: 104          moltype =    length =
SEQUENCE: 104
000

SEQ ID NO: 105          moltype =    length =
```

```
SEQUENCE: 105
000

SEQ ID NO: 106          moltype =    length =
SEQUENCE: 106
000

SEQ ID NO: 107          moltype =    length =
SEQUENCE: 107
000

SEQ ID NO: 108          moltype =    length =
SEQUENCE: 108
000

SEQ ID NO: 109          moltype =    length =
SEQUENCE: 109
000

SEQ ID NO: 110          moltype =    length =
SEQUENCE: 110
000

SEQ ID NO: 111          moltype =    length =
SEQUENCE: 111
000

SEQ ID NO: 112          moltype =    length =
SEQUENCE: 112
000

SEQ ID NO: 113          moltype = AA  length = 42
FEATURE                 Location/Qualifiers
REGION                  1..42
                        note = Synthetic hinge domain
source                  1..42
                        mol_type = protein
                        organism = synthetic construct
SEQUENCE: 113
AAAIEVMYPP PYLDNEKSNG TIIHVKGKHL CPSPLFPGPS KP                          42

SEQ ID NO: 114          moltype = AA  length = 28
FEATURE                 Location/Qualifiers
REGION                  1..28
                        note = Synthetic transmembrane domain
source                  1..28
                        mol_type = protein
                        organism = synthetic construct
SEQUENCE: 114
MFWVLVVVGG VLACYSLLVT VAFIIFWV                                         28

SEQ ID NO: 115          moltype = AA  length = 112
FEATURE                 Location/Qualifiers
REGION                  1..112
                        note = Synthetic signaling domain
source                  1..112
                        mol_type = protein
                        organism = synthetic construct
SEQUENCE: 115
RVKFSRSADA PAYKQGQNQL YNELNLGRRE EYDVLDKRRG RDPEMGGKPR RKNPQEGLYN       60
ELQKDKMAEA YSEIGMKGER RRGKGHDGLY QGLSTATKDT YDALHMQALP PR              112

SEQ ID NO: 116          moltype = DNA  length = 1467
FEATURE                 Location/Qualifiers
misc_feature            1..1467
                        note = Synthetic nucleotide sequence
source                  1..1467
                        mol_type = other DNA
                        organism = synthetic construct
SEQUENCE: 116
atggccttac cagtgaccgc cttgctcctg ccgctggcct tgctgctcca cgccgccagg       60
ccggacatcc agatgacaca gactacatcc tccctgtctg cctctctggg agacagagtc      120
accatcagtt gcagggcaag tcaggacatt agtaaatatt taaattggta tcagcagaaa      180
ccagatggaa ctgttaaact cctgatctac catacatcaa gattacactc aggagtccca      240
tcaaggttca gtggcagtgg gtctggaaca gattattctc tcaccattag caacctggag      300
caagaagata ttgccactta cttttgccaa caggtaata cgcttccgta cacgttcgga      360
gggggacca agctggagat cacaggctcc acctctggat ccgcaagcc cggatctggc        420
gagggatcca ccaagggcga ggtgaaactg caggagtcag gacctggcct ggtggcgccc      480
tcacagagcc tgtccgtcac atgcactgtc tcaggggtct cattacccga ctatggtgta      540
```

```
agctggattc gccagcctcc acgaaagggt ctggagtggc tgggagtaat atgggggtagt    600
gaaaccacat actataattc agctctcaaa tccagactga ccatcatcaa ggacaactcc    660
aagagccaag ttttcttaaa aatgaacagt ctgcaaactg atgacacagc catttactac    720
tgtgccaaac attattacta cggtggtagc tatgctatgg actactgggg ccaaggaacc    780
tcagtcaccg tctcctcaac cacgacgcca gcgccgcgac caccaaccac ggcgcccacc    840
atcgcgtcgc agcccctgtc cctgcgccca gaggcgtgcc ggccagcggc gggggcgca    900
gtgcacacga gggggctgga cttcgcctgt gatatctaca tctgggcgcc cttggccggg    960
acttgtgggg tccttctcct gtcactggtt atcacccttt actgcaaacg ggcagaaag   1020
aaactcctgt atatattcaa acaaccattt atgagaccac tacaaactac tcaagaggaa   1080
gatggctgta gctgccgatt ccagaagaa gaagaaggag gatgtgaact gagagtgaag   1140
ttcagcagga gcgcagacgc ccccgcgtac cagcagggcc agaaccagct ctataacgag   1200
ctcaatctag gacgaagaga ggagtacgat gttttggaca gagacgtgg ccgggaccct   1260
gagatgggg gaaagccgag aaggaagaac cctcaggaag gcctgtacaa tgaactgcag   1320
aaagataaga tggcggaggc ctacagtgag attgggatga aggcgagcg ccggagggc   1380
aaggggcacg atggccttta ccagggtctc agtacagcca ccaaggacac ctacgacgcc   1440
cttcacatgc aggcccctgcc ccctcgc                                       1467

SEQ ID NO: 117         moltype = AA   length = 489
FEATURE                Location/Qualifiers
REGION                 1..489
                       note = Synthetic amino acid
source                 1..489
                       mol_type = protein
                       organism = synthetic construct
SEQUENCE: 117
MALPVTALLL PLALLLHAAR PDIQMTQTTS SLSASLGDRV TISCRASQDI SKYLNWYQQK     60
PDGTVKLLIY HTSRLHSGVP SRFSGSGSGT DYSLTISNLE QEDIATYFCQ QGNTLPYTFG    120
GGTKLEITGS TSGSGKPGSG EGSTKGEVKL QESGPGLVAP SQSLSVTCTV SGVSLPDYGV    180
SWIRQPPRKG LEWLGVIWGS ETTYYNSALK SRLTIIKDNS KSQVFLKMNS LQTDDTAIYY    240
CAKHYYYGGS YAMDYWGQGT SVTVSSTTTP APRPPTPAPT IASQPLSLRP EACRPAAGGA    300
VHTRGLDFAC DIYIWAPLAG TCGVLLLSLV ITLYCKRGRK KLLYIFKQPF MRPVQTTQEE    360
DGCSCRFPEE EEGGCELRVK FSRSADAPAY QQGQNQLYNE LNLGRREEYD VLDKRRGRDP    420
EMGGKPRRKN PQEGLYNELQ KDKMAEAYSE IGMKGERRRG KGHDGLYQGL STATKDTYDA    480
LHMQALPPR                                                           489

SEQ ID NO: 118         moltype = AA   length = 243
FEATURE                Location/Qualifiers
REGION                 1..243
                       note = Synthetic amino acid
source                 1..243
                       mol_type = protein
                       organism = synthetic construct
SEQUENCE: 118
DIQMTQSPSS LSASVGDRVT ITCRASQSIS SYLNWYQQKP GKAPKLLIYA ASSLQSGVPS     60
RFSGSGSGTD FTLTISSLQP EDFATYYCQQ KYDLLTFGGG TKVEIKGSTS GSGKPGSGEG    120
STKGQLQLQE SGPGLVKPSE TLSLTCTVSG GSISSSSYYW GWIRQPPGKG LEWIGSISYS    180
GSTYYNPSLK SRVTISVDTS KNQFSLKLSS VTAADTAVYY CARDRGDTIL DVWGQGTMVT    240
VSS                                                                 243

SEQ ID NO: 119         moltype = AA   length = 106
FEATURE                Location/Qualifiers
REGION                 1..106
                       note = Synthetic amino acid
source                 1..106
                       mol_type = protein
                       organism = synthetic construct
SEQUENCE: 119
DIQMTQSPSS LSASVGDRVT ITCRASQSIS SYLNWYQQKP GKAPKLLIYA ASSLQSGVPS     60
RFSGSGSGTD FTLTISSLQP EDFATYYCQQ KYDLLTFGGG TKVEIK                   106

SEQ ID NO: 120         moltype = AA   length = 6
FEATURE                Location/Qualifiers
REGION                 1..6
                       note = Synthetic amino acid
source                 1..6
                       mol_type = protein
                       organism = synthetic construct
SEQUENCE: 120
QSISSY                                                                 6

SEQ ID NO: 121         moltype =   length =
SEQUENCE: 121
000

SEQ ID NO: 122         moltype = AA   length = 8
FEATURE                Location/Qualifiers
REGION                 1..8
                       note = Synthetic amino acid
source                 1..8
```

```
                        mol_type = protein
                        organism = synthetic construct
SEQUENCE: 122
QQKYDLLT                                                              8

SEQ ID NO: 123          moltype = AA   length = 119
FEATURE                 Location/Qualifiers
REGION                  1..119
                        note = Synthetic amino acid
source                  1..119
                        mol_type = protein
                        organism = synthetic construct
SEQUENCE: 123
QLQLQESGPG LVKPSETLSL TCTVSGGSIS SSSYYWGWIR QPPGKGLEWI GSISYSGSTY    60
YNPSLKSRVT ISVDTSKNQF SLKLSSVTAA DTAVYYCARD RGDTILDVWG QGTMVTVSS    119

SEQ ID NO: 124          moltype = AA   length = 10
FEATURE                 Location/Qualifiers
REGION                  1..10
                        note = Synthetic amino acid
source                  1..10
                        mol_type = protein
                        organism = synthetic construct
SEQUENCE: 124
GGSISSSSYY                                                            10

SEQ ID NO: 125          moltype = AA   length = 7
FEATURE                 Location/Qualifiers
REGION                  1..7
                        note = Synthetic amino acid
source                  1..7
                        mol_type = protein
                        organism = synthetic construct
SEQUENCE: 125
ISYSGST                                                               7

SEQ ID NO: 126          moltype = AA   length = 11
FEATURE                 Location/Qualifiers
REGION                  1..11
                        note = Synthetic amino acid
source                  1..11
                        mol_type = protein
                        organism = synthetic construct
SEQUENCE: 126
ARDRGDTILD V                                                          11

SEQ ID NO: 127          moltype = DNA   length = 1503
FEATURE                 Location/Qualifiers
misc_feature            1..1503
                        note = Synthetic nucleotide sequence
source                  1..1503
                        mol_type = other DNA
                        organism = synthetic construct
SEQUENCE: 127
atggccttac cagtgaccgc cttgctcctg ccgctggcct tgctgctcca cgccgccagg    60
ccggacatcc agatgaccca gtctccatcc tccctgtctg catctgtagg agacagagtc    120
accatcactt gccgggcaag tcagagcatt agcagctatt taaattggta tcagcagaaa    180
ccagggaaag cccctaagct cctgatctat gctgcatcca gtttgcaaag tggggtccca    240
tcaaggttca gtggcagtgg atctgggaca gatttcactc tcaccatcag cagtctgcaa    300
cctgaagatt ttgcaactta ctactgtcag caaaaatacg acctcctcac ttttggcgga    360
gggaccaagg ttgagatcaa aggcagcacc agcggctccg gcaagcctgg ctctggcgag    420
ggcagcacaa agggacagct gcagctgcag gagtcgggcc caggactggt gaagccttcg    480
gagaccctgt ccctcacctg cactgtctct ggtggctcca tcagcagtag tagttactac    540
tggggctgga tccgccagcc cccagggaag gggctgagt  ggattgggag tatctcctat    600
agtgggagca cctactacaa cccgtccctc aagagtcgag tcaccatatc cgtagacacg    660
tccaagaacc agttctccct gaagctgagt tctgtgaccg ccgcagacac ggccgtgtac    720
tactgcgcca gagatcgtgg agacaccata ctagacgtat ggggtcaggg tacaatggtc    780
accgtcagct cattcgtgcc cgtgttcctg cccgccaaac ctaccaccac ccctgccct    840
agacctccca ccccagcccc aacaatcgcc agcagcctc  tgtctctgcg gcccgaagcc    900
tgtagacctg ctgccggcgg agccgtgcac accagaggcc tggacttcgc ctgcgacatc    960
tacatctggg cccctctggc cggcacctgt ggcgtgctgc tgctgagcct ggtgatcacc    1020
ctgtactgca ccaccggaaa caaacggggc agaaagaaac tcctgtatat attcaaacaa    1080
ccatttatga gaccagtaca aactactcaa gaggaagatg ctgtagctg  ccgatttcca    1140
gaagaagaag aaggaggatg tgaactgaga gtgaagttca gccgacgcct cgacgccctc    1200
gcctaccagc agggacagaa ccagctgtac aacgagctga acctgggcag acgggaagag    1260
tacgacgtgc tggacaagcg agagggccgg gaccccgaga tgggcggaaa gcccagacgg    1320
aagaaccccc aggaaggcct gtataacgaa ctgcagaaag acaagatggc cgaggcctac    1380
agcgagatcg gcatgaaggg cgagcggagg cgcggcaagg gccacgatgg cctgtaccag    1440
ggcctgagca ccgccaccaa ggacacctac gacgccctgc acatgcaggc cctgcccccc    1500
```

```
aga                                                                    1503

SEQ ID NO: 128          moltype = AA  length = 501
FEATURE                 Location/Qualifiers
REGION                  1..501
                        note = Synthetic amino acid
source                  1..501
                        mol_type = protein
                        organism = synthetic construct
SEQUENCE: 128
MALPVTALLL PLALLLHAAR PDIQMTQSPS SLSASVGDRV TITCRASQSI SSYLNWYQQK        60
PGKAPKLLIY AASSLQSGVP SRFSGSGSGT DFTLTISSLQ PEDFATYYCQ QKYDLLTFGG       120
GTKVEIKGST SGSGKPGSGE GSTKGQLQLQ ESGPGLVKPS ETLSLTCTVS GGSISSSSYY       180
WGWIRQPPGK GLEWIGSISY SGSTYYNPSL KSRVTISVDT SKNQFSLKLS SVTAADTAVY       240
YCARDRGDTI LDVWGQGTMV TVSSFVPVFL PAKPTTTPAP RPPTPAPTIA SQPLSLRPEA       300
CRPAAGGAVH TRGLDFACDI YIWAPLAGTC GVLLLSLVIT LYCNHRNKRG RKKLLYIFKQ       360
PFMRPVQTTQ EEDGCSCRFP EEEEGGCELR VKFSRSADAP AYQQGQNQLY NELNLGRREE       420
YDVLDKRRGR DPEMGGKPRR KNPQEGLYNE LQKDKMAEAY SEIGMKGERR RGKGHDGLYQ       480
GLSTATKDTY DALHMQALPP R                                                501

SEQ ID NO: 129          moltype = RNA  length = 20
FEATURE                 Location/Qualifiers
misc_feature            1..20
                        note = Synthetic guide sequence
source                  1..20
                        mol_type = other RNA
                        organism = synthetic construct
ncRNA                   1..20
                        ncRNA_class = guide_RNA
SEQUENCE: 129
gatattggca taagcctccc                                                   20

SEQ ID NO: 130          moltype = RNA  length = 20
FEATURE                 Location/Qualifiers
misc_feature            1..20
                        note = Synthetic guide sequence
source                  1..20
                        mol_type = other RNA
                        organism = synthetic construct
ncRNA                   1..20
                        ncRNA_class = guide_RNA
SEQUENCE: 130
agagtctctc agctggtaca                                                   20

SEQ ID NO: 131          moltype =   length =
SEQUENCE: 131
000

SEQ ID NO: 132          moltype = RNA  length = 12
FEATURE                 Location/Qualifiers
misc_feature            1..12
                        note = Synthetic guide sequence
source                  1..12
                        mol_type = other RNA
                        organism = synthetic construct
ncRNA                   1..12
                        ncRNA_class = guide_RNA
SEQUENCE: 132
gttttagagc ta                                                           12

SEQ ID NO: 133          moltype =   length =
SEQUENCE: 133
000

SEQ ID NO: 134          moltype = RNA  length = 63
FEATURE                 Location/Qualifiers
misc_feature            1..63
                        note = Synthetic guide sequence
source                  1..63
                        mol_type = other RNA
                        organism = synthetic construct
ncRNA                   1..63
                        ncRNA_class = guide_RNA
SEQUENCE: 134
tagcaagtta aaataaggct agtccgttat caacttgaaa aagtggcacc gagtcggtgc        60
ttt                                                                     63

SEQ ID NO: 135          moltype = RNA  length = 99
FEATURE                 Location/Qualifiers
```

```
misc_feature            1..99
                        note = Synthetic guide sequence
source                  1..99
                        mol_type = other RNA
                        organism = synthetic construct
ncRNA                   1..99
                        ncRNA_class = guide_RNA
SEQUENCE: 135
nnnnnnnnnn nnnnnnnnnn gttttagagc tagaaatagc aagttaaaat aaggctagtc    60
cgttatcaac ttgaaaaagt ggcaccgagt cggtgcttt                           99

SEQ ID NO: 136          moltype = AA  length = 305
FEATURE                 Location/Qualifiers
source                  1..305
                        mol_type = protein
                        note = Human adenovirus type 47
                        organism = unidentified
SEQUENCE: 136
QLLFNKTKSV EFTFCNDTVV IPCFVTNMEA QNTTEVYVKW KFKGRDIYTF DGALNKSTVP    60
TDFSSAKIEV SQLLKGDASL KMDKSDAVSH TGNYTCEVTE LTREGETIIE LKYRVVSWFS   120
PNENILIVIF PIFAILLFWG QFGIKTLKYR SGGMDEKTIA LLVAGLVITV IVIVGAILFV   180
PGEYSLKNAT GLGLIVTSTG ILILLHYYVF STAIGLTSFV IAILVIQVIA YILAVVGLSL   240
CIAACIPMHG PLLISGLSIL ALAQLLGLVY MKFVASNQKT IQPPRKAVEE PLNAFKESKG   300
MMNDE                                                               305

SEQ ID NO: 137          moltype = AA  length = 323
FEATURE                 Location/Qualifiers
source                  1..323
                        mol_type = protein
                        note = Human adenovirus type 47
                        organism = unidentified
SEQUENCE: 137
MWPLVAALLL GSACCGSAQL LFNKTKSVEF TFCNDTVVIP CFVTNMEAQN TTEVYVKWKF    60
KGRDIYTFDG ALNKSTVPTD FSSAKIEVSQ LLKGDASLKM DKSDAVSHTG NYTCEVTELT   120
REGETIIELK YRVVSWFSPN ENILIVIFPI FAILLFWGQF GIKTLKYRSG GMDEKTIALL   180
VAGLVITVIV IVGAILFVPG EYSLKNATGL GLIVTSTGIL ILLHYYVFST AIGLTSFVIA   240
ILVIQVIAYI LAVVGLSLCI AACIPMHGPL LISGLSILAL AQLLGLVYMK FVASNQKTIQ   300
PPRKAVEEPL NAFKESKGMM NDE                                           323

SEQ ID NO: 138          moltype = AA  length = 18
FEATURE                 Location/Qualifiers
REGION                  1..18
                        note = Synthetic amino acid linker
source                  1..18
                        mol_type = protein
                        organism = synthetic construct
SEQUENCE: 138
GSTSGSGKPG SGEGSTKG                                                  18

SEQ ID NO: 139          moltype = RNA  length = 12
FEATURE                 Location/Qualifiers
source                  1..12
                        mol_type = other RNA
                        organism = synthetic construct
ncRNA                   1..12
                        ncRNA_class = guide_RNA
SEQUENCE: 139
gttttagagc ta                                                        12

SEQ ID NO: 140          moltype = RNA  length = 63
FEATURE                 Location/Qualifiers
source                  1..63
                        mol_type = other RNA
                        organism = synthetic construct
ncRNA                   1..63
                        ncRNA_class = guide_RNA
SEQUENCE: 140
tagcaagtta aaataaggct agtccgttat caacttgaaa aagtggcacc gagtcggtgc    60
ttt                                                                  63

SEQ ID NO: 141          moltype = RNA  length = 99
FEATURE                 Location/Qualifiers
source                  1..99
                        mol_type = other RNA
                        organism = synthetic construct
SEQUENCE: 141
nnnnnnnnnn nnnnnnnnnn gttttagagc tagaaatagc aagttaaaat aaggctagtc    60
cgttatcaac ttgaaaaagt ggcaccgagt cggtgcttt                           99
```

```
SEQ ID NO: 142            moltype = AA  length = 305
FEATURE                   Location/Qualifiers
source                    1..305
                          mol_type = protein
                          organism = Homo sapiens
SEQUENCE: 142
QLLFNKTKSV EFTFCNDTVV IPCFVTNMEA QNTTEVYVKW KFKGRDIYTF DGALNKSTVP   60
TDFSSAKIEV SQLLKGDASL KMDKSDAVSH TGNYTCEVTE LTREGETIIE LKYRVVSWFS  120
PNENILIVIF PIFAILLFWG QFGIKTLKYR SGGMDEKTIA LLVAGLVITV IVIVGAILFV  180
PGEYSLKNAT GLGLIVTSTG ILILLHYYVF STAIGLTSFV IAILVIQVIA YILAVVGLSL  240
CIAACIPMHG PLLISGLSIL ALAQLLGLVY MKFVASNQKT IQPPRKAVEE PLNAFKESKG  300
MMNDE                                                              305

SEQ ID NO: 143            moltype = AA  length = 323
FEATURE                   Location/Qualifiers
source                    1..323
                          mol_type = protein
                          organism = Homo sapiens
SEQUENCE: 143
MWPLVAALLL GSACCGSAQL LFNKTKSVEF TFCNDTVVIP CFVTNMEAQN TTEVYVKWKF   60
KGRDIYTFDG ALNKSTVPTD FSSAKIEVSQ LLKGDASLKM DKSDAVSHTG NYTCEVTELT  120
REGETIIELK YRVVSWFSPN ENILIVIFPI FAILLFWGQF GIKTLKYRSG GMDEKTIALL  180
VAGLVITVIV IVGAILFVPG EYSLKNATGL GLIVTSTGIL ILLHYYVFST AIGLTSFVIA  240
ILVIQVIAYI LAVVGLSLCI AACIPMHGPL LISGLSILAL AQLLGLVYMK FVASNQKTIQ  300
PPRKAVEEPL NAFKESKGMM NDE                                          323

SEQ ID NO: 144            moltype = AA  length = 6
FEATURE                   Location/Qualifiers
source                    1..6
                          mol_type = protein
                          organism = synthetic construct
REGION                    2..6
                          note = GGGGS can be repeated one or more times
SEQUENCE: 144
SGGGGS                                                               6

SEQ ID NO: 145            moltype = AA  length = 5
FEATURE                   Location/Qualifiers
source                    1..5
                          mol_type = protein
                          organism = synthetic construct
REGION                    1..5
                          note = GGGGS can be repeated one or more times
SEQUENCE: 145
GGGGS                                                                5

SEQ ID NO: 146            moltype = AA  length = 16
FEATURE                   Location/Qualifiers
source                    1..16
                          mol_type = protein
                          organism = synthetic construct
SEQUENCE: 146
SGGGGSGGGG SGGGGS                                                   16

SEQ ID NO: 147            moltype = AA  length = 21
FEATURE                   Location/Qualifiers
source                    1..21
                          mol_type = protein
                          organism = synthetic construct
SEQUENCE: 147
SGGGGSGGGG SGGGGSGGGG S                                             21

SEQ ID NO: 148            moltype = AA  length = 4
FEATURE                   Location/Qualifiers
source                    1..4
                          mol_type = protein
                          organism = synthetic construct
REGION                    1..4
                          note = GGGS can be repeated one or more times
SEQUENCE: 148
GGGS                                                                 4
```

| | |
|---|---|
| SEQ ID NO: 149 | moltype = AA length = 7 |
| FEATURE | Location/Qualifiers |
| source | 1..7 |
| | mol_type = protein |
| | organism = synthetic construct |
| REGION | 1..7 |
| | note = GGGGSSS can be repeated one or more times |
| SEQUENCE: 149 | |
| GGGGSSS | 7 |

What is claimed is:

1. An engineered T cell comprising (a) reduced expression of B2M, CIITA, and/or T cell receptor (TCR)-alpha relative to a control T cell, (b) expression of CD47 encoded by a first exogenous polynucleotide so that the engineered T cells comprise increased CD47 expression relative to the control T cell, and (c) expression of a CD22-specific chimeric antigen receptor (CAR) encoded by a second exogenous polynucleotide,
wherein the engineered T cell is derived from a primary T cell,
wherein the CAR comprises an antigen binding domain comprising:
 (i) a light chain variable region comprising a light chain CDR1, a light chain CDR2, and a light chain CDR3, wherein the light chain CDR1 comprises the amino acid sequence set forth in SEQ ID NO: 51, the light chain CDR2 comprises the amino acid sequence set forth in SEQ ID NO: 52, and the light chain CDR3 comprises the amino acid sequence set forth in SEQ ID NO: 53, and
 (ii) a heavy chain variable region comprising a heavy chain CDR1, a heavy chain CDR2, and a heavy chain CDR3 amino acid, wherein the heavy chain CDR1 comprises the amino acid sequence set forth in SEQ ID NO: 47, the heavy chain CDR2 comprises the amino acid sequence set forth in SEQ ID NO: 48, and the heavy chain CDR3 comprises the amino acid sequence set forth in SEQ ID NO: 49,
wherein the first exogenous polynucleotide is inserted into a locus of at least one allele of the engineered T cell, and
wherein the second exogenous polynucleotide is inserted into a locus of at least one allele of the engineered T cell.

2. The engineered T cell of claim 1, wherein the CAR further comprises (i) a hinge domain, (ii) a transmembrane domain, (iii) a costimulatory domain, and (iv) an intracellular signaling domain.

3. The engineered T cell of claim 2, wherein
 (i) the hinge domain is selected from the group of hinge domains consisting of a CD8α hinge domain, a CD28 hinge domain, an IgG4 hinge domain, and an IgG4 hinge-CH2-CH3 domain;
 (ii) the transmembrane domain is selected from the group of transmembrane domains consisting of TCRζ, CD5, CD8, CD9, CD45, CD22, CD32, CD33, CD37, CD40, CD40L/CD154, CD64, CD80, CD86, CD134, CD137, CD154, VEGFR2, FAS, FGFR2B, CD8α, CD8β, 4-1BB/CD137, CD28, CD34, CD4, FcεRIγ, CD16, OX40/CD134, CD3ζ, CD3ε, CD3γ, CD3δ, TCRα, and TCRβ;
 (iii) the costimulatory domain is selected from the group of costimulatory domains consisting of B7-H3, CD28, CTLA-4, PD-1, 4-1BB/TNFSF9/CD137, OX40/TNFRSF4, CD200, HLA Class I, HLA-DR, DAP12, CD3ζ, and an immunoreceptor tyrosine-based activation motif (ITAM), 2B4/CD244/SLAMF4, 4-1BB, 4-1BB ligand/TNFSF9, 4-1BB/CD137, a ligand that specifically binds with CD83, TCRβ, B7-2/CD86, B7-H1/PD-L1, B7-H2, B7-H4, B7-H6, B7-H7, BAFF R/TNFRSF13C, BAFF/BLyS/TNFSF13B, BLAME/SLAMF8, BTLA/CD272, CD134, CD134/OX40, CD137, CD154, CD16, CD160, CD2, CD22, CD229/SLAMF3, CD27, CD27/TNFRSF7, CD2F-10/SLAMF9, CD30, CD30/TNFRSF8, CD300a/LMIR1, CD32, CD33, CD34, CD37, CD3γ, CD3δ, CD3ε, CD4, CD40, CD40/TNFRSF5, CD40/TNFSF5, CD40L/CD154, CD45, CD48/SLAMF2, CD5, CD53, CD58/LFA-3, CD64, CD7, CD8, CD80, CD82/Kai-1, CD84/SLAMF5, CD84/SLAMF8, CD86, CD8α, CD8β, CD9, CD90/Thy1, CD96, CRACC/SLAMF7, CRTAM, Dectin-1/CLEC7A, DPPIV/CD26, DR3/TNFRSF25, EphB6, FAS, FcεRIγ, FGFR2B, Gi24/VISTA/B7-H5, GITR/TNFRSF18, HVEM/TNFRSF14, ICOS, ICOS/CD278, Ikaros, integrin alpha 4 beta 1, integrin alpha 4 beta 7/LPAM-1, integrin alpha 4/CD49d, LAG-3, LIGHT, LIGHT/TNFSF14, lymphocyte function-associated antigen-1 (LFA-1), lymphotoxin-alpha/TNFβ, NKG2C, NTB-A/SLAMF6, OX40/CD134, PDCD6, PD-L2/B7-DC, RELT/TNFRSF19L, SLAM/CD150, TACI/TNFRSF13B, TCL1A, TCL1B, TCRα, TCRζ, TIM-1/KIM-1/HAVCR, TIM-4, TL1A/TNFSF15, TNF RII/TNFRSFIB, TNFα, TSLP, TSLP R, and VEGFR2; and
 (iv) the intracellular signaling domain is a CD3ζ signaling domain.

4. The engineered T cell of claim 3, wherein the hinge domain comprises the amino acid sequence set forth in SEQ ID NO: 9, SEQ ID NO: 10, SEQ ID NO: 11, SEQ ID NO: 12, SEQ ID NO: 13, or SEQ ID NO: 113.

5. The engineered T cell of claim 3, wherein the transmembrane domain comprises the amino acid sequence set forth in SEQ ID NO: 14, SEQ ID NO: 15, or SEQ ID NO: 114.

6. The engineered T cell of claim 3, wherein the costimulatory domain comprises the amino acid sequence set forth in SEQ ID NO: 16 or SEQ ID NO: 17.

7. The engineered T cell of claim 3, wherein the intracellular signaling domain comprises the amino acid sequence set forth in SEQ ID NO: 18 or SEQ ID NO: 115.

8. The engineered T cell of claim 3, wherein
 (i) the hinge domain comprises the amino acid sequence set forth in SEQ ID NO: 9,
 (ii) the transmembrane domain comprises the amino acid sequence set forth in SEQ ID NO: 14,
 (iii) the costimulatory domain comprises the amino acid sequence set forth in SEQ ID NO: 16, and
 (iv) the intracellular signaling domain comprises the amino acid sequence set forth in SEQ ID NO: 18.

9. The engineered T cell of claim 1, wherein the light chain variable region comprises the amino acid sequence set forth in SEQ ID NO: 50, and wherein the heavy chain variable region comprises the amino acid sequence set forth in SEQ ID NO: 46.

10. The engineered T cell of claim 3, wherein the antigen binding domain comprises a linker, wherein the linker comprises:
(i) SEQ ID NO: 24;
(ii) SEQ ID NO: 30; or
(ii) a (Gly$_4$Ser)$_n$ linker comprising the amino acid sequence set forth in SEQ ID NO: 145, wherein n is 1, 2, 3, 4, 5, or 6.

11. The engineered T cell of claim 3, wherein the CAR further comprises a signal peptide.

12. The engineered T cell of claim 11, wherein the signal peptide comprises the amino acid sequence set forth in SEQ ID NO: 6, SEQ ID NO: 7, or SEQ ID NO: 8.

13. The engineered T cell of claim 3, comprising reduced surface expression of human leukocyte antigen (HLA) class I antigens, HLA class II antigens, and/or TCR-alpha.

14. The engineered T cell of claim 13, comprising no surface expression of HLA class I antigens, no surface expression of HLA class II antigens, and/or no surface expression of TCR-alpha.

15. The engineered T cell of claim 14, wherein the engineered T cell is a B2M$^{indel/indel}$, CIITA$^{indel/indel}$ cell, and/or a TRAC$^{indel/indel}$ cell.

16. The engineered T cell of claim 1, wherein the first exogenous polynucleotide encoding CD47 and the second exogenous polynucleotide encoding the CAR are inserted into the same locus.

17. The engineered T cell of claim 1, wherein the first exogenous polynucleotide encoding CD47 and the second exogenous polynucleotide encoding the CAR are inserted into different loci.

18. The engineered T cell of claim 3, wherein the first and second exogenous polynucleotides are inserted into at least one allele of the engineered T cell using viral transduction.

19. The engineered T cell of claim 18, wherein the viral transduction includes a lentivirus based viral vector.

20. The engineered T cell of claim 19, wherein the lentivirus based viral vector is a pseudotyped, self-inactivating lentiviral vector that carries the first and/or the second exogenous polynucleotides.

21. The engineered T cell of claim 20, wherein the lentivirus based viral vector is a self-inactivating lentiviral vector pseudotyped with a vesicular stomatitis VSV-G envelope and carries the first and/or second exogenous polynucleotides.

22. A pharmaceutical composition comprising an engineered T cell and a pharmaceutically acceptable carrier, wherein the engineered T cell comprises (a) reduced expression of B2M, CIITA, and/or T cell receptor (TCR)-alpha relative to a control T cell, (b) expression of CD47 encoded by a first exogenous polynucleotide so that the engineered T cells comprise increased CD47 expression relative to the control T cell, and (c) expression of a CD22-specific chimeric antigen receptor (CAR) encoded by a second exogenous polynucleotide,
wherein the engineered T cell is derived from a primary T cell,
wherein the CAR comprises an antigen binding domain comprising:
(i) a light chain variable region comprising a light chain CDR1, a light chain CDR2, and a light chain CDR3 of the light chain variable region sequence set forth in SEQ ID NO: 50, and
(ii) a heavy chain variable region comprising a heavy chain CDR1, a heavy chain CDR2, and a heavy chain CDR3 amino acid of the heavy chain variable region sequence set forth in SEQ ID NO: 46,
wherein the first exogenous polynucleotide is inserted into a locus of at least one allele of the engineered T cell, and
wherein the second exogenous polynucleotide is inserted into a locus of at least one allele of the engineered T cell.

23. The pharmaceutical composition of claim 22, wherein the CAR further comprises a hinge domain, a transmembrane domain, a costimulatory domain, and an intracellular signaling domain, and wherein
(i) the hinge domain is selected from the group of hinge domains consisting of a CD8α hinge domain, a CD28 hinge domain, an IgG4 hinge domain, and an IgG4 hinge-CH2-CH3 domain;
(ii) the transmembrane domain is selected from the group of transmembrane domains consisting of TCRζ, CD5, CD8, CD9, CD45, CD22, CD32, CD33, CD37, CD40, CD40L/CD154, CD64, CD80, CD86, CD134, CD137, CD154, VEGFR2, FAS, FGFR2B, CD8α, CD80, 4-1BB/CD137, CD28, CD34, CD4, FcεRIγ, CD16, OX40/CD134, CD3ζ, CD3ε, CD3γ, CD3δ, TCRα, and TCRβ;
(iii) the costimulatory domain is selected from the group of costimulatory domains consisting of B7-H3, CD28, CTLA-4, PD-1, 4-1BB/TNFSF9/CD137, OX40/TNFRSF4, CD200, HLA Class I, HLA-DR, DAP12, CD3ζ, and an immunoreceptor tyrosine-based activation motif (ITAM), 2B4/CD244/SLAMF4, 4-1BB, 4-1BB ligand/TNFSF9, 4-1BB/CD137, a ligand that specifically binds with CD83, TCRβ, B7-2/CD86, B7-H1/PD-L1, B7-H2, B7-H4, B7-H6, B7-H7, BAFF R/TNFRSF13C, BAFF/BLyS/TNFSF13B, BLAME/SLAMF8, BTLA/CD272, CD134, CD134/OX40, CD137, CD154, CD16, CD160, CD2, CD22, CD229/SLAMF3, CD27, CD27/TNFRSF7, CD2F-10/SLAMF9, CD30, CD30/TNFRSF8, CD300a/LMIR1, CD32, CD33, CD34, CD37, CD3γ, CD3δ, CD3ε, CD4, CD40, CD40/TNFRSF5, CD40/TNFSF5, CD40L/CD154, CD45, CD48/SLAMF2, CD5, CD53, CD58/LFA-3, CD64, CD7, CD8, CD80, CD82/Kai-1, CD84/SLAMF5, CD84/SLAMF8, CD86, CD8a, CD80, CD9, CD90/Thy1, CD96, CRACC/SLAMF7, CRTAM, Dectin-1/CLEC7A, DPPIV/CD26, DR3/TNFRSF25, EphB6, FAS, FcεRIγ, FGFR2B, Gi24/VISTA/B7-H5, GITR/TNFRSF18, HVEM/TNFRSF14, ICOS, ICOS/CD278, Ikaros, integrin alpha 4 beta 1, integrin alpha 4 beta 7/LPAM-1, integrin alpha 4/CD49d, LAG-3, LIGHT, LIGHT/TNFSF14, lymphocyte function-associated antigen-1 (LFA-1), lymphotoxin-alpha/TNFβ, NKG2C, NTB-A/SLAMF6, OX40/CD134, PDCD6, PD-L2/B7-DC, RELT/TNFRSF19L, SLAM/CD150, TACI/TNFRSF13B, TCL1A, TCL1B, TCRα, TCRζ, TIM-1/KIM-1/HAVCR, TIM-4, TL1A/TNFSF15, TNF RII/TNFRSF1B, TNFα, TSLP, TSLP R, and VEGFR2; and
(iv) the intracellular signaling domain is a CD3ζ signaling domain.

24. The pharmaceutical composition of claim 23, wherein
(i) the hinge domain comprises the amino acid sequence set forth in SEQ ID NO: 9,
(ii) the transmembrane domain comprises the amino acid sequence set forth in SEQ ID NO: 14,
(iii) the costimulatory domain comprises the amino acid sequence set forth in SEQ ID NO: 16, and
(iv) the intracellular signaling domain comprises the amino acid sequence set forth in SEQ ID NO: 18.

25. The pharmaceutical composition of claim 24, wherein the light chain variable region comprises the amino acid sequence set forth in SEQ ID NO: 50, and wherein the heavy chain variable region comprises the amino acid sequence set forth in SEQ ID NO: 46.

26. The pharmaceutical composition of claim 24, wherein the engineered T cell comprises reduced surface expression of human leukocyte antigen (HLA) class I antigens, HLA class II antigens, and/or TCR-alpha.

27. The pharmaceutical composition of claim 24, wherein the engineered T cell comprises no surface expression of HLA class I antigens, no surface expression of HLA class II antigens, and no surface expression of TCR-alpha.

28. The pharmaceutical composition of claim 24, wherein the engineered T cell is a $B2M^{indel/indel}$, $CIITA^{indel/indel}$ cell, and/or a $TRAC^{indel/indel}$ cell.

29. The pharmaceutical composition of claim 24, wherein the first exogenous polynucleotide encoding CD47 and the second exogenous polynucleotide encoding the CAR are inserted into the same locus.

30. The pharmaceutical composition of claim 24, wherein the first and second exogenous polynucleotides are inserted into at least one allele of the engineered T cell using viral transduction.

* * * * *